United States Patent
Laird et al.

(10) Patent No.: US 8,586,313 B2
(45) Date of Patent: Nov. 19, 2013

(54) DNA METHYLATION MARKERS BASED ON EPIGENETIC STEM CELL SIGNATURES IN CANCER

(75) Inventors: Peter W. Laird, South Pasadena, CA (US); Martin Widschwendter, London (GB)

(73) Assignees: The University of Southern California, Los Angeles, CA (US); University College London (GB)

( * ) Notice: Subject to any disclaimer, the term of this patent is extended or adjusted under 35 U.S.C. 154(b) by 657 days.

(21) Appl. No.: 12/520,841

(22) PCT Filed: Dec. 27, 2007

(86) PCT No.: PCT/US2007/088994
§ 371 (c)(1), (2), (4) Date: Jan. 14, 2010

(87) PCT Pub. No.: WO2008/083251
PCT Pub. Date: Jul. 10, 2008

(65) Prior Publication Data
US 2010/0172880 A1    Jul. 8, 2010

Related U.S. Application Data

(60) Provisional application No. 60/877,530, filed on Dec. 27, 2006, provisional application No. 60/882,948, filed on Dec. 31, 2006.

(51) Int. Cl.
*C12Q 1/68* (2006.01)
(52) U.S. Cl.
USPC .......................................... 435/6.14; 435/6.1
(58) Field of Classification Search
None
See application file for complete search history.

(56) References Cited

PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Bracken et al., "Genome-wide mapping of Polycomb target genes unravels their roles in cell fate transitions," Genes & Development, 2006, pp. 1123-1136, vol. 20.

* cited by examiner

*Primary Examiner* — James Martinell
(74) *Attorney, Agent, or Firm* — Barry L. Davison; Davis Wright Tremaine LLP

(57) ABSTRACT

In particular aspects, stem-cell polycomb group (PcG) targets are more likely to have cancer-specific promoter DNA methylation than non-targets, indicating a stem-cell origin of cancer, where reversible gene repression is replaced by permanent silencing, locking the cell into a perpetual state of self-renewal and predisposition to subsequent malignant transformation. Exemplary aspects provide methods for identifying preferred DNA methylation markers for a cellular proliferative disorder and/or cancer and markers for developmental lineages and/or stages, based on identifying PcG protein or PcG repressive complex genomic target loci within a precursor cell (e.g., stem or progenitor cell) population, and determining, in cells of the proliferative disorder and/or cancer or cell of the particular developmental lineages and/or stages, a characteristic methylation status of the PcG target loci. Additional aspects provide methods for validating and/or monitoring a precursor cell (e.g., stem cell) population. Diagnostic and prognostic methods for ovarian and breast cancer are provided.

45 Claims, 5 Drawing Sheets

SEQUENCE LISTING

```
<160> NUMBER OF SEQ ID NOS: 599

<210> SEQ ID NO 1
<211> LENGTH: 31
<212> TYPE: DNA
<213> ORGANISM: Artificial sequence
<220> FEATURE:
<223> OTHER INFORMATION: CXCR4: Forward primer

<400> SEQUENCE: 1
cgctaattct ccaaatacga taactactaa a                              31

<210> SEQ ID NO 2
<211> LENGTH: 21
<212> TYPE: DNA
<213> ORGANISM: Artificial sequence
<220> FEATURE:
<223> OTHER INFORMATION: CXCR4: Reverse

<400> SEQUENCE: 2
tcggtcgcgg ttagaaattt t                                         21

<210> SEQ ID NO 3
<211> LENGTH: 33
<212> TYPE: DNA
<213> ORGANISM: Artificial Sequence
<220> FEATURE:
<223> OTHER INFORMATION: CXCR4: Probe (5'-6-FAM; 3'-BHQ1)

<400> SEQUENCE: 3
tcgacgtcac tttactacct actaccgcaa cca                            33

<210> SEQ ID NO 4
<211> LENGTH: 19
<212> TYPE: DNA
<213> ORGANISM: Artificial Sequence
<220> FEATURE:
<223> OTHER INFORMATION: SFRP 1 Forward primer

<400> SEQUENCE: 4
caactcccga cgaaacgaa                                            19

<210> SEQ ID NO 5
<211> LENGTH: 16
<212> TYPE: DNA
<213> ORGANISM: Artificial Sequence
```

```
<220> FEATURE:
<223> OTHER INFORMATION: SFRP1 Reverse primer

<400> SEQUENCE: 5
cgcgagggag gcgatt                                                        16

<210> SEQ ID NO 6
<211> LENGTH: 24
<212> TYPE: DNA
<213> ORGANISM: Artificial Sequence
<220> FEATURE:
<223> OTHER INFORMATION: SFRP1: Probe (5'-6-FAM; 3'-BHQ1)

<400> SEQUENCE: 6
cactcgttac cacgtccgtc accg                                               24

<210> SEQ ID NO 7
<211> LENGTH: 18
<212> TYPE: DNA
<213> ORGANISM: Artificial Sequence
<220> FEATURE:
<223> OTHER INFORMATION: SFRP2 forward primer

<400> SEQUENCE: 7
aaacctaccc gcccgaaa                                                      18

<210> SEQ ID NO 8
<211> LENGTH: 22
<212> TYPE: DNA
<213> ORGANISM: Artificial Sequence
<220> FEATURE:
<223> OTHER INFORMATION: SFRP2 reverse primer

<400> SEQUENCE: 8
gttgaacggt ggttggagat tc                                                 22

<210> SEQ ID NO 9
<211> LENGTH: 25
<212> TYPE: DNA
<213> ORGANISM: Artificial Sequence
<220> FEATURE:
<223> OTHER INFORMATION: SFRP2: Probe (5'-6-FAM; 3'-BHQ1)

<400> SEQUENCE: 9
cgcctcgacg aacttcgttt tccct                                              25

<210> SEQ ID NO 10
<211> LENGTH: 20
<212> TYPE: DNA
<213> ORGANISM: Artificial Sequence
<220> FEATURE:
<223> OTHER INFORMATION: SFRP4 forward primer

<400> SEQUENCE: 10
tccgccgtct aacacacaaa                                                    20

<210> SEQ ID NO 11
<211> LENGTH: 21
<212> TYPE: DNA
<213> ORGANISM: Artificial Sequence
<220> FEATURE:
<223> OTHER INFORMATION: SFRP4 reverse primer

<400> SEQUENCE: 11
ttcgtaatgg tcgtggttgg t                                                  21
```

```
<210> SEQ ID NO 12
<211> LENGTH: 27
<212> TYPE: DNA
<213> ORGANISM: Artificial Sequence
<220> FEATURE:
<223> OTHER INFORMATION: SFRP4: Probe (5'-6-FAM; 3'-BHQ1)

<400> SEQUENCE: 12
caacgccaac tctcaacctt cgaaacg                                              27

<210> SEQ ID NO 13
<211> LENGTH: 21
<212> TYPE: DNA
<213> ORGANISM: Artificial Sequence
<220> FEATURE:
<223> OTHER INFORMATION: SFRP5 forward primer

<400> SEQUENCE: 13
gaacgccccg actaatccta a                                                    21

<210> SEQ ID NO 14
<211> LENGTH: 19
<212> TYPE: DNA
<213> ORGANISM: Artificial Sequence
<220> FEATURE:
<223> OTHER INFORMATION: SFRP5 reverse primer

<400> SEQUENCE: 14
taggcggtcg gagattggt                                                       19

<210> SEQ ID NO 15
<211> LENGTH: 24
<212> TYPE: DNA
<213> ORGANISM: Artificial Sequence
<220> FEATURE:
<223> OTHER INFORMATION: SFRP5: Probe (5'-6-FAM; 3'-BHQ1)

<400> SEQUENCE: 15
ctcccacctc gaaactccaa cccg                                                 24

<210> SEQ ID NO 16
<211> LENGTH: 21
<212> TYPE: DNA
<213> ORGANISM: Artificial Sequence
<220> FEATURE:
<223> OTHER INFORMATION: TP53BP2 forward primer

<400> SEQUENCE: 16 acccccctaac gcgactttat c                                                   21

<210> SEQ ID NO 17
<211> LENGTH: 22
<212> TYPE: DNA
<213> ORGANISM: Artificial Sequence
<220> FEATURE:
<223> OTHER INFORMATION: TP53BP2 reverse primer

<400> SEQUENCE: 17
gttcgattcg ggattagttg gt                                                   22

<210> SEQ ID NO 18
<211> LENGTH: 27
<212> TYPE: DNA
<213> ORGANISM: Artificial Sequence
<220> FEATURE:
<223> OTHER INFORMATION: TP53BP2: Probe (5'-6-FAM; 3'-BHQ1)

<400> SEQUENCE: 18
```

```
cgctcgtaac gatcgaaact ccctcct                                    27

<210> SEQ ID NO 19
<211> LENGTH: 17
<212> TYPE: DNA
<213> ORGANISM: Artificial Sequence
<220> FEATURE:
<223> OTHER INFORMATION: CCND2 forward primer

<400> SEQUENCE: 19
ggagggtcgg cgaggat                                               17

<210> SEQ ID NO 20
<211> LENGTH: 22
<212> TYPE: DNA
<213> ORGANISM: Artificial Sequence
<220> FEATURE:
<223> OTHER INFORMATION: CCND2 reverse primer

<400> SEQUENCE: 20
tcctttcccc gaaaacataa aa                                         22

<210> SEQ ID NO 21
<211> LENGTH: 20
<212> TYPE: DNA
<213> ORGANISM: Artificial Sequence
<220> FEATURE:
<223> OTHER INFORMATION: CCND2: Probe (5'-6-FAM; 3'-BHQ1)

<400> SEQUENCE: 21
cacgctcgat ccttcgcccg                                            20

<210> SEQ ID NO 22
<211> LENGTH: 14
<212> TYPE: DNA
<213> ORGANISM: Artificial Sequence
<220> FEATURE:
<223> OTHER INFORMATION: FHIT forward primer

<400> SEQUENCE: 22
ggcgcgggtt tggg                                                  14

<210> SEQ ID NO 23
<211> LENGTH: 16
<212> TYPE: DNA
<213> ORGANISM: Artificial Sequence
<220> FEATURE:
<223> OTHER INFORMATION: FHIT reverse primer

<400> SEQUENCE: 23
cgccccgtaa acgacg                                                16

<210> SEQ ID NO 24
<211> LENGTH: 32
<212> TYPE: DNA
<213> ORGANISM: Artificial Sequence
<220> FEATURE:
<223> OTHER INFORMATION: FHIT: Probe (5'-6-FAM; 3'-BHQ1)

<400> SEQUENCE: 24
cactaaactc cgaaataata acctaacgcg cg                              32

<210> SEQ ID NO 25
<211> LENGTH: 21
<212> TYPE: DNA
<213> ORGANISM: Artificial Sequence
```

```
<220> FEATURE:
<223> OTHER INFORMATION: SOCS1 forward primer

<400> SEQUENCE: 25
gcgtcgagtt cgtgggtatt t                                      21

<210> SEQ ID NO 26
<211> LENGTH: 21
<212> TYPE: DNA
<213> ORGANISM: Artificial Sequence
<220> FEATURE:
<223> OTHER INFORMATION: SOCS1 reverse primer

<400> SEQUENCE: 26
ccgaaaccat cttcacgcta a                                      21

<210> SEQ ID NO 27
<211> LENGTH: 26
<212> TYPE: DNA
<213> ORGANISM: Artificial Sequence
<220> FEATURE:
<223> OTHER INFORMATION: SOCS1: Probe (5'-6-FAM; 3'-BHQ1)

<400> SEQUENCE: 27
acaattccgc taacgactat cgcgca                                 26

<210> SEQ ID NO 28
<211> LENGTH: 23
<212> TYPE: DNA
<213> ORGANISM: Artificial Sequence
<220> FEATURE:
<223> OTHER INFORMATION: DIRAS3 forward primer

<400> SEQUENCE: 28
gcgtaagcgg aatttatgtt tgt                                    23

<210> SEQ ID NO 29
<211> LENGTH: 22
<212> TYPE: DNA
<213> ORGANISM: Artificial Sequence
<220> FEATURE:
<223> OTHER INFORMATION: DIRAS3 reverse primer

<400> SEQUENCE: 29
ccgcgatttt atattccgac tt                                     22

<210> SEQ ID NO 30
<211> LENGTH: 29
<212> TYPE: DNA
<213> ORGANISM: Artificial Sequence
<220> FEATURE:
<223> OTHER INFORMATION: DIRAS3: Probe (5'-6-FAM; 3'-BHQ1)

<400> SEQUENCE: 30
cgcacaaaaa cgaaatacga aaacgcaaa                              29

<210> SEQ ID NO 31
<211> LENGTH: 21
<212> TYPE: DNA
<213> ORGANISM: Artificial Sequence
<220> FEATURE:
<223> OTHER INFORMATION: DAPK1 forward primer

<400> SEQUENCE: 31
tcgtcgtcgt ttcggttagt t                                      21
```

```
<210> SEQ ID NO 32
<211> LENGTH: 19
<212> TYPE: DNA
<213> ORGANISM: Artificial Sequence
<220> FEATURE:
<223> OTHER INFORMATION: DAPK1 reverse primer

<400> SEQUENCE: 32
tccctccgaa acgctatcg                                                    19

<210> SEQ ID NO 33
<211> LENGTH: 21
<212> TYPE: DNA
<213> ORGANISM: Artificial Sequence
<220> FEATURE:
<223> OTHER INFORMATION: DAPK1: Probe (5'-6-FAM; 3'-BHQ1)

<400> SEQUENCE: 33
cgaccataaa cgccaacgcc g                                                 21

<210> SEQ ID NO 34
<211> LENGTH: 16
<212> TYPE: DNA
<213> ORGANISM: Artificial Sequence
<220> FEATURE:
<223> OTHER INFORMATION: TWIST1 forward primer

<400> SEQUENCE: 34
gtagcgcggc gaacgt                                                       16

<210> SEQ ID NO 35
<211> LENGTH: 23
<212> TYPE: DNA
<213> ORGANISM: Artificial Sequence
<220> FEATURE:
<223> OTHER INFORMATION: TWIST1 reverse primer

<400> SEQUENCE: 35
aaacgcaacg aatcataacc aac                                               23

<210> SEQ ID NO 36
<211> LENGTH: 24
<212> TYPE: DNA
<213> ORGANISM: Artificial Sequence
<220> FEATURE:
<223> OTHER INFORMATION: TWIST1: Probe (5'-6-FAM; 3'-BHQ1)

<400> SEQUENCE: 36
ccaacgcacc caatcgctaa acga                                              24

<210> SEQ ID NO 37
<211> LENGTH: 21
<212> TYPE: DNA
<213> ORGANISM: Artificial Sequence
<220> FEATURE:
<223> OTHER INFORMATION: DNAJC15 forward primer

<400> SEQUENCE: 37
tttcgggtcg ttttgttatg g                                                 21

<210> SEQ ID NO 38
<211> LENGTH: 28
<212> TYPE: DNA
<213> ORGANISM: Artificial Sequence
<220> FEATURE:
<223> OTHER INFORMATION: DNAJC15 reverse primer

<400> SEQUENCE: 38
```
actacaaata ctcaacgtaa cgcaaact        28

<210> SEQ ID NO 39
<211> LENGTH: 30
<212> TYPE: DNA
<213> ORGANISM: Artificial Sequence
<220> FEATURE:
<223> OTHER INFORMATION: DNAJC15: Probe (5'-6-FAM; 3'-BHQ1)

<400> SEQUENCE: 39
tcgccaacta aaacgataac accacgaaca        30

<210> SEQ ID NO 40
<211> LENGTH: 21
<212> TYPE: DNA
<213> ORGANISM: Artificial Sequence
<220> FEATURE:
<223> OTHER INFORMATION: DPH1 forward primer

<400> SEQUENCE: 40
acgcggagag cgtagatatt g        21

<210> SEQ ID NO 41
<211> LENGTH: 18
<212> TYPE: DNA
<213> ORGANISM: Artificial Sequence
<220> FEATURE:
<223> OTHER INFORMATION: DPH1 reverse primer

<400> SEQUENCE: 41
ccgcccaacg aatatccc        18

<210> SEQ ID NO 42
<211> LENGTH: 23
<212> TYPE: DNA
<213> ORGANISM: Artificial Sequence
<220> FEATURE:
<223> OTHER INFORMATION: DPH1: Probe (5'-6-FAM; 3'-BHQ1)

<400> SEQUENCE: 42
cccgctaacc gatcgacgat cga        23

<210> SEQ ID NO 43
<211> LENGTH: 20
<212> TYPE: DNA
<213> ORGANISM: Artificial Sequence
<220> FEATURE:
<223> OTHER INFORMATION: CDH1 forward primer

<400> SEQUENCE: 43
agggttatcg cgtttatgcg        20

<210> SEQ ID NO 44
<211> LENGTH: 21
<212> TYPE: DNA
<213> ORGANISM: Artificial Sequence
<220> FEATURE:
<223> OTHER INFORMATION: CDH1 reverse primer

<400> SEQUENCE: 44
ttcacctacc gaccacaacc a        21

<210> SEQ ID NO 45
<211> LENGTH: 21
<212> TYPE: DNA
<213> ORGANISM: Artificial Sequence

```
<220> FEATURE:
<223> OTHER INFORMATION: CDH1: Probe (5'-6-FAM; 3'-BHQ1)

<400> SEQUENCE: 45
actaacgacc cgcccacccg a                                              21

<210> SEQ ID NO 46
<211> LENGTH: 22
<212> TYPE: DNA
<213> ORGANISM: Artificial Sequence
<220> FEATURE:
<223> OTHER INFORMATION: ABCB1 forward primer

<400> SEQUENCE: 46
tcgggtcggg agtagttatt tg                                             22

<210> SEQ ID NO 47
<211> LENGTH: 21
<212> TYPE: DNA
<213> ORGANISM: Artificial Sequence
<220> FEATURE:
<223> OTHER INFORMATION: ABCB1 reverse primer

<400> SEQUENCE: 47
cgactatact caacccacgc c                                              21

<210> SEQ ID NO 48
<211> LENGTH: 30
<212> TYPE: DNA
<213> ORGANISM: Artificial Sequence
<220> FEATURE:
<223> OTHER INFORMATION: ABCB1: Probe (5'-6-FAM; 3'-BHQ1)

<400> SEQUENCE: 48
acgctattcc tacccaacca atcaacctca                                     30

<210> SEQ ID NO 49
<211> LENGTH: 18
<212> TYPE: DNA
<213> ORGANISM: Artificial Sequence
<220> FEATURE:
<223> OTHER INFORMATION: PTTG1 forward primer

<400> SEQUENCE: 49
gcgttcgttt atcgcggt                                                  18

<210> SEQ ID NO 50
<211> LENGTH: 16
<212> TYPE: DNA
<213> ORGANISM: Artificial Sequence
<220> FEATURE:
<223> OTHER INFORMATION: PTTG1 reverse primer

<400> SEQUENCE: 50
ccgcgaccct cccatt                                                    16

<210> SEQ ID NO 51
<211> LENGTH: 29
<212> TYPE: DNA
<213> ORGANISM: Artificial Sequence
<220> FEATURE:
<223> OTHER INFORMATION: PTTG1: Probe (5'-6-FAM; 3'-BHQ1)

<400> SEQUENCE: 51
actcacgcaa atcttaacaa ccgcattca                                      29
```

```
<210> SEQ ID NO 52
<211> LENGTH: 19
<212> TYPE: DNA
<213> ORGANISM: Artificial Sequence
<220> FEATURE:
<223> OTHER INFORMATION: SMAD3 forward primer

<400> SEQUENCE: 52
cgtgaagcgt ttgttgggt                                                 19

<210> SEQ ID NO 53
<211> LENGTH: 19
<212> TYPE: DNA
<213> ORGANISM: Artificial Sequence
<220> FEATURE:
<223> OTHER INFORMATION: SMAD3 reverse primer

<400> SEQUENCE: 53
ttaaccgcct tctcgcacc                                                 19

<210> SEQ ID NO 54
<211> LENGTH: 29
<212> TYPE: DNA
<213> ORGANISM: Artificial Sequence
<220> FEATURE:
<223> OTHER INFORMATION: SMAD3: Probe (5'-6-FAM; 3'-BHQ1)

<400> SEQUENCE: 54
tcctcctacc cgttctactc gcccttctt                                      29

<210> SEQ ID NO 55
<211> LENGTH: 19
<212> TYPE: DNA
<213> ORGANISM: Artificial Sequence
<220> FEATURE:
<223> OTHER INFORMATION: CXADR forward primer

<400> SEQUENCE: 55
tacgcggttg gagaagtcg                                                 19

<210> SEQ ID NO 56
<211> LENGTH: 21
<212> TYPE: DNA
<213> ORGANISM: Artificial Sequence
<220> FEATURE:
<223> OTHER INFORMATION: CXADR reverse primer

<400> SEQUENCE: 56
ataaactcgc gtcacttccg a                                              21

<210> SEQ ID NO 57
<211> LENGTH: 25
<212> TYPE: DNA
<213> ORGANISM: Artificial Sequence
<220> FEATURE:
<223> OTHER INFORMATION: CXADR: Probe (5'-6-FAM; 3'-BHQ1)

<400> SEQUENCE: 57
aacgacccga accgaactac gaacg                                          25

<210> SEQ ID NO 58
<211> LENGTH: 29
<212> TYPE: DNA
<213> ORGANISM: Artificial Sequence
<220> FEATURE:
<223> OTHER INFORMATION: MTHFR forward primer

<400> SEQUENCE: 58
```

```
tggtagtgag agttttaaag atagttcga                               29

<210> SEQ ID NO 59
<211> LENGTH: 18
<212> TYPE: DNA
<213> ORGANISM: Artificial Sequence
<220> FEATURE:
<223> OTHER INFORMATION: MTHFR reverse primer

<400> SEQUENCE: 59
cgcctcatct tctcccga                                           18

<210> SEQ ID NO 60
<211> LENGTH: 27
<212> TYPE: DNA
<213> ORGANISM: Artificial Sequence
<220> FEATURE:
<223> OTHER INFORMATION: MTHFR: Probe (5'-6-FAM; 3'-BHQ1)

<400> SEQUENCE: 60
tctcataccg ctcaaaatcc aaacccg                                 27

<210> SEQ ID NO 61
<211> LENGTH: 21
<212> TYPE: DNA
<213> ORGANISM: Artificial Sequence
<220> FEATURE:
<223> OTHER INFORMATION: CLDN1 forward primer

<400> SEQUENCE: 61
cggtgagtcg ttttgaaatc g                                       21

<210> SEQ ID NO 62
<211> LENGTH: 19
<212> TYPE: DNA
<213> ORGANISM: Artificial Sequence
<220> FEATURE:
<223> OTHER INFORMATION: CLDN 1 reverse primer

<400> SEQUENCE: 62
acgcaaaacc gctaaacgc                                          19

<210> SEQ ID NO 63
<211> LENGTH: 26
<212> TYPE: DNA
<213> ORGANISM: Artificial Sequence
<220> FEATURE:
<223> OTHER INFORMATION: CLDN1: Probe (5'-6-FAM; 3'-BHQ1)

<400> SEQUENCE: 63
gatttaaaac aactccgccc gcctca                                  26

<210> SEQ ID NO 64
<211> LENGTH: 18
<212> TYPE: DNA
<213> ORGANISM: Artificial Sequence
<220> FEATURE:
<223> OTHER INFORMATION: PPARG forward primer

<400> SEQUENCE: 64
gcgttcgcgt tcgttttc                                           18

<210> SEQ ID NO 65
<211> LENGTH: 16
<212> TYPE: DNA
<213> ORGANISM: Artificial Sequence
```

```
<220> FEATURE:
<223> OTHER INFORMATION: PPARG reverse primer

<400> SEQUENCE: 65
cgccccaaac gacgac                                                     16

<210> SEQ ID NO 66
<211> LENGTH: 20
<212> TYPE: DNA
<213> ORGANISM: Artificial Sequence
<220> FEATURE:
<223> OTHER INFORMATION: PPARG: Probe (5'-6-FAM; 3'-BHQ1)

<400> SEQUENCE: 66
cccgcctacc cgcgacgaaa                                                 20

<210> SEQ ID NO 67
<211> LENGTH: 23
<212> TYPE: DNA
<213> ORGANISM: Artificial Sequence
<220> FEATURE:
<223> OTHER INFORMATION: S100A2 forward primer

<400> SEQUENCE: 67
tgtttgagtc gtaagtaggg cgt                                             23

<210> SEQ ID NO 68
<211> LENGTH: 25
<212> TYPE: DNA
<213> ORGANISM: Artificial Sequence
<220> FEATURE:
<223> OTHER INFORMATION: S100A2 reverse primer

<400> SEQUENCE: 68
cgtatcatta caataccgac ctcct                                           25

<210> SEQ ID NO 69
<211> LENGTH: 28
<212> TYPE: DNA
<213> ORGANISM: Artificial Sequence
<220> FEATURE:
<223> OTHER INFORMATION: S100A2: Probe (5'-6-FAM; 3'-BHQ1)

<400> SEQUENCE: 69 atcctcccctt tcttatccgc caaaccct                                       28

<210> SEQ ID NO 70
<211> LENGTH: 19
<212> TYPE: DNA
<213> ORGANISM: Artificial Sequence
<220> FEATURE:
<223> OTHER INFORMATION: CLIC4 forward primer

<400> SEQUENCE: 70
ggcggtgttg aggagttga                                                  19

<210> SEQ ID NO 71
<211> LENGTH: 19
<212> TYPE: DNA
<213> ORGANISM: Artificial Sequence
<220> FEATURE:
<223> OTHER INFORMATION: CLIC4 reverse primer

<400> SEQUENCE: 71
ccgattcccg ccgtactac                                                  19
```

```
<210> SEQ ID NO 72
<211> LENGTH: 31
<212> TYPE: DNA
<213> ORGANISM: Artificial Sequence
<220> FEATURE:
<223> OTHER INFORMATION: CLIC4: Probe (5'-6-FAM; 3'-BHQ1)

<400> SEQUENCE: 72
cgctaaacta tccgaaatcg aactaaccac g                          31

<210> SEQ ID NO 73
<211> LENGTH: 21
<212> TYPE: DNA
<213> ORGANISM: Artificial Sequence
<220> FEATURE:
<223> OTHER INFORMATION: STAT1 forward primer

<400> SEQUENCE: 73
gcgtaggatt cggaagggtt a                                     21

<210> SEQ ID NO 74
<211> LENGTH: 20
<212> TYPE: DNA
<213> ORGANISM: Artificial Sequence
<220> FEATURE:
<223> OTHER INFORMATION: STAT1 reverse primer

<400> SEQUENCE: 74
aacaaacccc aaaccgaaca                                       20

<210> SEQ ID NO 75
<211> LENGTH: 22
<212> TYPE: DNA
<213> ORGANISM: Artificial Sequence
<220> FEATURE:
<223> OTHER INFORMATION: STAT1: Probe (5'-6-FAM; 3'-BHQ1)

<400> SEQUENCE: 75
aacgacccaa cgcgctcgaa aa                                    22

<210> SEQ ID NO 76
<211> LENGTH: 19
<212> TYPE: DNA
<213> ORGANISM: Artificial Sequence
<220> FEATURE:
<223> OTHER INFORMATION: PTGS2 forward primer

<400> SEQUENCE: 76
cggaagcgtt cgggtaaag                                        19

<210> SEQ ID NO 77
<211> LENGTH: 18
<212> TYPE: DNA
<213> ORGANISM: Artificial Sequence
<220> FEATURE:
<223> OTHER INFORMATION: PTGS2 reverse primer

<400> SEQUENCE: 77
aattccaccg ccccaaac                                         18

<210> SEQ ID NO 78
<211> LENGTH: 29
<212> TYPE: DNA
<213> ORGANISM: Artificial Sequence
<220> FEATURE:
<223> OTHER INFORMATION: PTGS2: Probe (5'-6-FAM; 3'-BHQ1)

<400> SEQUENCE: 78
```

-continued

```
tttccgccaa atatcttttc ttcttcgca                              29

<210> SEQ ID NO 79
<211> LENGTH: 20
<212> TYPE: DNA
<213> ORGANISM: Artificial Sequence
<220> FEATURE:
<223> OTHER INFORMATION: HSD17B4 forward primer

<400> SEQUENCE: 79
tatcgttgag gttcgacggg                                        20

<210> SEQ ID NO 80
<211> LENGTH: 21
<212> TYPE: DNA
<213> ORGANISM: Artificial Sequence
<220> FEATURE:
<223> OTHER INFORMATION: HSD17B4 reverse primer

<400> SEQUENCE: 80
tccaaccttc gcatactcac c                                      21

<210> SEQ ID NO 81
<211> LENGTH: 22
<212> TYPE: DNA
<213> ORGANISM: Artificial Sequence
<220> FEATURE:
<223> OTHER INFORMATION: HSD17B4: Probe (5'-6-FAM; 3'-BHQ1)

<400> SEQUENCE: 81
cccgcgccga taaccaatac ca                                     22

<210> SEQ ID NO 82
<211> LENGTH: 21
<212> TYPE: DNA
<213> ORGANISM: Artificial Sequence
<220> FEATURE:
<223> OTHER INFORMATION: NR3C1 forward primer

<400> SEQUENCE: 82
gggtggaagg agacgtcgta g                                      21

<210> SEQ ID NO 83
<211> LENGTH: 17
<212> TYPE: DNA
<213> ORGANISM: Artificial Sequence
<220> FEATURE:
<223> OTHER INFORMATION: NR3C1 reverse primer

<400> SEQUENCE: 83
aaacttccga acgcgcg                                           17

<210> SEQ ID NO 84
<211> LENGTH: 25
<212> TYPE: DNA
<213> ORGANISM: Artificial Sequence
<220> FEATURE:
<223> OTHER INFORMATION: NR3C1: Probe (5'-6-FAM; 3'-BHQ1)

<400> SEQUENCE: 84
gtcccgatcc caactacttc gaccg                                  25

<210> SEQ ID NO 85
<211> LENGTH: 24
<212> TYPE: DNA
<213> ORGANISM: Artificial Sequence
```

```
<220> FEATURE:
<223> OTHER INFORMATION: VDR forward primer

<400> SEQUENCE: 85
acgtatttgg tttaggcgtt cgta                                          24

<210> SEQ ID NO 86
<211> LENGTH: 29
<212> TYPE: DNA
<213> ORGANISM: Artificial Sequence
<220> FEATURE:
<223> OTHER INFORMATION: VDR reverse primer

<400> SEQUENCE: 86
cgcttcaacc tatattaatc gaaaataca                                     29

<210> SEQ ID NO 87
<211> LENGTH: 29
<212> TYPE: DNA
<213> ORGANISM: Artificial Sequence
<220> FEATURE:
<223> OTHER INFORMATION: VDR: Probe (5'-6-FAM; 3'-BHQ1)

<400> SEQUENCE: 87
cccacccttc ctaccgtaat tctacccaa                                     29

<210> SEQ ID NO 88
<211> LENGTH: 23
<212> TYPE: DNA
<213> ORGANISM: Artificial Sequence
<220> FEATURE:
<223> OTHER INFORMATION: CADM1 forward primer

<400> SEQUENCE: 88
gggtttcgga ggtagttaac gtc                                           23

<210> SEQ ID NO 89
<211> LENGTH: 23
<212> TYPE: DNA
<213> ORGANISM: Artificial Sequence
<220> FEATURE:
<223> OTHER INFORMATION: CADM 1 reverse primer

<400> SEQUENCE: 89
cactaaaatc cgctcgacaa cac                                           23

<210> SEQ ID NO 90
<211> LENGTH: 30
<212> TYPE: DNA
<213> ORGANISM: Artificial Sequence
<220> FEATURE:
<223> OTHER INFORMATION: CADM1: Probe (5'-6-FAM; 3'-BHQ1)

<400> SEQUENCE: 90
acactcgcca tatcgaacac ctacctcaaa                                    30

<210> SEQ ID NO 91
<211> LENGTH: 21
<212> TYPE: DNA
<213> ORGANISM: Artificial Sequence
<220> FEATURE:
<223> OTHER INFORMATION: TERT forward primer

<400> SEQUENCE: 91
ggattcgcgg gtatagacgt t                                             21
```

```
<210> SEQ ID NO 92
<211> LENGTH: 16
<212> TYPE: DNA
<213> ORGANISM: Artificial Sequence
<220> FEATURE:
<223> OTHER INFORMATION: TERT reverse primer

<400> SEQUENCE: 92
cgaaatccgc gcgaaa                                                      16

<210> SEQ ID NO 93
<211> LENGTH: 23
<212> TYPE: DNA
<213> ORGANISM: Artificial Sequence
<220> FEATURE:
<223> OTHER INFORMATION: TERT: Probe (5'-6-FAM; 3'-BHQ1)

<400> SEQUENCE: 93
cccaatccct ccgccacgta aaa                                              23

<210> SEQ ID NO 94
<211> LENGTH: 21
<212> TYPE: DNA
<213> ORGANISM: Artificial Sequence
<220> FEATURE:
<223> OTHER INFORMATION: CDH13 forward primer

<400> SEQUENCE: 94
aatttcgttc gttttgtgcg t                                                21

<210> SEQ ID NO 95
<211> LENGTH: 20
<212> TYPE: DNA
<213> ORGANISM: Artificial Sequence
<220> FEATURE:
<223> OTHER INFORMATION: CDH13 reverse primer

<400> SEQUENCE: 95
ctacccgtac cgaacgatcc                                                  20

<210> SEQ ID NO 96
<211> LENGTH: 20
<212> TYPE: DNA
<213> ORGANISM: Artificial Sequence
<220> FEATURE:
<223> OTHER INFORMATION: CDH13: Probe (5'-6-FAM; 3'-BHQ1)

<400> SEQUENCE: 96
aacgcaaaac gcgcccgaca                                                  20

<210> SEQ ID NO 97
<211> LENGTH: 19
<212> TYPE: DNA
<213> ORGANISM: Artificial Sequence
<220> FEATURE:
<223> OTHER INFORMATION: NCL forward primer

<400> SEQUENCE: 97
cgtgtcgttt cggttcgtt                                                   19

<210> SEQ ID NO 98
<211> LENGTH: 19
<212> TYPE: DNA
<213> ORGANISM: Artificial Sequence
<220> FEATURE:
<223> OTHER INFORMATION: NCL reverse primer

<400> SEQUENCE: 98
```

```
accaaaactc gcgaccgtc                                                  19
```

<210> SEQ ID NO 99
<211> LENGTH: 29
<212> TYPE: DNA
<213> ORGANISM: Artificial Sequence
<220> FEATURE:
<223> OTHER INFORMATION: NCL: Probe (5'-6-FAM; 3'-BHQ1)

<400> SEQUENCE: 99

```
ccataaacca atcgcgaacc tctaaccgt                                       29
```

<210> SEQ ID NO 100
<211> LENGTH: 19
<212> TYPE: DNA
<213> ORGANISM: Artificial Sequence
<220> FEATURE:
<223> OTHER INFORMATION: CYP1B1 forward primer

<400> SEQUENCE: 100

```
gtgcgtttgg acgggagtt                                                  19
```

<210> SEQ ID NO 101
<211> LENGTH: 21
<212> TYPE: DNA
<213> ORGANISM: Artificial Sequence
<220> FEATURE:
<223> OTHER INFORMATION: CYP1B1 reverse primer

<400> SEQUENCE: 101

```
aacgcgacct aacaaaacga a                                               21
```

<210> SEQ ID NO 102
<211> LENGTH: 20
<212> TYPE: DNA
<213> ORGANISM: Artificial Sequence
<220> FEATURE:
<223> OTHER INFORMATION: CYP1B1: Probe (5'-6-FAM; 3'-BHQ1)

<400> SEQUENCE: 102

```
cgccgcacac caaaccgctt                                                 20
```

<210> SEQ ID NO 103
<211> LENGTH: 21
<212> TYPE: DNA
<213> ORGANISM: Artificial Sequence
<220> FEATURE:
<223> OTHER INFORMATION: SLC6A20 forward primer

<400> SEQUENCE: 103

```
aggcgaatac gaattgtagc g                                               21
```

<210> SEQ ID NO 104
<211> LENGTH: 19
<212> TYPE: DNA
<213> ORGANISM: Artificial Sequence
<220> FEATURE:
<223> OTHER INFORMATION: SLC6A20 reverse primer

<400> SEQUENCE: 104

```
taaaacgacg cgcctaacg                                                  19
```

<210> SEQ ID NO 105
<211> LENGTH: 26
<212> TYPE: DNA
<213> ORGANISM: Artificial Sequence

```
<220> FEATURE:
<223> OTHER INFORMATION: SLC6A20: Probe (5'-6-FAM; 3'-BHQ1)

<400> SEQUENCE: 105
ccgcgcacta aaactaccgt accgaa                                          26

<210> SEQ ID NO 106
<211> LENGTH: 20
<212> TYPE: DNA
<213> ORGANISM: Artificial Sequence
<220> FEATURE:
<223> OTHER INFORMATION: TNFRST25 forward primer

<400> SEQUENCE: 106
gcggaattac gacgggtaga                                                 20

<210> SEQ ID NO 107
<211> LENGTH: 20
<212> TYPE: DNA
<213> ORGANISM: Artificial Sequence
<220> FEATURE:
<223> OTHER INFORMATION: TNFRST25 reverse primer

<400> SEQUENCE: 107
actccataac cctccgacga                                                 20

<210> SEQ ID NO 108
<211> LENGTH: 25
<212> TYPE: DNA
<213> ORGANISM: Artificial Sequence
<220> FEATURE:
<223> OTHER INFORMATION: TRFRST25: Probe (5'-6-FAM; 3'-BHQ1)

<400> SEQUENCE: 108
cgcccaaaaa cttcccgact ccgta                                           25

<210> SEQ ID NO 109
<211> LENGTH: 19
<212> TYPE: DNA
<213> ORGANISM: Artificial Sequence
<220> FEATURE:
<223> OTHER INFORMATION: UNG forward primer

<400> SEQUENCE: 109
gtttgacgga gggcgtgta                                                  19

<210> SEQ ID NO 110
<211> LENGTH: 27
<212> TYPE: DNA
<213> ORGANISM: Artificial Sequence
<220> FEATURE:
<223> OTHER INFORMATION: UNG reverse primer

<400> SEQUENCE: 110
acaacgacga ctattttaaa cacgtaa                                         27

<210> SEQ ID NO 111
<211> LENGTH: 27
<212> TYPE: DNA
<213> ORGANISM: Artificial Sequence
<220> FEATURE:
<223> OTHER INFORMATION: UNG: Probe (5'-6-FAM; 3'-BHQ1)

<400> SEQUENCE: 111
cccgaattta ccgaatcaaa aacgcga                                         27
```

```
<210> SEQ ID NO 112
<211> LENGTH: 23
<212> TYPE: DNA
<213> ORGANISM: Artificial Sequence
<220> FEATURE:
<223> OTHER INFORMATION: MBD4 forward primer

<400> SEQUENCE: 112
tcgtgtttat cgagtagggt tcg                                             23

<210> SEQ ID NO 113
<211> LENGTH: 23
<212> TYPE: DNA
<213> ORGANISM: Artificial Sequence
<220> FEATURE:
<223> OTHER INFORMATION: MBD4 reverse primer

<400> SEQUENCE: 113
tcgattacaa cccgataccg taa                                             23

<210> SEQ ID NO 114
<211> LENGTH: 30
<212> TYPE: DNA
<213> ORGANISM: Artificial Sequence
<220> FEATURE:
<223> OTHER INFORMATION: MBD: Probe (5'-6-FAM; 3'-BHQ1)

<400> SEQUENCE: 114
cacaccctaa acgttacgac gctaaactcg                                      30

<210> SEQ ID NO 115
<211> LENGTH: 22
<212> TYPE: DNA
<213> ORGANISM: Artificial Sequence
<220> FEATURE:
<223> OTHER INFORMATION: MSH6 forward primer

<400> SEQUENCE: 115
ggagtgtttc ggttcggtta gt                                              22

<210> SEQ ID NO 116
<211> LENGTH: 18
<212> TYPE: DNA
<213> ORGANISM: Artificial Sequence
<220> FEATURE:
<223> OTHER INFORMATION: MSH6 reverse primer

<400> SEQUENCE: 116
ctaccgccga cgcctaaa                                                   18

<210> SEQ ID NO 117
<211> LENGTH: 19
<212> TYPE: DNA
<213> ORGANISM: Artificial Sequence
<220> FEATURE:
<223> OTHER INFORMATION: MSH6: Probe (5'-6-FAM; 3'-BHQ1)

<400> SEQUENCE: 117
cccttccctc acgccgcga                                                  19

<210> SEQ ID NO 118
<211> LENGTH: 16
<212> TYPE: DNA
<213> ORGANISM: Artificial Sequence
<220> FEATURE:
<223> OTHER INFORMATION: OGG1 forward primer

<400> SEQUENCE: 118
```

-continued tagggtgggc gggtcg                                                    16

<210> SEQ ID NO 119
<211> LENGTH: 15
<212> TYPE: DNA
<213> ORGANISM: Artificial Sequence
<220> FEATURE:
<223> OTHER INFORMATION: OGG1 reverse primer

<400> SEQUENCE: 119
ccgcgaaacg cccaa                                                     15

<210> SEQ ID NO 120
<211> LENGTH: 21
<212> TYPE: DNA
<213> ORGANISM: Artificial Sequence
<220> FEATURE:
<223> OTHER INFORMATION: OGG1: Probe (5'-6-FAM; 3'-BHQ1)

<400> SEQUENCE: 120
caataccgac caaccgcgcg a                                              21

<210> SEQ ID NO 121
<211> LENGTH: 20
<212> TYPE: DNA
<213> ORGANISM: Artificial Sequence
<220> FEATURE:
<223> OTHER INFORMATION: MUTYH/TOE1 forward primer

<400> SEQUENCE: 121
tcgggtggat tcgagttacg                                                20

<210> SEQ ID NO 122
<211> LENGTH: 23
<212> TYPE: DNA
<213> ORGANISM: Artificial Sequence
<220> FEATURE:
<223> OTHER INFORMATION: MUTYH/TOE1 reverse primer

<400> SEQUENCE: 122
aaaattacct cccgcgaact cta                                            23

<210> SEQ ID NO 123
<211> LENGTH: 19
<212> TYPE: DNA
<213> ORGANISM: Artificial Sequence
<220> FEATURE:
<223> OTHER INFORMATION: MUTYH/TOE1: Probe (5'-6-FAM; 3'-BHQ1)

<400> SEQUENCE: 123
cgcgcccgac tttccgacg                                                 19

<210> SEQ ID NO 124
<211> LENGTH: 17
<212> TYPE: DNA
<213> ORGANISM: Artificial Sequence
<220> FEATURE:
<223> OTHER INFORMATION: NTHL1 forward primer

<400> SEQUENCE: 124
cgggacgtcg tcggaag                                                   17

<210> SEQ ID NO 125
<211> LENGTH: 17
<212> TYPE: DNA
<213> ORGANISM: Artificial Sequence

```
<220> FEATURE:
<223> OTHER INFORMATION: NTHL1 revese primer

<400> SEQUENCE: 125
ccgacctttc cgccaaa                                                  17

<210> SEQ ID NO 126
<211> LENGTH: 20
<212> TYPE: DNA
<213> ORGANISM: Artificial Sequence
<220> FEATURE:
<223> OTHER INFORMATION: NTHL1: Probe (5'-6-FAM; 3'-BHQ1)

<400> SEQUENCE: 126
cgaccctccg cgcataccg                                                20

<210> SEQ ID NO 127
<211> LENGTH: 24
<212> TYPE: DNA
<213> ORGANISM: Artificial Sequence
<220> FEATURE:
<223> OTHER INFORMATION: APEX1 forward primer

<400> SEQUENCE: 127
cgtatttgta tcggttcgat ggta                                          24

<210> SEQ ID NO 128
<211> LENGTH: 18
<212> TYPE: DNA
<213> ORGANISM: Artificial Sequence
<220> FEATURE:
<223> OTHER INFORMATION: APEX reverse primer

<400> SEQUENCE: 128
gcgcattctt cgaccacg                                                 18

<210> SEQ ID NO 129
<211> LENGTH: 29
<212> TYPE: DNA
<213> ORGANISM: Artificial Sequence
<220> FEATURE:
<223> OTHER INFORMATION: APEX1: Probe (5'-6-FAM; 3'-BHQ1)

<400> SEQUENCE: 129
caaacgcgcc tctaatcacg taaccaaat                                     29

<210> SEQ ID NO 130
<211> LENGTH: 24
<212> TYPE: DNA
<213> ORGANISM: Artificial Sequence
<220> FEATURE:
<223> OTHER INFORMATION: XRCC1 forward primer

<400> SEQUENCE: 130
cgttgttaag gaacgtagcg tttt                                          24

<210> SEQ ID NO 131
<211> LENGTH: 19
<212> TYPE: DNA
<213> ORGANISM: Artificial Sequence
<220> FEATURE:
<223> OTHER INFORMATION: XRCC1 reverse primer

<400> SEQUENCE: 131
gcgcgaaact cgaaccttt                                                19
```

```
<210> SEQ ID NO 132
<211> LENGTH: 22
<212> TYPE: DNA
<213> ORGANISM: Artificial Sequence
<220> FEATURE:
<223> OTHER INFORMATION: XRCC1: Probe (5'-6-FAM; 3'-BHQ1)

<400> SEQUENCE: 132
ccaatcgcgc ctctccaaaa cg                                               22

<210> SEQ ID NO 133
<211> LENGTH: 18
<212> TYPE: DNA
<213> ORGANISM: Artificial Sequence
<220> FEATURE:
<223> OTHER INFORMATION: PARP1 forward primer

<400> SEQUENCE: 133
cgggtttagg gagcgagc                                                    18

<210> SEQ ID NO 134
<211> LENGTH: 19
<212> TYPE: DNA
<213> ORGANISM: Artificial Sequence
<220> FEATURE:
<223> OTHER INFORMATION: PARP1 reverse primer

<400> SEQUENCE: 134
aaacgaccgc gaacccata                                                   19

<210> SEQ ID NO 135
<211> LENGTH: 22
<212> TYPE: DNA
<213> ORGANISM: Artificial Sequence
<220> FEATURE:
<223> OTHER INFORMATION: PARP1: Probe (5'-6-FAM; 3'-BHQ1)

<400> SEQUENCE: 135
cgctccgaaa acccgaaccg aa                                               22

<210> SEQ ID NO 136
<211> LENGTH: 18
<212> TYPE: DNA
<213> ORGANISM: Artificial Sequence
<220> FEATURE:
<223> OTHER INFORMATION: PARP2 forward primer

<400> SEQUENCE: 136
gggcgagagg ttcggagt                                                    18

<210> SEQ ID NO 137
<211> LENGTH: 22
<212> TYPE: DNA
<213> ORGANISM: Artificial Sequence
<220> FEATURE:
<223> OTHER INFORMATION: PARP2 reverse primer

<400> SEQUENCE: 137
tcgttccttt ctaactaccc gc                                               22

<210> SEQ ID NO 138
<211> LENGTH: 21
<212> TYPE: DNA
<213> ORGANISM: Artificial Sequence
<220> FEATURE:
<223> OTHER INFORMATION: PARP2: Probe (5'-6-FAM; 3'-BHQ1)

<400> SEQUENCE: 138
```

```
cccgcatacc gtcccgcgat a                                      21

<210> SEQ ID NO 139
<211> LENGTH: 20
<212> TYPE: DNA
<213> ORGANISM: Artificial Sequence
<220> FEATURE:
<223> OTHER INFORMATION: MSH2 forward primer

<400> SEQUENCE: 139
ttttagtgcg gaggtacggg                                        20

<210> SEQ ID NO 140
<211> LENGTH: 21
<212> TYPE: DNA
<213> ORGANISM: Artificial Sequence
<220> FEATURE:
<223> OTHER INFORMATION: MSH2 reverse primer

<400> SEQUENCE: 140
aaacgatcct ccgaaaccaa a                                      21

<210> SEQ ID NO 141
<211> LENGTH: 22
<212> TYPE: DNA
<213> ORGANISM: Artificial Sequence
<220> FEATURE:
<223> OTHER INFORMATION: MSH2: Probe (5'-6-FAM; 3'-BHQ1)

<400> SEQUENCE: 141
ccgcacaaac accaacgttc cg                                     22

<210> SEQ ID NO 142
<211> LENGTH: 27
<212> TYPE: DNA
<213> ORGANISM: Artificial Sequence
<220> FEATURE:
<223> OTHER INFORMATION: MSH4 forward pimer

<400> SEQUENCE: 142
cggattttag gagattttat agagtcg                                27

<210> SEQ ID NO 143
<211> LENGTH: 15
<212> TYPE: DNA
<213> ORGANISM: Artificial Sequence
<220> FEATURE:
<223> OTHER INFORMATION: MSH4 reverse primer

<400> SEQUENCE: 143
ccgatcgccc gcaac                                             15

<210> SEQ ID NO 144
<211> LENGTH: 40
<212> TYPE: DNA
<213> ORGANISM: Artificial Sequence
<220> FEATURE:
<223> OTHER INFORMATION: MSH4: Probe (5'-6-FAM; 3'-BHQ1)

<400> SEQUENCE: 144
aacgtaccaa aacaaataaa tacaaaaacc acctaaaccg                  40

<210> SEQ ID NO 145
<211> LENGTH: 17
<212> TYPE: DNA
<213> ORGANISM: Artificial Sequence
```

```
<220> FEATURE:
<223> OTHER INFORMATION: MSH5 forward primer

<400> SEQUENCE: 145
ttcgtggcgg tcggtta                                                  17

<210> SEQ ID NO 146
<211> LENGTH: 16
<212> TYPE: DNA
<213> ORGANISM: Artificial Sequence
<220> FEATURE:
<223> OTHER INFORMATION: MSH5 reverse primer

<400> SEQUENCE: 146
ccgccatcgc aacgtt                                                   16

<210> SEQ ID NO 147
<211> LENGTH: 30
<212> TYPE: DNA
<213> ORGANISM: Artificial Sequence
<220> FEATURE:
<223> OTHER INFORMATION: MSH5: Probe (5'-6-FAM; 3'-BHQ1)

<400> SEQUENCE: 147
cccgcctttt caataaccta atcgctaca                                     30

<210> SEQ ID NO 148
<211> LENGTH: 18
<212> TYPE: DNA
<213> ORGANISM: Artificial Sequence
<220> FEATURE:
<223> OTHER INFORMATION: PILRB forward primer

<400> SEQUENCE: 148
tcgtggtttg gcgtggat                                                 18

<210> SEQ ID NO 149
<211> LENGTH: 26
<212> TYPE: DNA
<213> ORGANISM: Artificial Sequence
<220> FEATURE:
<223> OTHER INFORMATION: PILRB reverse primer

<400> SEQUENCE: 149
cctaatacat cgaaataacg cgtacc                                        26

<210> SEQ ID NO 150
<211> LENGTH: 24
<212> TYPE: DNA
<213> ORGANISM: Artificial Sequence
<220> FEATURE:
<223> OTHER INFORMATION: PILRB: Probe (5'-6-FAM; 3'-BHQ1)

<400> SEQUENCE: 150
ccaacgatcg aaaccgcca aaca                                           24

<210> SEQ ID NO 151
<211> LENGTH: 20
<212> TYPE: DNA
<213> ORGANISM: Artificial Sequence
<220> FEATURE:
<223> OTHER INFORMATION: MLH3 forward primer

<400> SEQUENCE: 151
tgatgatggt tgcgcgtagt                                               20
```

```
<210> SEQ ID NO 152
<211> LENGTH: 15
<212> TYPE: DNA
<213> ORGANISM: Artificial Sequence
<220> FEATURE:
<223> OTHER INFORMATION: MLH3 reverse primer

<400> SEQUENCE: 152
cgaccgccaa accgc                                                        15

<210> SEQ ID NO 153
<211> LENGTH: 20
<212> TYPE: DNA
<213> ORGANISM: Artificial Sequence
<220> FEATURE:
<223> OTHER INFORMATION: MLH3: Probe (5'-6-FAM; 3'-BHQ1)

<400> SEQUENCE: 153
cgaaaccctc gcgcatccga                                                   20

<210> SEQ ID NO 154
<211> LENGTH: 18
<212> TYPE: DNA
<213> ORGANISM: Artificial Sequence
<220> FEATURE:
<223> OTHER INFORMATION: XPC forward primer

<400> SEQUENCE: 154
gtcgggtgcg ttattcgc                                                     18

<210> SEQ ID NO 155
<211> LENGTH: 18
<212> TYPE: DNA
<213> ORGANISM: Artificial Sequence
<220> FEATURE:
<223> OTHER INFORMATION: XPC reverse primer

<400> SEQUENCE: 155
ctacgcaatt cgcgtccc                                                     18

<210> SEQ ID NO 156
<211> LENGTH: 26
<212> TYPE: DNA
<213> ORGANISM: Artificial Sequence
<220> FEATURE:
<223> OTHER INFORMATION: XPC: Probe (5'-6-FAM; 3'-BHQ1)

<400> SEQUENCE: 156
accgcgcgtt tccgaaccat attact                                            26

<210> SEQ ID NO 157
<211> LENGTH: 22
<212> TYPE: DNA
<213> ORGANISM: Artificial Sequence
<220> FEATURE:
<223> OTHER INFORMATION: RAD23A forward primer

<400> SEQUENCE: 157
tatcgataac gggtatggcg tt                                                22

<210> SEQ ID NO 158
<211> LENGTH: 23
<212> TYPE: DNA
<213> ORGANISM: Artificial Sequence
<220> FEATURE:
<223> OTHER INFORMATION: RAD23A reverse primer

<400> SEQUENCE: 158
```
gcaaactaaa ctccgcgcta taa                                                23

<210> SEQ ID NO 159
<211> LENGTH: 30
<212> TYPE: DNA
<213> ORGANISM: Artificial Sequence
<220> FEATURE:
<223> OTHER INFORMATION: RAD23A: Probe (5'-6-FAM; 3'-BHQ1)

<400> SEQUENCE: 159
ttactcgacc cgcacacgta atctcctaaa                                         30

<210> SEQ ID NO 160
<211> LENGTH: 19
<212> TYPE: DNA
<213> ORGANISM: Artificial Sequence
<220> FEATURE:
<223> OTHER INFORMATION: XPA forward primer

<400> SEQUENCE: 160
cgcggagttg tttgtttcg                                                     19

<210> SEQ ID NO 161
<211> LENGTH: 21
<212> TYPE: DNA
<213> ORGANISM: Artificial Sequence
<220> FEATURE:
<223> OTHER INFORMATION: XPA reverse primer

<400> SEQUENCE: 161
caacatcaat acccgctacc g                                                  21

<210> SEQ ID NO 162
<211> LENGTH: 20
<212> TYPE: DNA
<213> ORGANISM: Artificial Sequence
<220> FEATURE:
<223> OTHER INFORMATION: XPA: Probe (5'-6-FAM; 3'-BHQ1)

<400> SEQUENCE: 162
ccgctcgata ctcgcccgca                                                    20

<210> SEQ ID NO 163
<211> LENGTH: 19
<212> TYPE: DNA
<213> ORGANISM: Artificial Sequence
<220> FEATURE:
<223> OTHER INFORMATION: RPA2 forward primer

<400> SEQUENCE: 163
tggcgcgaat ttgagtacg                                                     19

<210> SEQ ID NO 164
<211> LENGTH: 21
<212> TYPE: DNA
<213> ORGANISM: Artificial Sequence
<220> FEATURE:
<223> OTHER INFORMATION: RPA2 reverse primer

<400> SEQUENCE: 164
cgtataatcc caccctcgtc a                                                  21

<210> SEQ ID NO 165
<211> LENGTH: 30
<212> TYPE: DNA
<213> ORGANISM: Artificial Sequence

```
<220> FEATURE:
<223> OTHER INFORMATION: RPA2: Probe (5'-6-FAM; 3'-BHQ1)

<400> SEQUENCE: 165
cgcgacttct accgtcactt cctttattcg                                    30

<210> SEQ ID NO 166
<211> LENGTH: 19
<212> TYPE: DNA
<213> ORGANISM: Artificial Sequence
<220> FEATURE:
<223> OTHER INFORMATION: RPA3 forward primer

<400> SEQUENCE: 166
agcgcgattg cgatttagg                                                19

<210> SEQ ID NO 167
<211> LENGTH: 22
<212> TYPE: DNA
<213> ORGANISM: Artificial Sequence
<220> FEATURE:
<223> OTHER INFORMATION: RPA3 reverse primer

<400> SEQUENCE: 167
tttctcgaca ccaatcaacg aa                                            22

<210> SEQ ID NO 168
<211> LENGTH: 28
<212> TYPE: DNA
<213> ORGANISM: Artificial Sequence
<220> FEATURE:
<223> OTHER INFORMATION: RPA3: Probe (5'-6-FAM; 3'-BHQ1)

<400> SEQUENCE: 168
tccaacttcg ccaattaaat acgcgaaa                                      28

<210> SEQ ID NO 169
<211> LENGTH: 23
<212> TYPE: DNA
<213> ORGANISM: Artificial Sequence
<220> FEATURE:
<223> OTHER INFORMATION: ERCC2 forward primer

<400> SEQUENCE: 169
cgagttttcg aggatgttta cga                                           23

<210> SEQ ID NO 170
<211> LENGTH: 23
<212> TYPE: DNA
<213> ORGANISM: Artificial Sequence
<220> FEATURE:
<223> OTHER INFORMATION: ERCC2 reverse primer

<400> SEQUENCE: 170
ccgaccgaac tatacaacga aat                                           23

<210> SEQ ID NO 171
<211> LENGTH: 29
<212> TYPE: DNA
<213> ORGANISM: Artificial Sequence
<220> FEATURE:
<223> OTHER INFORMATION: ERCC2: Probe (5'-6-FAM; 3'-BHQ1)

<400> SEQUENCE: 171
acccgcctcc ctcataaata ttcaacgaa                                     29
```

```
<210> SEQ ID NO 172
<211> LENGTH: 28
<212> TYPE: DNA
<213> ORGANISM: Artificial Sequence
<220> FEATURE:
<223> OTHER INFORMATION: ERCC5 forward primer

<400> SEQUENCE: 172
taagcgtaga aaatatacgt tatgtgcg                                    28

<210> SEQ ID NO 173
<211> LENGTH: 18
<212> TYPE: DNA
<213> ORGANISM: Artificial Sequence
<220> FEATURE:
<223> OTHER INFORMATION: ERCC5 reverse primer

<400> SEQUENCE: 173
cccgctcgat ttccgtct                                               18

<210> SEQ ID NO 174
<211> LENGTH: 23
<212> TYPE: DNA
<213> ORGANISM: Artificial Sequence
<220> FEATURE:
<223> OTHER INFORMATION: ERCC5: Probe (5'-6-FAM; 3'-BHQ1)

<400> SEQUENCE: 174
cgacgcgcaa aacgaaaact ccg                                         23

<210> SEQ ID NO 175
<211> LENGTH: 17
<212> TYPE: DNA
<213> ORGANISM: Artificial Sequence
<220> FEATURE:
<223> OTHER INFORMATION: ERCC1 forward primer

<400> SEQUENCE: 175
gggcgagtcg aaggtgg                                                17

<210> SEQ ID NO 176
<211> LENGTH: 23
<212> TYPE: DNA
<213> ORGANISM: Artificial Sequence
<220> FEATURE:
<223> OTHER INFORMATION: ERCC1 reverse primer

<400> SEQUENCE: 176
ctccgaaaac tccataacgt caa                                         23

<210> SEQ ID NO 177
<211> LENGTH: 29
<212> TYPE: DNA
<213> ORGANISM: Artificial Sequence
<220> FEATURE:
<223> OTHER INFORMATION: ERCC1: Probe (5'-6-FAM; 3'-BHQ1)

<400> SEQUENCE: 177
cccaacgcta aaaactctat aacgccacg                                   29

<210> SEQ ID NO 178
<211> LENGTH: 19
<212> TYPE: DNA
<213> ORGANISM: Artificial Sequence
<220> FEATURE:
<223> OTHER INFORMATION: ERCC4 forward primer

<400> SEQUENCE: 178
```

```
tcgacggatt gttatggcg                                          19
```

<210> SEQ ID NO 179
<211> LENGTH: 22
<212> TYPE: DNA
<213> ORGANISM: Artificial Sequence
<220> FEATURE:
<223> OTHER INFORMATION: ERCC4 reverse primer

<400> SEQUENCE: 179

```
ccgtcaatat cgaacaattc ca                                      22
```

<210> SEQ ID NO 180
<211> LENGTH: 29
<212> TYPE: DNA
<213> ORGANISM: Artificial Sequence
<220> FEATURE:
<223> OTHER INFORMATION: ERCC4: Probe (5'-6-FAM; 3'-BHQ1)

<400> SEQUENCE: 180

```
caccaactat cgctcgtact ccaacaacg                               29
```

<210> SEQ ID NO 181
<211> LENGTH: 22
<212> TYPE: DNA
<213> ORGANISM: Artificial Sequence
<220> FEATURE:
<223> OTHER INFORMATION: NDUFA121 forward primer

<400> SEQUENCE: 181

```
ggttaaggcg tttagagtcg gg                                      22
```

<210> SEQ ID NO 182
<211> LENGTH: 28
<212> TYPE: DNA
<213> ORGANISM: Artificial Sequence
<220> FEATURE:
<223> OTHER INFORMATION: NDUFA121 reverse primer

<400> SEQUENCE: 182

```
tcatacgaca cttaaaatat caccgaaa                                28
```

<210> SEQ ID NO 183
<211> LENGTH: 30
<212> TYPE: DNA
<213> ORGANISM: Artificial Sequence
<220> FEATURE:
<223> OTHER INFORMATION: NDUFA121: Probe (5'-6-FAM; 3'-BHQ1)

<400> SEQUENCE: 183

```
cccttcactc taacatcgaa accctacccg                              30
```

<210> SEQ ID NO 184
<211> LENGTH: 25
<212> TYPE: DNA
<213> ORGANISM: Artificial Sequence
<220> FEATURE:
<223> OTHER INFORMATION: ERCC6 forward primer

<400> SEQUENCE: 184

```
acgtaagtag aaaggcgttg ttgag                                   25
```

<210> SEQ ID NO 185
<211> LENGTH: 26
<212> TYPE: DNA
<213> ORGANISM: Artificial Sequence

```
<220> FEATURE:
<223> OTHER INFORMATION: ERCC6 reverse primer

<400> SEQUENCE: 185
cgactccgac ttctactaat acgaaa                                    26

<210> SEQ ID NO 186
<211> LENGTH: 27
<212> TYPE: DNA
<213> ORGANISM: Artificial Sequence
<220> FEATURE:
<223> OTHER INFORMATION: ERCC6: Probe (5'-6-FAM; 3'-BHQ1)

<400> SEQUENCE: 186
cccgtaacgc atacgcctaa ctcaacg                                   27

<210> SEQ ID NO 187
<211> LENGTH: 27
<212> TYPE: DNA
<213> ORGANISM: Artificial Sequence
<220> FEATURE:
<223> OTHER INFORMATION: XAB2 forward primer

<400> SEQUENCE: 187
gacggatagg tttacgttat tgatttt                                   27

<210> SEQ ID NO 188
<211> LENGTH: 23
<212> TYPE: DNA
<213> ORGANISM: Artificial Sequence
<220> FEATURE:
<223> OTHER INFORMATION: XAB2 reverse primer

<400> SEQUENCE: 188
cgcatcttct aacgcctcta ttc                                       23

<210> SEQ ID NO 189
<211> LENGTH: 26
<212> TYPE: DNA
<213> ORGANISM: Artificial Sequence
<220> FEATURE:
<223> OTHER INFORMATION: XAB2: Probe (5'-6-FAM; 3'-BHQ1)

<400> SEQUENCE: 189
acttccgatc gctaacgtcg tcgaaa                                    26

<210> SEQ ID NO 190
<211> LENGTH: 16
<212> TYPE: DNA
<213> ORGANISM: Artificial Sequence
<220> FEATURE:
<223> OTHER INFORMATION: DDB1 forward primer

<400> SEQUENCE: 190
gggcggaggt agcggt                                               16

<210> SEQ ID NO 191
<211> LENGTH: 18
<212> TYPE: DNA
<213> ORGANISM: Artificial Sequence
<220> FEATURE:
<223> OTHER INFORMATION: DDB1 reverse primer

<400> SEQUENCE: 191
cccgtcgaaa ctcgaacg                                             18
```

```
<210> SEQ ID NO 192
<211> LENGTH: 23
<212> TYPE: DNA
<213> ORGANISM: Artificial Sequence
<220> FEATURE:
<223> OTHER INFORMATION: DDB1: Probe (5'-6-FAM; 3'-BHQ1)

<400> SEQUENCE: 192
ccaacaacgc gcaacgaact cca                                    23

<210> SEQ ID NO 193
<211> LENGTH: 26
<212> TYPE: DNA
<213> ORGANISM: Artificial Sequence
<220> FEATURE:
<223> OTHER INFORMATION: MMS191 forward primer

<400> SEQUENCE: 193
ttaggtagaa gtcggtaggt acgtga                                 26

<210> SEQ ID NO 194
<211> LENGTH: 23
<212> TYPE: DNA
<213> ORGANISM: Artificial Sequence
<220> FEATURE:
<223> OTHER INFORMATION: MMS191 reverse primer

<400> SEQUENCE: 194
ataactcgaa acgaactctc cgc                                    23

<210> SEQ ID NO 195
<211> LENGTH: 21
<212> TYPE: DNA
<213> ORGANISM: Artificial Sequence
<220> FEATURE:
<223> OTHER INFORMATION: MMS191: Probe (5'-6-FAM; 3'-BHQ1)

<400> SEQUENCE: 195
cgcctcccga accaatctcc g                                      21

<210> SEQ ID NO 196
<211> LENGTH: 19
<212> TYPE: DNA
<213> ORGANISM: Artificial Sequence
<220> FEATURE:
<223> OTHER INFORMATION: BRCA2 forward primer

<400> SEQUENCE: 196
cgttacggcg ttacgtggt                                         19

<210> SEQ ID NO 197
<211> LENGTH: 20
<212> TYPE: DNA
<213> ORGANISM: Artificial Sequence
<220> FEATURE:
<223> OTHER INFORMATION: BRCA2 reverse primer

<400> SEQUENCE: 197
ccgcctctac cgcctaattt                                        20

<210> SEQ ID NO 198
<211> LENGTH: 17
<212> TYPE: DNA
<213> ORGANISM: Artificial Sequence
<220> FEATURE:
<223> OTHER INFORMATION: BRCA2: Probe (5'-6-FAM; 3'-BHQ1)

<400> SEQUENCE: 198
```
cgcgccacaa acccgcg                                              17

<210> SEQ ID NO 199
<211> LENGTH: 18
<212> TYPE: DNA
<213> ORGANISM: Artificial Sequence
<220> FEATURE:
<223> OTHER INFORMATION: DCLRE1C forward primer

<400> SEQUENCE: 199
cgaagcgcgg gtgattta                                             18

<210> SEQ ID NO 200
<211> LENGTH: 22
<212> TYPE: DNA
<213> ORGANISM: Artificial Sequence
<220> FEATURE:
<223> OTHER INFORMATION: DCLRE1C reverse primer

<400> SEQUENCE: 200
aaaatccgaa aaccgaaaac aa                                        22

<210> SEQ ID NO 201
<211> LENGTH: 29
<212> TYPE: DNA
<213> ORGANISM: Artificial Sequence
<220> FEATURE:
<223> OTHER INFORMATION: DCLRE1C: Probe (5'-6-FAM; 3'-BHQ1)

<400> SEQUENCE: 201
atccgatcga attctaaacg cccgctact                                 29

<210> SEQ ID NO 202
<211> LENGTH: 16
<212> TYPE: DNA
<213> ORGANISM: Artificial Sequence
<220> FEATURE:
<223> OTHER INFORMATION: POLD1 forward primer

<400> SEQUENCE: 202
gggacgcgga ggatgc                                               16

<210> SEQ ID NO 203
<211> LENGTH: 22
<212> TYPE: DNA
<213> ORGANISM: Artificial Sequence
<220> FEATURE:
<223> OTHER INFORMATION: POLD1 reverse primer

<400> SEQUENCE: 203
gatctaaacg ccgcgattct at                                        22

<210> SEQ ID NO 204
<211> LENGTH: 25
<212> TYPE: DNA
<213> ORGANISM: Artificial Sequence
<220> FEATURE:
<223> OTHER INFORMATION: POLD1: Probe (5'-6-FAM; 3'-BHQ1)

<400> SEQUENCE: 204
tcctcccacc ctcgaatatt acgcg                                     25

<210> SEQ ID NO 205
<211> LENGTH: 20
<212> TYPE: DNA
<213> ORGANISM: Artificial Sequence

```
<220> FEATURE:
<223> OTHER INFORMATION: BCL2 forward primer

<400> SEQUENCE: 205
tcgtatttcg ggattcggtc                                                  20

<210> SEQ ID NO 206
<211> LENGTH: 19
<212> TYPE: DNA
<213> ORGANISM: Artificial Sequence
<220> FEATURE:
<223> OTHER INFORMATION: BCL2 reverse primer

<400> SEQUENCE: 206
aactaaacgc aaaccccgc                                                   19

<210> SEQ ID NO 207
<211> LENGTH: 28
<212> TYPE: DNA
<213> ORGANISM: Artificial Sequence
<220> FEATURE:
<223> OTHER INFORMATION: BCL2: Probe (5'-6-FAM; 3'-BHQ1)

<400> SEQUENCE: 207
acgacgccga aacaaccga aatctaca                                          28

<210> SEQ ID NO 208
<211> LENGTH: 20
<212> TYPE: DNA
<213> ORGANISM: Artificial Sequence
<220> FEATURE:
<223> OTHER INFORMATION: TSHR forward primer

<400> SEQUENCE: 208
ttgagggtta gaggcgggta                                                  20

<210> SEQ ID NO 209
<211> LENGTH: 28
<212> TYPE: DNA
<213> ORGANISM: Artificial Sequence
<220> FEATURE:
<223> OTHER INFORMATION: TSHR reverse primer

<400> SEQUENCE: 209
acaacgaaaa tcctcctcca aaataca                                          28

<210> SEQ ID NO 210
<211> LENGTH: 22
<212> TYPE: DNA
<213> ORGANISM: Artificial Sequence
<220> FEATURE:
<223> OTHER INFORMATION: TSHR: Probe (5'-6-FAM; 3'-BHQ1)

<400> SEQUENCE: 210
aacgacgact tcgaccgcac cg                                               22

<210> SEQ ID NO 211
<211> LENGTH: 21
<212> TYPE: DNA
<213> ORGANISM: Artificial Sequence
<220> FEATURE:
<223> OTHER INFORMATION: MBD2 forward primer

<400> SEQUENCE: 211
aggcggagat aagatggtcg t                                                21
```

```
<210> SEQ ID NO 212
<211> LENGTH: 21
<212> TYPE: DNA
<213> ORGANISM: Artificial Sequence
<220> FEATURE:
<223> OTHER INFORMATION: MBD2 reverse primer

<400> SEQUENCE: 212
ccctcctacc cgaaacgtaa c                                              21

<210> SEQ ID NO 213
<211> LENGTH: 27
<212> TYPE: DNA
<213> ORGANISM: Artificial Sequence
<220> FEATURE:
<223> OTHER INFORMATION: MBD2: Probe (5'-6-FAM; 3'-BHQ1)

<400> SEQUENCE: 213
cgaccaccgc ctcttaaatc ctccaaa                                        27

<210> SEQ ID NO 214
<211> LENGTH: 24
<212> TYPE: DNA
<213> ORGANISM: Artificial Sequence
<220> FEATURE:
<223> OTHER INFORMATION: HRAS forward primer

<400> SEQUENCE: 214
gagcgatgac ggaatataag ttgg                                           24

<210> SEQ ID NO 215
<211> LENGTH: 29
<212> TYPE: DNA
<213> ORGANISM: Artificial Sequence
<220> FEATURE:
<223> OTHER INFORMATION: HRAS reverse primer

<400> SEQUENCE: 215
cgtccacaaa ataattctaa atcaactaa                                      29

<210> SEQ ID NO 216
<211> LENGTH: 23
<212> TYPE: DNA
<213> ORGANISM: Artificial Sequence
<220> FEATURE:
<223> OTHER INFORMATION: HRAS: Probe (5'-6-FAM; 3'-BHQ1)

<400> SEQUENCE: 216
cactcttacc cacaccgccg acg                                            23

<210> SEQ ID NO 217
<211> LENGTH: 25
<212> TYPE: DNA
<213> ORGANISM: Artificial Sequence
<220> FEATURE:
<223> OTHER INFORMATION: TFF1 forward primer

<400> SEQUENCE: 217
taaggttacg gtggttattt cgtga                                          25

<210> SEQ ID NO 218
<211> LENGTH: 31
<212> TYPE: DNA
<213> ORGANISM: Artificial Sequence
<220> FEATURE:
<223> OTHER INFORMATION: TFF1 reverse primer

<400> SEQUENCE: 218
```

```
accttaatcc aaatcctact catatctaaa a                              31

<210> SEQ ID NO 219
<211> LENGTH: 37
<212> TYPE: DNA
<213> ORGANISM: Artificial Sequence
<220> FEATURE:
<223> OTHER INFORMATION: TFF1: Probe (5'-6-FAM; 3'-BHQ1)

<400> SEQUENCE: 219
ccctcccgcc aaaataaata ctatactcac tacaaaa                        37

<210> SEQ ID NO 220
<211> LENGTH: 23
<212> TYPE: DNA
<213> ORGANISM: Artificial Sequence
<220> FEATURE:
<223> OTHER INFORMATION: CCND1 forward primer

<400> SEQUENCE: 220
ggtaatttcg tcgtagggta ggc                                       23

<210> SEQ ID NO 221
<211> LENGTH: 16
<212> TYPE: DNA
<213> ORGANISM: Artificial Sequence
<220> FEATURE:
<223> OTHER INFORMATION: CCND1 reverse primer

<400> SEQUENCE: 221
gaacgccaaa cgccga                                               16

<210> SEQ ID NO 222
<211> LENGTH: 26
<212> TYPE: DNA
<213> ORGANISM: Artificial Sequence
<220> FEATURE:
<223> OTHER INFORMATION: CCND1: Probe (5'-6-FAM; 3'-BHQ1)

<400> SEQUENCE: 222
acccaaaaac catccctaaa acgccg                                    26

<210> SEQ ID NO 223
<211> LENGTH: 21
<212> TYPE: DNA
<213> ORGANISM: Artificial Sequence
<220> FEATURE:
<223> OTHER INFORMATION: CTSD forward primer

<400> SEQUENCE: 223
tacgtttcgc gtaggtttgg a                                         21

<210> SEQ ID NO 224
<211> LENGTH: 21
<212> TYPE: DNA
<213> ORGANISM: Artificial Sequence
<220> FEATURE:
<223> OTHER INFORMATION: CTSD reverse primer

<400> SEQUENCE: 224
tcgtaaaacg acccaccta a                                          21

<210> SEQ ID NO 225
<211> LENGTH: 19
<212> TYPE: DNA
<213> ORGANISM: Artificial Sequence
```

```
<220> FEATURE:
<223> OTHER INFORMATION: CTSD: Probe (5'-6-FAM; 3'-BHQ1)

<400> SEQUENCE: 225
cctatcccga ccgccgcga                                              19

<210> SEQ ID NO 226
<211> LENGTH: 19
<212> TYPE: DNA
<213> ORGANISM: Artificial Sequence
<220> FEATURE:
<223> OTHER INFORMATION: PGR forward primer

<400> SEQUENCE: 226
ggcggtgacg gtcgtattc                                              19

<210> SEQ ID NO 227
<211> LENGTH: 17
<212> TYPE: DNA
<213> ORGANISM: Artificial Sequence
<220> FEATURE:
<223> OTHER INFORMATION: PGR reverse primer

<400> SEQUENCE: 227
acaaaccgtc ccgcgaa                                                17

<210> SEQ ID NO 228
<211> LENGTH: 19
<212> TYPE: DNA
<213> ORGANISM: Artificial Sequence
<220> FEATURE:
<223> OTHER INFORMATION: PGR: Probe (5'-6-FAM; 3'-BHQ1)

<400> SEQUENCE: 228
aacaaccgct cgcgcccga                                              19

<210> SEQ ID NO 229
<211> LENGTH: 21
<212> TYPE: DNA
<213> ORGANISM: Artificial Sequence
<220> FEATURE:
<223> OTHER INFORMATION: MLH1 forward

<400> SEQUENCE: 229
aggaagagcg gatagcgatt t                                           21

<210> SEQ ID NO 230
<211> LENGTH: 21
<212> TYPE: DNA
<213> ORGANISM: Artificial Sequence
<220> FEATURE:
<223> OTHER INFORMATION: MLH1 reverse primer

<400> SEQUENCE: 230
tcttcgtccc tccctaaaac g                                           21

<210> SEQ ID NO 231
<211> LENGTH: 31
<212> TYPE: DNA
<213> ORGANISM: Artificial Sequence
<220> FEATURE:
<223> OTHER INFORMATION: MLH1: Probe (5'-6-FAM; 3'-BHQ1)

<400> SEQUENCE: 231
cccgctacct aaaaaaatat acgcttacgc g                                31
```

```
<210> SEQ ID NO 232
<211> LENGTH: 18
<212> TYPE: DNA
<213> ORGANISM: Artificial Sequence
<220> FEATURE:
<223> OTHER INFORMATION: FBXW7 forward primer

<400> SEQUENCE: 232
tgtcgttgcg gttgggat                                                    18

<210> SEQ ID NO 233
<211> LENGTH: 27
<212> TYPE: DNA
<213> ORGANISM: Artificial Sequence
<220> FEATURE:
<223> OTHER INFORMATION: FBXW7 reverse primer

<400> SEQUENCE: 233
cgaaaataaa taactactcc gcgataa                                          27

<210> SEQ ID NO 234
<211> LENGTH: 28
<212> TYPE: DNA
<213> ORGANISM: Artificial Sequence
<220> FEATURE:
<223> OTHER INFORMATION: FBXW7: Probe (5'-6-FAM; 3'-BHQ1)

<400> SEQUENCE: 234
acgccaaaac ttctacctcg tcccgtaa                                         28

<210> SEQ ID NO 235
<211> LENGTH: 30
<212> TYPE: DNA
<213> ORGANISM: Artificial Sequence
<220> FEATURE:
<223> OTHER INFORMATION: EPM2ALP1 forward primer

<400> SEQUENCE: 235
cgttatatat cgttcgtagt attcgtgttt                                       30

<210> SEQ ID NO 236
<211> LENGTH: 18
<212> TYPE: DNA
<213> ORGANISM: Artificial Sequence
<220> FEATURE:
<223> OTHER INFORMATION: EPM2ALP1 reverse primer

<400> SEQUENCE: 236
ctatcgccgc ctcatcgt                                                    18

<210> SEQ ID NO 237
<211> LENGTH: 22
<212> TYPE: DNA
<213> ORGANISM: Artificial Sequence
<220> FEATURE:
<223> OTHER INFORMATION: EPM2ALP1: Probe (5'-6-FAM; 3'-BHQ1)

<400> SEQUENCE: 237
cgcgacgtca aacgccacta cg                                               22

<210> SEQ ID NO 238
<211> LENGTH: 27
<212> TYPE: DNA
<213> ORGANISM: Artificial Sequence
<220> FEATURE:
<223> OTHER INFORMATION: APC forward primer

<400> SEQUENCE: 238
```
ttatatgtcg gttacgtgcg tttatat                                    27

<210> SEQ ID NO 239
<211> LENGTH: 19
<212> TYPE: DNA
<213> ORGANISM: Artificial Sequence
<220> FEATURE:
<223> OTHER INFORMATION: APC reverse primer

<400> SEQUENCE: 239
gaaccaaaac gctccccat                                             19

<210> SEQ ID NO 240
<211> LENGTH: 22
<212> TYPE: DNA
<213> ORGANISM: Artificial Sequence
<220> FEATURE:
<223> OTHER INFORMATION: APC: Probe (5'-6-FAM; 3'-BHQ1)

<400> SEQUENCE: 240
cccgtcgaaa acccgccgat ta                                         22

<210> SEQ ID NO 241
<211> LENGTH: 18
<212> TYPE: DNA
<213> ORGANISM: Artificial Sequence
<220> FEATURE:
<223> OTHER INFORMATION: MYOD1 forward primer

<400> SEQUENCE: 241
gagcgcgcgt agttagcg                                              18

<210> SEQ ID NO 242
<211> LENGTH: 17
<212> TYPE: DNA
<213> ORGANISM: Artificial Sequence
<220> FEATURE:
<223> OTHER INFORMATION: MYOD1 reverse primer

<400> SEQUENCE: 242
tccgacacgc cctttcc                                               17

<210> SEQ ID NO 243
<211> LENGTH: 30
<212> TYPE: DNA
<213> ORGANISM: Artificial Sequence
<220> FEATURE:
<223> OTHER INFORMATION: MYOD1: Probe (5'-6-FAM; 3'-BHQ1)

<400> SEQUENCE: 243
ctccaacacc cgactactat atccgcgaaa                                 30

<210> SEQ ID NO 244
<211> LENGTH: 23
<212> TYPE: DNA
<213> ORGANISM: Artificial Sequence
<220> FEATURE:
<223> OTHER INFORMATION: PTEN forward primer

<400> SEQUENCE: 244
gtttcgcgtt gttgtaaaag tcg                                        23

<210> SEQ ID NO 245
<211> LENGTH: 31
<212> TYPE: DNA
<213> ORGANISM: Artificial Sequence

```
<220> FEATURE:
<223> OTHER INFORMATION: PTEN reverse primer

<400> SEQUENCE: 245
caatataact acctaaaact tactcgaacc g                              31

<210> SEQ ID NO 246
<211> LENGTH: 30
<212> TYPE: DNA
<213> ORGANISM: Artificial Sequence
<220> FEATURE:
<223> OTHER INFORMATION: PTEN: Probe (5'-6-FAM; 3'-BHQ1)

<400> SEQUENCE: 246
ttcccaaccg ccaacctaca actacactta                                30

<210> SEQ ID NO 247
<211> LENGTH: 22
<212> TYPE: DNA
<213> ORGANISM: Artificial Sequence
<220> FEATURE:
<223> OTHER INFORMATION: CACNA1G forward primer

<400> SEQUENCE: 247 tttttttcgtt tcgcgtttag gt                                       22

<210> SEQ ID NO 248
<211> LENGTH: 18
<212> TYPE: DNA
<213> ORGANISM: Artificial Sequence
<220> FEATURE:
<223> OTHER INFORMATION: CACNA1G reverse primer

<400> SEQUENCE: 248
ctcgaaacga cttcgccg                                             18

<210> SEQ ID NO 249
<211> LENGTH: 25
<212> TYPE: DNA
<213> ORGANISM: Artificial Sequence
<220> FEATURE:
<223> OTHER INFORMATION: CACNA1G: Probe (5'-6-FAM; 3'-BHQ1)

<400> SEQUENCE: 249
aaataacgcc gaatccgaca accga                                     25

<210> SEQ ID NO 250
<211> LENGTH: 20
<212> TYPE: DNA
<213> ORGANISM: Artificial Sequence
<220> FEATURE:
<223> OTHER INFORMATION: MGMT forward primer

<400> SEQUENCE: 250
gcgtttcgac gttcgtaggt                                           20

<210> SEQ ID NO 251
<211> LENGTH: 21
<212> TYPE: DNA
<213> ORGANISM: Artificial Sequence
<220> FEATURE:
<223> OTHER INFORMATION: MGMT reverse primer

<400> SEQUENCE: 251
cactcttccg aaaacgaaac g                                         21
```

```
<210> SEQ ID NO 252
<211> LENGTH: 21
<212> TYPE: DNA
<213> ORGANISM: Artificial Sequence
<220> FEATURE:
<223> OTHER INFORMATION: MGMT: Probe (5'-6-FAM; 3'-BHQ1)

<400> SEQUENCE: 252
cgcaaacgat acgcaccgcg a                                          21

<210> SEQ ID NO 253
<211> LENGTH: 34
<212> TYPE: DNA
<213> ORGANISM: Artificial Sequence
<220> FEATURE:
<223> OTHER INFORMATION: PENK forward primer

<400> SEQUENCE: 253
ggttaattat aaagtggttt tagtagtcgt taag                            34

<210> SEQ ID NO 254
<211> LENGTH: 24
<212> TYPE: DNA
<213> ORGANISM: Artificial Sequence
<220> FEATURE:
<223> OTHER INFORMATION: PENK reverse primer

<400> SEQUENCE: 254
caacgtctct acgaaatcac gaac                                       24

<210> SEQ ID NO 255
<211> LENGTH: 21
<212> TYPE: DNA
<213> ORGANISM: Artificial Sequence
<220> FEATURE:
<223> OTHER INFORMATION: PENK: Probe (5'-6-FAM; 3'-BHQ1)

<400> SEQUENCE: 255
aacgcctacc tcgccgtccc g                                          21

<210> SEQ ID NO 256
<211> LENGTH: 19
<212> TYPE: DNA
<213> ORGANISM: Artificial Sequence
<220> FEATURE:
<223> OTHER INFORMATION: ESR1 forward primer

<400> SEQUENCE: 256
ggcgttcgtt ttgggattg                                             19

<210> SEQ ID NO 257
<211> LENGTH: 19
<212> TYPE: DNA
<213> ORGANISM: Artificial Sequence
<220> FEATURE:
<223> OTHER INFORMATION: ESR1 reverse primer

<400> SEQUENCE: 257
gccgacacgc gaactctaa                                             19

<210> SEQ ID NO 258
<211> LENGTH: 24
<212> TYPE: DNA
<213> ORGANISM: Artificial Sequence
<220> FEATURE:
<223> OTHER INFORMATION: ESR1: Probe (5'-6-FAM; 3'-BHQ1)

<400> SEQUENCE: 258
```
cgataaaacc gaacgacccg acga                                          24

<210> SEQ ID NO 259
<211> LENGTH: 26
<212> TYPE: DNA
<213> ORGANISM: Artificial Sequence
<220> FEATURE:
<223> OTHER INFORMATION: ESR2 forward primer

<400> SEQUENCE: 259
tttgaaattt gtagggcgaa gagtag                                        26

<210> SEQ ID NO 260
<211> LENGTH: 20
<212> TYPE: DNA
<213> ORGANISM: Artificial Sequence
<220> FEATURE:
<223> OTHER INFORMATION: ESR2 reverse primer

<400> SEQUENCE: 260
acccgtcgca actcgaataa                                               20

<210> SEQ ID NO 261
<211> LENGTH: 18
<212> TYPE: DNA
<213> ORGANISM: Artificial Sequence
<220> FEATURE:
<223> OTHER INFORMATION: ESR2: Probe (5'-6-FAM; 3'-BHQ1)

<400> SEQUENCE: 261
ccgacccaac gctcgccg                                                 18

<210> SEQ ID NO 262
<211> LENGTH: 23
<212> TYPE: DNA
<213> ORGANISM: Artificial Sequence
<220> FEATURE:
<223> OTHER INFORMATION: CALCA forward primer

<400> SEQUENCE: 262
gttttggaag tatgagggtg acg                                           23

<210> SEQ ID NO 263
<211> LENGTH: 19
<212> TYPE: DNA
<213> ORGANISM: Artificial Sequence
<220> FEATURE:
<223> OTHER INFORMATION: CALCA reverse primer

<400> SEQUENCE: 263
ttcccgccgc tataaatcg                                                19

<210> SEQ ID NO 264
<211> LENGTH: 30
<212> TYPE: DNA
<213> ORGANISM: Artificial Sequence
<220> FEATURE:
<223> OTHER INFORMATION: CALCA: Probe (5'-6-FAM; 3'-BHQ1)

<400> SEQUENCE: 264
attccgccaa tacacaacaa ccaataaacg                                    30

<210> SEQ ID NO 265
<211> LENGTH: 21
<212> TYPE: DNA
<213> ORGANISM: Artificial Sequence

```
<220> FEATURE:
<223> OTHER INFORMATION: TIMP3 forward primer

<400> SEQUENCE: 265
gcgtcggagg ttaaggttgt t                                             21

<210> SEQ ID NO 266
<211> LENGTH: 22
<212> TYPE: DNA
<213> ORGANISM: Artificial Sequence
<220> FEATURE:
<223> OTHER INFORMATION: TIMP3 reverse primer

<400> SEQUENCE: 266
ctctccaaaa ttaccgtacg cg                                            22

<210> SEQ ID NO 267
<211> LENGTH: 19
<212> TYPE: DNA
<213> ORGANISM: Artificial Sequence
<220> FEATURE:
<223> OTHER INFORMATION: TIMP3: Probe (5'-6-FAM; 3'-BHQ1)

<400> SEQUENCE: 267
aactcgctcg cccgccgaa                                                19

<210> SEQ ID NO 268
<211> LENGTH: 19
<212> TYPE: DNA
<213> ORGANISM: Artificial Sequence
<220> FEATURE:
<223> OTHER INFORMATION: HIC1 forward primer

<400> SEQUENCE: 268
gttaggcggt tagggcgtc                                                19

<210> SEQ ID NO 269
<211> LENGTH: 19
<212> TYPE: DNA
<213> ORGANISM: Artificial Sequence
<220> FEATURE:
<223> OTHER INFORMATION: HIC1 reverse primer

<400> SEQUENCE: 269
ccgaacgcct ccatcgtat                                                19

<210> SEQ ID NO 270
<211> LENGTH: 31
<212> TYPE: DNA
<213> ORGANISM: Artificial Sequence
<220> FEATURE:
<223> OTHER INFORMATION: HIC1: Probe (5'-6-FAM; 3'-BHQ1)

<400> SEQUENCE: 270
caacatcgtc tacccaacac actctcctac g                                  31

<210> SEQ ID NO 271
<211> LENGTH: 17
<212> TYPE: DNA
<213> ORGANISM: Artificial Sequence
<220> FEATURE:
<223> OTHER INFORMATION: CTNNB1 forward primer

<400> SEQUENCE: 271
ggaaaggcgc gtcgagt                                                  17
```

```
<210> SEQ ID NO 272
<211> LENGTH: 18
<212> TYPE: DNA
<213> ORGANISM: Artificial Sequence
<220> FEATURE:
<223> OTHER INFORMATION: CTNNB1 reverse primer

<400> SEQUENCE: 272
tcccctatcc caaacccg                                                 18

<210> SEQ ID NO 273
<211> LENGTH: 18
<212> TYPE: DNA
<213> ORGANISM: Artificial Sequence
<220> FEATURE:
<223> OTHER INFORMATION: CTNNB1: Probe (5'-6-FAM; 3'-BHQ1)

<400> SEQUENCE: 273
cgcgcgtttc ccgaaccg                                                 18

<210> SEQ ID NO 274
<211> LENGTH: 23
<212> TYPE: DNA
<213> ORGANISM: Artificial Sequence
<220> FEATURE:
<223> OTHER INFORMATION: GSTP1 forward primer

<400> SEQUENCE: 274
gtcggcgtcg tgatttagta ttg                                           23

<210> SEQ ID NO 275
<211> LENGTH: 23
<212> TYPE: DNA
<213> ORGANISM: Artificial Sequence
<220> FEATURE:
<223> OTHER INFORMATION: GSTP1 reverse primer

<400> SEQUENCE: 275
aaactacgac gacgaaactc caa                                           23

<210> SEQ ID NO 276
<211> LENGTH: 29
<212> TYPE: DNA
<213> ORGANISM: Artificial Sequence
<220> FEATURE:
<223> OTHER INFORMATION: GSTP1: Probe (5'-6-FAM; 3'-BHQ1)

<400> SEQUENCE: 276
aaacctcgcg acctccgaac cttataaaa                                     29

<210> SEQ ID NO 277
<211> LENGTH: 20
<212> TYPE: DNA
<213> ORGANISM: Artificial Sequence
<220> FEATURE:
<223> OTHER INFORMATION: CDKN2B forward primer

<400> SEQUENCE: 277
aggaaggaga gagtgcgtcg                                               20

<210> SEQ ID NO 278
<211> LENGTH: 21
<212> TYPE: DNA
<213> ORGANISM: Artificial Sequence
<220> FEATURE:
<223> OTHER INFORMATION: CDKN2B reverse primer

<400> SEQUENCE: 278
```

-continued

```
cgaataatcc accgttaacc g                                         21

<210> SEQ ID NO 279
<211> LENGTH: 29
<212> TYPE: DNA
<213> ORGANISM: Artificial Sequence
<220> FEATURE:
<223> OTHER INFORMATION: CDKN2B: Probe (5'-6-FAM; 3'-BHQ1)

<400> SEQUENCE: 279
ttaacgacac tcttcccttc tttcccacg                                 29

<210> SEQ ID NO 280
<211> LENGTH: 20
<212> TYPE: DNA
<213> ORGANISM: Artificial Sequence
<220> FEATURE:
<223> OTHER INFORMATION: SFN forward primer

<400> SEQUENCE: 280
gaggagggtt cggaggagaa                                           20

<210> SEQ ID NO 281
<211> LENGTH: 20
<212> TYPE: DNA
<213> ORGANISM: Artificial Sequence
<220> FEATURE:
<223> OTHER INFORMATION: SFN reverse primer

<400> SEQUENCE: 281
atcgcacacg ccctaaaact                                           20

<210> SEQ ID NO 282
<211> LENGTH: 25
<212> TYPE: DNA
<213> ORGANISM: Artificial Sequence
<220> FEATURE:
<223> OTHER INFORMATION: SFN: Probe (5'-6-FAM; 3'-BHQ1)

<400> SEQUENCE: 282
tctcccgata ctcacgcacc tcgaa                                     25

<210> SEQ ID NO 283
<211> LENGTH: 25
<212> TYPE: DNA
<213> ORGANISM: Artificial Sequence
<220> FEATURE:
<223> OTHER INFORMATION: KL forward primer

<400> SEQUENCE: 283
agtttggttt tcgcgtagta tgttc                                     25

<210> SEQ ID NO 284
<211> LENGTH: 15
<212> TYPE: DNA
<213> ORGANISM: Artificial Sequence
<220> FEATURE:
<223> OTHER INFORMATION: KL reverse primer

<400> SEQUENCE: 284
cgcccgactc cgcac                                                15

<210> SEQ ID NO 285
<211> LENGTH: 21
<212> TYPE: DNA
<213> ORGANISM: Artificial Sequence
```

```
<220> FEATURE:
<223> OTHER INFORMATION: KL: Probe (5'-6-FAM; 3'-BHQ1)

<400> SEQUENCE: 285
cgaacgacgc gacgaaacgc t                                              21

<210> SEQ ID NO 286
<211> LENGTH: 24
<212> TYPE: DNA
<213> ORGANISM: Artificial Sequence
<220> FEATURE:
<223> OTHER INFORMATION: RARB forward primer

<400> SEQUENCE: 286
tttatgcgag ttgtttgagg attg                                           24

<210> SEQ ID NO 287
<211> LENGTH: 21
<212> TYPE: DNA
<213> ORGANISM: Artificial Sequence
<220> FEATURE:
<223> OTHER INFORMATION: RARB reverse primer

<400> SEQUENCE: 287
cgaatcctac cccgacgata c                                              21

<210> SEQ ID NO 288
<211> LENGTH: 25
<212> TYPE: DNA
<213> ORGANISM: Artificial Sequence
<220> FEATURE:
<223> OTHER INFORMATION: RARB: Probe (5'-6-FAM; 3'-BHQ1)

<400> SEQUENCE: 288
ctcgaatcgc tcgcgttctc gacat                                          25

<210> SEQ ID NO 289
<211> LENGTH: 20
<212> TYPE: DNA
<213> ORGANISM: Artificial Sequence
<220> FEATURE:
<223> OTHER INFORMATION: TP73 forward primer

<400> SEQUENCE: 289
gggtcgggta gttcgttttg                                                20

<210> SEQ ID NO 290
<211> LENGTH: 19
<212> TYPE: DNA
<213> ORGANISM: Artificial Sequence
<220> FEATURE:
<223> OTHER INFORMATION: TP73 reverse primer

<400> SEQUENCE: 290
cgatttcgct acgtccccct                                                19

<210> SEQ ID NO 291
<211> LENGTH: 26
<212> TYPE: DNA
<213> ORGANISM: Artificial Sequence
<220> FEATURE:
<223> OTHER INFORMATION: TP73: Probe (5'-6-FAM; 3'-BHQ1)

<400> SEQUENCE: 291
aacctccgaa cgaatacgcg aacgaa                                         26
```

```
<210> SEQ ID NO 292
<211> LENGTH: 15
<212> TYPE: DNA
<213> ORGANISM: Artificial Sequence
<220> FEATURE:
<223> OTHER INFORMATION: DCC forward primer

<400> SEQUENCE: 292
gggttcggcg cgtgt                                                      15

<210> SEQ ID NO 293
<211> LENGTH: 29
<212> TYPE: DNA
<213> ORGANISM: Artificial Sequence
<220> FEATURE:
<223> OTHER INFORMATION: DCC reverse primer

<400> SEQUENCE: 293
cgaaaaatac aaaaaccaac ttaaatacc                                       29

<210> SEQ ID NO 294
<211> LENGTH: 28
<212> TYPE: DNA
<213> ORGANISM: Artificial Sequence
<220> FEATURE:
<223> OTHER INFORMATION: DCC: Probe (5'-6-FAM; 3'-BHQ1)

<400> SEQUENCE: 294
accaaaaatc gcgaacaacg acaacact                                        28

<210> SEQ ID NO 295
<211> LENGTH: 22
<212> TYPE: DNA
<213> ORGANISM: Artificial Sequence
<220> FEATURE:
<223> OTHER INFORMATION: ATM forward primer

<400> SEQUENCE: 295
acggagaaaa gaagtcgtgg tc                                              22

<210> SEQ ID NO 296
<211> LENGTH: 23
<212> TYPE: DNA
<213> ORGANISM: Artificial Sequence
<220> FEATURE:
<223> OTHER INFORMATION: ATM reverse primer

<400> SEQUENCE: 296
gcgacgataa ctacaacgca aat                                             23

<210> SEQ ID NO 297
<211> LENGTH: 22
<212> TYPE: DNA
<213> ORGANISM: Artificial Sequence
<220> FEATURE:
<223> OTHER INFORMATION: ATM: Probe (5'-6-FAM; 3'-BHQ1)

<400> SEQUENCE: 297
cgactcctct cgcctcctcc cg                                              22

<210> SEQ ID NO 298
<211> LENGTH: 19
<212> TYPE: DNA
<213> ORGANISM: Artificial Sequence
<220> FEATURE:
<223> OTHER INFORMATION: ATR forward primer

<400> SEQUENCE: 298
```

-continued agcggttttc gggaggagt                                          19

<210> SEQ ID NO 299
<211> LENGTH: 20
<212> TYPE: DNA
<213> ORGANISM: Artificial Sequence
<220> FEATURE:
<223> OTHER INFORMATION: ATR reverse primer

<400> SEQUENCE: 299
gaattcccga cgtctccaaa                                         20

<210> SEQ ID NO 300
<211> LENGTH: 23
<212> TYPE: DNA
<213> ORGANISM: Artificial Sequence
<220> FEATURE:
<223> OTHER INFORMATION: ATR: Probe (5'-6-FAM; 3'-BHQ1)

<400> SEQUENCE: 300
cgacgcccga cgaaaccgta taa                                     23

<210> SEQ ID NO 301
<211> LENGTH: 19
<212> TYPE: DNA
<213> ORGANISM: Artificial Sequence
<220> FEATURE:
<223> OTHER INFORMATION: RUNX3 forward primer

<400> SEQUENCE: 301
cgttcgatgg tggacgtgt                                          19

<210> SEQ ID NO 302
<211> LENGTH: 25
<212> TYPE: DNA
<213> ORGANISM: Artificial Sequence
<220> FEATURE:
<223> OTHER INFORMATION: RUNX3 reverse primer

<400> SEQUENCE: 302
gacgaacaac gtcttattac aacgc                                   25

<210> SEQ ID NO 303
<211> LENGTH: 25
<212> TYPE: DNA
<213> ORGANISM: Artificial Sequence
<220> FEATURE:
<223> OTHER INFORMATION: RUNX3: Probe (5'-6-FAM; 3'-BHQ1)

<400> SEQUENCE: 303
cgcacgaact cgcctacgta atccg                                   25

<210> SEQ ID NO 304
<211> LENGTH: 21
<212> TYPE: DNA
<213> ORGANISM: Artificial Sequence
<220> FEATURE:
<223> OTHER INFORMATION: STK11 forward primer

<400> SEQUENCE: 304
aattaacggg tgggtacgtc g                                       21

<210> SEQ ID NO 305
<211> LENGTH: 23
<212> TYPE: DNA
<213> ORGANISM: Artificial Sequence

```
<220> FEATURE:
<223> OTHER INFORMATION: STK11 reverse primer

<400> SEQUENCE: 305
gccatcttat ttacctccct ccc                                             23

<210> SEQ ID NO 306
<211> LENGTH: 17
<212> TYPE: DNA
<213> ORGANISM: Artificial Sequence
<220> FEATURE:
<223> OTHER INFORMATION: STK11: Probe (5'-6-FAM; 3'-BHQ1)

<400> SEQUENCE: 306
cgcacgcccg accgcaa                                                    17

<210> SEQ ID NO 307
<211> LENGTH: 25
<212> TYPE: DNA
<213> ORGANISM: Artificial Sequence
<220> FEATURE:
<223> OTHER INFORMATION: SEZ61 forward primer

<400> SEQUENCE: 307
gcgttagtag ggagagaaaa cgttc                                           25

<210> SEQ ID NO 308
<211> LENGTH: 22
<212> TYPE: DNA
<213> ORGANISM: Artificial Sequence
<220> FEATURE:
<223> OTHER INFORMATION: SEZ61 reverse primer

<400> SEQUENCE: 308
ataccaaccg cctcctctaa cc                                              22

<210> SEQ ID NO 309
<211> LENGTH: 27
<212> TYPE: DNA
<213> ORGANISM: Artificial Sequence
<220> FEATURE:
<223> OTHER INFORMATION: SEZ61: Probe (5'-6-FAM; 3'-BHQ1)

<400> SEQUENCE: 309
ccgtcgaccc tacaaaattt aacgcca                                         27

<210> SEQ ID NO 310
<211> LENGTH: 21
<212> TYPE: DNA
<213> ORGANISM: Artificial Sequence
<220> FEATURE:
<223> OTHER INFORMATION: RPB1 forward primer

<400> SEQUENCE: 310
cgcgttggga atttagttgt c                                               21

<210> SEQ ID NO 311
<211> LENGTH: 26
<212> TYPE: DNA
<213> ORGANISM: Artificial Sequence
<220> FEATURE:
<223> OTHER INFORMATION: RPB1 reverse primer

<400> SEQUENCE: 311
gatactacgc gaataataaa cgaccc                                          26
```

```
<210> SEQ ID NO 312
<211> LENGTH: 28
<212> TYPE: DNA
<213> ORGANISM: Artificial Sequence
<220> FEATURE:
<223> OTHER INFORMATION: RPB1: Probe (5'-6-FAM; 3'-BHQ1)

<400> SEQUENCE: 312
acgccctccg aaaacaaaaa actctacg                                       28

<210> SEQ ID NO 313
<211> LENGTH: 20
<212> TYPE: DNA
<213> ORGANISM: Artificial Sequence
<220> FEATURE:
<223> OTHER INFORMATION: ARPC1B forward primer

<400> SEQUENCE: 313
tgcgcgggta tcggtagtat                                                20

<210> SEQ ID NO 314
<211> LENGTH: 23
<212> TYPE: DNA
<213> ORGANISM: Artificial Sequence
<220> FEATURE:
<223> OTHER INFORMATION: ARPC1B reverse primer

<400> SEQUENCE: 314
acctaaaaca acgatcgcga aat                                            23

<210> SEQ ID NO 315
<211> LENGTH: 24
<212> TYPE: DNA
<213> ORGANISM: Artificial Sequence
<220> FEATURE:
<223> OTHER INFORMATION: ARPC1B: Probe (5'-6-FAM; 3'-BHQ1)

<400> SEQUENCE: 315
caaatcccgc cctcccttcg aaat                                           24

<210> SEQ ID NO 316
<211> LENGTH: 19
<212> TYPE: DNA
<213> ORGANISM: Artificial Sequence
<220> FEATURE:
<223> OTHER INFORMATION: CHFR forward primer

<400> SEQUENCE: 316
cgggagtttt tatgggcgt                                                 19

<210> SEQ ID NO 317
<211> LENGTH: 21
<212> TYPE: DNA
<213> ORGANISM: Artificial Sequence
<220> FEATURE:
<223> OTHER INFORMATION: CHFR reverse primer

<400> SEQUENCE: 317
aaccgtcccc aaaactacga c                                              21

<210> SEQ ID NO 318
<211> LENGTH: 25
<212> TYPE: DNA
<213> ORGANISM: Artificial Sequence
<220> FEATURE:
<223> OTHER INFORMATION: CHFR: Probe (5'-6-FAM; 3'-BHQ1)

<400> SEQUENCE: 318
```

```
cctcgaaccg ctccatcgaa attca                                     25
```

<210> SEQ ID NO 319
<211> LENGTH: 19
<212> TYPE: DNA
<213> ORGANISM: Artificial Sequence
<220> FEATURE:
<223> OTHER INFORMATION: VHL forward primer

<400> SEQUENCE: 319

```
cgggagcgcg tacgtagtt                                            19
```

<210> SEQ ID NO 320
<211> LENGTH: 19
<212> TYPE: DNA
<213> ORGANISM: Artificial Sequence
<220> FEATURE:
<223> OTHER INFORMATION: VHL reverse primer

<400> SEQUENCE: 320

```
ctccgaaaca ttccctccg                                            19
```

<210> SEQ ID NO 321
<211> LENGTH: 19
<212> TYPE: DNA
<213> ORGANISM: Artificial Sequence
<220> FEATURE:
<223> OTHER INFORMATION: VHL: Probe (5'-6-FAM; 3'-BHQ1)

<400> SEQUENCE: 321

```
cgaaccgaac gccgcgaaa                                            19
```

<210> SEQ ID NO 322
<211> LENGTH: 20
<212> TYPE: DNA
<213> ORGANISM: Artificial Sequence
<220> FEATURE:
<223> OTHER INFORMATION: TGFBR1 forward primer

<400> SEQUENCE: 322

```
acgcgcgttt attggttgtc                                           20
```

<210> SEQ ID NO 323
<211> LENGTH: 18
<212> TYPE: DNA
<213> ORGANISM: Artificial Sequence
<220> FEATURE:
<223> OTHER INFORMATION: TGFBR1 reverse primer

<400> SEQUENCE: 323

```
acgaacccgc aaacgaaa                                             18
```

<210> SEQ ID NO 324
<211> LENGTH: 27
<212> TYPE: DNA
<213> ORGANISM: Artificial Sequence
<220> FEATURE:
<223> OTHER INFORMATION: TGFBR1: Probe (5'-6-FAM; 3'-BHQ1)

<400> SEQUENCE: 324

```
taaatcccgc ttaacaactc gcgacga                                   27
```

<210> SEQ ID NO 325
<211> LENGTH: 25
<212> TYPE: DNA
<213> ORGANISM: Artificial Sequence -continued

```
<220> FEATURE:
<223> OTHER INFORMATION: COL1A2 forward primer

<400> SEQUENCE: 325
cggtagtagg aggtttcggt taagt                                    25

<210> SEQ ID NO 326
<211> LENGTH: 24
<212> TYPE: DNA
<213> ORGANISM: Artificial Sequence
<220> FEATURE:
<223> OTHER INFORMATION: COL1A2 reverse primer

<400> SEQUENCE: 326
cctaaatcac cgacgaaaat atca                                     24

<210> SEQ ID NO 327
<211> LENGTH: 32
<212> TYPE: DNA
<213> ORGANISM: Artificial Sequence
<220> FEATURE:
<223> OTHER INFORMATION: COL1A2: Probe (5'-6-FAM; 3'-BHQ1)

<400> SEQUENCE: 327
cgaacgcgaa catacaatcg taaccaatac ct                            32

<210> SEQ ID NO 328
<211> LENGTH: 15
<212> TYPE: DNA
<213> ORGANISM: Artificial Sequence
<220> FEATURE:
<223> OTHER INFORMATION: SCGB3A1 forward primer

<400> SEQUENCE: 328
ggcgtagcgg gcgtc                                               15

<210> SEQ ID NO 329
<211> LENGTH: 26
<212> TYPE: DNA
<213> ORGANISM: Artificial Sequence
<220> FEATURE:
<223> OTHER INFORMATION: SCGB3A1 reverse primer

<400> SEQUENCE: 329
ctacgtaacc ctatcctaca actccg                                   26

<210> SEQ ID NO 330
<211> LENGTH: 30
<212> TYPE: DNA
<213> ORGANISM: Artificial Sequence
<220> FEATURE:
<223> OTHER INFORMATION: SCGB3A2: Probe (5'-6-FAM; 3'-BHQ1)

<400> SEQUENCE: 330
cgaactccta acgcgcacga taaaacctaa                               30

<210> SEQ ID NO 331
<211> LENGTH: 19
<212> TYPE: DNA
<213> ORGANISM: Artificial Sequence
<220> FEATURE:
<223> OTHER INFORMATION: CDX1 forward primer

<400> SEQUENCE: 331
tgagcggttg ttcgtcgtc                                           19
```

```
<210> SEQ ID NO 332
<211> LENGTH: 19
<212> TYPE: DNA
<213> ORGANISM: Artificial Sequence
<220> FEATURE:
<223> OTHER INFORMATION: CDX1 reverse primer

<400> SEQUENCE: 332
aaatcccccg cgcatacta                                                  19

<210> SEQ ID NO 333
<211> LENGTH: 23
<212> TYPE: DNA
<213> ORGANISM: Artificial Sequence
<220> FEATURE:
<223> OTHER INFORMATION: CDX1: Probe (5'-6-FAM; 3'-BHQ1)

<400> SEQUENCE: 333
cctaaaaccg ccgctaccga ccg                                             23

<210> SEQ ID NO 334
<211> LENGTH: 21
<212> TYPE: DNA
<213> ORGANISM: Artificial Sequence
<220> FEATURE:
<223> OTHER INFORMATION: CRABP1 forward primer

<400> SEQUENCE: 334
tcgaaatttt cgttgttgcg t                                               21

<210> SEQ ID NO 335
<211> LENGTH: 19
<212> TYPE: DNA
<213> ORGANISM: Artificial Sequence
<220> FEATURE:
<223> OTHER INFORMATION: CRABP1 reverse primer

<400> SEQUENCE: 335
tatccgtacc taccgccgc                                                  19

<210> SEQ ID NO 336
<211> LENGTH: 27
<212> TYPE: DNA
<213> ORGANISM: Artificial Sequence
<220> FEATURE:
<223> OTHER INFORMATION: CRABP1: Probe (5'-6-FAM; 3'-BHQ1)

<400> SEQUENCE: 336 accatacccat acttcgccga cacctaa                                        27

<210> SEQ ID NO 337
<211> LENGTH: 23
<212> TYPE: DNA
<213> ORGANISM: Artificial Sequence
<220> FEATURE:
<223> OTHER INFORMATION: PLAGL1 forward primer

<400> SEQUENCE: 337
atcgacgggt tgaatgataa atg                                             23

<210> SEQ ID NO 338
<211> LENGTH: 20
<212> TYPE: DNA
<213> ORGANISM: Artificial Sequence
<220> FEATURE:
<223> OTHER INFORMATION: PLAGL1 reverse primer

<400> SEQUENCE: 338
```

```
ctcgacgcaa ccatcctctt                                              20
```

<210> SEQ ID NO 339
<211> LENGTH: 25
<212> TYPE: DNA
<213> ORGANISM: Artificial Sequence
<220> FEATURE:
<223> OTHER INFORMATION: PLAGL1: Probe (5'-6-FAM; 3'-BHQ1)

<400> SEQUENCE: 339

```
actaccgcga acgacaaaac ccacg                                        25
```

<210> SEQ ID NO 340
<211> LENGTH: 17
<212> TYPE: DNA
<213> ORGANISM: Artificial Sequence
<220> FEATURE:
<223> OTHER INFORMATION: LZTS1 forward primer

<400> SEQUENCE: 340

```
gcggcgttgt agggacg                                                 17
```

<210> SEQ ID NO 341
<211> LENGTH: 20
<212> TYPE: DNA
<213> ORGANISM: Artificial Sequence
<220> FEATURE:
<223> OTHER INFORMATION: LZTS1 reverse primer

<400> SEQUENCE: 341

```
cgcgcgctaa ctcttctacg                                              20
```

<210> SEQ ID NO 342
<211> LENGTH: 29
<212> TYPE: DNA
<213> ORGANISM: Artificial Sequence
<220> FEATURE:
<223> OTHER INFORMATION: LZTS1: Probe (5'-6-FAM; 3'-BHQ1)

<400> SEQUENCE: 342

```
attaccgcct ttaaactccg aaccctcca                                    29
```

<210> SEQ ID NO 343
<211> LENGTH: 18
<212> TYPE: DNA
<213> ORGANISM: Artificial Sequence
<220> FEATURE:
<223> OTHER INFORMATION: SFRP1 HB-201 forward primer

<400> SEQUENCE: 343

```
gaattcgttc gcgaggga                                                18
```

<210> SEQ ID NO 344
<211> LENGTH: 21
<212> TYPE: DNA
<213> ORGANISM: Artificial Sequence
<220> FEATURE:
<223> OTHER INFORMATION: SFRP1 HB-201 reverse primer

<400> SEQUENCE: 344

```
aaacgaaccg cactcgttac c                                            21
```

<210> SEQ ID NO 345
<211> LENGTH: 23
<212> TYPE: DNA
<213> ORGANISM: Artificial Sequence

```
<220> FEATURE:
<223> OTHER INFORMATION: SFRP1 HB-201: Probe (5'-6-FAM; 3'-BHQ1)

<400> SEQUENCE: 345
ccgtcaccga cgcgaaaacc aat                                           23

<210> SEQ ID NO 346
<211> LENGTH: 21
<212> TYPE: DNA
<213> ORGANISM: Artificial Sequence
<220> FEATURE:
<223> OTHER INFORMATION: JUP forward primer

<400> SEQUENCE: 346
ggatagcgaa ttgagttcgg c                                             21

<210> SEQ ID NO 347
<211> LENGTH: 28
<212> TYPE: DNA
<213> ORGANISM: Artificial Sequence
<220> FEATURE:
<223> OTHER INFORMATION: JUP reverse primer

<400> SEQUENCE: 347
ctcttcgcct tttattcgat tactaaat                                      28

<210> SEQ ID NO 348
<211> LENGTH: 19
<212> TYPE: DNA
<213> ORGANISM: Artificial Sequence
<220> FEATURE:
<223> OTHER INFORMATION: JUP: Probe (5'-6-FAM; 3'-BHQ1)

<400> SEQUENCE: 348
aacaaccgcc gcccgacca                                                19

<210> SEQ ID NO 349
<211> LENGTH: 28
<212> TYPE: DNA
<213> ORGANISM: Artificial Sequence
<220> FEATURE:
<223> OTHER INFORMATION: MT1G forward primer

<400> SEQUENCE: 349
cgtttaaggg attttgtatt tggtttat                                      28

<210> SEQ ID NO 350
<211> LENGTH: 17
<212> TYPE: DNA
<213> ORGANISM: Artificial Sequence
<220> FEATURE:
<223> OTHER INFORMATION: MT1G reverse primer

<400> SEQUENCE: 350
ccgctaaatc cgcaccg                                                  17

<210> SEQ ID NO 351
<211> LENGTH: 26
<212> TYPE: DNA
<213> ORGANISM: Artificial Sequence
<220> FEATURE:
<223> OTHER INFORMATION: MT1G: Probe (5'-6-FAM; 3'-BHQ1)

<400> SEQUENCE: 351
cgcgatcccg acctaaacta tacgca                                        26
```

```
<210> SEQ ID NO 352
<211> LENGTH: 24
<212> TYPE: DNA
<213> ORGANISM: Artificial Sequence
<220> FEATURE:
<223> OTHER INFORMATION: MT1A forward primer

<400> SEQUENCE: 352
cgtgttttcg tgttattgtg tacg                                                24

<210> SEQ ID NO 353
<211> LENGTH: 22
<212> TYPE: DNA
<213> ORGANISM: Artificial Sequence
<220> FEATURE:
<223> OTHER INFORMATION: MT1A reverse primer

<400> SEQUENCE: 353
ctcgctatcg ccttacctat cc                                                  22

<210> SEQ ID NO 354
<211> LENGTH: 27
<212> TYPE: DNA
<213> ORGANISM: Artificial Sequence
<220> FEATURE:
<223> OTHER INFORMATION: MT1A: Probe (5'-6-FAM; 3'-BHQ1)

<400> SEQUENCE: 354
tccacaccta aatccctcga acccact                                             27

<210> SEQ ID NO 355
<211> LENGTH: 24
<212> TYPE: DNA
<213> ORGANISM: Artificial Sequence
<220> FEATURE:
<223> OTHER INFORMATION: MT2A forward primer

<400> SEQUENCE: 355
gcgttttcgt cgtgtgtata gttt                                                24

<210> SEQ ID NO 356
<211> LENGTH: 19
<212> TYPE: DNA
<213> ORGANISM: Artificial Sequence
<220> FEATURE:
<223> OTHER INFORMATION: MT2A reverse primer

<400> SEQUENCE: 356
ttcccaaatc ccgctttca                                                      19

<210> SEQ ID NO 357
<211> LENGTH: 23
<212> TYPE: DNA
<213> ORGANISM: Artificial Sequence
<220> FEATURE:
<223> OTHER INFORMATION: MT2A: Probe (5'-6-FAM; 3'-BHQ1)

<400> SEQUENCE: 357
cgcgcgctaa cgactcaaat tcg                                                 23

<210> SEQ ID NO 358
<211> LENGTH: 25
<212> TYPE: DNA
<213> ORGANISM: Artificial Sequence
<220> FEATURE:
<223> OTHER INFORMATION: MT3 forward primer

<400> SEQUENCE: 358
```
ggttttaggg tttatgtcga ggaga                                         25

<210> SEQ ID NO 359
<211> LENGTH: 19
<212> TYPE: DNA
<213> ORGANISM: Artificial Sequence
<220> FEATURE:
<223> OTHER INFORMATION: MT3 reverse primer

<400> SEQUENCE: 359
ccgcgcgtcc aattactta                                                19

<210> SEQ ID NO 360
<211> LENGTH: 28
<212> TYPE: DNA
<213> ORGANISM: Artificial Sequence
<220> FEATURE:
<223> OTHER INFORMATION: MT3: Probe (5'-6-FAM; 3'-BHQ1)

<400> SEQUENCE: 360
aaaacccgtt caccgcctcc aactacta                                      28

<210> SEQ ID NO 361
<211> LENGTH: 25
<212> TYPE: DNA
<213> ORGANISM: Artificial Sequence
<220> FEATURE:
<223> OTHER INFORMATION: SERPINB5 forward primer

<400> SEQUENCE: 361
gaaaaggaat aggtaagcga ggagt                                         25

<210> SEQ ID NO 362
<211> LENGTH: 24
<212> TYPE: DNA
<213> ORGANISM: Artificial Sequence
<220> FEATURE:
<223> OTHER INFORMATION: SERPINB5 reverse primer

<400> SEQUENCE: 362
ataaaccacc gctacttcta ccca                                          24

<210> SEQ ID NO 363
<211> LENGTH: 27
<212> TYPE: DNA
<213> ORGANISM: Artificial Sequence
<220> FEATURE:
<223> OTHER INFORMATION: SERPINB5: Probe (5'-6-FAM; 3'-BHQ1)

<400> SEQUENCE: 363
cacgatcgcc tccacatcca aatcttt                                       27

<210> SEQ ID NO 364
<211> LENGTH: 18
<212> TYPE: DNA
<213> ORGANISM: Artificial Sequence
<220> FEATURE:
<223> OTHER INFORMATION: OPCML/HNT forward primer

<400> SEQUENCE: 364
cgtttcgagg cggtatcg                                                 18

<210> SEQ ID NO 365
<211> LENGTH: 20
<212> TYPE: DNA
<213> ORGANISM: Artificial Sequence

```
<220> FEATURE:
<223> OTHER INFORMATION: OPCML/HNT reverse primer

<400> SEQUENCE: 365
cgaaccgccg aaattatcat                                        20

<210> SEQ ID NO 366
<211> LENGTH: 29
<212> TYPE: DNA
<213> ORGANISM: Artificial Sequence
<220> FEATURE:
<223> OTHER INFORMATION: OPCML/HNT: Probe (5'-6-FAM; 3'-BHQ1)

<400> SEQUENCE: 366
aacaactcca tccctaaccg ccactttct                              29

<210> SEQ ID NO 367
<211> LENGTH: 22
<212> TYPE: DNA
<213> ORGANISM: Artificial Sequence
<220> FEATURE:
<223> OTHER INFORMATION: PAX8 forward primer

<400> SEQUENCE: 367
gttcgtagtt cgtcgagggt tc                                     22

<210> SEQ ID NO 368
<211> LENGTH: 25
<212> TYPE: DNA
<213> ORGANISM: Artificial Sequence
<220> FEATURE:
<223> OTHER INFORMATION: PAX8 reverse primer

<400> SEQUENCE: 368
cgcatctcat acccttctcc taaat                                  25

<210> SEQ ID NO 369
<211> LENGTH: 25
<212> TYPE: DNA
<213> ORGANISM: Artificial Sequence
<220> FEATURE:
<223> OTHER INFORMATION: PAX8: Probe (5'-6-FAM; 3'-BHQ1)

<400> SEQUENCE: 369
caaacgcgac ccgaacctac gaaaa                                  25

<210> SEQ ID NO 370
<211> LENGTH: 24
<212> TYPE: DNA
<213> ORGANISM: Artificial Sequence
<220> FEATURE:
<223> OTHER INFORMATION: TIFF1 forward primer

<400> SEQUENCE: 370
cgaaataaac cgaatcctcc ttaa                                   24

<210> SEQ ID NO 371
<211> LENGTH: 25
<212> TYPE: DNA
<213> ORGANISM: Artificial Sequence
<220> FEATURE:
<223> OTHER INFORMATION: TIFF1 reverse primer

<400> SEQUENCE: 371
tgttttgttg ttttagcgtt tacgt                                  25
```

```
<210> SEQ ID NO 372
<211> LENGTH: 26
<212> TYPE: DNA
<213> ORGANISM: Artificial Sequence
<220> FEATURE:
<223> OTHER INFORMATION: TIFF1: Probe (5'-6-FAM; 3'-BHQ1)

<400> SEQUENCE: 372
ctcgcgttta ttttaacccg acgcca                                   26

<210> SEQ ID NO 373
<211> LENGTH: 23
<212> TYPE: DNA
<213> ORGANISM: Artificial Sequence
<220> FEATURE:
<223> OTHER INFORMATION: PRKAR1A forward primer

<400> SEQUENCE: 373
cggatttgta gtagttgcgt tgc                                      23

<210> SEQ ID NO 374
<211> LENGTH: 21
<212> TYPE: DNA
<213> ORGANISM: Artificial Sequence
<220> FEATURE:
<223> OTHER INFORMATION: PRKAR1A reverse primer

<400> SEQUENCE: 374
accgaacaca aaatacgcga c                                        21

<210> SEQ ID NO 375
<211> LENGTH: 19
<212> TYPE: DNA
<213> ORGANISM: Artificial Sequence
<220> FEATURE:
<223> OTHER INFORMATION: PRKAR1A: Probe (5'-6-FAM; 3'-BHQ1)

<400> SEQUENCE: 375
catcccgacc atccgcccg                                           19

<210> SEQ ID NO 376
<211> LENGTH: 20
<212> TYPE: DNA
<213> ORGANISM: Artificial Sequence
<220> FEATURE:
<223> OTHER INFORMATION: TFAP2A forward primer

<400> SEQUENCE: 376 caccccata tacgcgctaa                                           20

<210> SEQ ID NO 377
<211> LENGTH: 24
<212> TYPE: DNA
<213> ORGANISM: Artificial Sequence
<220> FEATURE:
<223> OTHER INFORMATION: TFAP2A reverse primer

<400> SEQUENCE: 377
ggtcgttacg tttcgggtag ttta                                     24

<210> SEQ ID NO 378
<211> LENGTH: 23
<212> TYPE: DNA
<213> ORGANISM: Artificial Sequence
<220> FEATURE:
<223> OTHER INFORMATION: TFAP2A: Probe (5'-6-FAM; 3'-BHQ1)

<400> SEQUENCE: 378
```

```
cgcgctcaca cgctcaaaaa cct                                         23
```

<210> SEQ ID NO 379
<211> LENGTH: 19
<212> TYPE: DNA
<213> ORGANISM: Artificial Sequence
<220> FEATURE:
<223> OTHER INFORMATION: THRB forward primer

<400> SEQUENCE: 379

```
tcgtcgtcgt tatcgtcgc                                              19
```

<210> SEQ ID NO 380
<211> LENGTH: 24
<212> TYPE: DNA
<213> ORGANISM: Artificial Sequence
<220> FEATURE:
<223> OTHER INFORMATION: THRB reverse primer

<400> SEQUENCE: 380

```
gcgtctacga accgataacc taat                                        24
```

<210> SEQ ID NO 381
<211> LENGTH: 29
<212> TYPE: DNA
<213> ORGANISM: Artificial Sequence
<220> FEATURE:
<223> OTHER INFORMATION: THRB: Probe (5'-6-FAM; 3'-BHQ1)

<400> SEQUENCE: 381

```
ccctccaacc ctcacgacta tccgactta                                   29
```

<210> SEQ ID NO 382
<211> LENGTH: 19
<212> TYPE: DNA
<213> ORGANISM: Artificial Sequence
<220> FEATURE:
<223> OTHER INFORMATION: WDR79 forward primer

<400> SEQUENCE: 382

```
tttgttgtcg cgggatttc                                              19
```

<210> SEQ ID NO 383
<211> LENGTH: 19
<212> TYPE: DNA
<213> ORGANISM: Artificial Sequence
<220> FEATURE:
<223> OTHER INFORMATION: WDR79 reverse primer

<400> SEQUENCE: 383

```
cgaattccgt aaatcgccc                                              19
```

<210> SEQ ID NO 384
<211> LENGTH: 30
<212> TYPE: DNA
<213> ORGANISM: Artificial Sequence
<220> FEATURE:
<223> OTHER INFORMATION: WDR79: Probe (5'-6-FAM; 3'-BHQ1)

<400> SEQUENCE: 384

```
taatccgaaa tacgacgacc caatcgaaaa                                  30
```

<210> SEQ ID NO 385
<211> LENGTH: 22
<212> TYPE: DNA
<213> ORGANISM: Artificial Sequence

```
<220> FEATURE:
<223> OTHER INFORMATION: DLC1 forward primer

<400> SEQUENCE: 385
agtaaggatg cgttgaggat cg                                         22

<210> SEQ ID NO 386
<211> LENGTH: 19
<212> TYPE: DNA
<213> ORGANISM: Artificial Sequence
<220> FEATURE:
<223> OTHER INFORMATION: DLC1 reverse primer

<400> SEQUENCE: 386
acgactcgac ttccgcgtc                                             19

<210> SEQ ID NO 387
<211> LENGTH: 23
<212> TYPE: DNA
<213> ORGANISM: Artificial Sequence
<220> FEATURE:
<223> OTHER INFORMATION: DLC1: Probe (5'-6-FAM; 3'-BHQ1)

<400> SEQUENCE: 387
aacccacgac gacacccgaa acg                                        23

<210> SEQ ID NO 388
<211> LENGTH: 27
<212> TYPE: DNA
<213> ORGANISM: Artificial Sequence
<220> FEATURE:
<223> OTHER INFORMATION: LDLR forward primer

<400> SEQUENCE: 388
gatatcggtt ttttaattcg tgaagtt                                    27

<210> SEQ ID NO 389
<211> LENGTH: 22
<212> TYPE: DNA
<213> ORGANISM: Artificial Sequence
<220> FEATURE:
<223> OTHER INFORMATION: LDLR reverse primer

<400> SEQUENCE: 389
ttcaccgaaa acccaaatac aa                                         22

<210> SEQ ID NO 390
<211> LENGTH: 30
<212> TYPE: DNA
<213> ORGANISM: Artificial Sequence
<220> FEATURE:
<223> OTHER INFORMATION: LDLR: Probe (5'-6-FAM; 3'-BHQ1)

<400> SEQUENCE: 390
atcaaatcgc ctaccctaac gacactttcg                                 30

<210> SEQ ID NO 391
<211> LENGTH: 26
<212> TYPE: DNA
<213> ORGANISM: Artificial Sequence
<220> FEATURE:
<223> OTHER INFORMATION: SASH1 forward primer

<400> SEQUENCE: 391
tggaagagtt tattttgaag agaggg                                     26
```

```
<210> SEQ ID NO 392
<211> LENGTH: 24
<212> TYPE: DNA
<213> ORGANISM: Artificial Sequence
<220> FEATURE:
<223> OTHER INFORMATION: SASH1 reverse primer

<400> SEQUENCE: 392
gcgactcgtt ccttctaaca aatc                                          24

<210> SEQ ID NO 393
<211> LENGTH: 28
<212> TYPE: DNA
<213> ORGANISM: Artificial Sequence
<220> FEATURE:
<223> OTHER INFORMATION: SASH1: Probe (5'-6-FAM; 3'-BHQ1)

<400> SEQUENCE: 393
aaacccgaca aaataaccg cgaaacct                                       28

<210> SEQ ID NO 394
<211> LENGTH: 23
<212> TYPE: DNA
<213> ORGANISM: Artificial Sequence
<220> FEATURE:
<223> OTHER INFORMATION: GDNF forward primer

<400> SEQUENCE: 394
cggtagttgt cgttgagtcg ttc                                           23

<210> SEQ ID NO 395
<211> LENGTH: 23
<212> TYPE: DNA
<213> ORGANISM: Artificial Sequence
<220> FEATURE:
<223> OTHER INFORMATION: GDNF reverse primer

<400> SEQUENCE: 395
aacaaccgcc gctactttaa ata                                           23

<210> SEQ ID NO 396
<211> LENGTH: 24
<212> TYPE: DNA
<213> ORGANISM: Artificial Sequence
<220> FEATURE:
<223> OTHER INFORMATION: GDNF: Probe (5'-6-FAM; 3'-BHQ1)

<400> SEQUENCE: 396
cgcgcgtcgc gctcttaact aaaa                                          24

<210> SEQ ID NO 397
<211> LENGTH: 26
<212> TYPE: DNA
<213> ORGANISM: Artificial Sequence
<220> FEATURE:
<223> OTHER INFORMATION: CYP27B1 forward primer

<400> SEQUENCE: 397
gggatagtta gagagaacgg atgttt                                        26

<210> SEQ ID NO 398
<211> LENGTH: 20
<212> TYPE: DNA
<213> ORGANISM: Artificial Sequence
<220> FEATURE:
<223> OTHER INFORMATION: CYP27B1 reverse primer

<400> SEQUENCE: 398
```
ccgaatataa ccacaccgcc                                              20

<210> SEQ ID NO 399
<211> LENGTH: 30
<212> TYPE: DNA
<213> ORGANISM: Artificial Sequence
<220> FEATURE:
<223> OTHER INFORMATION: CYP27B1: Probe (5'-6-FAM; 3'-BHQ1)

<400> SEQUENCE: 399
ccaacctcaa ctcgcctttt ccttatttca                                   30

<210> SEQ ID NO 400
<211> LENGTH: 20
<212> TYPE: DNA
<213> ORGANISM: Artificial Sequence
<220> FEATURE:
<223> OTHER INFORMATION: LRRC41 forward primer

<400> SEQUENCE: 400
ttcggtttcg ggttttaacg                                              20

<210> SEQ ID NO 401
<211> LENGTH: 20
<212> TYPE: DNA
<213> ORGANISM: Artificial Sequence
<220> FEATURE:
<223> OTHER INFORMATION: LRRC41 reverse primer

<400> SEQUENCE: 401
cccatataaa cgctcaccgc                                              20

<210> SEQ ID NO 402
<211> LENGTH: 25
<212> TYPE: DNA
<213> ORGANISM: Artificial Sequence
<220> FEATURE:
<223> OTHER INFORMATION: LRRC41: Probe (5'-6-FAM; 3'-BHQ1)

<400> SEQUENCE: 402
cccgcacaac tcgaacaaaa cgaaa                                        25

<210> SEQ ID NO 403
<211> LENGTH: 28
<212> TYPE: DNA
<213> ORGANISM: Artificial Sequence
<220> FEATURE:
<223> OTHER INFORMATION: DLEC1 forward primer

<400> SEQUENCE: 403
tcgttgcgta tttaagatat ttcgtatt                                     28

<210> SEQ ID NO 404
<211> LENGTH: 22
<212> TYPE: DNA
<213> ORGANISM: Artificial Sequence
<220> FEATURE:
<223> OTHER INFORMATION: DLEC1 reverse primer

<400> SEQUENCE: 404
cgtaacgctc attctcgcta cc                                           22

<210> SEQ ID NO 405
<211> LENGTH: 29
<212> TYPE: DNA
<213> ORGANISM: Artificial Sequence

```
<220> FEATURE:
<223> OTHER INFORMATION: DLEC1: Probe (5'-6-FAM; 3'-BHQ1)

<400> SEQUENCE: 405
taatcaaact tacgctcact tcgtcgccg                                    29

<210> SEQ ID NO 406
<211> LENGTH: 17
<212> TYPE: DNA
<213> ORGANISM: Artificial Sequence
<220> FEATURE:
<223> OTHER INFORMATION: CDK2AP1 forward primer

<400> SEQUENCE: 406
cgcggaaagt ttgcggt                                                 17

<210> SEQ ID NO 407
<211> LENGTH: 24
<212> TYPE: DNA
<213> ORGANISM: Artificial Sequence
<220> FEATURE:
<223> OTHER INFORMATION: CDK2AP1 reverse primer

<400> SEQUENCE: 407
cgcacttttt attatcgacg actc                                         24

<210> SEQ ID NO 408
<211> LENGTH: 26
<212> TYPE: DNA
<213> ORGANISM: Artificial Sequence
<220> FEATURE:
<223> OTHER INFORMATION: CDK2AP1: Probe (5'-6-FAM; 3'-BHQ1)

<400> SEQUENCE: 408
cgacaaatat aaccgtccgc gcccta                                       26

<210> SEQ ID NO 409
<211> LENGTH: 24
<212> TYPE: DNA
<213> ORGANISM: Artificial Sequence
<220> FEATURE:
<223> OTHER INFORMATION: AXIN1 forward primer

<400> SEQUENCE: 409 cggttttgt agttgtttcg tgtt                                          24

<210> SEQ ID NO 410
<211> LENGTH: 20
<212> TYPE: DNA
<213> ORGANISM: Artificial Sequence
<220> FEATURE:
<223> OTHER INFORMATION: AXIN1 reverse primer

<400> SEQUENCE: 410
cgacgcgata accgcttaaa                                              20

<210> SEQ ID NO 411
<211> LENGTH: 24
<212> TYPE: DNA
<213> ORGANISM: Artificial Sequence
<220> FEATURE:
<223> OTHER INFORMATION: AXIN1: Probe (5'-6-FAM; 3'-BHQ1)

<400> SEQUENCE: 411
atccgaaacc tcgaacgcgt ctcg                                         24
```

```
<210> SEQ ID NO 412
<211> LENGTH: 19
<212> TYPE: DNA
<213> ORGANISM: Artificial Sequence
<220> FEATURE:
<223> OTHER INFORMATION: PYCARD forward primer

<400> SEQUENCE: 412
ttggagattt acggcgtcg                                                19

<210> SEQ ID NO 413
<211> LENGTH: 24
<212> TYPE: DNA
<213> ORGANISM: Artificial Sequence
<220> FEATURE:
<223> OTHER INFORMATION: PYCARD reverse primer

<400> SEQUENCE: 413
accctaatac gtaaccgcct acaa                                          24

<210> SEQ ID NO 414
<211> LENGTH: 27
<212> TYPE: DNA
<213> ORGANISM: Artificial Sequence
<220> FEATURE:
<223> OTHER INFORMATION: PYCARD: Probe (5'-6-FAM; 3'-BHQ1)

<400> SEQUENCE: 414
catctcctac aaacccatat cgcgcaa                                       27

<210> SEQ ID NO 415
<211> LENGTH: 22
<212> TYPE: DNA
<213> ORGANISM: Artificial Sequence
<220> FEATURE:
<223> OTHER INFORMATION: EBF3 forward primer

<400> SEQUENCE: 415
gtaggatatt gcgggatcgt tc                                            22

<210> SEQ ID NO 416
<211> LENGTH: 23
<212> TYPE: DNA
<213> ORGANISM: Artificial Sequence
<220> FEATURE:
<223> OTHER INFORMATION: EBF3 reverse primer

<400> SEQUENCE: 416
gcaacactca ctaccccgtt tat                                           23

<210> SEQ ID NO 417
<211> LENGTH: 26
<212> TYPE: DNA
<213> ORGANISM: Artificial Sequence
<220> FEATURE:
<223> OTHER INFORMATION: EBF3: Probe (5'-6-FAM; 3'-BHQ1)

<400> SEQUENCE: 417
tctttaaaac aaacgaaccg cgccaa                                        26

<210> SEQ ID NO 418
<211> LENGTH: 23
<212> TYPE: DNA
<213> ORGANISM: Artificial Sequence
<220> FEATURE:
<223> OTHER INFORMATION: PSAT1 forward primer

<400> SEQUENCE: 418
```

-continued tgggtttggt ttcgttaagt tgt                                      23

<210> SEQ ID NO 419
<211> LENGTH: 21
<212> TYPE: DNA
<213> ORGANISM: Artificial Sequence
<220> FEATURE:
<223> OTHER INFORMATION: PSAT reverse primer

<400> SEQUENCE: 419
acgtactccc gcctaaacct c                                        21

<210> SEQ ID NO 420
<211> LENGTH: 28
<212> TYPE: DNA
<213> ORGANISM: Artificial Sequence
<220> FEATURE:
<223> OTHER INFORMATION: PSAT: Probe (5'-6-FAM; 3'-BHQ1)

<400> SEQUENCE: 420
acgcccgctc gcgaaaactt actaaata                                 28

<210> SEQ ID NO 421
<211> LENGTH: 28
<212> TYPE: DNA
<213> ORGANISM: Artificial Sequence
<220> FEATURE:
<223> OTHER INFORMATION: ERBB2 forward primer

<400> SEQUENCE: 421
agtgtgagaa cggttgtagg taatttag                                 28

<210> SEQ ID NO 422
<211> LENGTH: 18
<212> TYPE: DNA
<213> ORGANISM: Artificial Sequence
<220> FEATURE:
<223> OTHER INFORMATION: ERBB2 reverse primer

<400> SEQUENCE: 422
ccctctcttc gcgcaaac                                            18

<210> SEQ ID NO 423
<211> LENGTH: 27
<212> TYPE: DNA
<213> ORGANISM: Artificial Sequence
<220> FEATURE:
<223> OTHER INFORMATION: ERBB2: Probe (5'-6-FAM; 3'-BHQ1)

<400> SEQUENCE: 423
aaatacgtcc ctcctaacgc cgaaacg                                  27

<210> SEQ ID NO 424
<211> LENGTH: 17
<212> TYPE: DNA
<213> ORGANISM: Artificial Sequence
<220> FEATURE:
<223> OTHER INFORMATION: PITX2 forward primer

<400> SEQUENCE: 424
agttcggttg cgcggtt                                             17

<210> SEQ ID NO 425
<211> LENGTH: 22
<212> TYPE: DNA
<213> ORGANISM: Artificial Sequence

```
<220> FEATURE:
<223> OTHER INFORMATION: PITX2 reverse primer

<400> SEQUENCE: 425
tacttccctc ccctacctcg tt                                            22

<210> SEQ ID NO 426
<211> LENGTH: 20
<212> TYPE: DNA
<213> ORGANISM: Artificial Sequence
<220> FEATURE:
<223> OTHER INFORMATION: PITX2: Probe (5'-6-FAM; 3'-BHQ1)

<400> SEQUENCE: 426
cgacgctcgc ccgaacgcta                                               20

<210> SEQ ID NO 427
<211> LENGTH: 25
<212> TYPE: DNA
<213> ORGANISM: Artificial Sequence
<220> FEATURE:
<223> OTHER INFORMATION: CGA forward primer

<400> SEQUENCE: 427
gggttttttg taggatgtgt ttagg                                         25

<210> SEQ ID NO 428
<211> LENGTH: 34
<212> TYPE: DNA
<213> ORGANISM: Artificial Sequence
<220> FEATURE:
<223> OTHER INFORMATION: CGA reverse primer

<400> SEQUENCE: 428
aactacaatt actaaaaact cataaaacga aact                               34

<210> SEQ ID NO 429
<211> LENGTH: 26
<212> TYPE: DNA
<213> ORGANISM: Artificial Sequence
<220> FEATURE:
<223> OTHER INFORMATION: CGA: Probe (5'-6-FAM; 3'-BHQ1)

<400> SEQUENCE: 429
tccctcttcg aatccacaat caaccg                                        26

<210> SEQ ID NO 430
<211> LENGTH: 20
<212> TYPE: DNA
<213> ORGANISM: Artificial Sequence
<220> FEATURE:
<223> OTHER INFORMATION: SYK forward primer

<400> SEQUENCE: 430
agggtcgttg ggtgtttgtg                                               20

<210> SEQ ID NO 431
<211> LENGTH: 21
<212> TYPE: DNA
<213> ORGANISM: Artificial Sequence
<220> FEATURE:
<223> OTHER INFORMATION: SYK reverse primer

<400> SEQUENCE: 431
aacataaacc gcatcgatcc c                                             21
```

```
<210> SEQ ID NO 432
<211> LENGTH: 31
<212> TYPE: DNA
<213> ORGANISM: Artificial Sequence
<220> FEATURE:
<223> OTHER INFORMATION: SYK: Probe (5'-6-FAM; 3'-BHQ1)

<400> SEQUENCE: 432
cgccaacgcg ataacttcta taactaccca a                              31

<210> SEQ ID NO 433
<211> LENGTH: 23
<212> TYPE: DNA
<213> ORGANISM: Artificial Sequence
<220> FEATURE:
<223> OTHER INFORMATION: ONECUT2 forward primer

<400> SEQUENCE: 433
acgggcgtta agcgtaatta ttt                                       23

<210> SEQ ID NO 434
<211> LENGTH: 25
<212> TYPE: DNA
<213> ORGANISM: Artificial Sequence
<220> FEATURE:
<223> OTHER INFORMATION: ONECUT2 reverse primer

<400> SEQUENCE: 434
ccacaaccac taataacttc ccgta                                     25

<210> SEQ ID NO 435
<211> LENGTH: 23
<212> TYPE: DNA
<213> ORGANISM: Artificial Sequence
<220> FEATURE:
<223> OTHER INFORMATION: ONECUT2: Probe (5'-6-FAM; 3'-BHQ1)

<400> SEQUENCE: 435
cccgcctccc gaaacaacta cga                                       23

<210> SEQ ID NO 436
<211> LENGTH: 22
<212> TYPE: DNA
<213> ORGANISM: Artificial Sequence
<220> FEATURE:
<223> OTHER INFORMATION: RB1 forward primer

<400> SEQUENCE: 436
ttagttcgcg tatcgattag cg                                        22

<210> SEQ ID NO 437
<211> LENGTH: 18
<212> TYPE: DNA
<213> ORGANISM: Artificial Sequence
<220> FEATURE:
<223> OTHER INFORMATION: RB1 reverse primer

<400> SEQUENCE: 437
actaaacgcc gcgtccaa                                             18

<210> SEQ ID NO 438
<211> LENGTH: 21
<212> TYPE: DNA
<213> ORGANISM: Artificial Sequence
<220> FEATURE:
<223> OTHER INFORMATION: RB1: Probe (5'-6-FAM; 3'-BHQ1)

<400> SEQUENCE: 438
```

```
tcacgtccgc gaaactcccg a                                              21

<210> SEQ ID NO 439
<211> LENGTH: 18
<212> TYPE: DNA
<213> ORGANISM: Artificial Sequence
<220> FEATURE:
<223> OTHER INFORMATION: TGFBR2 forward primer

<400> SEQUENCE: 439
gcgcggagcg tagttagg                                                  18

<210> SEQ ID NO 440
<211> LENGTH: 20
<212> TYPE: DNA
<213> ORGANISM: Artificial Sequence
<220> FEATURE:
<223> OTHER INFORMATION: TGFBR2 reverse primer

<400> SEQUENCE: 440
caaaccccgc tactcgtcat                                                20

<210> SEQ ID NO 441
<211> LENGTH: 21
<212> TYPE: DNA
<213> ORGANISM: Artificial Sequence
<220> FEATURE:
<223> OTHER INFORMATION: TGFBR1: Probe (5'-6-FAM; 3'-BHQ1)

<400> SEQUENCE: 441
cacgaacgac gccttcccga a                                              21

<210> SEQ ID NO 442
<211> LENGTH: 25
<212> TYPE: DNA
<213> ORGANISM: Artificial Sequence
<220> FEATURE:
<223> OTHER INFORMATION: THBS1 forward primer

<400> SEQUENCE: 442
gttttgagtt ggttttacgt tcgtt                                          25

<210> SEQ ID NO 443
<211> LENGTH: 18
<212> TYPE: DNA
<213> ORGANISM: Artificial Sequence
<220> FEATURE:
<223> OTHER INFORMATION: THBS1 reverse primer

<400> SEQUENCE: 443
cgacgcacca acctaccg                                                  18

<210> SEQ ID NO 444
<211> LENGTH: 19
<212> TYPE: DNA
<213> ORGANISM: Artificial Sequence
<220> FEATURE:
<223> OTHER INFORMATION: THBS1: Probe (5'-6-FAM; 3'-BHQ1)

<400> SEQUENCE: 444
acgccgcgct cacctccct                                                 19

<210> SEQ ID NO 445
<211> LENGTH: 19
<212> TYPE: DNA
<213> ORGANISM: Artificial Sequence
```

```
<220> FEATURE:
<223> OTHER INFORMATION: TYMS forward primer

<400> SEQUENCE: 445
cggcgttagg aaggacgat                                              19

<210> SEQ ID NO 446
<211> LENGTH: 24
<212> TYPE: DNA
<213> ORGANISM: Artificial Sequence
<220> FEATURE:
<223> OTHER INFORMATION: TYMS reverse primer

<400> SEQUENCE: 446
tctcaaacta taacgcgcct acat                                        24

<210> SEQ ID NO 447
<211> LENGTH: 29
<212> TYPE: DNA
<213> ORGANISM: Artificial Sequence
<220> FEATURE:
<223> OTHER INFORMATION: TYMS: Probe (5'-6-FAM; 3'-BHQ1)

<400> SEQUENCE: 447
ccgaataccg acaaaatacc gatacccgt                                   29

<210> SEQ ID NO 448
<211> LENGTH: 20
<212> TYPE: DNA
<213> ORGANISM: Artificial Sequence
<220> FEATURE:
<223> OTHER INFORMATION: GRIN2B forward primer

<400> SEQUENCE: 448
gtcggattta cgcgtcgagt                                             20

<210> SEQ ID NO 449
<211> LENGTH: 20
<212> TYPE: DNA
<213> ORGANISM: Artificial Sequence
<220> FEATURE:
<223> OTHER INFORMATION: GRIN2B reverse primer

<400> SEQUENCE: 449
ctaccgccgc gctaaaatac                                             20

<210> SEQ ID NO 450
<211> LENGTH: 29
<212> TYPE: DNA
<213> ORGANISM: Artificial Sequence
<220> FEATURE:
<223> OTHER INFORMATION: GRIN2B: Probe (5'-6-FAM; 3'-BHQ1)

<400> SEQUENCE: 450
acgcacgaaa cttcacctac aacgtatcg                                   29

<210> SEQ ID NO 451
<211> LENGTH: 27
<212> TYPE: DNA
<213> ORGANISM: Artificial Sequence
<220> FEATURE:
<223> OTHER INFORMATION: NTF3 forward primer

<400> SEQUENCE: 451
tttcgttttt gtattttatg gaggatt                                     27
```

```
<210> SEQ ID NO 452
<211> LENGTH: 20
<212> TYPE: DNA
<213> ORGANISM: Artificial Sequence
<220> FEATURE:
<223> OTHER INFORMATION: NTF3 reverse primer

<400> SEQUENCE: 452
ccgtttccgc cgtaatattc                                              20

<210> SEQ ID NO 453
<211> LENGTH: 23
<212> TYPE: DNA
<213> ORGANISM: Artificial Sequence
<220> FEATURE:
<223> OTHER INFORMATION: NTF3: Probe (5'-6-FAM; 3'-BHQ1)

<400> SEQUENCE: 453
tcgccaccac gaaactaccc acg                                          23

<210> SEQ ID NO 454
<211> LENGTH: 21
<212> TYPE: DNA
<213> ORGANISM: Artificial Sequence
<220> FEATURE:
<223> OTHER INFORMATION: DRD2 forward primer

<400> SEQUENCE: 454
gaagtcggaa attttggtcg c                                            21

<210> SEQ ID NO 455
<211> LENGTH: 22
<212> TYPE: DNA
<213> ORGANISM: Artificial Sequence
<220> FEATURE:
<223> OTHER INFORMATION: DRD2 reverse primer

<400> SEQUENCE: 455
atctcgaaaa aacacttccc cc                                           22

<210> SEQ ID NO 456
<211> LENGTH: 25
<212> TYPE: DNA
<213> ORGANISM: Artificial Sequence
<220> FEATURE:
<223> OTHER INFORMATION: DRD2: Probe (5'-6-FAM; 3'-BHQ1)

<400> SEQUENCE: 456
acacccaaac gcgaaacccg aaact                                        25

<210> SEQ ID NO 457
<211> LENGTH: 16
<212> TYPE: DNA
<213> ORGANISM: Artificial Sequence
<220> FEATURE:
<223> OTHER INFORMATION: GABRA2 forward primer

<400> SEQUENCE: 457
tcgtcggagg agcgga                                                  16

<210> SEQ ID NO 458
<211> LENGTH: 21
<212> TYPE: DNA
<213> ORGANISM: Artificial Sequence
<220> FEATURE:
<223> OTHER INFORMATION: GABRA2 reverse primer

<400> SEQUENCE: 458
```
aacctctcga aaaccccaac a				21

<210> SEQ ID NO 459
<211> LENGTH: 29
<212> TYPE: DNA
<213> ORGANISM: Artificial Sequence
<220> FEATURE:
<223> OTHER INFORMATION: GABRA2: Probe (5'-6-FAM; 3'-BHQ1)

<400> SEQUENCE: 459
acgacctcga aaacaaccc gaaactacg				29

<210> SEQ ID NO 460
<211> LENGTH: 20
<212> TYPE: DNA
<213> ORGANISM: Artificial Sequence
<220> FEATURE:
<223> OTHER INFORMATION: GAD1 forward primer

<400> SEQUENCE: 460
cgattggttc ggcgtagaaa				20

<210> SEQ ID NO 461
<211> LENGTH: 21
<212> TYPE: DNA
<213> ORGANISM: Artificial Sequence
<220> FEATURE:
<223> OTHER INFORMATION: GAD1 reverse primer

<400> SEQUENCE: 461
ccctccgata tacaaaaccc c				21

<210> SEQ ID NO 462
<211> LENGTH: 28
<212> TYPE: DNA
<213> ORGANISM: Artificial Sequence
<220> FEATURE:
<223> OTHER INFORMATION: GAD1: Probe (5'-6-FAM; 3'-BHQ1)

<400> SEQUENCE: 462
cccgcacaac tctcgcttct ctttacaa				28

<210> SEQ ID NO 463
<211> LENGTH: 23
<212> TYPE: DNA
<213> ORGANISM: Artificial Sequence
<220> FEATURE:
<223> OTHER INFORMATION: BDNF forward primer

<400> SEQUENCE: 463
cgtatcgggt tggttttttt gtt				23

<210> SEQ ID NO 464
<211> LENGTH: 16
<212> TYPE: DNA
<213> ORGANISM: Artificial Sequence
<220> FEATURE:
<223> OTHER INFORMATION: BDNF reverse primer

<400> SEQUENCE: 464
cgcccgctcg ctatcc				16

<210> SEQ ID NO 465
<211> LENGTH: 22
<212> TYPE: DNA
<213> ORGANISM: Artificial Sequence

```
<220> FEATURE:
<223> OTHER INFORMATION: BDNF: Probe (5'-6-FAM; 3'-BHQ1)

<400> SEQUENCE: 465
ccgtaacgcc tcgaactccc ga                                          22

<210> SEQ ID NO 466
<211> LENGTH: 19
<212> TYPE: DNA
<213> ORGANISM: Artificial Sequence
<220> FEATURE:
<223> OTHER INFORMATION: NEUROD1 forward primer

<400> SEQUENCE: 466
gttttttgcg tgggcgaat                                              19

<210> SEQ ID NO 467
<211> LENGTH: 24
<212> TYPE: DNA
<213> ORGANISM: Artificial Sequence
<220> FEATURE:
<223> OTHER INFORMATION: NEUROD1 reverse primer

<400> SEQUENCE: 467
ccgcgcttaa catcactaac taaa                                        24

<210> SEQ ID NO 468
<211> LENGTH: 20
<212> TYPE: DNA
<213> ORGANISM: Artificial Sequence
<220> FEATURE:
<223> OTHER INFORMATION: NEUROD1: Probe (5'-6-FAM; 3'-BHQ1)

<400> SEQUENCE: 468
cgcgcgacca cgacacgaaa                                             20

<210> SEQ ID NO 469
<211> LENGTH: 27
<212> TYPE: DNA
<213> ORGANISM: Artificial Sequence
<220> FEATURE:
<223> OTHER INFORMATION: NEUROD2 forward primer

<400> SEQUENCE: 469
ggtttggtat agaggttggt atttcgt                                     27

<210> SEQ ID NO 470
<211> LENGTH: 18
<212> TYPE: DNA
<213> ORGANISM: Artificial Sequence
<220> FEATURE:
<223> OTHER INFORMATION: NEUROD2 reverse primer

<400> SEQUENCE: 470
acgaacgccg acgtcttc                                               18

<210> SEQ ID NO 471
<211> LENGTH: 28
<212> TYPE: DNA
<213> ORGANISM: Artificial Sequence
<220> FEATURE:
<223> OTHER INFORMATION: NEUROD2: Probe (5'-6-FAM; 3'-BHQ1)

<400> SEQUENCE: 471
cgccatacga accgcgaaac gaatataa                                    28
```

```
<210> SEQ ID NO 472
<211> LENGTH: 23
<212> TYPE: DNA
<213> ORGANISM: Artificial Sequence
<220> FEATURE:
<223> OTHER INFORMATION: NEUROG1 forward primer

<400> SEQUENCE: 472
cgtgtagcgt tcgggtattt gta                                               23

<210> SEQ ID NO 473
<211> LENGTH: 25
<212> TYPE: DNA
<213> ORGANISM: Artificial Sequence
<220> FEATURE:
<223> OTHER INFORMATION: NEUROG1 reverse primer

<400> SEQUENCE: 473
cgataattac gaacacactc cgaat                                             25

<210> SEQ ID NO 474
<211> LENGTH: 26
<212> TYPE: DNA
<213> ORGANISM: Artificial Sequence
<220> FEATURE:
<223> OTHER INFORMATION: NEUROG1: Probe (5'-6-FAM; 3'-BHQ1)

<400> SEQUENCE: 474
cgataacgac ctcccgcgaa cataaa                                            26

<210> SEQ ID NO 475
<211> LENGTH: 21
<212> TYPE: DNA
<213> ORGANISM: Artificial Sequence
<220> FEATURE:
<223> OTHER INFORMATION: PSEN1 forward primer

<400> SEQUENCE: 475
gtcgggtgga gagagatttc g                                                 21

<210> SEQ ID NO 476
<211> LENGTH: 22
<212> TYPE: DNA
<213> ORGANISM: Artificial Sequence
<220> FEATURE:
<223> OTHER INFORMATION: PSEN1 reverse primer

<400> SEQUENCE: 476
aacacctacg ccctaaaacg tc                                                22

<210> SEQ ID NO 477
<211> LENGTH: 30
<212> TYPE: DNA
<213> ORGANISM: Artificial Sequence
<220> FEATURE:
<223> OTHER INFORMATION: PSEN1: Probe (5'-6-FAM; 3'-BHQ1)

<400> SEQUENCE: 477
tcgaacaaac aacatttccg aaccaaaact                                        30

<210> SEQ ID NO 478
<211> LENGTH: 19
<212> TYPE: DNA
<213> ORGANISM: Artificial Sequence
<220> FEATURE:
<223> OTHER INFORMATION: PSEN2 forward primer

<400> SEQUENCE: 478
```

```
gaggcgtgta gtaggcggg                                              19
```

<210> SEQ ID NO 479
<211> LENGTH: 26
<212> TYPE: DNA
<213> ORGANISM: Artificial Sequence
<220> FEATURE:
<223> OTHER INFORMATION: PSEN2 reverse primer

<400> SEQUENCE: 479

```
ccgatactaa aaaccgaata aactcg                                      26
```

<210> SEQ ID NO 480
<211> LENGTH: 26
<212> TYPE: DNA
<213> ORGANISM: Artificial Sequence
<220> FEATURE:
<223> OTHER INFORMATION: PSEN2: Probe (5'-6-FAM; 3'-BHQ1)

<400> SEQUENCE: 480

```
cgcaacgaaa atctccgacg aaaaaa                                      26
```

<210> SEQ ID NO 481
<211> LENGTH: 24
<212> TYPE: DNA
<213> ORGANISM: Artificial Sequence
<220> FEATURE:
<223> OTHER INFORMATION: APP forward primer

<400> SEQUENCE: 481

```
aacgaaatgc ggataaaaac gtat                                        24
```

<210> SEQ ID NO 482
<211> LENGTH: 24
<212> TYPE: DNA
<213> ORGANISM: Artificial Sequence
<220> FEATURE:
<223> OTHER INFORMATION: APP reverse primer

<400> SEQUENCE: 482

```
tcgtccccgt aaacttaaat catc                                        24
```

<210> SEQ ID NO 483
<211> LENGTH: 30
<212> TYPE: DNA
<213> ORGANISM: Artificial Sequence
<220> FEATURE:
<223> OTHER INFORMATION: APP: Probe (5'-6-FAM; 3'-BHQ1)

<400> SEQUENCE: 483

```
cccgcaaacc tcccgaaaat atcgtataaa                                  30
```

<210> SEQ ID NO 484
<211> LENGTH: 23
<212> TYPE: DNA
<213> ORGANISM: Artificial Sequence
<220> FEATURE:
<223> OTHER INFORMATION: HOXA1 forward primer

<400> SEQUENCE: 484

```
ttgtttatta ggaagcggtc gtc                                         23
```

<210> SEQ ID NO 485
<211> LENGTH: 26
<212> TYPE: DNA
<213> ORGANISM: Artificial Sequence

```
<220> FEATURE:
<223> OTHER INFORMATION: HOXA1 reverse primer

<400> SEQUENCE: 485
tcgaaccata aaattacaac tttcca                                              26

<210> SEQ ID NO 486
<211> LENGTH: 26
<212> TYPE: DNA
<213> ORGANISM: Artificial Sequence
<220> FEATURE:
<223> OTHER INFORMATION: HOXA1: Probe (5'-6-FAM; 3'-BHQ1)

<400> SEQUENCE: 486
tcgtacgcga tcaacgccaa caatta                                              26

<210> SEQ ID NO 487
<211> LENGTH: 26
<212> TYPE: DNA
<213> ORGANISM: Artificial Sequence
<220> FEATURE:
<223> OTHER INFORMATION: HOXA10 forward primer

<400> SEQUENCE: 487
tgtattgatg ggttaggaga cgtatt                                              26

<210> SEQ ID NO 488
<211> LENGTH: 21
<212> TYPE: DNA
<213> ORGANISM: Artificial Sequence
<220> FEATURE:
<223> OTHER INFORMATION: HOXA10 reverse primer

<400> SEQUENCE: 488
cccaccaacc acgttaaaac a                                                   21

<210> SEQ ID NO 489
<211> LENGTH: 29
<212> TYPE: DNA
<213> ORGANISM: Artificial Sequence
<220> FEATURE:
<223> OTHER INFORMATION: HOXA10: Probe (5'-6-FAM; 3'-BHQ1)

<400> SEQUENCE: 489
caactcccga ccttcgaacc aaaatatcg                                           29

<210> SEQ ID NO 490
<211> LENGTH: 21
<212> TYPE: DNA
<213> ORGANISM: Artificial Sequence
<220> FEATURE:
<223> OTHER INFORMATION: TMEFF2 forward primer

<400> SEQUENCE: 490
cgacgaggag gtgtaaggat g                                                   21

<210> SEQ ID NO 491
<211> LENGTH: 20
<212> TYPE: DNA
<213> ORGANISM: Artificial Sequence
<220> FEATURE:
<223> OTHER INFORMATION: TMEFF2 reverse primer

<400> SEQUENCE: 491
caacgcctaa cgaacgaacc                                                     20
```

```
<210> SEQ ID NO 492
<211> LENGTH: 26
<212> TYPE: DNA
<213> ORGANISM: Artificial Sequence
<220> FEATURE:
<223> OTHER INFORMATION: TMEFF2: Probe (5'-6-FAM; 3'-BHQ1)

<400> SEQUENCE: 492
tataacttcc gcgaccgcct cctcct                                        26

<210> SEQ ID NO 493
<211> LENGTH: 23
<212> TYPE: DNA
<213> ORGANISM: Artificial Sequence
<220> FEATURE:
<223> OTHER INFORMATION: SMAD2 forward primer

<400> SEQUENCE: 493
cgaggcggta ggtttttata ggt                                           23

<210> SEQ ID NO 494
<211> LENGTH: 21
<212> TYPE: DNA
<213> ORGANISM: Artificial Sequence
<220> FEATURE:
<223> OTHER INFORMATION: SMAD2 reverse primer

<400> SEQUENCE: 494
cgcattaaaa cgattcccga t                                             21

<210> SEQ ID NO 495
<211> LENGTH: 23
<212> TYPE: DNA
<213> ORGANISM: Artificial Sequence
<220> FEATURE:
<223> OTHER INFORMATION: SMAD2: Probe (5'-6-FAM; 3'-BHQ1)

<400> SEQUENCE: 495
ccgatccctc gccaacgtcg taa                                           23

<210> SEQ ID NO 496
<211> LENGTH: 28
<212> TYPE: DNA
<213> ORGANISM: Artificial Sequence
<220> FEATURE:
<223> OTHER INFORMATION: SMAD6 forward primer

<400> SEQUENCE: 496
atgttagttt agatattttg gcggtttc                                      28

<210> SEQ ID NO 497
<211> LENGTH: 27
<212> TYPE: DNA
<213> ORGANISM: Artificial Sequence
<220> FEATURE:
<223> OTHER INFORMATION: SMAD6 reverse primer

<400> SEQUENCE: 497
cgaccctaca ataaaacgta ttctcct                                       27

<210> SEQ ID NO 498
<211> LENGTH: 29
<212> TYPE: DNA
<213> ORGANISM: Artificial Sequence
<220> FEATURE:
<223> OTHER INFORMATION: SMAD6: Probe (5'-6-FAM; 3'-BHQ1)

<400> SEQUENCE: 498
```

-continued aaaccttatt tacgcaacaa tcaacgccg 29

<210> SEQ ID NO 499
<211> LENGTH: 24
<212> TYPE: DNA
<213> ORGANISM: Artificial Sequence
<220> FEATURE:
<223> OTHER INFORMATION: SFRP2 HB-280 forward primer

<400> SEQUENCE: 499
gcgttttagt cgtcggttgt tagt 24

<210> SEQ ID NO 500
<211> LENGTH: 24
<212> TYPE: DNA
<213> ORGANISM: Artificial Sequence
<220> FEATURE:
<223> OTHER INFORMATION: SFRP2 HB-280 reverse primer

<400> SEQUENCE: 500
aaacgaccga aattcgaact tatc 24

<210> SEQ ID NO 501
<211> LENGTH: 27
<212> TYPE: DNA
<213> ORGANISM: Artificial Sequence
<220> FEATURE:
<223> OTHER INFORMATION: SFRP2 HB-280: Probe (5'-6-FAM; 3'-BHQ1)

<400> SEQUENCE: 501
cgaacccgct ctcttcgcta aatacga 27

<210> SEQ ID NO 502
<211> LENGTH: 17
<212> TYPE: DNA
<213> ORGANISM: Artificial Sequence
<220> FEATURE:
<223> OTHER INFORMATION: SFRP4 HB-281 forward primer

<400> SEQUENCE: 502
gttgttcggg cgggttc 17

<210> SEQ ID NO 503
<211> LENGTH: 18
<212> TYPE: DNA
<213> ORGANISM: Artificial Sequence
<220> FEATURE:
<223> OTHER INFORMATION: SFRP4 HB-281 reverse primer

<400> SEQUENCE: 503
gcgaaactcc gccgtcta 18

<210> SEQ ID NO 504
<211> LENGTH: 28
<212> TYPE: DNA
<213> ORGANISM: Artificial Sequence
<220> FEATURE:
<223> OTHER INFORMATION: SFRP4 HB-281: Probe (5'-6-FAM; 3'-BHQ1)

<400> SEQUENCE: 504
aaacacgaac aacgccaact ctcaacct 28

<210> SEQ ID NO 505
<211> LENGTH: 26
<212> TYPE: DNA
<213> ORGANISM: Artificial Sequence

```
-continued

<220> FEATURE:
<223> OTHER INFORMATION: SFRP5 HB-282 forward primer

<400> SEQUENCE: 505
gcgtttgtag tttatcgtgt ggtaga                                        26

<210> SEQ ID NO 506
<211> LENGTH: 19
<212> TYPE: DNA
<213> ORGANISM: Artificial Sequence
<220> FEATURE:
<223> OTHER INFORMATION: SFRP5 HB-282 reverse primer

<400> SEQUENCE: 506
gaaccgctac acgaccgct                                                19

<210> SEQ ID NO 507
<211> LENGTH: 27
<212> TYPE: DNA
<213> ORGANISM: Artificial Sequence
<220> FEATURE:
<223> OTHER INFORMATION: SFRP5 HB-282: Probe (5'-6-FAM; 3'-BHQ1)

<400> SEQUENCE: 507
cgccgcaata ccttaacatc cctaccg                                       27

<210> SEQ ID NO 508
<211> LENGTH: 20
<212> TYPE: DNA
<213> ORGANISM: Artificial Sequence
<220> FEATURE:
<223> OTHER INFORMATION: FAF1 forward primer

<400> SEQUENCE: 508
cgttttgcgg ttttacgtga                                               20

<210> SEQ ID NO 509
<211> LENGTH: 22
<212> TYPE: DNA
<213> ORGANISM: Artificial Sequence
<220> FEATURE:
<223> OTHER INFORMATION: FAF1 reverse primer

<400> SEQUENCE: 509
caacgcaaaa atcctaaccg aa                                            22

<210> SEQ ID NO 510
<211> LENGTH: 28
<212> TYPE: DNA
<213> ORGANISM: Artificial Sequence
<220> FEATURE:
<223> OTHER INFORMATION: FAF1: Probe (5'-6-FAM; 3'-BHQ1)

<400> SEQUENCE: 510
cgcgcgctca acgcttaaca aaaaaata                                      28

<210> SEQ ID NO 511
<211> LENGTH: 26
<212> TYPE: DNA
<213> ORGANISM: Artificial Sequence
<220> FEATURE:
<223> OTHER INFORMATION: TNFRSF10A forward primer

<400> SEQUENCE: 511
agtttttggt atttagtagg cgttcg                                        26
```

```
<210> SEQ ID NO 512
<211> LENGTH: 25
<212> TYPE: DNA
<213> ORGANISM: Artificial Sequence
<220> FEATURE:
<223> OTHER INFORMATION: TNFRSF10A reverse primer

<400> SEQUENCE: 512 caaacccgc aataacctct atatc                                    25

<210> SEQ ID NO 513
<211> LENGTH: 21
<212> TYPE: DNA
<213> ORGANISM: Artificial Sequence
<220> FEATURE:
<223> OTHER INFORMATION: TNFRSF10A: Probe (5'-6-FAM; 3'-BHQ1)

<400> SEQUENCE: 513
attccgccac ccatccgtcc a                                       21

<210> SEQ ID NO 514
<211> LENGTH: 18
<212> TYPE: DNA
<213> ORGANISM: Artificial Sequence
<220> FEATURE:
<223> OTHER INFORMATION: TNFRSF10B forward primer

<400> SEQUENCE: 514
ttttggcggt tgcgtttc                                           18

<210> SEQ ID NO 515
<211> LENGTH: 22
<212> TYPE: DNA
<213> ORGANISM: Artificial Sequence
<220> FEATURE:
<223> OTHER INFORMATION: TNFRSF10B reverse primer

<400> SEQUENCE: 515
ctcatttccc ccaaatttcg at                                      22

<210> SEQ ID NO 516
<211> LENGTH: 29
<212> TYPE: DNA
<213> ORGANISM: Artificial Sequence
<220> FEATURE:
<223> OTHER INFORMATION: TNFRSF10B: Probe (5'-6-FAM; 3'-BHQ1)

<400> SEQUENCE: 516
atcctaacgc gaacaaaacc caaaaacaa                               29

<210> SEQ ID NO 517
<211> LENGTH: 19
<212> TYPE: DNA
<213> ORGANISM: Artificial Sequence
<220> FEATURE:
<223> OTHER INFORMATION: TNFRSF10C forward primer

<400> SEQUENCE: 517
gggaagagcg tatttggcg                                          19

<210> SEQ ID NO 518
<211> LENGTH: 19
<212> TYPE: DNA
<213> ORGANISM: Artificial Sequence
<220> FEATURE:
<223> OTHER INFORMATION: TNFRSF10C reverse primer

<400> SEQUENCE: 518
```

```
tccccctaact ccgacgacg                                              19
```

<210> SEQ ID NO 519
<211> LENGTH: 26
<212> TYPE: DNA
<213> ORGANISM: Artificial Sequence
<220> FEATURE:
<223> OTHER INFORMATION: TNFRSF10C: Probe (5'-6-FAM; 3'-BHQ1)

<400> SEQUENCE: 519

```
cgaacatacc cgaccgcaaa taacca                                       26
```

<210> SEQ ID NO 520
<211> LENGTH: 19
<212> TYPE: DNA
<213> ORGANISM: Artificial Sequence
<220> FEATURE:
<223> OTHER INFORMATION: TNFRS10D forward primer

<400> SEQUENCE: 520

```
gggaagagcg tatttggcg                                               19
```

<210> SEQ ID NO 521
<211> LENGTH: 19
<212> TYPE: DNA
<213> ORGANISM: Artificial Sequence
<220> FEATURE:
<223> OTHER INFORMATION: TNFRS10D reverse primer

<400> SEQUENCE: 521

```
tccccctaact ccgacgacg                                              19
```

<210> SEQ ID NO 522
<211> LENGTH: 21
<212> TYPE: DNA
<213> ORGANISM: Artificial Sequence
<220> FEATURE:
<223> OTHER INFORMATION: TNFRS10D: Probe (5'-6-FAM; 3'-BHQ1)

<400> SEQUENCE: 522

```
tacccgaccg caaacgaccc g                                            21
```

<210> SEQ ID NO 523
<211> LENGTH: 28
<212> TYPE: DNA
<213> ORGANISM: Artificial Sequence
<220> FEATURE:
<223> OTHER INFORMATION: IFNG forward primer

<400> SEQUENCE: 523

```
tgaagagtta atattttatt agggcgaa                                     28
```

<210> SEQ ID NO 524
<211> LENGTH: 29
<212> TYPE: DNA
<213> ORGANISM: Artificial Sequence
<220> FEATURE:
<223> OTHER INFORMATION: IFNG reverse primer

<400> SEQUENCE: 524

```
ttcctttaaa ctccttaaat cctttaacg                                    29
```

<210> SEQ ID NO 525
<211> LENGTH: 22
<212> TYPE: DNA
<213> ORGANISM: Artificial Sequence

```
<220> FEATURE:
<223> OTHER INFORMATION: IFNG: Probe (5'-6-FAM; 3'-MGBHFQ)

<400> SEQUENCE: 525
acaaacccat tatacccacc ta                                                22

<210> SEQ ID NO 526
<211> LENGTH: 25
<212> TYPE: DNA
<213> ORGANISM: Artificial Sequence
<220> FEATURE:
<223> OTHER INFORMATION: SMAD9 forward primer

<400> SEQUENCE: 526
cgcgaagttt tatcgttcgt attag                                             25

<210> SEQ ID NO 527
<211> LENGTH: 19
<212> TYPE: DNA
<213> ORGANISM: Artificial Sequence
<220> FEATURE:
<223> OTHER INFORMATION: SMAD9 reverse primer

<400> SEQUENCE: 527
cgaaaacgaa ccgcaaaca                                                    19

<210> SEQ ID NO 528
<211> LENGTH: 28
<212> TYPE: DNA
<213> ORGANISM: Artificial Sequence
<220> FEATURE:
<223> OTHER INFORMATION: SMAD9: Probe (5'-6-FAM; 3'-BHQ1)

<400> SEQUENCE: 528
aactccctaa ccgctttcca aatcgacg                                          28

<210> SEQ ID NO 529
<211> LENGTH: 20
<212> TYPE: DNA
<213> ORGANISM: Artificial Sequence
<220> FEATURE:
<223> OTHER INFORMATION: IGF2 forward primer

<400> SEQUENCE: 529
gagcggtttc ggtgtcgtta                                                   20

<210> SEQ ID NO 530
<211> LENGTH: 21
<212> TYPE: DNA
<213> ORGANISM: Artificial Sequence
<220> FEATURE:
<223> OTHER INFORMATION: IGF2 reverse primer

<400> SEQUENCE: 530
ccaactcgat ttaaaccgac g                                                 21

<210> SEQ ID NO 531
<211> LENGTH: 22
<212> TYPE: DNA
<213> ORGANISM: Artificial Sequence
<220> FEATURE:
<223> OTHER INFORMATION: IGF2: Probe (5'-6-FAM; 3'-BHQ1)

<400> SEQUENCE: 531
ccctctaccg tcgcgaaccc ga                                                22
```

```
<210> SEQ ID NO 532
<211> LENGTH: 17
<212> TYPE: DNA
<213> ORGANISM: Artificial Sequence
<220> FEATURE:
<223> OTHER INFORMATION: ITGA4 forward primer

<400> SEQUENCE: 532
tgcggaggcg tagggtc                                                    17

<210> SEQ ID NO 533
<211> LENGTH: 19
<212> TYPE: DNA
<213> ORGANISM: Artificial Sequence
<220> FEATURE:
<223> OTHER INFORMATION: ITGA4 reverse primer

<400> SEQUENCE: 533
caaccgaaat tccccaacg                                                  19

<210> SEQ ID NO 534
<211> LENGTH: 26
<212> TYPE: DNA
<213> ORGANISM: Artificial Sequence
<220> FEATURE:
<223> OTHER INFORMATION: ITGA4: Probe (5'-6-FAM; 3'-BHQ1)

<400> SEQUENCE: 534
cctacaaccg cgcgtaaaca aaaacg                                          26

<210> SEQ ID NO 535
<211> LENGTH: 17
<212> TYPE: DNA
<213> ORGANISM: Artificial Sequence
<220> FEATURE:
<223> OTHER INFORMATION: RARRES1 forward primer

<400> SEQUENCE: 535
ggcgagtcgg atcggaa                                                    17

<210> SEQ ID NO 536
<211> LENGTH: 22
<212> TYPE: DNA
<213> ORGANISM: Artificial Sequence
<220> FEATURE:
<223> OTHER INFORMATION: RARRES1 reverse primer

<400> SEQUENCE: 536
cgcaaactcc tacaacaaac ga                                              22

<210> SEQ ID NO 537
<211> LENGTH: 23
<212> TYPE: DNA
<213> ORGANISM: Artificial Sequence
<220> FEATURE:
<223> OTHER INFORMATION: RARRES1: Probe (5'-6-FAM; 3'-BHQ1)

<400> SEQUENCE: 537
cgcgcgacgc ttcacttctt caa                                             23

<210> SEQ ID NO 538
<211> LENGTH: 21
<212> TYPE: DNA
<213> ORGANISM: Artificial Sequence
<220> FEATURE:
<223> OTHER INFORMATION: GATA4 forward primer

<400> SEQUENCE: 538
```

```
gatggtggtc gcgtgaagtt a                                              21

<210> SEQ ID NO 539
<211> LENGTH: 23
<212> TYPE: DNA
<213> ORGANISM: Artificial Sequence
<220> FEATURE:
<223> OTHER INFORMATION: GATA4 reverse primer

<400> SEQUENCE: 539
ttccctccat atacgaacta ccg                                            23

<210> SEQ ID NO 540
<211> LENGTH: 24
<212> TYPE: DNA
<213> ORGANISM: Artificial Sequence
<220> FEATURE:
<223> OTHER INFORMATION: GATA4: Probe (5'-6-FAM; 3'-BHQ1)

<400> SEQUENCE: 540
cctatcccga atccgtcaat cccg                                           24

<210> SEQ ID NO 541
<211> LENGTH: 27
<212> TYPE: DNA
<213> ORGANISM: Artificial Sequence
<220> FEATURE:
<223> OTHER INFORMATION: GATA5 forward primer

<400> SEQUENCE: 541
agttacgtga ttttggtagg ttttgtt                                        27

<210> SEQ ID NO 542
<211> LENGTH: 19
<212> TYPE: DNA
<213> ORGANISM: Artificial Sequence
<220> FEATURE:
<223> OTHER INFORMATION: GATA5 reverse primer

<400> SEQUENCE: 542
taatccgaac tccgcgcta                                                 19

<210> SEQ ID NO 543
<211> LENGTH: 27
<212> TYPE: DNA
<213> ORGANISM: Artificial Sequence
<220> FEATURE:
<223> OTHER INFORMATION: GATA5: Probe (5'-6-FAM; 3'-BHQ1)

<400> SEQUENCE: 543
cccgtatcgt acgtccttat cgccaaa                                        27

<210> SEQ ID NO 544
<211> LENGTH: 20
<212> TYPE: DNA
<213> ORGANISM: Artificial Sequence
<220> FEATURE:
<223> OTHER INFORMATION: GATA3 forward primer

<400> SEQUENCE: 544
tgtatcggga cggaatcgtt                                                20

<210> SEQ ID NO 545
<211> LENGTH: 18
<212> TYPE: DNA
<213> ORGANISM: Artificial Sequence
```

```
<220> FEATURE:
<223> OTHER INFORMATION: GATA3 reverse primer

<400> SEQUENCE: 545
acgcgcgctc taaccctt                                              18

<210> SEQ ID NO 546
<211> LENGTH: 32
<212> TYPE: DNA
<213> ORGANISM: Artificial Sequence
<220> FEATURE:
<223> OTHER INFORMATION: GATA3: Probe (5'-6-FAM; 3'-BHQ1)

<400> SEQUENCE: 546
aaatataacc gcgactccta ccaattcatt cg                              32

<210> SEQ ID NO 547
<211> LENGTH: 20
<212> TYPE: DNA
<213> ORGANISM: Artificial Sequence
<220> FEATURE:
<223> OTHER INFORMATION: CDKN1C forward primer

<400> SEQUENCE: 547
tcgagtaggg cgcgaattag                                            20

<210> SEQ ID NO 548
<211> LENGTH: 18
<212> TYPE: DNA
<213> ORGANISM: Artificial Sequence
<220> FEATURE:
<223> OTHER INFORMATION: CDKN1C reverse primer

<400> SEQUENCE: 548
gtcccgaaat ccccgaat                                              18

<210> SEQ ID NO 549
<211> LENGTH: 31
<212> TYPE: DNA
<213> ORGANISM: Artificial Sequence
<220> FEATURE:
<223> OTHER INFORMATION: CDKN1C: Probe (5'-6-FAM; 3'-BHQ1)

<400> SEQUENCE: 549
aactaatcaa cgaaaaactc ctaaccgcgc t                               31

<210> SEQ ID NO 550
<211> LENGTH: 29
<212> TYPE: DNA
<213> ORGANISM: Artificial Sequence
<220> FEATURE:
<223> OTHER INFORMATION: CARD15 forward primer

<400> SEQUENCE: 550
gtctcacttc ccatctacat tctaaaact                                  29

<210> SEQ ID NO 551
<211> LENGTH: 26
<212> TYPE: DNA
<213> ORGANISM: Artificial Sequence
<220> FEATURE:
<223> OTHER INFORMATION: CARD15 reverse primer

<400> SEQUENCE: 551
gggttttatt ttcgggattt gaatat                                     26
```

<210> SEQ ID NO 552
<211> LENGTH: 29
<212> TYPE: DNA
<213> ORGANISM: Artificial Sequence
<220> FEATURE:
<223> OTHER INFORMATION: CARD15: Probe (5'-6-FAM; 3'-BHQ1)

<400> SEQUENCE: 552
caacccttac ccaaacccta cgaccaaaa                                   29

<210> SEQ ID NO 553
<211> LENGTH: 20
<212> TYPE: DNA
<213> ORGANISM: Artificial Sequence
<220> FEATURE:
<223> OTHER INFORMATION: CDKN1B forward primer

<400> SEQUENCE: 553
aaattcgaaa cccgacgcta                                             20

<210> SEQ ID NO 554
<211> LENGTH: 17
<212> TYPE: DNA
<213> ORGANISM: Artificial Sequence
<220> FEATURE:
<223> OTHER INFORMATION: CDKN1B reverse primer

<400> SEQUENCE: 554
gaggagcggg agggagg                                                17

<210> SEQ ID NO 555
<211> LENGTH: 19
<212> TYPE: DNA
<213> ORGANISM: Artificial Sequence
<220> FEATURE:
<223> OTHER INFORMATION: CDKN1B: Probe (5'-6-FAM; 3'-BHQ1)

<400> SEQUENCE: 555
gaattcgccg cgacgccta                                              19

<210> SEQ ID NO 556
<211> LENGTH: 20
<212> TYPE: DNA
<213> ORGANISM: Artificial Sequence
<220> FEATURE:
<223> OTHER INFORMATION: CDKN2C forward primer

<400> SEQUENCE: 556
aaattacaac gccgcgaaaa                                             20

<210> SEQ ID NO 557
<211> LENGTH: 17
<212> TYPE: DNA
<213> ORGANISM: Artificial Sequence
<220> FEATURE:
<223> OTHER INFORMATION: CDKN2C reverse primer

<400> SEQUENCE: 557
cgtgcgagat tgcgagc                                                17

<210> SEQ ID NO 558
<211> LENGTH: 19
<212> TYPE: DNA
<213> ORGANISM: Artificial Sequence
<220> FEATURE:
<223> OTHER INFORMATION: CDKN2C: Probe (5'-6-FAM; 3'-BHQ1)

<400> SEQUENCE: 558
aaaccgaacg ccgcccacg                                              19

<210> SEQ ID NO 559
<211> LENGTH: 20
<212> TYPE: DNA
<213> ORGANISM: Artificial Sequence
<220> FEATURE:
<223> OTHER INFORMATION: FGF18 forward primer

<400> SEQUENCE: 559
atctcctcct ccgcgtctct                                             20

<210> SEQ ID NO 560
<211> LENGTH: 19
<212> TYPE: DNA
<213> ORGANISM: Artificial Sequence
<220> FEATURE:
<223> OTHER INFORMATION: FGF18 reverse primer

<400> SEQUENCE: 560
tcgcgcgtag aaaacgttt                                              19

<210> SEQ ID NO 561
<211> LENGTH: 19
<212> TYPE: DNA
<213> ORGANISM: Artificial Sequence
<220> FEATURE:
<223> OTHER INFORMATION: FGF18: Probe (5'-6-FAM; 3'-BHQ1)

<400> SEQUENCE: 561
cgaccgtacg catcgccgc                                              19

<210> SEQ ID NO 562
<211> LENGTH: 18
<212> TYPE: DNA
<213> ORGANISM: Artificial Sequence
<220> FEATURE:
<223> OTHER INFORMATION: FOXO1A forward primer

<400> SEQUENCE: 562
gccgcgctcc aactaaca                                               18

<210> SEQ ID NO 563
<211> LENGTH: 18
<212> TYPE: DNA
<213> ORGANISM: Artificial Sequence
<220> FEATURE:
<223> OTHER INFORMATION: FOX01A reverse primer

<400> SEQUENCE: 563
tcgggcggtt tggtagtc                                               18

<210> SEQ ID NO 564
<211> LENGTH: 19
<212> TYPE: DNA
<213> ORGANISM: Artificial Sequence
<220> FEATURE:
<223> OTHER INFORMATION: FOX01A: Probe (5'-6-FAM; 3'-BHQ1)

<400> SEQUENCE: 564
cgaacgccgc gaaccgctt                                              19

<210> SEQ ID NO 565
<211> LENGTH: 17
<212> TYPE: DNA
<213> ORGANISM: Artificial Sequence

```
<220> FEATURE:
<223> OTHER INFORMATION: GSTM3 forward primer

<400> SEQUENCE: 565
gcgcgaacgc cctaact                                                    17

<210> SEQ ID NO 566
<211> LENGTH: 22
<212> TYPE: DNA
<213> ORGANISM: Artificial Sequence
<220> FEATURE:
<223> OTHER INFORMATION: GSTM3 reverse primer

<400> SEQUENCE: 566
aacgtcggta ttagtcgcgt tt                                              22

<210> SEQ ID NO 567
<211> LENGTH: 24
<212> TYPE: DNA
<213> ORGANISM: Artificial Sequence
<220> FEATURE:
<223> OTHER INFORMATION: GSTM3: Probe (5'-6-FAM; 3'-BHQ1)

<400> SEQUENCE: 567
ccccgttctc cgtcccttac ctcc                                            24

<210> SEQ ID NO 568
<211> LENGTH: 25
<212> TYPE: DNA
<213> ORGANISM: Artificial Sequence
<220> FEATURE:
<223> OTHER INFORMATION: HSPA2 forward primer

<400> SEQUENCE: 568
cacgaacact accaacaact caact                                           25

<210> SEQ ID NO 569
<211> LENGTH: 18
<212> TYPE: DNA
<213> ORGANISM: Artificial Sequence
<220> FEATURE:
<223> OTHER INFORMATION: HSPA2 reverse primer

<400> SEQUENCE: 569
gggagcggat tgggtttg                                                   18

<210> SEQ ID NO 570
<211> LENGTH: 21
<212> TYPE: DNA
<213> ORGANISM: Artificial Sequence
<220> FEATURE:
<223> OTHER INFORMATION: HSPA2: Probe (5'-6-FAM; 3'-BHQ1)

<400> SEQUENCE: 570
ccgcgcccaa ttcccgattc t                                               21

<210> SEQ ID NO 571
<211> LENGTH: 20
<212> TYPE: DNA
<213> ORGANISM: Artificial Sequence
<220> FEATURE:
<223> OTHER INFORMATION: LTB4R forward primer

<400> SEQUENCE: 571
gcgttggttt tatcggaagg                                                 20
```

```
<210> SEQ ID NO 572
<211> LENGTH: 19
<212> TYPE: DNA
<213> ORGANISM: Artificial Sequence
<220> FEATURE:
<223> OTHER INFORMATION: LTB4R reverse primer

<400> SEQUENCE: 572
aaaccgtaat tcccgctcg                                                  19

<210> SEQ ID NO 573
<211> LENGTH: 23
<212> TYPE: DNA
<213> ORGANISM: Artificial Sequence
<220> FEATURE:
<223> OTHER INFORMATION: LTB4R: Probe (5'-6-FAM; 3'-BHQ1)

<400> SEQUENCE: 573
gactccgccc aacttcgcca aaa                                             23

<210> SEQ ID NO 574
<211> LENGTH: 24
<212> TYPE: DNA
<213> ORGANISM: Artificial Sequence
<220> FEATURE:
<223> OTHER INFORMATION: MT3 forward primer

<400> SEQUENCE: 574
cgataaacga acttctccaa acaa                                            24

<210> SEQ ID NO 575
<211> LENGTH: 15
<212> TYPE: DNA
<213> ORGANISM: Artificial Sequence
<220> FEATURE:
<223> OTHER INFORMATION: MT3 reverse primer

<400> SEQUENCE: 575
gcgcggtgcg taggg                                                      15

<210> SEQ ID NO 576
<211> LENGTH: 35
<212> TYPE: DNA
<213> ORGANISM: Artificial Sequence
<220> FEATURE:
<223> OTHER INFORMATION: MT3: Probe (5'-6-FAM; 3'-BHQ1)

<400> SEQUENCE: 576
aaacgcgcga cttaactaat aacaacaaat aacga                                35

<210> SEQ ID NO 577
<211> LENGTH: 20
<212> TYPE: DNA
<213> ORGANISM: Artificial Sequence
<220> FEATURE:
<223> OTHER INFORMATION: OPCML forward primer

<400> SEQUENCE: 577
cgaaccgccg aaattatcaa                                                 20

<210> SEQ ID NO 578
<211> LENGTH: 20
<212> TYPE: DNA
<213> ORGANISM: Artificial Sequence
<220> FEATURE:
<223> OTHER INFORMATION: OPCML reverse primer

<400> SEQUENCE: 578
```

```
gaggcggtat cgggagaaag                                                20
```

<210> SEQ ID NO 579
<211> LENGTH: 23
<212> TYPE: DNA
<213> ORGANISM: Artificial Sequence
<220> FEATURE:
<223> OTHER INFORMATION: OPCML: Probe (5'-6-FAM; 3'-BHQ1)

<400> SEQUENCE: 579

```
aacaacaact ccatccctaa ggc                                            23
```

<210> SEQ ID NO 580
<211> LENGTH: 26
<212> TYPE: DNA
<213> ORGANISM: Artificial Sequence
<220> FEATURE:
<223> OTHER INFORMATION: SLIT2 forward primer

<400> SEQUENCE: 580

```
caattctaaa aacgcacgac tctaaa                                         26
```

<210> SEQ ID NO 581
<211> LENGTH: 17
<212> TYPE: DNA
<213> ORGANISM: Artificial Sequence
<220> FEATURE:
<223> OTHER INFORMATION: SLIT2 reverse primer

<400> SEQUENCE: 581

```
cgggagatcg cgaggat                                                   17
```

<210> SEQ ID NO 582
<211> LENGTH: 23
<212> TYPE: DNA
<213> ORGANISM: Artificial Sequence
<220> FEATURE:
<223> OTHER INFORMATION: SLIT2: Probe (5'-6-FAM; 3'-BHQ1)

<400> SEQUENCE: 582

```
cgacctctcc ctcgccctcg act                                            23
```

<210> SEQ ID NO 583
<211> LENGTH: 21
<212> TYPE: DNA
<213> ORGANISM: Artificial Sequence
<220> FEATURE:
<223> OTHER INFORMATION: TACSTD1 forward primer

<400> SEQUENCE: 583

```
cacacctacc cgacctaacg a                                              21
```

<210> SEQ ID NO 584
<211> LENGTH: 20
<212> TYPE: DNA
<213> ORGANISM: Artificial Sequence
<220> FEATURE:
<223> OTHER INFORMATION: TACSTD1 reverse primer

<400> SEQUENCE: 584

```
aattttcggg cggtgattta                                                20
```

<210> SEQ ID NO 585
<211> LENGTH: 29
<212> TYPE: DNA
<213> ORGANISM: Artificial Sequence

```
<220> FEATURE:
<223> OTHER INFORMATION: TACSTD1: Probe (5'-6-FAM; 3'-BHQ1)

<400> SEQUENCE: 585
cccttcccga aactactcac ctctaaccg                                          29

<210> SEQ ID NO 586
<211> LENGTH: 24
<212> TYPE: DNA
<213> ORGANISM: Artificial Sequence
<220> FEATURE:
<223> OTHER INFORMATION: TITF-1 forward primer

<400> SEQUENCE: 586
cgaaataaac cgaatcctcc ttaa                                               24

<210> SEQ ID NO 587
<211> LENGTH: 25
<212> TYPE: DNA
<213> ORGANISM: Artificial Sequence
<220> FEATURE:
<223> OTHER INFORMATION: TITF-1 reverse primer

<400> SEQUENCE: 587
tgttttgttg ttttagcgtt tacgt                                              25

<210> SEQ ID NO 588
<211> LENGTH: 25
<212> TYPE: DNA
<213> ORGANISM: Artificial Sequence
<220> FEATURE:
<223> OTHER INFORMATION: TITF-1: Probe (5'-6-FAM; 3'-BHQ1)

<400> SEQUENCE: 588
ctcgcgttta ttttaacccg acgcc                                              25

<210> SEQ ID NO 589
<211> LENGTH: 22
<212> TYPE: DNA
<213> ORGANISM: Artificial Sequence
<220> FEATURE:
<223> OTHER INFORMATION: ZBTB16 forward primer

<400> SEQUENCE: 589
atcacgacga caacgacaac at                                                 22

<210> SEQ ID NO 590
<211> LENGTH: 31
<212> TYPE: DNA
<213> ORGANISM: Artificial Sequence
<220> FEATURE:
<223> OTHER INFORMATION: ZBTB16 reverse primer

<400> SEQUENCE: 590
tgatttgtta atttcgtagt agagaggagt t                                       31

<210> SEQ ID NO 591
<211> LENGTH: 25
<212> TYPE: DNA
<213> ORGANISM: Artificial Sequence
<220> FEATURE:
<223> OTHER INFORMATION: ZBTB16: Probe (5'-6-FAM; 3'-BHQ1)

<400> SEQUENCE: 591
cgacaattcg caatacccgc tctca                                              25
```

```
<210> SEQ ID NO 592
<211> LENGTH: 15
<212> TYPE: DNA
<213> ORGANISM: Artificial Sequence
<220> FEATURE:
<223> OTHER INFORMATION: COX-2 forward primer

<400> SEQUENCE: 592
tgctgctgtg cgcgg                                                   15

<210> SEQ ID NO 593
<211> LENGTH: 21
<212> TYPE: DNA
<213> ORGANISM: Artificial Sequence
<220> FEATURE:
<223> OTHER INFORMATION: COX-2 reverse primer

<400> SEQUENCE: 593
ggttttgaca tgggtgggaa c                                            21

<210> SEQ ID NO 594
<211> LENGTH: 24
<212> TYPE: DNA
<213> ORGANISM: Artificial Sequence
<220> FEATURE:
<223> OTHER INFORMATION: COX-2: Probe (5'-6-FAM;  3'-TAMRA)

<400> SEQUENCE: 594
cctggcgctc agccatacag caaa                                         24

<210> SEQ ID NO 595
<211> LENGTH: 84
<212> TYPE: DNA
<213> ORGANISM: Artificial Sequence
<220> FEATURE:
<223> OTHER INFORMATION: HOXA10 amplicon

<400> SEQUENCE: 595
tgtattgatg ggccaggaga cgcaccccga caccttggcc cgaaggccgg gagctgtggg   60
ggctgcccca acgtggctgg tggg                                         84

<210> SEQ ID NO 596
<211> LENGTH: 100
<212> TYPE: DNA
<213> ORGANISM: Artificial Sequence
<220> FEATURE:
<223> OTHER INFORMATION: HOXA11 amplicon

<400> SEQUENCE: 596
ctctgcctcc gacccctagcc ggaaccccctt cggggccaga gtttgaagcc gtggatgtgc   60
ctgcctggtg gcttgtccga tttgcacggt gacttgatta                       100

<210> SEQ ID NO 597
<211> LENGTH: 82
<212> TYPE: DNA
<213> ORGANISM: Artificial Sequence
<220> FEATURE:
<223> OTHER INFORMATION: NEUROD1 amplicon

<400> SEQUENCE: 597
gcctcctgcg tgggcgaatt cctcgtgtcg tggccgcgcg ggcgctcagg ttatatagcc   60
cagttagtga tgctaagcgc gg                                           82

<210> SEQ ID NO 598
<211> LENGTH: 129355
```

```
<212> TYPE: DNA
<213> ORGANISM: Homo sapiens

<400> SEQUENCE: 598
gatcattttc tataatctgg gttttgtaaa actcaccaat accttaataa tcaatacagt        60
tgggacaaaa atgccatctt gtcctggaat atcagaaaaa tgatctcaat cctctctctt       120 cccttctgg atggacttat aagtgcaagt gaaagaaagt cacccctttc atcctcatac        180
aactgcctgc agcatgaagc taatgaatat tcccataccc ctcttttccc acaaaggaga       240
aatataagaa tttaccttaa atgatgatag tctgccattt gagattttgc agcttgacac       300
tcaatttcca ctgagagtct aggcattttt tttttttagc agacagccaa gatgctgtgt       360
ccttgcctga gaccacatta tttgcaagaa gatccctctc tcctccacag acttttccca       420
gagaatgcct ttcagaattg ctgttgaatt acaaagaagt atttattgtt tgaggtgatt       480
aatgattcct gggaaaattg ctattttcag cgtgatttaa ttttgtttta caagtgtgtg       540 tagtagggggg agggttaata agtttcagca gcagttgcat tgcctccaga aatccctggc      600
acccgttcac accttataaa atgcacttta tgccaggttt atcctgattt gggaaggtaa       660
gtgtgtattt gattgctccc gaattttctt ggctcttcag agactggtat ctatcacttt       720
cctctcaaat ctgatttgta ggtatagaac ggatcaccct tgtttgtatc acacacaggg       780
cagcaggggt gaaaggggta ccagctctga cactggctaa agggttttgc cactaatgag       840
agaaatgtgt ttaaaaattc tctgatattg cagaggcagg tgagcactta ctcccatcta       900
tgctaaaatt actacattac ttaaaagttg cacttttttca aggccaggtg acagttctaa       960
tattctgggg ctagtgtgca caggttttttg tggtcttatt gtagggaact ccctgcagta     1020
agcatcaaat ctaaatcagt aaacaaatac taggttata gagatcgaga agtgggtttt        1080
gattttcagc cttttggatc tagatctctg gaatcgagca gaaaattcac aaagcatttg      1140
aggaaagtga cccagtttgg ctattttcca gcagtaaact ctcccaggtc tactttgcat      1200
ggggtgaact ttaggggtat attatgcttt ttcctcagaa gagacattgg agagtgtact      1260
tgtaaaattc agtttatttg aaagctcttt cttcaaaaaa gagaaacaaa caagcaaaca     1320
aacaaaaatt cccagtctgt agttagtgaa gaggaccta agaacagcca ggaaacaaaa      1380
actaatctca acccttttgca caaactattt tttatctcct gggaaacagg cagattaagt    1440
gtgaaggtgc aacaaatacc aaataccaaa gagaccactt ctttccaagt gtgctcagag    1500
ttcagtgtgt agaacagctg cagaaactcc tgggcccaca gcactgcatg gtttcaactt    1560
tcattgcagg gaaggacacg tttctatgcc ttacagagac ttgaagcctg aaagcctggc    1620
caagtttggg aagaagagga gccctctcag agctcaagag ccttcctact ctttggaact    1680
tttccacagt aggccaagct tgacaagagt tcagctcaag ttgaacatac atacacacac    1740
tctcacacac aaattatgtg agccgtcaga atccaagtga atccagctca agctatctac    1800
aaggttttta catgcaaggt caagtatctc aatccagagg acttttgttt tcttaatgaa    1860
aagcttagaa aacacatgaa tcttagattt ttaatgtttt ttaaatggag tttattctta    1920
gcacatggct ttctatgtag ccacatcaca atttgtacag ttccacataa gtctaaatgc    1980
actcccctct ccccaaagac cgtgccccag aaggggacaa cagtatctct gtaacagtgt   2040
cttaaataaa tgcaagtaag aaaaactaac atgtcacacc taccatcaag gtctacacat    2100
cttaagaatt aaataatctt gtgaggtcca caatgtctac tcatttattc agttaaatac    2160
aagcttggat gagctgcctt aatggggggaa gaggaggtaa ggaaggtggg gaaagggtct   2220
gtcttcttct gctttcaaca aagatgcaag tgtatgtccc cactcagcat gggctgtcca   2280
```

```
gctagctgac tgtagccatc tcaaaagtat ttgataccaa gtagtccttc tcaggtatcc    2340
acacctggca gccttgtttc gggccagcag gttgttccac cagccagcat cctggacaac    2400
tgttctctct tgggtggcaa ccagcacaga ctcttaaccg gataatgtct tcttttttgat   2460 tattctttc accaatttgg gtttgttttg gtgtctatta tggtccagat ggggaggggt     2520
ggatgaggaa cggagcagga gaagagaaga gaaaagcagg taagggatag aaactggtta    2580
agatctctag aagattatat ggaggaggga acgggtgtgg aggtgctcgg gtgggggtgg    2640
ggatggaggt gtgggctctg agtttgtgct ttccctggtg ggccggcaga ggccgaggcc    2700
gaattggagg atcgcatctt ggtgttgggc agtttgtggt ctttcttcca cttcatcctc    2760
cggttctgaa accagatctt gacctggcgc tcagacaaac agagcgtgtg gcgatctcg    2820 atgcggcgcc gccgggtcag gtatcgattg aagtggaact ccttctccag ctccaagacc    2880
tgctgccggg tgtaggcggt tcgagagcgc ttaggctccc ctccgttata actgggtta     2940 actgaaaacc cagaacccg aaatagaagg ccaaggagga gggagcggaa gagagggaaa     3000
ggaggaggag agagaaggtg gggtgggaa gagcaattgg acatcatcat tatataataa     3060
cctgacacca agttcacgca agatacataa aacggcaaag aaaatgtttc acaggctatt    3120
gacaacggga aacacccgag agccataaag aatggtgctg ggcattgggg ctgaagaaaa    3180
gcttcaaaga cacatggcct gaagcctctg ccagggcaat taaatttatg ggggctataa    3240
ttactgccct aacagtttgg cgtctcgtaa atctcctgat aaagggaccc tgggtacaaa    3300
agggttctca tgttgggatc aggcggctgg ctggcgcgca catcccaca tctcaccgca     3360 gcccgggtca gatgggggct cccctcccga ggcccccttc ccctgagcct ctccctcctg    3420
accccgaccc tcgaacccag gcccagcccc ggcccacctc ccgcgcctcc caagcggcgc    3480
cacgtaccgg cgctgacatg gatcttcttc atccagggt acaccacggg ctccttgccc     3540
ttcaggccca gcgggctctt gtcggccaag agcagcgggc acgcggggc gctgcccct     3600 gccgggacgc ctggggtggc gggggccgcc tcgcagcgcc gcggggccgc tgggggcacg    3660
gcgcgaggct gcaggggcgg cggcagctgg ggctgcagga cgtggctcgc atgcaggccg    3720
tgcgctgggc ccttggcttg cgccggggc tgctcggct ggggcggccg ccggggctg       3780 gcgccgccgc ggtagccata ggggtaggcg gtgtccgcgg ccccatgcgc ggggtacagc    3840
gcggcagcag ggtaggcggg ctcgcgggcg gtccgcggcg cgtagtagga ggcagtgggc    3900
tctcggccgc cgcccgcgtg agggagctgg ggctgctgca gcggcaggtg ctgggtcggg    3960
ggcgctgggg gctgctggta gccggggccc ccgcccgggc cgccgtctgc gccgcccgag    4020
ccgctgtgct gcgcgtactc ctcgaaggga gggaacttgg gctcgatgta gttggagttt    4080
atcaaaaacg agctcatggt cattaatttg tgaagtgcaa aaatactaat ttttctcgcg    4140
ttgtcgtttt ttctgggctt gccgaggcc ctccccctcc tgcctcgctt cccatccccc     4200
tttcctctgc gcccttcccc tccccccgct gtcaagtgcc cactcctccc cctcccgcag    4260
acgccgccac caaagttcga gccgctcctc cccagcccag cgcgcgcccc gcccgtgcc    4320 ccacgtgcag cgcccccacc aatgggcgca ccgcgcgcgc ggaccggat caggaaacgc     4380 gcgggtgcgt gatggatgct gctgtccggc cctgggctg ggggagggag caggagcttt    4440
ggaccccagc ccccagctt tggttcccgc tgggaattca ggccctgtca ggctgtaggt    4500
cctctcggga gccctctgcc tgccctactg ctggcctagg cctcgggctg tctggcggcc    4560
gcgactcagc gctgacctcg ggcgcaaccc agtcaggctt cgtgtccttc aggggttcta    4620
ggctaacagg cgaaaggaag ggcgttggga ccgaggggca tcctggtttt tatgtacgcc    4680
```

-continued

```
actgagaggc caccagacac attttctcaa ccgcagatcc cccttcccca caccctgctc   4740
cttgcgtgtc agcctgagag cccttgcttt gagaagcttg gcagaagctg caaagggtgg   4800
gcgggcagct aagagaaatc gacccaagga tgtaaatcga ggccattcca ttataactgg   4860
atggacactt ttcattttt ccttctttca gagacaatct gtttcgtgtt ttcctaagaa   4920
aaattggaac cttcgtaata gcatctaatt tgacgggggt tgtcgatgtg agagctaaat   4980
atgcccgcat ttactaggtg cgattgtgag agagaaggtg gcccaaggat gggaatggat   5040
agaagcaaca cctccacaga accgagcttt gaaaacaata acttcctatt tcagaactat   5100
ccccaaacaa aaacaagcta agggtagaat aaacaccttg ccgggtctga tcgctgatgg   5160
gtcttttcca gctaagaatt tcatgttttc tcttttagat cctgctttct caggcagtat   5220
ctgaggctag agttatattt gcaggacagt ctataatttc tgaattgctg aaaattagcg   5280
tattaacgat atcagaagct ccggaaagga gggagaggag actgttgcct gctatttggt   5340
aattgaaatt tgatgggtac actaattacg ccattattaa caaataaatt acttattaat   5400
tccacctaat gttgatcttt gaagtaaata ctgatgcctt atttgtgctg tgtgcttttct  5460 cccttctttt tctgagtagt agacatatct agatcctcta cttttcagcc taaattaaag   5520
cagtgtaaac tagcatagtc accattctaa aaatatttc atattggcat gcaaaagcaa   5580 ggattttca gctggtgcac cttagttgat ttttcaaaga gcagtataaa cagccttctc   5640
acaactgagt ctggaacgca gacaaggaaa attatttcct aagcctggag cacttgaaa    5700 aggaatgtca attctatctt cattcatact ggttactcat atgagttact aaatgctgga   5760
atatatccat ttgatggata gtcacttaat gcttagccac ataaagccta ttatatggga   5820
ctaatcttta aactaattta ggaaaagagg ttaaaaggg gatcatatta gctttctaac    5880
tggaatcacc ctgaagaggt acaaagagat tttccacgtt aggtgtatat gagtgtgaag   5940
agtgctgtcc attcacatga ggcaccctga aatttgttt ttaaagaaat ttgagccaca    6000
gacagaaatc aacactgagt gtaatctta gccatcctct ctagactgga ggaaaattt     6060 agaatgtgat acatctacct gaaccaatat ctctccctag caagaaaaaa taatatacac   6120
ataggttata taaatgtaa tataaataat atatagacat acgtattaca aatctgaacc    6180
ctataagttt caggggggaca aaaagcatga caaggaaatc ttccctcctt ctcatgtcat  6240
cagccttgag tactagggtc ttaaccatat ctgtttaata tttacagaca ctaaaacaca   6300
aaattctgtt gtttagcctc agaaccttgt accaagtttc tatttttaag tattaacgag   6360
acataaacac tgttttgtat acggttaacc caaacgagtt agctgtgcct gtgttttgtg   6420
tgattctatt actttaggaa gatggcctta cacagaatcc cccaaggcct gtaacttgtc   6480
tttgtggttc gtatcataaa cacaaacgga gccaggacca ccaagtgtta tctcaacacc   6540 gacatttga cattttactg caagatttat ggctgtaata aacaatctca gtacctttc     6600 tgaaccttcc tcaatctccc tttgcaaacc atagcatcat tccattgaat caaataatct   6660
tttgaaaaac atttaaaaaa aatacctctt gcctttacac aatatccaag acaccaaagt   6720
aaagccagga agaaactaac tcaattaata aacaaactga gtttaccag cagcatctcg     6780 cctgagaaaa gatgggatgc cctgaaatgt agcagagagg gagcatgcta atcctcacac   6840
accaactggc tccagtccca agcggggtga aagcgttatc ctttccttag gaaactggtg   6900
agcacgtttg ctcatttcca cgtgcaggga taacatatat tcccaacaaa agctttctta   6960
aaatcccatt aggtgaaata acttttcatc atgtcctcga atcccagatg gagaagagtg   7020
aagggagtcg gagggagagg gagggtgcaa gggaggcaat gttttgcagc ttggtttgaa   7080
```

```
tctgatttga atcattttga atatatttgt aacagcattc cctcttgaat gcaaccctgt    7140
cccaagtttc aaagtgaccg aacagtgaca ccgtgtgcat tttgtttctt attaatctta    7200
cacattgaca gtctttgtta aatcacaagg cgcgcccttc actagccgac attttcatat    7260
ttgttagacg cactgacctg aagttcacct cggccttgga ctttgcgctt ctaaaaggtc    7320
tatacagtgt cttttagaga gcagggtgct ttgcccaggt cactccttct caggaaaaac    7380 caagggaaa agccaaagga aatgtaaacg ttatggaatg tattgactgt atttgtcctt     7440
tgttctttag agcgagagtc ccccagactg ttctctatct gatgcatgtc tctagagctg    7500
aacagtggaa tggcagaatt tcaaaacgcc tgatggtggc atttgaaggc ttccccacca    7560
cctacactag acacaagatt tgagaggaac aacactttac cagccatttg accaattaat    7620
tctttgggga taattttctt gtagtagttt aaaataatgc acacaacgca gggatgagga    7680
ctgatattca tattgggatt acacatgaat tttaactggg attgtttgag aggcctgagg    7740
ttcaaaatcc tccagataaa gcaagcacac taaaagcaat aaattctgca agtactcttt    7800
tcttttactt tgaagactag ctaagaggta tctatggttt ttgaagctga catgtctata    7860
aggtgtgtca catgttttta accaaaaagc acaataaaaa ggttttttccc aaagagacac   7920 gtaattgtct tgttgactca tcgaggggtt tcagttttcc tcatttcact agcccaaatg    7980
tggtgaaatg ttcactgctg caacagcaat caccacagtt gtttcctttc ttctgtttca    8040
tctggcaaac ccccatttgg cttcaagctc ttggccagag tgaaaacttt acacattgca    8100
cagaagcacc ctgattactt ccatgaaggc agtgtttgga aaatatttac tttaccactg    8160
aacatacctg gcaccattaa atccaatcaa ccaaaatatt gggatgatct taaacattcc    8220
tgcaagagtc cacattctga gtagatgaat tatttccaaa gttaaaaaag aaaaacctag    8280
ggaaaatatt tcacttttct cttctctgtt ttcctatact gatcccttga aggtcaattc    8340
atagaaaagg gaaatatgtc ctctggaaaa tagattctta cagcaccaac acttaaagcc    8400
attctagatg catgaaaaat aaaatattgt ttagctcttc agttgcaact cacacatgag    8460
gcatggttct agtcggcttc cttaatacac tattctcttt cttttctgct ctcccaccct    8520
tcttcttagg ttgctttatc ttctccttgg cttttttttt taattccacg tgtatcatta    8580
aaaagtacat tctgaagaat agaaaatatt ctattctgtc ctggtggtct tacagagtag    8640
cctgttattt gtggatttca cctttctgca ttccctacag tctagttatt cacttatagc    8700
ttgtagcatt tctcttacat tcaattgtgg tttaataata aacattaaaa aaatttccaa    8760
acaggaacat tttcatggca ccagtaagca ttttgtcact ggcagtggtg gtggaagggg    8820
tgaagggaga attctgtgtc tttcaggagg gtttccactt ccttccttcc ccttctcaga    8880
tctcagaacg ctttgcattc agcggactgt agtttcagaa aaagcatatt ctgtgtttga    8940
aaactgcaaa gattatattt tgcaagaagt gtctgtgttt gcatttattc ttacacactt    9000 tagggtcat catgtgtact aaaaagacaa aaaaccggcc aatcagaatc cctcttttca     9060
aataaaggag gtttcctgca ccattctgtt gcctttgaag gcataatgaa atattggaaa    9120
cttgtgacat tagttttttaa agctccacag atgagttttt agcattttta ttttgtgaca    9180
aacccacaga ctcctggttc tccaacacct aaggtgttga tgtttcagta atctatgcct    9240
atttacctgc tgctattccc tcagaatggg agcgataatt caagatgaga tacagcatgt    9300
attactcttg aaaagaggaa ttttctatcc tttcctccgt aattgaggtc attcaaccac    9360
tagggttcac ctggagtcca taccgtgata cacgcgtcac tctgagccat tttatctttt    9420
gtgctgatag tcaagatcac agctctaaca ttgacatcaa actctgtctg ggcagatgac    9480
```

```
taagagcact gcacaatgta aacttttgac cctcaacttt ttgacctgca gttgtaacgc   9540
actaaccgca aagatacaca aagccgagcc tcttctttca gggggaaggg gccccccagc   9600
atctcaggat gccctgcttc tgccactgcc atttgaaatt agagggtgaa atggatattt   9660
ttgtgtgttt gtgactgtac tttttgttaa atcagcctat gacctcttcg ttagcaccta   9720
ggaactagat taacttgaaa tcactcgtga ttctatttta caaggaaaat ttggagcaga   9780
atgggagaac cttgcaaaaa gtgaaagaaa agagaagatg ggggaaagca ggcaatggga   9840
ggtggagaca cttttttccct ttatttaaaa ctaaagacgc agccctaatt gttgggagag  9900
ctggcccaag cgggtgaatt gactgtgaac ttgtactaaa gcgtgctctg ctggcgattc   9960
ctagggtgtg cagatttatc ttctctgcat ttacttaacc cggcagtgaa ctgcgcgggc  10020
gtcatttgtt aggcgatgac agacttcacc tccagcaagg gctgcttcac aaaatcgcaa  10080
taattatcta ataaccttca taacaaatat tattattgaa aagactggtt tgtggggagg  10140
ggacctggtg ggagaacaaa tttatttgtg aacaacaaca aacaaaacaa acctgggcag  10200
accttcaagt tctggggctt agaatggctg gggctgtgga tcccctcccc tacttgggtg  10260
ggagcttagg ctgaccccct cagccctgcc tgggagcccc gtttatagtt ttgccattga  10320
ctagaaggaa actcctcctc agaaaccaaa gggagggagc ccacaatgct ctgcactctc  10380
catggtgggc aagccatgga cagaccccca gccaaggcag gggggaggct gagaagggca  10440
tcttttaagc taaaggatt gttttcctct ttaattgcct atcttttaag atgtgatttg   10500
ctttccactc actaattatt tcgatataat actctcagaa tctcaacaaa tgaacaggac  10560
tctgtttttt ggtgggaaat tctgtcttgc tctctcagag ccgccaacaa tgaagcaggg  10620
gaaagagcag gagaaaggga atcttggcat aatgttgtga aattagacca tggaaaccct  10680
aacaaaccac taagtaagtg tgaccagaag cttcctgttg tatttatagt tcagaaatat  10740
tgtctcttca gcttgtggga acaaacgagc ccccgcacat tgccgctgag gaggagcaca  10800
gacacgcact tctgccaccg gctgaggctg gatgtcttca taaagccctc agtgacagac  10860
atatttttc ttagtaagtt cctctgcaag aacaacccaa aagaatccac aaaagaaata  10920
acttatctac agaatgagca gaaaaccagc catcctcttt attatgcttc ctatgaaaat  10980
aggaagaaag aaaaaaatct tccagtaaca cataggtctg actgcatgat gtattttaa  11040
agtcatttta attccatgtg gccatgtggg tttgcctgct ctcttaaatt ctacttaagt  11100
tttgtgaaga ttaaaacaga cagaaataag caagctgaca atatttacag cctgtaattt  11160
ttctcattcc ttggaaagat tctctatgtt ctgtggtact ggatatgact tcaacaggct  11220
ttctgctcat tcccacaccc cagggtggaa tatggccatg aagtagtgtg gatattttct  11280
gtgtaagtaa ctcaaattaa actggcagaa tccccgtcac tctttttttt ttctaatttc  11340
aatcaccaag aaatcactca agcaagatca ccaaatcagt aactaaaatg gaaccataac  11400
gcaatatttt ccaataagga gcccaaaatt cagagcagca aaacaaggaa tccagtattc  11460
tcacagacac ataacattat aaaagagaac ccatacccat gtagagttta tatccttgtt  11520
cccactaaga tgtggacaca tcttcttgaa tgctgaaata ccaatgttta ctttaatagg  11580
ttacacacaa tgacttcagg attcttcacc ttgccactat tcatgagaag tagcacttgt  11640
gggagggttt tgatttttca aaaaaacttt ctaggttttg ctttctggac ctctgacttt  11700
agggacatct gttggactta tgttgagtgt aggtggcctc tgcacaataa gtttattgaa  11760
attccaaatc tatactttca attttttcac tttaagcact taataggtat ctttaccaat  11820
taatacttgc tgaaaactgc ccagctccta aggagaaaag cagatcctat tttttgtttc  11880
```

```
atttctgaat gcagtaggag aatttggctt aattcctaaa ataggattgg aggaaatcta   11940
ctgggtccct tgtgggtacc catccagaaa aagatcccag gacaggccac agtccccagt   12000
cactgggctt gggttttgcc attgaagaat atgggggggtt ggggccagaa ggggtgactg   12060
gggccaatat ggaattgtgc ccaggataaa cttatttcac cttacttcac ccattggtgc   12120
aattttggag actgttctgg aaatcataga ttatgtaaat ttcctgggat caaacagaaa   12180
gagcaactaa caaagaaag gcggaaatct cctactgaca aaggaccaat ttcttcccta    12240
aactaccgtt tatgatgtgt caggaaaaac aacctaatgg ctctggggac tttaagttg    12300 ggcactgaag acacctcaat ttcccccaaa actttagagc acagtttgga acagagaatt   12360
cgcctgtatg ttgaggggga gtgaatttct ccaatcttaa tgttatccag ggggccgcct   12420
aagttgcctt ctgagggtcc tgtgcgtaga tgttttttaat tctacaaaga aggagaggaa   12480
caggaaagaa gagagggaga agaaaggcaa agcggaagaa aagaaagcgc tttaccccct   12540
ttcaattagc ctggggattc aaagactaaa gttaaatccg gccataaagt ttattgcttc   12600
agactcacaa gcggctgaga acagtcccgc cgaaataaaa agaacatgca ggcaaacagg   12660
gttcagggcc tggtcccggg tgcggggag ggggtcctga acacccccc acaccagggt    12720 ggggatcctt ggtcctcagg gtccagtggg cgctagcagc ccaggatcca ccttgcaacc   12780 cggggggccca gcctggaggt gcagcccag cctcgccggc ctctgccacc ctcccgctct   12840
cgcgagctag cctgaaaccc ggccccgaag gccgccgcct caattcagcc ctgccaaatg   12900
accccggccc gcgaagacat attgccacag ccccgtaagg aatcccgcca gagtccgcct   12960
cggccctgcc ccggcctttc tttcaaactc ctgagcgcag cgcggccctc ggcgcccgcg   13020
gccggcgccc cactgtctcc cagccccgac cccagggctc cgcgacccc aggagctggc    13080 cccggccggc ccagcaattg cgcggggac tgggggtgcg gccctgccag gtccccacac    13140
acaggcccat tcgcacacaa aaatcatctt tttgcacgcc ggcgggagca gcggaagtca   13200
ttaacatccg cggttgtgct gcaattaaag ttaggcctgg ggatgcggcg cggccacagg   13260
cgctgctcac tctgctgcct ccgcagagtt ggctcctggc gctgctcttt tgggcagagg   13320
gaaagtttgc tctgcctttt cgaattcaga ggcagcctga gttattgaac cagagagaga   13380
gagagagaga gagagagaga gaaagttcc aaagtacaaa taaacttgaa agcgctcagg    13440
aggcgagctt accttaactc ggagggagcc atttttcaga gagttttgag aacttgtggt   13500
ttggacactt ctggacctaa aattgacagt ttgaatggcc aggcggcaca cgtagcctgc   13560
aaaagagtca aatggagtcc agcgttagtg agattatatg ttatgtggta tataatgttg   13620
gatgtcaact ccccaaaacc ataaaactta cttttaatggc cccacgtgac gtttttatagc   13680 cagtgagccg atctgtctgt gctatggatg attttacgat ctaattcata gacaaaaccc   13740
tattcatttg gcacccaaat gtcatatagc cggaactggg gcttataaag tttactgttt   13800
tataactttt aaaaggaaag acggcatcag tgtaagcagt cggtaaatgt gcaaatctct   13860
agttgcgctt tagctgctct gaggagtttc ccaatcgagc taggatgggg taagtacctt   13920
caatttgtag caaattaatt gtagcaaaag aagccaactg ggtcccgggt gaagagtggg   13980 gaagggtgc tgggatgggt taagggcaga gggtttgggg tccacagaca gacatagcag    14040
cgtcttcagc aagtggaggc ctaggacagc cttaggaaag aggcaggatc tgtgtggcct   14100
gagggcggct aacaaagccc tgggtttttt ctcctttttt cttgctcttt ctctcttttt   14160
tgtacccagc aagttaactt ggtttcctca gagatggaca gggtgttctg gggctttgga   14220
acagcctaca gcttttttcca ccttctgccc tgaactttgc aatgggtcag aggtagggaa   14280
```

-continued

```
gcgatgggac agtgttggta tgaggtctcc ctgcacaggt catctgctca ggtagcctca    14340
gacccaacag cttccaagac tgcacagaca gacagaaaag cagacagagc cgctcactat    14400
ttggcacaaa ccagaccaag agaacttaca atagaaagtt tattttttgt tccagtcagt    14460
attttttcct taaaaacaaa tacaaaaaaa aaaaaaaaaa aaaaaagct gatcacagtt    14520 tgcttaaaac agccagactt ggacaatatt tgtaactttg ttcacaaaaa catacatcac    14580
tgaagctgcg cttataagag ccacttccag agttcgtgca aagggtccta taaaggcacg    14640
cagggacaca ccgcttggag tcacagtttt catcacagag tcactagtca ctacacgtcg    14700
aacaagttgt gtctcatcaa gtcacctcta caacagcatt aattacacaa ggaatatagg    14760
tagtttgaat aaaaatatct ttaacagctt ggagctattg agacaggaac acttccacgc    14820
acatgcacag ttaaacaact tgagtgcaac acacaacatt ggcactaaac gagattgaag    14880
ggggactttt tgtgtgtttt tttttctctt ttcttttttt gttatagtta cttcaagtaa    14940
cacagcttgc ttcatataaa taagttaaaa catctatttt ttttcaagac aaagccattc    15000
aggacaaaga gatgaacaga aagcagatct acttatacag gcgctataat ggcaataaac    15060
aggctcatga ttaaaagatg aattagggca acgagaacag ggcttcttca cagaaggaac    15120
acaagggagt ttcagaaagt caccttagta ctgacactac gcgggatccg ctaatactgc    15180
tcagtacttt aaacgctcag atactcaggg acggaaggcc cctcctgccg cggccatgct    15240
catgcttttc agcttattat cttttttcca cttcattctc cggttttgga accagatttt    15300
aatttgtctc tcggagaggc aaagagcatg tgctatttca atcctccttc tgcgggtcag    15360
gtaacggttg aagtggaact ccttctccag ctccagggtc tggtagcgcg tgtaggccgt    15420
ccgggccctt ttgccttccg ggccgccat gttgtctgca atagaaaagt cagcggttta    15480
gccaccaact cctgtcttcc aaagtccgcc aggggggacaa gcttgggtca tgagcaggga    15540
acccaggcga aaagctcaac aagttctgcc taccagcccg cacacccctc ccgaatttcc    15600
ttctctcttc ctttctagaa agaaaacaat acgatttgga ccctgggaac aatctgccca    15660
tctgaggctg gggccgtgtc ccggcggact ccggcttttcc ctggcccctc tcctgccccc    15720
tccgccctgc cccgggcgcc ccgatcggga ggcacagccc tcccaggctg cccaccgcac    15780
agaaacccag gaagcaaggc cctttcctga gcgcccaagt ggccttcggg tcaccctccc    15840
tcaaagttcc agccccgaga gccgcctccc gtttccagcc tgcagggttg gggagcctgt    15900 tttcttttc ttccctttcc ttctctctcc ctcctgcccc caaaattcag aatcctgcag    15960
gctctcgcct cgattctttc ccccaagccc cttttcgggg gctgtaatta gtaacgctgt    16020
ttccccagcg tagccctcct cataaattat ccgccgtgac aagcccgatt cacggctgct    16080
acagccatcc tctacctctc tgcgccttgc tcggctggcc tgacccggga gcgcgtccca    16140
aggcgtgggg ttccagaggg gttttttgct tcctcccccct tccaacgtct aaactgtccc    16200
agagaacgcc catttccccc actatttgtg agcgcagggt gctcgcaaag aagaggagga    16260
aggaggaagg caggggaggg agaacggcaa ggagagctcc gcagggctgg gagaaatgag    16320
accaagagag actgggagag ggcggcagag aagagagggg ggaccgagag ccgcgtcccc    16380
gcggtcgcgt ggatttagaa aaaggctggc tttaccatga cttatgtgca gcttgcgcat    16440
ccaggggtag atctggggtt gggcgggcgg cgccgggctc ggctcgctct gcgcactcgc    16500
ctgctcgctg ctggcagggg cgtcctcctc ggctccggac gccgtgccaa cccccctctct    16560 gctgctgatg tgggtgctgc cggcgtcggc cgaggcgccg ctggagttgc ttagggagtt    16620
tttcccgccg tggtggctgt cgctgccggg cgagggggcc acggcggagc agggcagcgg    16680
```

```
atcgggctga ggagagtgcg tggacgtggc cggctggctg tacctgggct cggcgggcgc  16740
cgcgctggcg ctggcagcgt agctgcgggc gcgctctccg gagccaaagt ggccggagcc  16800
cgagcggccg acgctgagat ccatgccatt gtagccgtag ccgtacctgc cggagtgcat  16860
gctcgccgag tccctgaatt gctcgctcac ggaactatga tctccataat tatgcaactg  16920
gtagtccggg ccatttggat agcgaccgca aaatgagttt acaaaataag agctcatttg  16980 tttttttgata tgtgtgcttg atttgtggct cgcggtcgtt tgtgcgtcta tagcaccctt  17040
gcacaattta tgatgaatta tggaaatgac tgggacatgt acttggttcc ctcctacgta  17100
ggcacccaaa tatggggtac gacttcgaat cacgtgcttt tgttgtccag tcgtaaatcc  17160
tgcctgatga cctctagagg taaactcgtg cactaatagg ggagttgggt ggaggcgagg  17220
ggggtggcgc gcgcgccccg ggcgcgtgcc cgccgccagt tgccgccgtt cagccggact  17280
cgagcgccac ccgctggagg cagggctcat cgcccagctt ccgaccgggg gctgcaaggg  17340
ccggggtcga attgaggtta cagcccatta tggcaaaatt attgcatttc cctcgcagtt  17400
ccattaggat gtaccaattg ttaggccgtc agctgccgat cgcgcgcccg gcgaggatgc  17460
agaggattgg ggggaggtgg tgacttgcat tttatttaca acaactttat ttcccccgtt  17520
ttgcagcccc tcttattttt gtgtcgaggt tggggtcggt actgaccgtc ctgccagcag  17580
ctctgaattt tgaaaataca gatatcacct tcggggaagg gggaaagcca tttagccaat  17640
tggagaaata aatcctgccc gcagcagcag cagctacaat tacggctctg ttttgcgag   17700 cgcatgaggg acagtgtccc tgccgctctt aaatgacagg cgtctattaa agatagcttt  17760
tgtgtagtgt ttctccaagg cgaggtcaaa ttccatacac ttttataacc gtagtcgatt  17820
tttctttcgt gtgaatatgg ttttcgtgtc attagtttgc gatttgattt gcttacgtat  17880
ccagcctgga aaatcttcat cacagggtcc ggttcctcga gccagccggg ccccaagtcg  17940
gagggttctc cttgaaccca gcgagtgggc ccaggctccc tgcagccaca gaggctgcct  18000
ggggtctggg gatccgtggg gcgggttact ggggtcttgc ttagacctcc aggagtaaaa  18060

tgagggcgat aatggaagca ttccttggca gtgcctagta tctctgtagt тaтттттccac 18120 ggctccgaaa gactcaagta aatcacaaat atagctgaga ggcaagtgga gtctcccgc   18180

tggaggcccg gcgttgcagg cgcccctggc acgtctggaa gccaggactc tggcggctcc  18240
catggccctg ggcccctcgt tgggtcctga acgctgctgt ggcggcgacg cgggcgctat  18300
cggaggctgg gagcgggaat ccggagccgg gagcctaccc cgggctgtaa tgttccaccc  18360
gcgcccaggt taactcgcct cggctgaggc tgcttctctt ccactgacgg ttgcacacgc  18420
gggaccgaga gactgggctc tgttgggcc cctttgttc ctcgagcttc cttcctgttc    18480

tgggaggcgg cttgggaggc cgcgacaagg ccgggctcca gctcttagac cccctctttc  18540
cactggccag agatgattt atgatgccct tcgggactta ctggcgaggg acttaggcag  18600
agacgcccag acacgaaacg gggctcggcc cagggctctt cctcccag cagccccgcg    18660

tcccgaggtc ggggagctca gagacactag cacaggagcc ccagacgcat tcagggcgca  18720
ccccagaact ccggagccgg ttggcatc cttgtggagc gggactgggt gtgtgcagtg    18780
cgccccgctc caccgctggt attgctgtg tgtgaggtt tgtttgttt tgtttttgttt    18840

tgtttttgttt тgтттттgттт тgтттттgтaa gaaataaatg cacagacgct tgcaaagctc 18900
cgggctcccc tgaagctgcg gaagccccca gatgggagca ggcgggaga aaagttgggg   18960 aacaggcgag ggcaagggg caaagccgaa ggaggttgca gcgctggcct ggtccctgcc    19020
caggcatcta ctcgcccgcc tttgcctctg agtcctcccc gctgggctgc gtggaattga   19080
```

```
tgagcttgtt ttccttttc cacttcatgc ggcggttctg gaaccagatc ttgatctggc   19140
gctcggtgag gcagagcgcg ttggcgatct cgatgcggcg gcgccgtgtc aggtagcggt   19200
tgaagtggaa ctccttctcc agctccagtg tctggtagcg cgtgtaggtc tggcggcctc   19260
ggcgcccatg gctcccatac acagcaccta cgagcagaaa cggccgggcg ccggtaagcc   19320
agggcctgga gggttgaccc agtcagccca gtgcctccca caagaggcac ccagactaga   19380
aaccaccccg cctccactcc agcctctccc actatgtctg gggcccaaag catactgaat   19440
gggagattat ttcataccaa gcagatgtt ttccacctat aacgacttgg ggtggacatt   19500
atcgttttg aaaaatctgc ctcataggaa aaccattaca agcaaaataa cagaatgagc   19560
attcttaatt tgggatgccc aggtcgtgtt tttgtgggga tgcagggtgt gtgtgtgtgt   19620
ttgtgtgtgt gtgtgtgtgt gtgtctgggg tgggtggtgt ggaaccatgt aagtagtgta   19680
cacactctga attcatagtg gtctctctga ggatgctact gtgaccagcc atgtcggaac   19740
tcaacacatt ttttgaagag ttaaaaatgg tcagccctct tgaatcttta cacattctcc   19800
caaattatat gacccttctg agaaatgcag aactccccca aggataaagt ggatgttaat   19860
ggaaaacatt ataattttaa caatccgcat taggctctgt cctagggaat tcctaggagt   19920
ctttgggatt ccctgtggag tccttggaaa ccagaggcta agagatggag ctataggtag   19980
tctaggattt ctggcaatgt aggattgtgt tgggctgtct gatctggtgc caaagttccc   20040
caagggtggt gggggtccc tccaagacag gtgtatgaag ctcaggcatg ggctcagaag   20100
agggcagaag ttggctaaga gtgggcagtt gagtagaagc cggggagat gagggaggag   20160
agagaaaaaa atcctgagtc tggggctgtg gccctccaag gctttgggga gacactggaa   20220
gaggccaaat ggccaacctct ctgtacgggt ttctgaaggg cagaaaggag aggggggttgg   20280
gaagcaaagg gtatttatca gtgacgcagt gcaaaaggcc ctctggcttg ggaagctgag   20340
cagggtactc agggtgcatg gacaggctgt ccctccccac cagcctctct ctctcttcag   20400
gctgtccctg tcacaggtct catatacgtg ccagtgcccc catcctcccc taaggtgtca   20460
gcttacatgg acactggggc cttgcccttc ctctgccatg gcctgatagc cccattggga   20520
actgattttt tcttctcttt taagaagcca aagaaacttt gctggttctt tcatcctttc   20580
tttctctcta ttcctctttc tactctgttt cctccttctt tctttctttt cctgcctcct   20640
ttcccctctc cctccactgt cttgggatat gtcttacccg cgcaggagtt catccgctgc   20700
atccaagggt aaaccgggct cgtgtacttc cggtcggcgc cttcgtcatg gagtgctttg   20760
ccctgcccgc tgctgctgtc gggtttgtac tgctgctcgg gagaaaagtg caggtagtcc   20820
ccggggcccc tctgcttgcc actgcccgag ggcgaggcgc cactgaggtc cttatcagaa   20880
tagaaacacg aggccccgta ctcgtaggac gcccggttgc aggccaggac cgagttggac   20940
tgttggtaga aacaaggtga ggtgtacgtc ttgtccggga gactcgacgc cccgtacgag   21000
gccgggaagg gcctcagcgc gtcatagcca gcctggtaga ggggcagctg gcccaagaag   21060
gagtcctggc cgctgggaag gctcccgggg aaagtgggat tcacaaaata ggaactcatt   21120
tgcgcgcccc tctgcaggac tgtgatttgt tgtgtattag tacatctggc tataactatt   21180
agtagtcatc gaactggttt gtttctggat ggccgaacgc caaaagcgac agcagcaaat   21240
cgcaccagct gacgcggcgg cggccaatgg gagcgaacgc cggagcccgc tccccgggga   21300
ccgcggcgac cgaggcagca aagttacaaa cagcccccag cccgcccgcc gccgcccgc   21360
ccggcagatt aatgggcgcg cacagctagc cggcccggct ctcttcccga acgccagcgg   21420
cgggcacggc cctttcagtg gcgagcagat caggccagag tagggacact aatgcttggg   21480
```

```
ccgcctcaaa ggccccgcca ggtcccctcc ttcctcctcc ccttttttgct ttattgaatt   21540 ttgcgggttc cccgcccctc ctcctccaaa caggaaacct gaaggtcctg ctccaggagg   21600
ggcagtgaca aggtggctt tgctccctgc cggcctgcac tccaggcacg cccagagtt     21660 gcccctcccc tagcgctccc ctattcgtgg gtgcgagttc ttgagctgga gcaagggcca   21720
tgagaaacca ggccttcact ctatgctctt cactcgtgcg ccttaggaat cggtgaactc   21780
cctcattctc tccttctccg ctagcaccag gggcctgggc cttgcagccc agagctgaag   21840
gatcacctcg agctgaccag gactcagcca aacgtaggtt cttcccaccc attccctcct   21900
cccacataca catcctgttt gagtcccaag gggctcaatg gcccgcgcct gctggtgtc    21960 aaagcactcc ttccagctgg gcgtccccat cccacctttg aacccaggga attgaaaggc   22020
cagaaaccac tggtttcaac aagaaaggac cgacagagca gtggccgtga gactgggctc   22080
ctaagacagc cgaggacct gctcccctgc ctagcgcctg gggactcagc atccactgcg    22140
agaaccgctc agagctgagg cagataaaaa tccagatgtg gaatctctct gtccacattc   22200
cagaggcaca gaagacgcag aggccctggc caagctgggc acagagggca gctctgcagg   22260
gcccaaggcc gcgggataat tgatgggctc ggtttccggg gcgcccgaca accggcactg   22320
tcctggggcc gccctcttta ctgcccttcc tgggaccgca gggagggctg ccgcccctca   22380
gtcgctccgg aaccgggaat agtctcaccg gctccagaaa tcctgaattg ctttcactgc   22440
tgtcccaggc ctggcggtcc ccagacagga cattaaaagc ctgtcctgag ctgctcactc   22500
ttgcctgaga ggtgtgcctt cgagatagtt gacttttaca acacatggat caatctcgtt   22560
ttgtaaaatg tgatagcagc ccaatggcat ttttacaact gtgtttgttg ggcttgtaaa   22620 acccccttgaa ttagctttaa aatcctcaat tctgtggagg ttgaagaaag actatttacg   22680
tgatttggat ggatttctgg agactgttta caagatctgt aaaaccctgg ccaatgcagg   22740
ctcacccggt tcaggactta gtggggaggt ggcaattggc agtgttccag taggaatcta   22800
gtaatgactt agtctcttcc ttgcttttca atttttttcc tgaactctcc tcccacaaag   22860
ggaaaaaatt gggaaaggac tggcctaagg tcgacctccg aagagcccaa gaggcactcc   22920
tggaaggcgg ctgctagccc ggcaacgggg gctacccctg gaagccggat gcctgttccc   22980
cagtcgatcc gtcctggaaa gggtttactt tgcatataaa gcagggcctc gaatgagagg   23040
atagaattgg gcatttccca cacattactt cagggaaaga attcaatagg tgaaaatgaa   23100
aactcgagtc aaaaaattaa aagggacttt taaaaatagc tgtttgaaga aaaacatgtt   23160
tgtgttattt ttttcttaaa caaaattatc agacaacagt gattttaagc aagttattat   23220
ttaaaatgaa acaaccgtt tggagatgac aatcaatgtt tacatttatg atttcctttt    23280
cattccgcca tgtcccacat agtggtgggt cagtgtcaat ttactattat tattatttgt   23340
catgccttga ccaggattct cgatctaatt attgttccag ctaacaagag aatttgattt   23400
ctcagctaag aaccagaaaa cattatattt ctagcttcta taggcactaa gatggaaaaa   23460
catatattac attggaatct ttacatgtta gccaaggcta gtgcatatca tttctccaac   23520
cagatattct ctctctctct ctctctctag agagagaggg ctattccggc aagaataggc   23580
accccagacc ctccaaaggg cctcctctgc gatggtgaga atggccaccc cagggctctc   23640
tctcctccct gccaaagcca cgcagaaagc gacttacctt tcagtttctc tccaaggggg   23700
gcaggacggc gagctgggcc ccactgtctg cccttgccct gggctgccca ttgaacagct   23760
ccacctctgc cagcctggag ggtggtctgg gagtatgtag gtgtgggacc ttgaaggcca   23820
cctcggtcca gccagctcgc tagcccagac cagagcccaa agcacacagg tgcggcctct   23880
```

```
gcccttcaca gccctctcct ggagccaaag ccgtccttct ttgccatagc caatcctcct   23940
cagagcagcc aggcctacag gcctcaggac tacaggtagt ctctccgatt gcagaatccc   24000
aaagccagag tgttccctga accagcgtgc gcccccagaa cgccttggga cgcgcagttt   24060
ggacagaagc agccatgacg tgccaggcgg cctgtgcaac cagtctccat ggtgctggag   24120
tgggggtggg ggaggacccg agtctataac ggcgtccagc tccggtcagg ggtagccgag   24180
gcggggagat ttcccggcca tataggctct gggtgatcgc cccccaggtc cccttgcgtc   24240
cccctctacc ctgcttgctg ggaaatctct gaggggccag tacagcagtc gcgccaggct   24300
gcaagaggcg ggctgcagct ggcgccggtc ccggcgacgg ccacggcgtg gcagcagcga   24360
gcgccagcac ggtcgcaata aataatcggc ccgcggcagc cgcagtcagg aaggcggcgg   24420
acctaggatg caaatgcgcc gctttatccg ccccgagcgc acgcagagca cgggctaacg   24480
tcctaaacat ccacagcccc ttcctattta tcgaatccat accaagatat tgtctcaagt   24540
tggggaaaca acaacccaaa caaaaaacaa acaaaaagaa cctcggactc ttttcttgtc   24600
gctgtccgag gagttctcgg ggcaaatctg gtctgatgtg cacttaggcc gagctacagt   24660
tcgagccacc gcgctacgca aagccaccgc cagcagcacg ctctgcgctt cctcccgggc   24720
agctccacca tcctctcccc gctcgcggaa ggtggggagt gcggtcgcca gtccgttgcg   24780
ccaaggtgga ttggggggtc ccctatcgc ccagactcgg tttgcgtcct tccttcaacc   24840
ttagctgcgg gaccctgcca cgcgcgctaa cagcattatg tcctctgcac cgaaacttcc   24900
caccaagtaa cacccaatta atcccatcct ctcctccaac acagaattcc acccacgcac   24960
ctattccccc tcccagcgct tcagacacct ctctcatcga aaaccgggc gaagggaagc   25020 cggcaacgag cggagaactc tggctgaatt agtaagtttt tctgtttccc ccttctacct   25080
ttctctctga aaccaattcc cacggagtag aaagtgctgt gctgatgcta ataaaatgcc   25140
tgtggattaa tgcactttgc cctcacctct tcccaccttc ccaggtcaag gatggtctcc   25200
tcttgttggg gaatccaaca aaaccaaata gggccatgaa tgaaaacaca aaaatccaaa   25260
cccaaagggc tggcggggaa cacagtgtgc cgggccactt ccttttgggc ttcacggggt   25320
cgctagggaa ggggagagag acgacccaag ggatgctgcc ctgtgccttg gcgctgtgcc   25380
acggagggcc gaaggaaggc gggcacttac tgccaaggcg agccagggag gggagagaaa   25440
gggagtggtg tgtgtgtgtg tgtgcgtgcg cgcgtgtgtg cctgtgtgtg tgacgtgtgt   25500
gggctgtagt gtgtgatggg ggcaagtgtg aatgggtgag tatgggtaag ggggagtatg   25560
cccctcttaa agcctccctg ggtgccctct cccaccgcta ccgccgccgg ctgtcgcctc   25620
accacctttg ctcctatctc ctccccacat gtctcacctt cagacggtgg ctcccagaag   25680
ctcctgcccc tctgacagct gtcgcttggg cagcccgaga gaagaattgt cctctttcct   25740
ggtgccagag gacgcaggaa attagccagg ttgcgagttg caaagctgct gccgcggcgc   25800
cgggaacgga gcgcgcccaa tctccagcgg gagccgccag gcctggcctg gccggggctt   25860
cccttcgctc gccatctccg gacaaagcac agccgagccc ggctggaagg cagagctccg   25920
aagcaggcag gacggagcgg agcaaaagaa tgcggctcta ttctcgcaag ggaaattata   25980
aaaaagttca tgttcacggt tctcatccac atgaccgaca gcggccaatg gaagggccga   26040
acaactcata aagttgtatt gcaaagttgt aaattttcat aaacaacaac ggattttatga  26100 cccttttcccc atcactgaga ggaggcagct cttacaccgg cgccatctta ccaccgaggc   26160
cgccccgact tggggcctca ggttttacag acccttttgg gccaggtttt actaaaagag   26220
ccataagaag cgggcccagc ccaggcagga gactggagac gaggtcttgc aggcggaact   26280
```

```
caggatgctc tgagctgccc gcacaacccc tggaccttca cccctcgccc cttccccgca   26340
tccagctgcc ccagccctg cccaggctgc gtagcctagc gggggtctgc ggtcctagcc    26400
cctccccgcg ccacctactg cagtgccgga ccctggggcc ccctcgcctg gtctgcaggc   26460
ggggtgggga ccttaaatcc catttcctag cctggggctg ggttcagggc gcatgcgaat   26520
ccggaatcag ctctgggtaa tgccccttc caagcccact gctcagcctt agaggaaagt    26580
gtggatttga aatttcctca tggaattgat ggaggttttt aggtagattc atagaatata   26640
acgtatctac caaagattcc gttttcaagg gatctagaag atgttagtgc acacgcaaaa   26700
accagacaaa cgtctctaca cggataaagg cacatataca attatgcaca cagggaaggg   26760
catacactct attgtgggca cagaatgaca tgcaattatg gacacacaaa aacacatgca   26820
cccaattatg gacaccaaaa tatatacaat tgtggaatta ggtaaaaaca cacacagaa    26880 aatacataca cagaaaaata agcacatact catacaaata cacacataaa aatacattaa   26940
aaagatacat gacaccaata catgggtacc caacacttgg accatcacaa ggacagccac   27000 cccactttg cttccccact gcccctgcc ctccagccat actcacctcc cctttcccag     27060
tcccctctgg ataaggcagt ccacatttt ctttgtcacc acgcatcttt attttcggtt   27120
acataaaaca cagctgggct gggaagtgtg ccttccctga accccaggat ggagctgagc   27180
agggtacagg acaacacagg agatgaaggg cattgcggag ggcattggac ctccccaccc   27240
actacagtta actcaagaca ataccatg ctacaaagtc accccattaa cacatccttt     27300
ccaagtcaag acactgcctt acaaatgaac tccaagacta tagaaatgat aaaaaaaaat   27360
cttgttcaaa tatacagtat ctgctattat aggaaacatc agggcgtaca tatttaacac   27420
agctgaacag taagatacag gagccagagg aaaggacagc gaagctggaa gcatctccac   27480
agtcctgcta agcagaagct aacccacaga tctgcagcca gctcaggaac attcccctcc   27540
agaagtgggg gttgatgggc ctgagctgtg ggtgccaagc cagagaagga gggattgatt   27600
ctagggtgca agcacttagg atgcttttg gaataaatat attattttc gatttaaata    27660 gatgccaata ccctgatcct ggacctcagc acattctcag ggcagcctca gggaccccaa   27720
aagctgcggg ctgtaagcag caggggactt gcctgggagc agtcggcact aggtagcagg   27780
caagccagcc agcacaaaat aggtagtttt aggggagtag gtagtagtga gattcactt    27840 cttgcgggtc tgggagggtg gtgctgggtg tctgccagtg ttgggataca tagggacttc   27900
ctgggaatgg aggccctctg gggctggata catagttagt ttgggggtgc ctcgagcaga   27960
ggcctgtgct aggtagtatt ttggacgcgc cagagcaggg ccggctggcc tggggttggg    28020
ggtgtctttt ggggtcctcg gaggcagagg gaatccaagg cgacccagtc tctgcggccg   28080
ctcagtccac aaaagttggg agctggagta ggtgatgggg gtgggtagag tgcaggttgg   28140
ggactgggtt gctttttgt tttgttttt gttttttaca ttttcttta tttttcccat     28200 ttttgtaagt aaaaccagtg agtctcttaa agacgctttt ccgactgtcc ggtgcagaga   28260 gggcccgga tcggcccctc attcctcctc gtcttcctct tcttcatcat cgtcctcctc   28320
gtcggccttg tccgcggcag cagtggcggc ggcagagggc acggcgccct cgggagctgc   28380
ggcggcagtc ggaccttcgt ccttatgctc tttcttccac ttcatgcggc ggttctggaa   28440
ccagatctta atctggcgct cggtgaggca gagcgcgtgg gcgatttcaa tgcggcggcg   28500
ccgcgtcagg tagcggttga agtggaactc cttctccagc tccagcgtct ggtagcgcgt   28560
gtaggtctgc cggcccgct tcctgtcagg tcctgagaac agacatgcag acacatgaac    28620
acaaggacag acaagtagac agggcactcg ttaggctgct gtcccagagc ccgcaccttc   28680
```

```
ctcctggcct agtccccagc gagcatcccc ctctgcccca ggccccgaac tgagctaggg   28740 gaggagggggg agtgttaggg aaagacccca actgcagtgc cagacgcgca ggcagctctg  28800
taatgagcaa aggcacagaa tctcaacttt acaaccgacc tttccagccg gctaagcttc   28860
cacaatgtcc tgcttcctct gacaaaggaa aactgtaaat atagagtgtg agcaagtggg   28920
aaacgctgca cttttgccat tcaaagatga gcccggccat tcccctgcct tgctaggcaa   28980
gtgggcgact cttcccagca gcctgagccc tcatccccag gaccttccta gggcaccccg   29040
accctctgtc ctcattccct cgcccccatc ttgaaatgga ccctggcaca gggtcgggtg   29100
agaggccctg gagggcttgg ctctcctagc ttttgagaaa gaaatgtcag gcagcaagga   29160
aaatgaggag agagagaaga agaaagggag ggagggtgac agaggaggga gaaagagaga   29220
cagaatagcg aacaaactta atgttaaaat tccaagacaa atggagttaa ataaatttac   29280
gaggatcgaa cccattaatt gggccataaa aagttttatg agcctcattt acatacaatg   29340
ctatgggctc cacgcaatgg cgcctccgct ccaattaaaa ccagaaaggc tgcgccggga   29400
gtcacggggc taccggctcg caacagcctg gctccgctct tccggccccg cgccccgcgc   29460
tccgcgctcc ccagcgctgc gctccccgct cccggtcccg ctccgccagc ctggcccgcc   29520
tagcgactgc gcctacctga agaccgcatc caggggtaga tgcggaaatt ggcctcagcc   29580
gcgccatgca gcgcgccctc gtccgtcttg tcgcaggcgc cttggcgag gtcactgcag   29640 agcccgggga tgttttggtc gtaggaggcg cagggcaggt tgccgtaggc gtcggcgccc   29700
aggccgtagc cggacgcaaa ggggctctga taaaggggc tgttgacatt gtataagccc   29760
ggaacggtcg aggcgaaggc gccggcgccc gccccgtagc cgcttctctg tgagttggga   29820
gcaaaggagc aagaagtcgg ctcggcattt tggaacagag aagcccccgc cgtatatttg   29880
ctaaaaagcg cgttcacata atacgaagaa ctcataattt tgacctgtga tttgttgtcc   29940
ggcagctttc agtgtcggtt ttacgaggta gagtgatata tgataacatt acaccccccag  30000 atttacacca aaccccattt tcttttggac ggagctcgcc gcagcacgtg accgcccaca   30060
tgaccgcctc cgccaatctc agcagtcctc acaggtggtc tcgctccgca gggcccgcag   30120
ccgcctagaa tggaagggca agaggctcaa atatgcggcc aaagaatccg cccgcgcccg   30180
gcgggcctgg cgcgtcccgc ggaaaaagac ctggaggctc cgcggagcg cccagctggc   30240 ggccaacctc cgcactgggg tctgcggacg ccaggcggcc cggccccacg cagcacccc   30300 cacccgcccc cccgccgac tcctgctagt gagccctgga ccaagcttgg gatcctcccc   30360
atccctctcc tgtccgcctg cccagaccct ggaagggtct ctgtccccg caacagcctg   30420 ccccgcggtg gccttgtggg caggactcag ctatgagcag atcgactctg cccaagtctt   30480
ctctcaccca ggtccagtgg gcgacaggcc ggacttagac tcggatccag acggggaagg   30540
cgcagcatct cttgcagctg cagagagatt gccaccgcaa actggagcca tgtggttcga   30600
ataaagtcaa cgtctcccag cttcctttcc ttaatcggag gcacactgtt tatccgccct   30660
aaaggaagca gtgaaatatt tatctattaa tgagactcat ttgccaacag atttattaac   30720
gtggggttcc cctccctcct cccggacgct gtagtgctgc aggctctgtg ccttcgctcc   30780
tgggcacctg gctggctcca gcagtccgat aaattgctaa agattccttt gtccttcca   30840 caacttctgg ttcccctctg gcgcatgggg agccagggct gtttccccca gcttggaaaa   30900
atctcgggcc tgcaccccttc caggcactcc caatactgga aggtttctgg ggtaggccgg   30960
ggtgcctggg aacaatacat gctttagagc ggatttggag agggggctct ggcgtctagg   31020
gactgcaacc cactgtggac ttcctttct tttgaagaca ccgaaaacaa ataggggaaa   31080
```

```
ccacccccta aaggccaccc agctgtggag gcttcaccta tccaagtacc agctcacatg   31140
gagctgagcg cacagtggtc tcacttcctc ccatccaggc ctccaattcc taccttccag   31200
gcctccgacc cctgcaccat gttgcaccag ctgaagcccc tgccgcccac cgctcggtgg   31260
aggatggtgg ggagaaccct tcccctaaac gcctcataaa ctgcccggct gcgctggaag   31320
cccggccacc tttactgct cagctcgatt acacaccata aacccgacct cacaatggaa    31380
ttgccccgga aattctcctg taaattgtag agtttagttc cttgtgtact gagcacttcc   31440
catcactttc agagggtcca ggccgtcccc gtttaccgca ccctctcagg gggcccagg    31500
aatacaaaag gtggagggag ggttcagatc gggacgccac ggagcccag ttcctgcgca    31560
gtgaaccacc ggggcttggg taggaaggcg ggggctggtg gggcaggtgg gcgctgggct   31620
gtctcctccc gggccacgga agcctggggg taggggtgtg gagtgaggga caacatccgg   31680
ggacgccttt atggcggatc agatgatacc ttgtctccga tggagaatag agggagtaag   31740
acaaaagaa aagacctaaa taatcccagt cgcatcgcct tctggaagga aataaaaacc    31800
caagaaagtt aaaggaagat gaagcaaaca agaaggctag gagatcaaag aggcagaatt   31860
agaccgtttt agaccaataa attttctctg gggtgacaca cagcaagacg caaagagaaa   31920
agaccaaggc ccccgccgcc gccgtctgtc tagactcaag cgactgaagg ggccaacaga   31980
gctggtgttt aaagtagaac ctgcccagtc caacagcccg agcagggagc gatttcgggg   32040
atcgcgggaa ggaacgcact tcgccaaggg agggccgggt gccctcgcca ccggctcatt   32100
cctgctccgg ttttgcccga tgcgcgtcca ggaggttctg gcaggacgca ctgcccctct   32160
gccccggcca aggaggatgc ggatactgcc cgcaaggctt cggcctttat ggacccaagt   32220
cagccaactg ggccgagtcc tgcggacacc gaaacctccc tttcgtttcc aggcttcctt   32280
ctcccctctt gccctctgtg gtctgattta aaacgaaaag gtcggataaa atcaggcttt   32340
caataaggct tctttaactg tgtgttctct attcattggt tctctactta tttgactgaa   32400
aagacacaaa tgcactaggt tatgtgagat aattttcaca gaaatactca ttgaccctca   32460
gcctgaagca ggcacatgta ggcgggtttc taatcagtag agctatgttt agatagacat   32520
tttccactgc cgtccctgag cttccttcct acctactggc agagcgtgtt cactctgctt   32580
cttgttacca aataccaata tttaaattca attatgaagg taaagccagc tctaggcagg   32640
gaacagcgcc ttccagagat ttgggtggca ggcaaattgc ttcctaaagg tttccaccct   32700
tgcctctctc accagctgca tctgttcccc atccagtgag tgagtgatcc ctagcctggg   32760
tgcaaagaca aactcgtacc tgtcgtgtac aaatgagatt gggttggtgc ggggtcttgc   32820
ctgggtgaag gtccgcagcg gggaagccac tcccaggctt cccagaggaa aagcagactc   32880
ccagccacca gcctgccaag ggcaagggag gagccttggg acagtccacc caggcctggg   32940
agaccctggg cggcctgcac ctacctgagg cctccgtgat cagtggagag acgcagtcgc   33000
caccgatctg tgacttcatt tatttgtagt tacacaaatc gagctttctc tctgcatcca   33060
cggatctgcg acttcactat ttatttgcag ttaacataaa ttgagctctc tatctgcggc   33120
ttgaatacaa agccacggtt gactcccagg gaagctataa aaccctccct acaatcagac   33180
gttgtgaaat tatatacgga aatgtaatga aggtgtgtgt ctgtaatatc tgtatctatc   33240
tatctatcta tccatatata tatgtatatg tatatatgag atgagagaca gagagggaga   33300
gagagaaagg agagatattg tgtgtgtgtg aaaggaaaga gagaacaaac acccgggaga   33360
gacatcaacc aaaaatccagt cccccagtttt acagcgtgaa agcactggga tgcgggtcgt   33420
aaacattttg tgggcttggc ggagactatt acgacccaaa taaatgcact gtgtagcgtg   33480
```

```
ttcacagggc tccggggcct ttcgaaaggt tctctgtttg cttttgcgtt ttgcctctgg   33540
aaccattcga catccgtggc tgatgcgcgc acccgagagg aggccgaagc gtgttccccg   33600
cctagggtct gggagaggct gggcctggat tggggtcccc tcccttctgg cctcctgatg   33660
ggtgaacgcc agagcagcct cggttcctgt acagcggagg gcatgccgcg gccagagaca   33720
gcccgggcgg cttccacact gtgtgcgaca cttttggtgc tacggtgtga ttgttatatt   33780
aaacatcaca ttaaaaaaat aaccaaagca gtccctggtt tgtccccag  gattctcctc   33840 ccagccaact cggcccggcc cctataccta cagtggtcag acaccgagat tgcctttacg   33900
cccaattttc accgcctaat tttattgtct cgattcaagc cagccgagtc ccggggtcct   33960
ggctctgtct tgggttctgg ctcgccgggc cctgacccag gtcgcaggtt tcggggcct   34020 cctgggcggc cgcggacccc gcggtcacgg tgtgagccct cggcacgcac cgtgcacacc   34080
ctctgggcgg tcatcaagtt ctggggctgc aggcgttcct cctgtgtccg ccagtcagcc   34140
ggggctctct ggcgcctggc tgtgtcaggc ctgtcccagc tgaggacggt gaccctggag   34200
ccgcgcccgc gcctggagct gcagccccgc ggccgcccgg acagctgcag cccggcagca   34260
ctgggccccc gggatggggt cagggaggcg cgagcggtga gggtcgggca agcccccgcc   34320
gattccttgt ttcccagcga ggcttctagc caggcttgag cagcccagaa aatatagggc   34380
ggctgttcac taaaatctgg ggctcccatt ccagaaaggc tcgtgtcaag tcgacatctt   34440
aggaacttca caagggtcgc ggaggcggga gatggcggcg cggaagcctc ttgcatggag   34500
ccacactgcc atctgctggc cgccgttttgg tactgcagcc tcagctacct ccgccggcct   34560
gagctttggg agccgccggc tagcccaccg cacccactc  ccaaacgagg ggcgtgggcc   34620 taggtccccgg ggagtctgcg tggagcccgg aatctactgc agaggaggca atgccaataa   34680
aagaggtgtt tccgcagccg ctttatcggc ggcagacaga acaaatgaac aaatgaaagg   34740
gctttggtgt aatatcctaa ttggggctgg acagttgtaa actcattaag ggacgaattc   34800
cagacagttc gcagacccgg cctttatggc acactcttac tgcctattct ttgaagttcc   34860
ttctgtctgc aacaacagag ggcgtcccaa cctggcggcg gggtgggggt ggggttagg   34920 ggacgcctca tccacccgcg ccctggttcc ccttttaagc ttagaacaca tccaactttg   34980
cagaagtcgt ggagtggggg aaggggtcg  ggcgagggaa gcaaggggt ggaagcgagg   35040 ccgaaccctc cggccacatc tggaaagcgc tcaggcctcc gaagttgtgg ccgttccccc   35100 cccccgccc  ctcgtagccc tttacacccc ataaacggta acagccctca ttttcttta   35160 tggcgcttag gggctcgtca attgcctcag ccctgcctct gttaggcctt gtgctcgaga   35220
ggtgcttgca gtgcaggacc cagattctct tgggccaggc tggcaggact ccgcgggggt   35280
ggcgggcggt gcgaggatgc agggctttgt tcctttgcaa gccccaaaa  tgtttgcctg   35340 catggccacg ttgggccggt ggggctccta tttccctctt cagagcctgc ttagaaggcg   35400
gctcccagct ctctatcctg tcaccctctc ccccttttcc tcaccaagct aacgaaggcc   35460
caggtttggg aattttctcg ggggcaccaa ggtgagagtg gtctttccac tgctactggc   35520
cagaccagac cagctcctca ggggcttctc cgccgtcccg cacatagaca caaggccggg   35580
agcctggctc ctccgccggg tttcccagct ttttctcgcc gccaggcagc tggcctgttt   35640
gggagagctt agctcggcgg actggttgtg gcaggtcccg ctcctgaaag ccagccgag   35700 gcaaaattgg ggctctttct caccaccca acccgcccct acccagagac tctacatagg   35760
ctcccctgac ccagagaaga aggtgcaaag agcagacccg caaaaaatag aaaagaatca   35820 atatattta  tttggcaaaa agttaaatat catctcaaca caacaatttg gtcagtaggc   35880
```

```
cttgaggtaa ctattgcaaa atatacagtg taagttcagt ctgatggaaa ccccagattc   35940
atcaaggata caaatctaca gtagcccaat ggcggtttca tagtgtataa tttattatca   36000
ataaaattaa ctccgttaca atcagcattc atttcctcca attaaaatta agcataaacc   36060
ctaggtagta accttctgca catatgtata gctccgaatt tcctcactgt tcgtctggtg   36120
caaaaacaat attcaagctt gtctgattat gcatattttc tttaatcata tagattatat   36180
atacaataga caagacagga ctatatagat aatggacaga cttaaatgcc cgcatttta   36240 aggtggagaa aatgatgaat ctatgcatcc ccgagaacac ttaaaatttt tttttatttc   36300
actgggaaat tcttacagct actttacaat cataggttaa cagcctagtt atacagaaga   36360
catattccac tacagagcta tactctatgc aactgttttt ttcccctcat aaacaacctg   36420
agttcaaatt gaattctatc ttccacaatc acaatgggtg catcacccag tacacagaag   36480
tttgaatcac aaaacataat taccacaata aaacacagtg ttcaagtatc ttggcagagc   36540
aatctgccgc acaaactgca aattaaatta actacacaga ctaaaaacta tacagcctac   36600
catcaacagt tgtgcattat aaaaaggtag tttctttcct tttgttttaa gtcaggaaca   36660
ggtagatttt taaaaatata tatacaagct aacacacaca gctatcagca ctaatgcccc   36720
cccctcaact tttcctttt cttatagaaa atggaaagct tacaataccc cctccatcaa   36780
agcggcaggc ctacgagcca gcctgaacag ggtttgcctt ggaaaagatg tggcctgagg   36840
tttagagccg ctttgtgcgg ggatggtgga ggctagggtg ggggtgagag aagggagaag   36900
gcggaagggg gacggacagt tctttctttt tctctctagc ttacccttt ttctaaataa   36960 gcccaaatgg catcactcgt cttttgctcg gtctttgttg attttcttca ttttcatcct   37020
gcggttctgg aaccagatct tgacctgcct ctcggtgagg ttgagcagtc gagccacctc   37080
gtacctgcgg tccctggtga ggtacatgtt gaacagaaac tctttctcca gttccagggt   37140
ctggtgtttt gtatagggc accgctttt ccgagtggag cgcgcatgaa gccagttggc   37200
tgctgggtta tctgcgggga agagaaacac tgggtttagg agcagaagac gcacatcccg   37260
ctggggcaaa tgagcctcct gcatggggtc tctggccgaa gtgcagaact ctgctgaact   37320
ggttaggaaa ggcagtcagg cctcggacac aatggaaccc tggcagacag acgcacagac   37380
agtcacttaa aattgcacgc agtaaaaactt tggctcgccc tccccctccga gaccttcctt   37440 tctcctactc tgtcctcttg tccccttct ccttcctccc actctcaaaa cgctgtatag   37500
aatgaaattt ggaaacaggt ctccttgcca cgcagaggga aagcatgctg ccttgtgttc   37560
tgtagcaaga ttaggattcc tctgtcccgt tcactgactt cgtctttctt tcccaacctg   37620
tccctctacg ccccccactc cttatttaac cttcctggaa ggccttcgga gctgggcaag   37680
ccgtcagggc gccctaaggc cgctgatcac gtctgtggct tatttgaata atctgtcatg   37740
gggacccttg tggcccgggt cgcccgcagc ctcatcttgg caggatttac gccgccactg   37800
gccgaaggca agaagtggaa ggaatcggcc gtctccccca gcgtcccagc tccggctgcc   37860
ctggctgccg ccgctcacgg acaatctagt tgtacaaaag gctctctggg ctgcactgct   37920
ttcgaagaac ggcccaaagt atctcggtcc tgggcctggg cagccaagga gagggcggc   37980 cagtcttggc tcgtcccgaa gtgcccgccc cgcccctct cgctgcagca gccgcctcct   38040
ctcccgtagc cctgcgggcc gctcttcact gctctccaga cttggggccc tatctgaggc   38100
gtcccaaaca ccaacttctg gctcctggcc ccaactcgag aggcttccag cgaggacgaa   38160
ggcaggctcg agaaaacct ggcgggccag cagatccggg aggccggcgt ggaggcggcg   38220
gcggatttga agggaggaga cacttactgg gatcgatggg gggcttgtct ccgccgctct   38280
```

```
cattctcagc attgttttca gagaaggcgc cttcgctggg ttgttttttct ctatcaactg    38340 gaggagaacc acaagcatag tcagtcaggg acaaagtgtg agtgtcaagc gtgggacagt    38400
caccccttct ggccgacagc ggttcaggtt taatgccata aggccggctg gagggcaagc    38460
ccgcgaagga gagcgcaccg ggcgtgggct ccagccagga gcgcatgtac ctgccgtccg    38520
gcgccgccgc cgccacgggc gcctgggggt gcacgtaggg gtggtggtga tggtggtggt    38580
acaccgcagc gggtacagcg ttggcgcccg ccgcgtgcac tgggttccac gaggcgccaa    38640
acaccgtcgc cttggactgg aagctgcacg ggctgaagtc ggggtgctcg gccagcgtcg    38700
ccgcctgccg gggaggctgg cccagggtcc ccggcgcata gcggccaacg ctcagctcat    38760
ccgcggcgtc ggcgcccagc aggaacgagt ccacgtagta gttgcccagg gccccagtgg    38820
tggccatcac cgtgcccagc gcctggcccg cccggcccga cccacggaaa ttatgaaact    38880
gcagatttca tgtaacaact tggtggcacc ggggggaag tacagtcacc taataagttg    38940
ccggcgcccg cgccccatt ggccgtgcgc gtcacgtgcc cgtccagcag aacaataacg    39000
cgtaaatcac tccgcacgct attaatggtc cgatgttttg cagtcataat ttttatagca    39060
aaagccatat gttttatgt aaagggatcg tgccgctcta cgatgggtt tgttttaatt    39120 gtggccaacg acgattaaaa gatcaaatct agccttgtct ctgtactctc ccgtctcccc    39180
ccccatacac acacttctta agcggactat tttatatcac aattaatcac gccatcaaga    39240
aggcgcgggt cccgcgtgcg agtgcggcca gcggagcccc tcacataaaa ttagacaata    39300
attgaagcca taaaaagca gccaaatcgc attgtcgctc tactgtattt aaatctatat    39360
ttatgatatt tcataaggag ttattgtttc agaagccaca caggctggcg ggaagtcgga    39420
aacgaccaac agattcgttt gcctcgccgt ggctcccagc tgtaaaaatt tacgaggact    39480
tggaaaggtt agactgttgt gtttggttgg cgagctccct gtaaataatc cctgcggtcc    39540
ccgggagagg cgagtttacc cgcggccgcc ctcgaaaagt caaattcaac gcaggatccg    39600
tcccaaacgg agccgccgcc ggccctacca gggcactcca ggcagggacc ggccgctcag    39660
ggagtaccgc gggtgtaggt ccccacagct acccgcctgg agcgagggc gcccgggcaa    39720 cccttaaatt cgcctttgct acgaggaccc cacggaggag ctggccagga gggagcggcc    39780
agccgccacc agggcgaagg ttttgagggc ctggttggtt gtgcggcgcg ctcggtcccc    39840
ggccctcgac cccacgcaca cgcgcgccca gcccgccttt ctcatcagct ggcaatcagg    39900
attcccaggc gcaggcggct ggcgaccag ccctgtgctc cagcctcaga ggctctaacc    39960
atgagcgctg caagcctggt tgcgctccgt gaatcccagc tggggaaaaa actacaagtg    40020
gcatgaatgg aaggcaagtt cggtttggga aaaggcagcc tcgcctaaga gaccccgcag    40080
ctccggaacc tgggaggccc gcaccgatgt ggcctgtccc ggggccgcgt gagcctttca    40140
gggctccttc ctcccttttcc agctgctact ccgggcctcg ccttggttac ctacggggcc    40200
cggagactcg gcggagaggt acaaggccca aagagaggca gccacagctc aaggccaggg    40260
ctggaaatta gaacggggag gggtaaaagg gcatcgactc cagtcccatt cctgggcctg    40320
gccacgttgg ggaagtttat ttctcacccg ttgggggtaa attaaaaggt cgccgccact    40380
ccgttaattg gaaggaaact cccccctgccc ccaattccta acagaaagca gcgactccta    40440 gaacagggt aatcaaattc acgtgtggat actgtgcctg caacagtgtg ttttcatta     40500 gcccacttcc ctggcggcga ggctggcggc ctcgggcgct tccatctctc tctctctctt    40560
ttgccttcat cctcaccagc agttccagta atccccccct caaacaccct gacacacttc    40620
cggctgggac tcccaaatac cagcgaggct gccaagccgc gcggataccg actgggtgcc    40680
```

| | |
|---|---|
| ccttcctgca cccgcgcctg gaagagggaa gtggccgaca caatgaactc cgaaatggcc | 40740 |
| ccgtcctgtc cgcctcatct ccctccccct aatattttcc ttgccccata aattcctcta | 40800 |
| ggtcatgccc accccacca cagtccaccg tgtcctaaat accccgcagt ccgccaggcc | 40860 |
| tctgagattt tcatttaaaa aattaaccct ggaggaaacc ctggctccca attttaagtg | 40920 |
| tctgcaaatg ggctgggcat gtctggatgc cttttccacg ttttatgcct gagaagacac | 40980 |
| tgattatttc agtatttttt aagtaaaaaa gctgttcctt taaacagcct tagccccaaa | 41040 |
| ataagagagt tactgaacaa ttagcaggcg ttgagtgtta agcagatgtt actggtgcct | 41100 |
| agaaagcgga gaaaaatcag aaaccaaat attgtcttcc ttcagcccaa aggtttggag | 41160 |
| ccagaatagt ctgactttt tgtctgcttt tattttcgaa gtgaaagaga ttgcgtatgc | 41220 |
| ataaagaaat aataaatgag tataatttaa agcggcccct tctcgactga gatttctgaa | 41280 |
| actgtgatct ctgaaataaa tccaatgccc tggtccagaa aatggcaggg aggagttgaa | 41340 |
| gggaatgggg tgtgtggtcc tttcagacag caggtcggtg gctgtgcaac gaaagagttc | 41400 |
| ctgggcctcc agtccaggca gggaaaggaa acagctttgt gggcacgaat ctgtaactgt | 41460 |
| gtgtgttggg agtagggaga gatagtttgt tttctgtttt ctgtagggaa aatggtcaga | 41520 |
| ctggctccca tctgtagact acaatttgga acgatgactc aagtttatat caatggctct | 41580 |
| ggaatttggg attcttttg cccatttaaa acatactggc tcttggaagg gtccccttct | 41640 |
| ccagcaccca gctgcacaaa ggtgctgtat ggaacatatt ttgtacctaa tggaagccac | 41700 |
| tagtaagcaa gcagtcaagc tttgccctag ccagtctccc tcaatgcggt caaaccccaa | 41760 |
| gctgtgaccg gcaggccggg aagagccagc taagagcttc ccagcgaatg gccaggctcc | 41820 |
| agcgaggctg gttgggcctc agctccagtc cccagtgagg ctggcgaagg cctccctgcc | 41880 |
| ctcgatatgg gcacacaaag ctgcagcgaa tgtcccctaa tcagatctcc tagtcagccg | 41940 |
| ttagcgacag gcgaagaaac gcaaggctgc cgccatccgg tcgtgatcat aaccgaggcc | 42000 |
| ttgtctgcag agtaacacac caggcccaaa cccaccgccc tcggcagccg ccccacgcgg | 42060 |
| gcccttcctc ggcagacttc ccaacctcta cttgagccgc agaggaaagt gagacccct | 42120 |
| aggctctcct gaagccagct ctgggcccct ccccaaggat gctttgggaa ggagataagg | 42180 |
| aggtgagata gaatctggca gagacggaag atgaaaaaaa gaccaacgga agaaaagaaa | 42240 |
| gcaggaagga gcaaaggaaa gaagaaaaaa agaaagaaga gataaaagag gaagggaaga | 42300 |
| cagggaaaag aaggaagaaa agagaggcga ctcctagcag cggccgagct tacagagaga | 42360 |
| agggtaagtg acaaggccag gatcccagcc tgccctatcc ttcctagtcc agcctgagtc | 42420 |
| tccactggaa ggaggttctt tcctgagctc acacccggga ctggtgtgtg tgtgtgtgtg | 42480 |
| tgtgtgtgtg tgtgtgtgtg tgttccagcc ttacaagaga atggcaggag gtccctgggc | 42540 |
| aggcgcaggc ctccagtggg aggctcagga tggaagcggg cgcccctgac cttgaatggc | 42600 |
| ccaaagccca gaattcctac cacgccccg gcgtccgcga aggagcagcc aacctaaccc | 42660 |
| tacctgctgt gaccaggtgg aggtgtgtgg tggaaggga aagccggccg gctggcaaag | 42720 |
| cgctgcggag aaagacacga ggctcctgag cagggaaagc cgaggttgcc accgcaggcc | 42780 |
| tggcacgacc agggccgtga tgccccgccc ggcccgaccc ccgcgcgcag aggtacctgg | 42840 |
| agacgatttc aactgaagta atgaaggcag tgtcgtgctg tcgagagaaa ggtggatccc | 42900 |
| aacaacagga aactacctaa atcaccgacc agttctggtg ctgcccgcga agggctgcct | 42960 |
| cgcccgccgc cgccgccgcc tccgccgctg ccgccgccgc caaggagaga accctgccat | 43020 |
| cgcgcctggc ccggcccagc ccagccccta ggcaacctgc gcccgccagt gcaacagagt | 43080 |

```
gccccaggcg gccgcaaatg cgtcaaggaa ggggaagcca caggccccag taaggtattc  43140
ctgggaggga gagggaggaa aagagaggga ggaaaggcag ggagagagga ataaaggcgg  43200
ggagcaggcg agacgagagc agctccgaga agcagtgtgc gcgccgcttt cccaaatctt  43260
gcagcccagc gagccggcgc caagaggcgg tagccgtgga aggctcgaaa gcgccaggga  43320
cggtacagat cccggctccc tgtctggccc cggcctcccg cctctcgctc tcccctctc   43380
cctcctagct gcccgcccgc cggggcgcgc gctcctgcgc cccctcccct tagccccgc   43440
ccccccact ctggcaagca ggaaacgcgt ggccctaagg agtgccgcca ggtgggggag    43500
gccgtactgg gggaggggga ggcccccatg cagtccagcc cgggtccacc taaccgctgc  43560
ctccagcggc tagagatgcg ctgtgggcca ggcctgctcc ccgattcaga ttgagggtca  43620
tctgtgaccc agacacccgc aaaataaccg gcctctgcaa gcctcctgg ggctcccgaa   43680
agaaatcctg tttggcttcc tctgtctatg tagctcccct ctcaactgaa atcactggtc  43740
caagacagcc acaatccaga tatactagca agccataaaa ctgaacaaaa gccgacaaac  43800
cttacggcac cagggctata gggcccagac aaattacgac cgtctaggta atatttaaat  43860
agatgcctaa agtaattgca ggggctcggg ttagtcctcc tgttgtaaaa gtggtgaacg  43920
ggataaagtg gaaggtgaag ataagaagtc aaaaagagg taaaattaaa aagcttcatt    43980
ccacagcttt tattctataa gaacataaac atcgtctttt tccacgcaca gcagcaatac  44040
aatattaatt tattctgatt taagattaga agtaaataga gctagaacta acatttataa  44100
taacgataga atgcatttgc ttaaaacaag attggcaatt cttcataata atagacattt  44160
atacagattt gtatttatag ttttttttctt tttctgcatc tacaggtttg acccttttat  44220
gcatgtaact tcacagtata aaggaaatcc aaacaatgtc tcccttctct agtttattcc  44280
gcttacccca gtcctcctag gcttctgtga atttcagaaa gcaaaacaa acaaaaaaaa    44340
aacttttttgt tcaaggcgat ttaaaaaaac aacttcacaa gataggaga attgtggtgt   44400
gcttgtcaca tgttaccagt ggtaacaatt ttaatgacaa aaaaatccac taattccaaa  44460
tgcataaaca aaactacatt atttatctac agccagaagg atatggaaat ttagaggtaa  44520
atgaaacatt ttagtcaggc aatgtaagac cttacagaaa ctggaagaga agtcccctttc 44580
tcttggtaat tcttttttt tcttttaaa gctgggatat cttacagagg aaggaaaaat    44640
taaccttttt tactttcttt ctcacttttt aaatcagcca aagtcaagcc cgtttgccaa  44700
cctgcatgtc catgcctgta agcccttctc ttggccaagg aagaaaggaa gaaagaaaaa  44760
agaaacccag gggcctgtat cccctgatta acacagcac agcactccag gcagacatgc   44820
ccggtggcgg ctcctttgca ccattgacct caggccagac acctcagcgc caacaatggg  44880
acctcggcct tccggctagg tttgccccag gctgggcagg aaaccagctc ggccgaagac  44940
agggccatt tcgagcagtg ggaccccaag acagcaaacc cagcccagtc aggacttgac    45000
acttaggaca atatctatct ctatagaatt ttagcatgat atggcttttt cccccagaaa  45060
acaacaaata aaccagcacc aagcaaacac aaagaaacaa aaagtcagaa caaaccagcc  45120
ctgcacagat gtaacggccc aggagatggc gagtgtggga gggaggaaca gggctccagc  45180
acaggtgcga gttcctgggc agagcctgaa gacagaggga ggggaccagc gctcgggaag  45240
tgaaaaaacc gcgtcgcctg gagattcatc aggaaaaatt aaagttggct gtgagctccc  45300
ggatccggtt ttctcgattc atttcttca gtttcatcct gcggttctga aaccagattt   45360
tcacttgtct gtccgtgagg tggacgctgc ggctaatctc taggcgccgc tctcgagtaa  45420
ggtacatatt gaacagaaac tccttctcca gctccagtgt ctggtgcttc gtgtaggggc  45480
```

```
agcgcttctt ccgaccactc tttgccgtga gccagttggc tgcgttttca cctttggaat   45540
tgcctggcat gtaagagaat aaagagggga tgattaagtc gaggccacac gggctgcccg   45600
cgggggtgaa ttgcctccgt ttctcccata agagagatgt cccaagtcac agagaagaga   45660
gtcgtgcccc cgttttggc ttgctgagag caagcagttc ctccaaaagt catgacaaaa    45720
attgagtggg ccttcaatct acatgaccct tccaatttac atttccccca cttttccaaa   45780
cacctgtttt agcgctaagc cgtagatgct tgcagaagga aaggcctggg agggcaggct   45840
gtacatcttg aacttaacgc ttttctttgc ctcttgccat atggcagaca agcatttcct   45900
gtagccccca ggctaggagc gcgggtgct tacttggaag atgggccagg cagcttggct    45960
gtctcacccc agggccctga ttgcccaaga ctcgataagg ggagaaagaa gggcatcatt   46020
ggtccaatgg ggaaggcagg aaaaaccgat tcggggtca agggccctcc ctcaagtttc    46080
tccaggagcc aggatagat agctgggcga ttccgaggtc caggggaagg gaaatggccc    46140
ttctctggct ctcagctcag ggccccccgc ttccaggccg gatttgcctt ttcttcttcc   46200
cgcaacgaag attcccgccc ctcagcaact ttgaaaaaag catgggggat cgtaaactcg   46260
aacttcgccg gttaatgggc ttatttattg gcgctggcgg ctgcttattt tggatgcctt   46320
acaaacatcc gcgctatctg cgggcgagct actttccctc cctcccctc ccccgcgtg     46380 ggccgcgccg cgcaggctgg gcagggacca gggctctggg tcctcccggc cacaggaaag   46440
agcgcacagg aggggcctg ctcgctggtg tcctcgtccc tagtcagggg gagctgaggc    46500
cagcgccgag gacgtcttgc tgtggggcgc taagccggac atgaattta ctgcgtcccc    46560 acgcccaaat attaaaaagc aagttcacaa ggtcagcctg cctgcagctt gggccaaggc   46620
cggccggctg ctgcgcgggc tcctagtttt ctgatccttc cctccttgt gtctgcctgt    46680 ctgcccgcct gactgcagcc ctctgcagcc ctgcttaccc agggaatcct tctccggcga   46740
ggctttgctg ctctcggaag gggccgggga gagctcctcc gcggccgagg acgacgcgtg   46800
cgcctcctcg tcgccctgcg agcccccgcc gctgccgcaa gccagcgtgg ggggcggcgg   46860
cgaatcgagg gctcgctcct tccgggccga atcggccgag ccggaggcta gcgcgggcgg   46920
gagatcgaaa ccgcgccccg ggggctgcgc ggggaacggg ccagccccga gttgctgcgc   46980
gccgccgccg ccgctgccat agcccttggc ggtgccgtag gcctgagaaa ggcggaagta   47040
gccaggcact ggcaccccgc tggaggtgcc cagggcgcag ccgtcgggcg gcgggccccg   47100
cgggaaggga gccagttcgg cggcggtggc cgagactttg gggcatttgt ccgccgagtc   47160
gtagaggcag taggagctct cttctttgat gttctgcgcg aaagagcacg aggtggcctg   47220
cggcgctggc tggggtggtt cggcggggg cggcggctgc tgctgggggcg gcggcggcgg    47280 cccgtcaggc ggctccatcc ggcaagaccg gggcgcgtct agccacaggt ctatgggcga   47340
gggcccgtag ccgtgcgccc cgggacctag accccgccca ccgccaccgc tgccggcga    47400 cgctgcctca ttgcgcttgc cgcccagcgt ggggaagagc ccgcagctct gcagcccgta   47460
gggcaggtcg gcggcgggcg gcaggtagac cccgccgtgg gcgtagtaac cgccaccgcc   47520 gccgccccc gcgccaccac caccgccgcc tgcctgcct ctgcccgagc tgatgagcga     47580
gtcgaccaaa aaagagttcg cggcggggct ctccgagcat gacattgttg tgggataatt   47640
tggcgaaggg agcagatagc cctttctggc tgacatttct tgtgcaaaac atgctgaata   47700
cgattagcaa tcccccgca ccgcggcggg cgcccgcagc caatcccgag ccagagtttc    47760
cgcgcgacca ctcccagttt ggtttcgtag gcgcggggcc gctctccgag ggcgccctca   47820
gagcccgcga ttgatataaa tatgtaatct gtattgatgg gccaggagac gcaccccgac   47880
```

-continued

```
accttggccc gaaggccggg agctgtgggg gctgcccaa cgtggctggt ggggggcctg    47940
gccattgggc tcgccccgcc cctaccggga cgtgagcccc ataccggggt cccttagaag    48000
ggcccttggg ccccgcgcag ttaacaagtg gggtgtttat ggtgcgcgcc cagtctgcct    48060
tgggtgctca ccatccctgt cgcagaagct gccactagtc cccggtgtac tctaaccact    48120
gaagcggccg tgtcggggac tcacgcgctt cccattcagc tctggatctg gaactggccc    48180
cttgtctgaa ttctgcctcc tcaaaagtgg cgaacctggc cctatgccg tcaggatcct    48240 cagagtgtca ggagcccaga gtgaactaga agctgacttg cctctacttc cagtatccac    48300 agattttcc ccaaaatgca gtggttgttc cctagcccct aaccccaac acttttctcc    48360 cctagtccgt tgatccagtt aggatcttct cctctggtgt tgtgctcacc cggcttgcct    48420
tctctacaac tcctgtcagt ggactttggt gggctggcgg gactggggt gggaagcggc    48480 tgccagcctt gatggaaaga cggcccact cccactccca aggccagagc cagatccaag    48540
catcccctca tcacctaggg aagactctaa gcccacagtc atttcgggga agtaaaatgc    48600
tggccttggg gtccttggct ggccaaagt gagagacttg gaggggtgtg cccggtgtac    48660
acctccgctg ctttatgttc ctgctctcct gttagctttg gcactcatat gctcctggag    48720
gctacaacaa gaaccagtgt cactacactc ctacctctct gtccctccc ctcttcccct    48780 ccctcccata ccctcagcta gggcagtcct tgctcctgca gtgtgtgcat tttaacgagg    48840
cctcggtgag gaaatccttt ccctgcaagg ccgggctggg ctcatggtcc tgttataaga    48900
gcatgtggag gtcaggccct ttgctcagca ggctcagggg ctctgtttta gccaactgga    48960
aatggccggc ctggggtgct agcccccaag tgtgagcctc atgctagtct caggaaatgc    49020 aacctttcc ggccagatcc agtggagccc ggaggtcgc tgccttgccc ctggcccgtg    49080
ggctacaggt ctccaggata ctctaggcct gcccgcccct ccggcccag tcggagctgg    49140 cattactgaa cgccggcatc ccaggaaata daccgctcag gccgctgcct tcagctggga    49200
aagactcttg catccgggtc atacgcggca cttttgcctcc ttcctcccag tgtgaatcca    49260
gcccaaggtg gaagaggagc ctgagaggac cctgaaagcg cagagagagc tggctaggta    49320
gagctccagc tctggcttct gagattcaag cagctgcggt cgctgcgggc agtggctgct    49380
ccgagctccg ggcccagaag gccgctccac cgctagcgcg cgctccagc cacttcaacc    49440 tcggcgcccc acggtgaccc ggccgtaagg actgagcatc agggtgcgga ggaggaggat    49500
ggagagaaaa agagagagat agaaggagag acggacagag ggagagaaaa gagagagaaa    49560
caggagggga gagagaataa gaaagccagt tctctccagc ctgacagggt cttgaagctg    49620
cagcagcggc tttagaggga tcaagacagg gtctgtgcca agagatcatt aactctcctt    49680
cgctcttcgc atgctcctgc gcccaaggcc aaggcaaatt ctctaccctc taggcccatg    49740
agacggacga acctgagtgc agaaaagctt cagagcaccg cagccagtgg ccctatcttt    49800
agcttcccgg atctgcctgg tccttaccct gctcaccaga agggtggaac tggctgggac    49860
tgttgccctt agcaatgcca cctgaaaatg ccacagagct gggggctgcc taggaaggaa    49920
gctttgctct tcagcactgc ccatgcctct cagaaaagct gtgtcatttg gcaagtgggt    49980
cccaagacct tcgaggtttc ctcaaggata atgagccgtg gcaggtcagt gggccaggac    50040
ctgggcctag agtcatgcct ctccaggcta aatgcagaaa gcaacttccc aggccgacat    50100 ctggaaggt ccagtatata tttgagatag tggaggctat acaaataaag taaaagacaa    50160
tgatcttaac ctatctttcc taacctttta gggagtcagg accttctgg aaaatccaag    50220 taagttttga ctcattctgt gaaaaatgca tatctgtata ttcccacaat ttgatccatc    50280
```

```
atttcgaagg agttcacaca cccctcagtc ttttccttgg gtcttccaga gtcccccagt   50340
gtcctgggac ttgggggccc tgccaatttg gctggcaaga caagctgggt gccctgcagc   50400
agacagctca ggtcagggcc ccgtagggca gccaaatggg cttctaggct ggatagaatc   50460
cagggacctg cacgtgccaa ccaaggttac aaaagtcagt ttgtatcgca tctgctacaa   50520
aaggctgccc cagccgaaga gtagaggagc tgggaggcct gctatgggcc tcgcaagccg   50580
tggcgttggc acttgggtct tcagtgacct ttctgtggtg agccagatgt gtttctttag   50640
tatgactttt tccccttgt aataaaccaa acgggatgtt gggcttgagc tccttctggc    50700
ttttaaaaag agtgtgtaag ctcatgtatg gcagcccctc tctggcccag gactgccttc   50760
caactcccac cagggcttgc tgagtgggaa acgcagcgag acactgccgg tgagctggcc   50820
ggctgcaggc gggccggctg ctgctggttc aaatgagagg atactaacgc agcagaagct   50880
caagttaaac gcctccttgg ccctctcagt tggtctccta gccccagca tccctgaccg     50940 accccccaagg ctcccatgct ctctagactt taacactgga gtgttaggtt tctcaataaa  51000
atattccatt tattgagcgc ctcggctttc ctgagattcc ccaccccaag agatgaagaa   51060
agcgattcag ttgtagtgtg ggtcggcttc caagcacttt tcctccctcg tgctcatttg   51120 ccttcttttct tttttgccat tcttcccagc tactaaattt ctccctctcc ctcagggtaa  51180
ctttgaccta aatcttcagt gcctgcttgc ctcaaccagg ccttatgcag cggttacaca   51240
gtcacctcca gagcccatgt tttatttagg aggaaatatt gcccatttct acccgggtaa   51300
taacctgcca gccctatggg gccaaagtaa acaccaggcc catggattaa ggccttcggc   51360
aaggattagg ctgcagttca ctaggtactc cttctgagta ggcccttgta agcagtgaga   51420
aataaactat tatgaaaaac aagttcctaa tgaaaagata ccaggtcctg agatcgaaac   51480
tgctagtaaa caatttatat ctggagggca ctctcaatgc tttcaagact ctgaattatc    51540
cagcggtgga gttgggctgc agtcccacag aggaaaaata aaggctgctt ttacatatct   51600
ggctttagca aaaaagaaa aaaaaatcag agcttctcat atccatgcat ttatgcatag    51660
ttagaaaatt ttttccacaag caatgatgtt cttttcccat tcatctttaa gaatgtcaac  51720
attttcaggg atatttgatg tgtctgtttt gaatctatca ggtgcaatct attactaaac   51780
aacatacttt taaagttttc taaatccaac cattaagatg gcccttcccc tgttagggaa   51840 gtgttgggc cttttcacac acccttgaa ttgcaatatt cttagatttg ttcataataa     51900
acagcctctg gccttagaac tggaggcggc tctggcattg tagggagggc tcccgctgca   51960
gagagcagct cactgggtgg gcgctcattt cttgccttgt tgctttgctc cgtcatagtt   52020
tgggagccag ccttcaacaa agactagtaa ctatgatagg caaaatttac gcaacaaaca   52080
ggcagtgcct actttctctg ggattcaccc cactcaccac gcactgtata tttgggaaaa   52140
gaaaaagatg tgggaaacta atggaaaaat agtagaaaaa attaaatata ggagaaagag   52200
ggaatttgaa tcgatccttc aaaatgtaat ggaatttttt catttaaaat gtgtttgatg   52260
acaaccccaa tggagtgatt gctccgtcaa aatttatcct cggttccagc ttttaaaaa    52320 agtattagta tttaccaata cattttttgca tatttgcaaa atatcttcta caaaagatct  52380
aattttcata tgtaagaaat tgctgcgaaa ttgcagctgg gtttataaca gcgtactcca   52440
agtatgcaac acagagactt gtctggcact ctcaaaaatc acatgcgact tctccgaatt   52500 ggccttttc ggaacaaagg ttttctccaa gctgccgggc agacatagag atgcacctag    52560
taggaaacca gtgacctcca ggacttctgc ccctgggaat aagctcgcct tagcggccgc   52620
agacttctac caccccattg tttagaatgg aaactttgtt ttcctcaacc cgcgatcacc   52680
```

```
tttttttttt tttttgccct cccacaaccc cctatcgcag cacagctgga acactttcgc    52740
ctagatgcct ctcatccta gcccattcta ttctgtgtat ttctacaaaa tcgaaagatt    52800
cgccttgagt gaaatgctgg cgcaaggagc taaaatcctc aacttttcta cttaggcctc    52860
cccctgcttt ccaaccttag ggagcaatgg ggtgggggct ccctaccgcg tcaccccaca    52920
aacccagcca cgttcccgag agccctgctt agacatcggc cacctcccca ctcccgcccc    52980
accagactga aattgctaaa cttgtggcct cttaccttga cacatttccg aaatcactgc    53040
caagggacag ctggcttctc cgcgcggcga cgctcgcgag gcctagcgaa tgcgcgttgc    53100
tttaaattac cataccaatc acttcttgag ggtgagtccc cttttctgt tatgaagggg     53160 agcgggacaa gtgaaataat gtaccgtgct gctcttagta tcagaagcga acaaaggcca    53220
agaatcatgc tggggttccc ggctccccgg cggctttgac attgatcgga agtgcgccat    53280
ctcgtggcgg ctgcgcgcct aggttgggcc ggagttccag ccccgagccg agagacggaa    53340
accagctccg ggcagagaga aaggagagag ggagaggatg tgcccagccc gctgctattg    53400
agatctcatt tttacatcta agaaatcgct gcaaaacccc agccgggttt atagcggcgc    53460
attccaaata tgcaaattgg ccggcccgg acgggtttac gaccacattg tcacagccat     53520
cggaggatgg gcttttatag ggctcagaaa tcaaaccgc gcccgcccgc cgcccgcccg     53580
cgagcagtcc tcctggctag actctctcta gcaacttgag agactttggt taatcttaa    53640 ccatcccaaa ggaagtcttt ccctaaaccc aggcttccca gcccgcccc tccctgcccc     53700 ccaggagggc cttgttcat gtctgcgtgt ctgcctatca acctagacat tcatctctag     53760
atctgtccca ctacccttc agctcgattt ccccagtcgc gccagttaga caaacacaca    53820
aacaaataaa cagagtgggg tctgggcct ctctccaaat gcgaccctat ctgctgctct     53880
ggccctgcct gggtggctga agagagggtg gggtgggcaa caaagggctc tgtcctttca    53940
gcccttctcc tcaaggttat gggtgatgtc caatttaag gcagaagttc aaaggcagca     54000
aacaaagagg aaatcggcat ccttttttt tcccccaaag ggaaaaagca gcctcagctg    54060
ggagctgggg agaaagcacc cttagaggct cctgggagtc tgctctgcct tggaacccag    54120
accaggctcc ctcttgttga agcctccacg ggcccccgga cggtcccact gcaggcctac    54180
ctgtcctgag gtgagcgagg gcagcctggg gtctgacctg ttggccacct caggcccaa     54240 ggccctctcc agggctgaga tcagtctgag gggataaagt cctatattcc aggccctgag    54300
ataccaccca ggtccccact tcccacaagg acgtagccaa ccaccttggt ttcctaagcc    54360
tggcttctgt tgtagccaat tcctgactca gtcaccttct caccccctca ggggcctgat    54420
aacttgctcc tcaactaggt aaggcatttt ttgggggggt gggggagggg gggcagacat    54480
ttggtagtaa aaggcgatca gggagaggaa tgtcacacca ggatactcaa atttccaccg    54540 tcttatttt ccttgtgccc agttgcctgt ataagtgctg caacacacac ggtgggtaag     54600
aaccagaatt gaggacaggc caacactccc agtacaaatg gagccaacag acatttctta    54660
acacagggag gcaaggaga ttcaatggga gggtgcctgg ctttcccaga tgagatcccc      54720
aggccggcca ggccgactgc ctctgagcat ttccctaact ctttccaaat gttgcaagag    54780
attaaaaaga ccattctcaa tacctttttcc acccctcca acaccctaaa ggaaatcaac     54840
taatggcaaa agaaaaaaga aaagagaaa gaaagaaaag aaaattgatt atggttcctt     54900
tatttacaag ttttttgaac accatccctg tatgaagcat acattcaaat attcttagca    54960
gtgagcgagt ttaccacgg aacactgtaa acagataggg cctttaaata ttttcatcat     55020
ctcttttccc ctctacattg catctttaa aattcgcttt ggttccttca gggaaatata     55080
```

```
tatatatata atataatatt tatcttttaa aataattcca cctcactctc aggctcttgg   55140
aaggtcacca gaagcttcca agctcagttc aagagccaat gagggctgag tgtggtgctg   55200
gaacccggtg ttttggggga ctcaaggccc tcatagccaa agctggggac ctgctggcca   55260
ggcccactgc tctgcagcca gacactgagc aaatccaagt ttcattacgt gtggtggaga   55320
gtttgccaaa ctgccacact ccacagccat ttcctgcaga gatctcaggg gccagtggcc   55380
tggctgcagc ctcttggctt ttccacatct cccacctcag ggaacagtcc actctgtgtc   55440
gaggctttgg gcctgagtgg caggctgaa ccaagaccct catttggtag aaagaaaagc   55500
caggtgggct gtaggaggcg gtggctagga actcagggct ggatcagtgt ggtgggtggc   55560
taggaggagt ggaaagacac tgatgccacc tggaatcata gatttctttt cccacaagga   55620
tttgcagccc tcttccacct caaagctacc tccaagtcca gccgctgttc acattggctt   55680
tggaaagcag cctcattctg ggcacctagt aatcctaccc cttcctcctg cccctgtccc   55740
caagctgaac tgggcttgga gagcacacag cttttttact caggggtcct gggggtgggt   55800
aggctcccag tagagggagg gtgtggtggg gttagtctcc aggggtctg gcaggggccc   55860 aatccccagt ggagaccaca cccagcccgc agctctgcag gctccaagag tgaaccacca   55920
ggggtcccaa acctgtcatt ctagctgatg cacagctctc agaatccaat gattattagg   55980
aatcttaacc actgagatct taatcaagag agtcccagac cacctcctgt ggggctatct   56040
ccatgcatcc ctctcttgca cacctctttt caaaagtcac catgtggctt gactttgtca   56100
agggcaaaat ctgcatatta tctcatgtgt atgaagcccc ccacccaatt ccagccgctg   56160
gagtcttaga ggagtggatt tgctgagtag tactgtaaac ggtctctgtt aatttttttt   56220
tccttcattc tcctgttctg aaaccagatt ttgacttgac gatcagtgag gttgagcatg   56280
cgggacagtt gcaggcgctt ctctttgtta atgtagacgc tgaagaagaa ctcccgttcc   56340
agctctcgga tctggtactt ggtataggg cagcgctttt tgcgggtgcg ttggccacct   56400
gtggagggag aaaaggcatg gggtgagcca ggtgtggggg ctgcaatcca ccccagagcc   56460
catagctgag gagaagggct gccatgggga ctggtggtcc agcccaagcc ccgtcaaagt   56520
ctgcccaggc ccctgccttt aacgctccga ctgcatgctt ggaacggccg cagttggagg   56580
ctcagccaca gataaaagcc agctccctaa ataggccccc ggggaagctg ctcccgctgc   56640
ccccagaaca gaaaggagag cttcgcacag caacaggcga gtttgcgctg cctaagcctc   56700
tttgaaagca gccaagtggg ggttgccggc tgcctctcgc aggccagact aaacaaacag   56760
ccgcctgcgg acatttcacc ttccagcacc tgggctgccc cttcccaagg cagtaaaggc   56820
ggctccagtc ccagtctttc ccggctgcgg ccaagactgg gcagtcctta acatctgggg   56880
cggctgccgg gtctttgtca gcctgagtcc tggccaccag cttctgcctc cccggccagc   56940
cttccggctc cgccgaggtg gggaggtggc ggcggaagcc ccctacccta ggccttcgct   57000
gagcaccacg gccacacggc catcctgcac acggcagagc agcggctcta tcttaggtag   57060
ggtgaaggga aaggggcttt cccgaagctg cgggcaggct ctacttgctc cccctttaaa   57120
aaaaaaaaaa aaaaaaaaa aaagacccac aagacaaaaa aaaatcgct tttgacagat   57180 tgaataacaa ttgtgaataa catgcagttg ggcagaagga ggcacgtaat tgccaccacg   57240
ccagaggaaa atggcttcct ttggacaaaa aggccaactt tgggttaatt tgttctttta   57300
atatattgct agagctaagc gggctacttt atctgttaaa cgcgctccta gcgccgtcgt   57360
taaacagcga cgcctttgaa tcccggccgg gactggagtc ccggcgcaac acatggcttt   57420
tataaaaatc tccggattac ctcgctatca aaagctcccg aagcccttgc agggggaatt   57480
```

```
tacaggcgcc cacctccggc tccccagcct ggagctggcc ccgagcgggg tcgagctgct   57540
gggcttggga gctgagaagg gaaaaaaggg aaaagggag ttgttttttt ttgcaggcat    57600
gccttggccg gtgggtattt cacggccaat ttcagcactc gccacgtgat cccgccttt    57660 ataacaaagt tttgttgggg gaaacctaaa ggcccttcat aaaccttata tgcttataaa   57720
acagcatata aaaatttaac agcggtgctg cgctagattt ccaactcccc tttcataaag   57780
cgcagggcgc tgcctttata cgtactggag ccgccggcct tgtcctcagt gtggccggaa   57840
gacgactcgg ggctgctgct gctctcgggg cgccgccgcc gctctttctc ctctgctgcc   57900
gccgccgtct cccggcagcc gccgccgccg ccgctgtccg aacttgaagt tgccggcgcg   57960
cccgttgcag ccgccgccgc cgccgcggag gtcgccgtgg ccgccggggg cccttctcg    58020 gcgctcttgt ccccggggta gtcggaggag gcgaggtttt ccggggtgcc gtaggctgtc   58080
tcgaaaaact ggtcgaaagc ctgtggcagg acgccgttcc tgcccacggt gctatagaaa   58140
ttggacgaga ctgcggggt ggggtggtgg tagacgttgg ccgagctctt ggccagcacg    58200
tcgccaggca cgccggccgc gctgggcgcc tgcaggcagt ctctgtgcac gagctcctcc   58260
gcggagtagc agtgggccag attgccgcgg gggtgccatt tagtggcggg ctcaatggcg   58320
tactctctga aggtcacttc gcgcacgggt tggacctggg gcaggttgga ggagtaggag   58380
tatgtcattg ggcgcgaaga cggggtctgg ggcagaaaag aagggaggct ggagaaatct   58440
ggacccgaga cgtagtaagt acaacttggc aaatacatgt tagaggagca gggaccacgc   58500
tcatcaaaat ccattattgg gctaccttgg gctctccgca gtagccgagc ttaacatgat   58560
tctccactgc agctgcctct ttgaagcgga tccgtgaagt agaaatttgg agacgtaagc   58620
tgacgtggaa atctatcccc atccttagca gggaggtgct ggtcatgtga cccgatgttg   58680
aaattgacaa gctgctagct agtccgggcc ttttccccc cccttttcctt ttttttttt    58740 cctcctctcc cctccctccc ggcttccttt ctttgtagcc acctcagggg aagcaacaga   58800
tcgtcactcg gtgttctcac cgaaagcacg taatcgccgg tgtaactcat gttggctggg   58860
gggcctcccg gcgcgcgcgg agaggctggg gtgcgccccc atgcagcatg cttgtgctca   58920
attgcagggt cctcgttctc gagtgtgcag agggcggtga gagctcaact ctcgtcccca   58980
cctcccaccc gcagctcccc gggtgggtga gggatgccct ggactgggga tagccaggtg   59040
ggagtccgtc gctgtgtggc ctgtggtctc ggagtctgtt ctcctggagt ctcgcatttg   59100
cacccccttc ttcgcagtcc ccctcccata gacttgctct gggaagcgcc tctgcctccg   59160
accctagccg gaaccccttc ggggccagag tttgaagccg tggatgtgcc tgcctggtgg   59220
cttgtccgat ttgcacggtg acttgattac actctctcat tcatggtcac ttccgaagcg   59280
ctttagtgcc ttccgtccct aaaccgccaa cagccagaac ggcttctccc cgcggtttgt   59340
cactgatccg cagggcccgg aagggccttc gtcttacccg ggatccacct ctccctcat    59400 cttccctgcc tacctcttca tcccacctt  tgtccttgga gaaactccct cctcctcgct   59460
gcctgccggg cttcggagtg actcggcaga gacagaggca caggggctgc cctgctgctc   59520
accggtccac ccatctgcct ggtcttctgg agctgaggac tcgggaaacc atgcaattga   59580
ggcaagcctt gggctgcttt agaggcgctg acatccgagg agacttctcc tgggtatgct   59640
gcatcttcgt gggggggccca tcaggctgct tacagagctc caggggtgtg gggagaatgg   59700
aggtggaaag gacgggctga gggccaagga gaggtggctg agaaaggggt aacccaccta   59760
ctctcctact ctccttcctt gcaatgtgtg agagtgaaag caaggatgt gcagggcaaa    59820 aactcagaga gctctgtgcc tttcctactg ctcattccac aggaggaata caataccaga   59880
```

```
gaaaggagag gtgcttcccg aactccctgc acctggggaa acagggatgt ctttaaaaag   59940
ctaggtttgt gctaaggata gagagaggcc atagcaatac tctgagtcta gctttcttga   60000
gaagaggaaa aaaataaat taagaaggca aaatatgctc cccatcctgc aggattgaag    60060
gagcaatgtt tggaggaagc gaaagaaagg agaggacaca gagcacagag cagccaggca   60120
gagccaggag ctgagaaggg cccagacctg aggcctccca acaactctct tcttggaagg   60180
atctgggatg ttgctgaagg aaaataaaaa aatatgtaaa aagataaccct tttgtttttc   60240 cctctccagg aaatagccaa agttatttac atatcttggg gagatttaga gtataaactc   60300
taagatcttt ggtatttaag tgtcaacatc gatttattta tttattgctg agctgactgt   60360
aactgactca ataacaaatc taatcgtgta ttgcactgga aaagaaatat tcttattatg   60420
tattttctcc aaataatggc ctaccattgc atttgaatac ctgctgtaaa tatcaataat   60480
atgaagtaat tactctgtag tcgagtaaac taatttatta gcattaatgt ttatgtggct   60540
ctccacctcc ccccaccacc acctttacaa ggattgctta tcacaaatca agctacttgg   60600
acacattggt ttaatgaact ctttattcaa gatttgctac aagaattttc atgtcctttg   60660
aatccctgag aactgaactt gaaattattt gtgcatcttc agcttgacat atttgtccac   60720
tgtggcttgt ccagagggca gcagtgctgt gagtgagaag gtccagtggg aaggaaggtt   60780
attggagaag agtagcctca gacctcctaa agctgggaag cacatttaca gaattgccct   60840
gcagcgaaaa aacttctatt ccagcagtg accaacaagg caaaatgttt gtttctccac    60900
agcatctctt ttttagagac agaatataaa agacagaagg agaggtttca aacagcggta   60960
ttcgagctgt tccctggctt gattttggct atcccaagct ctctctctgc agcccaccca   61020
gtccacgcca cccctacctt cgaacaaaag gaatgcatga agggtttcag tgactttgcc   61080
ataacaaagg cgccaccatt gcggggctcg ccccgcccct gggtgaaggc aaacaaattc   61140
ttgcacttgt attagggctt ttaagaccat aattgaaccc gggggcgtct aggaaaaccg   61200
aaaacagttc tagacagacc tgcggtttta tagcagtttt ggcagtcaac ttcagcttgt   61260
gcctgagcag acggggttgt ggtggcccgc cagcggggga tgccaggcca cctcccccag   61320
cggcacgcag cccctctctt aattagatcg ttttccccct ggtgtccggg agagcggtcc   61380
cggcagaaag gtcggtatgg gggtgtgcgc tgttccgcat aaccactgcc tcccatgtcc   61440
tcctcgaggg ccgaaccgag agggtgctgg cagggctgga tccacgggt gtccgcagga    61500 gacaaaggcg aattccggag aaaaggctgg ggctgagaaa ggcgctccgg gagcggctgg   61560
cagggcaatt cggcaggctg caccgaagcc gagtgcccgg agggacttgc cgcccggaag   61620
ggggtgtgtg gggcgctgc cgtgaagatg gatgagggaa aaggttttttg atatcagcag    61680 aagggaaaac gcctggagtg gccgaacact tttagttgcc cagcaggaat aggagacggg   61740
tactcagctc cccaaggctg cgcaatatcc cagctttgcc cgctcctgcc ctcgtgttcg   61800
gaatatgctg gcggtgtgaa tgtgaaggtt ctccaggca ggcggctggg gcgaggggtg     61860
ggcgcagctc tgaggatcag accaaatcta ggggaaaaag gggaggcaga ccttcgggtc   61920
cttggttttg actttgctct gagcctatga ttgactcttc cgctttgcag gaggtccaac   61980
agccgagctt agcccaccgg gctctgggaa agacccgact gaggctaaag ccgcccggga   62040
aggccaagtc cgagttccat ttcttgaaga ggccggcgcg cgtaaggctg tgacattggc   62100
cctggcgact ggcttcccag gagctgttct ttctcaggag ctccacagcg cgggccatct   62160
ccagaaaact gtcttcagag tgtatttcct tttatcgtca acccagagcc ccaccgcggc   62220
taatgcaaga ggccaaaaaa tgtttggagg aagaaaaaca aaggcaggaa gtggcggcgg   62280
```

```
cctgacggtg cgtgtgtgtc tgcagagaag ggagggagcc ggctcagtct cttcttgttt   62340
ttccaaactt caaggtccag gcagccctct gcagggccgg gccccattgc tccccgcgcg   62400
gcattggagg tggccgcccg gagaggagaa ggccaacgcc tgcgccaggc ttgtcaggcg   62460
gaaacggcta acaaggagat tggtcagca aaacagaccc agcctttccg aggcttcgtc    62520
tgacttggcc cgaaaggttg gggaggggg gcttgcgcag agcctcaggg accctcctct    62580
ctggggacta ccatccctga gccttacgct tctttccaca gcctttgcag gcggaatatc   62640
ggaataaagt gggtccaggc gcctctgccg cctccgcttc ttcttgcagc ctgaatggtc   62700
cgggaggcag cgggagggcg ccggcgggca gtgcccaggc ggggtcgcct cgaggccgtc   62760
ggtgagcacc gggcaatgcg aggccttgtt accgaggttg ttgtgctggg ggcgtttcca   62820
gcacagtcat tcaagggacg tgagctgcaa ggatcgtcac ttgacaggcg gcttaacacc   62880
ctctcactcc aagggaggat acagctgggt ggccgggagc acctccacac tccaggcttc   62940
ccagctccaa ctggcaaagc tgctgggcca ccctcttctc tccctgggc tggcttggga    63000
ggcagcagct gctccttgtc ccagaaatct gagaattcga agtccccagt acttgcacat   63060
gcagcccttt aaatgcccag catttgtcca cagtctcaat gtcaatgcca agctgcccca   63120
gtcaccactg tccttctcaa gggggtcctg tccctctaca gttcctgatc ctgctcctgt   63180
cccccctaca gttcctgtct cctgccctgc tccttccag ccattctcac ctgctgggac    63240
ctcctgtctc ttccctacct cttttgatgc ctctgctaga ctgagcaaca gctgaggtgc   63300
cactggaggg catccaatac tcaggcgcag agaagagggg ctgttaggtc cctgactctc   63360
ccccaacttc gggcttccac cagagcctga actgagtctc ccacctcctt cttaggaata   63420
ctccacctca aggccccacc aagtctggct tatctccctt cctctcccct cccttctcta   63480
ccctcctttc ttccccaaca cttcctcctt ctcttctgcg acccagctg ctgcttttct     63540
aggctgggca acccagatgg gataggcctg ggaggggtca ggaccacttt gacagactga   63600
atctcactcc cagatggcta cagttaagtt tctctcttgg tggattgctt agggcaccat   63660
cattattttg cctcctcctg cttgcctaat cccttacttt cctctgtcca caaatgtcac   63720
actgttttcta gaaagctaca cagaagagta tttcaaccct ggtgaccata ctgcacacag   63780
gtgcaagaac tggcccggag gccccgggta gaaatggcaa cagagctctt ctccattaca   63840
ggaatatctc cttccaaatc aaagggttcc tgtgggcaca tctgtcttat gtggtgagct   63900
aggggagatg ggttgtctgg gaaggcccag gagatctcca cgtatttgtt ctcagggcat   63960
ggcttattgc cagatcatag acaatccatc acattttcca ggcgctgccc agaggcagca   64020
ctgaagcttc aattaaaaaa tcaagagatc acctctatca ctaccaggtg gaggcagggg   64080
ttaatttgtc cctttgttga gacacctcac cctccccgaa ggtccccaac acttcctaaa   64140
agctcagaaa caggtaatgc cctgaagtgg acctcataat tctgcttggt ctgactggca   64200
gtttcagtca tccttcaaag cccctaaata tctgaaaagg cccatacact tcccctggcc    64260
actgcagagt ggggcacagg gctcagctga gggtctcaag tacctaagca atctagttat   64320
catttacttt agtggatccc aaactgaagg gagaagagaa gattacttcc tttaataact   64380
attttattt ttattgttgc caattattag acttcttttt cctatagcat gggaacaaat    64440
gggggtgggg agactttgaa gggcgaagcc ctagttctca gtgtctgcct tccattcccc   64500
atgcagcttt ggcccaaaca ggtttcccag cagagtgtgt ctgagataaa gaagacaaaa   64560
gggggtggcc caacccgaag gttggctctg gtccttgggt ctcggtctct acagccgtag   64620
ctcacaggaa gcccccacgc cacaaagctc caactgcttc ctagggcagc tccatttcca   64680
```

```
ctcagtgctc atgttggctc acattccagg cttgagaaga gccatcaccc catccagccc   64740 tcctcccta cacacccttc caggcagttc tgcgatggga cccattcaca gatcattgtt   64800
tctgctatat atgccccac agcccagccc agcccatcca cgcagcccta ggggtacaat   64860
ccagattttt ggcttccgcg aaaagaaatc ctttgcatgt cctctttggt tcacctggag   64920
agataggctc agcggcagat cacgcttaag ctaacgttta ccgcagggcc tgatgctctg   64980
atctgctgga ggcaggctat aggcaggggg taagggctc tctccctcgc agagcgcagt   65040
gaaggattct tggggctgg gagtcaggag ttttaccttt ggaagagtgc gcctcacatc   65100
tgtgtggatt ttaggcagga aagagcatc aagggtctca ccaaaggctt gccactcact   65160
gagggagagg cctggattct gggaccccag gagagtctct ccagcagggt cttggctccc   65220
ctatcctctt ccctgccaag tcggccctat gttcctacca ggacccagaa ctccgatcca   65280
gccacgtcct ttccctggg cttgcaggcg ctccctctcg ccccgctag gccttagcgg    65340 gctccgaagt ctgctggact ggggcaaacc ccgctcttct gggacgggga cacggcctgg   65400
gccacccgtg gctgccggga ctcctttcca acagggctgg ggatgggaga gttggaaatc   65460
aagaaagaac ctctgcctcc agtgcacgag cccagagccc aggctaccag aacccgcttg   65520
cagcaaggta actgtgcgtc ctgtgccttc ttgaggcggc ggcagcgatc ggccctgacc   65580
atagaggcgg ccgtggcgcg gaggacttga cctttacggc acgagaggag ggcgctggct   65640
gagccgcagg gaggggacg ctgctctctc cagcctcctc cacccaatag cagtccgctc   65700
gacccacgcc agctgcgcgc tcaccccctt tcccctccca ttttgtgcag tgtccgcaga   65760
cccgcggccg gaaacaaagc ccccagccct gctctcacca cccttcttgc aagctgctgt   65820
cgccaacccc ccagaccaga ggctcagagc taacgctaag ccccttaagg ccctctccag   65880
ggccctcttc tctcgccagc cgccctcagc cagctcctga ccccagccgc cctcagccag   65940
ctcctgggta ccactctggg tgccaaccgg gacctgccgg tgccacggtc ccgtgcgccg   66000
ggtcccggcc tcgggctgcg ggcggcttcg gggcctacag cccagcggcg cggagcgtgg   66060
cagaggcgcg gggcgcagcg cagcccgagg ctgcctcccg cccgggcgga cggcgcggcc   66120
gctggggtgc acagcgtagc cccgcgtgcc cggctcgctc tccgttccct cggatagctc   66180
ccaccgctcg gctccgggct cagaaagcgg aagtatttgg tagagaaaaa cacggtttct   66240
tttcagctcg tctcaaaatc ccttttagag aaaatgctcc tgtcaagttt tatttcccgt   66300
tgcaaaccac cttccacgct gccaagaatt aagaccggga gagattaaat acccgattat   66360
tctcctgggg agggcgggc ggggccggga agtgggcacc cacaccaaac attccttgaa   66420
gtaggcttgt cctgatccag ccgcgcccgg ggagccccac gaaggcccgc gcggcctgcg   66480
gtgacgtcag cctgcagttg cggggccact cacccgcaca gacacggccc ttgctgttcc   66540
gcgccgggac ctccgccagc cgtcctgccg cagcccgac tggcccgcgt gccgtcagag   66600
ggaggcccgc tttacaccgg cctgagcctc cattttgagt aggggttct tgtagaagcg    66660 tggagggttt ggggccgcgc ctctgtcccg gagggcgcg acatcaggta gctctccgag   66720
ttcacacccc agtacctggg ggaggaccta tgtcgccgca taaccgcccg cagaggtttg   66780
gaaatctctg agaccgttg taattatttc tgcccagtgg atccggctct tcagcgtcac   66840
gagagccggg cagaaatgaa atcaactgtg gcaaggcctt ggctgctttc acggaggagt   66900
ttttctgcgc cagtgtcttt ttccttccct ttaaaataaa attaaaaata gcaagcactt   66960
ctcaggcatt catcagagat agatagatgc acgaggattg agtgggcatt ttcataaaga   67020
atgaggccgg ctgttataga ccggcggcct agcagatgaa aacttaatta gcgtgcctgt   67080
```

```
cctaaaacct aggcataaat ctccctctgc cttttggata acgctatatc tttgcttatg   67140
agaaatggga tgtgagcaac tcgctgcaca tttctctgat tctccaggtc ttggtcggct   67200
gacacgcatt cgatcaagtt taaaggaatg cgcataaatc agcaagcccc tagcgtctcc   67260
ttgggagagg tccgcaaatc caggagggcg cctctgaacc caccgggtct ggggattagc   67320 agtccaggge aacctccgtc tctgctcctg aactcgggaa ttcacagagg aagcaagaca   67380
ctgcatcttc accaaggcct ccaaacacat gcagcagagt gcaatctgca cttacatgta   67440
ttacaaagtg aaatctgtgt caactctccg cacacaaatg ttgcatctgc agctgaattt   67500
cactgcctag tggtgaattt ttaagaaaag atttcaacta ggttgtttta atttttttct   67560 tccctttttct gttaatttttt tttaaaaacc cacaacttga ataacttgaa tgggtggctt   67620
cagctctgca tcagtcacaa ataggagtga aatgcatagc acatttaac aatcatccac    67680 ttaaaataag taaataaata tgatagtact gagagcagat agaaaaagta gcgttttttt   67740
ttaaagtccc attttattt tcttaattca ggaagagttt tcttttaga aaaaaatact    67800 ttaatcaggc tttcaacaac attatccatg ggtcagtggc tgatactatt attcctattt   67860
ttcaggaggt ggctggtctc tccttgattt ttgttttgt ttttgttttt gttttaaggt    67920
tttagactga ttgctatttg ggcattaaag gagccataat aaataatcca tgcccacttt   67980
aggttatctg gtagatccac agaaatttta aataggagga gagttaggta agatcgacac   68040
tatcaatgac catttttagaa ctgggggggaa aaatcccca caacaaccct gaaatgtctt   68100
ctgtcattac agtttcaaaa actagagaga gaaaaaaaga aggctactac tttacccagg   68160
gttcctgtag tggtgatggc tttcgaaagg ggcgggatcc cggctggaga gctgctgttg   68220
gcctccttcc taggctcgag gctcagaata tttcttacat ctaaagaaaa atatcccctg   68280
tcaacagaag agtccctttt ggagctgttc ttaaacacac agtttgatcc agctttgagg   68340 ggatttttcca ccactttaaa cattttggga gaaagttgtt actttggctt gatggcagct   68400
catttggaaa tggagtactg tttggaacaa gaggtggaga ggtgggtctg aagcaacatt   68460
atcatttgtt tccacaagtg gagtgaaaat cctcagggca gcaaaatata attgaatttc   68520
tcgagacctt tcgatatgta tgtttcaaca ccagcctgtt tttgagacag ctttagagac   68580
tctttcgtaa ttctcatcta taagaagtt gtgagtcctc aggagaggtt ggagaggttt   68640
ccggcagcca cttttgtaac caatcaatat tattttccat aaaatgatga atctggttct   68700
tccattcact attactttcc tctaacgtaa agataaaatt agcctgcatc tcacaattct   68760
gcatcccacg gctactgatt ccaccaacat tttaatacat atgcgcatag catagatttg   68820
acaaaaacac attatcctat gtgtatatta aatatacaaa catacatatg tattctttat   68880
gactctgaat acagcacctg attgttgtta gaggtcaaca gtagatataa tattattatt   68940
atagttttga tggaagttgt taatattaaa catatttatt tatcctacaa atcaaatggc   69000
agattcacaa gcatcaatat aagattgcac accaccctgg agcagtactc agctctgagt   69060
tatccaggat aactctcgtt ctgtatccaa tcctgtggtc attttgtaga tatgaaatat   69120
taagtcctct ttactgacct ctcaagaggt gggtttctta gactttctga aacataactc   69180
tagaactcta gacttagcaa ggcatctgaa tcttaatttg ctgtaaagac tcctcaatag   69240
ctctaattac agtgtgagac caccctggag ggtgaggacc aggaaggaat ggtgatttaa   69300
gaacacatct tagactgtaa caaaaatgta cagctttaaa gcagatctgc agaaatctga   69360
tgcagagcaa gccactgtga agacaaatca aatttggcca ttagagaaaa ggaacaaggc   69420
ttcatcttgt aaagtacatt ttgtacctca attctagaaa tcaccttaaa ttacaatatc   69480
```

```
ttgcgtcatt agcaattaat gatatgatat ctgtacagat tctacaaata tatatacaag   69540
cacacacaag cactaatatg caaatgtata catgtgtaca catattatat atatttacat   69600
atatacaggg acatgtataa tttacatata ttcaaatttg ctccagctgg agccaaataa   69660
ttgagtactg aatctctaaa gtcaaggagg taagagctct tgattccctt ggttgaagaa   69720
ttacaaggag gcttgtcaac gcgaggtggc gcccttgatc tactaatcca gctaaggcca   69780
attcatgagc tgtcaaaagt caaggtcaca aattgtcttt tttttcgtca aggtcaaggt   69840
ttaaggcctt tcgtagtcct gtcatttcaa caaatatcaa aacctgccct ctcagacaca   69900
tgcagaccca acagcagatt ttaaaatacg acagcctagg cattgctgct acaaaacaac   69960
tggttttcat tttccacagg gagcctggga attcatacta tctcttcctc ctttctttc   70020 tctccctttt gtaatacctg acactttaat ctccttgaag cacttatcat tttttaggat   70080
tttagttatg agggatttct ccctttctt aaaaatttgg tagcaaaaga agtactgaat   70140
aataataaag aatggtcctt ggtttatata agataaacct gctccttttc tttctgtgca   70200
gtgcacattt agcataggaa agtaaagagt attttctgca gattttaatg gcagtgacta   70260
ttttattaac aattaatatt acgatatcac tatctacagg tctaagggtt tttttttttc   70320 attttttagta gaaatattta aaaagcaggt gcacaaatac attttcacag tgtgctgaat   70380
gtctttattt acaagatatc attctatagt gaatatgaac aaaacgaatg tgctggttga   70440
aataactgct tgattaaaaa tgtgctgtga agatgaatca ctaatctttc taatgcactc   70500
tgataacaca ataaacatgg aaaaatacta atcccttaat agatcaaaat atagaatata   70560
gacacctaaa tatttcaggg gaatgaattt tcattctgag ttttctaaaa agaaaaaag   70620 aaaaatgatt tctccagcaa atgtttagca aatattggga aatgccaatt caatgaaaa   70680 aacgaattgt gttcaaacca aagtccatca tgttgggatg gaaactctcg ggagatctca   70740
cataaagtga attctgtgga tcatctgatg atgtaaacat tttcaaaaag atacaaaatc   70800
ctttggaaaa taacggatat tggagcagta aatatagttc aaatgccaca aaatatgctt   70860
gttataagca attaaaaatt attcttaaaa agacattacc gacccgggtt ctcttgtagc   70920
ctgaaaggtt cagctggttg gttttactat actaccaaga caaatgatcc tcagaagagt   70980
tttctctccc tttctccctt cacagcaaat attccaagat cattatttca gtaccttctc   71040 gtttccccctc taaatctata cataaaatgt tttgcagaac gtacaacaac ggtaggaatt   71100
tcactaagat ttacctgagc agacgcttaa catgcaaagg gaatggcgac ctaagaagga   71160
caagcagatg tttacaatgg cctcttgcgt ttgtaaccaa cttccagatt attaccatct   71220
aacgcagtgt cctaaaatgt aacgatcact taaatactta caagatttca gtaactgcgt   71280
aacttatctg aaattgcgta ttttgggggt tgacgtttga catttaacgg gctgggctga   71340
tggggttggc ggaagaactg gcagtctttta cctttcttaa agttttaaaa cagttgtaga   71400
ttccattaaa gagaaagaga tctccttcgg gagaggaaaa tgccagtctc tgtctctttc   71460
tctttcccat tcttcaatta ttattaagca ttattatcat tatctgggca aagcaacgag   71520
ttctgaagcg tttcttcaag ttgccttctt gctctatttt taatccatta actagtggtt   71580
ttcagtttgt tgatgacttt tttctcttta accctcctgt tctggaacca gattgtgacc   71640
tgccgctcag agagattcgt cgtggctgat atccgcctcc gtttgtcctt agtaatgaat   71700
ttattcgtgg cgtattcccg ttcaagttct tttaattgca ccttggtata aggcacgcgc   71760 ttcttttctcc ccctcctata ggagctggca tccgagggat gggagaccac gtctagaaga   71820
caagggagaa ggcaagttac acagggatcg gaccccagcc agggcatagg cgacagctcg   71880
```

```
atctgagcca cccgccttgc agcgcccggc tgctctttgc cacccgctgt acaatcctgt   71940
cttctgctaa agcctagagg gtcagtgggg aaggtagtta gttctgaact gaaatgaaat   72000
cacccagggc tccagtgact tccccaaccc ggccatcctg caggagcagc gcgtaggcag   72060
cctcgagtga tagcctggtc caacggccca caccttagcg ccaggctcaa ggtacaacac   72120
ttctgtgcct gcctcctttc tgggtgcccg tcccaatact cgaagcttct acactgaagc   72180
cattttttgag agaatgaata gggaggggca atttggggag ctgttttctg gtcaatttct   72240
catccttaaa ttggtgtcag gggctgggga gggcggggcg cagagggaga gggaagctag   72300
ccgaggtctc cacaagccac ccctcaccca gggagagcca gggaccagct caactcgagg   72360
cagtgcaggc agaccagcc agccatgctc gggctcccag gggtgcagag ccgctagggc   72420
agaccaggaa gagaacagaa acgcacccgg gatcgcccgg gtgcgagcgg agaagaagct   72480
ggagcagagc cggaagacca gggctgggaa taggtcgtca tttaccgggc agagtggact   72540
tccagaggtg gggaggctgc gcctgctctt tgggcagta catttggccg ttccagccgt   72600
tgggcagcgc ccagggctgg tagctttcca tgggaagacc caagggttcg tggcgcgact   72660
cgccggggcc cccgaggccc ggcaccactg gcatatccag gtagccaggc atgggctgat   72720
ggtggtggta aggcccggct gcgtagccct ggtggtagaa ggcgaactcc ttagcgcggg   72780
agctgaactc ctcggcagct gggcggcgg tatccatgta cttgtccgcg aaggcggcgg   72840
cggcggcgc cgaggcgggc tgcgcgcacg acttgatggc gttggggtgc gggcccatgc   72900
gggcgcacgg gtagtagccg ctgccgaagt agccataggg cagcgccgcg ggccccgacg   72960
agctctgcgc cgctgccgag caggggctgc attgcttggc ggcctctgcg cccgccgggc   73020
ccgccgggcc gggacctccc gaggacgacg cggcggcggc ggcggcggct gcagcggcag   73080
ccgcggcagc agcggcggca gccgacgggg gcgcctcccc gggggcgctg ctgtaggcgg   73140
acgcggctcc tggcgccaag ggcgccgggt gcgccatcag gttgcggcac tggttggccg   73200
cggccgccgc cgcagccgcg gccgccgccg ccaccgagaa gttgccccct gccgccgcag   73260
ccgccgggtg ggggaagccc ccgccccgg ccccggcagc cgccgccgct gcagccgctg   73320
ctgcagccgc cgccgcccct tccatgttct tgttgagctc gtcggccacc aggccgccgc   73380
cgttgtcgta gagaaacatg acggtgggct cgatccagcg ggggtggagg agcacggagg   73440
ctgtcatagc ccgagccgca tggagaagac cccagtggcg ctgttttaaa aagcccccaa   73500
gaagtgaaga gcgcgcggcg cggggccggg gcccgagcga gggggcgga tcgcgccccg   73560
cggggtcgcg ccaggcggcc gcccattggc ccggcccccc cgctccgccc acggcgtatg   73620
caaagcgggc ggctccgact ccagctctgc acggtgcacc cgtcgtcccc gccgcggccc   73680
gcgccgtccc cagcgccagc cgcgcggccg cgcaccattc acccggggga gaggcggagg   73740
aacgtgcggg tggggcaggg aaggaaggcg gccccatctc cgccccccttcccttcctttt  73800
atcccagtgg ggcccagacc cgcgcaacca ggcggggagg ggaggtgggc gcgcgattgg   73860
gttgcgatct ggagcagtgg ggacaggtca ggtaattctg ccggcggtca gggatgggag   73920
agtggggagg acgggaccag cctagctcag aatgggtgtt tcttggagcc tctgggactg   73980
tttttctttcc aggaaccggc gcgtatttct gcagtgagac cacaggacgg acatcggcgc   74040
cttcggcttc gatggagttg cgattttgct ctttccaggg aaacagtggc agggtgtttg   74100
ctgcttatcg gttcctgcgg atatgcctgg gtcccaggac attccactgg aggcttggac   74160
tgcatttagg agccccctatc ccttccctgt ccacactgtt agtgagcaat tcatatgtt    74220
tgcatttaga cccatagact cagaacgact catcacacac acacacagtg tacactgaca   74280
```

```
cactcacatt cgcacactta ggtatacagc ctgatccttg ctctgacctg gtaacaacgc    74340
ttcctcctcc agagactttg agatagagcg agcgatccct gtgcaccatt catccatgct    74400
cccacctcgc cagtatggct ggcttagttc tggaagggc ttaagaggaa caagccccag    74460
ctgtgcttct ggctgggact taaaccccc ttctgggccc taaagccacg cttctttgtg    74520
gaccggacct gactctccag gaatctggga acccgctatt tcactctatt ttgggacaag    74580 aaaaggggc tctttggggc cacttcctgc cttcccctca gtaggatct ccagcctgca    74640 gagggtgcct agtccttctt tgcccaagaa ccagtccaag aagcctttcc tctgtgcctg    74700
ggaaatgcaa ccttttcttg ggagcatggt agggtgttgg tgctgaagaa ccaagcagcg    74760
acccgtcttg tagctgccat gttttgtcga ggggttctgg gggtcctgct gctttagagc    74820
cacatacttc cacttcctga ttcactactg tgagctggtc agatgcctag aagaggaaca    74880
agcgttcaaa gtgaaagtgg gcacattacc ggaatagtgc tggggagagt gctggattct    74940
tttccacccc aggcggactg gtgagaagcc aggcttggac ctgtcctctg ctcctagctt    75000
gcacactcag ccctaaactc agagcagcac gcataccacc cctcacacac accccaccat    75060
ctgctgtcta aggcccctgg gcttcctgca ggatccagac caatgtggct gggcttgggc    75120
ttttatctgt cctgatcctg gatttgtcct gaccaatgta agtgtcgccc aataaaacct    75180
tctatgaccc ccacaccagc cacccccca ccaagtgtgc cctttccttc ttgactttt    75240 agcagttctg ggtaaatatt gatttgcccc cagtttacct tctccctgac tggccatttg    75300
cagactcagg aactagcctc tgtagggact tgatttttct gttactttct ggccgtttca    75360 ccaccccct tcctccctcc aagtggcatt gtaaaactca cagtgacaaa gagacagagt    75420
agggttctag gcccctgttc ctggggactt gaaggcggtt ttacatactg gtcagacacg    75480
gctggaggcc aaggtcaagt tgaaagttgc agtccagcca gcatgagaac tgccatgcga    75540
gcgtagagac acaggcagca gcaaaaggcc cattgcccac atcccctcac tcttaatttt    75600
ctctctcttt ttaaaattct cgcctctgac tctgttcggc tgcccagaat ttttggtgc    75660 cttcgtgggg ttttgggc ggtgtttacc gactcttctc tgcctccgcc ctgctcagcc    75720
agggctttga gcctcttcgg ttttccggcc agacccggaa aaacgaaaac acagcttggg    75780
gagcccccac tagccggcgc ctgtgccagc tcacctctgg ccatggcgca gctgccggtg    75840
cacacggcgg ccaaggccag ctccacattc ttccctcccc ctcccacttc accgtagccc    75900
cgaaccctgc gcgcagagaa agggtctcag ctccacagac gactgggtcc ctcctcacca    75960
aaaatggtga gacaagattt catctgtcgg ccgaggagcc acaagcaggt ttgtctgaga    76020
gggatggtgc tgggggaagg ctttggattg catctcaaat taagctttgc tccttaaatg    76080
tggcgctctc gccaagaaaa agcttgggga ctgaattctt gagatttatg gtgcaccta    76140 ttgatcaaat ttatctggac tttttttagt tccccgatgt gtccctatca ttaaaaaaaa    76200 aaaaaaaaa aaaaaccccc tctcaagaca tgcttattta gaggaaggca ccctgcttgt    76260
tctcttcttg tcttggatct caacatgtat cttatttttc taccagacat gtccatggcg    76320
tcctggcatg ccccactgtt ttcaaatgtc tgcatgtcct gtcagtattg agttgtagcc    76380
accaatcagt ggaggtcgtt tatagaagga gaacgagctc tgaataattt gggtctgagt    76440
ttcagaattt ctactcactt ttaagcaaga ataatcttcc ttccctgtct tctgctaagg    76500
gagataagat atttattaat gtttcccaat atgatttctt tccctgccag gcagccaaca    76560
aactgacttg ctgtggcaaa agaaagtttg gaggacgatt gagacgggtg tgctctggga    76620
agcaagcaca gaccctccta gcattttccc tcttttccca acggcaaggt caagatttgc    76680
```

| | |
|---|---|
| ttgcctgcca aggtagtggg tcctgatctt ctgagctgtc tgtccctctg attttttgtt | 76740 |
| ctccaggctc aggaattcct ataggattgc agaggcacct tcaacctgat aatttttatat | 76800 |
| tctcaggctc ctcctgggtt agactgggga agccagggca cccactagga tcggccggca | 76860 |
| gcggtggcac cttaggcatg acagccaagc agagggctgc atgagtagag gtgggagagg | 76920 |
| tgggagaggc tgcagtcact tcccaggtac tgtctggtgc actgatttcc cggaggagc | 76980 |
| cctgagaggg cagtgcaggc aggaccggag ggtagtttct gcagcacggc ctttatttca | 77040 |
| ggaatcacca gagcctttct cagtgttcca aaatgccttg gctgacaagg cttcttactt | 77100 |
| cctggggtag gccagggtgc cctgcaggga ctggttgccc aaaaacctct cactgaagaa | 77160 |
| aaaaaccgca gctaggtttt ctgggtgggg gaactggatg ccagcctggt ccacgcggct | 77220 |
| ctgggctccc agcattggag aagaaaagga aaaaggaaa ccaggtttta atcgagcttg | 77280 |
| attttcatta gcaaatgaaa tttacctgct ctcactttaa ctctgaggag gctgtcagca | 77340 |
| ctgctccctg gcactatttc tttgcatcca tccagcacta ggataaacat tccttggttg | 77400 |
| attctaaaga cactttgtat ttcaggatat tcatgtgctt ttaatgtatc caagcagctt | 77460 |
| tacaagccac ttttgcagaa catcttaacc ctctctctcc caccctaggt gggctggggc | 77520 |
| acagagataa tggcaaagga agaaagatcc agaggaaaaa ctggttgagg ggctgaggag | 77580 |
| agagaaagag aaaagacgaa atcgtcaaac agtgtagcac ctctgaagcc aaacttgagc | 77640 |
| agatcatttg ggaaaggagc aagtggggga ctgctctgct tatggaggga attttgagtg | 77700 |
| tccccatcag gtagaagctg taccctcttt cttaagggga aagggttggt aggtcctgag | 77760 |
| atctgggctg aagttggcca gcggacaggg aaatggtgca tcgagtcact cactcaacct | 77820 |
| tttgttccag atttttgtgc atttgaaaca ataataaggc agtaaaaggc ttgaggctgt | 77880 |
| gggatagttt tgggctattg tcactgtggt gaccaaatgt taacatggtg aaagtggaag | 77940 |
| tgcaaggtcc aggaagatct acagggaccc ccactttgcc tttaagatcc cttcatgggg | 78000 |
| tggatctcaa ggacagcagg ttttgtggagg agcagctctc ctgctgcctg tagagttttt | 78060 |
| tgttttgttt tgttttttca ggtaccacaa agccactagt gcacagggac tcagaaaaga | 78120 |
| cggcaggagc ccaaggaaaa ctccaatttg agtacagccc tgccttgttt cccccagaga | 78180 |
| gtccctgagc aaggagacct ccaccccaca cacaccattt cagaacaacc aggttccaga | 78240 |
| ctcccatgag gagcatctcc cactgcagag ccttggccag ccgcgcccgg actcctcaga | 78300 |
| gctggcgcaa actccgtcct ccaaaactcg gctctgggag gcctaagtga ctccgaagcc | 78360 |
| ggcggcagcc gcggcagcgg ccgtggtggt ggaagagctc ttttcccga cagtgccact | 78420 |
| gatcgctctt cactggagct ggaaacagcc ttcgcgaaaa ggaccggagc atgcgttaga | 78480 |
| agcagaggga gcttggtgaa gggctcggct ggaaggagga aacgccttct cgcagtgcgc | 78540 |
| ggccagcccg cggggacac cggcttgctg gactgcaggg gcccgtgcca cccaggaagt | 78600 |
| gacctgcggg tcactcagcc ggggcgctgg gcgagcgcgg gacggcccgg agaattccgt | 78660 |
| gcggctgcga cggaaaagg acgagggtc tctgtacccg acgctgccac tggcccaaag | 78720 |
| gaatttacc cgcgagcgcc caccccaccc tagcttgatg cttacgcccg caacaaaaca | 78780 |
| ggaaaccagg actgggcagt gcattccttta agtcaacaaa tacactgaag acttcgagcg | 78840 |
| tttgaaggaa ggagggggtt tgcacgtaag cctggcccg ccgggctcgg cttttctcgct | 78900 |
| gagaaagcgg cgcaggcagc caggcggcct gggcccgcgg gggtccatct cgccctagac | 78960 |
| tcctaagaac tcccacggcc ctgttcccag ctgcgaattc ttaatgcaca acgcgacgga | 79020 |
| gggaaggaaa ttcaccagcg cagcgacgag gaaggggaac tcaggacccc ttcaagtaca | 79080 |

```
cactgaggtg tgatcagagt tttatgggca ctttatatgc tgtaatcata acgatgtgtg   79140
tgccttgata tgcacgcata ttcacgcatc aaacgtgcat acacacacag agtgaatgtg   79200
cgcatccaat gtcatgtggg tgaaatacaa gcatcatacc cagccctacg aaaaaaaaat   79260
tcaccctgtc ggaccaggct ggtgacatac ttcgctggcg catctcctta ctcactctta   79320
cttttccgac ccctcaccat tccctctcct gtggcttggt aaatacacct gccctccgtg   79380
gaaggtgagt cctggactgg cgttgccagg ttcgcatgtc ctccccagaa cctccgtctg   79440
gctccaggga ctctcactga gcgggtctag agcacccagc acttttcaag gaacagccgc   79500
ggttcctttg tcccgcggct ccagccccgt tcggcccagc tctcagggaa acgaagcgct   79560
cagtaagaac ttttgatatt agtttgtatg ggtatttaca ctctggtgag gggagctgag   79620
tacggaagtt ccattaatca tactccaacc ttgggtttag atattcagtt tatgggttgg   79680
gagagggagt ttgccggaaa gaaagcatca aggttggccg ctgactccag agaaatgaaa   79740
agggagcaag gtcgttttct gtttctggaa atcaagaatt aggaatgggc aactacaggt   79800
gctaaccaac agaccacttt tttgttttttt ggtagcccctt tggcagggat agttttttcca   79860 cctttgcccg atacaattta aaaaaaaaaa tcctttttatt atggaatttg tcaaacacac   79920
acacaagcat aacaaacccc taggtaccca tctccaagtt ttgaccccta ttataatttc   79980
atcttcagtg ttttattatc cacttcctct ctctctatct ttagtatttt aaagtaaatc   80040
ccagatagca tcacatcatt tcaccccccac cataggattt caaagatctg ttatatttca   80100
agattgagta aaagggcttg aaattgggtt attgcaatga aactctagaa aaagcttgag   80160
ggttcaccca ggagtaagct ggacaaaaaa ggggtttgag gggtggaccc atcttgccta   80220
aaaatcttgt ctcatctttc taaaaattac atatgaaaga ggaagattta tgttactttt   80280
ttatatgaga gaatcgtcct ttaatagaaa atttctattg ctgcatcaga attatggagg   80340
aacacaaaaa acatacctca gtccttagtg tgtcctaaat taacacatat tcacttatta   80400
gtgggtaaat gactatattt catttcagca caacttctcc cctggtagaa acacaaaaga   80460
aatttctaat gattaaacta ggaaagtttg cactgaattg atggcttatc agagcaaccg   80520
cagttttcag gaagaaattc aatgccatgc gttgaaaata tcccccctagc aataagggat   80580 tatttttaaa aaagaatgaa taaagatgtt ctggtttctt ttgttttaat ctggtagtct   80640
catttacaac gagcatgatt ctccctgtcg aactctgaaa gtgacttaac tgaaaggctt   80700
ggcaacttca gaaagcaaaa aggtaaaaac agaaaatagc acacggttga atttgacaac   80760
ttttacacta cccggctgct taataaattc taaccccact tgtctgagtg gatactgatc   80820
atcttttcta tggcagtatt ttgtatttgg gttgttatg gtttcttaat taattttttt   80880
gagtagtgat taaatatctg ggatgctttt acactaagca tataaattct catggtatta   80940
gaaaagagct atttgatgaa actcataagg ggtatgtaaa ttaaaaaaga gaagaaagtg   81000
tgtgtacata ttttacaata atctcgaacg actccaacta tatgttgcag aagccatgag   81060
ctctctgccc actgtctgtg gggtatcagc aagattgact cctaccaagc cttgggcaca   81120
gtggtgggtt taagggtccc atgtctccag atcctaagat ggagttcacc gcaggggtga   81180
gggctcgggt cagggtaagg gtggggactg cagaagtcaa acaattcgga ggaagaggga   81240
gaggggaaga gagaagccac agacaagcca ggagacaaag aggaagggag agatgggagg   81300
gagaagaata agaagcaatg aaactgtaat tctccacaaa aatttaagct acagcagctc   81360
aaagaaggcc tgttttttaaa gcttagcaga agcccattct ccgctgaagc ctgttctttg   81420
tggaagcctg gctggggggc agtgggggcg gtgccactgt cgagtgttcc ttgccattta   81480
```

```
ggtccaaagc ctccctgtga tttctgtaac tgcacaaaaa caatctgggc tttaagaacc   81540
tgattattgt ccagagttaa atgcaggctc gaccttctgc ccatagagag tccaaacgca   81600
tgaattcctg ctggtatcag cttcggaggc agaggtcgcg agctgagctt gggacaaccc   81660
ttcaagcctg ctagcaatta cctgctctca gccactttta aaaggccata tttctttaca   81720
tttctaggat ctaatgtgag gttatgtcag gtcatgggac cctaggctgg tgcaaagtaa   81780
tttgatgtca ccaagagcaa gcagactcgt ttgtcaccct gaggaataga agtccctgtg   81840
atttctgctg ggagcagagc agggttgctt ggctggggt gtggaatcca gacaggggtc   81900
cagtgtgggc ctaaccaggt gagctgggag gggactttct ggatcgtgtg tgtgtgtgtg   81960
tgtgtgtgtg tgtgtgtgtg tgtgtgtgta tgtttgtctg tctcaggttg agaggattaa   82020
gggatcagct ctgctccaag ctcacacagc agcccattgg aactcagcat gtgacctgga   82080
ctgatccagg cccttggatc ccaggttcac ttgtgacatg atctgggtct cagttttct   82140 gaagctaaat ctggttagcc cacctgcagt cctttcttcc cctagccctt acccactgct   82200
actttaatag tctgtagctg attaaataaa caacggagt cttcctacct gaggtttatc   82260
cagccattag gtgattggtg ggagcacaga aggagtcata gcccttgtac ccctttgggg   82320
aaacacttct gtgagtgata agagacggct aatgtctcag tgaagggctt caaggcattt   82380
gctagaatgc cctcttccac tatttccagt tcttccattt tttcaaggg ggtgggggtt   82440 gtaggggtt gtgtaacaaa gccaaagaac agggtccctt aagccttcat ttgagaatca   82500
gggagagtgc gaaccctgga ggagtatggg taggcaactt gatgggtaaa atggaaaagg   82560
aagaggccgc ttcccagagg cctggccgat gctaggtccc agagacttga gcatgacagg   82620
gtggggggcc tcctacagaa gccctggaaa ctctatcggt agagctgcct gtgggggctc   82680
cacaatgtcc tgggattcat acattgaaat gtggagcatg gttccttggc cttctatatc   82740
attcccaaaa ggagtatact ggtgccactc ttcctgacaa ttctaggatg atctaatgcc   82800
acaactaata gactgagaga gcctgggcaa catggagaaa cccagtctct ttaaaaaaca   82860
caaaaattag ccaggtgtgg tagcatgtgc ctgtggtccc agctactggg gaggctgagg   82920
tgggaggatt gcttgatccc cagcaagttg aggctgcagt gagccatgat agtaccacta   82980
tgttccagcc tgggcgaaag agtgagaccc tgtctcaaaa aaaaaaaaaa aaaaaaaaaa   83040
gactgaagga gagaactcag actcagactc agccaaagtg gtcagcaagg aggcacaccc   83100
ctacaaggcg gaccccattt gaagcaggcg aaggcaccca atagagaacc tgcagtgagc   83160
atctcagagg cacatggaga ggcctgcaca gaattctcta tcttttggcc ataaggttag   83220
gaggtgctgg tggggccaga ggagctcaga taagagccag ctctctatat gtggggctca   83280
tttccatggg gttgtgagag aggccaatcc ttcacagaaa ttagaatctg gatgcaagaa   83340
ggcagccagg atcagatctg gccagatggc cccacggcag agatggggaa aatgtcacct   83400
tcgaatccta agaagctagg ctcctgtgct ttgccaaagg cctcgtgggc agcagtctgt   83460
agctccagcg gttttgcatg ccagcctctg gactcactta acttctgcag caatctgttg   83520
gtccccagag ccactctgca ccctccagga gaacctacat atgggcgctc cagggatttg   83580
cccgcattag gatcaggagc cccaggaaga gttagatggg aatccaggca tcctgggccc   83640
tgtgctttcg gtgacagct agatcttcct tgtcaaggtg gaaatagcgt ctctgccctg   83700
ggtgggaacc cagacccagc cctgcaatca cgcaggcaat aaagtaagca ctccactgtc   83760
gacggggagg ccagggagag agaggcttct ctttgaggcc tcccacccc atccaatcca   83820 ggaggttgca gtcgctgtgg gcggcggcgg aggatgctcg caggacaccg ctgcagttgc   83880
```

```
gacctcttcc cactagatgt cttcccagtt aatcggaact caagggcgct gtctctgctc    83940
ctcgggccga gactcggttt ccctgccgc tttttgaagt ctagcattcc tctgtgaaag     84000
ctggcttttc ccttttttc ctatactccc cttcccgccc tgcgctctaa atcctggctc    84060
tggaaatcca ccagaatcaa atgctggctc cctgcgggcc cgcgtcggag cggctcacgc    84120
cattggaatc tttttatgac ctttgatgtg tttaaataac atggcaagtc tgagcacaca    84180
cctcggatta aactttaatc ggctgcagtc aaggtcgccc aggtggtaaa agcgtttcct    84240
ccgacgtctc ctggcagacg ctgcgggtc caaggtctgg ggcaaagccc taggcccccg    84300 ccatacccte ctgcctctgt caggcctggg tgggggccag gcccagggcc accccatcga    84360
gctccaaaga ggactaagga aatgggatcg gaggtagaca ctcagggtgg gctaatgacc    84420
tgagcacagt ttttatagct gctagacaga atagttaaaa attccaagaa gcactttcaa    84480
tttcccctga ctccagaaac tggttgaagg tctagtcatg gtcagtgcct tattgcctcc    84540
tccccatggc tctgctcccc tagggagaaa ggggtgctg gtaatgatgt tgcggccaag     84600
ttagctgact gtttttaagg tcaccaaacc cattaactgt gggccaggat ctagaaccca    84660
ggctaaagca gcccttctgt gtgtcaggct agacaaggtt ggcttcaatt ttatctggga    84720
tgagcatatc tttctgagcc agtatacctg tcatggagaa ttgtcatggg cagtatttag    84780
gaaaagctcc aagaacaggg cagcatatgt agtgagagct taccactgtg ctttttaaaaa   84840 agaaggaatg tacaaagggg ctagaaggac agacaagtca tcagtaacag tgcttcccct    84900
gggaagaact ggtgttcaga ggatctgagt agagaatttt ttttctataa aatcttttg    84960 tagtgtttgt gaagtgcacc aattgtatgt attagctatt gaggttatac ttttcagaaa    85020
actggttacc ctatgtatct catggccaca tattcctttg gggaatttcc tccacacatc    85080
ataccagcct tggattcagg ggagaacact gaaataagtt accccaaggc ttgaatctta    85140
gtcttacgga catcaactca gatttccatc ccctgggaga ggttctcagg cctctctctc    85200
tgggcttacc cctaacttgt aaatgaacat gccagcccca gccattcaca aaagagaatg    85260
cgttgtctca aaacgaatta aagcctgatc ttcaattttc ccccaatccc tgagtgccta    85320
ggggtttgca gaaaaggccc acaaatgctc ctccagacca gagattccca cagcccttg    85380 acatgtatat ttggtttgtc aattcttgtc ttgaagacac tatcaagtgt cttcaagggc    85440
cacatactag actgacctgt tgatctcttg acttagagat aacactatca ctgtctaaaa    85500
ttagttctca tagtgcttct tcatggcctt ctgggggctg ctaatactct ttatcttgat    85560 cttttgtagta gttacacaaa tgtatacata tataaaaatt cagtgaactg ggggcttaag   85620
atttgtatgc tttgctatac gtaagttata tggcaataaa aaatttta agtgcttcct     85680 cctaacaacc tgtgaggttg gtcccaaggt tattacaatc atctccattt tacagacaaa    85740
gcaactaaga ctcaagggaa gctagggtcc caggcatctg tggaagaaaa taaccagcca    85800
gagactaacc agcagcttct tcctctgggt cttgctgctt caatatccag ctttctttc    85860 cagcagattt ctcaggtgac aggagccggt tcagtataga gaggctcttt ttagagagat    85920
tgtgaggtag gaacatgtgg tctgagtctt caaattttt agtcttggcg tagggagtca    85980
gggagggcac gcgcccagag ggtgtggggc ctagagggcc ccacttgtgt gcctctaatg    86040
aggaagaggg ccctcaggc ttggaacata ttttcttctt attccagtcc tccaagccca    86100
cacgcacccg aggctcagga gacctcttca ggcgaccgca cccttccgct gaagtcccc    86160 acttctgccc ctccgaggtg gggtgggggt gttctgaaat aacggtggct gcagttagat    86220
ggctgaggac atagaaagcg gttgttattt attccaggca ccatcacaaa aggcttccaa    86280
```

```
aaatatcgag ccgagatatt ttattgtcca gcctgtctgc agcctgtaat tatgcgttca   86340
agatgtttaa tgtgtgcaaa tgcattagcc gctttcgctg gtgaaaaccc tagctggggg   86400
cggggtagag gcaagtctgg agataattat gtcgtacagt cgcaaacatt attccgttct   86460
tactgtaaac ggccccggcc acctttacga gaaaccagga aacttctgag agttactagc   86520
agcgtttacg cgggcaaact gagttctttt tctttctctc ccggattgtt cgaagtatct   86580
atcgggcggc ttcgatgcca ggttcagagg cgcgccaggg agagggcgcc ccgcagagga   86640
gcgcagcgga gaggcctacg caggtccccg gtgcccgcgg ccctcggagg ccgggccctg   86700
cgtcttggcc aggcactggg tggcagctga ggctggtggc ccggagccct cgcggccgcg   86760
ggcaggcccc ttcttgggca gggtcgggca ctcccgctgt ccagggctct tcggcaccct   86820
ccttccaatc aggtcgctct cccctgctcc ccagactcaa ctcctccgaa gctgctccag   86880
gttgaaatgt gaccgctagg ccgactccct gggcccgcga gcagttctcg aaaggtgcgg   86940
actgagccct ttctggggtg gggtgcgggt tggttctcgc aagtgtgacc cagggtgaac   87000
ttgctatttc gggtcccggg tgctgcaggg ccaggagaac agctggatg ggggacccc    87060 gcctccaccc tcgggccggc acgtccgcgc cctgtcaggt ccccctccct cctctatgat   87120
ggccaaggcg tgcgccaggg ctatccggga accttgtaag gcctcgtgct ggcacctaac   87180
cccactcgcg gcacacttcc tctatgtagt ctgcggcccc gcctgccaaa tgagagtgac   87240
cagtgcaggg acagaatgcc aggctggtgg ccgaccgcct gagggacaaa ggcgagcatt   87300
cacaagccaa cagcagaccc ctgccccca tatttccatt tcgctcaggc ttttaggaca    87360
aaatcaacaa ggccgcagag tggtgcaggc gctcaccccg ggtgacagcc tggggagcca   87420
ctggttccgc gaccctgggc atgaaactcc tcaaggcgg ccctcgagac gcaggggaga    87480
ggatgctgcc ggcgcctgcc cgagggcttc tctgcgggaa gcgggcaggc accccaccgg   87540
agtcattgcc gggaccctca gcgcaacgcg ggcctgtgtc ctctcgtttc tctttagaaa   87600
aagactggat tttaagactc gttttaggcc aatgatttaa acaaaaccaa accaaacta    87660 ctgggcgctc gaggagtagt gtgggacaca tttaaaaaaa aacttgtgtg ggatccaggg   87720
tgcattttct ggggcctggc agcgctgctg cagccccagg gcatggagaa caggggaca    87780 tggaaagatc tgggaggatg atgaaacccc agggagggaa acgctcacac agagaggaaa   87840
aacaaaaccc actagacgtg atttgttcct gctccaaatg aatcatctaa agagaatccc   87900
tctgggctac atttactggg gcttagggtc tggggccctc agatccacca gtggtggggg   87960
tagttccctg aaatttgcac tcccaatctc ccccgtgaag gtgcaagctg tagctacaaa   88020
gggaaaagga gaggaagagg ctagtaggat tcctgggtgg ctgcagcccc aaagtaaacc   88080
ccatgctttg agtgcctctg cataacaaag tttcccaggc ccccagact tggaggggg     88140 tggttagtta tgcagcaact agacgtttgg gaacagcaag accctggcag gaggtgcaga   88200
ctaaagcttt caggttccta cctcttgttc tttcctaccc cctgtgtctg cctttctctc   88260
tgccaccttt ccagagactc aggcctccag gagcaagtgg ctttgctctg aggccctacc   88320
tggatgggcc agagagactg ggaagtttaa ggacaggtct cacacttggt tcagatttca   88380
gacacctcag aggtggctat aacttaaagc ctgcaaaaat aaactttaac cacattcgag   88440
cgtcccccaa gcctatagtt ttgaaggcct aaaatgtgcg atcttttaac tcagaggttg   88500
ctggttgcct gagaggctga gcagaatttc ccaagcaaga ggggacaggg aaaaaggcca   88560
ttgtttctgt agatatccag gatcagttca aaatcagggc tcactgaaga gggcatgtgt   88620
cctgtgactg ctctcttgaa tgtaatttt gtctctctct ctctgtctct cttgctccca    88680
```

```
tagaaccgtg ccctcacagc aatccagtgt tgattctcc ctatagaaag tgaatctgat   88740
cagggccttc ttcactctcc tcctccttct cttctgttct gcagctcatt caaaagagcc   88800
catagaaaca cagagagacc catgaggagt ctcttgccac tgggactgac tctgcctggg   88860
acccagagac cagaaatggt gagtggtttt tcttcaaagg ctgctgggtc ctgaggctgg   88920
gattgcctgc acagcgagag ggcctcccct gcagctgcac ccaaccaggg aaaggggtgg   88980
aaagagtttt tgaaggactc tagaagatgg taagcagggc cacctcgaag acctagattt   89040
ctcaactcta catctcctgg aggagggatt ctctactggg agtgatcagt gccaattcca   89100
gtttccagat ttggtttgcc tgcctaggaa aattggagcc tcatttaaat cttttcctag   89160
aagtcttgtg ctcattcttt ggctttctgt tttctattag ccagagactc atgtaagata   89220
atctgggttt ctccctccga cctctgaaac atgtaatttg ggggagatac tgtatttaaa   89280
atgccagtcc cagtaatgag cccagcttag cagtgtgagc tcccaccctc cccttaatga   89340
acagagctgt cgagaaataa tttcactttg atctagtttg tgacctgagt ttttggctta   89400
aagaagactg ggcagctaat tggattcttc agttgccttt aatctccacc tcaacacttg   89460
gaacctgacc aagctgaatt aaaacaagtc tgataaacaa gatgtagctg gctcccaggt   89520
taacagtaac aagaaaatcc ccaccaccac tgttgggttt aatgatcaca gcatggttgg   89580
cacctcacaa aaaacatgag gctgtaggcc cgcagaacct gcagcacgga agtcttcaga   89640
atcctttccc ctccctccta gccccctgga tgtagcttaa ttagaaagag aaggaggggt   89700
agagggaggt ggggaagaaa aacttacagt tggtgaaaga atcaggttgg gggttcatct   89760
caaagggagg caggacgttg aggagacttt gtccctggga gaggaagcag gccgagcctt   89820
tgagggctgg acagtaaaga ttgcaattttg aatttccaac tgtgtttcaa gaatgagggg   89880
atgcaggagg gaaataggat atgaggggca gggttatgca gcctggcggg ctgggaatca   89940
tggattgtat ttaatctttt cagatgccag ggttttgtgt tctaggagca aagcagaagg   90000
aggaagaagt ctgctagacc tccccattct tagtttgggg cctgagaagg gattctcttg   90060
gactcccctc tggatgctcc tgtctgctgc ctgcctaagt ggctggagga gttctgaggg   90120
aatgctttct ccaaggcagc aggggtttgg tctaggctag gatttctcaa acctccacaa   90180
tattgatgct ttgggctgga tgattaattc cttgtcgtgg aggctgtcct gtgcgttgta   90240
agatgtttac cagtatcttt ggcctctact tacagatgtc agtagtgcct accccagttg   90300
tgacacccag aaaagtctcc agacactgcc aaatgtcccc tggggggcaa aaattgcccc   90360
cacttaagaa ccaccagtgt agacctctgt gaggcaggca tttctgggaa aaaagtgtag   90420
tgctttgctt gaaatgatct ttgtatagtt tcagagagct aggggagcag ggcggggtac   90480
tcccgctcct tctttgaacc tctccagcag ggcagatcat gaattccttc ccagggctgt   90540
cttgatctcc ttactgtagg tgctacacct tcattaaggc tttgagcaag gacatagctg   90600
ccagggcata taatcctaat cttagacac actgaatcca ggataagtgt gtgtgtgtgt   90660
gtggggaagg tggtgggtgg gtaggtgtat atatgggtct gtataagata aatgctaggc   90720
aaaagagatc caggcctcac cttttcctgc agctttgaaa gctctttctt tggcatactt   90780
ggccttgaag tgggaaacag ctgggttttc ataaaatggt tgttgaggtt atcagggaat   90840
ggaaagccta ttcacatat tgaggtgaga ggtagtgtct aggatgctgt taccagattc   90900
ttatgcagta ggtggtctta cagctcctac ccatctcttc cctctagctc tgactctcag   90960
caagctcttc tcacacaggc tttctggaaa ctgttaagat cctagaaagt aggagcttga   91020
cataatttat tgaacacttg gtattactat tataatgctg attgaaaata tttaaaaaaa   91080
```

```
taggaggctg ggcacggtgg ctcacacctg caatcccagt actttgggag gcagaggcag   91140
gtggatctca atgtcaggag tttgagacca gcctggccaa tatggtgaaa ccccgtccct   91200
actaaaaata caaaaattag ctgggcatgg tggcgggtgc ctgtagtccc agctactcgg   91260
gaggctgagg caggagaatt gtttgaaccc aggaggcaga ggttgcagtg agccgagatt   91320
gcaccactgc actccagcct gggggacaga gtgagactcc atctcaaaaa aaaaaaaaaa   91380
aaagaatttt tatcacaatc cagacatctc aaccagatcc acccatccct tttctttctc   91440
tcttctttct ttctctcttc tttctttttc tctttctttc tctctttctc tcttctctt    91500 tctcttttc tttctttctt tctctctctt tttctttctt tctttccctc cttccctccc    91560
tccctcctta cctacctccc ttcttccctc cctccctccc atcctccctt tgtttcttcc   91620
tttcattttc tttccagaat gtgttcacat agaacacaaa tgaaggatgg taaagattaa   91680
gagaaactga ttaactgaca aagacaattc tatcaagttt gcattgcatt aatagcaata   91740
acaatagggt taagttatgt gaccctata tatattttc acatctagag tgggttatag     91800
tcacttaggg ctaggcatat ttagctgtca gcattgccaa atgaattaag ctttaggtat   91860
ttgactaaaa tcactggtcg aatgcttaca gagtggtcat cactttacaa atattaactc   91920
atgtaatctg ttgaacaccct ctaggaacta ttataatcat cttcatctca cagatggtga   91980
aacagaggcc tagaaagctt aagtaacttg cccaaggtca tccagctact aagggacaac   92040
actaggattg gactgaggca ttggatttag ggtccatatt ttctattttc tttctttctt   92100
tccttttttt tttttttctt tctcaataca gagtttcact cttgttgcct aggctggagt   92160
gcaatggtgc gatcttggct cactgcaacc tccgcctccc ggattcaagc aattctcctg   92220
cctcagcctc ccgagtagct gggattacag gcatgcgaca ccatgcctgg ctaattttg    92280 tattttagt agagacaggg tttctccatg ttggtcaggc tggcctcgaa cttccgacct   92340
caggtgatct gcccacctcg gcctcccaaa gtgctgggat tacaggcgtg agccacctca   92400
cccagctggg tccatatttt caatgactaa tttctgctgc caattgttaa tatgctgggt   92460
agggacagtg gcccagggga cagctgttgg ggaggtgggc atctctaagg atgtagccac   92520
tgctctggaa gcctcattct gagctttggg gccggattcc ttgtccacag tgtgtctatt   92580 aataagcc tttctgataa ttgaaagtaa gttatgggaa atgtaatata tatccccggt     92640
atttactgcc tcgggaacaa gggagacata atgaaggagg gaagtttgta attgcagaaa   92700
aacatcagtt ctaggaacag aaatcagtgg cagccagaga cgttctcccc aggtttccgg   92760
ccctgctggt ggcccctcca ccaggctcca tacaggcagg aaccccccaga agaggaaagg  92820 ggcctgtaat aggagtcatc aacctgtcac cacggctagg gtgaatatgg cctctgagtt   92880
gggggaaggg gggaggttta ctctttagca ccaccagctg cagggatggg gaggggctgt   92940
ggagggtggg gtggggaggg gaggctggag gtggagctgg ccttctctat ccacagccca   93000
cagcctcctc agaacagaca ctgggctagt aacgtgcgat gctgcggtct aggtccctgg   93060
ccccacttgg cactaaggtg agcatggtgg tccttaccct caggcagcct tcacatctat   93120
aagaatgtgc atacatgcgt gggtttgcgt gtgaaggaaa catggagggt gacacagcta   93180
cataaatgat tgcaccaaag gctgagataa gaacctaggg atggagcagt atgaaccggg   93240
tgccaagtgg tgtggggtgt cagggtctgg ctgagggtgg gcagcaagga ggctgagata   93300
atgacctgga caggtgggaga ggggccgtcc caggtggaga tgcaaggagg atgctgggaa  93360
caaactctgc ctcttgggct agaggggaag ggagggtaaa ggaggcattg tctggcacct   93420
accaggtgct gtgctttgca gggatgatct catcgaaccc tcacaatatc cccatgtggt   93480
```

```
aggtacttgt gttacccaaa ttctacagat gaggaaacag gcagagaggg tcagtgactt   93540
gggcaaggtc ccgtggctgg gtggcagaga gcctctgtga gttgctctga accggtccat   93600
aggaggaagc ccagcacctg cagtgaagcc ctggtaaagg ggaaacttag ttgggaggct   93660
ttgattttga attgaggcct tgcttgcttt aagaaggttc tcataaggaa aagctgcatg   93720
cgtcttacat ttctgtattt cccccgtgcc actgccagcc ccatcttata agttatccgc   93780
gagtgatgag aagtccccccc tcctcccccgg ggtgagtgag agggcaccat ccctggggca   93840
agggccccca ggcgcaggat gcacgaaccg agggacacac cgccgccaga ctgacctggt   93900
gtggcggtcg ggcggggccg ggccaggccg cgaccgcgag aaaccacagc cccacggagg   93960
aggccgggcc gcggggctgg cggggaccct gcaggccggg ccgaggtgcg gtgaggcctc   94020
ctcccgacct ggccgcgtcc tcagagttcg ctcggggctt cgtgtttgca gagcagcctc   94080
ccgcctgccc ggcttgcccg gggatgtggg tggacccgcc ccgcgcggcc gcggcccagt   94140
gcaaaccgtg atccaccctc ttccgctcgg tgggaggaac ccggggcttt gcgcccctaa   94200
ccagcagcgt gaccctcgca gtcagggaac ttctcatctg tgaagaaagc ttaagaatga   94260 caccccctgac aggagcatac gtgcttgcct gcccataggg gacaggaaca aacgagatca   94320
tgtattccat gaacacgctt ttaatgccca cctactatat gacaggtgct gtgctaggca   94380
cttctgtatt cattctaaaa tattaatttt gcatcgtgtc cttttggtat actttattga   94440
aatactatgt acaaaaagtg caaagtcat aagatcatct aacaccaaca aatatttatt   94500
ttcattcaac aaataaatga ttctgtaaaa cttattggca atgtgtgaga gtattgcaca   94560
ctgcaataaa gtgttgtcag taagaggcct cttctctaca ttacctgctg ttgatctggg   94620
atgaatttac ctgagtactt gcttcttctg ggactggaga tgggttttcg gctccattct   94680
gtcactaaac accctggcta cctcctgtga tctctctgga actcctcagt ggaatgaggc   94740
ggctggcctt cacactaagg accctacttc ctgtgactga tgagggtggc ttgggtgtat   94800
ttcagaaata ataggacaca atttgagtgt ggcttcttgt atttatgatt actaacacaa   94860
atgttatcca cacattcatg ataatacaca tttgcaggtg aatgtctttg gcagagctgc   94920
tggaagaaat gtgaggcctg tgactcatca tgaaatccca agaaggtttc actactttac   94980
caactgagaa gttctcatag gtggctttag agaagagcgt ttcttcttgt gcaaatagaa   95040
tccttctact gagcagtctt ctaaagcagt catctcaaaa atgaagataa taacactact   95100
cattttatat tttatgcaga aagctttag aacagtgcct gggcacacac tgagagttta   95160
ataaaagtta gccacaatta ttattcactc tttgacactc cccaaaagc ttatttgtct   95220 ccattcttcc ctcttttaaga aaggaggtag taggttggaa ggtctagcct aattgttata   95280
aggtgctgcc atgaatccca acctaaaaat taacagtagg aggcatagat ccctaagtag   95340 ttttctcccct acacattcat cccttgtgaa tacaggatga ttgggtaaag gtccaacctc   95400
ccttcctggg ctccctggcc tggagaggca ccagggcact ccctaaggca acctcatcag   95460
aaatcagaat cctcatcagc agacctaagt ccttcaggcc accagtgcct tcccaagggg   95520
gttaaaagtt ctctaacaag ggcagtgtca ggtatggaga aaatgatgga gtaagaattc   95580
cttccatatg agtggagatt tacagttgac aaagcactgg ccatttctcc atgtttagtg   95640
gggttgatag gaagacttcc ctgggttttg tgtgtttgtt ttcgtgatga tggaagggta   95700
ctgagtgcaa agagcctttg gtgtttttgaa tgcaaggtga ctctgtcttt ggctctggag   95760
ttacagacac ctagatttga gccaccactc tgccatctat ttgctttgtg accttcggca   95820
agtctgttta tattttttctt aactttagct tcctcaactc gaaaatggat gtaacaatat   95880
```

```
cacctagtta gcccataagg ctgttgtgca gtttaatttc tatgatgcaa ataaagcact   95940
tagctcagtg cctaaagtaa tgtagatgca atactagtta gctttcaata tatattatca   96000
atattcttat atgattctct tagacatggc agaaaaaatt cattctgatt ttataggtga   96060
taaaaccgta tggaactact gatatttact atagcatgga tgaacctcaa aaattgtgct   96120
aagtgaaaga agccagaccc aacagactac ctgttgtgtg attatgtctg tctaaaatgc   96180
ccagaaaagg taaacttatt aagatagaac attagcggtt gcctcaagct ggacgtggaa   96240 agggaatta acttaaaaaa aaaacgaggg atctcatggg ttgagaagat gaaaatgttc    96300
tgaaatggat ttatcgtgat ggttgtacca cttggtaaag ctactactaa aaatcattgt   96360
tttgtacacc tgaagtgggt aaatgttatg atgcataaca tatacatcaa taaagttgtt   96420 ttaaaaccc aaaatatcac aggagaagag ggggaataga atctaggttt cctattaggt    96480
gttctttaga ctctgctacc tcccattggg taggagagag aaggcaaaca gcagggagg    96540 agctatggtt agaatctccg ttaaataaga gaatggaact aagacaattc tgagaatgtg   96600
gaggtggtag tttcttaaag agggaagaat ggagagaaat aagcttttgg gggagtgtaa   96660
aagagtgaat aataattgtg gctaactttt gttaaactct cagtgtgtgc ccaggcactg   96720
ttctaaaagc tttctgcata aaatataaaa tgagtagtgt cattatcttc attttgaga    96780 tgatgaactt gaagcataga gaatgtaaat accttgacca cagtcataag ctaatatatg   96840
gcagggtcag gatttgaacc caagtagctt gttccaaagc acctgcattt taccctgatg   96900
ctattaatac atataaaaag aaggagagaa atgtcaggtt tctgggcaaa aatctggagt   96960
tacattgtgt ggatgcgtga gcctggaaca ttctgagact ttgctttaaa aatgtgatgt   97020
tgttttatat ataaatatga accacaccag atatcttgct gggggggtgg atttgctcca   97080
ccatctattg catggataat atgcagcatg gatatcattt ttgtatatga atatcttaaa   97140
atgccagaca atcccttcac ttctgtgttt gaagtgtggc tatgctcatt tcccagagta   97200
tgaactgagc tcacgttttg ggaacaacat tcagactgat gtaaacaatc tcagaattac   97260
ttggaccatg ttgccaagct ccatttcccc tcccccagtc tcattccggg tgcctccttc   97320
atccctgtgc cctttgcctc attcctgtcc ctctttaccc ttccaatgct cttttctcca   97380
tgaaataggg agtctttctg gattgaatag aaaaattatg ccttaaagat ccattctttt   97440
ggtttgctgc attgaggaag aatatgtgtg cagctagaag aaaaaacagg tcatatctat   97500
acagaacttg aaaagtaagg attaaaaatt tcaatgcttc caaggcccaa aaaatattgc   97560
actatttttt catttaaatt atatgtatag attaagtgaa aataatattc ccatttcttt   97620
cattcttttg gttaagtga tttaaaacta tttgcatgta taaaacaggc aacttgtaaa    97680
tttaagtgaa aggaatgcag atttcttgga tgctgtacag ggagggagag gttgaaaaga   97740
aaattaacat agtaatgaaa agattagaga aaagtggtca agtgatcaca atctggtggc   97800
cttgggatgg ggaagaggta taattttta aaacctttat tgttttgtgt gggaggaaat    97860
acacaactaa tgcatgttca tttaaaaaga taatcagttt ttgaagaaat agtgtggcaa   97920
gttaatgccc catatgcccc cataatccca aagtaacagt tgaatgtata ttcctccata   97980
tctatgtgca tataaaatat acatatattt cctatataac tatccatgaa attaagtcac   98040
taatcatatc tgattgcttg cagacatttg cttacaattt ctttctccat ttttacaaat   98100
gtggaatcat attacacaaa ctattctttt tgcaatttat ccttttcat ttaaagtaag    98160 cttagacctg tttgcctgtg agcacacaga tctcgtctga atatagagta ttcctttata   98220
tgaatgttca tcattttatt taaccatcat tttatttata aattgatgac tgtcagctat   98280
```

-continued

```
ttccactttt tccttatcac taaaataatt tagtgaatat tcttgaatgc attcattcgg   98340
gaatatttac tagattattt tagtgataat gaaaactatg caaattttca gaagtgacat   98400
ttcagggaca aaccgaataa taactgtaaa ttcataaatg tcaaaattgc cttcaaaaag   98460
gttttgccgt tttgttttt gtttgttta acgttccacc aatggttttc gggtgacggt    98520
gtccttgcac gatgtagtcc gtcttcaaag ttcttttaca caacgtgaat tatattgaaa   98580
ttgggctact tcatagagct tcgcctcagt ggaggacagc ctggaatagg tgaggggtc    98640
tcgaaaggaa taccaggccg gggagtactg caagtgtcg gaggggaagg gcaggtcggg    98700
gagaggatcc ccaggggctg ggtgtctgca gggctccccg taactcagag gggccggcgg   98760
ccgccgcccg aagcctgagc ttttctcagc agatggagaa ttcatttta accccaggaa    98820
aggaatgggc tgagacatca gaccaccgct cctagagggt caaatttcct ccccataaat   98880
ccaaaacatt ctctttaggg agttccctcc gtggcgcgca acccgggaa gccgcgcgcc    98940
ctggggttc ttggcgggcc gtgcgcgcag cctgaaccgc caaagtcgcg tcatcccgca    99000
tttgcctgca cccaggagtt tgcaacccgc agagcccgca gaggccaccg ccaagagtgc   99060
gcgccttggc gccccgtcgg cctctacttc ctcggatctg agccagcgcc gctaatccgc   99120
aggctgcagc agaacctgtc gccagcttgg agagtccctc gcgctgccct ggcttccccgg  99180
tccgcgggcg actcgcgctg ctcccgggtt tgtcggacc ccaggagggc gctcaagcct    99240
gtcggcccct acttgtgtgt agagaatagg cccgggtaca ccacctcaga aatgcagagg   99300
aagccgggga cactgaagcc cgggtggttg cagtgaggct gaggatctca gatgggtgac   99360
ccccagctct ggccagtatc tgaggccact gcacgtgggg gacactgccc cccaggttcc   99420
cacctagttg gtctcttcct tgggtcagtg gactgcagat gactccaatt ggcctagtgg   99480
gccatttctg tcctagagtc atttttggc tgatacagaa ttttataata attcaaatta    99540
gttgccaaca tgtagaaaca cttgaaaatg aaatatctaa caatgatatc agctggagct   99600
gaattctgtg actccagtct tctcaattcc caaatgtgac catggccatt tctctcattt   99660
ctgttacatt tctgttacca gcccactcct gtaggcattg atgtgtgtcc cctgttggag   99720
tcatagaata ccatggtggg ggcatgaaaa tagaatatat tttcatatat ttcagaaaaa   99780
tagacccttt agctcccact gatatttgat gctgtgaatt ggtcaaggtt acccagggtg   99840
tggcagagtt gagattagca ctttattcac tgatgagagc ccagaggagg gaagagactt   99900
ctgcaggacc acccagccag agagcggcag gggcacgcct agagcccacg tttctgacca   99960
ttagccccctt ctcctgaccg cacaggggcc ccagtaaaac acagcctatg accaaagagc  100020
ccttgcttgg gctctcaggc tttgacccaa cacctagtca ttggtcagac caactgagct  100080
tccactgcct ctgtctgtag ctatagaatg gagggagtcc atgagggctg gcttgtgtct  100140
tgctgtcagc ttccaggttc tgggttcttg cctaagaaac aactgcatcg aactgtgggc  100200
agatattcct tatcttcttg catagtctaa aaatacacct ggccatacta tagcaattgt  100260
atttgaactt actgatccaa tcccattgga aatcagtgca tctagctatt aggggaatgt  100320
ttcccaaacc ttcatacttg ccacctccag ggtaaaggga gactggaaaa gaaacagcca  100380
tgtcacttgc cagccttgtc acagttctga gttctgtcct acattttca tttgggagcc   100440
agaaagaagt ggctagacta tcagaaggcc catagggtg gaaactccct atcttaaaac   100500
cagtacaggg aaacacagtg aagggaaaat gaatggctgg agataacagc cagtgtgggg  100560
aaaagaagta cgtctgaaat ggcttcttat tttacttggg agcattccct acccaagact  100620
aaagcatgca aagcaggcca gagactttga tgtttctcct taaggaaatg aaagtttgag  100680
```

-continued

```
gcatttatgt taacatatgg aatatctatc tgtgactgca ttagctcttc agacgtatct 100740
tcttacctcc ctaggagtaa gtgaacagct tacaaaagct gcagtttctg tgggagaaac 100800
tcaatttgga tctgaaatca agaaggctta acaacaccca ctctgtatga aattaccacc 100860
ccattttaat aaagtccaag atgtttaata gctcacttaa ggtcttacag cacattggga 100920
gcagaaatag aagagttaac tgttttttctc atttggtctc ctgagaaagg cttgttcatt 100980
ttaattctat ctccagaaaa acgttttatt tgtcctcttc acaatccctc cttaatatct 101040
cacttaggtg ttatcactgt gcaggtaaaa taatttatt ttaaagtggc atgttgtaca 101100
cataaaaata attgagtctg ccggcctgga aaaaggttca gctgcctgcc tggaaaaagg 101160
tttactgtag cctaaatttc tatgaagatg tataatttgt cagtgaaaaa tatatatgaa 101220
cacacatgca tacccctta ttaccactca gaaagacttg ggaaacttac attttcttct 101280
tctctctctc tcatttggaa aacatggctc cttcatttcc cattctcttg tagaccttcg 101340
gtccttgtga ccctgttctc tttaccttta tgtttgcaag gcagagtacg gcacaggcat 101400
accatattct catcacctat aggccaagaa cttggtctca gataatagtg ctagtaagga 101460
atagctctgg cttccagtct tagaaaactt aaaataacca gggcttaaac aggataaaag 101520
tttacagttt tccacctaaa agcctggata ggggctccag ggctggtgtg atgcttcatg 101580
atgtcagaga tctgagctgc tactatcttg ttgctctacc ttatccaggc ccaggatgtc 101640
agtagacaag ctccaggcgg cagaatggag ggataaagaa aaccactggc cggatgcggt 101700
agctcaggcc tataatccca gcactttggg aggctgaggt gggtggatta cctgaggtca 101760
ggagttcgag accagtctgg ccaacatggc gaaaccccat ctgtactaaa actacaaaaa 101820
ttagctggat gtgacatgca cctatagtca cagctactca ggaggctaag gcaggagaat 101880
cacttgaact ggggaggtgg atgttgcagt gggccaagat tgcgccactg cactccagcc 101940
tgggtgacag agtgagactt tgtctcaaaa aaaagaaaa agaaaagaaa gaaaaaaaac 102000
catgcaaaga gcttgtacat ctctgtcttt taaggagtgt gcctggattt tgctacagga 102060
catttctgct gacattccaa tgggccagaa tttatttggc tctaaatata agtggccacc 102120
cactagtata tttgttccag gtatggagtt gttgcttcat tcctcttcct ttcagtatat 102180
aaacttactg aaattcctta ggctcacatt tagggaagta acatgcgaca atagtaatag 102240
ctaacattta ttgaggatta gtgagtgcta gatattcttg gaagtgctct gtgtgtacta 102300
actcatttta ccctcatatg tccccgtttt acagatgggg ccaaattaga acccaagcag 102360
tctaatttaa gtatgggcac ttaaccatta ttctaaattg ccactataat taagacggca 102420
acaattgtac cctgttatta tttatggatc atcttacgcc tttactacaa aaggaacatt 102480
cccttatcac accgggcatg ccttgatttt cttctcacta ttccaaatcc cagtgaatgt 102540
cttttgcaaa aaggacacaa aatcctggat gccatttact atagcactgc aaagatagca 102600
gccagataat tctttatttc aatttcacat ttaccatctc cacatctgct gctttccaac 102660
aaatgcatta atgcacccta gttttgctct gtagttattt atttctgggc atatgttaac 102720
caccacatag ggagaggggg gcaaacatgt gatgtgattc cctgagcacc attcaccctc 102780
acttctcatc cacagctgct tttcactcag aagagtggaa tgttgagaaa aagaatcaca 102840
gacatagtag agagtgaagt aggggaccg tcaaggtgag agagaagcag taacttgcat 102900
ttgcggagta cccattgtag gccagacact gtgcaaggcc cttccatta gaacggctct 102960 gaaaggtagg ccttgtatta ttttagatct gacatcctgc agctttggtc tgcccaaggt 103020
cactggtgag taagctccag agctgaggtt caagctcagg actgtctggc ttccaagtcc 103080
```

```
aggttcttga catgtcatca actacctctg aagtaccaga aatcttggct gggcaagttt   103140
gagagcactg ctccaccgtt gattctgttc tcctagctgt tacagaccag tttccatctt   103200
cccaaatttc cctgggatct gtctgtcttc ctgctggact caaaatccag gcctcattcc   103260
accacacacc agcttttgc tgctcctctc ctgctgggtc agaagatctc acaatatata   103320
ttcatagaga aagtggattc atggctattg gaagtaagat ttggtgttta caagcatggg   103380
tttttccttg actctcccac ttactatctg tgtgagctca ggcaagttgt ttaagttctt   103440
taggcttcag tttcctcatt tgtaaagtgg ggagacccat acctccctct gagggttgtt   103500
ataagactta gagccagagc acatgggatt tttcttttc cattgcctgt actgggaaaa   103560
ggtgagggtt atgagggaag gacagttcta ataaaaggaa aattggccaa tttttggagt   103620
gaatctggct tttcagttgt taaaggtcca tatctaagag aaaatcatca cctgactgtt   103680
gccacttgta aaagtgatac caccctttcc tcagggctca agaccaggac agagttaaat   103740
cctggatctg ggttcaagag atcttcccac ctcaacctct tgagtagcta ggactatagg   103800
tgtgcaccac catgcctggc taattgtttt taatgttttg tagaaacagg atcttgctat   103860
tttgtccatg ctggttttga actcctgtcc tcaagcaatc ctcctgcttt ggtcttccaa   103920
aaatgccggg attataggcg tgagtcactg tgtccagcct catgcctatt tttgaaacaa   103980
ggacctatct ttcatctttg attccttcct tccttccttc cttccttcct tccttccttc   104040
cttccttcct tccttccttc ctccctccct ccctcccttt cttccttcct ttcttttctt   104100
tcaagttttg ctcttgttgc ccaggctaga gtgcagtggc acaatctcgg ctcactataa   104160
cttccgcctc ctggattcaa acaattctcc tgcctcagcc tcccgagtag ctgggattac   104220
aggcaccaac caccacacct cgctaatttt ttgtatttgt ggtagagatg aggtttcacc   104280
atgttggcca gtctggtctc gaacccctga cctcaggtga tccacctgcc ttggcttccc   104340
aaagtgctgg cattacaggc gtgagccact gcacccggcc tgaattattt ctaagaatag   104400
taaggtaaac tccagaataa ttaggaaaac gaagttacta tattgccaat aatggaagtt   104460
atgaaacaac tttaagtcca tttataataa aatatacatt aacaatacat tggtcaggca   104520
tggtggctca cacctgtagt cctagcactt tgaaaggctg aggcgggtgg atcacctgag   104580
gtcaggagtt caagaccagc ctggtcaaca tggtgaaacc ctgtctctac aaaaataca   104640 aaaatttagg ccaggcgcgg tggctcacgc ctgtaatccc agcaatttgg gaggccgagg   104700
ggggtggatc acgaggtcag gagttcaaga ccagcctggc caagatggtg aaaccccatc   104760
tctactaaaa atacaaaaat tagtgctggg cacaatggct cacacctgta atcccagcac   104820
tttgggagac caaggcaggt ggatcacctg aggtcaggag ttcgagacca gcctgatcaa   104880
catggagaaa ccccatctct actaaaaata caaaaaaaaa aaaattagc tggtcatggt   104940 ggtgcatccc tgtaatccca gctacttggg aggctgaggc aggaaaatca cttgaacctg   105000
ggaggcggag gttgcggtga gctgagattg caccattgca ctccagcctg gcaataaga   105060 gtgaaactct gtctctaaaa aaaaaaataa aataaataca aaaattagcc aggcatggtg   105120
gcaggcgcct gtaatcccag ctactgggga ggctgaggca gggaattgct tgaacccggg   105180
aggcggagtt tgcagtgagc cgagattgtg ccactgcact ccagcctggg tgacagagca   105240
agactctgtc tcaaaaaaaa aaaaaatta gccaggtgcg tggtgcgtg cctgtagtcc   105300 cagctactcg ggaggctgag gcaggagaat cacttgaacc caggaggcgg agattgcagt   105360
gagccaagat tatgccattg cactccagcc tgggtgacag agcaagacac catctcaaaa   105420
caaaaacaaa aacaaaaacg ttacgccatg tgtaattaaa agtgttggta gcatttcaca   105480
```

```
accatctgcc ttttgtttgt gcatctatca gtatttccag gcctcaagga tgaggcaggg   105540
actaagaata atttattcat tctgtagaat tctttacaaa attcatactc ttgctccatg   105600
aagagtctga gactgattct tgtcatggct ctgtgaactt ggccaagtcc tctgaactct   105660
ctgaatcttg gcttcctcaa ctggaaactg aaaagaacaa ttctggcccc tccaacttta   105720
ttaggaacct ggagaggagc taataaaatg ctggacatgg ccgggcatgg tgactcacgc   105780
ctgtaatccc agcacttggg taggatgagg caggcagatc acaaggtcag gagttcaaga   105840
ccagcctggc caacatggtg aaacccccatc tctactaaaa tacacaaatt aataggccag   105900
gtgcggtggc tcacgcttgt aatcccagca ctttgggagg ccgaggcacg tggatcacct   105960
gaggtcagga gttcaagacc agcctgacca acatggagaa accccgtgtc tactaaaaaa   106020
aatacaaaaa attagccggg tgtagtggcg catgcctgta atcctagcta cttgggaggc   106080
tgaggcagga gaatctcttg aagccgggag gcggaggttg caatgagctg agatcgtgcc   106140
attgcactcc agcctgggca acaagaacaa aactctgtct caaaaaataa ataaataaat   106200
aataaaaaat aaaaatacaa aaattagcca ggggtggtgg tgcacacctg tagtcccagc   106260
tacttgggag gctgaggcag gagaattgct taaagatggg aggtggaggt tgcagtgagc   106320
caaaatcatg ccattgcact ccagcctggt gacagagcga gactctgtct caaacaaaac   106380
aaaacaaaac aaacaaacaa gaaaactgct ggacacagaa gtccacctga gcagcctaaa   106440
gtaatagatg gaagttaagg attaatatga tgatctgtga atatgtgtct gaagtggaaa   106500
tgaaagaaaa ataagaaaca gagacaacgt agtcaaaagg agtaacggtg ttccctgatt   106560
tgccatgtat tagctgagtg atcctaatct ctctgggtct cagcttcctc atctgtaaag   106620
tggggattat aataatagct gctctttcca tttgataaga ctattgtatc aaatgggtca   106680
gtgagtgtga aaatgttact tggaagagac catctaactg ttaattatta ttaatactga   106740
tagtagttct cctagaagaa gttccagtgt tcttccaggg cttcaactag tttggtcacc   106800
tttggaaatg aaatctatct tttgagatca cacggtagtc acaggcaggg actgagccta   106860
atgagtagga gcctggctcc tggcatgaca ctgctaggat tcaaatttca tctctgccac   106920
taataggcta tgtgatcctg agcaagcatt taacccttct ttgacttagc ttctccatcc   106980
atagaatggg gatgataatt atgtagtctc ttacctgctg gagttgtaag aattaagtgc   107040
cataatacat gtgtgctatc cagtacacag aagatatttg taggtatctt tattcttgga   107100
tatagggtat tactctcggg tattcttggt ggcaccttgg ccccatactg cctaatttac   107160
aacatttgct gtaactttaa cttatcaaat agcatcccag agtaagcctg atactagaaa   107220
aatatgactg aatgaaaaag catctatatc tacagctaca tggctgaggc ccttttggct   107280
cctactaaaa ccatttgctt tcttttttgag acagactcta gctctgtcac ccaggctgga   107340
gtgcagtggc atgatcttgg ctgcaacctc cacctccctg attgaagcaa ttctccccgc   107400
ctcagcctcc cgagtagctg ggattacagg tgcccactac catgcctgcc taattttttgc   107460 attttttaata gagacagggt ttcaccatgt tggccaggct ggtcttgaat gcctgagctc   107520
aggtgatctg cccgcctcgg cctcccaaag tgctgggatt accgccgtga ccaccatgc   107580 ctggccttct ccattttaga gccagcaagc caatcatatt tcaaggcctc tggtccccctt   107640 ttgtgaaaga atctctagg tagggcaagt tttccaccct cctccagctc ctgcagttcc   107700
agagcagttt ctaacctgct gtcacagagt gaggatttcc atgtccttag gcagtggatg   107760
aatgagaggg tgagtgagaa gctaagttag ataatggcat cattaggtaa taagttagtg   107820
cacaaagatc tacatggagg tgataaggtg gaaggagcag ggggtaacag atgcataaat   107880
```

```
ctgtactagg gatttttttt tttttaaag atacactttc aaaaagccat tccaggctgg 107940 gtgcagggc tcatgcctgt aatcacagca cttgggaggc caaggtggga ggaatgcttg 108000
agcccaggag ttcgagacca gcctggacaa tacagtgaga cccccatctc aaacaaataa 108060 cataaaaaa aaaataaagc cattccaggc agaatggaga atcacagaaa cttatcaagt 108120
cgaataatga aattcgtagg gctgcagttc ttaaacttga gtgtgcatta gaatcacttg 108180
aagggcttgt taaaacattg ctgggcccac ccccaaaatt tctgattcaa taggtccaga 108240
gtggggcctc aggaattgca tttctagtta gttcccaggt gacgtgggga ccacaatcac 108300
tgtcataggg aatctgagaa gagttgctgt aaggctgtct tattagaaat ggtcctcaga 108360
cgtaagtgag gcccaagaaa gagtccaagg agctacagag ataggagagt ccaggggctt 108420
cccacagcct ggacttcctg agccacaaca aatgggcct actagtgtgt tggtggcatg 108480
attgaacata taggctgacc aggcactctc acccatgaga ctctccttat ccagaccttg 108540
gctgatatgt ggtggcgggg ggagtttggg ggaaagtgtt cagcgtttcc tctcaaacga 108600
cagggcgggg tggggtgggg ttgggaggaa ggagctcgca ggagaactgc ttgatacttc 108660 ccgcccacc gcggttaatc actgtctaga gaagccgagg ttaagtggct ctgacctatc 108720
acccatcccg cttagggtcc agctcagaga gcgggcgcat agggcctggt ggaacaggct 108780
gccctctggg gatgggggat tggggccgct gctccgggca gagccgcggg atccgagcca 108840
gcaaggatgc tgggactcgc cgcgacttcc gcctctggcg atcggcagtg gggggcgcac 108900
caagacagca gttcgggagc tgcgctttgt caccgaggcg gcgaggggcg gagggcgcag 108960
aaaggggccg cggagaaagg acaaggcggc cgaccagctc ccaggatgga aagggaccct 109020
caaggggctc caggcagcac ctggggcaag gggagggact gatactcccg gccggagccc 109080
aacctgtggc gcgtgcttca gtcctgagcc agcggctccc tggcttctgg gctggcatcc 109140
gtcctaccct cctcccgctg caacacgccc ctgatagccg ctcccccacc ctctgaaact 109200
cacccgcaca gactcaccgc caggcttctg ggctgggatc gcgcagtccc tccacgtcgc 109260
ggcgccctga ggcccctccc ggtgagccac ccggccttcg tgccttgctc cccgatacc 109320 aacctcacct ggctcccgcg cgtcgctcac cgcccgcggg gacagcggcc gcatccgccc 109380
aacccacttg ggaaggggga tccctatctg ggtctttcaa tcatacccaa ggcatcgcag 109440
ttttctgtct gggtgttagg gaaagcagtc catggtcctg gggcacggcg ttaatgtcag 109500
aggagaatct ggcccttgga gtctggacaa cttgcgttaa aatcctggct tggcctcttc 109560
cccactgtgt aactctgagc aaattcctca acctctcggg gagtccgttt tcccgctgca 109620
cgacgggagg gactgtgcct cgtcggacgc tcagaagctc agtaggaggg gagtggggac 109680
tagtctgggc caggaggggt ctctaggcaa gtcagtcccc agaactccgc atagagagag 109740
ttttccattt cacgggaggg agaggctaag ccagcccaac cagctggact tccttgcctg 109800
gggtggggaa aggggcgtc ggggcagttc tctcatccca cacctggtaa accgactcct 109860
ctactcctta ttaggcgcca ccgagtcttc cgtcttccgg gcccaggaga ggggaagggg 109920
ctttggcctc ctcagcttgg gaactgagag agacacaggg tcagagagca cacagagaca 109980
gagagacacc cgcaccctgg aggaagaatt ttgggaccat cgagttgtcc tctactactc 110040
cacagcccga aatgatgcct ccacccagat ttgtggtcct gcattgccct tgttgggtgg 110100
ccctgacagg cgctgcagtg ggcaggttcc ctcttacagt gcaggggtgg aagagggtgg 110160
agatggtgcc ccatgcagg ggactgggag taggggagc aaggtggtca ggtttgtctg 110220
gcccttggat agcccagtgc ttggaaagga tttgtgcctg gacaaaatct attaaaaaca 110280
```

```
aacaaaagat cctgaaaaca tatcctcccc tgaccccact ccaatctctt ctcaataatg   110340
taaatgaagc aatgttgtaa tacagtgata ataacaggac agttccctgg actctgggtt   110400
tcctttatcc caaaggaagg tcagcccaag ccgagtcctg tcttttacag gagaaacccc   110460
agcggggtga ttctctccct gatgcaggtc cagagcctag aggtttggat ggaggcacat   110520
gcagaacata aaggatgtcc ccagccaggt tgcaggtgtg accaggcctg ccagactct    110580 tgggttttgc cccttggacc aatcaatcct ggaggtcaat ttgaaggggg tagcagccat   110640
gtaagggaaa ataccctggt aaagggtact ctatgaaatg gctcagggaa ttgtgcctgg   110700
agtatggtgg ctccaagggt gtggggatc  tgggaactga aggccaactt ctctgcctct   110760
gcattttcgt gggaagaggg ctgatggcta tgtgaagggg ccatacctaa gaggttaaaa   110820
ctgcctgggt gaccttggtg agtcctgctc ctttccagaa atgttctcag gcctcagtg    110880 gattgcaatg gtcagagagg gactgggctt tgtctcttag ggtctccagg atcagcagct   110940
gcactgatat ttctgacatt ctggcctcag gccctgagac ccttcccaca tgcttcggca   111000
gagcagttct cctaccctac attcctgagg gtggctctcc caacccctc  catgagttaa   111060 tctagaaatg aggtagagaa gaggccttgg tcacaaaaaa tcacaagata aattttggaa    111120
agagaagtct cagaaggcaa tgcttagcac cttcctaatt ctcaaattgt gaaagtggcc   111180
tttgagctgg agggagggt  tgaatcctga tgctcattta cacatcagct ttctgtctgt   111240
gctttgggtt tctcagccac aaaatagaga tgattcatgc tgtcttcctc agagcctgtt   111300
gtgaggctgg agagctaata catgtgaaac gcttagagca gtgactgctc ttatcatgtg   111360
ggaactccag acttctaaga gggatttctc tttgccctcc tggaaaagta tgtgtggtgt   111420
gggtgaggga tgggggtggc agggtgagga ctagtccatc cagctgtgtg ggccctgagc   111480
cttccagcca tgcaggtgct tctaagggca ggagggacac tctctgagag gcccacagac   111540
ctgcctaaac cccagtaaag gctgaggctt tgtggagggt tgccttatgg agagttaaag   111600
cattgctggg ggttgaggca tccctgaagg ccagggaggg acatggcctt ggaagggaga   111660
ctgagcttgg tttgacactc agccctgacc tagctatctg agtcaagacc actagtcatt   111720
ctacaactgt aggaaaaaat gcactgtgga ctcttgaggc cttttaaagg actgttaaat   111780
taaatgagat tgttagatta aatgagaaat gggtgttgat gttctttgta ataaaagcaa   111840
acttcaggac aataatgaag aagaagaatc catagcatct ctgctagggt tgaggaggga   111900
gatgtctgag cctttgggtg cttgggtgtt ggagaattgc tcttggacac aaactgcact   111960
gggcccttcc agtcagtggc tgaggtggca gcaaaccttg agcttgggga ggtcttcagc   112020
tgccagtctc accctgggtc ctccagccct aggatgggcc agtggtggga atggggatgt   112080
ggaccagaca tccttagcac agggccagga agctaccagg ctggccttaa ggagcccagg   112140
cagacaggtg tacaggcagg agtgcagcag ggtcagctgc ctcccaggac ctggccctcc   112200
attccaggag ggtggagagg aggggcact  cttcaaaatc agagttccag aagccgcagt   112260 ttcccctgt  ctgaaggaga aagtgttcca cggtgcctgc cacagttaca cagctgccac   112320
cgactttctc agcagattcc actgcagtgc aaggaggtga caggagtggt caaccctcat   112380
ctacctgcaa gtgtgagatc cactcgacct tattccccag gggtgcaccc agcagtggca   112440
ctaggttccc aaaagggcat cagcagctgc caaggcagaa gggggaagcg ggtcccgaaa   112500
ccacccacct ccggctgtcc ccaccgcgag gacccagcag tctggcgccc ccaccacggc   112560
ctggaagatg acgagggcc  caagactaat attcacgaca gccagaccac gcttattgtt   112620
tagaaggaag ctccctttgt tcttactttt taaccaaaga gaagcgaaaa catttttttc   112680
```

-continued

```
ctgatcacat tttcaccgac acctgagccg acaagccagc tcctggcccc cggctcagga   112740
ctcctcgctc tctcccttct cggggccctg tcgccgttga aaggcccgct gcaggctggg   112800
gagggtgatc ggggccgcgg gccatctccc ccgagccggg cggcagact gcggaggcag   112860 gccccacacg cgccgctttt ccgagcccgg ttttcttcag gagcgaagct gttccagctg   112920
acccgcgcgt ctggggcct atgcccggct tccgattcca tttaaaacga cccgcgcatc   112980
ttatctccgt cgcctccccg ggttcccac ccaccccct ccggcccggg ccaggccagc   113040
ccagccccgg cggaagccaa gctgggagct tttgaagtcc ggagaatttc aatccgagag   113100
gagccggctg gaccggagcc cgtcgcccca gcggggaag ggacgggggg cctgccgtgt   113160
ggcaggtggg ggatgggtgt cccccgccgc gagaaatgag aagccgccgg gcctggagcg   113220
gcctccacct cagctgctat caccccctct ccgctgtcat gggattgccc aggcttaatg   113280
gggttgtgca gggcttcact tgctctcgga atttaccttc cttctcgagc cgtgccgcga   113340
ataaccttca cgacacagtg ataacgatgt tattaaatac tccccccaca ttcaccgccc   113400
aaaaaaccaa aacagtgttc ttatccagtc ctctctttt ttgtcttctt tcctttaaaa   113460
acccaaccgc tcttaatgtg aggttgatga aggatgctt ttggaagaag tgacatttgg   113520
ttaaaacgtt ttccccctaa tgcgccggtg gaaaggggcg ggggtgggtg tggttcccta   113580
ggctcctaag actggccagt cagctttgaa agagcgggc agaagtcggg agagggctgg   113640
ggaaggcttt gggctgaggg gatgtgtccc tgaagcttca gatctggagc ccaagggagg   113700 caacctcct ctgaaaagcc ggtcctcagc tccatccagc cctctccgcg ggatgtaagc   113760
cctgctccgt agggcccgac ccaggaagca gactaagtgg cactccttga tctctcactc   113820
ctactcggct ttcatctcac ccagaagaaa agcggatcaa acagaggatt cccattgaat   113880
gcagagctgg gggcggggtg gggagccagg agtccctctg aggacccagc ccccaggaga   113940 tggggggcagc aggctactca cgagaaggtt aagcgctcaa ggaggaaagg agggtgggca   114000
cctcaaaggc ccagtgctgg agggccctat agagagtagg caaccttgga agctctaaga   114060
cagatgccca gggggcttgc cattgacagg aaagagagca agccaggtgc tccctcaggc   114120
tgtggctgct ggtagggagg acagagaaag atagaatacc tggacagctc tccaaggcag   114180
gaaaaggttc taggatttga ctcccctcac tcccaattga tcctctcacc tctaaaacat   114240
ttccctggat tttggggcta gcagtgctca gcatatagtg gcttcaggag tcccaaggag   114300
tagaaatatc tatgtggaca ctaccttccg gatcccgctg cctccgcccc caggcaagat   114360
taatgaacat cgtcttagac tgaaagagaa gtggaaagcc ggagtgaaga ggaaactttg   114420
tctttctttg gacccttac ttcctctacc ttccttaacc ctatggatag gaagatggag   114480
gagagaagca agaaggaga agaatacaga aagagaaaaa ggaggagaga aaagtaggag   114540
ataacagata aaaaggtcac ggaagaggac ttacctgtaa aagctggggc tttgctaggg   114600
acacagaaag gagggaggtg ctgggctgcc cttttgcagct ggctgcctag ggctagaagc   114660
tcttcgggag gaggcggaga aaggggggtt gagcatagaa ggtgcccacc tcctgctctc   114720
agcaatgtgg ggatagactc agcccaccca cctggccca gcacacttgc ttggagctca   114780
aaaagggtca gttttgaagga gttttatacc agcttcttcc ctgggagagg agccaagaga   114840
ggcctatggc agcttccaga tattaagttc cacaaccct gccccacct ccagcccttc   114900 atcagagtcc ctacttactt gctgtttag ggcattttca gcgacttcac tctcttctac   114960
ctcaaacgcc atccactttt ggagacaggt accactgccc ctaggcaggg acttgggaga   115020
ggaccttatg agtcaaacct ctatgaaccc caacctttt gtactcgggg aggctgaacc   115080
```

```
cctgcccaaa atagcgcggt gaaagctact gccttctccc aagtaggggc ctccagtact   115140
gccacagcag gggccgcatt cctggcgcct cttcattcga aaaacctctt tccaggagac   115200
ttcgctgatt ctgaacgaat actttaaaat atgggcaagg gaaaaaaaaa gacaactctt   115260
agaaactctc cccacccaac atacctggag tgcaggcgag gtccaggcaa acgggaaagc   115320
gacttcttgt acgaatagcc atctcaagat gaagccaggc tgtggaaaac ttaaggccat   115380
ctagatggga aggaggtatt taaaagaaat cagcacacac tcttacagaa gccaaggcgg   115440
gtctttaaat taaaaaataa taataaggta tttatttctt gccccttagg gaagaaaaat   115500
agcaaagttt ggttcgcagg agtaaggaga cagaggtggg tagggagagg gaggagaaaa   115560
gaggaaaaga tggcccagcc tcaagctctc cagtcaactt ggggcggggg aatacatttt   115620
tccgtagctt gtaaaaagac ttttcagcca gtttgaggtt agctgccagg ggcagacagt   115680
tgtaataatg ccgacagaat tgaggcttgt aagccgggct tcacacttct aaaatgcagt   115740
tatggattct ttcatcggtg ttagatcaag gcaccaagtt aagaaaacaa aagtcaaaac   115800
aacaataaaa gaaaaaatca aaagcttatt taattaccga gtcccgctgc ccctgcggaa   115860
ctcgccgcgc gcgttaagct ctcttttctt tctgcggaat tccatttgca tccctctgc    115920
ctgggtgtct ccctctctca gtgtgtgtgt ctctctgtct gttttcacac tctcctcccc   115980
aatcgagcga ggcccacacc tggcgcatca ctgccgagcc attagctgcg ggtttccttt   116040
catcttcgct gtggcagacg tttctattta tccacttgcg ctcgccgagt ggcgtcacca   116100
gcggtactgt aatgacgatt gcagcaggag gatgacagct tagaaagaag agggcaatgg   116160
ggcttcctcc cagaggcggt gcggcacaga ggagcgctcg cttcacaagg tgaccctagc   116220
tcccaccgcc accgccgcgg tcgcggtcca gaccgcgctc cagcagctcc gcgccctccc   116280
aggcacccgg cctttctttc tccctcttgc aaccaagatc cgtccggccg ctggagaccc   116340
agggagccgg ggttaggaac tcacttgggg ctttcccctc ccccaccgga gagccccggg   116400
atggagagcc gaaaggacat ggttgtgttt ctggatgggg gtcagcttgg cactctggtt   116460
ggcaagagag tctcaaattt gtccgaagcc gtgggcagcc cgctgccgga gccgcccgag   116520
aaaatggtgc cccgtggttg cctgagccct cgggccgtcc ctccggccac ccgggagcgc   116580
ggcggggag gcccggagga ggagccggta gatggactcg caggcagcgc ggcggggccg    116640
ggcgccgagc cccaggtagc tggggcggcc atgctcggcc caggaccccc ggccccctca   116700
gtcgacagcc tctccggaca ggggcaaccc agtagctcgg acaccgagtc ggatttctat   116760
gaagaaatcg aggtgagctg cacccccggac tgcgccaccg gaacgccga gtaccagcac   116820
agcaaaggta gccaccgtgc ccctccgctc cccgggcctc ccactgcgcc cacccttcac   116880
ttcggcgcag gccaggagga agacactccc ttcccctagg gcaggatggc tgggggggacc  116940
cacctgagca actctctctg ctatctgcgt tctggcgggg gtctcctact gtgttctggc   117000
attggcggga ctgagggtga cagcagtgcc ttgagtgcgg ggtgctgagg gggcggatgc   117060
aagtcctgga cttgggggat tcgaagctca ccccaagcac ccagtgtttc aactgctcgg   117120
ggaatgcttc aattgctcgg ggaagacact ttccccaggc gagggcaaga tcaaacgccg   117180
atccgggcag tttgtggctg gcagggtgta agaggcatgg aggcgcggaa gccaggagtc   117240
cataaaggac cgtaaaattg cggcccactt gggcagcccg ggtgctgcag ccctccgacc   117300
agtttgcacg tcggtcagag gtccaaatta ccttgtcact tcccgggctt cgcggcgcca   117360
ggtcggaaat ggtcccaatg gtctaattgc ctttggtctc cggttgcatt tgaaaaggca   117420
gagatcgggt cctccccccct tccccttttcc ttcctagtcc cacttctcca cccaaaggaa  117480
```

```
aaggagctgc agggggctgg agccccaccc ttctcagagg taggcccaaa gggggctgg    117540 tttaactgga gaacccctcc ccaccaaagg ctaatgggaa aggggtggat agcccggaag   117600
ggagtttccc tctgtgccaa caatcacctc cccagaaggg ggtagaaaac tgggcgcggg   117660
ttggtggggg ggaggagagg ggagcccacc agcagacact cctccacaga actgtaggag   117720
tgggtggaaa gagcctgggg gcgggggga gaaagaccac cccctggtct tggcagccaa    117780
cgccttgttg aatacctgca cctacccctt actatcttat caccgatttc acccagcctc   117840
cttcccataa ccctcagaac aacctggact ccactcacat atactaaggt aataaataag   117900
atactcaaca tgcattctca ctccagccct gcaatacacg gaacctagta cacattccca   117960
cacctgttct ggcagcccgt cacacataag agcaaggaaa ctctctgaat gcccagcata   118020
ctacaatgca cttgacccag agtttacaac cctctagcac aaaggtgcat ctcaactcat   118080
gtgcctgtca gaagtgcacg ccctgccaac gggaggcaga aatctcacct atgctccagg   118140
gcaggtggga agggcggctg ggaaccctg tacccaggat gccttagagg aagggaaggc    118200
ctccccaaag acctctacct acccaatcaa gggcaggccc ttattttccc ttcttgggtt   118260
ccccagaggc cgcagtaccc tagcagaaac agttactgag gtggctgaca gggtgtccct   118320
tcccaaatca ccctcccacc ttaggcctac agccccactt caatggcgtt tgtgtgtctg   118380
tgtctgtaca cgcctgtgct ctggactcgc tgtgcagggt ccggctccga ggcgctggtc   118440
ggcagtccga acggagggag cgagaccccc aagagcaacg gcggcagtgg tggggcggc    118500 tcgcaaggca ccctggcgtg cagcgccagt gaccagatgc gtcgttaccg caccgccttc   118560
acccgagagc agattgcgcg gctggagaag gaattctacc gggagaacta cgtatccagg   118620
ccgcggagat gtgagctggc ggccgcccta aacctgccgg aaaccaccat caaggtatgc   118680
ggggtccagg ctggggaggc gggtgtgcac ctatttagcg ggaagtaaat gccaactgcc   118740
aactccctga aacgcaggcc aggaatctgg gcctggggtc tccctgcccg gcgcgtgcag   118800
attgaccctc gtgacagctc ctaggcaggc attgctgcca tgtggctgac tctgtccctt   118860
tcctggttaa atagacaagg ggtgggcgtg ggggaagggg atagagtgcc tgtgcgggtg   118920
acaaggaagt ttctggggac acgctctctg cggccgcaga ccaattgagt ccatgtcctt   118980
tcactgctcc tcccatacac acactggcct ctggcacccc gggggcctgg ccacctgggc   119040
agaaggaagg agggagcggg ctggagtcac tccccaaacc tctctcggag ggattccagc   119100
tccaggtggt ggtggtgggg tcggtctcta cccggctggt gtctgctttg gctgttcctg   119160
ccctgcgaac actgtccccg gagcgggacc agactactgg cctctgagca tcgggccaag   119220
tccagctact gaacctgctc cgctcctctc cccaggtgtg gttccagaac cggcgcatga   119280
aggacaagcg gcagcgcctg gccatgacgt ggccgcaccc ggcggacccc gccttctaca   119340
cttacatgat gagccatgcg gcggccgcgg gcggcctgcc ctaccccttc ccatcgcacc   119400 tgccctgcc ctactactcg ccggtgggcc tgggcgccgc atccgccgcc tccgccgccg    119460
cctcgccctt cagcggctcg ctgcgcccgc tcgacacgtt ccgcgtgctg tcgcagccct   119520
acccgcggcc cgaactgctg tgcgccttcc gccaccgcc gctctacccc gggcccgcgc    119580
acggactggg cgcctctgcc ggcggcccct gctcctgcct cgcctgtcac agcggcccgg   119640
ccaacgggct ggcgccccgg gctgccgccg cctcggactt cacctgtgcc tccacctccc   119700
gctcggactc cttcctcacc ttcgcgccct cggtgctcag caaggcctcc tccgtcgcgc   119760
tggaccagag ggaggaggtg cccctcacta gataaggggc cgccggctgg ctgccggctc   119820
catgacgccc gtgggtcac ccccggccc cgggactcag ccagcctcgc tcctcgctcc     119880
```

```
tcgctcctcg cccctaggac gccaagggg aaaggagagg gcggaaaagg accagcggga    119940
tccggccgca agaattggaa agcctaggaa gtggcggtgg ctggcgcgtt tggggagcag    120000
gagtgggat agggaagcag agcttgagag accttcctcc gggcagcct ccggacccac    120060
cgcccccac cagggtcgag gctgtagctc caaagctaaa caaaacttag cagcaacagc    120120
aaccaatatc cagtccctcg gccctcggc ccctcaccct ccacctcaca ctcccttctc    120180
accgggcccc ctctcccag ccaaggccca agcactggaa agggaaattg ctgtctctct    120240
gaacaaaatg ctgtgtatgc agagcaggta gagattaatc tttgccagct tttccaaggc    120300
atgacaaggg gctggtggat ggcaacatac cagtcatttg gaggagagag tgagagatga    120360
tttactacca gggagaatcc agccccttgg catgggacct ggagcctcga ctacacagca    120420
tcttctgggt ctggcgtctg ccagcacctg atctctttcc tcattcccag ctttgtgaca    120480
cttctcaact tgcggctcca tctctccctg cccccacttt tttgttggcc agggaggctg    120540
cagatgcccc aggagccctt tgccgcttct atgaggccaa gccttttttc cctgggccca    120600
gcacacaccc tgattagcaa gtgatgtgtg cgaggagggt ttgtgaatgt tgaatgtgta    120660
ataatgatca ccatggagct ggccactgac cccagagctg agctgttaac aaggcgccca    120720
gggaagagct tagggagtgg gaacttcacc tccctctctc ggtatctggc ggtaaattag    120780
aggcaattt catcctttgc ttgttcacct tcacttcacc aggaactttc tggccctacc    120840
ctttgcattg ggtatttac aactttctct cattttcttc ccaagctacc actggagctt    120900
gactttcaga taccagtggg agccttctgt ccctttggg gaccctgtct gtggcctcca    120960
ccagggtttg tttagagcca ctcccaaatc ctcactccca cactcatcct tgcagccagt    121020
ttttgaggaa gaggagaacg tgtaaccca atgcaagctt cacccctgact gagaggtagt    121080
ggttcttcct gtagggaatg aatttggttt gatttgggt tttcctttga gcccaaaga    121140
acttgctgtt atgattcgtt aaccatattg caataaaagc tggacataat tctcactta    121200
cattttagtt tttgtggcag caggcagctc ttaactgaat tttaaagttg ctattcagc    121260
caccatgggt tcgaataggg aaggaaccaa aagatggacc cacagagtct tccaagccac    121320
tgtttgtcac tggtaggctc caagcagcca ttgcatggag gtggagaaga caggctccaa    121380
gctgccctgg ggtgcatgtt tccttaattt tgggtatgtt gggaacagtt ccttggtaaa    121440
gtggcagcag agtgctgcca ggggcccacc cctgtggttt cttctccagt tgttccaatc    121500
ctttgagcaa cagaaagggg acccaggttg tggtctctga gcaacctgcc tccaccccag    121560
cccaaaggga aggtgagtgg ggcagtggca gtagagcctg agtactgcag agacctgagt    121620
tttctggtca aactgggtct gcacttgagg gtggaggaca gcaggagga aggtccttg    121680
gttgggatca tcttggtctg aattgtcctc atactggaag tcatcttgag ggtgggattc    121740
tgagggtta ggacaagagg aaaggagtgc tcagcagcta ccttccagcc cgcacctgca    121800
tcccccacag gagagccaaa tgtggctggt tgtggagttc cacttaagca ggggagagat    121860
gggtgccttc tgggagtcca ggaggctctg gattgcatag acacgaggag tcctctgcca    121920
ctgtctttgc cagcacatag agactcctca aatgccctcc tccctccttg gttccacag    121980
caaatcctcc tgcacacagt agcaggtgcc ctcccaagca aattgtgccc tgaggttcc    122040
agcaccccct ctcctgcagc caaaagctcc tgagtgccaa atcctggtaa attttgcagt    122100
tgctccatat tgggcagaga ttgcttgcga caggtaaatg ggctgcatgt tgccttaatg    122160
ccaggcgtat tttcagttaa tagggaggga aaatgaggtg tctgcagaga tattggaaag    122220
tacaagatcg atgatccagc ttcgtgtcca atcagcagcc tttaattgac tgtatttct    122280
```

```
gggtaattga gcctctcttc ctccaaattg aagtggaaga tataacaata catcttgcca    122340
ggaggaatta ctcattactt cataatgaaa tttcccttttt gccaaggttt gcggtttggc   122400
gctaggcacg acttctcact cccctctcc cccaaatat tcttagccca cttgcatcag     122460
gctaccccat ctggcatgac acgttccatt tgggtggtgg cagggaggaa gtgggagttg    122520
acttgaagaa gatactgccc cttcacaatc acagcctcct tatctgtaaa atgagaaggc    122580
tagaccaggg cctagcatga tgttgttttc atttttcaac tctctcagtg tctctactta    122640
gctttgcctc atctcggttc cattttgcag gagggaaaac ggaggctcca ggtctacaca    122700
gctattagtg gccgatgtag ctatgagctc cgggctccca cttcctcttc tcttaccctg    122760
ttctggggca cagattctga ggtaacccc agtgaagcct gacacctcac tcccgactca     122820
cgctttccca gggctcttca atcccggcca gccggcaggg cctgggagcg cggtccagcg    122880
cccagcccag attcgcccag ttgggcaagg ctggccaccc cgcagcccga gtgtgcaccg    122940
gcccccggca attgctggct tgttagcgtg tgattgattg ccttattaaa gcgtgttctt    123000
gtaagtgtga ccaaactgat tgcattgcat atgtttggga taatgctcat tttaaacaac    123060
aggataaaga ggatgagctc cgcagagcct tgaagacaaa atgattctgg ctagcagctc    123120
cctaactatg gcattaaatt gctcagttac atagcaaatc gctacttggt ttctgcatcc    123180
ttgtccgtat ttttttttt tctgtcctac agtttgatcc tgtctcccaa tgtggcatgc     123240
cccacgaacg gtttctttag tgattatgtt gactccacct tcctagtttc aaaccctgca    123300
cccgcactct ccagacagga agtccctctc cctcgaccag ggattgaggg agaagagatt    123360
cagaatgcat ctccttgccc taggcctttc ggggggggaca tggccttaga cagtcacccc    123420
gaaattgggc tcaggtcctc acagtaagtc gagtgtcccc ccacatcccc aaccccggcc    123480
ctttcactaa agtttaaaag attcttttgt tcctcaggct tctcccgctt ggttgcttcc    123540
attattcccc aactgcggaa acaccagcca ccatatgtcc gccggagaat aagcgtgagt    123600
gtcgcggtgg acagttgccg ccaaaggtgt ccagacggat ggcattctca aagtagggat    123660
cttagcatcc tctccataca tcatcaccca agaatggtag aggaaagagt aggagtgggg    123720
ttacagatag gagagaaagg aggttgaggc cacaaaattg gcatttctct aattatcaac    123780
cccctcctcc accatcctgc caccatttgt tatggcaaag ttctcttttct gtgcccctcc    123840
cctaataaag aaatcctcag tcagcctcca cctactcctt ttgatttgca ggaagccaaa    123900
ctgccagcag attgagcttt ctaagggata cctttgggat atgttggaat tctgatttgt    123960
tcaagatgat gacggtcatc agtacaaatc agaaacaatg ccactcttca gggtgtcatt    124020
tgtaagtgca ataacacgga ttcatttgca aacccagct aaactgcgtc tggataagtg     124080
actagatcca aacgacaaat ttcttccatc actcagctcc tcccaagctc tgcggggca     124140
gcacagaaga ctgctttagg gtgaaactaa ggctcagctc accatttgtg ccagcttgag    124200
ggaccctgga aatgttgact ctgagaaaaa gacaaaacaa aacaaaacaa aacaaaaccc    124260
aatcacaaaa catatcctac tgtctacaaa gcaaacagaa acacaaagtt gtttccaaaa    124320
tcaccttttc agcaaataag tatgtgatat tctgagcagg agcaggaggg agagaaagac    124380
tgccacttaa aaaacatga aagcattaag taataattta aaacacggct gtttagaaaa     124440
atatttatat ttattgcagc tgctcaattg gcctcgttaa agtcggcaag catttaaatt    124500
gtgttacaat ctcatttaaa tcccgttccg ttccagcagg ctgaagagct tgaatagacc    124560
aatcacttca taatgatgat gaatgagaaa ttaattcaga tacaagcaag acaatttagg    124620
ccttcatctg tttaaatagc cttccaatat tattcgccat cgcgggtcac agattgaatc    124680
```

```
aattgtccaa tcttgtgaaa gtcatatcct tgcgtcttca tcgagattat ttatagcgca  124740
gtgagcgctg ctgaaaggta tacgctgtta acagggacaa ttacttaaag ggaagcgttt  124800
gtaaaatgga aaacaaatgc cggggttggt aacaaatggg atcaaaagca gccattccaa  124860
tctggctccc cgagggaaag gagcgggcgt ggccctgtag gattaggggc gcttctgacc  124920
tccccaagac ccaggtgagg ccgagggtcc ccggcgcgcc agcctgcgcc gtggctgtgg  124980
ctgcggtggc gactcgggcc gggcctcgct ctcgccggct tcaggttccc gcctccctcg  125040
cgcaggcagc gggcgcgtgt ggcccgggct gggcaagccg aggaacagcg agccccggga  125100
cgctgactgc aggacgtccc agtttgtgcc cgggtctccg tccctccccg tacggggctc  125160
gtacccccgg gcctgggtct gacccacagg gcgctgaggc ctttgtagct gaagtcggaa  125220
ggcctcgttg cgagcgcggc acaggttgct ggtagcttct ggactctgga ggcttggcct  125280
tccttctaag ccgatggcgg ggaaagaacc tcgtttccac agcttccccg accccgccg   125340
cttgccattt ggggacggga agcgcgcccg ggtcgcttca cgtccctctg ggccggagcc  125400
ctttccatgg ctggctcctc tgggggccct tgggcctgtg agcagcgtct acttccctca  125460
gagaagaatc ctttccttcc cccatcgaag tgtccctttc tgtatcctga ataacccct   125520
cctgggtgag gccagttccc ctctgtcgcc ctcctcccgc aggcgtccgg gagcctcgtg  125580
aggacccgt gcagttgagt ccaggcgaca ggtgcctccc caggtgtcta cttgccctcc  125640
ctcaacctgt ttagggaaag accagaacga tgtgcgcggg gaggtggttt tgtttctccc  125700
gaaactggcg ctcttgggta aaaccgcgtg ccgcgtctac gcgggctctg ttagtgtgcg  125760
tgtcccagaa gagtgggcct tctaggcggc actctttgga gaagtaagtg aggtgaactc  125820
agaacagaga agcgggaacg atcgtttgat gtgccgagcc ggaaaaagag aggagaggga  125880
gaggctccca gcgagcgcgg agacagagga gcccacgcgg cacagcacga gccctactct  125940
tgcccgcgta gaggtgtgtg tgtgtgtgtg tgtgtgtgtg tgtgtgtgtg tgtgtgtgtg  126000
ttttcctctg tatttctgtg tttgaaacaa agcccaact aacggattcc tggtgctctg    126060
aggactcact cccgggagcg actttgatgt attgctgtcc aattagtgcc tttaattggt  126120
gtcctcggag acaggcaggc ccggagctgg gacagagcct cctctcgcct ctcctgcaca  126180
ctggaaaggt aaaatttata acacactgtg gccaccccct gggagagcga aagagagtgg  126240
gaggcaggga agaaagggag agatgcagct gtttgcagag gacggagcct ccagccccgg  126300
gggtcgtggg gaagggccca gaccaccggg ttcgactcag ttttctgtgt aagagggttc  126360
gggccggctg agtcgctgag gattatgaat ttgctcgcag aaaggcctag ggagctctca  126420
ttgtctgtac aaacccaccc catgtggtct accatctcgt taataatggc tgtttgttaa  126480
caaggatgcg gaggttaaat aatccgggtg gaagattaaa cacgtctcat caaggcgctt  126540
ggaagccgcg cggtgcagag acctgcgctg gagccgcctg gctcactgga gcctggaggg  126600
agatgggagc acagtctgca aggagccccg gggtagaaga ggaggcaagg tctagtctcc  126660
ctcttcaggg tgtcctgcta tgccaggaca ggtctaactc ttccacatgt caaacagaaa  126720
atccacatag aagtcagccc caatgaggtg tggaggtcaa accctcggag tagttggctg  126780
gagggcagac atggagcatc tggggtctga accaaaggcc ccttttgag gagggggtggc  126840
catcccctgc ctcccagtcc ttacatgtca tgcatctggc aatttgtgcc tacatgggat  126900
tagcattgga ttagaagaca gaagatgtgg tttctagtct gggttctgcc cctaaatcac  126960
tgtagaattt ttattacatt attctcccag cttcattttt ctactgtgta agagaaagga  127020
gatgggcctt gatgtagatg atgtacagca tttcttcttt tgtccagctt cccaccagag  127080
```

```
ttagggaact gaacacctta taagatgctc tgtctcccct aaaccttgca ggatgcagtc  127140
aaaaagaatt ttatttagca aatatctgag ggcctactct gcaccagtca tggtgcagta  127200 tgtattttt  aactgagagc agaatatcag ttcatattcc cctgttattc tcaaatataa  127260
tgttttataa caaaagatga aagagaaaga acttcaaaga gaatagaata ggatgggtat  127320
gtatgtacag ggtagagaaa ctatggaggt aaaggtaaag gcattgacaa agctgtgaa   127380 gaacttgttg aactggcaag gaagtcagtg gataaatact gcagaagtag ctccttaaca  127440
gagatactat gtaggagagt agagagaagg tcccctcctg aatcctggtg atttggcaga  127500
gaacaaaagg gtaagggttg cagaatttga ctaggaggcc caagttgtat gcatctaata  127560
ttgccaattt ttggtttata tattctttca gtagttggaa tttctctctc tctctctctc  127620 tctcttttc  ttttttgagat ggggtcttgc tctgttgctc aggctggagt gcagtggccc  127680
catcaaggct cactgcagcc ttaaactccc aggctcaagt gatcctctca tctcagtctc  127740
ccgagtagca agggccacag gcatatgcca ccatgcctgg ataattttt  ttttttggttg  127800 aggggtacag atgggtctt  gctgtgttac ccaggctggt ctcaagcttc taggctcaat  127860
gaaccctccc accctggtgt cccaaagtgt tgagattaca ggaatgagcc actgtgcccg  127920
gcctaggaag tttactcttt agctaatttt gaaacattac tttctgaatc caccaatcag  127980
gaaactcggc tgctaggctg ggactcttca agcttctggg tgatgggcat ttagcctcaa  128040
ggaaggcaat gatgcttaaa tcactaaacc atgtctcagt ttctgtgagt caggaatcta  128100
gtgagcttag ctgtgtgtcc ctggctccag gctattccac tggggttgtg gtcttatcta  128160
aagactcagc tgggtgagga tatgttccgg gctcactcat gtggttgttt ggcaggattc  128220
agttccttgc tggtgggcta tttggctgaa ggcctcagtt ccttcttggt ggttggccag  128280
aggtttctct gttccttacc atatgagcct ctctataggg tagcttataa agtggcagct  128340
gtctttcctc agactgagta agcaagagtg agagtggagg ggggagaaag cacccaagac  128400
agaagctaca ctcttttggt catctaatct tggaagtgac tttccatcac tatgccatat  128460
tatatttgtt agaagtgagt cactagatcc agcccacact aaaggaaagg ggattacaga  128520
aggcatcaaa tccaggaggc agggatcact ggggactgtc ttagaggctg ctgcccagac  128580
cccttttata taacagctct gaggcttata tggttttata tttatgaaga gcttaggaca  128640
gcacctgttt gctctgatca tcagcatgag tgatccttct gatccaatgg agcacccatt  128700
tcttcatcta gaccctccta tgtcaacagt tctaattttt tcctgcaaag ccctgtaaaa  128760
gagtgtagga aaggcaagac agtaactgct gcaaggaaag aggctgagga aacagaatag  128820
aaaggggata ggatgggaga tcctgaaaaa ctctggggga gggtgcctag agacaaaagg  128880
gaaagtagga gacccttgtc tcctatggtg ggctttacac tttttttttt ttttgagaca  128940
atgacttgct ctgtcaccca gaacccaggc tggagtatag tggtgtgatc tccaatcact  129000
gcaaccttca ccttcagagc tcaagcaatc ctcctgcctc agcctcctaa gtagctggga  129060
ctacaggcat gtgccaccac actcaactag ttcatatata tatatatatg tacgtatata  129120
tatatatatg tatatatata tatatatata tatagagaga gagagagaga gagagagagt  129180
atgtatatat gtatattggt agagaccagg ttttgccatg ttgcccaggc tggtcttgaa  129240
ctcctaggct caagtgattc gcccacttca gcctcccaaa gtgctgggac tacaagcata  129300
agccactgtg cctggccagc tttacactgt ttagagtatt tccacataca tgatc        129355
```

<210> SEQ ID NO 599
<211> LENGTH: 152306

```
<212> TYPE: DNA
<213> ORGANISM: Homo sapiens

<400> SEQUENCE: 599
tcttatcaaa atcaaagttt caaaaagtaa cattttcaga ggatggtaga ctaaaggata      60
tgtagtttat tcatctctgt aatttgtcta gattttaacc ctagatcaaa caaaaacatc     120
actcattaag ctgaataaat atttggacat tgttttttgt tgttgttttt gtttttgaca     180
agtccctcta ctcctataaa attgctttta ctgaattgag ctttgttgtg atgtcctctg     240
cttcttactt tctcttggtt ttatggctga gatatattga ggaagttgcc tcagtgtagc     300
ccttcataag ccccatggga gaagagttcc tcagaccta agcgcaagaa tgagctttga     360
ctctcctaat taaatgacat atccttattt tatagacaag accatgcaag ttttatgtat     420
tcctggtcat gttaatcaat ttacttccac tgaaattatt aatttcatt tttactttt      480 aaatcacttg acataaattt caaataacac tgtaaaggat tcactattaa agtgctttta     540
tttaattata catattctct atgtttccag agagataaac taaactacag cctctgtggg     600
ttcttgtctt cttgaaataa ccaagtcttc ttggaagtcc caaggggct agcagggaag      660 catggagcca cttagtaaga gggtcttcca attttaatgt aatgtcactt cagctcatct     720
cgcatgagca tagctttatt ggctggctgc ctttgatcaa cttgggtcct catggttttc     780
ttcatcaatg atgctggaac tggaaatttc taacatgcct ctgtgactgc tctttgtcta     840
gcacccattt ctatcctgtg ccatctaacc ctaaactgtg ccatcaacta caagctgc      900 ctctactctg atctgactga tgcagcaaac aagaagaaat gaattaacag aaaaacaagc     960
aagattcata atctaagac aaaaaaaata aatcctaaga tcatatttta actagataac      1020
ttctagaaat ccaaattgca ttatatttgt acttatgaat tgcattatat ttgtacttat     1080 gaatttatt tagtatgcaa aatatgaaaa tgtcatttag aaatttcaga tacactgaat     1140
tcattaagag atatatccta ataaacatgt tctcttttct ctggaaatta acctttagaa     1200
aaagctactg tgaaataggt aattctcaat taccagagta taaagcatgg cctcttaaga     1260
ttattcaaaa aaatcttatt ttcaggccac agagtacaaa tacacacttg ccatcaatgt     1320
gtgagtggaa ggagaataca ttcttatata gttcaaaaaa gacattaata gaaaaataaa     1380
tacgcttcta aaaacaactc tcaggtgaac taaattattt aagtatttta tttcagatta     1440
ttgaagcttc ttcatgaaaa tagtcattca agagttactt cctaactcat tctatgaggc     1500
cagtattacc ctgatgccaa agtcagacaa acagtacaga aaaactacag aacaatatgt     1560
tttatgaata ttgatgcaaa catactcaac aaaatattaa caaaccaaat tcaatagcat     1620
ctttaaaaga ttatacacca tggccattgg ggagttattc ctggaatgca aggatgttaa     1680
acatatgaaa atcaattaat ataagatacc acattaacag gatgtaggga aaaatatgat     1740
tatctcaatt aatgtagaaa aagtatttag caaatttcaa cactttctca cgacaaaaac     1800
taggaacaga aggaaactat ctcaacatca ctaaagttgt tttactcaa aacatgtcta      1860 gattaatcat gtatatcaag gaaactgggc tgattaaaat ttcccatgag gagtacttac     1920
ctgccaatat tttcttgaac tgtctaaacc atatgtcaca gtggtcttca cttaaattaa     1980
taagatcaag tgtagaattc tttagtttat tttgttcctt tttcaagcag atgaagagtg     2040
tgatacctaa taaagtacca cttctctgct gtttaacaga acaacgccgt tcagtttca      2100 cagagaatat gtctttgagt tcaataaatt cttctttaca tagcaagtca tacttagaat     2160
cacctgaaaa aaaataaat tttccaatta aaaccattgt gtttcataga gaggaacaac      2220
agacactggg gcttaccaga gggtagaaag tgagcaaagg gagaggatca agaaaaataa     2280
```

```
ctaatgggta ctgggcttaa tacctgggtg atgaaataat ctgtacaaca aaccccatg    2340 acacaaatgt acctatataa caaacctgca cgtgtacccc agaacctaaa agttaaaaaa    2400
taaaatgaat tactagtaag aaataaaaat tgtgaccata tcttaaatgt atgaataata    2460
gttaaaacca aaaaaattca tcatttgtaa ttttatggat tgcccttat gccagtccct    2520 acgtgagatg gaaaggggaa gaaagaaaa attgggttta ttttgtcaag aattagatta    2580
aaaatagaat aaatggaaga gagtccctgc cacacaggcc tacaacattc gacatctgag    2640
gatagtcaat gtatgaagaa ttccaagaac ataaacaaag cgacatttta gtaataaatt    2700
ggtgtcacat aaggagctct ttggtactaa ggatagagta aagtaacaga aaaaatagaa    2760
ttcactaaca gaagtgactt tatgacaaat tgttgaaggc agccttaacg aaaaggaaat    2820
atacattccc attaaagtaa cacatgcaaa gaggaagcag aagtacaatt attgtgagta    2880
ggaaacatta taaactctgt caatctagga ggaaatagcc ccctgaattt aaccataatc    2940
agacttaaaa aaaaatagtg gcataaaatt ttcatgactt atctttaaac cataggtcag    3000
aaaataatta ttgtggaaaa gaccatttca attgactctc aaagtagaag tgttttagac    3060
cttaaaaaaa gacttccaaa acttctgctt tggccaatgt ggaataataa gaaactagtt    3120
ttacctttca cctaaaacta caaaagcaca caagatacgt gaaacagtag ttttcagaca    3180
ttggacatca ggtaacacag gacagtgaag ccgaagagga ggaaaacaaa gtggacccta    3240
cgaccgcccc aacctattgc ctgcagagaa tctccaggtc acagggcaga tacaggaatc    3300
ctggtggggc ctggtgatct ccctgagtta aggagaactg ggggtcagg aaggctaagg    3360 ggactagagt tcactgtgca atttactaca gaagagaaag ctgaacagtg aacactgtag    3420
atttgcagag gtccccttga acttttagct gaaagtattg atcagcagat gtacaaagcc    3480
agataagaac tactagaaga attaacagta caatgcttag agatgacaca ggtgttccta    3540
ccagctgaag tggaaaaaca tggaaattca tatgacatta tggtaagtat ttagaagagt    3600
attggtcctt agtgagctgg ctaaagactg ctgtgattcc acctaacaaa acttaaaagc    3660
aagcctctca aaaggatgtc acttttttcca ggtaacttaa ctacatccta gaacaatgcc    3720
aaaaaaatat ttacaggaat agaaaaaaaa ttcagccatc ctgcacagta aaattcacaa    3780
tgtcactcat ctaatccaaa atcactagac aagcaaagaa gcagaaaaca tatgaaccaa    3840
aataggagaa aaagtaatca gtagaaatac atgcagaaat gactcgagtg ctaaaagtaa    3900
cagaaagcag agaccctctc tcagcttttt agtccttgaa gtatgaacaa tgttatcctc    3960
cgattggagt gaggatgttc atatgctcac taagaagttc cttgcttgca ttctcagggg    4020 cattttggc ctctcccaac tattctgcaa gctatagtct gattgctcac aaagtataca    4080
taccactaaa aaaagaaag catggaagga atgaaagaga gaaggcaagt aaaagggaaa    4140
ttaaaaaaag gaagagtgaa aaagaaagag aaagaaagaa aaagacagaa ggaaaggaaa    4200
ggcaagacag agagaagggg acaaggagaa ggagacagac ggagagagg gaagacagga    4260 aggaaagaag aaaaaggaaa gaaaggaaaa gaaagacagg aaggaaagga aggaagggag    4320
gatggaagac aaggaggaag acaggagtg gggggtggga ggaagacagg gagggagggg    4380 gaggggaca gagaaggagg ggaaaggttg ggaggggtta gggagaggag gggagggag    4440 aagagggga ggaggaggag ggaggaggga gggggaggga ggggaggga aggggagag    4500 aggggaggg gaggggag agagggag gggagaggag gggaggga gggagggga    4560 gaggagaggg taggggagac gaggggagg ggagggggga ggagagggta ggggagagga    4620 ggggagggg aggggagg agagggtagg ggagaagggg gagggtaggg aagagggaac    4680
```

-continued

```
ggaaaggcct ttttctcaat tattgtggtc atgggatagg gtaacactaa acattttttg    4740
gtcttctatt tcttagaagg ctcaagtttc agttcttctc ctggtccatt tctacagtca    4800
cccagtgacc taaaactcaa caccctcaaa gtatcaattc aacaggctct ttttccttca    4860
ggtatcagaa aatcaaacaa tcattactat tactaaaatc accacttaat cagagtaaaa    4920
gtattttagt gaaatgctct gtgtgtcttt ataaaatgaa tggtttgtcc tgtcccggtc    4980
agtaaatact aattgattaa ccctcatcag taagactgac ttttctctag aacatcaatt    5040
cccaaactct ttagtctcag gccccactgt gcacccttaa agactgaggg ccgcaaataa    5100
ctttggttta tgtaggttat atctatctat aattattgta ttcaaaatta aaaccaagca    5160
tttttaaagg acaaaaatgc aaagcacaaa gcacacactc cattagggca aggctatcgc    5220
cacatatccc atagcttctg gaaaactcca ccgtatcctt ggagagaagg agagtgatat    5280
acattcttag caatattata aaaacagttg tgacctcacc aaccctgaga gtccctggac    5340
cgcactttga aaatgctact ttaacacatt ttagattgct tgttcccctt gatcatatta    5400
tgaagttata gccttttaca aattcaacat tacaattaac taaaattctt gtctccattt    5460
taacactcat gcttgtcaca gactgaacag tgagagtccc ttcaatctaa ctcctttgtt    5520
acgaactata gatgttttg aaaacagccc ttctcttata aaaacagtgt ttcaagctca    5580
tctggattcc ccaagaagtc ctggttccct taaggaagaa tatattagaa acaaaaagct    5640
ggatagtata tgcaaaggaa accaaactca gtcacagcaa atcattggtg gtacacttgc    5700
atctggtcag catattacca gtcatttgca cctgttgagc aagtaggctt atggccaggg    5760
tccccaaaat gcttgggaga gaccagggaa gtcttgcacc cttcctctac cctcaagaat    5820
gaaagcaagc aggcttacca aaggtcctga aaaatcctca ccctatgatg gactacatgg    5880
gaaatactgt cctgtgaagt ttaaggaagc ttgtcttcca cacggggggtg ttactgggtg    5940 tccgcttcac ataggtgaat gcatatagat aagatgtatc tcttacccac cttaaaataa    6000
cttgtaggct tggttatatt tgtgggtatt ttccaaaaat cagctagtca acaattaat    6060 gaaactgaat atcttttcat ttctttttct ttaagacaca gagtcttctt atgtttgccc    6120
agtctagaat ggagtggtta ttcacaggtg tgactgtggt gcactacagc cctgaactcc    6180
tgggctcaag tgatcctcct gcctcagcct cccagtaac tgggaccaca ggtgtgcatc    6240
atcacaccca gctcactttt tttttttaa gagttgcctc tacacatgct ttgccttatt    6300
ctaaacggtt gtctattttt ttcttaccaa tcttttaaagt ccttcaaata atcttgaaat    6360
tagtccctta ttatataggt tgcaaataac ttcttctaga ctaattttat aatattagtt    6420
atggtcttgt atcacatata aattgagagt ctctttttat gtagtcaaac ctagaacaat    6480
aagagcacaa aggaaggaag ctgggggatg gagcggggtg gggggagggg acaaacagcc    6540
actgagggaa agaaaaaatg aaagtgatga aataaactct tttaactttt cattgaagtc    6600
ctgtacttca gtctgaattt aacatgtttg tgctttactt aacaactcaa tgactattcc    6660
aatgtaaaat atcttgtaaa ttgcaaattt aaagatacta aaccaaaagc caacatcaca    6720
cttactgaaa tccagaagga tttccaaaaa cagggcaaga atacctatta ttactcatag    6780
cattcaatta ttctaggcat tctagtcagt acataaggaa agtgaaataa aagacagtaa    6840
ttgatggatt taaggggaaa ggaggagttg aaactaacta tttaaagatg ttatcataat    6900 ttttttttgta aaatccaaaa taataaactt aatgccatta ggcctaataa aaatatgca    6960 gtgaggaagc tggctacaaa tatgtctaca cccaagaaga aggtataatg gagataaaaa    7020
aaattcccat atcaattagc atattatatc taggaataaa cttagcaaaa tgattctaga    7080
```

-continued

```
ctcgtgtggg ataaagagcc attcaaaatc tactgagaga caaaggattg aataagtgga    7140
gatacaacaa gttccaagat tacatatttt ccatgccagt attctcttta ttttcttttta   7200 ttattatact ttaagtttca gggtacatgt gcacattgtg cagctgagtt acatatgtat    7260
acatgtgcca cgctggtgtg ctgcacccac taactcgtca tctagcatta ggtatatctc    7320
ccaatgctat ccctccccccc tccccccacc ccaagtaact acttataata gaacttcaat    7380
caaaatctcc gtggtatttt ttgatgtaag gaatggacaa ggaatctcat aaaatatttg    7440
aaaattctct tggaataaat atattacagt aagaaaatgt tttaaaagca atgaggggggc   7500 caggcacagt ggctcacacc tgtaatccca gcactttggg aggccgagaa gggcagatca    7560
cctgagatca gaagttcgag accagcctgg ccaccatggt gaaaccctgt ctctactaaa    7620
aaaaaaaaaa aaaaaaaaaa tttgccaggt gtagtggcac acacctgtaa tcccagctac    7680
tcaagaggtt gaggcaggag aatcccttga acccaggagg cggaggttgc agtgagccaa    7740
gttcatgcca ctgcactcca gcctgggtga ctgaaactct gtctctaaat aaataaataa    7800
ataaatgaag taatgagggg gagtacacac cctatcagat atatttggta aagctattac    7860
aatagaagta tctaggaata gagaaatgaa tagatcagga aacaattaca catttaaaaa    7920
ttcactgatg tgataatggt ggcatctaag cgccgctaga aatagcaaag gatgattta     7980 aactgactaa tcttttgtaa agaaaaatag ggccctattt cataatatac accaatattt    8040
gtatattaga aatttacgta accttaaata gaaaagccgt aagacacaaa ggaagacaga    8100
catcaatata tttaacatta aaattattga atacctaata aagacctcaa aagtcctaaa    8160
gactcataaa aagtcataag caaaggccaa atggacagaa atatttgcaa catatgacag    8220
ttacataatc tatttaatca agaaaaacac tttaatggta aagtacataa aagacccaag    8280
caggcatttc acaaaagaag aaatgcaaat tgaccaatga acaaatgaaa aagttcaatc    8340
taattagtaa tcaaagaaat gcaaattaaa acaacaagat accactttttt gccttttaga    8400 ttggcacaag atcaaaaata atgctaaatg atggtgcaac taaagggaag tagccccagt    8460
gctggtggga atgcaaaaat ggtaattgct ggagaacaag ttgggaatat gtatcaaaag    8520
actttaaaat gttaattgca ctaatatta taataacaaa agtatctgaa gcaatattca    8580
tgctcttcaa taggagaatg gttgaataaa tcatagtcat cttctgcagc tcataaatga    8640
gtaagtgaaa tctctgtatt ctggtctgga aagacattca tgctaagagg tatgaaaaag    8700
tagaataaaa gcaagttaca aagtaatctg agggatctga tcctgctttt attaaaggag    8760 ataaaagaa atcccagtgg aaaacacaca acaaatttaa cactggttac ctattaaata    8820
tgcaatatga ggtatgaaat atgagactaa ttttttctta tgaagctcca taattttcct    8880
ttcttgtaat cagaattata attatttttta atgtagaaaa ggaaaattct ttaaaatata    8940
cctggttttg atccagcaat ttacttccag gaatttactc taagggaata aatatgcaca    9000
atttagctaa aataatactt atccaggcca gacgtggtgg ctcacggcct gtaatcccag    9060
cactttggga ggctgaggtg ggcggatcac agggtcagga gtttgagacc agcctgacca    9120
acatgctgaa atcccatctc tactaaaaat acaaaaatga ccaggcatg atggtgtgca    9180 cctgtaaccc cagctactca ggaggtggag gcaggagaat cgcttgaacc caggaggcgg    9240
aggttgcagt gagccaagat cacaccattg cacttcagcc tggcaacag agtgaaactc    9300 catctcaaaa aaataataat aataaataaa aatacttact tacccaagca ttatttgagt    9360
gaaacttgga aacaacctaa atgtacaata atggagtatt ggttttgtta aaaaaaagta    9420
tattcatata acagaaggct actcagctat taaaatgtag aggtcagtgt agtggctaat    9480
```

```
gcctgtgatt gcagtgtttt gggaggctga ggcaggagga taacttgagc ccaggagttt    9540
gagaccagcc tgggcaacat agtgagacct catctctaca aaaaaataaa aaataaacaa    9600
acaaacaaaa taaaccaaat aagctgggca tggtggtgct ttcctgtggt cccagctact    9660
caggaggctg aggtaggagg attcctttag cccaggacct ccagcctcca gtgagctgag    9720
atcacactac tgcactcaag cctgggcaac agagtgagac cctgtctcaa agtaaataa    9780 aatgccgggc tgactagaaa gatgttcaaa atagtacagc acatttccat tactgttttg    9840
tatatattta tagaatacat atgtgtaatg ctttcatatg catgtaagca tgaatatgca    9900
tatgaaaatt tgaatggtaa tgacactgta gtttgcttat ataaatgtct aatttgtctt    9960
cagtgaaaat atttctgtga tcgattgaaa aaaagattgt ttcacttgct tatcctaaaa   10020
tagtttgatt agtttaaatt taaaaatttc cattctctaa aaaataaggg tagctaataa   10080
tgaacatgtg ttacacacca aacgctgttc tctgtacttc atttgtatta tctaatttaa   10140
tctctacaac aaaaactaga tgcttttttcc taaaagagaa gaaactgaag acggaatgta   10200
agtaacttgt ctgtggtcac acatctggta ggaacagatc taagatttga atccaagcat   10260
tttggatgat ttttactaca actcgttaac aacagaccca tgtaaagacc ttcttcaagg   10320
aaacaatcac taaccctgtc atctgttttg tttttattta aggtataaat taccaacaaa   10380
aattacagat ttgtaagggc ataattccat gagtttttt aagtatatgc actcacataa    10440
ccactatccc aataaagata cagaatttttc ccactattat agaaagctcc ctcataccac   10500
tctctagtta ttccctcagg accatgattt ttttactata gctaagtttt gccttttcta   10560
gaacttcata taaatgtaac cataaagtat gtgcttcttt gtatctggtt tatttactc    10620 aactttaagg tttttagatt tatccacagt gttctcatac ttaattggat taataagtgt   10680
caagaaatta acatattaa atattataag attaataatg gacttttaaa aaaaactaat    10740
gtatgactct ccttggagga cttattggtc ccatcttcct caatctccaa ccacttgcta   10800 atttttttctt ccaaattatt ttttaattac aactttatttt tttgctgttt tattacagta    10860
taattgacca atgaaaatca tatatattta tgtatatatt acaatataat tgaccactaa   10920
aaattgtatc tatgctgtat aagatattat aaagaaaaag cagtatttt ctgattcata    10980 tggaaaatga aatgaggtac aagatcagta ccatacacgt ttacaatgtg aaatgattaa   11040
aatcaagcta agtaacatat tcattacctc acacctttt ttggtgtgtt gtaagaacat    11100
ttaagacgta gtctcttagt gattttcagg tattagcaat tttcaagtat acattattag   11160
ccatagtcac aatgctatac aatagatcca gaacttattc attctgtcta actgaaattt   11220 tatacccttta accatcatcc ccttgcttcc cctcccccag ctcttgacaa ccgcaattgt   11280
actctctgct tctataagtt tgactttttt ggattccaca tataagtgag atcatctgtt   11340
tttaaatcta gccaaattta aaacagtagg tgaaccacag ttctgcctgc agtccttagg   11400
aaaacagcaa gacagcatat gtataaatta actgaagagt atttcatcag aaactggggc   11460
tgccttcaag gagatgcgag gttagactgc agcaaccagg aggacccaac agtgaaaatt   11520
ctgaaaatcc ttgtaaggct ctgagcagta tttcctgctt ttccagctca gcttccaat    11580 ctctactcct gcatttgtgt acagatcaaa atctgaggtt ttcacacgaa tggtcttttt   11640
gccaatgtta caagaagaaa ttaaaaagaa aaactgtagg cttagaagaa attaaaaaga   11700
aaaactatag gcttagaaga aatatttagt tcttatttga aattagtaat ttgtgaattc   11760
ttttacaaat gtataacaat agacaaatgt tcttcagcac tccatttttc acaacagtga   11820
aacactgtaa atctctcagg tgtcaatatc tcacatagaa aatctgatct attactcatt   11880
```

```
ttggcaatat taaccattta tgctacatga ataaatgtga ccagttctaa tcacaagagt   11940
cacttgattt tgcatataac tagttcctaa catatatgaa catgtatata atattagttt   12000
taaggaaaat tgttttctca ctctgaatat agtctttggg aataaaactt gttagtattc   12060
tataaacaag cttaaaatgt ttttatttaa agtcttgagc catctaaata ttgtttaatg   12120
agttatcaga ttagatggtg ctttgctatg tctttgtatt gttaccgaag ttcttatatg   12180
aggagtggac cagctggctc tgtggggtcg caggccactg gcttcctaga cttgagagag   12240
agctaaagca gaaggcttct gaggtttctc aggtttccag gtgaaaagcc ctccagctaa   12300
cttcagtgaa ggttgaaggt tcaaggttct agagatcatc tgataagatc agctgaaatc   12360
taaaaaggtc tttctttctt ttcaaccccc actgcaaaac atttattttt tggacattct   12420
tagaatatac aaatacttat gggaaacata attaaagaga aaaaagggaa aacaaaccat   12480
actgagagaa aaaactgttg tcttgggtat atttaaaaat ggacttctta tctatacacc   12540
tttacggtat caccttaaga atgactcaga ctcattttat tttccatatg aatcacaaaa   12600
atactgcttt ttgtttataa aattttactt ataaatttt gagtgctgaa aaaatattac   12660
atcttttatg tctgcttcag ttgtcatcta caagataact actctgattc ccatgctagc   12720
cacttctgtt atagtacaag tttctgctag aaataaaagc aattgttttc ctaattgtat   12780
gtaaaagcta catttccata tacagcccaa tacatacaga cagtatagta aaagaggagt   12840
taaaaaaaaa tcaccacata ctttggggca tgtattttaa atataacttt aattctacct   12900
taatgttaaa acatacccttt attggtaaaa aatatgaagt gaaactctat tcataaattg   12960
atatttgata tcagtagata aaaatataga aatcatctat tgacacttttt ttgcaagtta   13020 tgataattaa atccttatga atgacatata attttgcttg gcggcatgtg gtttattatt   13080
tgaaatctac tggttcatta gtatcatact ggttatagct agttgtttca gaacattaac   13140
tgtcctctca cattacttac agagatactg gggaccatct gttcttgcaa ggaacttaag   13200
tatacatcta ctgggtatca tgctatttat ttaattcagc acccacttcc tattgttgta   13260 ttttttttggg gggaaaagtc aacttaatta cagggaataa agataacctc tcctggcagg   13320
ttaccttgtc accatgagag caaagcggga cctgcttaaa gtaggttact tacggtggtt   13380
aataagaaga gcaaaaccaa caagacttaa gaatatttag caaaggttta acaaaaatag   13440
aacagcgaat ggcacttta aaaatattac tgtaagcctc gggcttgtct aaatcaatct   13500
tggcacatct gtctgatgta gaccgtaaac aggattagag ctggatttat ctgcttggcg   13560
ctaattgtgc tcacagtttc tgcacatgtc cactttttaa aatactgcct gaaaaacagg   13620
cctgcctgat agatggctcc cacaacatag tgtatacaca cacttatggt atattagatg   13680
gttaagcaat gtgatgtcta acaattttt tggctcttca gaattggtta tctaatcccc   13740
taattaaaaa tacaaaattc tgtttgaata caccacatac tgagataaat ctgtgaagca   13800
agggaccaat aaatttaaac acactttaat tgttagaaga aaacacaatt taattgttaa   13860
taatcaggtt aaactagggt ttaaacaaat agggctgctc ctgtagttta ctgaaaaccc   13920
atcacaatat aatactatcc tcaagaatta tgacataaca tttattagca gaaaagctta   13980
agttcctaaa tacatacata tatcaagagt tacaacgaag taggcttctt atctagtaaa   14040
agaattagag ggaaattttt gaacttattt tcagagagaa agacagaaaa ttacagtcca   14100
atcgcaaatg tcacattgtt atcggatcaa ataaaaata gtgaatttcc aactgcaatt   14160
tttttccatt tagttgtttc tatcatgtgt aaatggctga gatacttctt aagaatgtaa   14220
gcatttgagg atatacagat attttcatgt gaagtctaag atgaatcaat gaaacagtca   14280
```

```
aaaatctaaa tttttttttt tttttttttt tttttaagac agagtctcac tctgtcaccc   14340
aggctgaagt gcagtggtgc gatcttggct cactgcaagc tccgcctccc aggttcacac   14400
cattctcttg cttcagcctc ccaagtagct aggaccacag gcgctcgcca ccatgcccgg   14460
ctaatttttg tattttagt agagacggtg tttcactgtg ttagccagga cggtctcaat   14520
ctcctgacct cgtgatccgc ctgcctcggc ctcccaaagt gttgggatta caggtgtgag   14580
ccaccgcacc cagcctaaat gttattcttt gagctttaaa atacagacaa taaaaatgct   14640
aatctttaat acctatgatg taaaagtgac attaaaaatg ttaaattaca tggtgtatgt   14700
ttaatcataa ataccacata aaattggtaa attcttgaa aaagaacagt ataatagaaa   14760
tgagagctgt ttgactttca atcatagaca atcttctaaa gcttttttct ggatatatga   14820
tttattcaca ttccaaatat cctggctagt tcttagaaat taattttcct agatctctac   14880
cattaataaa aaggtaggtg tatacacata gtcttgtttt atataaacaa atattcagga   14940
gaaattggtg aattaagtaa atcttttcag tgcttatgat aaattaaaac accttcatca   15000
gcaattctca atgtgtagtc tcaaagagta tacagggtaa aaacgatttt tataataata   15060
ctaaagatgt catttaccat tcctaccata ttaacatttg cactaaaggt acaaaagaaa   15120
tagtgggtaa aactcctgga gtgtcagtat gaatcaaggt ggagcaccaa atttactaa   15180 taattgctgc attcttcatt aactcaaact cagtttaaaa aatccagttt catttaactg   15240
ttcttgatga agcaataaca cttatttta aaaaaatctc cacccttgag tatattttta   15300
aaaatgttat gagtaataac aatggaaagt atacatacag catttctgct acaaatcgaa   15360
gtggtggttt gctccaggag aaacacttat atcatttcag tcgcagctga actagctgtt   15420
tttcatagaa caccactttt tacttgaaag atcaactgac aatacagact ctggtattga   15480
ggcagcagca tttggtaaac actttctgga aaatgaacaa agtgagtcag tcactaagca   15540
aagcaactga gagctttgtc aatgataaaa tataaagttt tgagtaaaat taaaattttg   15600
taaaacttgt aagtgtgatg atgatcttaa cagcttttcta atctcaaaga attttctgat   15660
gagactggca gtgacattag actttttaaa atatattata ataaaaatta tcaacattta   15720
gaaactgtat aatagtaaac caaattttcc aaaaggccaa tacaggatgt tataaaatca   15780
tacgtgggca aaatatccat tcaaagtaca agacagacca ataaattttc aaatagcaaa   15840
ctacaattaa atagatatgt tttcagattt caaattataa ccagccttta agaaattagc   15900
acttgataag ttttgctata gtatcaaagg acaatatcca caattatctg aacatattaa   15960
aagatgtttc cttttcagct gcacatctgt gtaaaactgt attttcctta gatacttgaa   16020
tcaaagcaac atattcacaa cagactggat gaagaagcat tctgagattt cagctgtctt   16080
ctattaagcc agagttgaaa aaactcagaa agtcaaatac cacatgttct cactttaagt   16140
gggtactaaa taatgtgtac ataggaacag agtgtggaat gatagacaaa ggagactcaa   16200
gagagtgaga aggggtggg tgttgaaaaa ttatttaatg ggtgcaacgt atgttatttg   16260
ggtgaagata cactaaattc tcagacttca ccactaagca atatatccgt gcaacaaaat   16320
tgcacttgta cccttaaac ttacacaata tttttttttt tttttagaa aagggagatt   16380 tgaaaaatt taaaatagaa gagtggtact gcttttttga ttgttttgga aaatagttat   16440
ttttaataca aatatgttat ttatgttaat atgcaatgaa cttactgtta ttttattt   16500 tattttttt attttttga cagagtctc cactctgttg cccaggctag agtccagtgg   16560
cgcaatctcg gctcacggca acctccatct ccctgggttc aagtgattct cgtgcctcag   16620
cctcctgagt agctgggatt acaggcgccc accaccacac ctggctaatt tttgtatttt   16680
```

```
agtagagaca gggtttcacc atgttggctg gtctcgaact cctgacctca agtgatccac   16740
ccgcctcggc ctcgcatagt gttgagatta caggtgtggg ccaccatgcc catcttttg    16800
gttattttta aatagtaaat attttaatg tctatttaat ttctaataca acaaatatca    16860
atggttataa cttaaataaa tggtctttgt ggttttcaac gatttaagag tataaaggg    16920
ttccaagacc aaaaagcttg agaactcctg gtatatagtc ttataaagac aggcatagcc   16980
ttatgaaaat taagcctaaa atggcatgat ttatgcattg catctttctt caccttgtat   17040
taaatacccta agattttatt actagattgt ttttacacca tctatgcaac aagttcctac   17100
tacatctgaa acatcatgaa ataaagcaat tttaaatatt tcatattcta taccccaagt   17160
tcatcatgca atgtgattgg ctttcatcat tttcattcat ttcaagaagg gcaattttgt    17220
tgagatcatt tgttccttga ttttactacc tacttatgta tttgcccaga cctttccttt    17280
tatatgtcca cttccatctc agtccctcag gaaaaacatt tataaatgta tagggttggg    17340
ggaggtctcc aagaatggca ccaacagaaa acatgacctt aatggattca tcttaatcaa    17400
aaacctagtc ttttttttt tggcattatc agttcagcta cacagatcag tttgtatata     17460
cagttcatat atatcatacc agatgatctt tgcaccaatt cctcctgagc ctcagattat    17520
ggtaattggc cctttctcca gcttctcagc aattcacttc aacaatatct tcatcattat    17580
cttcatctct aatctctgta tcccagcacc tagcttaatg cttcaaacac aggctaggct    17640
tccaataaaa gttttttatt gactgtattt actatcaatc agaaaatccc ttaatcacac    17700
tgtatacatt tccacctctg gacctttgct ccttcatttc ctagcacatg gaaggctttc    17760
ttgactctag tcttttcaaa tattaaccaa ctgtcgaagc acattgagcc actcttctaa    17820
acaataaccct tcatttctca gtccctctga gctcttaggg cccactacta ctcagttgac   17880
atttaatcgc atatcagaag ttattaactt accagagggt gaaggttcaa aggtctttga    17940
aagcctttaa taacttgtta taaaatacta attaaatggt ggttttaaga tggtagtagt    18000
gggagaggtt agagaaagaa taaaactgta gtagttcaag gtaagtctga aagtttactt    18060
cttcattta acaagtttga atacctacta cattcgaggc acttctttgt gtatattaaa     18120
atgttaatat tagtgtaact gaacctccat gggcaactgt tgctatgaga acaaaggaaa    18180
aagtgcttaa acctttttgtg gcctgaactt gctggactgt aggaacagga tgagatgtaa   18240
accacaatga tggtttctat tgccagggtg taaggattat gtctgggcat gggcttcctt    18300
attggtaaag acccttacat acagttcaac tcactaatac tcttttttc ctgaggacct     18360
caaggatagt catatgtact ttgctctcac ttttgtcatt attgtcagcc aaggtagtac    18420
ctctgcaggt cagatcccat tacttcccag cagtcacggt gaggatatcg cacagccctc    18480
taaattgtcc aaagggttct gctacttaga aacactaaaa gtctgacttt tataccatgc    18540
ccattcagtt atcccctcaa tgctctcaat atttgatcat aagatgacaa aaagtattc    18600
agaacaactg ttgaaagttc agagtatttg aactcggcac aggcagatct gtgttgctgg   18660
aagggagaag aaactttacc tgagagatta aagtaattgt tattttact tgaagtgtcc    18720
agtggtccta ggaccaggaa agaggtagaa gagattcacc taacagcctc taggatacct   18780
gaactcctca gtctaccttc ctgatgccag caatgggacc actgtggtca gggatcactt   18840
tggggtgcac agtggcaggg aatagaggga agataaaaag aaactgtcag aagccttgtt   18900
gaccgaacat ccaaaagtaa gcttcaaaca cacatataat tcaagatgtt ctaaaaagta   18960
tttgtaaaac tttatttatt catatgatga gtatttttag gcccagactt actgaagaca   19020
aagggaaggt gataagcaat tttaatatag cttataattg gtttgatttt taaaatccaa   19080
```

```
gttaacaaca ttcaagacaa aggtcatgtt tatttttaat atgctaggca aatgggggat   19140
atgaaccttt catttccaca attaaaagaa tatagttgac aaatatattt ggttttcatt   19200
tttgccattg aaaaaagagt taagtaaatc agtaagaatt gtttccacaa gaaagaaaaa   19260
ttacaaggaa attacttata aaatgtagtc aaatttccta agtctctaag ttattttcag   19320
ttggacttac tcaaaatgta aggaaaaaaa ttaagtctta ataaaattgt aagtcttaat   19380
aaaaacttta aattttaata aacacacata taattcacaa attatgccag tcagctgata   19440
tagtttaggc tcctagtcac atgaaatatg atacccctaca acgtatttga agtaaaacaa   19500
aattttaacc attttggagt agaaattaga ggaagccaat tttattgaaa aagccttaaa   19560
ttgattcaaa gagtctgata ctaaaataag ctaaatgttt ataccttggc agtctacata   19620
gatggtaatt atacaagtgt gtctccactt tataatagtt ttaaaattat aatttcttct   19680
ccatgccttt catcataaca caattactac cgcatagtta gtactatgat aagaagccaa   19740
aactaaaggt gaagttgaga aagtattacc tgatgagaaa attttggaga aaacataaac   19800
attctagatc aagtattta tatacttagg tacattatgt agcatgtaat caatgtaaaa   19860
tagcttacag gattacagca agccatcttc tcctctgtgc tgtaatactg tcagtttttt   19920
tttagaaaga taaatttgat atcaatacga tgtgacacaa ctgcatcaaa ccttaatttc   19980
actcacagta agaagtcaca ggattaaata acactgtgca gtcttttaga aaagtttatt   20040
gcttccagat ggattcaagt ttcctttcag ccctgattac atctaatatg cacagggtgc   20100
caacattata aaggacagag tcaaaaatat catttatata gatagcaaga ggtgaagcag   20160
gggaactctg gcttctaaat aggttctgct aatcaagtct taactatttt taagaaatca   20220
caatcagcat ttaatgaaaa acaaacatca tactatataa atgtcttcaa taatggctgt   20280
tccacagaaa aacacaaatc tacactaaag tagccataaa gtgactccta gctcaagccg   20340
catgctcttt gcccccatgt tgggctgtgc catgtgtcac accgcatggg gcttgctacc   20400
aacatgtcca cctgtgcctc tgtggcagaa gaggcatcca tttttatttc atttagtagg   20460
aggactattg aatataagcc attgcaatca gatataaaga ccttcaaaaa tagtgactac   20520
tcaaaggcat gtttgctaac ttgaaggctg cacacaaatg accactatat ttaaaagaac   20580
attttcttat gcaactgaag taccactaac aaaataaatg aagtctttt cataaaaccc   20640 cccaaaagta ctctccataa tgcaaattaa aaataaaatc acatccattc tatctaatct   20700
tggggagaaa aacaaaaatg attgaaggat ttcagtcagt agatcacatg tcatcttttt   20760
aaaatatatt aaaactaaga atacttctgt atttcccatt ttcttaaaaa ttgttcaaat   20820
gtcaccctga aaaatttata caaattacaa agttgattga atataaatgt taaacaattt   20880
attatgattc cttaaaacag attagcaatt taaatacaat tatggtccca aagctctgaa   20940
gaggaggaaa atgatttctg gaaacacata aaatctttct tactggagaa ctgtttgaga   21000
atgtgggact acaataattc ctgctcatgc ctaactttct cctgtggagt acacttaacc   21060
aaaactaaga caaatatcat tatgatactt tattactcat aattcttag agagactaag   21120 ttcctctatg taaggaaagt gaatgctaaa atttcaggtg atcctcacaa gttttttcact   21180 atcttgtatt ttcgattcgt tccataagtc atacttaaaa tgaatgtagt aaaaatttta   21240
agtagattaa aatagtgata atatctttta gattgaaata gtgataatat ctttcaacta   21300
tctatcaact gcttaaaaat gcttgaagac acaaggtgat cagaaaagga tgaaattaca   21360
ttaaaatgta acttgaagtt acaggccaaa tcaataatag atcaataaaa cagagttcaa   21420
ccagttaggc taccaggaac taaaatggat aatgggtttt atgtcagcac atgactcatc   21480
```

```
cattaagtat ttcacatatc cctaatacta ataagtgttt gtgttaacta tccctaatca   21540
aatagtactt tgtttccaat aatgattatt cttaaactgg ccactgtctt ctaaatagta   21600
tgtatttgag tgaaaaatga tttgagcttc actctttcaa tatcgttaat tggaaacctt   21660
ccacatgcca gtcttgttcc acacagagaa gccttttaga cagagatctt ccttgactac   21720
ccaataaata atcgttgaac aaagattgga acaaaataag ggagcatgct gtgtaggtac   21780
gggtctagaa tctctcatct gcaattctga atccccaaa gctccaaaaa catttttttc   21840
ttaagtcatt tggcagcaaa tcttgagctg acctcattct gcagctgaac tgacaatgag   21900
agttgagtct ttactcatcc ctcttagcat gggcattctt aatgtttcat tcagaaatat   21960
tatttaatta tgaaatgcta ccacaaacca gctgtgagtg ttatgtaata tattatatat   22020
accccatttt agctctctaa aatcagtaaa tatctgaatt ttaacacata gctggttcca   22080
agggtttctg ggcaaaggga acagtaagca tcaaggtcct gtggcaaatg catacttggt   22140
gtgttcaagg aacggtaaga tgtggctggt gctagtgaga aagcaggaga gggataagac   22200
ataagagtag agggatcagg cacaagtagc ccatgtaggg taatatagac tacattaagg   22260
acattggatt ttatgctgaa catgcagaag aacgatgtgc tctaatgtac actttaaaat   22320
taacatctgg gccagacatg gtggctcatg cctataatcc caacactttg ggaggctggc   22380
acagaaggat tacttcaggc caggagttca agactagact gggcagcaaa gggagacccc   22440
atctctagta aaagttaaaa aaaaaaaaaa attagtcaag tgtggttgtg tgcctgtagt   22500
cctagctact gggagaagcta aggcaggagg atcacttgag cccaggaatt aaaggctaca   22560
gcgagctatg atcaccagtg cattccagcc aaggcgaaag taagacccaa tcttaaaaca   22620
aacaaaaacg aaattgctac atggagaaca gactgatggg ggacatcgtt ggacagacac   22680
tactccagat gagaaataca atactccagg tgagaaatga gagtgtataa caccaagtgg   22740
tgacaatgat gctgctcaag cgtggatata tttccaagga agaggcaaca ggatttgttg   22800
ataggttgga tgtagaatga aagacaaagg gtggaatgta gcaagtctcc aagtgttttt   22860
ggtttggaca atcagaataa tgaagttccc acttactgaa atgggaaaat ctataggagg   22920
tacatattta gaggctgcag gagaaaatgt ggagtttgtt gtagaacata agtttgagaa   22980
gtttattaga cctctaatat ttaagtagaa gatttataaa actggaattc agaggagagg   23040
tctagactag agttacaaat ttgaaagaca tgagcattta gatagtattt gaagccagaa   23100
actagagaag gtccaaccag agaaaacaga aacagagaca ataagaagtc agaggacaga   23160
catgggaaaa tgagaatacc caagaatgga gactgggaaa aagcagccca atggggtagg   23220
aggagaacca aaagaatgac atccaagaag gtaggtgaag aaagctgtat caaggagcat   23280
agtgtgacta cttgtcagac tcttagtagg tcaagtcaga tgaggactga ccttgacgag   23340
taagctgtag agtgacaggg gtcaagtctg gccacaggag attcaagaag gaatgaaaaa   23400
cagagtgaat gtataagtta tctagctaga aagttgggg gtggggtgag caaaaaaaaa   23460
aaataaatgg gaccaggtgc tctacaaaga ttagttcagt taatcctcac aatagttcta   23520
taaggtagaa atcacctcac tttacatatg aaaatgtaga agacaaatgg tatgccatgt   23580
tttaaatgag aatgttagaa tttgatagca agtataccttc attatcaaag tttatcctct   23640
tatagtacca cacagcttcc taccaattta ccatataaat aaacaaatat tgagaaaatg   23700
gcatcgtgtt ctcagaaagg acactggtgt aggaagagaa agccttagat ttagtcccca   23760
actctgtcac caatcttgag ggaaatgctt tcacttttga gcctgacggg tcattcctaa   23820
aacaagagga ttagaataga tgcattcatt cattcaacga atatttgttt aatctctatg   23880
```

```
tgctggaaac tattctagga gttagagaaa cagggggcaaa caaaacagaa acttaccctg    23940
tggtaagaaa aatgatattt aatttaatct aaagtttctt tcatgcctaa aacgctatat    24000
tgtttaatag acaaaaattc tgttctatgt agtgcaaata agtttagatt aattgtgtca    24060
gtgaatgctc actacaccat aaactgggtg ccattattat gatcccattt tacagattgt    24120
gaggaaggac agataagctt agagtttaaa tagcttgccc cagtctcaag agtggcaaat    24180
tccaaattct aacagatatt ctgacccccaa aaaaccaccc ttcaattact ttaaagagta    24240
tagtaataca ctattataat acttcatttg actggtgttt acctctccct tcctgttatt    24300
ttactttttt tgatggatct ctgaatgttc aaaatggaaa acaatgaaga ctaagagaaa    24360
aagcgaacaa cagaggaact gcagtagaag tgaataatga tatttgcttg aaaaaaactc    24420
aagaaaaacc aatatagtgg agtaacaaga acaaaaaaga gatctgagaa ggcacaggaa    24480
ggaaagaaca gccgccattg agatggtggc tctggtcagt cacccactga tgccacatgc    24540
ctaattgtac aggacagtta gcaggtgggt caaccacagc tccccaggtt tgctctatca    24600 gagggggactg gcttctccta ttctctgcca aatcacccaa acaagttgtc catttaagaa    24660
cccgaccaag aagccaaacc tctaatgagt ctgacaaagt aaatatgctc cctaaattcc    24720
tcagaaagga aatcaaggta ctgttagata cattttggta tgatcatgtt aaaaaggaaa    24780
gcaattcttg agagtgggta ctgggggaaaa aggagagatc cttatacaaa tcagaagagg    24840
ataaaagatg cagggatgag tcactggcct tactaccaga gaggtcatct tctgattttc    24900
agcagacaac cagtatctgg ctcttgcctt tggattaggg atctccagcc agcactaggt    24960
ccacatggac tctcactggc tggaagccag tttatcttcc ctagctttca acatagagag    25020
gtgatatgag agtagctgga tttccttttc tgaagaatta ttcttataat acagtatttg    25080
cccctagtag tctgaagata tttagagatt gtattggttt catattgctt gtagaggcaa    25140
gaaacatatt ttctatcaat aatctattta gctgcaaaat ttgagtgtct cttctatgcc    25200
aagtgttttc tgacctaaat attgaggatt tgaggttgat taaatatggt tctttccctg    25260
tagcagtttg gtacaatgga gaatggaaac taaccgtcac gtggaccttc accaagttct    25320
tattttcaat ttactgcctt acaaaagggg gcatcctgag tgcctcctaa agcaaactag    25380
gaaaccctca ttagtaaaaa ggttctacta agaaatttac aggatacatt aagaggagaa    25440
acatagaaat tgagagatac agaaaagaat gaaaagatat cattgaaata agagcaagaa    25500
gaaaaaatta ccaggagttg cctcatgtga tgctgctact cttgctgttc ctagggagga    25560
ataaatcttt tcccaaacat tttggggaaa tctatcaaat tccatttgta ctcatcctaa    25620
aaacttttag gtgtcctagt cacaatgcaa aattctttac caattccaac ccaggatagg    25680
atgagtattt cttttgacga aaactaataa tcatgtagtg gggaatagaa atttgatgac    25740
aatcatctgg tttcatcatc ttgtggtttt cctctggatc ctgagagttc agctatagaa    25800
atacacagac tttgccgaag aggaaaacat tcccacaccc catggctgta aggaacactg    25860
catacatcac tgtcctcagt actaaaacac tagatgttgc gatagcacac cagccctgaa    25920
atgtgccact cttattagtc accatctttt cttaacagat ggcaaaactg tgctacagca    25980
atattctact gatgaaggag ctgttaggaa ttagaaacta ggtgatagca catttataaa    26040
atcatcatca acaacaaaaa atacatgctg atcattaaga tatgtaaaat aagatacacg    26100
acaggaatca tttaagaaca ttctcaaaac ataaatgtct tgtcctgaag gtttcatttg    26160
tgctcagaac attttttttgt gttaaaaaaa aattagatga ccttggtagt aatcagctat    26220
ttagaccatg accactgaca aactcttatt taagcttcag actccaaaac gcaacaccat    26280
```

```
caacttcaga aatttttgta aggacaacct tgtagctact tatttaagaa atggtttgca   26340
cagtggttct caaattgacc tccagataat tctccataac ccagtcctaa ggagctctgt   26400
cgtactttac ctattgggag aagagaaaga gggtgtttta aaatggcctt ggaatggaag   26460
agataataca gaaagtactg ttttaataca gtcattggta aaaataacta tggatttgtt   26520
ccaaagagtt actggcatgc ttaaagatca gagatcagtt catttgtttg aaatgctcta   26580
ttttcagtgg gcataaaaaa ggcagtaacc cccaaagatt agtccaaagc ctcagtatca   26640
atacacatat taggatttgg aatcctggaa acctcttcca aaaagctgtt caaacaactt   26700
tcaaataatg aaattgagat cttttctgct cttcaagggg atacatgatc taaagtttgc   26760
gcaagttcat tttccttta atgtacgtat tttagaatta gattttgtaa tatatgcatg    26820
cagttaccac ctacacaaga ttattataat ctaacccaag taattactgc tgagatcagc   26880 aagtaatgt cctttgtttg ccaaattttt gtttccccaa gaacaaatcc cactcaataa    26940
agatgtgttt ccaggataca tataattatg ctgggtacaa catctgttgc tttgcatttt   27000
cagagcctta ccaaatcaag ataagaacac gcttctatgt ctactttaga gagaatgact   27060
agagtagtaa aagcttaaat actcagaaga ttttttcaaaa agcagtattc atcaaaaaca   27120
gaagcaaatt ctaatttaac tatttccaaa ttgaattaac tcattttagt ccttatcttt    27180
taacacaatt atatcatttt tcaatatgat tcaataatcc tgaaaattat ctttcctatg   27240
attttatata agaatcttag ttctattaac ttcaacctca gttatctttc agaagcagaa   27300
tgcctaacca aaaaaaaagg taatcactta tgatcaagaa cagcagaaaaa ataatattgg   27360 tgccctcttt tctggtattt cctctcagga acacagtgga tttagataac agggcagtgt   27420 tgcacttta aatgtaggtc agtattctga ttgtagtagg aaagtaaatg ctcagacctg    27480
aataaagcag ggtaatagcc acctaagtca atgttctgca tggccttta aggttgcccc    27540 cagcaacctg gtaatcctaa gaacttttca gtatggaagg taattactta ttggcaagat   27600
ttatcaggaa gacacaaaat aaacactgat ttcagtacca aaatatgaaa taaacatgta   27660
ataaatgggg gggtggttct gacactactc tctcctcaaa cattagtagt cataggcaaa   27720
aaaaaaaaaa ctcagttatg aattcatact ttcagaaaac tttagaacaa gcaaattcat   27780
gacattgtta gtgatattca gatgtatttc actatctttg agggctacta tttctcctgt   27840
ccatataact attattattt gtgctatatt tagactgatt agattgacca agttccacag   27900
agttagagtt gagaaaacct acttaaaatg taaaaaatta cccatctttc caagccattt   27960
taatatgttc cttctcactt aacaattctt tatttcttag tgttatatat cattttaag    28020 taatcacaca ttaaccattg tcttggaaaa aaaaaaaaaa aacacaagaa gcctcacctc   28080
actattaata ggaatttaag gggaagaata aaacccactt ttttttttct ttgagacaag   28140
ttctcactct gtaacccagg gctgaagtga agtggtgtga tctctgctca ctgtgacctc   28200
tgcctcctgg gctgtagcaa tcctccagcc tcagcctcac cctcttgagt aggtgggact   28260
agaggtgaac gccaccaagc ccagctaatt cccccactcc ccctgccccc ccagagtcgg   28320
ggttttgcca tgtttcccag gctgatcttg aacttctggg cttaagcaat ctaccttccc   28380
tggcctccca aagtgctggg attacaggtg tgagccacca cacctggcca aaatccactc   28440
tcaaggttgg aaaagattta ggtaaaggaa actatagca aatcacgtgt tatggactga    28500
cttgtgttcc cctaaaatat gtttaagccc taaccccag tgtgactgta tttagagaca    28560
gggccttaaa tagggtaatt aggttaaatg aggtcatagc atagggtcct aatccaatag   28620
gactggtgtt cttacaagga agacaccaga gatctctatc catgcaggca aaaagaaaag   28680
```

```
gccacgtgag gatgctgtat gaaggtggcc acctgaaagc caggaagaga accctcttca   28740
gaaaccaacc ccaatggcac cttgatttg gacttctagc ctcaagaact gtgagaagat    28800
aaatttctgt tcaagcctcc caggctgtag tattttgcta tggcagctgt agcagactcc   28860
tatactatcc tgccttgact tatcttcagt tttaatttct actttagcat ctctgaattt   28920
tcttcaaagg gtgacctgtt gtcgtattgc catatcaagg aaaacatggc aagcagagaa    28980
actgattgta tctttttca tttctgtgtt ccaatatttc caaatgtggg cactgaagaa    29040
tatttaacgc caatgagtga aaaaccaaat aatttcttag cttattaatt agaatgccag   29100
attatattgg gaggccattg aattatttta ggtgggaatt agtcaacata gcaagggatg   29160
caatacagtc tagggagtac aaataaaggt aactgagaac cttgtgtaag atttgaaagc   29220
accatttaca agaatttctc atgctgccca cttgaaaggt aaagatgaaa tttctcaagt    29280
cttctatatt tttactccca ggttttcact ggttctttaa aagtcttttc ttcattactt   29340 tttaaaaat tgttttattt ttctggttct taaaagtct tgtgattgaa ctagaaccag     29400
agcttctcag agcttccaaa cccaggagaa atcagcatag atacacacct ggaaagttaa   29460
gagtcaagat tagcccaggg ctaagtggag aaacaggcac actggaaaag gttcatcaaa   29520
gcccagaggc caactagaaa aatggcccctt taaccacttc acatctcatt ccctttacac   29580
ccctccaccc caccttcccc catgctaatg ctgcttttg caccttacac ccctccacag    29640 caccccctt catgctaatg ctgctttcca catgacctct gtcctaggag ctcatgctct   29700
catttaaagg gtttgaaggg agggcttgag gaaggtccca tatggaggaa aacttttgcct  29760 caagcaaagc actctcccct tttaccaccc accctgctat ttatcctctc caaggcccaa   29820
acatgactta agagtctcag aaaagggctc tcgagtatgg aaaggggaaa gagaaggaaa   29880
tgggaataga gtttattctg agtttctcta aaggtaacca agctgggctg tcacattttg   29940
cttttcccta tgtcattttt accccaacca ttgttaaact aaaccatctg tagatattaa   30000
aataccattt tcaggaaagc atttatctga aagaagaaaa tatatagtac taaatttagt   30060
attttgagga caaatttaaa taaaactatg taaatagtga gtttatttat atttctgaat    30120
aatttattgc aaagataaat acatcagtat tttaaaagtg tttccagttt gttgttttc    30180 actagttttt gtatctttgc ctttgccaaa tctaaaattc tcaaccttac attacattct    30240
atatcatcca taaactttga gaagtattat taaatttcag tggttaagag aacttttaa    30300 tctaaaaata tttatcctaa gacaccatta gattttttc tcatatagag ggattagagg   30360
aacaaaggaa agaaatccaa ttatttaaaa cagaaatccc ttaacactgg gatttttgttt  30420 taattataaa gagtgtgtct tattaaaaac aaaacaaagc cttgtccttt aagggagaaa   30480
cgcaatgttc ctctagtgaa cgagcatgca agagttccca tagaatgatt aaacaaatta   30540
actttgctat tcttcaattt ccgatgatat aattgactta ttaaaagaa catcaagtaa    30600 acaattacgg gtgcacctgt tcagggtgtc ataccaagca ccatacaaag ttaatgggaa   30660
tatttctatt ttcttcaccc ccacgatagg caaaacttac tgtactaaaa ccaaacaagt   30720
ataggcagta gtaagtatca gaggaaaatt gttaaagagt cttttaaact ttaaatgtta   30780
ctccagacat acccagtacc tgaaggcgct tttccatgaa tctcctccct catcctgtgg   30840
ctcctccagg gccttggata gggtagtggg gacagacaga tgggaagcta caactcaaag   30900
taaatggcct gctcctcagg aggcagaaag gtcactaggg actttcctta cttggtccta   30960
ctccagtcct actcataggg aaactaaacc acaatttagg gaaattatac taaccagctg   31020
acttaaatgg ttgagtgctg ggcccagaga gctgagggaa atctctcttt ctcaggggac   31080
```

```
acagaggcgc ctgactctcc tatttcaggc ctaaatgaaa gctacttaga cactcagcat   31140
agccacgctt gggttttgtc actgaaacta aagcttccag tcaccctgcc acctctggca   31200
gaatggagtt tggagtagaa ggcacacaga tatcacagag gcccaaactg agccatgaaa   31260
ggtgccacac ctaatgcaac tggcaagggc ctcagctcag tttcagccaa gtggggacag   31320
aaggttgtcc taatgacata agtcacccaa gggacaaaaa ggggactaag agcagcaagg   31380
atgactgaat gagcacggag atggaaatga tgacatgctt cgaggctgag ggaggacaac   31440
agctgataca cagaaagcag atgagtagaa aataaaagta aattgttcta gttattatct   31500
taaacagagg gataggctgt aacacaggac acactttctt gggtttaggt ttggtatcaa   31560
gtgtgaacat aatacaaaat tgtattgata gcatcctcta ataaaataaa tttggaaagg   31620
tagttttgtt tgttctttgt tttgttgatg ttccaggttt aagtccaata aataaaagtt   31680
catattgttt ttgaataaat agctgtcttt aaaaatgcaa gagaaacaaa aagaaaagca   31740
gaagagaaag cgtcgggcaa tggaaatctc aattgttgct tttcagtcaa gatcatgaaa   31800
agcaagtaaa agaagggatc ctaactacaa tagaatgagt gtcttctttt acttagaaat   31860
ttctctagtc tccataaagt aaagatttca cagttttgta gaaattccac ttcctttttc   31920
tttgcctgtc ttcacacacg catcaaagaa actaagtaag attagcaatt agcacaggat   31980
ataaactgac caaggataca ccacaactac tacatactta tcaaattcag agagtacttt   32040
caggaccaat agacagaaat tttcaactta agattttgga acctaaagga tccattaaaa   32100
gggcactttt caattttaaa gtgtcaatca atgacaaaaa tttaaaggca caatcatcat   32160
gaaaaaggta ttttttaaaat aacatccata gacagcttcg gtttctctct gaattatgcc   32220
ataaaactga ctcaattttg ttaatatcaa tagcataaaa acgagaaagg aatacaactc   32280
aaatattgta gattcacgtt aaaaagtgac tgacaggtca aattctaaaa aagaaacagt   32340
agataccacc acaaaactag cagatgtttc ttggggtcat ttgtacaaaa acataagcat   32400
atgttaaaga aatctgacac tatcatggaa tcagttggtg tctaaaataa tagcagctcc   32460
ttatggcaat atgataatat ccgtatcaaa tgcacaacac attatgttgc aacagtatgt   32520
gcagacaaaa gagcatcagt agcagcagta atgaccagtg gtctcattaa ggtgaaaaaa   32580
attttttcca gtgcatagta ctggttaaca gtaaattgaa catgatagac agtacgtaga   32640
attttcagag tttaaattta cctgatttta ttgaaactct tataaaggga cttaccaaat   32700
aagactgaag ttttttacagg gacctctaac atgggttttc tgatttatcc agtctactca   32760
agaataatga aaaagatcat tgttattctc aaagttaatg aacatacttg gttagtttaa   32820
gatataaaca agaactcttc acttcaaaat cagttatttc aacctgatgt cctatacccg   32880
ctagttaagc aataagtaac tgctgcaaca ttattttaat gtaaagcaac acataactta   32940
gtagtgtatt atcaccttca atagcagaag gctgagatct tctagaatat tcctttggaa   33000
ctagccatat cacacaaaaa aggacaatgt acacaatgaa tgctaattaa acattactga   33060
ctgaaaatct ttgaaaagta aaggccaaaa ggcattccat agtttttccta attgttggga   33120 ctcatattat tctctaagaa ggtcaaattt gaaaaggcac ttagaatttc aatgcacata   33180
ttttccatgc agaagaactg gatgtaagat gagtctggca tgtacctaca aaggtcttca   33240
agtgccaaga acatttcata aaaataaagc tcacccatga gatatttcca gagtaggttt   33300
gatcccaatg aaaaacatta aaataacctg taaaatgaca ggtgtgttat tagttcagaa   33360
gctagggtac caagacatat tgtttttcc tcaaatatga aaaatgctaa atttaaaaaa   33420
taaaaataac ttttagagaa atttatttct acttttttaaa aaacataaat cacatgacaa   33480
```

```
aaatgtatcc atgttattta ttttactgtg tctaaatatc tagataaatg ggtgaggaat   33540
ggaaatttta aaatgtatta tgttcaccaa gatttcaact gtaataagtt tttatctgta   33600
tgatgaaaac cacaacaaaa catactgtca tccctttaca ccttcaaaac atgaaaacat   33660
acttaaaata taaggaaacc aatacatgct aacagctgct caattgtatt gatcttattt   33720
ttcctgcaca gatggacact aaacagtgct ttgaattatg tttgtaacat ttagtaaact   33780
taaaagctta atttggggta aatattaatt acttgtatta gacaaaataa taccaacatg   33840
gatattttaa gaagtaaatg aagaactttt aagcttaaaa tggtatgaac agctattttc   33900
cacagataaa aactgacatc tttacaaatg actatttcac tgacttttta cactccaata   33960
atgcagaaat attatgaatg tataaagatt acattattta ctaacatcta atgaataatg   34020
ttttctgaaa atagagcgct ttaaactatg attatttta agtagcctct actctaataa    34080
gaaacaggat acacaaggaa agagcctagg gctcatagga aatacagatc ttaggcttaa   34140
aagggttcaa cttacagtcc ttcaggagca atttctccag tttgtgtact tttcaagcta   34200
cttcccttct gtttacatat tttgctagtc actagcacat ttgatgctaa gatttggtag   34260
aatatatttc aaataagatg cttctcattc tgctgattta aaaacgaatt tgcgcagcgt   34320
ctactatcta tcccactgcc caagctagaa atctcaccat caccattatt tatttccctt   34380
ttaagcctca catcccccaa attttgtctt tgacaatatc ccttgcatcc aggcttacct   34440
tgccattctc ccagctttgc agccactgcc ccctgatctg ctggatcagc catcacactg   34500
ggctcctcag tgtggagccc atttataatc tatcctgcta cctaatttac caaaaaaaaa   34560
aacagaaata cttgatctca cctaatgccc agcctttgtc acaccttcct caattttcag   34620
gttgagacgc caacttcctt gcatgctatt caaagtcctg tataaactac tgactaaaaa   34680
caaagcactg tcatctcccc cataaataag acaatgttat tttccaaata ggccaaagca   34740
tccttttctg gagattttc aaaatttct ttttctagaa tggtttcctt gctcctttgt    34800
ctgtcttgct aactccaaat catacttcaa ggcccacatt aaagtttacc ctcgaacctc   34860
tctgtagctt ttcctgactt cccccctcagc ccgcccaaca gagaatgatt ttctccttta   34920 cctattttc catgtgcatt tataatgctc tgtaagtact aagttgcaca caaaatagat   34980
catgtagtta ttcttttgtc aatatatctt cctgaagatt gtgaatatct gaagacagaa   35040
atcatgtcaa attgattaca gaatcctgga accttctaga gaccccataa ttggtgctcc   35100
ctaaatgtta ggaggactac agtaaaaaca tgaatgattt aacaagaaaa atgcaaattt   35160
aaactatgct gagatatcat ttattatgta tcaggctgtt tttttaaagt ttggcaataa   35220
actcttctgg agaaattttc aggaaataca tgcccttata caataatgat tttaaaaagc   35280
aaaattgcac aacccttttg aaagaatttg gtaatattga gcaaaattat taacacattt   35340
attctttgac tcaacaatct cacttctagg catctatcct aaaagcacat tgaaaaacaa   35400
aaaacggaaa gtaaagttttt ttattaaacc actatttgcg ataacaaaaa tgactagaaa   35460
caatccaaat ttctccaaca gagaggtcaa taaacgatag tacataatgg attttgatgc   35520
tgatgtaaag cgctacagag tgaacttctg ggcatattgc taagtaagaa agaaatcaag   35580
gtagaaaaac acatatattg tacatgtgtt taagacggtg ggtactgtgg gggtaatgaa    35640
aagaatatat gcacatgttt atttatataa aataaaagaa caacccagag ctttgaggaa   35700
caaataagct ttcctaccta caggaaggaa ggaaaagcat agaagggaaa cataaaagct   35760
atacttccta gaatatagtt tgtttagtag atttgatttt ggaaccatat aagtatttca   35820
cgtaattata aaattgattt ttaaaaaaga aatgcctaaa catcaaaagc aaaatgaaac   35880
```

```
aataatacaa aaaacaaata agttgggggt ataacttcac agatatgaat tattccaagt   35940
gtctttaaaa catagtaatt tgactacacc tccctagtag tgtacactct atgaacaaaa   36000
aaaaaaattg caggactatc ttaagtgggt ttcagtaatt atactttga ttggcagcat    36060
tggtgttgtt actctattgt gtctacataa tgcaggataa agcaaatgag taatgatgtt   36120
gttatagtta ggaatcagga ctttaagggt aggagaaaag agacaatgtg aaaagcttag   36180
gcctgcactt gaattggaag tatcagcata atcctatgat acattttttc tttaaaaaca   36240
aaacaaaaaa acccaacata ttttctagct ctgttctttg aaaaacctaa gtaacaaggt   36300
acacataggg gaagttttag caatgatgtt gcttagttct caaattgagg tctctaatac   36360
cactatccag taaaaggaac caggaccctc tgatgatgag cttgattcca tatctcaagc   36420
atgaaatgtt caagatgaac ctggaatatc ttgccattcc agaaagcagg gaagctatca   36480
gacagctgag tgaatgtcaa aagaactcag aagtcaagat gaaggggctc ccattggtct   36540
aaaaatccaa aatgtgacaa tttgaagatc agtaaaaata atcattgctg tgaattgaaa   36600
aacatttaat aggtttaaat ccttgagttt atagtgatca taacaataaa aaaacctcat   36660
tggtcatggt ggatgctagg atccatcttt gaggatgaac ttgccatgcc atcccaatga   36720
gtgtagtcat tataatggcc accagggatt cgtaccctca agctccacct caacttcaga   36780
ggagttgagg tcctacattt ccaaggcagc ccacagcctg tgacagcaca gctgaagttt   36840
ggccactttt gcccaaggca ggactcctaa tgggcaatct ttttcccaag tcctcaccct   36900
aggtaagcaa aaatcttgtg acatctgatc atggtctgag gctctccctt ccccaacctg   36960
cctcatcccc tttacgggta tcagagtgat ggccatccca gtctgaaggt tattcttgcc   37020
catgagaaac tataggccaa actagtttgt tcaaaacata aattgaaagg aaaaaaaagg   37080
aagaagaatc tgtggatgag aaaatttaaa aggcatagcc atcagctata atatggacct   37140
catttcaagg ttgacatatt taaaaaatag agaaaatatc aggaaaatct ggacactaac   37200
tggatatgta aaactataaa gattattta aatttgaaga gtagtaatat gattttttag    37260
aaaatcttta tctcctagag atacatgctg agatgcttac agatgaaatt atatgatgcc   37320
taggaattac ttcaatcatt ccaggggaag aagggatgtg ggtagagtat agatgaaata   37380
agactggcca taaattgaaa actgtttaaa ctcagtaatg ggtcacatag agcttcaccc   37440
ctcttagggt tgaacatgag gacttattac ataattattc ctacatttgg gtatgtttgg   37500
tggtttccat aaaaaaaatt agatttaaaa aaacttgtta aaaactccaa tttatcactc   37560
ccattttctt catttgttca gaaactggaa gtggccagag aaatggaata agctgttgat   37620
gatggaactg tcttaaaagc ctgaaagaag tcagataatg ttgtttcaaa ggtttttatt   37680
attttggttc agaccatgat gctttactac caccaactca gatgtcagat agactcttgc   37740
ttgcttaact ggggaagcaa cataaccaaa tggggacagt gcaggctctg gagtcagact   37800
gcctagcttt gaacccccagc aactgaaatt actggtatga ccttgggcaa gttatttaac   37860
acctctgggc cctagggata aaaattctat ctagactaca tagtttcttt gctaaggtta   37920
aacaagataa gatacttagc acagaacctg gcagagtaaa caaatctaag tgttcactat   37980
tttcagtcaa gcactgggca ctgctgtgta gcagcagtgg tagttccag aacactgttt    38040
ctaatgaaaa tctaggaatg tacatgggaa ttccctgatg ccagctggta cattatttta   38100
gacttaccct taggcttaac ataagttcat aacaccatgc caatgacaaa aacaaaaacg   38160
ctcaccaatg gtaactattt ttggtgccta taccttcctg attgcctgtc tacctctgaa   38220
ttcagtcacc cattacacta agtttcctca tattctggtt tgcatgccaa aagtttgcaa   38280
```

-continued

```
atggtttaat gtccttcaac ttcatgcctc tctctccttt gtgtttctcc tcctagctta    38340
taccaatttt ggccaacaca agagcattta gagtcatggc tgagagttcc ttcctgttgc    38400
tcaccacacc cacgtacaca tgtagacaca cacaatcaaa actcacctgc tcagcatata    38460 ctaccccgt cattggcata gtgcttctaa aacttgggta ggaatacggt cagaagtctg     38520
tgtttaggat tttaatgatg cttgtagact tgtcaatgtc tgaaatgtaa tctaataacc    38580
caatcaagtg gcaggctagg tgggataaca agtgatatgg ttatgatcag tattctagtg    38640
ctgagattac acaactgcaa tgaatttatc tactacatcc ctgaccattt caacaaggac    38700
ggtccatttt ctcaaattac agagggtaca aaaacatcca gtctaggcaa tagcatcttc    38760
ctgcataccc aattgctctg ttctctatat ccattgccct ggttctctat tcctttagct    38820
ttgccatgtt tggatttctg caattcactt cagaacttcc tactttggac aaccccatct    38880
ggattgccct ctctggttta atgaccttgg tccagtctat ctgattctca atttgtgtgt    38940
cccttggctt caatgaaccc actcctaggg gaatagttct gtgccagttc cagccccaga    39000 gggcccatc cgggatgcag gaaagagaga gaggaagggt ccacaaaagt agatcagttt     39060
taaaaagtgt ttgccttcag atgctgccat gtggacatag catatttagg aataacatta    39120
gtctccagac gttcacaggg tcagagtaca cagactaaga gagttaccat ttcaaatcta    39180
tgtactattc ttgtagtaag aaacagattg aatttgccaa atttcagttc aaacaatgta    39240
tcacaatgac catgaaaaat acaatgattt ctatagacaa gacttcaact ttactagtaa    39300
ccaactaatc tacacataat aaaaatattt tttgtacaca caaatatgt taatatatgt     39360 gtgtatatat gtatatatgt gtatgcatat atatatatat atatatatat atatatatat    39420
atatatatac atatatatac acatatttt tccctgaga tggggtcttg ctatgttgcc      39480
caggctggcc tcgaactcct gggctcaagc aatcctccca tctcagcctc ccaaagtact    39540
aggattacag gtatgagcta ccgtggccag cccacgaaat atgttaaagg actctgccac    39600
tttgaaatct ctaaactcag ttgctttatc tttaaatagg cagctcaaat tgcataacca    39660
tatcagttct acattcaggt tcattttca aaagctatat cttccttct atgtagaaac      39720 aaagactaaa atgaaaactt gggaagaaag taaacaaaca ttttcaactc tccatgtgtc    39780
agagctgtgt tgtacaatgc agttgccact tgctacatgc agttattgaa ttcaaattaa    39840
taaaaattaa atataattaa aaattcagtt tctcagtcac actagccatg tttctgttca    39900
atagccacat gtagctggtg gtaactgtat tgaacacttc agatatagtg cactcccatc    39960
atttcaggaa gtctaactgg acagccctgc tttagaaaat tcactctaca tttgtttct     40020 gtgagaccca acctacccta acaaaaagct aaaacttttg aggctatttt tatgataaat    40080
tagtagacct gtcaaaacat tttaaaactt tataagcaga tagtatttgc agttactatg    40140
gaaatttgag tctttgcata catcttaaaa atttcctcaa atttgacagc ttagaaacag    40200
aactaaattt ttttctaaag aggcttttt cttaacgtgt agactgatga atcaaagcat     40260
catgttttac tgagtaatta gtccttcaat aattcacatg agtaataggt catattgggg    40320
tttaacccct gcttccatta tttctgacca cacagtctac caacagatgt ctcacttggg   40380
gtgtacacaa cagaacaccc ggtatccatt tcacgtacat ctgttcccaa acagcttaga    40440
cagattaata cttagaatat actttgctct actaagtctc acgtaatcac caactcttgt    40500
tttgaaattg ttttttctca ttttcatatt tttgcacatt atctttaaa ctgctaagtg     40560 tcaagtaaat acttacataa acttaaagct caagaaaatc attttgactc tcttgtaaca    40620
ataagaaaca ctttccagac cttattttga agctcagcct tctcagattt tctagtcact    40680
```

```
gctctaattc agctgagctc tgagttgtgg caggaatact cttttgaaaa aaacataaca   40740
tgaaatttgt aacttgagat agtaagtata tgaaaaatag agttataagc cataattatg   40800
attcaaaggc ctagttttat ttttttttaaa atctttgaaa catactattt gaatgctaat   40860
caagcattgt ataaaatctt tactcagaaa tttgatagag gatacagaga aacgaatgaa   40920
gaatggatga gctagtcctt ttgtccatca tgaaatagct gcttaaagct agcctcaacc   40980
aattcttttc ctccagaaaa tggtttcttc cttttccaatg acaataccta caccaaagcg   41040
attgcccacc tctagtcact gtgccctaaa gctgagtaag gcgagcaaag ggctttgact   41100
tatatttccc aggtggttcc tctaattaga aattcatgag ggctctgaag ttcctgatgt   41160
aaaatacaac acccctccac acacaccaga cagtgggccc cattgaccat caaaccttac   41220
tgagatttat ttaatttgac aaaattccct aatgcctaaa ggccatagaa ataggtattt   41280
tctttaaaat gaaagttcat aggtggtcag aactgatagt acttagagac aatataatat   41340
aagcccttca ttttgccagt gaataaacag taactcagac atgttaaaca acctgtccaa   41400
agtctgttat gcaccttgct atctgttgag acaagatctt agggccttca gcggccactg   41460
ctgaaatctt tcctacacca cagatgggag cagattatag agagctggag gagggaagct   41520
ataaaagatc ctgtagtgct tttcatactt caaggtgtta tccattagga aattgtgaag   41580
ttaatttcac aaatcataat gagcatttgt ttgcaatgga aacagagcat atcagagtga   41640
ctcttaaatg gcaatggtaa gaattgtttt gtgaaacttt tgttttagac aaatcacata   41700
tcagcacaga aatctgtata gtatctgtca atccctaaag ggccgtcatt tcagaggact   41760
gaggaaaagt ggaggagaca catgtttcca acatgagata gcactgtgag catttggcat   41820
ctctgtcaca gagatcccta aattgatcac tcttaaacat actaatatat gagcttaaca   41880
ttgcctaatc ttacccatta cttactctcc ccatcagctt ttcctttacg ggaaataatg   41940
acattatatt tattcacaca ggacagtaaa caaatctttc tttggggagg cacaaaaaaa   42000
tgcctgactc ttctgcttta atcgaacatt tcaaataaaa gcttacccct tgttaaacag   42060
atgtcccaaa agttttttcct tggttgagat gtaaaacaat gccaacaggt gatcagcgat   42120
gcttttgaaa atactgaact ctgaaaatat ctgatccagt atcagcacaa gctaagggct   42180
aaatcatgaa atacgcaaat aagtctgtgg catctgtcca tgtcccctttt ctgaggtgta   42240 ttcttaattt ttgacttctc acacccagtc cctggcacca tactgggggt tggccccact   42300
gggcacagca cttgacctgc tctgccttgg cagggtccca tgacccagag tggtctgacc   42360
tttcacactt gacttcaaaa acagtcacct gatcccttca tcatttcttc aggatttttc   42420
tcataggtca cagctagctt gataattacc ttatttaac ataaataaac ccatgtatga   42480
ttctataatt aaaatgacca taatttaaga ttgtaataga aagatcatca ggcaccactg   42540
tagtcaatga aaaagatatt ttctgaattg atgatgctct ttcgtaaaca cagtttatat   42600
tataatggca gcatcctaat ctatttaagc cctgctcagt attttctact ctgcagctga   42660
gcaacatgga accttcctgc catgaacctc acatcagaga agtggatgaa ccttaactct   42720
tacgatagaa atcctggaat aacgcaaagt tgaaagaac ctcaaggagc ttaacatata   42780 atggggggaaa aaaacaatca aagttgcatt caatgtctca gtataggaga tccaattatg   42840
cctaaagaga aaacaactgt aatgaatctt cattaatttt aatgaatgta aacatgaatc   42900
attcaaataa aaaaagcac aaaggaagct aattcccagc agctggaaca gcaagaaagc   42960
ttgtgtagag aactagtttt gtaattcttt caattacagg atggtaaaat atgaggaaac   43020
tactgagaaa tgaggatgca gagataggca ggagccaagc atggaaatct tatgccatgt   43080
```

```
tgaagagtgt gtctctcatc ctgttttcta cttcagtggg ctttaaacaa gacagtcaca   43140
ttcctgctag gcaaagaggg aacccaaaca gacagactca ggatcattta cccaccactc   43200
caatcaaggc acccatactt ttatgtgtta tatactggcg attcatttaa gaatttttt    43260 taaaaaagag ttttgatgtt taaaaagggg gagaggggaa tactgccttt gtagttaatg   43320
aggagttggt atcaagtata taggaatgta gtcaccaagt tataatagaa taggcaaaac   43380
taaagttcat gaggccagta aaccagtaac aaattcattc attcaataaa tattatctat   43440
atgccaggca ctcttcaagg tgctgacagt aaagaaaaaa catattctga atatcttccc   43500
tctcctccat ctagatttag tttctatcct ccacctgccc tgttcactgg gaggccatac   43560
tgcatggact gcatcaagtg ctccccttgc cctctggctt aaagttggct ttggactgtg   43620
aaatgggcca gaaaagaagg aacttgggta atttaggatt agtgaggatt agtgaggtaa   43680
tcagccaagc tgaggcaaag gccacagctc ctgcctagtg gcctcctcta catagtctct   43740
ctgaatccag gttcaggcac ctgctctttc actatgccct tttgggctta aaaatggtat   43800
cacctgccca atgattacta gtcccaagag tacttcacta tctctatatc tacagcttta   43860
taaatactga cttttaaaaa ttcttctcaa gttactctaa tataaatgtg ccatttttt    43920 tcctattagg acagtcacta atataacaga caaatccttg ccatcttgaa gtggggtggt   43980
aatagaaagg acagagatca gaaattatat agtatacaag gagataaatg ccactgagga   44040
atataaggca atacagggaa ccaggaagta tgtagcagat gggaattta tacaggtgac    44100 cagagaaagc cttactaaga agctaacatt tgtgcacagg ttcaaaggag gtgaaggagt   44160
aggtcaagtg agagactttg aaggcctgag ctagggtagt gattggtcgg acagagaagg   44220
atggcagatt ggagaaatac caagtaaata agtaggcag gattggtggg tgtttagaaa    44280
tagtgagtaa gggacagtga ggctagagtt accttcagaa tcctgactta gataacattc   44340
cagatagctt cctaaatact ccttcactta ttaagccaaa atattcacta cttacatatg   44400
caattgtatt atctaaccca cataagctac aagctaattc tagttatcct agttattgtc   44460
ccataactta cacaaaccta aatagcaaag ttaaacattc tgacagctga tgctgaataa   44520
ttagtgagtt ccataaccat gatagggaac aaaagatcag agttagtcta cggagcaagg   44580
aaagttgctt ttcttgtaaa cttactaaat atatggcact tctggaggta gatgatggta   44640
gatgagaacc acagtgtgca atactgacca gaaagcatgt aatgaggaac agcagatcag   44700
accacagtcc ttgggactcc accatttggc aggcagatag aatgaagttc ccatgagaga   44760
ctgataaact aggtgctggt ggtattacaa aaaccaagag agttaagtca aagtcaaatg   44820
aaggagaaat acagaaaata aggactgaaa atttccactt cattgagcaa ttagaagact   44880
tctgctaatc tctgcctgaa gagtttcagt agagaaagaa caaagccagg tctcagatgg   44940
ttgaagaata attaagaggt gaactaatgg agatggtcag agtaagccaa ttttctagg    45000 agattatcag agcaagtgag aaaaaaataa aaataaaaag caaggtagca gctaaagaga   45060
aaagcttgta ggatcaaggc agggaactgt tagaatggga gagtcttgaa catatctctg   45120
cttaagtgaa agagctggta gagaatgaag gctaaaaacc aaagaaagaa agtgtaacag   45180
atgaaacaaa tttctagatg aagctgaaga gatgggatgg gtttgccttc aatagagatg   45240
actacatcta ttctgtggtc atgaatggaa gcgaatgaag gctgaaggtc actaaaatgg   45300
aaaaggtcta gaaagtctga agctgtaata atgattgcaa tatgaccacc accactggct   45360
agactttaga taaagaacac tgtgagccag acaacaaagt tttaaataaa catagaagaa   45420
aagctggaaa atcatacttt ctcttccctg gggagcccaa aagacagctt gtcagccctc   45480
```

```
cgagcctgca agtgtccagc ctgacaacta gcatgacatg cctgtcccta gcaaaactat   45540
accaccatca aaaactcctg cagcctaggc cactgaggaa atcagacatt gctgtgaaga   45600
ttacagctga cgaaactaca cagagaccat ggtactgaat ccaccccaaa ccaaagccaa   45660
tgtaccatac ccaaccaaca ctctaggacc catctacagg aaaagtctct ccctgtgaaa   45720
gctactgcat acaactggaa aatgtgacta ttccactaga tgtgcagatg tcacaagaaa   45780
catgaaaaag caaggacaca cgacactgcc aaaggaacac agtgagtctc tagtaacaga   45840
ccccaaagaa aagggtgttt ataaaatgcc tgaaacaaaa ttaaaaataa tgatcttaaa   45900
aaaattcagc aggctacaag agaatacaaa caacccaatg aaatcaggaa agttataaaa   45960
tgagaaatta aaacaagatc tatcatttaa aacacagaaa tctgaagaat gcagtgaata   46020
aaagacacaa tcgagagctt caagaataga ccagatcaag cagaagaaag aatttcaaaa   46080
tctgaaaata ggttttgtga ataacccaa agtttaaaaa aaactaagca aagaaatttt    46140
tgcattatag aactggcaga tggagaaaag ttgaagaaag gcacagaaaa cctatttaat   46200 gaataatag ctaaaaactt cccaaatatt ggggagata tagacatcca gatgaaggaa     46260
ccacaaagat tcccaattag attaaaccca aaaagattct ctctgtggca cattatagtc   46320
aaactgtcaa aagttgaaga cagagaattc taaaatctgc aagagaaaag catcaagtta   46380
catgtaaggg aatcctaatt agactatcag tagatttctc atcagtaaca ttaaattact   46440
gatgtatgcc aggagagaaa gggataattt attcaagatg ctaaaagaac aaaaaaaaac   46500
gagtctcggc caaggacaaa agatactata tccagcaaaa ctatcctgga ggagaataaa   46560
ggccttccca gacaaacaaa agctgaggga attcactcct acaccagcct acaagcaat    46620 gtttacagga gtgctacagc tgtaaatgaa aaaatgataa ctatcatgaa cacatgtgag   46680
aatataaacc tcaccaatag aggtaaatgt ataaatccaa ctcagaattc cccagtgata   46740
tcatgttact atgtaaacct gtcgatcctc tagatgaagg tttaaagtac aactggtcaa   46800
aaacaacaac agctacaatg gctagggaac acatactaaa gaaataaagg caacaaaaat   46860
ataaattagg gatggcggag gaaaaaagtc tagagtattt ttatgtgacc aaagttaact   46920
tgctatcagc ttaaaatagt ttattataac tacaagactt tttatgttag ccccatggta   46980
cccacaaaga aagcaattac aacagataca taaacaagag atagaaggaa aacaaagctt   47040
aggaccacag aaaatgacca aaccacagag gtaaacaaga gagaaagaag aactgagaat   47100
ctacaagaca accagaaaac aagtaacaaa atgggagaaa taagttctta tcaataaaaa   47160
ccttgaatgt aaataaatta tctaatgaaa agatataaag tagctgcagg actggaaaaa   47220
aaactcagct acatgctgcc taaaagaggc ttacctcacc gttaaagaca gactgaaagt   47280
gaagaaatgg aaaaagatat tccatgcaat cagaatccaa aagtgagcag gagtagcaat   47340
actcatatca gacaaaatag acttaagtc aaaaactgta aaaagagaca agaaggtca    47400 taatatgata aagggatcaa ttcaacaaca ggatataaca attataaaca tacatgtacc   47460 taataccaa gtacccagat acatacagca aatattcaac ctaaagagat aaactccaat    47520
acaataatag taagagactt taacagccca ctttcaataa tgaataaatt atctagacat   47580
acatacacaa acacacacag agagatcaag aaatattgga cttaagctga accatagacc   47640
aaatgcacct agcagacact tacagaacat tccgtccaac agctgcagat acacattctt   47700
ctcaaatgca catggaacat tcttgaggag agatcacatg ttaggccaca aaacaagtct   47760
taacaaattt taaaagatta agataatatc aagtatcttt actgaccaca gcgttataat   47820
actagaaatc aggccaggtg cagtggctca tggctgtaat cccagcactt tgggaagcca   47880
```

```
aggtgggcag gttgcttgag cccagcaatt tgagaacagc ctgggcaaca tggcaaaacg   47940
gcgaaagcca tctctactaa acatacaaaa caaaacaaac aaaaacaaaa aacaaattta   48000
accaggcaca gtgacacaca cctgtaggca cagtgacaca cacctgtagt cccagctact   48060
tgggaggctg aggtgagagg attgcttgag cccaggaggc agagattgca gtaagccaag   48120
atcgtgcctc tgcacttggg cctgggagac aaagcaatac agaagggagg gagggaggga   48180
gggagggagg gagggaggaa ggaaggaagg aaggaaggaa ggaaggaagg aaggaaggaa   48240
ggaaggaaag aaggaaggag aaagaaaaga aataaactag aaatcaacaa tgagaaaaac   48300
tgacaacttc acaaatcatg gagacaaaat gctcctaaac aaccaatggg tcagtgaaga   48360
aattaaaaag gaaattaaaa tttttcttga dacaagtgag aatgaaaata taccataaca   48420
aaacctacga aacatagcac aagcagtttt aagaggtaag tttatagtat taaatgccca   48480
tatcaaaaaa dacaacagat ttctgacaaa cagcctaatg atgaacctca aggcactaca   48540
aaattaagaa caaactaatc ggccaggcat tgtggctcat gcctgtaatc ccagcacttt   48600
gggaggccac ggcaggcaga cacctgaggt cgggagttc gagaccagcc tgaccaacat   48660
ggagaaaccc cgtctctact aaaaatacaa aattagctag gtgtggtggc acatgcctat   48720
aatcccagct actcaggaag gctgaggcag tagaattgct tgaacccagg aggcagaggt   48780
tgcggtgagc cgagatcaca ccattgcact ccagcctggg caacaagagc gaaactccat   48840
ctcaaaaaaa aagaaagaaa gaaaaaaaag aacagaacaa actaatccca aagttggtag   48900
aagtaaggaa gtaattcaac tcagaggaga aataaatgaa atagagacta aaaataattt   48960
caaaagatga acaaaattta gagttggttt tcaacaagtt tcatcaaatt tgataacata   49020
gaaaaaacga agtccccgac acatacaacc tatcaagatt aagttaggaa gacataaaat   49080
ctgaccagac caataataag tgaggaaatt gaatcagtaa taaagtcttt catcaaagaa   49140
aggcccagaa acgaatggct tcactgctga actcaaccaa acatttaaca aaccaatatc   49200
aattcctctc aaaatatttc agaaaactga agcaaaggga atacttccaa actcatttca   49260
tgagtcaagc atcacccctaa ttccaaaatc agataacaat acaacacagg aaactatagt   49320
acaatatccc tgatgaacat aggtgcaaaa attctcaaga tattagcaaa ccaaatccaa   49380
cagcacatta gaaagataac ttgctacatt caagtgcgat tcatcactgg gatcagaggc   49440
atgcaagaat ggtttaacat acacaaagca gtaaatgtga tacacattaa caaagacaaa   49500
aactgtatga tcattttaat agatgcatta aaagcctttg acaaaatgtg gcataatttc   49560
atgattaaaa acccaacaaa ttaggtatgg aaagtttgta cttcaacaca aaggccacat   49620
atgacaaatc cacagctaac atcatactga atgggaaaag accaataacg agatcaattc   49680
taagatcaat aacaaggaaa ggatggccac ttacacaatt tctattcaac atactactga   49740
aagttctagc cagataaact gggcaagaga aagaagtaac gagcatccaa attagaaaga   49800
agcatgtcaa actgtccctg tttgcagaag atatgatctt atagatagaa acccaaaat   49860
gctccacaaa agaactgtta gaattcagta aagttgcaag acacaaaatc aacatataaa   49920
aatcagtagc atttctatac actaatattg tactatgtga aaaatcaaga aaacaattcc   49980
atttatagta cttttttaaa aaaaagata cctagaaata aacaaccaag gaagtgaaag   50040
aatctctaca ctgaaaagta taaaactttg atgaaagaaa ttatcttccc acatcaataa   50100
atgggaagat agtacatgtt catggattga aataattata ttgttaaaat ggccatacta   50160
cccaaagtga tctatggatt taatgcaatt gctatcagaa taccaacacc attctttaca   50220
gaaatgttac aatctgaaaa ttcatgcaga accacaaaaa aaaccccaaa tagccaaagc   50280
```

```
aaccctgagc aaaaagaaca aaactggaag tatcatacta cctgacttcg aaatatacga   50340
taaaactata tcaacacagc atggtactag cataaaacca gacagaccca tgaaataaaa   50400
tggaaagccc agaaataaat ttttgcacct acaacagcca actgaattt taagatgtca    50460 agaacatgca ctgggaaaaa gacagtctct tcaacaaatg gtactaggaa aatcagatat   50520
tcacatgcag aagaatgaga ttaaaccct ccctctcacc atatacaaaa ataaaaatag    50580
attaaagatt taaaatgtaa aacttgaaaa ctatgaaatt acaagaaaaa agggaaatta   50640
ttctcgacac tgacctgagc aaggattttt aaaataagac ctcaaaagca tagacaaaat   50700
aagattacat caaactaaaa aactttgcac cttgaagaaa actattaaca aagtgaaaac   50760
agctgcagaa tgggagaaaa atatttgcaa tctatacatg cgacaaaggg ataaaatcca   50820
aaatatataa gaaaattaat tcaacagata aaataataat gacttttttt ttttttgag    50880 atgaagtctc actctgttac caggctggag tgcagtggca ctatctcggc tcactgcaat   50940
ctccacctcc tgggttcaag caattctcct gcctcagcct cccaagtagc tgtgactaca   51000
ggcatgtgcc accacacccg gctaattttt gtattttag tacagacggg gtttcatcat     51060
gttggctagg atggtctcga tcttctgacc tcgtgatctg cccgcctcgg cctcccaaag   51120
tgctgggatt acaggcgtga gccactgtgc ctggccaact tgatttttta aatgggcaaa    51180
cgactttaat tgataggtct caaaagaaga catataaatg atcaacaggt gcatttaaaa   51240
gatacttgac atcactaatc atcagggaaa tgcaaatcaa aaccacaatt agatacacct   51300
cactccagtt agaatggcta ttgccaaaaa gacaaaagaa aataagtact gacacagata   51360
tggagaaaag ggaacactta cacccggtg gtatgattgt aaactagtac agtcaatatg     51420
gaaaacagca tggaagttcc taaaacaatt aaaaatagaa gtatcatatg atccagcaat   51480
cccactacca ggtatgcatc caaggaaat aaaatgagta tgttgaagag atctgcaatc     51540
ccatatttac tgcagcacta ttcacaatgg ccaagatatg gaatcaacct aagcgtacaa   51600
caatggatga ataaagaaaa tgtgatacag aaacataatg gaatactagt cagccattaa   51660
aaaataaagt cctgtcaatt gtgaatgcta agcctggagg acatcgtgtt aagagaagta   51720
acccagacac agaaagacaa ataccacatg tcactcacat gtagaatctt tttctattat   51780
aaaaggttga tatagataag gcagagatta gaatagttac cagagactgg aaggggagg     51840 ggagaaggaa ggatggagag aggttagtca aaagacacaa agttacaact aggtaggaag   51900
aataaattct ggtgttttgt tgcatagtat ggtgactatg gttaacagta aaatactata   51960
tattacaaaa taactagaag agagtctttt gaatgttcta acccacaagg aaataatgaa   52020
agtgtgaggt gaaggataac taactacttt gattggataa ttgtacaacg taaatatcaa   52080
aacatcaaat agtatctcat aaatatatac aattacaatg tgtcaattaa atttttttaa   52140
acaattaaaa agttattaga ccagctgttg gatctggttg agttaatgtg cttaagaagc   52200
acatgcataa ctttatatca cacatttaaa atatttctct acttaaaaaa aaaaaaaatc   52260
cccaaaaagc gctgatactt tgtgcctccc aaattgactt atagcctctt ttcgaaagcc   52320
tcacttctac agggaagggt aataacacat ccattattcc aggtcatccc tgaacccaat   52380
aaaaagaact acaattacta cggttatgct catttaccct gccaacaaga ccatcaattt   52440
gtcccaattt tggcagtcag agccttcata aaatacatta atgtctttgc ttattactca   52500
agatggaaaa ttagaaaaag atcacatagt attttatttc atcagtgaaa acaaagtact   52560
atgaggttta aaaactaagc aatcttgaaa acatacgtat gttctaataa tctccagtga   52620
tctcccctac ccaccctcat ccttttctga ggcagccagt cacttgccaa ccagcaatgg   52680
```

```
acatgctctc ccccccaccac atcctaccat atcatgtcct cccaagtaca gtaactttga   52740
tgtagctccc tcttccattt aatcttttac cactcacatc taagcttatt caacaacaga   52800
gcatttctaa catttaaata tatcatctct taatatctcc ttcttatttc ccagtgtttg   52860
tttttgtttg tttgttgtgc ttttttgagat ggagattcac tcttgttgcc caggctggag   52920
tgcagtggtg tgatctccgc tcacagcaac ctccaactcc caggttcaag caattcacct   52980
gcctcagcct cccaagtagc tgggattaca gggacacacc acgcctggct atattttacc   53040
taaataaaac atctcttggt ttcttccata aacagaagta cttactaagg ctctaggctt   53100 ctgtgcccc aattttagag gcccaaagtg gtttgaatac caggtattaa ttacaaagaa   53160
aaagggtaca cctgtatgaa ggaaaagacc accaaatggt tttagggcat aattaaacaa   53220
agaatcagta cttgcaacct ttaaagttac aaatctgtca agatgtattt taaactctac   53280
tgccaggggt gcactaatta aacctatttt accttaatca ccactcaata taaaacagca   53340
tttcttttct catgtcattg tttgctttt ttgtacacaa atactgcaac attggtttgt   53400
atgacctctc attgcacaat gtctcatttt aattctatag catttcagct gcactgtagg   53460
ttaaactggc tctttgggct aatccaaact gtaattataa acttctatat tgcataactc   53520
gaattgcctg aaagacttac aaataattcc atagctatat ccctagcttt taacttaaaa   53580
ggttcaagaa aatactacac cttggttttt aaaacacctg aaaacacttt aaggtcaaag   53640
actgttttcg tgaagcgagc gagcatggca catgcagcac aggcagaatt cacaatcgca   53700
accagtgctg aatccctggc tagttggttt catttttgtta gacttttgag caagacttta   53760
agacagtgag tctattctgt aacataaata ccacactgtg tcttgttttc caacagggga   53820
aggcaatttt tttaatttca taaatttgta tttagctaaa agaggttgaa taccaaattc   53880 catctcccc aagtcatctc ctcgcaagta gagtaacctt gatgtagttc ctcccccatt   53940
tcatctgtct ttcaccgctc acatctaagc taattcaaca atggggagta tttctcgagt   54000
ttggacttag aaataagact atatgaaagt ctacttataa gacttgcaaa atggtcttta   54060
taaaatatct gttaagtcta taaggctatt tgactaagac gtgaaaatag actcgaagta   54120
tttgttgtaa actacagcat tataactttt ttaggtaact aaaattttaa gtcaataaaa   54180
ggcaaacgtt aagcaaaccg cttgacgtaa ctaagcatcg caaaactgtg atccaataat   54240
ctagggtcaa tattaaaaat caaaagtttc tagaccgagc ctgaagaagt cttaattcta   54300
gacaatggca aggaaggtga ggggcagaaa aaaacccaga aacactccca aagctctgga   54360
gttacatttt caagtcagca aaatgagagt tggattcaga actcttgtgt aggcataatc   54420
tgtgagatgt ttatagtttc aatgtaccat caaagttaat ggattaaaac ttttcaact   54480 tggaggggag gagtagttga ccttctcaca tttgtaaatt acctcccctt tgggctcaa   54540 gattttctgc tgagactctg agcaaaagct gcttgtgacg tttgcccggg gaaggtctcg   54600
gaggcgggaa aaggctaggt agcgaaagaa tccctggggg ttctgggatg gggcgagagg   54660
cgtgagttcc cagttgggaa ggaggaggcg gcgacttggg gactcggtaa cctgtccggg   54720
cagtgaggcg agcacgggga ggggaggcga gaaaggggga gggtggagca aaagctcgtg   54780
ggtgtaggcc ttgggccggg gagagggagg aagcgcggag ggaggcgaag acgcttgggg   54840
ccgggcactc acccgccggg cgctcgggct gaatgggccg ccaccgcagt gctcgctcgc   54900
tcagcaccac gtcacaactg tccctcccga tctcgaagat gccccggagc agaatccgct   54960
cggccgccgc ctccgtctgc tgcggggacg ttaacagcgc cggaggcaca gcggcagcct   55020
ccgggggcgc ctcttcctcc cggccgccct ccagggcact cacccggttc ctgcgcctcc   55080
```

```
tccagggcat ggcggagtcg caggctgggc ccgagccagg ggtccgggga ggcctttgga   55140
gaaggaggtg gagggcgcgg cagccccagc tctagccgcg tccagcgctg ccacagcaac   55200
ggcgcgcagg gcagggaccc aggagggagg cggggccgcg cctgacccag tccagcaccc   55260
tggcctgcca gcctcgccgc ttcgccactc accacaaaaa gacccagctg caagaggaag   55320
aataagtggc tccctccgcc tagcttctcc tgtaaagtac gatttcgtac ttttcgttac   55380
cctcgagtta aaccagccct cctcaatctt aaacttgcat ataatcgctt gggcatcttg   55440
ttcaaatgga gattcttatt gcataggtgt gggactggcc cccagatacc acatatctaa   55500
gaaaatacta ggtgatggat cccactggcc aaggaacaca cttagagttg caagggtgga   55560
agcctctgtt tttccacctc ctttccagag ggttccctgg agagcacagg tgacgcttta   55620
caaccctgtt tcagagtagt agcgcacttc ccaaaacccc tgaggggaag ctagagataa   55680
ggccctggtt tgcatagaca aatttgcatc tgacaaattc agtattaaag gtaagtgcct   55740
ccaggtgtaa gtatttaggg tcctactttc ccccaaggta gcgcctctgc agtcttgtct   55800
ttgcctggat cttgcactcc cttgagggag attacaagca gcagggcttc actttcacgc   55860
actgccataa agaagtgtca cctggaaaag gagaagagcc ctgggggggt tcacccttt   55920
ctcctgataa ctgagatttc taaaatcagc tgctcattaa ttttgataac acagagagtc   55980
tggaggctag tgattctcaa ttgtggttgc acattaaagt tacatagggga acttttgaaa   56040
acccaaatgt ccaggccacg ctcaagacaa ctaagctgga atctctggag gcgagaccca   56100
gacttccgga tttttaaaag ttcccaggta attccaatgt tcagccaagg ctgataatgg   56160
ctgctctaag cagggtgata aaacagggag ctgagtactt gtaatgggga agcagtcagg   56220
aagaaagtga gtccctggga agaggagcag agtgggaagt aaagcagaag cttttttttt   56280
tttttaaaca agatcattat catcatattg aaaagaagga gtagggagt tgaaaaggaa   56340
attaaattca tagggttgta gatctagttc cagtgttcta gtgcctaaac agttctatca   56400
tagaggcagc aaattcttaa ttctgtcctc attcctggtc acactgcaga gtcacagaaa   56460
gagctaacta tagcaggagt ttctcaaggt tcttagctca gacggtttgt aggcctaacc   56520
aaatccctac caaacataaa gcactgtgca ccagttaagc taggactctt actgtttaat   56580
gctccgacaa taagtaccca agcttcgagg aaaagcaagg aagagcttca gtttgatctg   56640
actgcagtga gctatttctt agagcagaag tgcagctgct gctaaacccc atgcaggctt   56700
caggtggctc tgttcagcag tcattagagg gaaaaggacg gtgcccttcg cagaatgagt   56760
tgcagttctg gagtcagcat cttgtattca cagctgttag gcaatcaaca caattagagc   56820
tcactggcat tttaaaagct cacccagagc cagtgcaaac aggccaagcc aatggctact   56880
ccttaggagc tttgcaaagg ggcaagttgc cattttttcaa gcttcactca agccaggaag   56940
tcaaaaacac tggctttgaa ttgtcctgaa gatggaagta ataaggattg tgtttccttc   57000
tttctttctt tttcctttga taagctgcct tcttccaggg ctggagtgcc ctagggctct   57060
ctttaggatc tatccacaca ctgtcccgtg ctttatgtac catccagggt tctgcaaatg   57120
atgtcaccag ctccaaccac tctcctgaac tttaggtatt atgtccagct ccctacctga   57180
catctctact tggctgtcca ataagcttct aaaacatatc taaaaccaga ctcatgattt   57240
tccatcacaa acctgtccct ctcagaatgt ttcaaatctg tagtatcaaa atccttgata   57300
tcatccatgt ctcctttgtc tcatgccttc aatccaatct accagcaaat cctgtccatt   57360
ctgtctagaa catatagtcc tttctgcctg ctgtcattgc agtctgcact tctgcacccc   57420
tcagctggac aacttcagtc tccgctctcc caacccagct ctctgctttc ggtttcccct   57480
```

```
gtgctggcac ctccagccca gagccaatttt tccattttgg agttacattg tgcctttaaa    57540
aaataacgag agcatataac cctgctcaca gccttccatt gacttcccat tattcttgga    57600
ataaagtcaa aatgcttagc aaggcgagag gtcctttata atctggaccc tggctatgtc    57660
tccgagatca cctactaact ttttcccctt gctcattcac acaaagcctt cttgccagtc    57720
ctcaaacaca ttgagaagaa taatcccttc tcagagcatt cgcttttgct gttccctctg    57780
actggaatgc ttttctcccc accagatggt tcattctttc actttgctca tttttctgtt    57840
taaaggccac cacctcaaag aggccattcc tgagcaccct ccataattca ccatcctgta    57900
aacctgtgta ttcatttctt actgctgctg tatctaatta ccacaaattt agtgacttga    57960
aacaaaacca atgcattgtt ttacatttct ggaggtcaga atccaaaat cagtttcaca    58020 ggactaaaat caaggtgcca gcaggcctat atattccttc tgtaggctct agaggaaaat    58080
atatctcctc ttttctggct tctagagcag cagtccccaa cctttttggc accagggact    58140
ggttttgtgg aagacagttt ttccacggat gggggcagtt tgaaggggtg agcattttgg    58200
aggcattaga ttctcataag gagcacaaac tagatcccctt gcatgtgcag ttcacagtag    58260
gattcaggct gctatgagaa tctgatgctg ccactgacct gacaggagac agggctcagg    58320
tggtaaaact tgcttgtcca ccagtcacca ctcaccgcct gctgggcagc ctggttccaa    58380
acaggccaca gacaggtact ggtccatggc ccagagactg ggacccctt ttctaaaggt    58440 cacctgtgga ttttgttttg ttctgttttg tttgttttgg ctcatgttca cttttttccaa    58500 cttcaaagcc agcagtctaa catctctcct ctttgcttct atccttaaat cgtctctttt    58560
cctctgtctt tgacctttgt cccccgtctt agataaggac tcttatgatt acattgggcc    58620
tgcccagata acccttaatt atgttttcaa agcctctttt gctatgtaag gtaacatatt    58680
cacaggttct ggggattgaa acatggacat cttcacgctg ccattaatct ctctaccata    58740
acctgcttta gtattcttta cagcacttac tattaattct tattacatac ttctttgttt    58800
attgtctagc ttccccacta agttagtgta cttagtaaca atactgaaat acagagaaca    58860
ctcagtaaat tttaagtttg ttagaatata agccccctga tggcagagaa tttatcttgt    58920
tcaccattaa atccccagta tctatcacag ttcttagtac acagtaagtg ctcaattaat    58980
atctgaaaga atgaacttct tcaacattta tctataacaa taataccaag ataccccaat    59040
tatttcacgt tagttcctga agatcaattg tctcattagt gattcatgtg tatatatata    59100
tatgtttata tatatgtgtg tgtgtgtgtg tgtgtatata tatatatata tatatgtaaa    59160
atactaatgc atgaaaattg ctttcaaaaa actttcagga agcttcctga acatagcttt    59220
ccctcctttg gctgaagctt gggtatttgt ttccagagca ttaaacagta caggtcctag    59280
tttaaaaggc actttgttgc tttatgtttg gaagggattt gactagatct ggaaacacag    59340
tctccatccc tggttcttaa aaatccaagt ctgagtagaa gactgtaaaa tatatcctgc    59400
tattgttaac attgctttca ggaggccttt aagtatgctc tgaaaacaaa tacccaaact    59460
tccagaagaa gggcagcaaa tccccaagta ataggccaat gagacagact ctggaagtct    59520
gggccacctt ctcagtgcca cagatagagg gagaaaaatt cacagccgac agagacattc    59580
agacccactg caatgagggc aacagacaag gaagtctaat tccagtcagg accaactgcc    59640
atggatctga attttagcca gtgggtaatc ctgtggtagt ccctttgatc tccctgagtc    59700
tctgctgaag tttggagttt atgtgacaag tgattgaggg cttatgctat catcaacata    59760
gttctttctc aaactccagt ttatagaatt ttttttttat taagaacttc tcactgcagg    59820
tagaataaaa tccaaacttc tattatgaca tatgagacac catgttgtcc aattcctgcc    59880
```

```
cacctgctca aaccctcttt tctatcagtt ttctcctatt attagtatgt gtcctaccac   59940
actggccttc attctactct ccagataagc caagtgcatt ctcatttagg gcctctgctg   60000
ttgctgtcta ctctgtctgg aacacttttc accatggtag agctccccat ggtgcccagg   60060
ccaacttctt gtcacctcag aaggtcttcc ctgcccaacc attccaaaat tgacctctat   60120
tcaataatat tttcttaatt gcactttaca ccatgtaaaa gtatgtagtt gatttataat   60180
gtttacttat ttctgtctcc tctcttatat cagattagta cctcagttga gaatagtgat   60240
ttaatctgct tatttatggc tctatctctt gtgcctgaaa cagtgcattt atataacaga   60300
tgctcaataa atgtgttaaa tgcatgataa gtaaactttt taaatttaat tcctttatta   60360
atttcagata tttaacatgt ctcaatggtg agaagaaagg ttaataacag caaattgtat   60420
ttactttctc cgtgtcaata tatattttga gtgaggtgag ttttagttgt gtccacctct   60480
caaacacttg taatgctaag tgggcacatc atcagtgtat caaggggact gcttccctct   60540
catgctgagt gggaattttg tcagaatgtt cctgctattc tggctcctgc tgcccaaaag   60600
gtacagggcc atatgtccct acaacaatta cagaaaaaaa tagaacaaat cctagaatcc   60660
cgccaagtca gaatatcaag ttttctgcac ataccagttt tttgtactca gatggaaact   60720
gttaaaagtg aattgctcag ctgtattcta agacacatct cacccaatat gatctctagc   60780
atctcaatca gcagtaacaa gaaataacac aggcaagaaa agtaggccct ccctttttcct   60840
ttcctcaagt ttttaaaagc tccttttttag ataggttcta atattcataa acttggaaca   60900
aaaaaatgaa atgtatttcc agcaaatagg gagcttgaaa tattctcaca gtaattgcta   60960
gcaatgctgt attgtagagt cttgaattag gtgtaaccag gcacacaaat gaaataggca   61020
gtttaagtca gaaatctatc ctcatttttct atactatatg tatatatggt ttctatgata   61080
gctatgaaaa aggcattata ctaagtggca acatcccttc tcactattga aaatagctga   61140
ctaatgtata catctatata cccacaaaaa taaaaataaa ttttaaaaag aaagaaaata   61200
gctcactttc ttgaacttct tacccatagg catcaaaaaa tttgacacta gacttgctgt   61260
ctttgacttt tgcctcatta ttcatcacca tttggaggca cttcagtgcc tgtgtcaaca   61320
acctgaacaa ctaagagtgg tttacaaata agatttttatt tctgacatta aaagaggtcc   61380
agagtcaggc tgttcctggg ttggttcatc ccatatgatg tcattagaaa tcaagagctt   61440
ttgtaggttg cctgttcact ctgatggtag tttcttttgc cgtacagaag ctctttagtt   61500
taattagatc ccatttgtca atttttgtctt ttgttgccat tgcttttcgt gttttagaca   61560
tgaagtcctt gcccatgcct atgtcctgaa tggtattgcc taggttttct tctagggttt   61620
ttatggttttt aggtctaacg tttaagtctt taatccatct tgaattgatt tttgtataag   61680
gtgtaaggaa gggatccagt ttcagctttc tacatatggc taaccagttt tcccagcacc   61740
atttattaaa tagggaatcc ttttccccatt gcttgttttt ctcaggtttg tcaaagatca   61800
gatagttgta gatatgcggc gttatttctg agggctctgc tgtgttccat tgatctatat   61860
ctctgttttg gtaccagtac catgctgttt tggttactga agccttgtag tatagtttga   61920
agtcaggtag tgtgatgcct ccaagctttg ttcttttggc ttaggattga cttggcgatg   61980
cgggctcttt tttggttcca tatgaatttt aaagtagttt tttccaattc tgtgaagaaa   62040
gtcattggta gcttgatggg gatggcattg aatctgtaaa ttaccttggg cagtatggcc   62100
attttcacga tattgattct tcctacccac gagcatggga gaaattttt gcaacctact   62160
catctgacaa agggctaata tccagaatct acaatgaact caaacaaatt tacagaaaaa   62220
aaaaaacaac cccatcaaaa agtgggcaaa ggacatgaac agacacttct caaaagaaga   62280
```

```
catttatgca gtcaaaaaac acatgaaaaa atgctcatca ccactgacca tcagagaaat   62340
gcaaatcaaa accacaatga gataccatct cacaccagtt agaatggcaa tcattaaaaa   62400
gtgaggaaac aacaggtgct ggagaggatg tggagaaata ggaacacttt tacactgttg   62460
gactgtgaac tagttcaacc attgtggaag tcagtgtggc gattcctcag ggatctagaa   62520
gtagaaatac catttgaccc agccatccca tcactgggta tatacccaaa ggactataaa   62580
tcatgctgct ataaagacgc atgcacacgt atgtttattg cggcactatt cacaatagca   62640
aagacttgga accaacccaa atgtccaaca atgatagact ggattaagaa aatgtggcac   62700
atatacagca tggaatacta tgcagccata aaaaatgatg agttcatgtc ccttgtaggg   62760
acatggatga aattggaaat catcattctc agtaaactat cacaagaaca aaaaaccaaa   62820
cactgcatat tctcactcat aggtgggaat tgaacaatga gatcacatgg acacaggaag   62880
gggaacatca cactctgggg actgttgtgg ggtgggggga gggggagggg atagcattag   62940
gagatatacc taatgctaga cgacgagtta gtgggtgcag cgcaccagca tagcacatgt   63000
atacatatgt aactaacctg cacaatgtgc acatgtaccc taaaacttaa agtataataa   63060
taaaatttaa aaaaaaaaaa aaagaaaag aaatcaagag ctttgtagct ttctacttca   63120
ctatcaccag gtagcaacaa ggattctatt gttggccccg agatggctgc aggagtgcta   63180
agcatcatac cctctcccaa aaaatgtcca aaagcaagaa tggaaggggc atttgtaggt   63240
tttccttggg catttctttt ttcttaacca gaaaaaaaaa tattttcaaa aatcccaccc   63300
agcagacctc ctatcatgtc ctattgttta gaattgggca acatgcctgt gctgtagctt   63360
ccagagagac tgggaaaggt gttttcagct tccaggtggg aggtgagacc tactaaaaag   63420
gaaaaagaat ttggggatga atattgatga ggcaactaac agtgtgctat ctcctttttc   63480
cccccaggct gtataattca tctacaactg gataacaaaa aaactttaaa tgtattgact   63540
taaagcaaca atgatttgtt attcattatg attctgtgag ttggatgaag tcagctcagt   63600
agttccgctc tatgaggtat caactgaatg tacttacatt tagctggaag ctcagctggg   63660
gctgaaatat ccaagatggc ttcatttgca tgtctggcat ctcatctgga gcggctggaa   63720
tgggtggaaa ctagctgggc ctatctcttt tcatgtggtc cctcatgatg agtagtctag   63780
cctgagcttt taaaaaatga cattgagttt caagagagta aaagcagaag ctgtcatgcc   63840
tcttaaggcc caggtctaga attggaatag cattactttt gcttcttgct gttagtcaaa   63900
caagtcacaa ggggaaatgg aaataaagcc cttcagttgc tggcaggtga acagtcaca   63960 ttaaaaaagg gaatgtatat atggacagaa ggaattttg gcagccgtct ttgcagatag   64020
gctaatacag tggaccctgt gggtgtggtt gtcagtggtt aacatccctc ccatttgcaa   64080
aatatgttca ctttctttca agtctcaccc aattatgata tcaagtgaaa aatccagtat   64140
ctcataaatg tcgctctttg agtgtgctcc tcttattctg ggaacctagg aactaaaaac   64200
acatgttatc gtcccacaca aatccaacat acaataatga gacagaggat aatcaagata   64260
gatgcaccca ttcaaagggg aaaaatatag aaagcatatc acagtcactg gtccatagca   64320
attctgaaat tcaggagagc atatgttgcc agtttcatag accctgagaa agaaaatgtt   64380
cctatctcac atccagatct gctctctgag agtggttccc taattcatca ttctcagcag   64440
ctcttggctc tagcctctgg gcttttggtt ctgcctccat tttattcttc ttttcagcaa   64500
gaaatggccc atgattacag ccaagtagct ttttcagcct tcttttgtc cataaaacat   64560 tggaggtaca gaggctttta atgttaaact tgtaaaccaa acataaaatt ccaagccacc   64620
caaccatctc aatggacccc tcctctcagc caaggacatt ccaaagttaa cctgaaaaac   64680
```

```
tagttcatgc catgatggga aaagggactc agacatgcct cattatactc tcctcccttt    64740
tggaattcag gcacagctga ccagcattaa catcaacact gagacctaaa gactgttaga    64800
acagactctt ttaagtctga taagaaacct ttacaatcta atgtctctga agcctgctac    64860
ctaaagcttc atctgcatga taaattccct tttattaatt ccaggtctta agataataac    64920
tcaaccaatt cccaatcaga aaacctttga atctgcctgt gacctgcaag cctccacttt    64980
cagtagtcct gcttctctgg actgagctaa tattcatctt acatgtatcg attgatgtct    65040
tatgtctccc taaatgtata aagccaagct gtagcctgat caccttgggc acatgtcatc    65100
aggaccttct gaggctgtgt cacaggcatg tccttaacat tggaaaaatg aacttctaaa    65160
ttgactgagg cttgtcacag atacttttag cttacaaact gtttgtaaat ggacaaaact    65220
cctacagaaa ctttgtgagc ttactttatg tagttcactt atcttacgga tatcatgtac    65280
atgtgtgaat tgtgatataa taagaaatat gtattttgat cttcatcact ggcttctgga    65340
cagagctcct aaaatccttg taattcccaa gagataaaag caaaaattga attttttgtt    65400
gttgttgtta tagtattagt cttttgtccc tagctcctga aacaactcag aaagataaag    65460
gaaaaaggcg catcttttgt tattcaaaac atccctttca accacacctg agtttatgat    65520
aatgaggtga ctttcagaag ccccctaagg atcaggggac tagttgccag ggaagctcac    65580
cctgtgatta cagagttgga acttttagct tcaccccccaa tgttgaggga ggggaaaggg    65640
gctggaggtt aagttaatca ccaatgccag tatttcatga atcattccta cttgataaag    65700
ctccataaaa gccctaaatg aaggagttct gagagcttct gggttggtga acacatggag    65760
gtgctgagag agttgtgctc catgcctctc ccccatttt cacccctatga atctattcca    65820
tttggctgtt tctgagttat atcctttata ataaattggt aaccataagt aaatgtttcc    65880
cagagttttg tgagccattc tagcaaatta ttgaaagaaa gaggggtttc ctccaatgta    65940
tagctcgtcc ttcagaagta aatgaagttg agacttgtga ttgacatcta aagtgggggg    66000
tagtcttttg gggctaagcc tttaatctgc gggtctgcac tgactctggg cagttgtgtg    66060
agaatcgagt tgaattgtag gacatccagg aagtgtccag caagaactaa agaattgctt    66120
agtgtgtgaa aaactccaca tttgttgtca gaagggttat atgaaagaac ggaaggaaaa    66180
acagggtttt ttttctttt aatatgatat atatgtatatg taacagatat gtatataaag    66240
tatcatatta tgcaaaagca attccctcaa atttttttga gactggcctc tctcaacttt    66300
gggtccaagt caggttattg tggtatatgc tcctaatatg cttagaagca cttttgtcca    66360
ggtgagctgt gccttctagc cacactcttg attgaggctt gcccttatga catgtttaat    66420
tggaagtacc ctacttttca tctttgcttt ggggctaatt tcttgctatc agaataattt    66480
tccagccaga gagtctgcct gggaccccct atagttcttc taaattatgc tcgcttatct    66540
ctcccttgta aaaccctatc tcatatagtt aagagaagcc aattagcctt acaatattct    66600
gccaaaaatc tccttaccca gatctacaag ttcgttaggt atttttttcta tcttccaact    66660
tactgcagaa ttgttcagga ccatccttgc ccatgtacca gatggatcaa ctctgctttt    66720
ctgagcccca tggtgtttca cttcaacgtc tctcttacca gtgctttcac ttctgttgtc    66780
caaatgccat aaaacactac cactgctaag tattggccat tgagaaaatg ctgaaaaatt    66840
agatggatta agaccactac aaactactat aatatcatgg tctctgaatt tgcttggccc    66900
taagccctgc tgccctatta ttgatgagtc ttgatgaaac tttctctttc tatccttaga    66960
gacattattc taaaccttca gtgttctcct ttaactcccc tagtcagaag gtcaacatgc    67020
ctccactgtc acataacagg acctggtaag aataaacttc tgctactctg ttacccttac    67080
```

```
tgctaacatt ctctctttct accctgactc ctatatctgg atataagtcc ttccagttta   67140
atgtaattct gtacctatgt tacaggtctt ctaccctcca ctctacccaa caccttcctc   67200
aatttcgtct tcactatgtc cagggttttc tccatcttag tgtataaaaa tgagcaagca   67260
acaacaaaat caaagcctct cttgtatcag gcaattcttg tgtgtgacca aaaacccatc   67320
tcaaaccagc ttaagttaat aaaacctact tagaggcgta gggatggctt atggaaagac   67380
ttaatccaca gttcaaataa tataatgcaa aaaacaattc ccctttcttt cttcactctg   67440
ctttctactg ggtgagaatc atcctctgct ccccgtctat cttctaccc tactctaatt    67500 ctcccctcca agtactgaaa tgctgccaca ttccagacct ctaatccaca cacataccac   67560
atttgtcaca agaaaggcac atgtctctgt tgatatttct tacataaaaa ggatgtttct   67620
ctattccaat aaagtcttct tgcataacat tttgtcttaa taagttagca ttttatcag    67680 tcagcagagg cagagttatg atgtggtttt taaattttt cagtggctta aaaaaataaa    67740
attttattcc ttactgatgt tcacctgact aaggtgggc acaaaatgaa aagaaagca     67800 agcataagaa atgaaagtac caactatccc aaaacaaaca gaccaatcaa gattaaaaac   67860
aagacagatc cccagatcta cataaaacca aaacttataa tgaaatacat tcagatgaaa   67920
tacacactaa cttgtattta gagcaatcaa aatagacaaa taatcagatg aaagccccat   67980
ataactaaag gtgaagtctt agcctcttaa gctcaccaga agagtactgg ctcaaggtcc   68040
tataaaaccc aaaaatagag acagaatttt tagaagtcat ggcacttaaa ttcatttgga   68100
ctagaatttt tttaaaatta tgtactttaa aatatgaact tgtgtgttaa atgagtgtct   68160
atgaaatcgg gaaagtgcta catttgttct ttcaaaagct ctattaatat atatgctaat   68220
ccacaaatca aataaatatg acatttttctt cacatgaaga atacataata gctgatattt   68280
gataattttt tgtgagttca aagatgagac tttaaaaaaa ttacccatag tttattggct   68340
aggcccattc acacttcact aaatgtgtagat gtcagtttaa gtcattcaca tgaataataa   68400
acaataaaac ttttatataa ttcagatgtt tattaaacag ctgttttttg tcagcttgtt   68460
taaatgtcaa acccgatacc aactacgtat actggttgtt atatactgta tcattaaaag   68520
tttaagaaga cattttcaga agaatttaaa tgaactctcc tatacttata tatatttaac   68580
atcaattcat tagagatttt agtataccta tcagtttcct agggctgcca taacaaatca   68640
ccagcaactg ggtagcttaa gacaacagaa atgtattata ttacagttct ggagacaaga   68700
agtttaaaat caaggtgtca gcagggttga ttccttctta gggattcaga aggagaagct   68760
gagaattcct gtctctttcc cagcttctga tgtgggcccc aaatccttgg ggcccttga    68820 tttgtagaca catcactcca gtctctgtct ttgccttcac atgccattct tcctgtatgc   68880
tgtgtgtctg tgtgttctgt ctgcttctta tcaggacatc agtgattgga tttagggccc   68940
accgtaatcc agcatgaact tgtatcaatt tacatcttat atcttaatta aatctggaaa   69000
gacaatattt caaatgaggc cacattttga ggttctggat ggacataaat ttgggagaga   69060
ggtgggcaag ggaagggggat actactcaac caagtatagc atatgtgtgc acacacacac   69120
acacacacac acacacacac catatataca catatatata tatacgtttt cccttgacaa   69180
tatgttttaa tataaatgca ccagtagtta attagacaaa aaataaaacc tgggaagcaa   69240
agatctcttc gcttaatatt tttaatatgc cagtcagaat caaagaatca ttaattattt   69300
tatccaaaaa tcttatgtta ttttaaggta tctaaacaag tagccttgcc tctattaaca   69360
aagaaattct tctagtaaag aaatattgtg ataaatatca ctactaggt ttagttataa    69420 tttatatcca tttgtactat catttattat gtatttaggc actggctaga ataaagatta   69480
```

```
ttcagttaac aaacaatgac aagtgatgtt atctcaaatc attttttttt tgagacaggg   69540
tctcactttg tcacccaggc tggagtacag tggtacaatc acgtctcact gcagccttga   69600
cctccccagg ctcaggtgat cctcccacct gagcctcccg agtagctggg actatagatg   69660
catgccatca tgcaccacta gttttttgtat ttttttgtaga cacgaggttt caccatattg   69720
cccagactgg tcttgaactc ctaggctcaa actatccacc cccattggcc tctcaaaagt   69780
gctgggatta caggtgtgag ccactgcacc caaccaccga attttctttt tagaacactc   69840
tattatcctc tttctgcttt gatgttaaca ttacttagtc acgtacctgc tatgaataaa   69900
caagcactac aattgttagt gacaccagtg gaaagggatt aacagttctc ttaagcattg   69960 caataccct tcattgacgt caccaaaagt gatggtgatc tcttaactga caccattgag   70020
cgcgaacact aaaagatag tattgatgtg ctaagtttat acactgaacc cttcaaaata   70080
gaaattatga gctacagtaa ttttacataa cactaaaaat agaacaagtg caattactga   70140
aagaataatg aacagaaagg aaaaataat atgcattgaa atacatggtc tggaaaaagc   70200
ctataatagt ttttctttta ttccaattcc agattatatt taaccaattg atatcaataa   70260
aaagaaacaa tgacagacaa ctcatgatcc tcaaaaagga agtgggggga gtttggtgcc   70320
atgcaatata ataagaaatt agtttcaatt gttttctttt tatagaatta atgtttataa   70380
cacttgctgg actgaaaata atttgtggtc ctctccattc tcaactgatt tgacttatag   70440
catagtggtt aaggcaacag gctttagcat cacattagtg ctcttcagtt cccttggaaa   70500
gttaatattt attgaggatc ctctaggtct tctaagcacc agaggaacag caacacacag   70560
aagagacaac tttgtctctg tttctcaggt gctcagaaga cctagagata gatagtttaa   70620
aattaagcta tacaagtaaa tacataagat aacatttgat aggcaaatgc tctggaaaga   70680
gggaggggca atacagtgat tttggtggag ttgaagtcag ttgctatttt aaatgggaat   70740
cagtaaaagc ttctttgagg aagtggcaat gaaagaaaaa cctgaatgaa gaaggaaga   70800 caggaatgca aatatctagg tatctcaact tcctgaagtt tccccatcta taaataaggc   70860
aggagggtgc tttgatgatg aaatatgaaa gtgaatgaaa agcacttagc agtgggctag   70920
tgtgtgaagc catctctctg gttggctgtc cttagacatg aaagtgtaaa gcaggttagc   70980
ttttgatctt gttaaaagaa aagtcagtta ccaaattact tcatatatgc tagattgaac   71040
ttactctatc tctccatatc atttcacaat tggatccatc tcttagaatt gtggatctgt   71100
agagatggtt attgtcacca tccatctacc tctaaattaa ctgggcaaat aacataataa   71160
tgcttagatg gccaaatcca catttaatgt atctgaagat ttaatccagc attaacataa   71220
tactctgcat tttaaaatta gcaatttctc ctgaagtccc cagagactgt ggccctgtct   71280
tgtcaatgcc actagtttgg ctgcacagtt aattccatca gagccactgg accaagcctt   71340
agtgtatgtg aagagagtcc atgagtcaat tgccagcaca gaattcttcc tgtcatagga   71400
aggcagatga tctcaacttt tgagtgcata cagtgcagat ttctagttga atggttcttg   71460
acaatagtgt cctctgaaac ataatgcctg gccaggagcc aatgattatg ccaccataca   71520
aatcactgtg catctgacgc cagaacgcct ctttgcaatg gtaacaacaa gagttctcag   71580
tcctggtgtt ccacaagatg ttgcattggc tctttattc ttcatcagac cctggaatta   71640
aatattttat ttagatgatt ttcaggaaat aagtggtgtt agagagagag aaaaggagaa   71700
gtgaggaggt ttttgtgtag tttaagaagc agttttgcta ttttacatt cccattagga   71760 gaaaattagc caatatttg aaacctagtt ttattaattg cttaataggt attttcactt   71820
taaatttctt gtataattat agaactaaaa cagcttgatt caaactgtta gctaatgatc   71880
```

```
catatatcat tttagtaatt gctagcttct ttcagaaaat gcattaattt tgtaagaatg   71940
taaggacttt caaatgtaaa aacagagaga ttttaagata aattagaaca caaaatttat   72000
ttcaaatggt attttactgt aacatattat aaacctaaaa ttagtagaac actcttgata   72060
ttataatctt tcattttaat ttatatataa ttgttttaat gattaaaagt agatagatca   72120
tactatatag ctgcaattgg ttatataaag taaaatatgt tatgtgaagt gttcctattc   72180
aatagtaatt atgcatgtta caatatttag cccaatttca tctttatgaa atttccccct   72240
gattttacat accagctttt tctagaaata actattcata ggattttcac attaaacaag   72300
tatacctaag catcttattt gataggaata gtcgtggctc aagatgaaga aacagataga   72360
atcccaaata ttattcatga caagcattaa acagcaaaac taaacgaaat attttttcca   72420
gtgaagccaa acttgccagc attttttttt ggttggtttt catttagtaa aatatgttct   72480
tttcttacaa actgggtata agcattagcc aattacaaaa actgtaagag tctcttttaa   72540
atatgggtag gaattcataa aagaagataa tttaaaatgt ttcttatggt ttgaaaatgc   72600
cttccaaata ttcattaaac atttaagtga gtaaatttgt agaatatgtt tctgacattg   72660
gcactggttc tgtggtattt ctctgatcag atggaagtgc tatgtgttat gcagagtgca   72720
tgcagttcat tcatgcataa acaatatcat tttcataaat taaatcctcc cctgcagaag   72780
gaacatctgt gcctgccttt gaataaaaga tggtggcatg tgagttactc cttgactgac   72840
tgaaagaatc cctatgtttt agaatgaagt tgtattggca aaatgggaag aaaaaaaaaa   72900
aaaacctaac ttttagtctt catttctacc ttacaaaaga acacagtcta gatttccctg   72960
tttgctattt tggaagctgg aattctcaaa atggcattct tttatttctt ctcttcacta   73020
cagcaacaga ttttagtttg catgaagatg tctaatttta attgcaggtg aaattgagct   73080
acttaatagg ttagatcaga tctgaatgct cacttcatta cctcctacac tggaaggctg   73140
gtagtattca agtatcatat cagtattatg tctcttaaag taagaacagt gagaacaatc   73200
caggatatag aaagcaacag cttgattcca aaataacaac tctgattcac ttggaatgag   73260
attgctgcat tttagataaa gttgggacta acttaaaagt attctgtca tgtgatgaag    73320 gctgatagaa acatgttaa aataatatat tttaaattgc tctcaaacat ttttttaacg     73380
tcgaagtatt ccttactgct tctgtcacag cttgacgcag cctcattggc aatgttatta   73440
gtatggctaa ttgttcctgt ccattacatt actcacattt ttctggagca gcttgctaaa   73500
tgaggtcagc tttctggaac ccctaaatca ccaatgagaa ggagattaaa ggaacaagct   73560
tgggaagggg ggtagtcatc caatgtggca cccgaatcag agtagaaaca atggagttac   73620
taatgacagt aatcagagca ccacagtaga gccagggcac aagtgccaaa atgatattcc   73680
ctaggaatca tgactgtcag tcaatacatc cagaggaaaa gaaatgccaa actgtttttt   73740 ttttttttgaa gtggacttaa caatagacag aatcatccat aagttttttcc agtgagttgt   73800 gttcatgaaa caacagaata gtgccccaaa gggtgggggg aggaaataat tacacctttcc   73860 taaatacagt acaaatagtg tgttcttcag tacaaataat ccattatgct tttcttgga    73920 aaaatgatgg aaatcatcac aagatgttaa tagaacaatt ataaaatgtt acttctcttg   73980
gattctttaa attaattaac tcatttccct ttggtacttc ctaaaggtgt ataaattttt   74040
ctgggacagt actagtttgc aagataaaac tgtttagttc agaaaatgt acagataaca    74100 gaagaccaag aaaatagtaa tgttttatac atcttaaatg tatagacaaa ctaagctagg   74160
atacttgttt atgtcttgct tgttaataat tattaaaatc cacctttaa aaaagaaat     74220 agaagaaaac atgtaacaat catttttaaa aatggaaata aaaaacctaa aggctaagcc   74280
```

```
acttaaaaca aagaaaaaaa cacactgttt gtactgccgt ccagtcccat attccaaata   74340
atgaaatatc agttaggtct tttcattatc tacatagaac tggtgactcc ctgtgcaaga   74400
taaacagaca agagcatatg ccaaggtaaa cttttttctt ttctttattt ctacatatag   74460
tgtttagtat tttttaactc agcaaaaaag caactacttt ccccaaaaat aaaaacagaa   74520 tcccttttaag aagaaatgca acaattgctc tcactttcaa tactatttta ttgcaactgg   74580
atgaatgttt tctaaattgt gcattacacc ataatataca ggattacaaa caaaattaca   74640
gtacagatcg attccagtgg taccagcatc acatctcaaa cagcacttat tctggactgc   74700
attttacatg caatagctat tgttctaatt atgaattaaa tggtttgaat ttatttaagc   74760
tactgtacta attgactact atagatataa atcccaacat taacaacctg attagattta   74820
ggctcagatt tattacatga atatatgaca aaccaccatt tttgtgacta tgtataaaat   74880
catgcattta tattttctgg aaacatcaat agcttcagat tctctgtaaa atcatggaat   74940
gcaaaggagt aaaagactaa aaagtaacag tgcaaattgt atgtgatagt caagcagctt   75000
ttgatttaaa gaagggtatg ttggcattta tttataatat gtatatacaa gcttgtgcaa   75060
gtaatgtgtt gaattgatat gttttgatag ggaatgtatc tcttaatttt ttcttctctt   75120
gaaaattatg attctggttt ttattttagg gagacggaaa gactttaaag tgaaatgaat   75180
tgctcaaatt gtgcaatttt tttttttttt tttttttttt tttttttttt acaattggag   75240
aggaaagaag tgctaaggca acacaataac tttctaagca cttttctgct ggtttaaatt   75300
agttaaatta ttttgtataa attagatata attctacttt tctgatatgt ataaaaattg   75360
atgaagctgc atggttttaa aataggaaat ccacattata aaaagtcatt aaaaattctg   75420
tacaaaatca caacaaaata attcagcatg ggaaaggtaa caagtagtaa aatgctggtt   75480
gaaaaatata tatttatata tattttaatt ggcccattac tagtttaaaa attgcataga   75540
tcctaattat tgcttgtgat tttgttatcc cgatcagata attaatacga tctgaataca   75600
gccacaccaa attcgtggtg tattttttaa actttactgt atttttttat tttttaaata   75660
gaagagctat agaaaataat acataaggtg aacaggaact ttgatcccct gtttcttcca   75720
aaggcagtaa tgacaataaa tacatatatc acttgaagct tggagtattt gcactttgca   75780
gcagtagtac ccaaagggct gccttttgta aacacgacag tcactgtaag cacagtgggt   75840
tcgtttcccg gaaatggtga aactggcgtg cctctaatca tgaaatatgg cattgagctg   75900
ggcactcatg actcgctcat gatgtgaatg gctatcgaag gacataatat tgtctatggg   75960
gatctcgcag cgaggggcag cggtgcctga gaagattgat ccgtggcttt gggcccctgc   76020
cagtgtcgct gcaggatagt gcatggtaaa ggcataattt ttctcaaact cggcggacgg   76080
ttcgtgtttg aaagagaagt tgccattgat gctgagcggc gggctgaggg gtccatcaaa   76140
ggaagggctg gtgcaatcag tcagagggct ttcaaagaag ggctccagcg ctgcgctgta   76200
ggcgtgcggc ggaggcttaa cgtggaagac atgggagctg tccatggtac cgtaaggcgg   76260
actgggcagc ccaggcgact ggtaggagta ggggtgtaca gggaaggaag cgctggccgt   76320
cggcaggtgg gggggcatgt cctggttctg ctcaggcaga aaagtccgag gattgagttg   76380
caggcagccc gcaaccaggt tggtggtggg ttgggataag cccttgcaaa gcgtctgaac   76440
gaaggagacc aggtctgggc ttttgcctga gcgcaggatc tccgacagag cccagatgta   76500
gttcttggcc aagcgcagag tctcgatttt ggacagcttc tgcgtcttag aatagcaagg   76560
caccaccttg cgcaggttgt ctagcgccgc gttcagtccg tgcatgcggt tccgctcccg   76620
ggcgttagcc ttcatgcgtc tcaatttaaa acgctccagg cgagccttag tcatcttctt   76680
```

```
cttttttgggg ccgcgtctct tgggcttttg atcgtcatcc tcctcttcct cttcttcctc    76740
ctcttccagg tcctcatctt cgtcctcctc ctctcccccg ttcctcagtg agtcctcctc    76800
tgcgttcatg gtttcgaggt cgtcctcctt cttgtctgcc tcgtgctcct cgtcctgaga    76860
actgagacac tcgtctgtcc agcttggagg accttggggc tgaggctcgc ccatcagccc    76920
actctcgctg tacgatttgg tcatgttccg atttcctaca ttcaacaagg gagaggcaaa    76980
cagaaagaaa agcagaaaaa cgctatattc aaaagccaga tacgccttca gcttccactc    77040
cctaaacctg tacaaatgct tgcgaaaagt acctgcccat tacaaaatga atgcctctga    77100
gaaaaagtta aatgcagtgt tttataatgg cgcgtgcgtg tgccccgcta gtacgtagga    77160
gtgaggacag gactggggga gggtagtgaa tatgtatatg tgtacaccac tcacgcatat    77220
gtgtttgtat cctagtgatt aacttaaatg tgtttatggt ggttgcccga caggataatg    77280
tgtgtggaaa tgactgtaca tttcagcgac ttcatgttta tccaaatgtg ttcaaagtta    77340
ctcacaactc cataaaaaaa aaaaaaagct gtaaaatcac acattctact tccatttctg    77400
tcctggcttc cagatactta gcgatttaag ttgaacagcc attgcgtaat ttactaatac    77460
tggcagcgat ttttaagaag attacatcga cgggatactg aaaagcaaat gcagaaagga    77520
ggaaaaatag tttccaccaa attgtttcac catcaatgta acatttggca acaaaagtgg    77580
acagggtctt ccaccccctcc ctcgcctttc ttttcttgcc ttccatctct ggcccaccgc    77640
taaatttcca ccttgtacaa aagcgctagc tgcagggcga gggctggggg cgcggcgcag    77700
agcgctctcc cacgcgccgg ggatcaggtg cggaaggctc ctctctaata aacagcccat    77760
tgaaagggcc gcccgctctt tattggggct tttcaaagtt cgcctcaaac ctcccttaa     77820 aagattgagt aattataatg gtcagcgatt ggcaaccgcg aagttgccgc ttctagtaag    77880
gaaaataaaa agcctttagt aaaacaactg aatttctggc tccagtagtg gctgctgggg    77940
acttggccgc ctctggagcg gtaacaggta gcaggagtga gtccctctcc ctttctccac    78000 tttccccct ctcaactaaa ctatctctga acctgattta ttttccatgg tgtgaatact      78060
caaggtatcc atgtcccttt cattcactga aaacacagct tgacactccc aatgtgcgta    78120
aaatacatgc acacaaaata tatattgata acatagattt ttttttctta ctgtaagaag    78180
tgagaaagtg aagtcattat tgcttttggg actttaaaat cagcactagc agataatcat    78240
agttaccgtg cattcttta aaaatccaa gaagctccta tgctatccac aaaagaaacc       78300 caaatttta aaatttaaat tagaaagcct gcagggggta cttgagtgac acgactcatt      78360
atgtgtgagt acttatgggc aattatggag ggggatgctg gtctcaatac acatacacac    78420
tctcgcaaac gcacacatac agaatatgta ggttcatcag tcttcagtta ttgcttctat    78480 tctgggcaa aaaatgaaa gaactgtaat tacctttgtt gttagtaggt cctgagcagt       78540
gatagtctca taaccctggg gcctccggac gccgcgcctc ctgcgtgggc gaattcctcg    78600
tgtcgtggcc gcgcgggcgc tcaggttata tagcccagtt agtgatgcta agcgcgggcg    78660
gggccgctag ctgaggggct agcaggtcta tgcgcctgac gcctgcgcac gcgtccaggc    78720
tgtgcgctcc ccgttctccc ctcctcccca cttctcccca cgccttgctc gtctcccgcc    78780
ctcctccgac aaccgctccc ctcacccctcc accctaccc ccgccctcc tccttcctcc     78840 ccggcatgcg ccatatggtc ttcccggtcc agccaagagc ctggaaccac gtgacctgcc    78900
catttgtatg ccgcggagcg ctccattccg gcccctttgt ggccagaaga agtgggccca    78960
tctgtcgcca gttagagact ccgcggacct gtttttaccc gcaggagaga ttaacccttt    79020
caggcggcag aagggacggg gatagagggg ggagggggatt tgagggaagg aagggaaaag   79080
```

```
ctaatgttaa ctaggtctag atcagagcga gtggcctgct ttcgcgccgg aagtaggaca    79140
gaggtgaaag aggcagaagc ggggagactg aggcacgcag tgaagagtcc tcgctccttt    79200
cgatttcttg tcctgacact ggcatccaga gcagcatgac tccttgccct ctctgaaagg    79260
cccatcccct tggcttcttct ccttggcaga cgctttgatc attggcgcca aaggatggct    79320
tctcctaatc tccgtcggcc cctctaagca aacatatacg ccatataaaa gcggcttcat    79380
ctgtaaacgc agcgttgaga ttagttcccc aacctcccta accggatcgt cctctcccag    79440
ttccttcagt acagaaaagt tgtacctgcc attctatccc taccatacgt gcaattcttc    79500
atgtcctgac cttcagctac gactgttcct ccagaccctc tcactacgtc agtccccacc    79560
tccatcccca ggatcttgtc ctcaaagcga gctagttctc gcgaggaggc cttggttcca    79620
ttggcctttg cgctctctta tgtgggagct ggggacttct ttgacggttg tattctgcct    79680
tttaaccatg gccactgggt tgctggaaag ggcaccctca ctcagccagt ccagggacgc    79740
ttctggttcc ctggccagcc cgccctggac ggcctcggct ctctagtcca ggcattgacc    79800
acaagtacgg tggtggacac ctcgccacag ccggacctgc gctcttgctc ccctcagtct    79860
cgggtctgta taagatactt gattcagaca agcgttttca aagagaagat gcaatgggcc    79920
tgtgctgaac gggtctttcc gatctctttc tagaaacgcc tttagcacaa ccccggaagg    79980
attaatggct gcgaactcct ccagacttca aagcctctga tttgaaactc ccaacttgaa    80040
ggtcaagcaa agaccacaga aattctcgac cagttctgaa ggagccatat gttgcccaa    80100 atagcaattc tttactcttt tcgaacaagg gttttccaga ataatagatt ttaaaaagaa    80160
agaaagaaac tggcctgtct actcgttctt tcccagcttt gcctctaatc cttcattaac    80220
taactcctta cccctccca gacctgaaac cctctgcaat aaatacctct tacgtgaatt    80280
gcttatttaa aggcaattgc actaaacatc cctcgagttt gcaaacagcg acagggttga    80340
gaggctggat tgggtgcat ctgggagagg gtggggacgg gaggagagag taggggtaga    80400
ggaagagggt cctagccaga tccccggtgt ctgaaggtag caggtgcagc cttccctgca    80460
cagtactaat ctaaagggg aagaaaagag ttgtgccacc gaagcgtggc gtgaatcgtt    80520
gtggggttct ggagttttgc ttgcttttct acattcactt ggctgacaaa gcgcataggg    80580
gaggataaaa taattcaccc aggagcctgg gcccaggatt tacccctgta ctgtctgtat    80640
cttcagtgtt gggctaaaac tcgagggcgt cggagtacta gcccttagaa gatagtacac    80700
agcccgacgt ttgcggcagg gccaggttaa gtactgcccc tcaccggca gctgccccga    80760 ctggcagcac actatgccgc aggcatatgc aactcgtgcc taggctctca tttttccaac    80820
tttggggagt tccggaggag aactggggac ggagtgggag aaaggactcc agctagcttc    80880
gaggtcaggg gtagcctaga ggtccctctg ctaaatcctt gtcctcaccc ccagaaagca    80940
gaaacctcca gttcgcgaca tcctgtgcaa tacaggagaa ttatggtgga gtcagatgtt    81000
cttgagcaag agggacgccc gagtgttttg ccagacggag actcaaatgc gtaaagtgcg    81060
ggaattacta gtctgtttcc tccctctacc cttgataaat tcatctctaa tcccactgcg    81120
cgttgttcgc tcaggcctgg agatttgtac aaaggaaagg ccactccagg atgtttcaga    81180
gacagggctg aggttgggtc tcacggtagc tgtccttggg cttcccatcc cgcagcgctc    81240
cgatgtgacc ctcctctgcg cggaaaattt cgacccgggg cgccggcatc gcgacgctca    81300
gccagtgccc gcgaggctcc caggagatgc ggggtagtaa ggccctaaaa agaggagcct    81360
ggacacggcc tggattgagg tgcgttttgt ttggggttga aggcgcgaga aattgggcg    81420 agagaagaga gtcagccgga tcccggagag gacagagctg aaggcgcggc ggggcttagc    81480
```

```
actgaggacc ttctccgcgg ccccgctcct cctccttatt ttcttctctt tggacttgtt    81540
tggacggttg cacactttc  cccctcctga ttccctaagt tttttgtctc tccctcgct     81600 gcccgttagc tgtactcccc cagctcccgt ccctactggg cgctgcaggc tacccagcgg    81660
cacgcgaacc gcacgcgcgg acaacaaaag cctctttcat gactcactgc cctcgagcaa    81720
tgccccaaat ctgccgcctc ccgggtcccc gctctgagcg cgcggcgcgg gccgggcgtc    81780
ccggccgtta cagcggcagc cggagcgccc gcgggaaggg gggcgggagg aggcgtgtgg    81840
ccaggggtgg ggagagggga gtgtggcctg ggccgggcgg aggggaaggg ggaggcatgt    81900
gggaggatgg gggtggggaa gggatggagg cgtgtggccc ggacgtaggg ggtgggaagc    81960
gtgtggctgg aggcgaaagc ggggagcggg aggtcggggg cgaagcattc acagggccaa    82020
gataaagcgc aggggccggg ccggcgtccc tggcggtgac ctgtttctca gggaaacaga    82080
tgctcgctct tgcaaaggga ggtttgcgtt caatgaaagg atcaagtgtg gccagggcag    82140
cccggccgac ctcgagaggt tcccgcgtcc tctccccgcc ctgcctagga gtggggtgtc    82200
ggggcctggg cgcggggagag cggagtgagg gggccgggtg gctgaggggc ccgcgagacc    82260
gtggggctca ggggccgcag gaacggaggg ctgagagctg caggtcctgc acaggctggg    82320
tagctcggag gctcttgaga gcttcggggg atgaagggggg gttgatgcgg gttctgacca    82380
gaccgccgac gcggcgcctc cgccccgggg gaggcagttg ggctcccggg tcctggcctg    82440
aggctggagc tgcccaggct cgacaggcag gcgacccggg agagccaaga gcaacgagag    82500
acgctattaa aatgcctcgc cgtcgccccg agcgcaaaac ccatcctccc caaatctcct    82560
gggcttgcgg cataatctta attaagataa ttgattcata ttgcacctgc gagaacggaa    82620
aaaattgatt tcaaccccca accccacaaa tcgcttagag ctattggatg gagcacgacg    82680
cgactgtgat ttagggagtg atttagtgcc gggcttcccc agctcggcct gcctgggcct    82740
ttttatttat tatttatgcc ctcccggtcc cgacggggct ttggtggctc ctttgtcggc    82800
tcccacaggc cttggaagga cttgtctctg attccctgtc aggatccagg ggctttcctt    82860
aaaccatcca acactcagaa tcaacaacgt aaaatcaact cagtaggagt atcttggcag    82920
tcgtaggtca cgggcacaat tgctcaaggc ctcgtgcgtc cgatgccctg tgtgtgcaaa    82980
agtgtgtgat tgcacttgaa tgtacgtgtg tgaatccgtg tgtgtgcaag attatgtgaa    83040
tgtgtgtgca aatcgtgtgt gcatataatg agtgtgtgat tgttagtgtg tatgtgaaca    83100
tatgagtgtg tgcaggtgtg tgtcaatgaa tgtgaatgtg tatgtgaaag tgggcataag    83160
tggatgggtg tgagagtgtt aagtgtatgt ccacggtcgc acctgctttc gggtgaggag    83220
cgtgagcaga gggcgcacac ctgtttcccg gggatcgagg aacagcttgc tgtccaaagg    83280
ggatcgcagg gccagggaac tgacaagcac acgctatttg ccaacctttg ccttaataga    83340
aagaagcaag caaacaaaaa tcctcggtag ctgtgtgtag cttcaggagt ggagagccga    83400
gacacaccga cggcgccgga gcgtcgcaag aacaatggtt gctgcagtgg gttgggagag    83460
aggacccgga caagttccta aaggcacggg aggaacgcgg gcaaaccagg tttagggccc    83520
caggcgaatt gtgaaggaa  tgacttcctc aacctatcag caccgtggac aattcccact    83580
ccaacggccc tgaccttcgg cctactagat tcagcaaaaa tctctcttcc tcccttgctt    83640
cctcctttcc ttcctccctt cctcctttcc ttcctgcctt cctccctcc  ccttcctcct    83700 cctttccttc ctttcctccc tcccttcttc cctcctttct ttcccttcct cctttccact    83760
cttccctgtt tgctttgttt caaaacaaa  aacaaacaaa caaaaaacat ggggcgccat    83820
gactgagctt ttagtcaaag agacctgtaa gtctgcatct aattaggcac atattcacag    83880
```

```
taagtttcct ataaaactag gtagccagat ttaggggcaa ggaaagagct taaactataa   83940
tttgagctgg ctagtctgaa acaaagacag aaatcataaa ttgaatagct ttcaaaaaga   84000
tagtcattat tccaatattt gcacttattt gccacacagc ttcaaaacca aaatgaattt   84060
cttgtttact gtccatagaa ataataaaat atctctaaaa atgtttttga ttttgcttgt   84120
gttttatgga gtataagttt tattgaaaat ataaaatctt tttcaccacc actttatcaa   84180
catttcagtt atttcatact gtaaacaatt tctggtaaat tcatgaaaaa ataagccaac   84240
agaagttaaa tggcattatt cactcagatt cagtgagcca cacaattagc taaatcatgc   84300
cagatctaaa atattgcata atgagtagtc ataacttatc cagcatatac tggaaaagtc   84360
tagtaaagac ataactgaga agagaaagct cctttggtac tttgaacatc tgagaaatat   84420
atacaccata tcccctccc ccaccacaca cttattgatg taattttcaa aacatcatta    84480
ttattagtaa acagaatcct tatcaagtat tattcacact tcactgtaat gagaaatata   84540
atcatttttg attaaagaat tcatccctgg agtctcacct tctttaaata aaatgtcttc   84600
tttcctttat aacaaatgca tttcactcaa attaaatatt gataatttga ccttttatgt   84660
ctttaactaa tcaaggggg aaaattccaa atgtagatct cggagtttgg ccttggtggg    84720
tctttccgct tgagtaggca ctgagattaa aggagtcaaa cttcctcttt cactgctctc   84780
tccttgcact aattgcttat gcaaaaaatg cagatttgta ttaattagta actccactga   84840
ttagttctgt ggtattttca cataataaat catgctgcag acatgaattt tggcacatca   84900
cccagtggtg gctcggctgc aatacgggtt tcttattaaa ataaaatctc tgactaaatc   84960
tacctttcgg atgtaggtac tgtgagcagc cacctgctgg gagcacctgc catgggaaat   85020
tactttcact cagtgacaaa ccactttagg ggctcaaaca gaacaatttg attatgaggt   85080
taggctctaa taataaacaa atagttaaac acatacatac atacgtgaca caaatgtgtc   85140
taagctttag acacattttg cagaccatga tgtaacaaca gataatttac ttgtaatggg   85200
actagatgtt taaaaacaac ttcccaagtc atcaataaat acctcagtct gttttcctcc   85260
tgtaacatct ttgctcattt gtgagatggt ctggtatttt gagactctca caaaactcac   85320
ccttattgac tttacccact ccccaggcag gcaagctagt tctggaagga aaagagccac   85380
aaaagtatca aggagaggaa tatgaatgcc aacagccctc ccagagggaa ctgggcaccc   85440
ctgccatcct agcatcagat gagaagctgt gaggccagac acctacagtt gcgtgatgtg   85500
aggcaaattc ttcctttccc attgttcact atacaaactt ttacacaact tcttcctttt   85560
gaaaagtatt taatttgata aagcagatta caaccaatct tgccaagact atgaattagg   85620
cccaggtgtt ttctgtgctc ttttaaccct ttacgtgccc ttgttttcta atcactagtg   85680
acgcctttcc aagacccctc aggtgctctc agcacctta tgttctttct gttacctgcc    85740
aatctatacc tgctgcttgt tgcaaggaac ctggaaattt acgcatctta agaggttgag   85800
aatgacgctg aatctgatgc ctgtacctgg ggaggttgca gaatcacaag gtacaaagaa   85860
aaaaaataaa aatattgaca ttcagagatt aataaaggct aagaaaggta tatttcagat   85920
ggaggctggg acatgacatt ctgttcagtt tgtgctaacg caggtcacag cctccatctt   85980
ccttcatgac ttgtcctgag gcaggtgggt atgtggaggc tgggaattgt gaagcctcta   86040
gggaggctct ctctctctct cgacatcatt tactaaccct ttcaaactta ggtggtgaaa   86100
ggaagaggtc atttattttg tgatgttttt atttatttgt cttcgatgtg ggcaattatt   86160 tatttatttta ttttgagatg gaattttcgct cttgttgccc aggctggagt gcaatggcac   86220
gatctcggct caccacaacc tccgccttct gggttcaagc aattctcctg cctcagcctc   86280
```

```
ccgtgtagct gggattacag gcacgtgcca ccacgcccgg ctaattttg tattttggt    86340
agagacgggg tttccccatg ttggtcaggc tggtctcgaa ctcctggctc tggtgatccg   86400
cccacctcgg cctcccaaag tgctgggatt acaggcgtga gccaccgcac ctggcctggc   86460
agttttttaa agaagttaac ccaaaagtca ggaaagaaca taaaatttaa agcagctaag   86520
tcaaatatgc ttttctcct ttgaatttac cctggatcct acttcttctg gaatcacatg    86580
gactagatta atagtctctc atgaaaaacc aacagacaaa aacaaaaca aaataacag     86640
tcctaaattt ttatgtttgt ccacaatgct agtgtggtag acaatatgga gagcaccagg   86700
gctgagcata agcaaaggct ataaaactga ttcaggtttt cttcagagag cttgtctcct   86760
ccttcccctc ctttcagaaa ctgctgattc actgggcaat aagcgtatta gcaaatctat   86820
attgaatgcc attatgtgcc aggcactgtg ctgctaggtg ctaggggcac aggagtaaat   86880
agacattaga ttcagctttc ttgacgcttt cttttctagtg ggagagatgg actttaacga  86940
ggtttactca caagtgagta tgtacctacc caacttgaaa caagtgcagg agtactcaat   87000
acccaatctc acttccttct tgtgtgcctt tctagagtaa acagtctgga aaattaaaac   87060
aaataaatta attaaaagtt tcctatgtgt cctagttgtg gtatacattc tgctaatcag   87120
atgcattaga ctttattca gaaccagtta cttgagagag ccaggagaca gaagatttat    87180
ttgtctggca caaattctag tgcaagtaaa gccagcaagt gtggtgacag ctttctgatc   87240
aggactcaag caaaggtgga agctttctta gcctagtttt gtggtatggt ttttgatact   87300
cttcctggaa tctcaggcta gagtctgttt cttcaagcct cctaacacat ttcttgtaaa   87360
gctctccagg tgatgaggga cactaaagtt tgaaaacccc taatggttct caataacaca   87420
ccacacctat cttctgatct cttacatcaa ggagcaaaaa ctgagaatta taatgacaac   87480
atttgggaag atttaaatag ctccagctac tctgaatact caagttccac tgaaagcctt   87540
cttttacaac ataagcactc cctcctgcca tatcaaatga ggctgatctt ggtttgcttg   87600
aaggttcctc tgacatactc aacttgcaag aggatgtaaa tcctctttat aacccattcc   87660
ttcccctac tattgcttcc aacctgtgac taatagggct caggtaggac aagaacaatt    87720
ttgtacctag aagaaggcta ctaagtaatt gcaagatttt gttcattttt atcgtgctca   87780
atgtgggggc aaatgtgcgg gtatagattt tgcagatgct agcctggggg gatagaatat   87840
tactttagat caggctgaat ttctgaatac tgttgtaatt gttattaatt ctggattcaa   87900
agtgctgctg aaacctctga gtatagtttt cattgtctgc tccgaaggtt gaataaaata   87960
tacattcaaa gctgacctac attgcatgaa gcttaaatac caaaaatttc tcaaagtgat   88020
gtagaaaaag caacccaaag ttttagacag aaaaggttag agtcaattca ttataggcaa   88080
acttctcacc tacctcctaa ctatcctcaa cacatgtgca tttccttggg agggacagca   88140
tctttgaaaa atcccccttca ggctgggaag gaaggtggac aatgttacta ttaaatggga  88200
tccctgatag aaattgggat aattggtttc tgggatgacg gtccaggggg cacacaaaag   88260
agtcagagac aaagtgggat ttttactaca acccacagta attggggtga tctaacacag   88320
gaaaacctgt ggcagtgtct taacctttca tgggattcat ataattgtat gaggtctgaa   88380
aaataataac aataatacat gggatgataa aacctgatca aggcttgtca tgaattacca   88440
tgatgtcatg atagctgctc actcaattct gaaacttgag tttatttcca aacattgaat   88500
atagaggaag ccaggtaacc tgaagaagga ccttgtgata tcatcagaag tacttcctgt   88560
aaatcttct cccagccttc tccagaagta tctttggtta tttaccatgg taactgtgta    88620
gtgggagatg ggaaatagcc agatctttca gggagtattg gctcctgaat ataaatgaac   88680
```

```
acgatgcaga atgtcactgt gatgtatctg gcagaatctg ggatgcatgc agtttaggtg   88740
acaattggat ttgcgggcct aattctgtca caatggcact tataggtctg taaaagcatc   88800
ctgtgattgt ttccacattt ccttcatata gagatgagtg aatgtccatg cttcctttct   88860 gaccccaaa atgagggtca ttatgggaga aaaagtcaaa tcttgagctt cctcttctta    88920
ccaaaagtac aactgcacac tgggggaatt gcagagattg atcagcatca aagatttgaa   88980
agacgtcaag tgatatgaca gtagccacta gttatctccc attagctgta ctctcttttt   89040
ctctcacaga aagaatatct ccaaatttta cctagggtaa cagtcattct gaaaaaagac   89100
tacatttcct gtcacattgc agctgcatat gaccatgtga ttaagttttg gccaatggga   89160
tgtgagtgac agtgacgaga acaactcctg gatcttgtca ttaaaataaa gtgatgtgtc   89220
tataccttct tctttctcct ttgtgctggc tgaaatgcag acccaaggca ccaccataga   89280
gacaatgtgg ctggcaataa gatagaagga attgggtcat tgatagcata accatactag   89340
ctctagtctg cttacacaag gactttcatt tgaatgagaa agaaatttt attttgttta    89400 tgctgtatca ttgtgaatct ctctccagca actgaattca tatgctaaca aacataggta   89460
gtgatccctg tcacatctcc attatagaac ccctttcctt gccttgtgca gatgagaatc   89520
tttaagaatg tcagtagaat tactgtacac ttattcttgg cccactgcaa cctccacctt   89580
ccgggctcaa gagattctcc agagtagctg ggattacagg cacccaacac catgcccagc   89640 tattttttt tttttaaatt tttagtagag atggggtttc actatgttgg ccaggctggt    89700
tttgaactcc tgacctcaag tgatctgcac accccggcct cacaatcaag tagtgatttt   89760
tcaatgcaga tgctattcca catgatatct tttagttgag taaatcaaca caatcctgac   89820
acgtgacatt cagcgtttgt tctggcaatt ttttttataa gaggaaaagg gtctcactat   89880
gttgcccagg ctatctcgaa ctcctggcct caagcaatcc tcctgccctg agtagctggg   89940
attacaggct tgagccataa tgccaaacta aaaacttttt gaaaaatccc aataagtaaa   90000
gagcacaaga agtagcttgc tttgagatat tctatttcag gtataccaac tatttcactc   90060
cttgtaatat aggaggtggc agacacccta attgcatcaa aaaggtgcat gattgacaga   90120
gagtgaggag taaatccaag gaaaatttag ggtcctgata tctcagtgaa aatacgggg    90180 atcaaatgaa atggggcaaa ctgagattct tccaaaataa aaagcaattt acttcacttt   90240
gcaccatcta tgactaatat attttgcaga gttttcctcc caagattatt aaattagatt   90300
aaattaattt aattgaagag aaagggaagc taaataaagt cactgttctt atccatatct   90360
aacttttgat ttttttttg gtggttataa acagcctgga caaatggctt gaaatatgaa    90420
agacctagta cttttcatag tttgaataaa ttctatacag tgtgggatag gaaagccaca   90480
aatgatttgc aatgtgaaga aaacttattg tatagatagt taggagataa ctttaaaaat   90540
gtgaaataag gaagtcaaag atgcaaggaa gaaatgtgca cggttaaata aaatgagaaa   90600
ctagaagaat aaaatgagta aaattatata tatgtaaggt ttttgaaaaa gaatcttcac   90660
aaatttccca tggaaatgta aactggtatg gccattgtag aaacattcac atggtttctc   90720
aaaacgtggg agttaacata tgactgagca attttactcc taggtatatc cctaagaata   90780
gggaagaaat atccctaaga aactagaaaa tatattatcg taaaaacttg tacacaaatg   90840
ttcatagcaa cattatttgt aatagttcaa aagtagaaac aagccaagta tctatcatct   90900
gataaatgga taacaaattt ggtatatcca tacaatagaa tattattcag ctataaaaat   90960
aataaatgct acaacaaaaa caatcacttg agacactatg ctaagtgaaa taagccaatc   91020
acaaaaggac aaatactgta ttattctacg tatatgaggt atctagagta gttacagtca   91080
```

```
tagagacaga atgcagttta gtgatttccc gggactggaa ggagggaaga atggagagta     91140
aacagctagt gggtaatggg tttctttcca gggtgatgaa atattctgg aattagataa       91200 tggtaatggt tgctcaactc tataagtaca ccaaaaacca ctgaattgta tacttcaaaa     91260
tggtgaatct tatggaatgt taattagagc tcattttaa aaaatgagtg ggaaatgcaa      91320
ttgcaatatg tcttctctta ccttgtatga caccatatgc tcttgttttc tctttacctc     91380
ttcgaccact ctttatgagt tactgtgcag atttctcttt tgctcatccc ttaaatcttt     91440
ggttttcctc aggattctct cctaggcttt cttctgtttt cttcttacac aatctctgca     91500
ttagttagta aggcagttaa tgctttgaac aattttcata tgcacaaatt tcatttatta    91560
ctgttcagtt aaatgacact agaccccaca tggtttaaat ttcagttacg cagtgtatta   91620
attgtgagta actgcttaac gtataagctt cactgctagc tctttagtac acgaatctct    91680
atgtaaataa cagacatata tcatggtcag tgaccaatca catcagttgt ttcaaattct    91740
gttagtgatt ggtcactgcc catctgttat ttagtttatg cacagacagc aaagccttag   91800
ttgggtggcc tccttctttc ctagtattaa acccatatga cattaaagaa atgaatatta    91860
gagaaaagtg accaacagca attaaagtgc agcaaataaa ttaaaaacga taatgctgga   91920
agtgaaattg aatgtgatga ggagatttga aaatggagac agcaaagtga agacaggatg   91980
agacctaggc ctgcctgaag ctagtgaaca atgatgttg aagaagtcag atcattcaaa    92040
aacaaggtaa tgtagcttca acattgttta gtttaagttg cactcagaac agaaagctgc   92100
ttagggtaaa aatggagcat ttacttctac ttaggattga acagtgtagt gaaaacaaaa   92160
acccaatcag cttaacaact atcatgcagg ccaaactctg aagtcaggtg ctgcattgaa   92220
aggaatcagt aattacaagg agaccgaaga taaatgtttc cctgacagtg aaggcagatt   92280
ttagtgtttt agaaactggc atgacttcac agtgtttgaa ttgaacatta atgggatttt   92340
ggaagaaata gctgactggg aatgttgaca cttgctattc aaaagactct aggctggcag   92400
ccacaggaac ttcattaagg caaatgtata gacttaaaag agtaaagtgg ttgtgacaaa    92460
aaggatgaca atatcccaga ggaagtaacc acagtaaaga aaaacaggcg ggccgtagga   92520
ggaagatggc ggtggggtcg cgcgttaccc gggaggagat taagacggag ccagagaacc   92580
cgatcaaccg tgagaaaaca tgcctgctgc tgctgcgcat cttcaccacc aataatggcc   92640
accaccaccg aacggacgag ttttcccggg gaaacgtaca gtccagagag ttgcagatct   92700
acgcttggat ggatgcaacc ttgaaagaac tgacaagctt ggtaaaagaa gtctacccag   92760
aagctagaaa gaagggcact ctcttcaatt ttgcagtcgt ttttacagat gttaaaagac    92820
ctggctatcg agttaaggaa gttggtagca ccaagtctgg cagaaagggg actgatgatt   92880
ccatgaccct gccgtcgcag aagttccagg tagattactt ggacatagca attacccctc   92940
cgcatcgggc accacctcct tcagggcaca tgagaccaca ttaaattcta tttactattt   93000
cttgtgttta ttttttggtc agttatgtaa aataaactta ctcttttttcc tccccagatt    93060 attgtcatta agcctttgaa ttctaagcaa attataatcc atcatctatt taggaattag   93120
atttggatgt gctattgtat aattactaat acaaagtcca tatgtttcca gccttttgt    93180 aaaatatgaa gaaatgctct tagcattcta tgtaaaactg tactgttaaa tatatgtgtg  93240
taataaaaaa agcaacagaa aaacagacaa aaacccttca aattaaagga aatctcgag   93300 atattttaca gcattgaaag ggcaaaaagt aaaatgttgg aaggtgatcc aaacttataa   93360
aggagtgtaa taattcacta agaaaaaatg cttgtccaaa ctactttga tacacttta       93420 caaagaaata caacatttga acgcttaatt atctaataaa ttttagtata ctaaataaat   93480
```

```
attaatttta taagtttttta gtttctcaaa ataagagtct tctttaatat tttaacaaaa    93540
aaatctaaag gtcttggacc aactttttcag agtttcagct tgtaaagtca ttttttattta   93600 tttatttatt tttaagacag agtctcactc tcacccaggc tggagtgcag tggcatggtc    93660
tcggctcact gcaacttcca cctcctggtt tcaagcaata ctcccacctc agtcctgagt    93720
agctggaact acaggcatgc gccaccacac ccggctaatt tttgtatttt tagtagagac    93780
agcgtttcgc caggctggtc tcgaactcct gacgtcaagc gatccgctgc ctcaccctcc    93840
caaagtgctg ggattacagg catgagccac tgcacctggt ggtaaagtca ttttttatgg    93900
tcctgcacta ctatgcagag ctagggctgc ctatattcat taggatacaa ctcaaactgg    93960
tataagaaaa gcaggcactt cattggctca catatttgaa atgcctagtc tttggtcttg    94020
cttcaggcat ggctggattc agatttgaaa tgacataaaa agaactcaat taccccttcat  94080 ctcaaactta tatattagat tccttctcag gctcaatgtg atggcctcca gttactatca    94140
tcctcatggt ggcaagatgg cttcaacagc tctaatttca tattttttcct ggttcctagg    94200 aaaacctggt tcctggttca tattttttcat aggttcctag tctaatggaa ttgagtggag    94260
tagactttta tttctaagtc agcaactcct gcacacatcc ttagactgac atttacttta    94320
ctagttgagg ctgccaacct tacacccccaa tcactgtggc caggtgtgtt tcatattcta    94380
tccttgggga caaatttagg cggagcccca tccaaatcac acagattatt ggtgaagaaa    94440
tgcaaaatac tccaaaaaat taaggagaat atgctggcag acagacaata aacatctatg    94500
aactaccctt ggtcctacac ctttaattat cccccacatg agaagggctc caagatctgt    94560
ccagaaatta tgaagtatgt tccctaacaa gacaactccc cttggattcc ctgcaaatac    94620
ctcaaaatca atgtgtttga aggtgaacct cttatgtcct ccaccccccaa ccccaaccaa    94680 gtctatgtct cctcttcgtt ctctatctca atgcatgtca tcactatcca cgttagttgc    94740
tcacactaga aatctgggaa atagcttaac tccttactct ccctcaccca agactaaaat    94800
taatcaccaa tagactcttg ttaactgtaa ccctggtatt ttttaattca acctatttct    94860
cttcatcaat acttctcttg tctcatttca gctgccatct ttatcttttg cctgcatctc    94920
agcaataacc ttttttaactt aatgcccagt cattgctttt ggtttttaaa aggtttgtta    94980
aaacacacat gacataaaat ttgctttttt tttttttttt tttggtggaa actctctctg    95040
tcgcccaggc tggagtgcag tgttgcagtc ttggctcact gcaacctccg cctcctgggt    95100
tcaagtgatt ctcctgcctc agcttcccaa gtagctggga ccaccggtgc atgccaccat    95160
gcccagctac tttctctgta ttttttgtaga gacagggttt caccatgtta tccaggatgg    95220
tctcgatctc ctgcgcttgt gatctgccca ccttggcctc ccaaagtgct gggattatag    95280
gcatgagcca ccgtgcccgg ccatcttaac cattttttaag tgtacagttc actaatatta    95340
aaaacattca cattgttttg caaccgtcac caccattgat ttccagagct cttttcatct    95400
tgcaaaactg aaactctcta ccagttaaac gataattccc cttttttctt ccctatccc    95460 tggcaaccac tattctactt tctgtctctc tgattttgac tattctaggt acctcatata    95520
agtgggatca agtggtattt gtcttttctgt aattagctta tttcagttag catgtatcag    95580
aatttccttc acttttaagg cttgaatgac accctgttgt atgtatatat catattttgc    95640
ttacccattt atctatctat ggatacttgg ctagctttca tgttttagat attgtaaata    95700
aggttgttat gaacatgggt gtacaaatat ctctttgatc cttcttttcaa ttctcctggg    95760 tatatatcca gaagtggaat tgctggacta tgtggtaatt ctattttttaa ttttttgagg    95820 aagtgccata ctgctttttca cagtgactgc aacatttttat gttactaaca atagtgcaca    95880
```

```
agggtttcag tttcttcaca tcctcaccca ccaatacttg ttctgttctg tttttttttt    95940
ttttttgata gtagccatct tatgggtgtg agacactaga caattgatta tcttctaaac    96000
tttttccata ctgtagccag aattatcttc agtaaacata tcatgatcac gtaaccttca    96060
gttgcatgtt taaatccttc agtggcttct cattaacttc aggatagtct gacctccttt    96120
aacatgtttt ataaaaactc attcatgatt tcttccctgg ctaactttc tagccttact     96180 tctcaactgc tccctttcc acctcttccc cctatagctc atcctccact tcctatatac     96240
acatatacac tctatgcatc agtcactctg aaatttgttc aggtctgtga aaatgctata    96300
cttcccctca tccccaacac tattccttct gacagatgcg ctttctccct catcacctgg    96360
ccaactcctg cttatccttg aggtctcaag atagcatttt ctccaggaaa attccttaat    96420
aaattccctc caccaagctt cattagtacc cttactgtgt gttcccagag cactcaacct    96480
ttgccctaac aaagtactct gtgtcaatca cactctgtaa ctgtctgctt acttatcacc    96540
tttcctctaa ttccatgctg gcctatgtgg ctcttggaca ctaaactgta actagtatga    96600
ctgaggaact gaattcttaa tttcaattgc tacaaattgt aaattaacac tgatatctga    96660
atcagttaca gtaaaaattt aaagatgttt ggaacaactt gggtatgtga gtctactttt    96720
tcaactgtaa gttgatgaga tctaaataca gatgagaatt aagcatctga attgagatgt    96780
gctgtaagta taaatacat tgaattttga agacttagta caaaataagg aatataactt     96840
tttagatagg ttacctgtag aaataatatt tttgatatag cagtttacat aaactattta    96900
aatcaatctt atttataatt cagtcacttt ttagtatagc cactagaaat ttttaattac    96960
atatgtggct taccttatat ttctattaaa cagcactgac ctagactata aattctgtgg    97020
agacaggaat cacaactgtc ttctttactt attttttaaaa ttttttatagc attcaccatg   97080 cgttgggtgt taatctatgc attaactagg aattgcaagc attaactatt ttgatccttt    97140 taacaaccttt tgagctaag tagtatcatt atccacatta tacatatgaa gaaatttaca    97200
caaaaggatt cacttaacta gatcaaggtc acagagttga ccctatggag ttagactgta    97260
gaggggatac agaaattata ctcccaataa ctttgttata ctgtttcttg ttggttctct    97320
tattacaggt gtccagagaa agaattacta cccaactttt taaattaaca accatcatga    97380
ttcaattact cttttaaaat taatcaatct gttcattcca taagtattaa ttgaactctt    97440
agtgccaggt actgtgctgg gtaataagga ctctaagttg agtgaaacaa atgctttatt    97500
tataaagaaa ctcttttctga tggtggtgac aatcatataa tgaaataata ataacaaaat    97560
attatacaac acaaatatac atgaagaatc acccatatca gcctggagaa gaggaacagg    97620
agggaaaaag tgagagaaca tcttgaacaa tgagtaggag taaactaaaa gtcggtgagt    97680
gggaggggag aggtagttga agcaggcgag aaggtgagca gagctaagaa atagcctggt    97740
gttggccagg cacggtggct cacacctgta atcccagcac tttgggaggc cgaggtgggc    97800
agatcacaag gtcaggagat cgagaccatc ctggctaaca cggtgaaacc ccatctctac    97860
taaaaatatg aaaaattagc cgggcatggt ggcgggcacc tgtagtccca gctactcggg    97920
aggctgaggt aagagagtgg cgtgcaccgg gcaggcggag cttgcagtga gcagagatca    97980
cgccactgca ctccagcctg ggtgatagag caagactccg tctgaaaaaa aaaaaaagag    98040
cctggtgtcg gtcatggaag tggcttaagg cagtacataa caagttcata tttacctaca    98100
taaaagatca ccctgggtga agttggaaaa gagattggtg gaaagtaatt atcacttaaa    98160
ccagagaaac aattaaaagc ctattgctct agctctgaac acagatgaca gtagtttaca    98220
ttaaaatggg ggcagtggtg aaggaataga catatttca agatatttaa aggataagac     98280
```

```
ccaacttgat atttggttgg cagaaaggtg ggggcgggga tttgttgcag atatttcaag    98340
ttatttagtc aatatgtatt ttcactttt tcctgctaaa ggaactctgg ctttctgagg    98400
agccaatgtg ttcatcttga ataaatggat cttgtttgga atagttcaat tataacaatc   98460
ctgttccctg ttttctcagt ctcccttata gctggggtag tgatccggcc tattctgcac   98520
agtgaactgt aaagagaagt ctactaggag gctcttcagg aaaagctgtt tccttgtaaa   98580
agagactcac aagactgctt ctttctactt ctttttttt tttttttt tttttttt       98640 tttttgagac ggagtctcgc tctgccgccc aggctggagt gcagtggcgc gatctcggct   98700
cactgcaagc tccgcctccc gggttcacgc cattctcctg cctcagcctc ccgagtagct   98760
gggactacag gcgcccgcta ccacgcccgg ctaatttttt gtattttag tagagacggg    98820 gtttcaccgt gttagccagg atggtctcga tctcctgacc tcgtgatccg cccgcctcgg   98880
cctcccaaag tgctgggatt acaggcgtga gccaccgcgc ccggccttct ttctacttct   98940
gtttcttttg aacatgaagg agatgcagtt ctttctcaat tccatcaggg aataccacac   99000
gaattgtaga atattgctg gacatttta ggttattgaa tcaacaccac agcaatctgc    99060
cttgaaccta cttatgtgag aaaaagaaaa caacaacatt taagctactg taaattgagt   99120
tgtccataac ttgtaactgc acataactat ttgatattgg gttaaatgag tagtcaaggg   99180
ttttctctgg tttctgattt aagcaattag gtaagtggta cagggaagtc tgggagtaga   99240
gcaaggttaa tgagaaattt gttgggctaa agactgttta tgctaagttt gatggttgtg   99300
tgcacatcca ggtgacaagt ggaccatttg atatacatgt tcaaattttg aaagagagct   99360
ctgcccttga gacacagatt tgggacacat gagcatagta gcatcaattc atctagaaag   99420
agaaagatac ataaagaaa atatattgc atataaaatc ataccttca agtcaaaata     99480 tgacatgcaa ttaccagcct cacctcaaga tatgtagagc tgggatgtta tctggctgcc   99540
tagtttgaag ataggataca acatcacttg aatatagact agaagcatgt aagaaaataa   99600
tgaaatccag tagcaatatg taggtttggg ttccttaaaa gtagaccctg agacaaaaat   99660
tcaagttatt tgtgaagtta tcccagcaca cataggtagg agagtggaga gaagtgattt   99720
aggaaaatta aggaagttaa caaaggatgt gttatcaggc aattacttct gtgggtaact   99780 ggagcttta ctgctggaga aatcacagag ccattatgca acatatgcct cagagttatt    99840
ccacctgggt atgagagacc tggcctgtgt ataggccaat ttctgttgat tagtactaaa   99900
ggctgctcct acgtgcacag gcagaacagg ctctacaatg agatgcaggt gctggcagtt   99960
gaaagtctgt ctagcataca ctgtaatggt aaggtccaag gattatgggt gaggattatt  100020
gtcagcatct gagatggagc ataatcaaag ccaggaaagc cataggataa caatggggcc  100080
attagaaaag gataagaaga gttaaaacaa aaaaggagac agagtctaag ggaatttct   100140 gagttaaaca aggtgtttac agtgactcag attattccag ccatcttggg tatcagcaag  100200
aagagaccta aggaacacta tgctataaaa ctgcaacttt ggtggcattt gaaaagtaat  100260
tcctgctttt actactaact cttaattctc agcagactaa aaatacattt tcccatctta  100320 aaaagaaca gtccttgaga gaaatgaaa caaagcaacc aaaacctctg tccactccta   100380
aaatatttca ctccatcttg tttttcttct tgtagttgtt ttgtaatttt aaaaaattta  100440
actttcattt taagttcagg tgtacatgag caggtttgtt tcataggtaa aactgtgtca  100500
tggggatttg ttgtacagat tatttcatta cccaggtatt aagcctagta tccattagtt  100560 attttcctg atccctctcc cctcacttct cccaccctcc aacctccacc ctccaatagg   100620
ccccagtgtg tgttgttccc ttctttgtgt ccatgtgttc tcatcattta gctcccactt  100680
```

```
ataagtgaga acatatggta tttggttttc tgtttctatg ttagtttgct aaggataatg   100740
gcctccagct tcatcaatgt tcctacgaag ggcatgatct tttctttttt catggctgca   100800
tagtattcca tggcctatgt attagcctgt tttcacactg ctataaagaa atgtccgaaa   100860
ctgcataatt tatgaagaaa agaggtttaa ttgacttaca gttccgcatg gctggggagg   100920
cctcaggaaa cttacaatca tgtgaaatgg gaagaaggca catcctacat tgcagcaggc   100980
aagagaagtg aagtgcaagc aaaggaaaaa ctgccacttt taaaaccatc agatctcata   101040
agactcactc actataatga gaacagcatg ggggaaaacg ccccccataa tccaatcacc   101100
tgtcatcatt tttctcccett gatacatggg gattataatt caagatgaga tttgggtggg   101160
gacacagagc caaaccatat aattctgcca ctggcctctc caaaatgtca tgtcttcaca   101220
tttcaaaaca caatcatgac ttcccaacag tcccccaaag tcttaactca ttccagcatt   101280
aactcaaaag tccaagtcca aagtctcatc caagacaagt cccttccacc tatgagcctt   101340
aaaatcaaaa tcaagttggt tactttcaag atacaatgag ggtacaggca ttgggtaaat   101400
gttcccattt caaatgggag aaattcgcca aaatgaaggg gccacaggcc ccgtgcaagt   101460
cagaaaccca gccaggcagt cattaaatct taaaactcca aagtaatctc ctttgactcc   101520
acgtctcacc cagggtactt tgatacaaag gttgtactct caatgccttg ggtagctccc   101580
tcatgggctg gcgttgagtg tctgcagctt ttccaggtgc aaggtgcaag ctgtcggtag   101640
atctacattt ctggagactg gaggatggtg gccctcacct cacagctcca ctaggcagta   101700
ccccagtggg aattctgtga gggagctcca accccacatt tcccttccat actgccctag   101760
cagaggtttt ccatgagggc tccaccectg cagcagactt aggcctggac atccaggcat   101820
ttccatacgt ccgccgaaat ctaggtagag gttccaagc tcaattcttg tcttctgtgc   101880
aactaactgc aggcccaaca ccacgtggaa gctgccaagg cttgcagctt gaaccctctg   101940
aagcaatggc ccaagctgta ccttgacccc tgttagccac agccagagct agaacagctg   102000
ggatgcaggg caccaagtct tgagactgca cagagttgtg gggtcctgga cccagcccac   102060
aaaaccattt ttccctccta ggcctggcct gtgatgggag gggctgctgc aaagatctct   102120
gacatgccct ggagacattt tccccattgt cttggctatt ataataacat ttggctcctt   102180
gttacttatg caaatttcat atccagcttg aattcctccc caggaaatga gttttttctt   102240
tctactacat agtcaggctg caaattttcc aaacctttat gctctgcttt cattttatac   102300
gtaagtttca atttcaaacc atttatttgt gaaggcataa aactgaaagc tttcagaatc   102360
aaccaggtca cctcttgaat gttttgctat ttagaaattt cttccaccag atactgttgc   102420
aggaagtcag gaaccccaaa tggagggact ggctgaagct gcagcaaaag aacataaatt   102480
gtgaagattt catggacatt tattagttcc caaaattaat acttttataa tttcttacgc   102540
ctgtcttact ttaatctctt aatcccatca tcttcataag ctgaggatgt atgttgcctc   102600
agaaccctgt gcttactgtc ttcttctgag ccctccaaac tattccaact tttgcctgtt   102660
acccagctcc aaagttgctt ccacattttt gggtatcttt atagcagtat cccactctgc   102720
tcgtaccaat tctctgtatt agtccatttt cacacagcta aaagaaatg cctgagactg   102780
ggtaatttaa aagaaaagag gcttaattga tcacagtatt gcatggctgg aaggcctcg   102840
gaaacttaca atcatggtgg aagggacac agggacatct tacatgctga catgcaagaa   102900
aactgaagtg taaacacagg aaaaactgct acttttaaaa ccatcagatc tcatgagact   102960
cactcactat catgagaaca gcatgggga acagccccc ataatgcaat cacctcccat   103020
caggttccta ccatcacaca tggagattac aattctagat gagatttggg tggagacaca   103080
```

```
gagccaaacc atatcagtgt atatgcacca cattttcttt atttatcaat gatgggcata    103140
aaggttgatt ccatgtcttt gaggaatcac catactgtct tccacaatgg ctgaactaat    103200
ttacactccc accaagagtg cataagtgtt catatctctc tacaacctcg ccagcatctg    103260
ttattttttg acttttagt agcagctatt ctgactggtg cgagatggta tctcgttgtg    103320
gttttgattt gtatttccct aatgagagtg ttgttgtgct ttttttcata tgcttgttgg    103380
ccacatgtat gtcttctttt gaaaagtgtt catgtccttg cccactttt aatgggattg     103440
tctttgaaac taatgagaac aaagataaaa cataccagaa tctctgggac acagctaagg    103500
caatgttaag tgggatattt atagcactaa atgcccacat caaaaagtta gaaagatctc    103560
aatttaacaa cctaacatca caattaaaag aactagagaa acaagagtaa accaatccca    103620
aagctagcag aagacaggaa ataaccaaaa tcagagcgaa ctcagaggag attgagacat    103680
gaaaaaccat taaaaagatc aatgaatcca ggacctgttt ttctgaaaaa attaataaaa    103740
tatatagact gctagctaga ctaataaaga agaaaagaga gaagatccaa ataaatacaa    103800
tcagaaacaa gaagggtggt attaatactc accacacagt aatacaaata accatcagat    103860
aatattatga actcttatat gcacataaac tagaaaatct agaagaaata aatacattcc    103920
tggacacgta caccttccca agaccaaacc aggaaaaaaa ttgctccatc tattttagtg    103980
gaaggaacat tctcaataca attcttttga gattttggaa gataaaatga aagtactcct    104040
attttttgtga taatttgtta gtgactgact tatcttaggt tcaatgccaa tacattgatg    104100
agctagaatc tttatatga catttctatg ccagaaaatg ctgttaaatt cctgaaaggg     104160
ctagtatatt gtgatgtgaa ttatatggaa ctgaaggagg gccacatctg taatcagaga    104220
tgaaaatatg ttgctgacag tctgattttc gcagtttgct tatggagttt gttttaata    104280
actggataac ctatatgcag tcatacttct cattgagttt gaaattttgc catgtgggaa    104340
tccaaaagag gcttatgcta aaggatggct gatgtgccct gatgatttag aatacatcag    104400
actcaaatga cccagtattt gataagctgt ctgtccccaa ggtcaggctt tcctgctgac    104460
atttcagagg cttcctatga atgcagataa acctgaccat tacaaaagaa ctgaaagttg    104520
gttgatccat gaatactta tttgaaggag aatatattat gttatatctg gctacaaaag     104580
cccaagaaat ttaattgact attctgaaac atctcacaca tttcttgtga ttgcttatat    104640
ggtagggtaa tgtttgaaac accattgtag gacagcatgg tggtggtcct ggctttgatc    104700
taatgcctga tgtgtgtaga acacattgta aacacctaag agaaagactt ctttttttcag   104760
ggggaaatct tagttccttg tagcacaaca ccctgcatgc tgagtacaca caacattttt    104820
ttagagaaag aaaatacaaa atctcttagt gcattctctg tgaataactt tccccaaatg    104880
gtgatgagaa catagcaaaa tcatgcacaa gttaagtaac tgtgataaac agcttctaaa    104940
aagttgtgat tcgagtaaga acattagaat atgcattgtt ttcaagcaga aattttcaaa    105000
attgaatgaa ttattgaggc atatctattg taaatctctc agtttcctgc tttaataaaa    105060
aagcctaaac caaatgcaa taaaacaaat gtaaataaaa acatcagatg gctagcttag    105120
gcagagtcag gaaatacaag gcttaagttc agcaccttag ttgtcctgtt ttgacacctc    105180
caaatgtgtc cttaagggaa tgagaagttt gttttgaaaa tatctgccat acggcctatc    105240
tgttcctcct cctgctctcc caacgatgc tgattcaagt cttcttttaa aacaaagcta     105300
atattcaaat ttttaactac tcacttggga ttaaggacta atttacattc cagttcaaac    105360
agaaggagaa gacttggctg gaggtggggg tagtgggtgg attgtggtgg ttgggagggg    105420
tgttccatag tcgttcatgc ctgtaatctc agtatttgg gaggccaagg tgggaagact      105480
```

```
acttgaggcc aggagtttga gaccagcctg ggcaatatag ggaaaccacg tctctacaaa   105540
aaattaaaaa attaaccggg catggtggtg ctcacctgtg gtcccagcta ctgggaggct   105600
gaggtgggag gatcacttga gcccaggagt tcaagcctgc agtgagctat gattatgcca   105660
ctgcagtcta gcctgggcaa cagagatctt acctctaaaa acaaaacaaa aaacagaaag   105720
gtataattaa taaagacaaa ataaaggggc aagaaaaacg ttttgcaatt cattttgaac   105780
ataaattctg gctataagta ttgtatttgg agaggagaaa aagaggatg catcactgca    105840 gtgctttagt ctgtcctttt ctacccaggt acaaatttaa ttccaggacc tttcctaacc   105900
tagaacttac tttccacatt ctatcagagt ccaactctca ctttctttca atctcctctt   105960
atgtaatcta ggtatattcc tatactacac ctccaggcaa catgtttgca ttataataag   106020
ggccttctgg aaataatgca ttttaccaaa ggagtcattc aaatggtggg aatttggagt   106080
agtataacag gccatagaaa gatacatttg ggaaagtagg tcttttcaaa tcttgtacat   106140
gttccatcca gacccgcacc agtgttctta gaataggact tcctaagata tatgttgcaa   106200
aatactagta cttggaattg ctgtatagga gaatgaattt gcatgatcaa gtaaaacacc   106260
tggtaccatg tgtcccctgg gagggtcaca aggacaaagt aaaggtccta agaaatcctg   106320
tagtaaatgt tagggttagg gaatttactt cacttcaaac tatcaagata gtctgtcacc   106380
ttttcatgga tgctggcaga agacatgaga ttcctgggtc agaaataaag aacatgacga   106440
tggcacagca tgtagcatga gcatcatgcg aaccttgatt ctccttgcct tctaagaccc   106500
acaaggagat gcagagggga cccactggat gctgtccatg caatgggttt atgttgcagt   106560
cagagaattc acctttaagc ttggggaatc caactctttt ttttagcaag cccatttta    106620 tcccagagag agactttacc tcattattca cggtaatggt tacccactgc caatacaacc   106680
atgataaatg tgctaggaaa agagtgatca gggtcttaca atggtgcctt ggctggcaac   106740
aatatacagg gttgctctgg gacgatagga gattacttct cctaacagta acaaaatgta   106800
ctcactgtta tttaatctag aaattcccaa tatgtttgac tagacaacaa cattcagtgg   106860
aacatatttt gagaaagtcg atttccattt gttctcaatt ttggacttca cataatggaa   106920
gtgggtcagg gcttttgact ttaggttcct ccatgttttt tttttttaatt tttaaaaatg   106980 ttattaatat aagggagagt ttttcaaaca tgggaccaga caggcaattt tttccaggat   107040
ttacacttcc tcccagtttg tctttgaacc aaatatagat ctcatatatg cttttcgttt   107100
tccagtcaat gcataagata atcacttaca agaccaaata aaaatgattg cagaattttc   107160
tgtgattaat tataattcta gttttatcat ttaggcttct attgagtgga atccccgctg   107220 gaatttttaaa taacacccct gttactgaag ctctgtttca ttctgcccgg cctttatctt   107280
tctcctaata tgaagaatct ccaaaaatat aactcccttta accaattcca gagatcattc   107340
ctttagagta aagaagagaa ttatagctta gttatatgat tcattcatc ccttggccac    107400 cttttttcatc tttctcctga accttgatca tacctctcta cccctttcatc ctgacctctt  107460 ctgattgtgg agaattcttc tggaagtcat tctttgtgtt tccacctctc tctcttttcc   107520
ctccattttt gggggcctgg gtgctatttt aattaaatta ccatgtagac tttcattttc   107580
tcatctgttg aattcactcc agcaatgtgc aattgatggc tgctcttctc ttgttccttt   107640
tctcaaactt tatcttttttt taaccggttc ataatatttg tacatatttg tggggtgcat  107700
gtgatatttt gatacatgca tacaacgtat aatgactaaa tcagggtaat cgagatatcc   107760
atcacctgta acatttatct tttctgtatg ttgggaacat tccagttctt ttcctttaat   107820
tattttaaat gatatgataa attacggctc aaactttatc ttgatcattt acagcctaat   107880
```

-continued

```
tgtcactcgt atcttcatca ttgttagaat gtctctaaat agcagacttt tcaacctcct 107940
tttaaaattg taatcccatg accttctttt tgttgttaag tcttgcatta ttttgtaaag 108000
atgaaaaggc atgagttgat ctttcaaatc ttgtacttat acacccagta aaacatagca 108060
ttagattttc cttttggctt taattaacta agatatatat cttctatcaa aaatttaaat 108120
ttttgtatat aaagatactt acttttacct ttattttat tttgtattat aaatgattgt 108180
tctcagttct ctctgtaaca atatttcaca tattcaatag aactgtgttt aattgcagtt 108240
ccaacatgat atttccttga aattaagggt ggtaaacatc tgtttgctta tcttataact 108300
ctaaaagtgg aagctgaatc aaatgtgcat gataaatcat tagccatgaa tcagtcttac 108360
atatggtaag actgttgttt tccctagat cattgcaggg tattggaatt tttcaaaatg 108420
actacatacc tatattgcag tcatttaacc tgattcttct ttgacatttc ctcattagga 108480
aattgggcca catctaaacg catagctggt ttggctttag aaaccacaca tttctacaca 108540
aatgatcaag ctggccatac agccaagcaa acacatttct ttcagtatag gaggtgcccc 108600
agtgacttga gggaatcaga gtttctctga atatctcatc aaataacaga agataagag 108660 acccttggaa ctatccaggt ggagacattt ttttaataag attggtagct ctggcctcat 108720
gccacatatt cagttagttt tcaggaaatt tattatttgg aagcagctaa aacctacagg 108780
gcctcagtaa atttctgctt ttatattttt atgggaaagt ttattttag gtctgatttt 108840 tctgccctac caccaccctc caaaaagca ttcttgttct agaaatagga aactaaagta 108900
atcagaggga gggaagactt tccaggtgaa gataaaattg tcccccaccc ctcacaaact 108960
agaatgattt agtaccaaga aagatgaaaa aaatgagtcc atgaaatcac taggacagag 109020
ctaggatgaa taattccgct gactactttg tgctactcca ggtgcacaga tcagagacaa 109080
aaatacctgc cctcatggag tatatacttt agtggaggga gacagacaat aaactatgaa 109140
agtgtattga tatggtttgg ctctatgtcc ccacccaaat ctcatcttga attgtactcc 109200
cataattccc atgtgttgta ggagggacct ggtgggagat aatttgaatc atgggggtag 109260
tttctcactt actgttctca tggtagtgaa taagtctcat gagatctgat ggtttatcag 109320
gggtttctgc ttttgcatct tcctgatttt ctcttgctgc tgtcatgtaa gaagtgccct 109380
ttacctccca ccatgattct gaggcctccc cagccatgtg gaactgtaag tccaattaaa 109440 cctcttttc ttcccagtct tgggtatctc tttattagta gcatgaaaat gaactgacac 109500
agtaaatttg taccagtaaa gtggggcatt gctgaaagat acgcaaaaat gtggaagcaa 109560
ctttggaatt gggtaacagc agaggttgga acaatttgga gggctcagaa gaagacagga 109620
aaatgtggga agtttagaac ctcctagaga cttgttgaat ggttttgaca aaagtgctga 109680
tagtgatatg agcaataagg tccatgctga agtgctctca gatggagatg aggaacttt 109740 tgggaactgg agcaaaggtg actcttatta tgttttagca aagagactgg tggcattttg 109800
cccctgacct agagatttgt ggaactttga atttgagaga gatgatttaa ggtatctggc 109860
ggaagaaatt tctaagcagc aaagcattca aaaggtgact tgggtactgt taaaacatta 109920
catttaaaaa aggaaacagc ataaaagttc aaaaaatttg caggctgatg atgcagtaca 109980
aaagaaaaac ccattttttt gaggaaaaat tcaagttgtc tgcagcaatt tgcgtaagta 110040
acaaggaggc gaatgttaat ccccaacaca ttggggaaaa tgtccccaag gtatgtcaga 110100
ggtcttcacg gcagacccac ccatcacaga cctggaagcc tagaaggaaa aataattttt 110160
gtgggccggg cccagggtcc ccatgctgtg tgcagccttg gaacttggtg ccctgcatcc 110220
cagctgctcc agctgttgct aaaagggggcc aaggtacagc ttggcccatg gtttcagagg 110280
```

```
atgcaagccc cagattttgg cagcttccat gtggtgttga gcctgcgggt gcacagaagt   110340
taataactga ggtttgggaa cctccaccta gatttcagaa tatgtatgga aatgcctgga   110400
tgaccaggca gaggggtgg ggccctcatg gagaacctct gctagggcag tgcaaaaagg    110460
aaatatggag tcagaacccc cacacagagt ccctactggg gcactgccta gtggagctgt   110520
gagaagaggg ccgccatcct ccagacccca gaatggtaga tccaccaaca cttggcacca   110580
tgtgcctgga aaagccacag acacactcaa tgtcagccca tgagagcagc cagtagggag   110640
gctgtaccct gcaaagccac aggggcagag ctgcccaaga ctatgggaaa ctacctcttg   110700
catcgccgtg aactggatat gagacatgga gtcaaaggaa atcattttgg aactttagta   110760
tttgactgcc ccgctggact tcagacttgc atgggcctgt aacccctttg ttttgaccaa   110820
tttctcccat ttggaatggc tgtatttacc caatacctgt accccattg tatctaggaa    110880 gtaactagtt tgcttttgat tttacaggct catagacgga agggacttgc tttgtctcag   110940
atgagacttt ggactgtaga cttttgggtt aatgctgaaa tgagttaaga ctttggggac   111000
cattgggaag gcatgattgg tgttgaaatg tgaggacatg agatttggag gggtcagggg   111060
tggaatgata tgttttggct ctgtgtcccc aatcaaatct caccttgaat tgtattccca   111120
taattcccat gtgttgtggg aggggaagga cctggtggga gataatttga atcctggggg   111180
cagtttcccc catactgttc tcgtggtagt gaataagtct cacaaaatct gatgtttat    111240 caggggtttc cacttttgca tcttcctcat tttctcttgc tgctgccagg taagaagtgc   111300 cttttcaccac ccctgccatg attctgaggc ctccccagcc atgcagaact gtaagtctaa  111360
ttaaacctct ttttctcccc agtctccagt atgtctttat caacagaatg aaaatggact   111420
gatacatgta ttaggtgtaa taagagctaa ggagaaaaat aaagcaggga gagggatagg   111480
aacattggcg gtgggtaggg ggaatggatt cgatggtcag aaaatactct acgctgaatg   111540
ttgcatttga ataaaaattt gaagcaggta agggagagag ccacacagaa atctggggga   111600
agtgcatttt aggtgcaaag gccttgaggc aggatcatgt ctggcagtta cagaagaaac   111660
aaaaaggcca agctagagga agcaagttag aagaacaagc aaggaggctg aagcaaagaa   111720
ataaaggaga gtctcagctg acaaagtcag aaaggtaacg tgagggaggc agatgatata   111780
aggctgatat ggtttggctg tgtccccacc caaatctcat cttgaattat agctcccata   111840
attcccacac gtcattagag ggaccctgtg ggaggtagtt gaatcatggg ggcaggtctt   111900
tcccatgctg ttctagtgat agtgcataag tctcaagaga tctgatggtt ttataaggga   111960
gagttccctt acacaagctc ccttgcctgt tgccatattg gatatgcctt tactcctcct   112020
tcaccttcca ccatgattgt gaggcctccc cagccatgtg gaactgtgag tccgttaaac   112080
ctctttttct ttataaatta cccagtctcc ggtatgtctt tattagcagc gtgagaacgg   112140
actgatataa aggccttata ggacattata agaatgttgt gtaagaacat cgtccctgcc   112200
ttcacagagt ttataataga ggagaaaata aacaataatg ataaaatgag atgcctatta   112260
aaattaggaa agtacatgat gctatggagt cgtagagtgg tgggtcctaa tgtgctctag   112320
tgaactcttt ctattaagaa ataatgttct cattgagatc tacaatgtga accagaatta   112380
gatagatgga ggtgtggtgg ctatgcctat agaagaggag taaattgcag ctgctgctgg   112440
agcacaagca ggatcaggaa aaataaacaa tcctgatgtg aacatactag gaactggaaa   112500
gaaatcttat gaccgaagtt aaacaacaag tggggtagtt gttgttgcaa gatgaagcta   112560
gaaaactgga agacagctag attctaaaaa aggcttgtag actacaagag tgtggatttt   112620
acttgaaagc actagggagc catagaagat tgtaaatggg tggggggtg cattacatga    112680
```

```
tcaggtctat ctttctgaaa gatcactcta gatgaagaga gcagattgag aggagcaagc  112740
tgtgtgaaag gggaaacagt taacctactc gtgcaatact gcagggagga ggtaatggtg  112800
ctgttgaact ttactggtag cagtgggaat ggacagagac agacatggac acaactgaga  112860
catttaggga ttagaacaga taggactggg agattgattg ggatgtggag tttctggtac  112920
ggaaggttaa aatagaaaga aggatcaaag acgtcattca aatttctgac ttcgaccact  112980
tgatggatgg ctacaaatag ggaacaaagg agaaagtaca agattagaga tggaatttgg  113040
ctttcagaaa atgccactga tgtacctcag aacagcaatg actgtatttg ttttccgtaa  113100
ttccttctcc taactgaaaa tttaaagata attgaatcaa attgttcctt gggtgactta  113160
gttttatatc tatacttaac acaggaatat catttcaagg tggcatttcc tacagatctt  113220
cccataagtc tgtgtatgtt ccttagacag tggtttcaga aatcaccaaa tgatacaggt  113280
agaaaacata gctaagcacg tggcgccatc ttcaggacag tttgttaaaa gcttataaac  113340
caaccagact gaaaggcaag tttctcacaa cagaacactg actgactcca tcttgtttgg  113400
taataaggag ctgaaaaaaa tgtttctgcc agctccaatt gtgtgaccaa actctttgtc  113460
ttcatgagaa ctgtagttta tcacaggata tagaaaagat ggtagcagat ttttcttcaa  113520
aatccttcca gtttgaaagt gtctgtgagc tggaaaatga gcttttgctg tggaggagac  113580
aagaaactat ggcaccatcc cttcaggttt tttgccttgg tattcagatt ctctggtgat  113640
tttcccattt tagatattta tgttctgttc tttactaggt gcttcattaa atatgtggtc  113700
aagtggaatt taacttataa gcattcacaa tgctttacaa atgcatgaat ataaaaagta  113760 gggggggaaaa catttgtcag attttgtacc caaggttttg gttcagggaa agcagtctta  113820
tagatttata cagtctccat tttaaaaata aaaggttgtt aataagaaat caatagtaga  113880
cccatagcta accacataag aaagacaaat agagcttact agatgacttt tattttttcaa  113940 atcctctcag cttgtaatta ttctatttga gtaagctcca ccttttcttt gtgcagagtt  114000
gggctataaa gacacacaca tatacatgtg tttgtcataa tgtatctgcc acctttctgt  114060
gctggatgtg gtgtttaacc tacactgagc atttggcatg gcctcgctga ataactggga  114120
ggtaaactgc ttggcttta catggaggca aatgctttct accatcttgc agcattcact  114180
cacaaatggg ctttctttct aaactttttct cattagaatg tatgccttgg gttgaggaat  114240
cttaaatccc agagttcctt tcaatcctga agaggtaac atgttaagct aaattccatt  114300
tctgtataaa ctgaggccct ggccgcccca tcaatgatgg gttgggtttt cctagagtct  114360
gaatggggct tatgacaggt gggcagaaag agggtataca cagaaggtat agtatcttat  114420
agtaattacg tgtttacaac agaccaggtg ctttacatgg gttatttcac gtaatcctca  114480
taacaaccta tggacacttt ttaaatgaat gagtattttt aatatctgta ttttacagat  114540
caggaaacaa aaacagagaa tgaaataatt tgcccaaggt cttacactct cctttaaagt  114600
aaacttatag aaatgaattc taactcaggc attcaccctc taaacccgac aagcttgata  114660
gaaacctcaa actaccctta aattgaaaat atccttatgg cacagacctg aaataaaccct  114720 ccaatcaaga atcaagccaa taattcagta gaagattcag agagcaaaag atttggaact  114780
gaaggcagag ggcagaaccc ggaatgattc tctggagtgc agaagttctt tttaatggtt  114840
cgagagtctt ggaactgctt gggccacatg tgacaacaca ggtccttgag acttcagagg  114900
gtgagtgtgg gagagactgg cactgccaca gatgagcctg gaggaatccg ggaatttacc  114960
attgtcctct tcacaattgt ttttaggatc aagcctagag ataaagagcc atggtctctg  115020
aaaataatgt tgaaaacaca cttacaacac agcagaagca gaaataaatg acatatttca  115080
```

```
ctctgttcat tcaggcagag gtgggtgcac agaacatggt gctgcaatgg tctcctgaag   115140
ctgaggccag ctaacaggcc cgcaggcaag tcaatgggat gaccagcaag tgggtggcac   115200
cagcaacagg gacaagcata cggcttagag tctgaaaccc tggttccagg ctgaacactg   115260
tcactgacta tatgactctg ggcaattcat ttaaattatc tgaactttaa tttactcagc   115320
tgaaaaatgg ctgtaatagc caccaaatag gattgttggg gtatcagaga aatcacgtgt   115380
gtgaaacact gtacgcttta atactcactg agggccttgt gtgtgctaca cattaggaat   115440
agaaaattga gacacagttc ttgctctgaa gaagtttgca atctaatgat atacactgta   115500
aatgttcatt ctctttattc ttataagccc ctcttctttc taattctccc ccatcccctt   115560
aatttggatt ttgtcttaag tttaggtttt ctcaaaagca gatccttagg caaggacttg   115620
cacacaaggg gtttatttgg agatgcaaat aaacagatga ggtgagaaaa agtgacatag   115680
gaaaggcaaa atcgccaata tagggtgcac tgttaagtcg actaccatga caggccactc   115740
tggaaaatgc tgcaaaacac acaactcaga gattttctta cttgaggcag cggggagcta   115800
gagtattttt acaccaactt ccattcatca atagtagaag gcttctttta ctgggtgtca   115860
actcccaggc acttttgtcc tgccaggtgt atgggcagaa tgtatctcgc agcagcttct   115920
gaaaaaggtc ttggtcaaag aaatggagat actggcagtt ggaaagtggc tggtgcacac   115980
tgaggtcaaa agagccaggg actgggcagg gtgttgacag catctgcaaa gattggccca   116040
ttcgtccgcg ggttcctggg tgggctccct ctttccctac cacccaaggc aaaaccaaga   116100
gagaaggatt tttcaacaac actgtagagg caggaaataa aaagatgtgt ggattggtgg   116160
ttcttaaatg tatgctaatg ctgtctagtg gcaactttga ctcatgaatc attgcgcttt   116220
ttcagaaatg aggcagaact ataggtcagt agaactattg tttaatggtt caactttctg   116280
tgataataga aatattctat atcttcactg tatagtatag tagccacaag taacttgagc   116340
ccatgaatgt ggtaggtgtg actgaggaac tgcattttca cttttattta atttcaatta   116400
atttaaatca cctgtggcta gtggctacca tattagacaa tatagcttta gagtatttaa   116460
aactatgttt cattattcac aagtcatctt aataattttt aaaataaagg atagaggtaa   116520
ataagttata ttaatgagtg ttaaaatcaa tattaagctg atttttttt tttgagatgg   116580 agtctcactc tattgtccaa gctggagtgc agtggctcaa tcacagttca ctgcagcctc   116640
gaccacttgg gctcaagtga tcctttcacc taagcctcct gagtagttga gaccacaggt   116700
ggacatcatt acgcctggct aattttttttt attattattt gtagagatga ggtatcacta   116760
tgttgcccag gctggtctca aactcctggg ctcaagtgat cccctggcat tgacctccca   116820
aagcgctgag attatgggca tgaaccaccg caaccagtct taagctgctt ttaacaacat   116880
taaatggaaa ttgagctgag gtcacaacca aatatcacta ttctaataga aactttggga   116940
catgggaata aatatgaaat cttatctaca tttattataa aatctatgat aacaatttta   117000
gtagtcaaat ttctaaagtt tgacataata ctgtaggaac aataatatct cagcagctct   117060
actgcatatt gatgattcta agtaaaggat cactttggat tgattactgt tgatggagga   117120
gaaagatatt ttgagataca ggattttttct ttataatctt ttcttcacaa tctcactaat   117180
tatatctcat attattatac aaatttctat aaatatttgt cgactcaaaa tctatatata   117240
gcatacttta caattttaac tgtttactag atttacattc tctcttaaaa gtcatattaa   117300
ttgtaatcta gtttccactg taactatttg aaagtctttta ataattgttt ttgtacctaa   117360
ttaatagctt tcagaatcat cattattgcc atattttacg cctacagttt gttctactat   117420
aatatgtgtt tctgcactgt gaatcagctc atatgcacta ggatcagagg atggtgttat   117480
```

```
cttggggatc acattggttt acatggaata ttttccagca tattaatgtt ttgtaccagt 117540
gtgtaatggc atctgaatgc aaagtgcact aacccagctg aatgtcttga gctgggttgc 117600
actgtgccat tcattcacca tgctcctctt ggctccctgg caacatgctc tttcctggag 117660
gtacttatgg catggttctc cctgatcttt gtgtactttg ccctcatctc cataactcag 117720
cagccccaat ccttcatcgt attcccttcc acagattagt tttagggttt tgttgttatt 117780
ctttgcgaag tcctatttat acagtagtat ttcttatttt attagtcatt taacttttca 117840
atagctgtgc tggcattttt actaggatta tcattttgt tagcacatta attataaagt 117900
ttgtatgttt tgagtggaat tgcatacaat tagagtgact tcaccctgat actattttgc 117960
atctattgtt tttagtgtat aatcttgtag acttgagttc acttcttttt aaagaaatac 118020
atttgttgca ttaaggcaaa acaactgtgc atcagttttt caattgaatg agaagatagc 118080
aacaaaaaca ataacaaaaa tcataaggag gtctagactc cagattgcga ttagaatgat 118140
tgcctacatt tgaaagtgaa tattcagata tgaacgatgt ttcaaattat atgctttgtt 118200
tatgttattg gttttcttaa gccaattaga tatgatggta atttccaaat aatctcactg 118260
gtcacatata agtcctggga tgccagaaat gacagtgaag ttggttattc atgatcttcc 118320
aaaatcctag atcaaagaca aatgaaagca tagatgttgg ctgaatactt aggccaaaga 118380
caaagttcta tgtctctatt agaaagaaat aaatgcacac tggcctacat aaatttttatt 118440 tatatataaa atttaagtat atgtaagtat atatatatgt ataatttaag tatatttgta 118500
tacatatatc ggtttttttt tttttttgaga ttttggtaca tgttcttttt aggtcctaaa 118560
aagcctaaag aatggccagg tgtggtggct tatgcctgta atccccacac tttaggggggc 118620 taaggtgggt ggatcacaag gtcaggagtt cgagacctgc ctgaccaaca tggtgaaacc 118680
ctgtctctac taaaattaca aaaattagct gggtgtggtg gcaggcgcct ataatcccag 118740
ctactcagga gactgaggca ggagaatcac ttgaactcgg gaggcagagg ttgcagtgag 118800
cctagatcac accattgtag tccatcctgg atgacagagt gagactctgt ctcaaaaaaa 118860
aaaaaaaaag cctgaaaaat ataacacact tcttccccat ttagggggcc tcctctttgg 118920
ccaaatataa tgctgtttct tagaatatat atgtagaaaa agcatccatg aatggcatgt 118980
tcattctcag gagtttgagt gcttgtatct cagatcaaag aagtttgtta gcaagtggta 119040
ttaatatttt gggagaagtt gtttcctagg tgtatgtttg tagggaggca gtataaagat 119100
caattcatat gtacccaact cagtttagtg cccttaaggt atttgtcttt tgaagaaaac 119160
tacaataata ttaacatccc ttaaaatgta tgtgcattaa tttcagttac atacttttaa 119220
ctgcctgcca tcaaatttag ggcttcacac tgccagtata actcaggaat gctgcccagt 119280
ggcaaacagc aaagactaag atgaatttgg agcttgatgc aaaatgttct ctgggtcagt 119340
atccaccatt ccaggtgcca tctggagatc aagtgcctgg agattgtgcc ttgagacatt 119400
ctattggtta gaaaggcaga ctctgggttc aaagctcagc tacgtcacct ctctgctgtg 119460
taaacttggt aaattactta atatctttgt ctcaattttc tcttttttga agtctgggt 119520 aaaatgattc caattatttt gggttgctga gaggattaaa tgaaataaac attaagtaat 119580
tagcataatg cctggcacat tataaatgtt tgatgcatgc tagccttcat gatgatgagg 119640
ttttctgagt gttttttttc caagttataa gtaaaatcgt gactgtgaaa tagctagtat 119700
tgcaaagagg ctcccagctg aaaagccata gaatgctgtc atcactggag tcaggattaa 119760
ggtaatcagt catattgaaa aggcaaactg atcaccagca ttgattaact acatggaagc 119820
agagcatctg accccataga caagaggatg ttacattatg accaaacaaa aattcctgtc 119880
```

```
aaaaagaaca tgggaactaa tgcaactaat ggcctaggct aataactacc atgcaattgg  119940
atacgccagt gacatttggt ctatctcatg aacaagcatt ttgatatatt cttttttcac  120000
aacccatata tttccagtat acattcatgt gatataccct aaaaggacat aatgtctatg  120060
accacatgtt gagaactcat ggagggcatg ggtaagagta caggctctgg tttcacattt  120120
tccagctctt ccatgaacca gatgtgtaat tctggcaaat tgctaaagac tctgagtctt  120180
ggttttctca tctgtacaat ggaggtaaaa atgattccta ctgcatagat ttattatgat  120240
gactatacag tttaattgac atcgaatata tggtgccttg gcataatta aatagtcaat  120300 aaatactacc tattaatagt tgtaaattat cattattttt aagcatttat aagtgatcca  120360
ccattttaca gagacttaaa catcacctat gtccagagtt cctgctatgc atgttaggtc  120420
atatatctga aaatgagtgg aaatggcagt taagaaggag gcacagagca agtttctatt  120480
tctaaatgga aatagagtta gaaatagaat ttctctaaca gtgagttaga ctagcattcc  120540
actagtcaga atctatgacc ttacaacatc taattgtgtg cccaagagga aaagacatga  120600
gttttgaaac ggatcctagc ctctgcccca gacactttg tataaagtta ctatattacc  120660
ttttaaaata gggaccataa tacaaatttg taatctaact aggaacaaga gaaaactgaa  120720
ttgtagctgg agattcagga acaactgaac tcaatatatc tcattactac agaataaaga  120780
tctatgaatt aatttttatg caaatcaaaa ttcaatttct tcggaaagct ctttgatgat  120840
tacaagaaca aaaactagca gttaattctt aatctggatg aggcactgtg ctaagagctt  120900
tatacattta tctaatttac ttactgttgc tataccttaa tgaagtagga gtgattattt  120960
ctattttata tactgaattt ctattttata ctgaatccca agaaagtcaa catccaagaa  121020
atgtactgcc ttgcccaaga tcatagagac agtacaaggt ggaatacagg ctgggcgcgg  121080
tgactcacac ctgtaatccc agcactttgg gaggctgagg caggcagatc accaggtcag  121140
gagatcgaga ccatcctggc caacatggtg aaaccccatc tctactaaaa atacaaaaaa  121200
attagccagg tgtggcagcg tgctcctgta gtcccagcta ctcaggaggc taagacagga  121260
gaattgcttg aacttgggag gcagaggctg cagtaagccg agatgggcc actgcactcc  121320 agcctggcaa ctgagtgaaa ctccgtctca aaaaaaaaa aaaaaaaaa agaagtggaa  121380 tagaaatgca aacacaggtt ttgttcccaa agccatgaga ctctactgct tcttgtaact  121440
tctaatcatt cctctattca gaaatccttg tgtataacca tctgatgctc ctatatgtct  121500
ctctgcaaat gttgatttct aagctgtatt ggttaattat tactgtgtaa caaacactct  121560
taaagtactg agctttaaag caagaatgac ttgttatttc tcaagattct gcaggttcac  121620
tggatggttt ttctctttca gttgggattg gctggagtca catatgaagc tgtatccaac  121680
tggtggctgg ctgggctggc tggagggtcc aagaaagctc ctctcacatg cctggggccc  121740
ttgtgttatc agctgtgata cctaaattct ccttcatgtg gagtctctcc tcatagcttt  121800
ttctcttcca gaacctctcc actattttta tagaatagtc tggaattcct tacagcatag  121860
aggctgtctt ccaatagcaa gaaaatagag gctcccagtc ctctttaggg cgaggcccag  121920
aactggctca gcatcacttc tgccgcattc tattggtcaa aggagtcatg agcctagctc  121980
agattaaaag agtggggaaa gagatttcac tgctcagtgg aagaagcagc aaataattta  122040
tggccatcct ttaatccacc acatgccatt ctttgtagga acatctggca ctgccatcca  122100
actaaacccc tgaagggaac atctggatct tcttgaggtt gcaattggtt cttaacagct  122160
agaactatgc tcttctgcac acaatgagtc taaaaaattt tgattaattg aaagtagaaa  122220
aaccacaatc tattaaattt ccgtgggaga aaaagcagct agaacactca caacagaaca  122280
```

```
gagaccctga ggacatctta ggcttatcac ctgtggaatt tgttaaataa ctccttccaa   122340
tcattttctt tccagagaaa ctgtggcaat gcacctacat cgctttatgg gttctctgct   122400
tctgtgcatg cccagtctta gaggctcacg gatcatctac ttgtctgagc tgaaatatgg   122460
aggctttcta ctgatttgca tctgaaaatc acaaaaagtg gtacatttgg aatttagggc   122520
aaatgataat ttaacattgt acaatgaact aacaatcgca tcaaaagatt ctgctaaaat   122580
gattgtccat tttttgttgg ctgtctatta gaagaaaaag ttacttaggg cacacataaa   122640
aaatatgttg gctctcacat gatctatttt caagcatagg tggctaatag ggctcaccct   122700
agacatgata atcttggcta tagagtatgg catcagccct taattgttca ctactttata   122760 agggatttt tttctaggta aggcatacac acacatgtgt acaagccaat aaataaataa   122820 taaaggtga taaagttgta agttgtacaa gtataaaact atgagactga ataggaatca   122880
gcaattgggt aaccttatca gtaaaacaca gggatgcccc ttgtgaaagt gaaacagctt   122940
ggttaaattt gccctgtctt tctttgcagt aaacatccaa aaccatgcat tcacatatgg   123000
tttgctgtag tagaagtaac acctttttgct tccattccag cctccttatt tgccaagatc   123060
cctgtaagca gataatgaca aaaatttatg agggttagat ccaaaaacaa aggcctggag   123120
gcatattgtt ggaaagataa aaactgctttt tttgggactt ctctatttct ttattacctg   123180
agaaaagatg gagtagtaat tgacatgtgg ttccttgacag atgttgacaa gggaaaagca   123240
tgtcactaag cccctcggag ttttttgcaaa ggattatgat gcttgtctcc atgttccata   123300
acctcaagag tacaatcaaa tatcctccct tactccaagt gccaaacaga catccatgca   123360
gatgctatag gactatatca gcatctggcc aaagaatata attctcttgt ctcacataaa   123420
gggtatacac aatagagacc attgaaagtg gagtgagtgc tttgatatat tctattgtta   123480
atctctcttg aaatagagtg atttttgtgg agaagtaatt caccaaaaat ttccttttt    123540 aacactcaga gcttgtatcg tggcatgcac tataaaatta aacaatttat tgttttgctc   123600
caaaattgta tccatatttt tattagataa atagtagga tgataggaat attaacaaat    123660
atgctattag aatagtactg gatgagagta agaattgat ttagacagga aacatttct    123720 ccgtatttgc caaacatcca gatgaaaagt tgaaaatttt tcagtcatgc agatgttcta   123780
aatatccaga tgttatgtag agaagatatt tggcaacaaa caaaactttc tttattcatc   123840
catatgtttc attctacttt catttttgtag aaaaattgtag aataatggaa attacaagca   123900 tatttagtt tatgaaacca aaaatcaagc aaaatgtagt aatactatt tcacatttct    123960 tttcagtatg tctgcggtag taaactaaga attcctaggg ctttaatgaa agaagaattg   124020
tttatgattt taaaaaatca cactgatctg atttcagtat gcgctgtatt cctttctcac   124080
tttatattac tccatgtttt aataatatgg ctaaataatg atttgagatt ttcatttgct   124140
ttagccctta tattttaag tttacctctc ttttctgtat taactccagc agtagtttct    124200
gtggttctac cagagaggga gtacatatca gagtgaaggg cacaaatagc tataaatcac   124260
cctaaatttg gtttccaaaa cttaagcctc aaagaaaaga gtctggttaa tatgaggaaa   124320
aataaagaca cacatttttt cttggacttc taaatttgtg ggcagataaa ctaaaattga   124380
atagtgcatg cagaggttat actatcatga ttgtatcagt cagcttaggt gagcttaggt   124440
atgctttagg aacaatcaag tccaaaatct cttcgtaaaa gcaaagggtt atttctaaca   124500
ctacatgtct gctctggatt ctctctactg gatatttaaa ctgaaggaga acctccttgt   124560
tgaaacaatg actttcctgt gacaaaaggg ggaaagagcc aggcatattg gcacacatcg   124620
gtaatcccag ctcctcagga ggctgaggtg ggaggatagc ttgaacccaa gagttcaaga   124680
```

-continued

```
cccacctggg caacatagca agattccatc tcaaaaaaaa ggggagagaa aaagaataat 124740
ggtggatccc acaatggctc ttaaatcttc tgttcagaag taacctatgc tacttctgct 124800
caaaaataat tggacgaatc aagtcatatg accaatcctg atatctttgg ccagtaatta 124860
caatcttaat attgggacag gctctaaggg aaagatttgg cagggagtgg aaacattttt 124920
acctcaatac aataccacag ttctcatttt aagcatgcat tatgtgctta attgttcata 124980
tttctgggtt agatgtgtca aaatagttat tcatctacat tttccccatg ggagaatgta 125040
aaatatgaga gaaacaaca cttaagacag atagaaaaca ggatgaaaag agtgaagcag 125100
tgttggatgt ttccagataa gtatgcagta ttgttttata aatcacatac agaaggacag 125160
taaattcatg ttcagaatag aggaaactgg tctccatctt atcaaattga aaaagtttg 125220 tgaaggaaaa gtttgtggct taggagccat ttgaatgggg gagaaaagta ataaataatg 125280
ataactaaca tttgagtgtc ctcttacaat ttataactgt aatttatt aatacttta 125340 gcaaccacct gagggagata gcattgcttc catttacaag tgaggacact gaggctcagg 125400
ttaaatggtt ggcccacatt ttcagaataa gtttcagaag gagaatttga gcaattgctc 125460
tacttctgta cattgtatgc tttacacaca gaaaaggatg agccaggaaa agcatgtggc 125520
gtacgtcagg agagggtccc aaatgagggg atagaatgga aggaaatggc ccaagcacag 125580
tgttggattt ggttggtgga attctcctat gtgagaatat gaaggaagtg aagcagtcag 125640
gtatatgtga cctcaagtgt tttgaagtcc ttaattggtg atatgggaag aaatacaatg 125700
atttacttaa gaaatatttg ttgaagacct gcagacaaga tgatagacaa ggaaggcatt 125760
gccaatacag attgtggaca tggaagaact tagctgcgcc taaaagttag gttaaaattt 125820
tttttttttt tttttttttt gagacggagt ctcgctctgt cgcccaggct ggagtgcagt 125880
ggcgcgatct cggctcactg caagctccgc ctcccgggtt cacgccattc tcctgcctca 125940
gcctcccgag tagctgggac tacaggcacc cgctaccacg cccggctaat ttttttgtatt 126000 tttagtagag acggggtttc accgtgttag ccaggatggt ctcgatctcc tgacctcgtg 126060
atccgcccgc ctcggcctcc caaagtgctg ggattacagg cgtgagccac cgcgcccagc 126120
caggttaaaa tttttaataa tttaattcta ttttccatcc cccaccttca gctgccttag 126180
gctagcagga tattaagcaa aactgttcat aattattaga attataagga aagattggaa 126240
aatgggtctt ggttctcttt ggagaaggat attgattcct gtcgttagtg gaaagagcca 126300
gggtactagc attgttgaaa aaaatcgtga ggttgaccac ttctggccag agacaacagt 126360
gaggaatgtt ccaatggatt tggtttctgt gttcattcaa gtcttctgag aagtagtcac 126420
caagatgaga ctagacctgc aagagatatg tttggtgaaa aacctatgaa ggatagcagg 126480
gagggagcag gagaaggtag ggaaagcact cagactatga tgcaggtctc acacttgtga 126540
aagagagggg aaacagaaga gttgggtaga aagggtctca ggttgcagtg gagttttaag 126600
aaagttttgg ccaggcttga gaagctgggg tgttctcaaa ccaaaatggc tagacacagg 126660
aattctgtgt ctagtgggaa tgggctggga atactaccct cgttccactc agtctttggc 126720
tggcagctcc cagtggaaga tgtggcctca gtgtgaacac agtaatggat ctagaggagc 126780
aggaattggg gccatcagtc aactatgctc cccacagcag gagatatgta ccaccacagt 126840
ccaccccttg cactgcgagc atctacttct ccattcaggt ttgggggaga attcctccat 126900
ggctcccatc agcctccctt catgagggga tcttagaggg aagttagtgg aacacattat 126960
ggtccctgtc actgcagttg gtctcagggc tataactggt attcatcccc ttactcctct 127020
attatgaatt ctaaattccc tgcctccccc gccctcgctc agctaccacc ttggcatgtg 127080
```

-continued

```
taattgcctt acctggtgat attatctgaa tctttatttc taaggtatct gggcttctgg   127140
caataataca tttctcagac caggttgctc tacatgtttg ttaaccacta tagtgggcca   127200
aagatgtatc aggaggtgcc cagttggatc acctgagttg tacacatatt ccttcctagc   127260
cctattggtt aaaagcagcc ctacctcctc cggctgatca tggtaaatta ccctgccaga   127320
aaggttattc ttttcctgat ctgcttgtcc atggacacaa ggagtccaaa gtgccctggt   127380
agaagtcaga gcttatagtt taatggtaac cttttctttag ctcctgaaat gagagttctc   127440
tctttgcaga ccagtacttc taagcttgta gagttcataa ctgtgggaaa tatgagaacc   127500
accccctcta gtgtattgtt tggaaggatg gtaagtggga ccaatcctgc ttctactcct   127560
tggttcccag ttccatgtag ttttcctgtt aggaatacag caccatatgg aagtttctga   127620
tttaatgcac atactgcatc ctgaagaatg gtaccctatc ttttcagaga attgcctctg   127680
agctgaagct tcatctatgt ctttaggagg ttatccaagt actctctaag gctggctgct   127740
tatgcatgtg cttatgcata agatcagtgg atgcgatggt cttgtcagag atccagcctt   127800
ctgagtaggg tggtatatga caagatcagt gtatcttatc caatgtgtcc agtcctgtac   127860
ttccttcatt ttgaagtggt taccctggtt ggatgctatg ctgcacagga tccatgcctg   127920
tggattaagg cagttcataa gtccctagat agcagagctg gctaaggctc tgtaagcagc   127980
aaaggcaaat ctacacttga aatgggtatc ctttcctgtg atgatgaacc aatggcttct   128040
ctagaatgga cggagcccag tgtagccaat ttgccatgaa gtagctggtt ggtctttatc   128100
aaatatagta ccatgccagg ggcttggtat tgaaattcag aggcagagat aattacattg   128160
gccttgtaaa taggagtcta tgctgatgga cttgcccaca gcctttgtac tcacaggctg   128220
tttctggagt ggccaatgag aaagaatagc taacatcaac caggcaaatc attttgtgga   128280
ctttgttgtt caatacttct tcaatggtag atgctttctg gtggcagtta acatgtaata   128340
caaaaacaca ttttgcgcaa ctcccacatg tcccacatgc ctctcctgac aacttcttgc   128400
atcttatttt ctagtccttt ttcttccaag cccctaccaa ttggccaatg tctaggaatc   128460
tttatatatt ctcaccttgg accacttctc cttgcatatc aaaagaataa tcaagtacac   128520
tgttcttagc tgtgcccaat gggaagattt tttcctttcc actgtttctc aagggtaccc   128580
ctgaatgtgt ctgtaatgca gtcactgtcc atttgcagtc aaattctggt cctacaccat   128640
atgggtcctg cagtcaaggg cctctctaca ccatatgccc taactatgaa atgagcctgg   128700
aaaaaacttt tcaaatagat atttctcatg ctgtagcata taagttatgt attttctttt   128760
cttagtctct tattttatat gcatttgatg cctcaaaaac aagaattgta tattctaatg   128820
aataaaccaa aaatatacat atcttcttcc aaggtgccaa acttgacagt attcaggaat   128880
atatcttatt tgcatgcaca tttgtgttta ttctaaatta aagaaaata aatgtataca   128940 agcccaatcc ttgcttgcat gaatatcttt ctcactaatt gtttcctact gtatttccac   129000
ccagaaaagc aggaagctga aatcatttac agttagtaaa gcaataccat tgccatgctt   129060
tttaatacac aacaaaccat aattggatga tcaacaattt ctgtatgctt tagcaacaat   129120
caagtccaaa atctctttgt aaaagcaaag gattatttct aacactacat atctgctatg   129180
gattctctct actggatatt taaactgaag gagaacctct ttattgaaac actgactttc   129240
ttgtgacaaa agggggaaag agccaggcat agtggcacac atctgtaatc ccagctcctc   129300
agaaggctga ggtgggagga ttgcttgaac ccaggagttc aagaccaacc tgggcaacat   129360
agcaagattc catctcaaaa aagggggggag aaaaagaata atggtgcacc ccacaatggc   129420
tcttaaatct tctgttcaga agtgacctat gtcacttctg ctaaaaaata attggagaat   129480
```

```
caagtcatat gactaattct gatatctttg ggcagtaagt acaatcttaa caggctctaa   129540
gggaaatatt tggcagggag tggcaatatt tttacctcaa tacaacttgc cacaattctc   129600
attttaagca tgcattatgt gcttaattgt tcagatttct gggttagata tgtcaaaata   129660
gttatttgtc tatattttcc ccatgggaga atgtaaaata aagagaaaa catcacctaa    129720 gacagataga ggttccgttc caaggcggcc gaataggaac agctctggtc tacagctccc   129780
agcgtgatcg acagagaaga tgggtgattt ctgcatttcc aactgaggta cctggttcat   129840
ctcactggga ctggttggac agtgggtgca gcccacagag ggcaagccaa agcagggcgg   129900
ggcattgcct cacccaggaa gtgcaagggg ttgggggatt tcccttttcct agccaaggga  129960 agccgtgaca gacggtacct gcaaaaatgg gtcactcctg cccaaatact gcacttttcc   130020
aatggtctta acaaatggca caccaggaga ttatatccca tgcctggctt ggcaggtccc   130080
atgcccagag agccttgctc actactagca cagcagtctg agattgacct gcaaggcagc   130140
agcctggcat ggggcggggt gtctgccatt gctgaggctt gagtaggcaa acaaagtagc   130200
tggggaagct cgaactgggt ggagcccacc gcagctcagc aaggcctgtt gcctctgtag   130260
actccacatc tgggggcagg gtgtagctga acaaaaggtg gcagaaactt ctgcagactt   130320
aaatgtctct ggctgacagc tctgaagaga ccagtggttc ttccagcatg gtgtttgagc   130380
tcgaagaatg tacagactgc ctcctcaagt gggtccctga cctccgtgta gcctaactga   130440
gagaaacctc ccagtagggg ctgactgaca cttcatatag gcggatgccc ctctgggaca   130500
aagcttccag aggaaggatc aggtagcaat atttgctgtt ctgcaatatt tgctgttctg   130560
cagcctctgc tggtgatacc caggaaaaca gggtctggag tggacctcca gcaaactcca   130620
acagacctgc agctgaggga cctgactgtt agaaggaaaa ctgataagca gaatgaata    130680 gcatcaacat caacaaaaag gacatcaaca aaaggacat ctacaccaaa accccatctg    130740
tagctcacca taatcaaaga ccaaaggtag atgaaaccac aaagatggcg agaaacaaga   130800
gcataaaagc tgaaaattct aaagaccagg gcacctcttc tcctccaaag gattgcagct   130860
cctttccagc aatggaacaa agctggatgg agaatggctt tgacaagttg acagaagtag   130920
gcttcagaag atcggtaata acaaactttt ctgagctaaa ggaggatgtt caaacccatt   130980
gcaaggaacc taaaaatctt gaaaagagat tagatgaatg tctaactaga ataaacagtg   131040
aagagaagac cttaaatgac ctgatagagc tgaaaaacct ggcacaagca ctatattacg   131100
catgtacaag cttcaatagc caattcgatc aagtggaaga aagggtatca gtgattgaag   131160
atcaaattaa tgaaaaaaag tgaagagaga agtttagaga aaaagagta aaagacatg     131220 aacaaaagct ccaagaaata tgggactatg tgaaaagacc aaatttacat ttcactggtg   131280
tccctgaaag tgacagggaa aatggaagtt ggaagacatt cttcaggata ttagccagga   131340
gaaattcccc aacctagcaa ggcaggccaa cattcaaatt caggaaatac agagaacacc   131400
acaaagacac tccttgagaa gagcaaaacc aagacacaca attgtcagat tcaacaaggt   131460
tgaagtgaag gaaaaaatat aagggcagc cagagagaaa ggtcgggtta cccacaaagg    131520
gaagccaatc agactaacag tggatctctt ggcagaaact ctacaagcca gaagagagtg   131580
ggggccaata ttcaacattt tcaaagaaaa gaattttcaa cccagaattt catatccagc   131640
caaagtaagc ctcataagtg aaggagaaat aaaatctttt acagacaagc aaatgctgag   131700
agattttgtc accaccaggc ctgccttaca agagctcctg aaggaagcac taaacatgga   131760
aagaaacaac cggcaccagc cactgcaaaa catgccaaat tgtaaagacc atcaatgcta   131820
tgaagaaact gcatcaacta acaggcaaaa ttaccagcta acatcaaaat gacaggatca   131880
```

```
aattcacaca tgacaatatt aacctaaaat gtaaatgggc taaatgcccc aattaaaaga   131940
cacagactgg caaattggat aaagagtcaa gacccatcag tgtgctgtat tcaggagacc   132000
catctcattg cagagacaca cataggctca aaataaaggg atggaggaag atttaccaag   132060
caaatggaaa gcaaaaaaaa agcagaggtt gcaatgctag tctctgataa aacagacttt   132120
aagccaataa agatgaaaag agacaaagaa ggccattaca taatggtaaa gagatcaatt   132180
caacaagaag agctaactat cctaaatata tatgcaccca atacaggagc acccagattc   132240
ataaagcaag tccttagaga cctgcaaaga gacttagact cccacacaat gataatggga   132300
gactttaaca ccccactgtc aatattatac agatcaacaa aacagaaggt taaaaggat   132360 atccaggact tgaactcagc tctgcaccaa gcagacctaa tagacatctt cagaactctc   132420 cacccaaat caacagaata tacattcttc tcagcaccac attgcactta ctgcaaaatt   132480
gaccatgtaa ttggaagtaa agcactcctc agcaaatgta aaaaacaga aatcacaaca   132540 aactgtctct cagaccacag tgcaatcaaa ttagaactcg ggatataaga aactcactaa   132600
aaaccacaca actacatgga aactgaacaa cctgctccta aatgactaca gggtaaataa   132660
cgaaatgaag gcagaaataa agatgttctt taaaaccaaa gagaacaaaa ctacaccata   132720
ccagaatctc tgggacacat ttaaagcagt gtgtagaggg aaatctatag cactaaatac   132780
ccacaagaga aagcaggaaa gatctaaaat caacacccta acatcacaat taaaagaact   132840
agagaaacaa gggcaaacaa attcaaaagc taggagaagg caagaaataa ctaagatcag   132900
agcagaaacg aaggagataa agacccaaaa aaatccttca aacatcaat gaacccagga   132960 gctgattttt tgaaaagatc aacaaaactg atagactgct aactagacta ataaagaaga   133020
aaagagagaa gaatcaaata gatgcaataa aaaatgataa agggggatatc accactgatc   133080 ccacagaaat acaaactacc atcagagaat actataaaca cctctatgca aataaaatag   133140
aaaatctaga agaaatggat aaattcctgg acacatacac cctcctaaga ctaaaccagg   133200
aagaagttga gtttctgaat agaccaataa caggctctga aattgaggca ataattaata   133260
gcctaccaac caaaaaaagt ccaggatcag ttggattcac agccgaattc taccagaggt   133320
acaaagagga gttggtacca tccttctga aactattcca atcaatagaa aaagagggaa   133380
tcctcgctaa ctcattttat gaggccagca tcatcctgat accaaagcct ggcagagaca   133440
cagcaaaaaa agagaatttt agaccaatat ccctgatgaa catttatgtg aaaatcctca   133500
ataaaatact ggcaaccaa atccagcagc acatcaaaaa gcttatccac catgatcaag   133560
tcagcttcat ccctgggatg caaggctgtt tcaacataca caaatcaata acataatcc   133620 atcatataaa cagaaccaac aacaaaaacc acatgattat ctcaatagat gcaggaaagg   133680
cctttgacca aattcaatat cccttcatgc taagaactct caataaacta ggtactgatg   133740
gaacatatct caaaataata agagctactt atgacaaacc cacagccaat atcatactga   133800
atgggcaaaa gctggaagca ttccctttga aaactgggag aagacaagga tgccttctct   133860
caccactcct attcaacata gtgttggaag ttctggccag ggcaatcagg caaagaaag   133920 aaataaaggg tattcgatta ggaaaagagg aagccaaatt gtccctgttt gcagatgaca   133980
tgattgtata tctagaaaac tccatcatct cagcccaaaa tctccttaag ctgataagca   134040
acttcaccaa aggttcagga tacaaaatca atgtgcaaaa atcataagca tgcctatacg   134100
ccaataacag acaaacagag agccaaatca tgagtgaact cccattcaca attgcttcaa   134160
agagaataaa atacctagga atccaactta caagggatgt gagggacctc ttcaaggaaa   134220
actacaaacg actgctcaac aaaataaaag aggacacaaa caaatggaag aacattccat   134280
```

```
ggttatggat cgcaagaatc aatctcatga aaatggccat actgcccaag gtaatttgta  134340
gattcaatgc catccccgtc aagctaccaa tggctttctt cacggaattg ggaaaaacga  134400
ctttgaagtt catatggaac caaaaaagag cccacatcaa gacaatccta agcaaaaaga  134460
acaaaactgg aggcatgcta cctgatttca aactatacta caagactaca gtaaccaaaa  134520
cagcacggta ctggtaccaa aacagagata tagaccaatg gaacagaaca gagccctcag  134580
aaataatacc acacatctac aaccatttga catttgacaa atctgacaaa acaagaaat   134640 ggggaaagga ttacctattt aataaatggt gctgggaaaa ctggttagtc atatgcagaa  134700
agctgaaact ggatcccttc cttacacctt atacaaaaat taattcaaga tggtttaaag  134760
acttaaatgt tagacctaaa accataaaaa ccctagaaga aaacctaggc aataccattc  134820
aggacatagg catgggcaaa gacttcatga ctaaaacacc aaaagcaatg gcaacaaaag  134880
ccaaaattga caaatgggat gtaattaaac taaagaactt ctgcacagca aaaaaaaaa   134940 ctaccatcag agtgaacagg taacctacag aatgtgagaa attttttgca atctatcctt  135000
ctgacaaagg gttaaaatcc agaatctaca aagaacttaa acaaatttac aagaaaaaaa  135060
caaacaaccc catcaaaaag tgggtaaagg atatgaacag acacttctta aaagaagaca  135120
tttatgcagc caacagacac atgaaaaaat gctcatcatc actgatcatc aaagaaatgc  135180
aaatcaacac cacaatgaga taccatctca caccagttac aatggcgatc attaaaagt   135240 caggaaacaa cagatgctgg agaggatctg gagaaatagg aatgctgtta cactgttggt  135300
gggactgtaa actatttcag ccattgagga agacagtgtg gcgattcctc aaggatcgaa  135360
ctagaaatac catttgaccc agtgatccca ttactgggta tatatccaaa ggattataaa  135420
tcattctact ataagacac atgcacatgt atgtttattg cggcactata cagaatagca   135480
aagacttgga accaacccaa atgttcatca atgatagact ggataaagaa aatgtggcac  135540
atatacacca tggaatacta tgcagccata aaaaaggatg agttcatgtc ctttgcaggg  135600
acatggatgc cgctggaaac catcattttg agcaagctat cacaaggaca gaaaaccaaa  135660
caccgcatgt tctcactcat aggtgggaat tgaacaatga gaacacttgg acacaaggtg  135720
gggaacaaca caccccgggg cctgttgtgg ggtgggggga ggcgggaggg atagcattag  135780
gagaaatacc taatgtaaat gacaagttaa tgggtgcagc aaaccaacat ggcacatgta  135840
tacatatgta acaaacccgc acattgtgca catgtaccct agaacttaaa gtatatatgt  135900
atataaaaaa aaagacagat agaaacagg atgagaagag tgaagcagtg ttggatgttt   135960
ccagataggt atgcagtatt gttttataac tcacatatag aagaagagta aattctgtgt  136020
tttctttttc ttttttttccc cctcaaggat gtgacttcaa agattatagt ttattgtaac  136080
cttatttggc tctgagtgct ttcagtggtg aaggctctgt atgatttcct tggttatagg  136140
aagtctttct cagatgctgg ttgtattaat gatgtgctga atgtgtaagc aggtttactg  136200
tatactgtgg ggttgggatg gcagaggtct catgatgctt atctcattct ccagtggtgt  136260
ccttttaatt tatttttttcc ccagtatttt attcattggt ttgagctgtt caggttttag  136320
gccagtagga gatgctcacg gataaaagcc agctgtggct aaagcaggtg gtaaatgcaa  136380
tacccaatgg tgggcagagt tatagaacat cttaaaaaaa aaaaaaaaaa gagtcatagg  136440
tttaaaccag aagctaatag ccatgccaac tttgtcagac tacaccatt tctcctctat   136500 aaatgggaat gataataata tgaaccctgc aacgttttgt taaagtttaa tataaaaaac  136560
atgtaactaa tagaatgcct agcacatagc tgtttaataa aatttcctat tatactctga  136620
ttttatgcag ttaaacctta tgaagctgcc aacatttgat ctttttaacc tacaaaaatt  136680
```

```
gtaatttcaa tgtttcatga aaggagaaca ggttaacact cccctatccg gcctttgggc  136740
ctaatagcat acatacagtt caggcattgc caccttgtgg aatctaacca tcattttac   136800 aaagttccag ttagatcaca ggaataagct ttagtgatct attgcactgc gtcttgaaca  136860
tggttaatga tatggtttgg atctttgtcc ccacgcaatc tcatgttcaa ctgtaatcac  136920
cagtgttgga ggtggggcct ggaaggaggt gattggatca aagggtgga gttctcatta   136980 gtagattagc actatctcct cggtgatgtt cttgtgatag tgagttatca tgagatctgg  137040
ttgtttaaaa gtgtgtagca cctcttccct ctctctcttc ctcctgctct agccttgtga  137100
gatgtctcac tcctcctctg ccttctgcca tgattgaaag atccctgagg cctcaccaga  137160
agcagatgct gccatgcttc ctgtacagcc tgcagaacca taagccaatt attaatcctc  137220
ttttatttat aaattaccca gtctcaggta tttcttgata gtaaaacaag gatggactaa  137280
cacagttaat aacaatgtat atttcaaaat cgctagaatg atagatttt aatgttctca   137340 ccacaaaaaa atgatgtcag atgatggcta tgttaattag cttgactgaa tctttctatg  137400
ctgtgtatac atatatcaaa ccatcacatt atactacata aatatacaca attatttgtc  137460
aattaaaaaa tggtaatttc atgtgatcta acctgttatt aacaaggta tgtataattc    137520 aatcccaatt cctaaaatgc ctaagattct aagaatcaga tttaggatct aatgtttatg  137580
atttgataaa catcaaatca taacaatttc taagaattct tttgatttct aagaattatt  137640
tattgtttta tagcaaaaaa ataggatgat aatgtagaag ttagaattct tcttttggt    137700 tccatgccat ttcaaatgat taggattacc tctgatctgt ggtctatgcc ttgggtgtaa  137760
actccttgat tagacagaat tccaaaaccc acatgactgg gaagtacatc tcacaaacta  137820
aaggtggggg aggacggaag gaagggagat acgtgaacag agaagtcata tagtacatct  137880
tccattcccc agccttatgc tctgacaatt aaagccaatt accaaggaga attcaggcaa  137940
taatgttaac tgatggtgtc catgtcaatt tgttctctcg aagcagctga aaaaaagtgt  138000
gagaataaat ggacatttct gtaaataatt ttttttttg caaattctgg catatttctt   138060
acaagtgttg gagctttagt atttgtactc tcccatgggc tagaattgaa atttctatt    138120 ataattactt tcagctactg aagtcatgta ggtccatttg aggtatttgc ataagtgtat  138180
tttaaggcaa tctatttct aacattaagt aagtgcttga cactttaatt ataactcatc    138240
aagaaagacc atctatttac ctgtctgtta tcaaaatttc taaattatag attgaggaaa  138300
aatgtgaatg ccagctgtac ttaaaagaaa taataataat ttacttatgc aagaaaatta  138360
tagagtgcat acactaagct acgatggata atgctttggt aaactaattg gatatatcag  138420
ttatatcatt attctagaac ctatatttct aaccactcat attaaaatac aacaaattcc  138480
cactacctgg attcttttaca tatacaaaga aaggcacaag tcataaaaaa agaaaaaaa   138540 agaaactac ctataaaaat gactactaat aactaataac ttatagctta aatgacaact    138600
taaactataa tctattgctt tagcagagat atcactatta taattgttca tttatacttg  138660
gaatgaccaa aaaatgtttt ttttttagat gacaaacagg cacagttctg aaaatgaaa   138720 aactttctgt accagcaaag ctgagaagat gaatcctgaa acatttaatc aattttaaaa  138780
aatttcctca tagatcaaag caaagattac tgcaaagttt tatgaatcaa cattgggttc  138840
atagcttagg tctaagagag gggaaaaaat atatcaggaa acaaacgaac aataagtgca  138900
gccagttgtc agtctagaaa tatggcagat ggttaaaatc agaagtcata tagttaactc  138960
aaagagccaa ggtccaaacc accaggcaga agttatgaga agaacaccac tgagttccaa  139020
cctccaaact gggatagaa gctgagcaga ggtgcctagt cacagaaccc aaaaggtagt   139080
```

```
tgttttttgt tttctgtgct ttaaaaatac aacagaagac aatggctggc cctctctggc   139140
atggtcagtc tacagccaag tatgagctga ttgagtgttg cacctgtcca acaaaatcag   139200
gacgtgttct tatttcctag aggtcattgt aagggactgt gagggtgtag acaagtcagc   139260
agcaatcaga tacactgaac actcttggac taactcacct tgcccaggtg acattttttgc  139320 atgtttgttt atttcaggac aggagaaaga gaaccagaaa tttgagctgt tttgcatggc   139380
aaatgtggac aatctttaga aaaaaaaatt tctcgttatt acttttagtt ggcattagga   139440
ctggactcca gttctctcct caggaaagta gagtgttggg cctgtttggc tccttcattg   139500
gaaccaatag gagagaagca acaagtgaag ggggaaatga cttaattgaa tagtttgtaa   139560
ctttgaaaca tgccataatc cgtttccgta ttccacagag aacgcacttg attttccttg   139620
atgattttcc actcctgccc tgagcatttg cagagtgtaa atcagagact gagaggcacc   139680
agcagcccat tctactcctg ggataataaa aacacatgcc ctagagcttc agttagtggg   139740
ttcccaaccc atcaacaaat ggaatttcta acattgctcc ctagtgattg tattaatggg   139800
ataattttct ctgacaggat gtattttttc tgaaattatc tgaagtttcc tcttccaaac   139860
tctatcttac tgcccactcc catgattatc tccttgtgca atggaaaaca atatcaaccc   139920
ccatgttagt tttctatttt tagacctggt ttggtcagtc tatacagtaa aatggtttat   139980
atttagctcc taagtttctc ctgttagtaa ttcagactcg tcactccctt agtcattttt   140040
attggctggt tggttgtcag tttcatgatg cttgacctaa gaatgaagac agtatttcca   140100
gggatagctc ataagggtgg ggtcagatat ttttgtctat agactataat gaatctatat   140160
ataccttgga agccagtcta acttcttacc cttttttcaac ccatatattt ttagcctcac   140220
atgataaatt ctgagttatt tttattaatg atatcttctc atcttggaaa acagttccta   140280
tggtatgttg ttatccctag aacttagccc atatgcctgc aacatagtta gaactcaaga   140340
tatacttgat gaataaatga ataaataaat gattcaaaca ttactggtaa gagttatttc   140400
caaattattt tttgtctgga tttataagat taaattttttt ttctattttt ctttaacatc   140460
ttttagtgtt ttacttcaat tgaggtgtgt tatcagttca actattagag tacaatctca   140520
tactctacaa gcacatatgt ccatgttttg cataaaattt gtggggtcac atgacttcaa   140580
tgatctttgc cataggattt ctggcctggt aagtgacttt agaaatcatc tggtctgatt   140640
ccaacatttt gtagacttta aacctgacaa ctaggaaaga ttctacggga tatagttaaa   140700
tgttttctat tataatcttc tcttttgttc acactttatt ctttgtattt gaagaccata   140760
ccatgtcgtc cggaatggtc aactctttca taccactcaa acatacattt ttttcttaca   140820
tttgaaaatc tagctactgt tttaaaggac ttatctccat ctgtgtttca aattcagcaa   140880
tttgcaagct ctctggtgat ccactgatga tccctgaagt ttcctagatc aaaacggtta   140940
attctagata gttaaaagtt gaccttttag agttctgaga ttcattgagg tccataatca   141000
gcatccatct gaggttcttg ctgtggtctc ttttctgcat gtaattattt ccttcgtat    141060 gtttgccctt ttgattatac gtggaatttt gaggttggtc gcttggtggc actgtagtta   141120
atagcttgat tttcttgtgt attttttccac tgccttcata gcttttgttt ttaaattgca   141180
attatgtgaa atatgtgcga ctttttaaatt ctgctgcagg tgaaatgatt taatgactct   141240
tgacttctgg attaatttta agcattataa acattgtgaa aacagactct tgctaataat   141300
gatcattatc gtaatggctt gaggcataat catttactaa cattagccaa gtgattaaaa   141360
tccatcatga gtttaatttg aaaaaatttt gttcctttgc aataaatggc taatgatatt   141420
agcctcatct ttgtgaggcc aaaacttatc atatgacttt gtactttcac tacttgatag   141480
```

```
aaatcttctc tttttaacac aggccatatt atccctattg tttaccaagc ctgtggtgtt   141540
ctctatattg gtactgaact gggccatgtg gtgcacaatg tacatgcaat tgtcacttttt  141600
cttttatggc cctgctattt gataatttgt cattttacaa agcaagtgac cttaacagat   141660
gttaaaatta attaccatgg ccagtcaaac ctgtagggaa agggaaacat tctcattta    141720
tgactcattt ttgtcaaaac tggttatgat atttataata atcagatttt ttgatatatt   141780
tgtataactt tgtaacgatg cctttaaaaa gtgtccaatc ttaaagttag taataatttt   141840
ccaaaaatat tatctttcaa ctgatttttt ttctttctac ctcttctctc tacaaccctc   141900
tgccctgctc acagaccagc attctggaga gactgagttt tgaaacaacc gaaggaaagt   141960
gattagagag caagtgtgta gttgccattt ttttcccccc acaaagaacc tgagtctgga   142020
cttttaaattt acttactgcc tcattatttc ctttgatgaa tcgtgcaaaa atcttgacct  142080
tcaagggtac tctacccagc agatgcccat gaggataatg atcttatttc caaacaccct   142140
taaacaatta gaaaaggaaa aaaataagta taacaaacaa cccccagaat aaacaaactt   142200
tggcaactgt ggaagggaaa aacctgtatt tcttaatggg tactattttg tttccagaag   142260
ttttccccaa acgaaacaac caggtgaata tcgcacactg actgatatta gagattagcc   142320
ttccacaggc tcactgatga actgtaatct ttatggctgt gttagctgtt tcctcttcaa   142380
aacaagtcaa tgttgttatt ctcatttttt aaagaaccag agagacccac gatggagaat   142440
taacatgccc aagattgttt agtgagtggg tagaaggcat gttaattggc cattgaatgc   142500
tatgtaaaaa ctacacactt gctctctaat caatttcttt cagttatttc aaaactcaat   142560
ctcttcagaa tgctggtctg tgagcagggc agaggattgc agaggtaaga ggtaaaaaga   142620
ataaaaatcc ccgaaggaaa atcataaaat ttaaaagtca catacagaat ttactattac   142680
atatatgtgt gtgtgtatgt gtgtgtgtgg tttttttta atttttttttt ttgagatgga   142740
atctcactct tgttgcccag gctggagtgc aatggtgcaa ccttggctca ctgcaacctc   142800
cacctcctgg gttcaagcga ttctcctgcc tcagcctcct gagtagctga aattacaggt   142860
gcctgccacc acgcctggct aattttttgt atttttagta aagatggggt tttctccatg   142920
ttggccaggc tggtcttgaa ctcttgacct taggtgatcc accccactcg gcctcccaaa   142980
ggcctgggat tacaggtgtg aaccactgcg cctggcctac tataatatct taatgaggta   143040
aaagtcacag atttttcagtc aaattatgag cattagtaac tccctgagct aaagctagcc   143100
attaattatt caaaaacata gtgtgcagca cctactccat gtaacatgtt gggcattagg   143160
gacactaggaa agttagtat agccaaggtg acccctctaa tgatttataa tactgcaaac   143220
ctgccccaaa tacttgtgtt acatggttaa atagcatgtc ttttagttaa cagtaaagtc   143280
aaaatatgga atctagcaaa atttattaga atagaatcaa ccataagaaa actagttcca   143340
gaaaactgag ttccagaaaa gtaacaccac ttattcaaga tctcatagct agacagtggc   143400
aaagagaagt tgattaccag tattttattt tattttattt ttattttatt ttaatttttg   143460
agacagggtc ttgctctgtc acccaggctg gagtgtagtg tcgcaatctc ggctcactgc   143520
aacctctacc tcctgggttc aagcgattct tgtgcttcaa cctcctgagt agctgggatt   143580
acagacgtgc accaccacac ccagctaatt tttgtagttt tagtatgaat ggggtttcac   143640
catgttggcc agtctgatct cgaactcttg gcctcatgtg atccaccac cttggcctcc   143700
aaagtgctgg gattacaggc gtgagccacc tttgcccagc cttgatttcc acttttttaag  143760
agttcactct attgtaaaat actctttttcc aaagaccatc caaaataaga atcttaattc   143820
cccaaaccta tatataataa gtgtatactg agatagattt ttttaacctg tgggatgata   143880
```

```
caatagaatg taataatgat ttatgtttgt atgaatgtgc atctcaatag gaactaccca  143940
atgaaatttt atatggctta aagatatgaa aattgttttc gctgtgtttt atgaagcctt  144000
aataatgact ctaatgcatt tgtggactga aaattttccc ttttcaaata aagagggaaa  144060
aacatatcct tctacaggaa atagcgacca taaatctgtt ttgtggtaac agatttatta  144120
tttccaatac attttttaaa agtgcttttg gttgttgctg ctgttgtttg aaagttcttt  144180
gttctagtta tttagtacct ttcagccaat aaaagtttat aaattcacat gtcaagtttt  144240
ataaaacttt tcatttcctt attaaggtgt ttttaataat tattttaata tttctaatat  144300
ttaagaacaa ttaaactatg atgatgatat taaaatcata ctatgacaaa atccagactc  144360
tgtagagcaa aatggggttt caggacaggc ggagacagac tgagctgctg gtccattaag  144420
gctgccaggt aatggtctga ccacttatct gctgaatttc ctgctagcca gacatgatca  144480
catcaatttc cttcataggc aattcttaca cagttataac tttgagggg agcaaagtca  144540 ttttagaatc tgaacaccag gaccaggagt taattgagcc cctccaccag gaaggaacag  144600
taactcctac cctgtttgga aaatttcatt gtgaagaatg tagtgtatgc cacattgtga  144660
aagatgtctc acaaaaaact cagaaattaa accacatata ttttatttcc tttgttgttg  144720
ttcgattggc atgaaaaaat tttgccaagg aaagaggatt taagatttt atttttcctt  144780 ttcttttaa aaaatcccca aatgacaaga atgtctgctt ttcgcaaaat atgtacataa  144840
aagtttatct tgatggccat actactttc tcagttaggg gaaacagcta taccaactgt  144900
tgtgtccatt tattcagttt ttcttttaac aattcattgc ttttcttgat cactttacta  144960
aatctctaca gaaatgactt taaatttgcc tagattcgaa cttcatataa atggattcat  145020
atgctctctt ttgtgatttg cttccttcac tcagcattat gtttccaggt tcttccatgt  145080
tgacaaatgc tttctatgag tcatcctttt gcactgttat gtagttttct attgtacgac  145140
tagcaacatt caattatcca ttctgtagtt aatgtacata tgagttgttt ccagcatttt  145200
gctgctgtga gtagaacttc tctaacattc ttggacttga ctccagatgc acatgtctaa  145260
cagtttttct aagctgcata cctaagaata aatttgctga gccagagggt atttttccca  145320
aagtagttgt accaattacc cacccacaag caatggataa gagctctatt gctccaaccc  145380
aggcaagact tgaaattctc caactttaaa aaattgtggc caaacagaag agtaaaaaat  145440
tggtatttca ctgtggttct aatttgcatg tctttgattt ctaacaaggt tacatattta  145500
tgttttctgc ccactttcct actacattat tcatctttcc ctattaactt ataggttttc  145560
tttaaatatt ttggattcta atcctccact ggttatgctc ttataaatat cttttgccag  145620
tttgtgactt gtattttaac tttttaaaaa acagtacaca taataaatat gtgctcttaa  145680
ttttaatgta gtaaaaatta tctgtattag accattcttg cattgctata aagaatactt  145740
gaaactgggt aatttataaa gaagagagat ttaattagct catagttctg caggctttat  145800
gggaagcatg gtgctgacat ctgcttctgg tgaggcctca ggaaacttac agtcatggca  145860
gaaagcaaac ggggaggcag catgtcacat ggcgagagca ggagcaagag agtgaggtta  145920
ggggaggtcc tagactttta agcaaccaga tctcacatga tctaactgag tgagaactca  145980
ccaccaagga gatagtgcta aactattcat gagggatgat ctgcccccat gatcctgtta  146040
cctcccaaca ggccacacct ccaacactaa gaatcatatt ttagaataaa tatgatgtga  146100
tgctgagaag aatttatatt ctgttgattt tgggtggagt gttctgtaga tgtctattag  146160
gtcctcttgg tccagagttg agttcaagtc ctgaatatcc ttgttaattt tctgtctcgt  146220
tgatctaata ttgacagttg ggtattaaag tctcccacta ttactgtgtg ggagtctaaa  146280
```

```
tttctttgta agtctctagg aatttgcttc atggacctgg gtgctcctgt attgggtgca    146340
tatatattta ggatagttag ttcttcttgt tgcattgatc tatttaccat tatgtaatgc    146400
ccttctttgt ctcttttgat catctgtttt atcagagact aggattgcaa accctgcttt    146460
ttttgctttc catttgcttg gtagatcttc ctccatccct ttattttgag cctatatgtg    146520
tctttgcacg tgaaatgggt ctcctgaata tagcacacca atcggtattg actctttatc    146580
caatttgcca gtctgtgtct tttaattggg gcatttagcc catttacatt taaggttaat    146640
attgttatgt gtgaatttga tcctgtcatt atgatgctag ctggttattt tgcccgttag    146700
ttgttgcagt ttcttcatag catctatggt ctttacaatt tggtatgttt ttgcagtggc    146760
tggtactatt ttttcctttc catatttagt gcttccttca ggagctcttg taaggcagtc    146820
ctggtggtga caaaaatctc tcagcatgtg cttgtctgta aaggatttta tttctacttc    146880
acttatgaag cttagtttgg ctggatatga aattctgggt tgaaaattct tttctttaat    146940
aatgttgaat attggccccc tgtctcttct ggcttgtagg gtttctgcag agagatccac    147000
tgttagtctg atgggcttct cttttgtggg aacccgacct ttctttcaga ttgcccttaa    147060
catttttttcc ttcatttaaa tcttggtgaa tctgtcaatt atgtgccttg ggggtgctct    147120
tctcgaggag tatctttgtg gtgttctctg tatttcctga atttgaatgt tgtcctgtct    147180
tgctagttgg ggaagttctc ctggataata tcctgaagaa tgttttccaa cttggttcca    147240
ttctccccgt cactttcagg tacaccaatc aaatgtaggt ttggtatttt cacatagttg    147300
catatttctt ggaggatttg ttcattcttt tttctctaat cttgtctgca ggctttattt    147360
cattatgctg attttcaatc tctgatatcc tttcttccgc ttgattgatt cgactattga    147420
tacttgtgtg tgcttcacaa agttctcatg ctgtgttttt cagctccatt gggtcatttg    147480
tgttcttctt taaactggtt attttagtta gaaattcctc taaccttttta tcaaggttct    147540
tagcttcctt gcattgggtt agaacatgct cctttagctc ggaggggttt ttattattca    147600
ccttctgaag cctacttctg tcaactcgtc aaactcattc tacttccagt tttgttccca    147660
tgctggcaag gagttgtgat cctttggagg agaagaggca ttctgttttt cggaattttc    147720
agcctttttg cactggtttt tcttcatctt cctggattta tctaccattg gtctttgatg    147780
ttggtgacct tcagatgggg ttttttgtgtg gatgtccttt tggttgatgt tgatgatatt    147840
cccttctgtt tgttagtttt ccttctaaca gtcaggcccc tttgctgcag gtcgctggag    147900
tttgctggag gtccactcct gaccctgttt gcctgggtac aaccagcaaa ggctacagaa    147960
cagcaaagat tgctgcctgt tccttcctct ggaagcttcg tcccagaggc gcacctgcca    148020
gatgccagct ggagctctcc tgtatgaggt gtctgtcaat ccctgctggg aagtgtctcc    148080
cagtcgggag gcacaggggt tatggaccca cttgagcagg cagtttgtcc cttagcagag    148140
ctcgagctct gtgctgggag atccaatggt ctcttcagag ccagcaggca ggaagtttaa    148200
gtctgttgaa gctgtgctca cagccacccc ttccccagg tgctctgtcc cagagagatg    148260
ggagttttat ctataagccc ctgactggga ctgctgcctt tctttcagag atgccctgcg    148320
cagagaggag gaatctagag aggtagtctg gctacagcag cttttttggca ctgtggtagg    148380
ctcctcccag tttgaacttc ccagtggctt tgtttacact gtgagggaa atctgcctac    148440
tccagcctca gtgatgccag atgccctcc ccccaccaag ctccagggtc ccaggtcaac    148500
ttcagacggc cttgctggca gcgagaattt caaaccagtg gatcttagct tgctgggctt    148560
tgtggggtg ggatccgctg agctggacta cttggctccc tggtgtcagc cccctttccg    148620
gggaagtgaa tggttctgtc tcactggcat tccaggcgcc actggggtgt gaaaaatact    148680
```

```
cctgcagcta gcttggtgtc cgcccaaaca gccgcccagt tttgtgcttg aaacccaggt    148740
ccctggtggt gtagacatcc gaggggatca cctggtctgt gggttgtgga gatggtggga    148800
aaagcatagt atctgtgctg gaatgcacca ttcctcatgg cacagtccct cagggcttcc    148860
cttggctagg ggagggagtt ccctggcccc ttgcgcttcc ctaaaggaag taaaccatgc    148920
aaaccaaaag aaagcctgat ttttgagaca ttcagttctt tcaaggtcta tataggaaca    148980
aaagaaagtg ggaaaagaag cctttgaaga ttgactcctg cctacatttc agcctgttt     149040 ctcttgctac tccactggag cttcccacat gcctactagt ctgaattgct ttcatttctc    149100
ccaactgcca tgtttcattg cttccgcacc tttgtacaga ctgtttctcc tctgcctgga    149160
atgcctttct gtcctcttca tccttcccat ggctaacttg aactcattgt tcagcactgg    149220
gttaagcctg gtctccttca ggaagccatt actaaaggag gtgcctattc tccatggctc    149280
tgtgacccct ttattagtcc ttgctttacc tatgctgcaa ctgcctgtgt acttgtatgt    149340
ctccccagct gtaaattagc accttcaggg caaagactgt atcctttatc atggtactat    149400
gcacatctaa tatttgttag atcaatggta aaatttgtgg atttgttata cccttgggt     149460 atcattgtaa tgattgccat cagtagagtt aagatgaaat atcctagagc tgggccgggt    149520
gcggctcagg cctgtgatcc cagcacttta gcaggctgag gtggctggat cacctaaggt    149580
caggaactgg aaaccagcct ggccagcatg gtgaaattcc atctccacta aaaatacaaa    149640
attagctggg catggtggtg ggtgcctgta atcccagcta ttcgggaggc tgaggcagaa    149700
gaatcacttg aaccctggag gcagaggttg cagtgagcta tcatgccact gtactccagc    149760
ctgggcaaca gagcaagact ctgtcaaaaa aaaaaaaaa  agagaaagaa aggaaggaag    149820
ggaagggaag gagaagggaa tgggaagaga aggggaaggg aatgggaagg aaaagggaag    149880
gggaagtgaa gggaaaagga aagggaaagg aaggggaagc gaagggaaaa gatcctagaa    149940
cctggggccc tgagttcttg gtgttcttgg gagttgtccc tttgcggtgc tggtctcact    150000
ggaacatctg aaaattgtca ctccgtataa cttttggtgt tttctttcaa cttctggtca    150060
aatgatcata gactgcccta cactgtgctc aggaatttaa gggttaaaat aggaagaaat    150120
tcttgtattc agagatgact gtgcttctgg aaatctacct acccgtctgc tactgacacc    150180
tattttaggc atggtatgta caatggaagg cccattcttt tattagggaa actttcatgg    150240
gctatgtaca catatatatt attgatgatg aacatgagaa tgtccctagt tcaagtcgtg    150300
ggcattgtag aatgaacata atagcttttt tcttctgct  aaatcacatg gtagaactta    150360
aagcttcatt ccacagcatt tttgccttat ataagagcaa ccctctcttc cccaaaagat    150420
tcagccataa tattctttat ctttgaaggc tgcttgtgta gtttgcatag ttttctctgt    150480
ctcttcctga ttagaggttg gcatctaaat actttctctg atcttatcac tgctgcaatg    150540
tattcctcga acagagtgtt gcaatttaga tttcttttgt ctcattaacc aagtgatttg    150600
ctggaatact atcagcagtg acatcatcac atttgctttg gtagttgaca tcttaggtta    150660
tcaatggaag cattgtaaga aactgtacag ggtcaagatc cattttgttt agagaatttg    150720
tacagtatgt gggctgagaa ttctcaaagc ccatgcttca taggatgtga agggaatctc    150780
aaatattatg ttcttaagtt cagcatggct attatacact gcactttatt tctccctgag    150840 gatagggggtt gagaacgagt tgatacaaaa acaaagataa attactgata ctttctattt    150900
aatgatgtgt tgtaacagat aaaattatct gagaactaat tgttctcaat cttggcaggc    150960
actaagtttc aaatgtacct attgatatta caggagtgaa gcagtcctga aagtgttggt    151020
agctgctttt gatgcagtgg aatgaatttg tttcctgtgc aactctgcaa gggtaagatg    151080
```

-continued

```
gatataaaac ttgcagacaa gactaccttc agaaactgaa tagggaatga aaaatctatg  151140
aaacatcaga ggtacctttt agtctcaacc tttttgaaaa atcggtcaca gtgtgccttt  151200
atcaattctt tgttcagaaa ttttccctgt ggttcatatt gcttttgtaa aatatcagac  151260
actggctcta attgtgggtg gatacagagc tatctaaatg tttatatatg gagacccata  151320
caagatccac ctgttccaaa atgcctcctt caaggaccta aaattcccat cctttgagac  151380
atttctatgg attaagacat agtgtccaaa tgttcccaca acaggttctc atgtcagtag  151440
aaaagagaag ccatcaggac tagccctgtt ccactaaacc tattaataat caatacatat  151500
caatatattg gttttgttgt tattttttgtt tggtttggct tggttttagt tttgtgtgta  151560
atttattgga accactagtt gtcatcttgg aaatcaggag agagtacatg caataaataa  151620
ggtaagattt gttttttcca gtgctaagaa acttgttcca cttattttta gggtagcact  151680
aacactaaaa atgcaatttt gaagtagaaa gaaaagtgtc acccacaaat agaatcccag  151740
atgtgcccag gtccggaagc aggtaaaaac acagcttctg ggaaagaaac ctagaaagtg  151800
actgaaggcg attgaaatcg acccaataat agtttaggga aaagaatcag aagagagaca  151860
gcacaatctc tacaccgggt tgtggggctc agacaagttg ctaacattgg cttctttgtg  151920
ttgctgctga aatggcatcc atgtcccaca agttttaagg ggaagccata tgagctcctt  151980
ggaatgctgg gtgttgagta actgtaggaa gattagcctc attatgtttt ctgagaatgc  152040
cttttgttga ttccactgcc ccaagcattt ggaagataaa tgtttaaatt cagaatttag  152100
gctctcatca agctcttgga acatccacga aaattacaac tatcattact atactatact  152160
attttctcct atctctcttt acttttactc aaaaacatcg atcaaatttt caagtcatag  152220
acagaactgg gctgtacaca gtgactctga attcaaatgc tgagttcctt ttataaacct  152280
gttaccttgg ttgctggcta gaattc                                       152306
```

DNA METHYLATION MARKERS BASED ON EPIGENETIC STEM CELL SIGNATURES IN CANCER

CROSS-REFERENCE TO RELATED APPLICATIONS

This application is the United States national phase of International Patent Application No. PCT/US2007/088994, filed Dec. 27, 2007, which claims the benefit of priority under 37 U.S.C. 119(e) to U.S. Provisional Patent Application Ser. Nos. 60/877,530, filed 27 Dec. 2006 and entitled DNA METHYLATION MARKERS BASED ON EPIGENETIC STEM CELL SIGNATURE IN CANCER, and 60/882,948, filed 31 Dec. 2006 and of same title, all of which are incorporated herein by reference in their entirety.

STATEMENT REGARDING FEDERALLY-SPONSORED RESEARCH

This invention was made with government support under Contract No. CA075090 awarded by the National Institutes of Health. The government has certain rights in the invention.

FIELD OF THE INVENTION

Particular aspects relate generally to markers (e.g., diagnostic and/or prognostic DNA methylation markers) for cellular proliferative disorders and/or cancer and markers or for developmental lineages and/or stages, and to precursor cells (e.g., embryonic stem (ES) cells, somatic stem cells, cancer stem cells, etc), and more particularly to methods for identifying preferred DNA methylation markers for cellular proliferative disorders and/or cancer or markers for developmental lineages and/or stages, and for validating and/or monitoring of precursor cells (e.g., embryonic stem (ES) cells, somatic stem cells, cancer stem cells, cells of a particular developmental lineage and/or stage, etc), particularly of precursor cells to be used therapeutically. Additional aspects relate to method for diagnosis or prognosis of ovarian cancer comprising determining the methylation state of a HOX genomic DNA sequence. Yet further aspects relate to methods for predicting the response to neoadjuvant and/or adjuvant chemotherapy in a solid tumor.

BACKGROUND

Cancer and Cancer Stem Cells.

A long-standing question in cancer research has been whether cancer arises through mutations in stem cells, or whether transforming differentiated cells reacquire stem cell characteristics through a process of dedifferentiation (Houghton et al., Semin Cancer Biol 4, 4, 2006; Passegue, E. Nature 442:754-7555, 2006). Tumor heterogeneity and shared features of normal stem cells and cancer cells have recently given rise to the concept of cancer stem cells (Pardal et al., Nat Rev Cancer 3:895-902, 2003; Jordan et al., N Engl J Med 355:1253-1261, 2006). However, it has been challenging to obtain firm empirical evidence supporting a normal stem cell origin of cancer and this question remained open.

Epigenetic Alterations in Cancer and Gene Silencing.

In the past decade, it has become clear that cancer arises, not only as a consequence of genetic alterations, such as mutations, deletions, amplifications and translocations, but also as a consequence of stable epigenetic changes in DNA methylation, histone modifications, and chromatin structure, with associated changes in gene expression (Jones & Laird, Nat Genet 21:163-167, 1999; Laird, P. W. Hum Mol Genet 14, R65-R76, 2005; Baylin & Ohm, Nat Rev Cancer 6:107-116, 2006; and Bird, A. Genes Dev 16, 6-21, 2002). In recent years, the disparate fields of chromatin structure, histone modification, DNA methylation, and transcription regulatory complexes have come together to provide an integrated view of epigenetics (Laird, P. W. Hum Mol Genet 14, R65-R76, 2005; Ordway & Curran, T. Cell Growth Differ 13:149-162, 2002; Freiman & Tjian Cell 112, 11-17, 2003; Felsenfeld & Groudine, Nature 421; 448-453, 2003; and Jaenisch & Bird, Nat Genet 33:245-254, 2003). This elaborate mechanism for regulating areas of the genome for transcriptional activity, repression, or silencing participates in mammalian development (Li et al., Cell 69:915-926, 1992), genomic imprinting (Li et al., Nature 366:362-5, 1993), X-inactivation in females (Zuccotti & Monk, Nat Genet 9:316-320, 1995; and Boumil et al., T. Mol Cell Biol 26:2109-2117, 2006), in silencing parasitic DNA elements (Walsh & Bestor, Genes Dev 13:26-34, 1999), and in coordinating cell-type specific gene expression (Futscher et al. Nat Genet 31:175-179. 2002).

Cancer cells contain extensive aberrant epigenetic alterations, including promoter CpG island DNA hypermethylation and associated alterations in histone modifications and chromatin structure. Aberrant epigenetic silencing of tumor-suppressor genes in cancer involves changes in gene expression, chromatin structure, histone modifications and cytosine-5 DNA methylation.

Epigenetic Mechanisms in Embryonic Stem (ES) Cell Differentiation).

Embryonic stem cells are unique in the ability to maintain pluripotency over significant periods in culture, making them leading candidates for use in cell therapy. Embryonic stem (ES) cell differentiation involves epigenetic mechanisms to control lineage-specific gene expression patterns. ES cells rely on Polycomb group (PcG) proteins to reversibly repress genes required for differentiation, promoting ES cell self-renewal potential. ES cell-based therapies hold great promise for the treatment of many currently intractable heritable, traumatic, and degenerative disorders. However, these therapeutic strategies inevitably involve the introduction of human cells that have been maintained, manipulated, and/or differentiated ex vivo to provide the desired precursor cells (e.g., somatic stem cells, etc.), raising the specter that aberrant or rogue cells (e.g., cancer cells or cells predisposed to cancer that may occur during such manipulations and differentiation protocols) may be administered along with desired cells.

Therefore, there is a pronounced need in the art for novel, effective and efficient methods for stem cell and/or precursor cell monitoring and validation, and for novel therapeutic methods, comprising monitoring and/or validating stem cells and/or precursor cells prior to therapeutic administration to preclude introduction of aberrant or rogue cells (e.g., cancer cells or cells predisposed to cancer).

Ovarian Cancer. In the US and Europe, epithelial ovarian cancer causes more deaths than cancer in any other female reproductive organ. It is estimated that there are about 20,180 new cases of ovarian cancer and 15,310 deaths in the US per year (1). Due to the current lack of early detection strategies, many ovarian cancer patients present with advanced stage disease, and the overall 5-year survival for these women is less than 30% (2). Despite the development of new therapeutic approaches, these survival statistics have remained largely unchanged for the past three decades. The most important prognostic parameters for this disease are age, stage, grade and optimal cytoreductive surgery (where all visible cancer in the peritoneal cavity is removed). Beside molecular genetic changes and expression profiling, studies have also begun addressing the epigenetic components of ovarian carcinogenesis (3-5). Changes in DNA methylation status (predominantly at CpG) are among the most common molecular alterations in human neoplasia (6). DNA methylation changes promise to be important screening markers for carcinogenesis.

Therefore, there is a pronounced need in the art for a better understanding of the molecular pathogenesis of ovarian cancer and identification of new drug targets or biomarkers that facilitate early detection.

Breast Cancer.

Breast cancer is the most frequent malignancy among women in the industrialized world. To date the presence or absence of metastatic involvement in the axillary lymph nodes is still the most powerful prognostic factor available for patients with primary breast cancer (1), although this is just an indirect measure reflecting the tendency of the tumor to spread. Chemotherapy can be an integral component of the adjuvant management strategy for women with early-stage breast cancer. Recently applicants showed that RASSF1A DNA methylation in serum is a poor prognostic marker in women with breast cancer (2) and that this cancer-specific DNA alteration allows monitoring of adjuvant Tamoxifen therapy, which is applied mainly in ER positive tumors (3). To date, however, no tool is available to sufficiently predict or monitor efficacy of neoadjuvant or adjuvant systemic chemotherapy which is frequently applied in ER negative breast cancer. Therefore, there is a pronounced need in the art for a better understanding of the molecular pathogenesis of breast cancer and identification of new biomarkers that facilitate early detection and treatment of breast cancer (e.g., ER negative breast cancer).

SUMMARY OF THE INVENTION

Stems cells rely on Polycomb group proteins (PcG) to reversibly repress genes encoding transcription factors required for differentiation (Ringrose & Paro, *Annu Rev Genet* 38:413-443, 2004; Lee et al. *Cell* 125:301-313, 2006, incorporated herein by reference, including supplemental materials thereof). While the present applicants and others have previously hypothesized that acquisition of promoter DNA methylation at these repressed genes may potentially lock in stem cell phenotypes and initiate abnormal clonal expansion and thereby predispose to cancer (for background, see also Schuebel, et al., *Nat Genet* 38:738-740, 2006), supporting empirical evidence for this idea has been lacking and this hypothesis has remained as mere speculation, until the instant disclosure herein. Moreover, recently, it has been reported that differentiating human ES cells acquire epigenetic abnormalities that are distinct from those observed in cancer (Shen et al., *Hum Mol Genet* 26:26, 2006).

Aspects of the present invention provide the first real evidence that stem-cell polycomb group (PcG) targets are substantially more likely to have cancer-specific promoter DNA hypermethylation than non-targets, thus providing, for the first time, effective and efficient methods for stem cell and/or precursor cell monitoring and validation, and for novel therapeutic methods, comprising monitoring and/or validating stem cells and/or precursor cells prior to therapeutic administration to preclude introduction of aberrant or rogue cells (e.g., cancer cells or cells predisposed to cancer). Specifically, according to particular aspects of the present invention, applicants report that stem-cell polycomb group (PcG) targets are up to twelve-fold more likely to have cancer-specific promoter DNA hypermethylation than non-targets, indicating a stem-cell origin of cancer, in which reversible gene repression is replaced by permanent silencing, locking the cell into a perpetual state of self-renewal and thereby predisposing to subsequent malignant transformation.

Exemplary aspects provide methods for identifying preferred DNA methylation markers for cellular proliferative disorders and/or cancer, based on identifying PcG protein or PcG repressive complex genomic target loci (collectively, PcG target loci) within a precursor cell (e.g., embryonic stem (ES) cells, somatic stem cells, cancer stem cells, progenitor cell, etc.) population, and determining, in cells of the cellular proliferative disorder and/or cancer (e.g., colorectal, breast, ovarian, hematopoietic, etc.), a characteristic (cancer-specific) methylation status of CpG sequences within loci corresponding to the precursor cell PcG target loci. Specific embodiments provide a method for identifying, screening, selecting or enriching for preferred DNA methylation markers for a cellular proliferative disorder and/or cancer, comprising: identifying, with respect to a precursor cell population, one or a plurality of genomic target loci for at least one polycomb group protein (PcG) or Polycomb repressive complex (collectively referred to herein as PcG target loci); obtaining a sample of genomic DNA from cells of a cellular proliferative disorder and/or cancer; and determining, by analyzing the genomic DNA from the cells of the cellular proliferative disorder and/or cancer using a suitable assay, a cancer-specific methylation status of at least one CpG dinucleotide sequence position within at least one region of at least one of the polycomb group protein (PcG) target loci, wherein the presence of said CpG methylation status identifies the at least one region of at least one of the polycomb group protein (PcG) target loci as a preferred DNA methylation marker for the cellular proliferative disorder and/or cancer.

Particular embodiments provide a method for identifying, screening, selecting or enriching for preferred DNA methylation markers for cells of a particular developmental lineage or stage, comprising: identifying, with respect to a precursor cell population, one or a plurality of genomic target loci for at least one polycomb group protein (PcG) or polycomb repressive complex (PcG target loci); obtaining a sample of genomic DNA from cells of a particular developmental lineage or stage; and determining, by analyzing the genomic DNA from the cells of the particular developmental lineage or stage using a suitable assay, a lineage-specific or stage-specific DNA methylation status of at least one CpG dinucleotide sequences within at least one region of at least one of the polycomb group protein (PcG) target loci, wherein the presence of said CpG methylation status identifies the at least one region of at least one of the polycomb group protein (PcG) target loci as a preferred DNA methylation marker for the particular developmental lineage or stage. In particular embodiments, determining the lineage-specific or stage-specific methylation status of the at least one CpG dinucleotide sequences within at least one region of at least one of the polycomb group protein (PcG) target loci, is determining the DNA methylation status of a locus that has a cancer-specific DNA methylation status.

Additional aspects provide methods for validating and/or monitoring a precursor cell (e.g., embryonic stem (ES) cells, somatic stem cells, cancer stem cells, progenitor cell, etc.) population, comprising screening or monitoring one or more PcG genomic target loci of a precursor cell population for the presence of absence of target loci methylation status that is characteristic of (disorders-specific, cancer-specific) the PcG target loci in one or more cellular proliferative disorders and/or cancers, or that, in certain further embodiments corresponds to (is specific for) a particular developmental status (e.g., lineage or stage). Specific embodiments provide a method for validating and/or monitoring a precursor cell population, comprising: identifying, with respect to a reference precursor cell population, one or a plurality of genomic target loci for at least one polycomb group protein (PcG) or polycomb repressive complex; identifying one or a plurality of said target loci having a characteristic (disorder-specific, cancer specific) DNA methylation status in a cellular proliferative disorder and/or cancer to provide a set of preferred disorder and/or cancer-related diagnostic/prognostic loci; obtaining genomic DNA from a first test therapeutic precursor cell population of interest; and determining, by analyzing the genomic DNA of the first test therapeutic precursor cell population using a suitable assay, the methylation status of at least one CpG dinucleotide sequence within at least one region of at least one of the polycomb group protein (PcG) preferred diagnostic/prognostic loci, wherein the first test therapeutic precursor cell population is validated and/or monitored with respect to the presence or absence of the characteristic (disorder-specific, cancer-specific) DNA methylation status of the one or a plurality of said target loci having a characteristic DNA methylation status in the cellular proliferative disorder and/or cancer, or with respect to the presence or absence of cells of the cellular proliferative disorder and/or cancer, or with respect to the presence or absence of cells or cells having a predispostion thereto.

Further aspects provide a method for validating and/or monitoring a precursor cell population, comprising: identifying, with respect to a reference precursor cell population, one or a plurality of genomic target loci for at least one polycomb group protein (PcG) or polycomb repressive complex; identifying one or a plurality of said target loci having a characteristic DNA methylation status (lineage-specific, stage specific, etc.) in a cell of a particular developmental lineage or stage to provide a set of preferred lineage or stage specific diagnostic/prognostic loci; obtaining genomic DNA from a first test therapeutic cell population of interest; and determining, by analyzing the genomic DNA of the first test therapeutic cell population using a suitable assay, the DNA methylation status of at least one CpG dinucleotide sequence within at least one region of at least one of the polycomb group protein (PcG) preferred diagnostic/prognostic loci, wherein the first test therapeutic cell population is validated and/or monitored with respect to the presence or absence of the characteristic methylation status (lineage-specific, stage-specific, etc.) of the one or a plurality of said target loci having a characteristic methylation status of cells of a particular developmental lineage or stage or with respect to the presence or absence of cells of the particular developmental lineage or stage, or with respect to the presence or absence of cells or cells having a developmental predispostion thereto. In particular embodiments, determining the lineage-specific or stage-specific methylation status of the at least one CpG dinucleotide sequences within at least one region of at least one of the polycomb group protein (PcG) target loci, is determining the methylation status of a locus that has a cancer-specific methylation status.

In yet additional embodiments, various stem or precursor cells are used to identify transcriptional repressor occupancy sites (e.g., by chromatin immunoprecipitation chip analysis) and status for not only polycomb repressive complex 2 (PRC2), but also for other repressors and repressor complexes (e.g., repressors of developmental genes) as well, and these ChIP-Chip targets are then used as a means of enrichment for cancer-specific DNA methylation markers as taught herein using the exemplary combination of embryonic stems cells and PRC2 targets. According to further aspects, therefore, the instant approach has substantial utility for various types of stem and precursor cells (ES cell, somatic stem cells, hematopoietic stem cells, leukemic stem cells, skin stem cells, intestinal stem cells, gonadal stem cells, brain stem cells, muscle stem cells (muscle myoblasts, etc.), mammary stem cells, neural stem cells (e.g., cerebellar granule neuron progenitors, etc.), etc), and for various stem- or precursor cell repressor complexes (e.g., such as those described in Table 1 of Sparmann & Lohuizen, Nature 6, 2006 (Nature Reviews Cancer, November 2006), incorporated herein by reference), and for various types of cancer, where the requirements are that the repressor occupancy sites/loci and corresponding occupancy status are defined/established, and a characteristic DNA methylation status (e.g., disorder-specific, cancer-specific, etc.) (e.g., DNA hypermethylation) is established at corresponding sites/loci in one or more cellular proliferative disorders or cancers of interest, or, in particular embodiments, characteristic lineage-specific, stage specific, etc., status in cells of a developmental lineage or stage of interest.

Yet additional aspects provide a method for the diagnosis or prognosis of ovarian cancer comprising: performing methylation analysis of genomic DNA of a subject tissue sample; and determining the methylation state of a HOX genomic DNA sequence relative to a control HOX genomic DNA sequence, wherein diagnosis or prognosis of ovarian cancer is provided. In particular embodiments, the HOX genomic DNA sequence is that of HOXA10 or HOXA11, and hypermethylation is used to provide the ovarian cancer related diagnosis or prognosis. In certain aspects, the HOX genomic DNA sequence is that of HOXA11, and hypermethylation is used to provide a ovarian cancer related prognosis of poor outcome. In particular embodiments, the diagnostic or prognosic marker is for at least one selected from the group consisting of: for stem cells that are unable to differentiate; for stem cell that are resistant to therapy; for residual tumor after cytoreductive surgery; for cancer stem cells; for mucinous cancer cases; for serous cancer cases; for endometrioid cancer cases; for clear cell cases; and for tumor distribution.

Further aspects provide a method for predicting the response to neoadjuvant and/or adjuvant chemotherapy in a solid tumor, comprising performing methylation analysis of genomic DNA of a subject tissue sample; and determining the methylation state of a NEUROD1 genomic DNA sequence relative to a control NEUROD1 genomic DNA sequence, wherein predicting the response to neoadjuvant and/or adjuvant chemotherapy in breast cancer is provided. Additional aspects provide a method for determining chemosensitivity in breast cancer, comprising: performing methylation analysis of genomic DNA of a subject tissue sample; and determining the methylation state of a NEUROD1 genomic DNA sequence relative to a control NEUROD1 genomic DNA sequence, wherein determining chemosensitivity in breast cancer is provided. In certain embodiments of these methods, NEUROD1 methylation is a chemosensitivity marker in estrogen receptor (ER) negative breast cancer. In particular aspects, methylation analysis is at least one of: methylation analysis in core breast cancer biopsies taken prior to preoperative chemotherapy with complete pathological response as the endpoint; and seroconversion of NEUROD1 methylation in serum DNA during adjuvant chemotherapy with survival as the endpoint. In particular implementations, the chemosensitivity is with respect to at least one of cyclophospamide, methotrexate, 5-fluorouracil, anthracycline, and combinations thereof.

BRIEF DESCRIPTION OF THE DRAWINGS

In FIG. 1A, genes are ranked by decreasing cancer-specific DNA methylation as defined by the differential mean PMR between tumor and normal samples with a 'cutpoint' of 2.

DETAILED DESCRIPTION OF THE INVENTION

Stems cells rely on Polycomb group proteins (PcG) to reversibly repress genes encoding transcription factors required for differentiation (Ringrose & Paro, *Annu Rev Genet* 38:413-443, 2004). Lee et al. have identified genes targeted for transcriptional repression in human embryonic stem (ES) cells by the PcG proteins SUZ12 and EED, which form the Polycomb Repressive Complex 2, PRC2, and which are associated with nucleosomes that are trimethylated at histone H3 lysine-27 (H3K27me3) (Lee, T. I. et al. *Cell* 125:301-313, 2006, incorporated herein by reference, including supplemental materials thereof). The present applicants have previously hypothesized that acquisition of promoter DNA methylation at these repressed genes could potentially lock in stem cell phenotypes and initiate abnormal clonal expansion and thereby predispose to cancer, but empirical evidence has been, until the instant disclosure herein, lacking to support such a hypothesis (for background, see also Schuebel, et al., *Nat Genet* 38:738-740, 2006). Moreover, recently, it has been reported that differentiating human ES cells acquire epigenetic abnormalities that are distinct from those observed in cancer (Shen et al., *Hum Mol Genet* 26:26, 2006).

The present applicants have recently described the promoter DNA methylation analysis of 195 genes in ten primary human colorectal tumors and matched normal mucosa (Weisenberger, D. J. et al. *Nat Genet* 38:787-793, 2006, incorporated herein by reference, including supplementary materials thereof). As described in detail herein, the present applicants identified and correlated cancer-associated DNA methylation with the stem cell occupancy by SUZ12 and EED, and the H3K27Me3 status for 177 of the genes described by Lee et al (Supra). Of these 177 genes, an astonishing 77 displayed evidence of cancer-associated DNA methylation, when compared to matched normal colorectal mucosa (FIG. 1A; see also working EXAMPLE 2 below and Table 1 thereof).

Figures 1A, 1B:
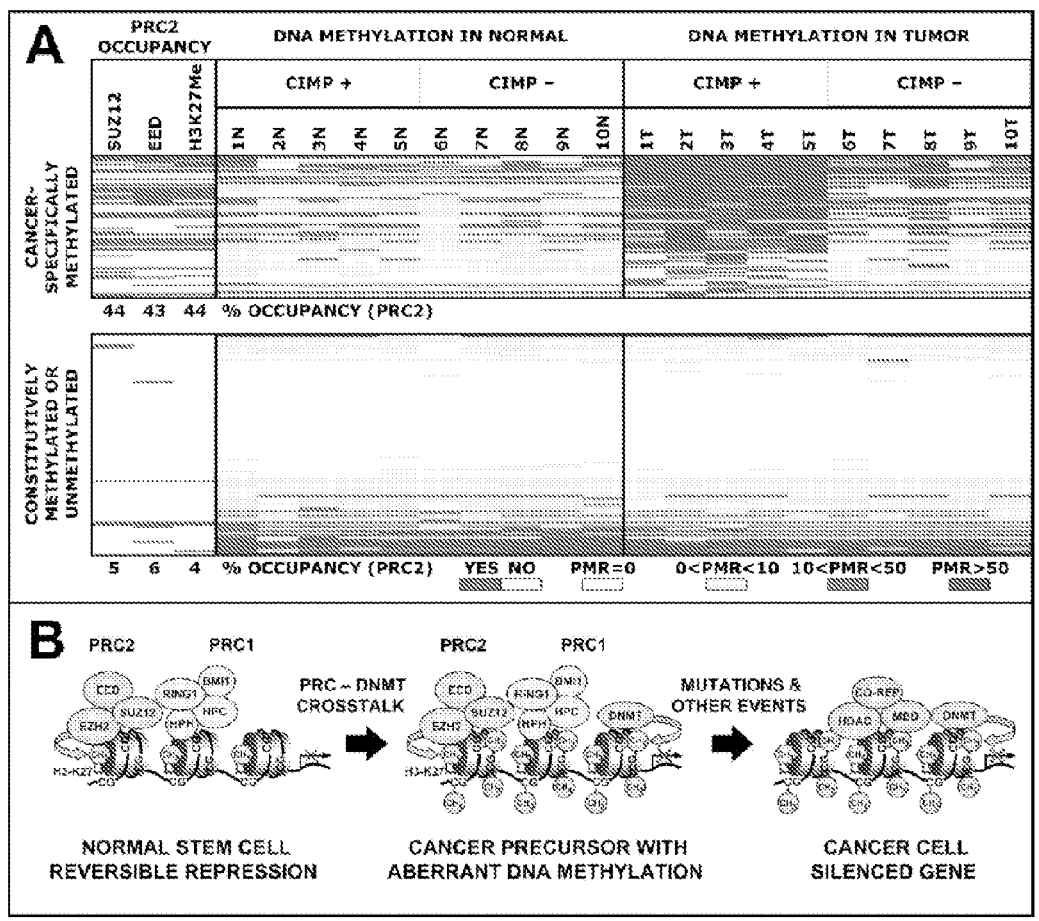
FIGS. 1A and B show, according to aspects of the present invention, PRC2 promoter occupancy in human ES cells and DNA methylation in human colorectal tumors and matched normal mucosa, along with a progression model.

FIG. 1A shows, according particular aspects of the present invention, SUZ12 and EED occupancy data and H3K27Me status for 177 genes (as reported by Lee, T. I. et al., *Cell* 125:301-313, 2006), as indicated by blue bars in FIG. 1A and in the legend at the bottom thereof. Gene identities and primer and probe sequences are supplied in the working EXAMPLES disclosed herein below. DNA methylation data was as reported by Weisenberger, D. J. et al. (*Nat Genet* 38:787-793, 2006, incorporated by reference herein). PMR values are indicated by colored bars in FIG. 1, and in the legend at the bottom thereof. Genes are ranked by decreasing cancer-specific DNA methylation as defined by the differential mean PMR (see Marjoram et al., BMC Bioinformatics 7:361 (pages 1-9), 2006, incorporated herein by reference it its entirety) between tumor and normal samples with a 'cut-point' of 2.

FIG. 1B shows, according to additional inventive aspects, a model for the progression of epigenetic marks from reversible repression in ES cells to aberrant DNA methylation in cancer precursor cells, and persistent gene silencing in cancer cells.

Strikingly, approximately 44% of these 77 genes contain at least one of these ES cell repressive marks, while 32% of these genes contain all three marks (see working EXAMPLE 2 below and Table 1 thereof). Only about 5% of the 100 genes that are either constitutively methylated or unmethylated contain these marks, while only 3% contain all three marks, close to the average of 4% of the 16,710 gene promoters reported by Lee et al (Supra). The difference in ES cell repressive marks between cancer-specifically methylated genes and constitutively methylated or unmethylated genes is highly significant by Fisher Exact Test (P<0.0001; Odds Ratio: 12.1), whether the analysis is restricted to tumors with CpG island methylator phenotype (CIMP) (Weisenberger, D. J. et al., supra) or not.

This astonishing association was independently confirmed for both ovarian and breast cancer-specifically methylated genes (see working EXAMPLES 3 and 4, respectively, below). Hatada et al. (*Oncogene* 9:9, 2006) used a DNA methylation microarray to identify hypermethylated genes in lung cancer cells. According to additional aspects of the present invention, of the 273 hypermethylated loci with known gene names and PRC2 occupancy, an astonishing 96 (35%) had at least one PRC2 mark. This result contrasts to only one gene with a single mark among the 23 known genes showing DNA hypomethylation in this study (P=0.0019; Odds Ratio: 11.9).

According to additional aspects, the predisposition of ES-cell PRC2 targets to cancer-specific DNA hypermethylation indicates crosstalk between PRC2 and de novo DNA methyltransferases in an early precursor cell with a PRC2 distribution similar to that of ES cells. The precise developmental stage and type of cell in which such crosstalk occurs is unknown, and is not likely to be an embryonic stem cell. Other stem and embryonic cell types display a similar PRC2 preference for DNA-binding proteins and transcription factors (Squazzo et al. *Genome Res* 16:890-900, 2006; Bracken et al., *Genes Dev* 20:1123-1136, 2006, both incorporated herein by reference in their entireties). In contrast, colorectal and breast cancer cell lines display a markedly different set of PRC2 targets, enriched in genes encoding glycoproteins, receptors, and immunoglobulin-related genes (Squazzo et al. *Genome Res* 16:890-900, 2006), which are not frequent cancer-specific DNA hypermethylation targets. This indicates, according to particular aspects of the present invention, that the 'crosstalk' leading to DNA methylation predisposition likely occurred early in oncogenesis, at a time in which the PRC2 distribution resembled that of a stem cell (see, e.g., applicants' model of FIG. 1B).

According to further aspects, where such crosstalk occurs at low frequency in stem cells, this phenomenon is observable in enriched adult stem cell populations. In specific embodiments, the high sensitivity of the MethyLight™ assay allowed for the detection of low frequency dense promoter methylation in CD34-positive hematopoietic progenitor cells (see working EXAMPLE 5, respectively, below). Stem-cell repressed genes, containing at least two of the PRC2 marks demonstrated detectable DNA methylation in CD34-positive cells in twice the number of subjects compared to genes lacking these marks (Mean: 6.1 vs 3.2, respectively, P=0.02).

According to additional aspects, the first predisposing steps towards malignancy occur very early, and are consistent with reports of field changes in histologically normal tissues adjacent to malignant tumors (Feinberg et al., Nat Rev Genet 7:21-33, 2006; Eads et al., Cancer Res 60:5021-5026, 2000; Shen et al. J Natl Cancer Inst 97:1330-1338, 2005). The instant results provide a mechanistic basis for the predisposition of some (e.g., a subset), but not other promoter CpG islands to cancer-associated DNA hypermethylation. Indeed, since some of the PRC2 targets with tumor-specific promoter DNA methylation, such as MYOD1, NEUROD1 and NEUROG1, are not normally expressed in the epithelium, the instant teachings indicate a residual stem-cell memory, rather than selective pressure for silencing of these particular genes during the transformation process in epithelial cells.

According to certain aspects, aberrant PRC2-DNA methyltransferase 'crosstalk' occurs at low frequency in stem cells, and does not disrupt normal differentiation if the silencing affects a small number of PRC2 targets that are not crucial to differentiation. However, if a sufficient number of a particular subset is affected, then the resulting DNA methylation 'seeds' prevent proper differentiation, and predispose the cell to further malignant development.

Applicants note that not all cancer-specifically methylated genes are ES-cell PRC2 targets, and therefore, according to yet additional aspects, PRC2 targets in other stem or progenitor cells contribute to the diversity of DNA methylation targets observed among different types of cancer.

In further aspects, other, and more tissue-specific repressive complexes are capable of causing a similar predisposition to characteristic DNA methylation status (e.g., hypermethylation).

According to yet further aspects, screening for PRC2 target promoter DNA hypermethylation has substantial utility for therapeutic applications involving introduction of precursor cells derived from cloned or cultured ES cells (see, e.g., for background, Roy et al. Nat Med 12: 1259-1268, 2006).

In additional embodiments of the present invention, various stem or precursor cells are used to identify transcriptional repressor occupancy sites (e.g., by chromatin immunoprecipitation chip analysis) and status for not only PRC2, but also for other repressors and repressor complexes as well (e.g., such as those described in Table 1 of Sparmann & Lohuizen, Nature 6, 2006 (Nature Reviews Cancer, November 2006), incorporated herein by reference), and these ChIP-Chip targets as then used as a means of enrichment for cancer-specific DNA methylation markers as taught herein using the exemplary combination of embryonic stems cells and PRC2 targets.

Further embodiments provide a method for identifying, screening, selecting or enriching for preferred DNA methylation markers for a cellular proliferative disorder and/or cancer, or for selecting or enriching for preferred DNA methylation markers for a developmental cell lineage or stage (see, e.g., EXAMPLE 8).

Particular embodiments provide methods for validating and/or monitoring a precursor cell population, for example, with respect to the presence or absence of cells of a proliferative disorder or cancer, or cells having a development predisposition thereto, or cell of a particular development lineage or stage (see, e.g., EXAMPLE 9).

According to particular aspects, a preferred marker is a marker that is a developmental repressor locus (e.g., for PcGs, and PRC1, PRC2, etc.) and that further comprises at least one CpG dinucleotide sequence position having a DNA methylation state (e.g., DNA hypermethylation) that is cellular proliferative disorder-specific and/or cancer specific.

Particularly preferred is a marker that is a PRC1 or PRC2 developmental repressor locus with occupation by at least one of SUZ 12, EED, and H3K27me3, and that further comprises at least one CpG dinucleotide sequence position having a DNA methylation state (e.g., hypermethylation) that is cellular proliferative disorder-specific and/or cancer specific.

More preferred is a marker that is a PRC1 or PRC2 developmental repressor locus with occupation by at least two of SUZ 12, EED, and H3K27me3, and that further comprises at least one CpG dinucleotide sequence position having a methylation state (e.g., hypermethylation) that is cellular proliferative disorder-specific and/or cancer specific.

Especially preferred is a marker that is a PRC1 or PRC2 developmental repressor locus with occupation by all three of SUZ 12, EED, and H3K27me3, and that further comprises at least one CpG dinucleotide sequence position having a methylation state (e.g., hypermethylation) that is cellular proliferative disorder-specific and/or cancer specific.

Particularly preferred are subsets of any of the above preferred markers that also bind at least one of the transcription factors OCT4, SOX2, and Nanog.

In additional embodiments of the present invention, various stem or precursor cells are used to identify transcriptional repressor (e.g., transcription factor) occupancy sites (e.g., by chromatin immunoprecipitation chip analysis) and status for not only PRC2, but also for other repressors and repressor complexes as well (e.g., at least one transcription factor of the Dlx, Irx, Lhx and Pax gene families (neurogenesis, hematopoiesis and axial patterning), or the Fox, Sox, Gata and Tbx families (developmental processes)), and these ChIP-Chip targets as then used as a means of enrichment for cancer-specific DNA methylation markers as taught herein using the exemplary combination of embryonic stems cells and PRC2 targets.

EXAMPLE 1

Methods

Colorectal Cancer Methods

Colorectal Cancer DNA Methylation Data and PRC2 Occupancy.

The full methods for the colorectal cancer data have been published previously (D. J. Weisenberger et al., Nat Genet. 38:7, 2006; incorporated by reference herein in its entirety).

Methods Applicable to the Previously Unpublished Data for Ovarian Cancer, Breast Cancer, and CD34 Positive Hematopoietic Cells Patients:
Hematopoietic Related Patients.
CD34 pos. cells isolated from stem cell apheresis collections from nine women were analyzed. The samples were collected during treatment at the Division of Hematology and Oncology, Innsbruck Medical University, Austria. All patients signed informed consent prior to apheresis.

Ovarian and Breast Related Patients.
Ovarian tissues from 40 patients and breast specimens from 30 patients were collected during surgery at the Department of Obstetrics and Gynecology of the Innsbruck Medical University, Austria in compliance with and approved by the Institutional Review Board.

Sample Preparation:

Apheresis Samples.

Peripheral blood progenitor cells (PBPC) were collected in these patients to perform high-dose chemotherapy followed by autologous stem cell transplantation to treat different diseases (n=9; age range: 20.1 to 49.4 yrs.; mean: 35.6 years; 3 breast cancer patients in a clinical trial setting, 2 patients with acute myeloid leukemia, 1 patient with B acute lymphoblastic leukemia, 1 patient with medulloblastoma, 1 patient with T non-Hodgkin's lymphoma and 1 patient with idiopathic thrombocytopenic purpura). Mobilization of PBPC was performed by administration of chemotherapy followed by G-CSF. The harvest of PBPC was performed as large-volume, continuous-flow collection using a COBE Spectra® blood cell separator (Gambro BCT, Colorado, USA) through bilateral peripheral venous accesses. During the first apheresis, the blood was processed at a rate of 50 to 120 ml/min. A second collection was optional and depended on the yield of CD34 pos. progenitors cells obtained during the first procedure. In addition, the CD34 pos. cells were isolated with CD34 conjugated magnetic beads (Miltenyi Biotec; Bergisch Gladbach, Germany) according the manufacturer's instructions. CD34 purity was controlled by flow cytometric analysis. Only cell fractions with >90% purity were further analyzed.

Tissue Samples; Ovarian and Breast.

Applicants analyzed patients with ovarian cancer (n=22; age range: 30.1 to 80.9 yrs.; mean: 61.8 yrs.; 7 serous cystadeno, 6 mucinous, 6 endometrioid and 3 clear cell cancers) and patients with normal ovaries (n=18; age range: 24.1 to 76.9 yrs.; mean: 61.6 yrs.; 13, 4 and 1 had endometrial and cervical cancer and fibroids, respectively). In addition, patients with breast cancer (n=15; age range: 30.3 to 45.7 yrs.; mean: 38.0 yrs.; 13 invasive ductal, 1 invasive lobular and 1 tubular cancer) and patients with non-neoplastic breast tissue (n=15; age range: 19.8 to 46.2 yrs.; mean: 35.0 yrs; all of them had an open biopsy due to a benign breast lesion) were analyzed. Tissues were immediately snap-frozen in liquid nitrogen, pulverized in the frozen state, and stored at 80° C. until used.

DNA Isolation:

Genomic DNA from cell and tissue samples was isolated using the DNeasy Tissue Kit (Qiagen, Hilden, Germany) according to the manufacturer's protocol.

Analysis of DNA Methylation:

Sodium bisulfite conversion, MethyLight™ analysis and nucleotide sequences for most MethyLight™ primers and probes has been described (Weisenberger et al., Nat Genet. 38:7, 2006; Muller et al., Cancer Res. 63:22, 2003; and Fiegl et al., Cancer Epidemiol Biomarkers Prev. 13:5, 2004; all of which are incorporated herein by reference in their entireties). The following primer and probe sequences were used for the ovarian, breast, and CD34 positive cell analyses, and differ from published reactions for these loci:

```
CXCR4:
                                       (SEQ ID NO: 1)
Forward: CGCTAATTCTCCAAATACGATAACTACTAAA;
                                       (SEQ ID NO: 2)
Reverse: TCGGTC GCGGTTAGAAATTTT,
```

```
                                       (SEQ ID NO: 3)
Probe: 5'FAM-
TCGACGTCACTTTACTACCTACTACCGCA ACCA-3'BHQ1;

SFRP1:
                                       (SEQ ID NO: 4)
Forward: CAACTCCCGACGAAACGAA;
                                       (SEQ ID NO: 5)
Reverse: CGCGAGG GAGGCGATT,
                                       (SEQ ID NO: 6)
Probe: 5'FAM-CACTCGTTACCACGTCCGTCA CCG-3'BHQ1;

SFRP2:
                                       (SEQ ID NO: 7)
Forward: AAACCTACCCGCCCGAAA;
                                       (SEQ ID NO: 8)
Reverse: GTTGAACGGTGGTTGGAGATTC,
                                       (SEQ ID NO: 9)
Probe: 5'FAM-CGCCTCGACGAACTTCGTTTTCCCT-3'BHQ1;

SFRP4:
                                       (SEQ ID NO: 10)
Forward: TCC GCCGTCTAACACACAAA;
                                       (SEQ ID NO: 11)
Reverse: TTCGTAATGGTCGTGGTTGGT,
                                       (SEQ ID NO: 12)
Probe: 5'FAM-CAACGCCAACTCTCAACCTTCGAAACG-3'BHQ1;

SFRP5:
                                       (SEQ ID NO: 13)
Forward: GAACGCCCC GACTAATCCTAA;
                                       (SEQ ID NO: 14)
Reverse: TAGGCGGTCGGAGATTGGT,
                                       (SEQ ID NO: 15)
Probe: 5'FAM-CTCCCA
CCTCGAAACTCCAACCCG-3'BHQ1;

TP53BP2:
                                       (SEQ ID NO: 16)
Forward: ACCCCCTAACGCGACTTT ATC;
                                       (SEQ ID NO: 17)
Reverse: GTTCGATTCGGGATTAGTTGGT;
                                       (SEQ ID NO: 18)
Probe: 5'FAM-CGCTCGTAACGAT CGAAACTCCCTCCT-3'BHQ1.
```

Statistical Analysis:

Descriptive analysis of obtained data was performed and median as well as interquartile range was given. Differences of PMR values between normal and cancer tissues were analyzed by means of Mann-Whitney U test. All statistical analyses were done applying SPSS Software 10.0.

SUPPLEMENTAL REFERENCES
(INCORPORATED HEREIN BY REFERENCE)

R1. D. J. Weisenberger et al., Nat Genet. 38, 7 (2006);

R2. H. M. Muller et al., Cancer Res. 63, 22 (2003); and

R3. H. Fiegl et al., Cancer Epidemiol Biomarkers Prev. 13, 5 (2004).

EXAMPLE 2

Colorectal Cancer DNA Methylation Data and PRC2 Occupancy were Analyzed

Table 1 lists the 177 MethyLight™ reactions from Weisenberger et al. (2006) for which the PRC2 occupancy could be established from the data published in Lee et al. (2006). Of the 177 reactions, 164 (93%) are located within 1 kb of the transcription start site. Of the PRC2 targets, 95% are located within 1 kb of the transcription start site. See Table 5 herein below for primer and probe details.

TABLE 1

Colorectal Cancer DNA Methylation Data and PRC2 Occupancy

| HGNC SYMBOL | REACTION ID | PRC2 OCCUPANCY ||| PRC2 TOTAL | DNA METHYLATION ||| 
|---|---|---|---|---|---|---|---|---|
| | | SUZ12 | EED | H3K27Me | | MEAN PMR (N) | MEAN PMR (T) | PMR(T) − PMR(N) |
| CANCER-SPECIFICALLY METHYLATED GENES |||||||||
| GATA5 | HB-326 | YES | YES | YES | 3 | 35 | 514 | 479.00 |
| SFRP5 | HB-282 | YES | YES | YES | 3 | 3 | 446 | 443.45 |
| IGF2 | HB-319 | YES | YES | NO | 2 | 2 | 368 | 366.11 |
| TWIST1 | HB-047 | NO | YES | YES | 2 | 9 | 294 | 284.89 |
| EBF3 | HB-229 | YES | NO | YES | 2 | 13 | 287 | 273.78 |
| HIC1 | HB-168 | NO | YES | YES | 2 | 90 | 356 | 266.16 |
| SFRP2 | HB-280 | NO | NO | NO | 0 | 7 | 187 | 179.71 |
| SFRP1 | HB-201 | YES | YES | YES | 3 | 29 | 177 | 148.52 |
| NEUROD2 | HB-260 | YES | YES | YES | 3 | 26 | 173 | 147.11 |
| SCGB3A1 | HB-194 | NO | NO | NO | 0 | 7 | 143 | 135.44 |
| RUNX3 | HB-181 | NO | NO | NO | 0 | 2 | 135 | 133.22 |
| OPCML | HB-209 | NO | NO | NO | 0 | 40 | 144 | 103.57 |
| GATA4 | HB-323 | YES | YES | YES | 3 | 7 | 102 | 94.68 |
| NR3C1 | HB-067 | NO | NO | NO | 0 | 0 | 94 | 93.43 |
| HRAS1 | HB-144 | NO | NO | NO | 0 | 639 | 731 | 92.27 |
| GATA3 | HB-327 | YES | YES | YES | 3 | 3 | 93 | 89.90 |
| TERT | HB-074 | NO | NO | NO | 0 | 0 | 89 | 89.06 |
| ITGA4 | HB-321 | YES | YES | YES | 3 | 2 | 86 | 84.62 |
| KL | HB-175 | YES | YES | YES | 3 | 1 | 86 | 84.62 |
| CACNA1G | HB-158 | YES | YES | YES | 3 | 1 | 80 | 79.23 |
| SFRP4 | HB-281 | NO | YES | YES | 2 | 7 | 78 | 70.74 |
| BCL2 | HB-140 | YES | YES | YES | 3 | 0 | 65 | 64.79 |
| TMEFF2 | HB-274 | YES | YES | YES | 3 | 29 | 89 | 60.51 |
| MYOD1 | HB-154 | YES | YES | YES | 3 | 8 | 65 | 57.31 |
| GAD1 | HB-256 | NO | YES | NO | 1 | 9 | 64 | 54.85 |
| GDNF | HB-221 | YES | YES | YES | 3 | 6 | 58 | 52.57 |
| HOXA1 | HB-268 | NO | YES | YES | 2 | 0 | 53 | 52.54 |
| CHFR | HB-190 | NO | NO | NO | 0 | 1 | 52 | 51.41 |
| SEZ6L | HB-184 | NO | NO | NO | 0 | 1 | 52 | 50.89 |
| MT3 | HB-207 | NO | NO | YES | 1 | 0 | 50 | 49.60 |
| TIMP3 | HB-167 | NO | NO | NO | 0 | 2 | 51 | 49.13 |
| PENK | HB-163 | YES | YES | YES | 3 | 48 | 95 | 46.68 |
| MT1A | HB-205 | YES | YES | YES | 3 | 12 | 57 | 45.36 |
| NEUROG1 | HB-261 | YES | YES | YES | 3 | 0 | 45 | 44.70 |
| RBP1 | HB-185 | NO | NO | NO | 0 | 1 | 45 | 44.16 |
| CDKN1C | HB-329 | NO | NO | NO | 0 | 1 | 44 | 43.34 |
| EPM2AIP1 | HB-152 | NO | NO | NO | 0 | 0 | 43 | 42.93 |
| COL1A2 | HB-193 | NO | NO | NO | 0 | 28 | 70 | 42.37 |
| ESR1 | HB-164 | NO | NO | YES | 1 | 15 | 56 | 41.29 |
| CRABP1 | HB-197 | YES | NO | NO | 1 | 1 | 39 | 38.62 |
| BDNF | HB-258 | NO | NO | NO | 0 | 1 | 37 | 36.44 |
| CDH13 | HB-075 | YES | NO | NO | 1 | 3 | 39 | 36.35 |
| NEUROD1 | HB-259 | YES | YES | YES | 3 | 24 | 56 | 31.57 |
| ABCB1 | HB-051 | NO | NO | NO | 0 | 7 | 38 | 30.72 |
| SOCS1 | HB-042 | NO | NO | NO | 0 | 0 | 30 | 30.10 |
| GABRA2 | HB-254 | YES | YES | YES | 3 | 8 | 38 | 29.93 |
| DCC | HB-178 | YES | YES | YES | 3 | 14 | 43 | 28.99 |
| CALCA | HB-166 | YES | YES | YES | 3 | 4 | 30 | 26.53 |
| TITF1 | HB-213 | YES | YES | YES | 3 | 5 | 30 | 25.47 |
| ESR2 | HB-165 | NO | NO | NO | 0 | 0 | 25 | 24.55 |
| PGR | HB-149 | YES | YES | YES | 3 | 0 | 24 | 23.90 |
| CYP27B1 | HB-223 | YES | YES | YES | 3 | 5 | 29 | 23.50 |
| MLH1 | HB-150 | NO | NO | NO | 0 | 0 | 23 | 23.24 |
| MLH3 | HB-099 | NO | NO | NO | 0 | 0 | 23 | 23.00 |
| RARRES1 | HB-322 | YES | NO | NO | 1 | 1 | 24 | 22.52 |
| MGMT | HB-160 | NO | NO | NO | 0 | 0 | 19 | 19.45 |
| MSH6 | HB-084 | NO | NO | NO | 0 | 13 | 31 | 18.02 |
| DLEC1 | HB-225 | NO | NO | NO | 0 | 0 | 18 | 17.65 |
| DRD2 | HB-253 | NO | NO | NO | 0 | 2 | 16 | 14.88 |
| GSTP1 | HB-172 | NO | NO | NO | 0 | 0 | 13 | 13.47 |
| IGSF4 | HB-069 | NO | NO | NO | 0 | 4 | 15 | 11.70 |
| TP73 | HB-177 | YES | YES | YES | 3 | 0 | 11 | 10.98 |
| THBS1 | HB-247 | NO | NO | NO | 0 | 0 | 11 | 10.94 |
| DLC1 | HB-218 | YES | NO | NO | 1 | 1 | 11 | 9.18 |
| THRB | HB-216 | NO | NO | NO | 0 | 1 | 9 | 8.59 |

TABLE 1-continued

Colorectal Cancer DNA Methylation Data and PRC2 Occupancy

| HGNC SYMBOL | REACTION ID | PRC2 OCCUPANCY ||| PRC2 TOTAL | DNA METHYLATION |||
| --- | --- | --- | --- | --- | --- | --- | --- | --- |
| | | SUZ12 | EED | H3K27Me | | MEAN PMR (N) | MEAN PMR (T) | PMR(T) − PMR(N) |
| SLC6A20 | HB-079 | YES | NO | YES | 2 | 0 | 9 | 8.55 |
| CYP1B1 | HB-078 | YES | YES | NO | 2 | 0 | 8 | 7.64 |
| TSHR | HB-141 | NO | NO | NO | 0 | 0 | 7 | 7.44 |
| MT2A | HB-206 | NO | NO | NO | 0 | 2 | 9 | 6.81 |
| ERCC1 | HB-110 | NO | NO | NO | 0 | 1 | 7 | 5.64 |
| HOXA10 | HB-270 | NO | YES | YES | 2 | 44 | 49 | 4.26 |
| CCND2 | HB-040 | NO | NO | NO | 0 | 0 | 4 | 3.99 |
| TNFRSF10C | HB-308 | NO | NO | NO | 0 | 1 | 5 | 3.86 |
| FHIT | HB-041 | NO | NO | NO | 0 | 0 | 3 | 2.75 |
| SERPINB5 | HB-208 | NO | NO | NO | 0 | 85 | 88 | 2.54 |
| PFTX2 | HB-235 | YES | YES | YES | 3 | 4 | 6 | 2.30 |
| PYCARD | HB-228 | YES | NO | NO | 1 | 0 | 2 | 2.29 |
| % OCCUPANCY | | 44 | 43 | 44 | 31 | | | |
| CONSTITUTIVELY METHYLATED OR UNMETHYLATED GENES ||||||||||
| SMAD3 | HB-053 | NO | NO | NO | 0 | 19 | 21 | 1.97 |
| APC | HB-153 | NO | NO | NO | 0 | 1 | 3 | 1.85 |
| JUP | HB-203 | NO | NO | NO | 0 | 0 | 1 | 0.97 |
| RPA3 | HB-104 | NO | NO | NO | 0 | 0 | 1 | 0.53 |
| GRIN2B | HB-250 | YES | NO | NO | 1 | 0 | 1 | 0.49 |
| SMAD6 | HB-278 | YES | NO | NO | 1 | 0 | 1 | 0.34 |
| RPA2 | HB-103 | NO | NO | NO | 0 | 0 | 0 | 0.32 |
| STK11 | HB-183 | NO | NO | NO | 0 | 0 | 0 | 0.08 |
| MSH5 | HB-097 | NO | NO | NO | 0 | 0 | 0 | 0.02 |
| XPA | HB-102 | NO | NO | NO | 0 | 0 | 0 | 0.02 |
| ATM | HB-179 | NO | NO | NO | 0 | 0 | 0 | 0.02 |
| TFF1 | HB-145 | NO | NO | NO | 0 | 5 | 5 | 0.01 |
| ERCC4 | HB-111 | NO | NO | NO | 0 | 0 | 0 | 0.01 |
| CTNNB1 | HB-170 | NO | NO | NO | 0 | 0 | 0 | 0.01 |
| MUTYH | HB-088 | NO | NO | NO | 0 | 0 | 0 | 0.00 |
| ERCC2 | HB-105 | NO | NO | NO | 0 | 0 | 0 | 0.00 |
| MSH2 | HB-095 | NO | NO | NO | 0 | 0 | 0 | 0.00 |
| DPH1 | HB-049 | NO | NO | NO | 0 | 0 | 0 | 0.00 |
| DCLRE1C | HB-133 | NO | NO | NO | 0 | 0 | 0 | 0.00 |
| TYMS | HB-248 | NO | NO | NO | 0 | 0 | 0 | 0.00 |
| STAT1 | HB-063 | NO | NO | NO | 0 | 0 | 0 | 0.00 |
| CTSD | HB-147 | NO | YES | NO | 1 | 0 | 0 | 0.00 |
| CXADR | HB-054 | NO | NO | NO | 0 | 0 | 0 | 0.00 |
| PPARG | HB-060 | NO | NO | NO | 0 | 0 | 0 | 0.00 |
| CLIC4 | HB-062 | NO | NO | NO | 0 | 0 | 0 | 0.00 |
| NCL | HB-077 | NO | NO | NO | 0 | 0 | 0 | 0.00 |
| UNG | HB-082 | NO | NO | NO | 0 | 0 | 0 | 0.00 |
| MBD4 | HB-083 | NO | NO | NO | 0 | 0 | 0 | 0.00 |
| OGG1 | HB-087 | NO | NO | NO | 0 | 0 | 0 | 0.00 |
| APEX1 | HB-090 | NO | NO | NO | 0 | 0 | 0 | 0.00 |
| XRCC1 | HB-092 | NO | NO | NO | 0 | 0 | 0 | 0.00 |
| PARP1 | HB-093 | NO | NO | NO | 0 | 0 | 0 | 0.00 |
| PARP2 | HB-094 | NO | NO | NO | 0 | 0 | 0 | 0.00 |
| PILRB | HB-098 | NO | NO | NO | 0 | 0 | 0 | 0.00 |
| ERCCS | HB-113 | NO | NO | NO | 0 | 0 | 0 | 0.00 |
| DDB1 | HB-116 | NO | NO | NO | 0 | 0 | 0 | 0.00 |
| BRCA2 | HB-126 | NO | NO | NO | 0 | 0 | 0 | 0.00 |
| POLD1 | HB-139 | NO | NO | NO | 0 | 0 | 0 | 0.00 |
| PTEN | HB-157 | NO | NO | NO | 0 | 0 | 0 | 0.00 |
| ARPC1B | HB-186 | NO | NO | NO | 0 | 0 | 0 | 0.00 |
| VHL | HB-191 | NO | NO | NO | 0 | 0 | 0 | 0.00 |
| TGFBR1 | HB-192 | NO | NO | NO | 0 | 0 | 0 | 0.00 |
| PRKAR1A | HB-214 | NO | NO | NO | 0 | 0 | 0 | 0.00 |
| TP53 | HB-217 | NO | NO | NO | 0 | 0 | 0 | 0.00 |
| UQCRH | HB-224 | NO | NO | NO | 0 | 0 | 0 | 0.00 |
| CDK2AP1 | HB-226 | NO | NO | NO | 0 | 0 | 0 | 0.00 |
| AXIN1 | HB-227 | NO | NO | NO | 0 | 0 | 0 | 0.00 |
| RB1 | HB-245 | NO | NO | NO | 0 | 0 | 0 | 0.00 |

TABLE 1-continued

Colorectal Cancer DNA Methylation Data and PRC2 Occupancy

| HGNC SYMBOL | REACTION ID | PRC2 OCCUPANCY | | | PRC2 TOTAL | DNA METHYLATION | | |
| --- | --- | --- | --- | --- | --- | --- | --- | --- |
| | | SUZ12 | EED | H3K27Me | | MEAN PMR (N) | MEAN PMR (T) | PMR(T) – PMR(N) |
| TGFBR2 | HB-246 | NO | NO | NO | 0 | 0 | 0 | 0.00 |
| PSEN2 | HB-264 | NO | NO | NO | 0 | 0 | 0 | 0.00 |
| APP | HB-266 | NO | NO | NO | 0 | 0 | 0 | 0.00 |
| SMAD2 | HB-275 | NO | NO | NO | 0 | 0 | 0 | 0.00 |
| FAF1 | HB-304 | NO | NO | NO | 0 | 0 | 0 | 0.00 |
| TNFRSF10B | HB-307 | NO | NO | NO | 0 | 0 | 0 | 0.00 |
| SMAD9 | HB-315 | NO | NO | NO | 0 | 0 | 0 | 0.00 |
| XPC | HB-100 | NO | NO | NO | 0 | 0 | 0 | 0.00 |
| RAD23A | HB-101 | NO | NO | NO | 0 | 0 | 0 | 0.00 |
| FBXW7 | HB-151 | NO | NO | NO | 0 | 0 | 0 | 0.00 |
| XAB2 | HB-115 | NO | NO | NO | 0 | 0 | 0 | 0.00 |
| MMS19L | HB-117 | NO | NO | NO | 0 | 0 | 0 | 0.00 |
| ATR | HB-180 | NO | NO | NO | 0 | 0 | 0 | −0.01 |
| PTTG1 | HB-052 | NO | NO | NO | 0 | 0 | 0 | −0.01 |
| NTHL1 | HB-089 | NO | NO | NO | 0 | 0 | 0 | −0.02 |
| ERCC6 | HB-114 | NO | NO | NO | 0 | 0 | 0 | −0.02 |
| HSD17B4 | HB-066 | NO | NO | NO | 0 | 0 | 0 | −0.03 |
| MBD2 | HB-142 | NO | NO | NO | 0 | 1 | 1 | −0.04 |
| VDR | HB-068 | YES | YES | YES | 3 | 0 | 0 | −0.05 |
| S100A2 | HB-061 | NO | NO | NO | 0 | 2 | 2 | −0.07 |
| ERCC5 | HB-109 | NO | NO | NO | 0 | 0 | 0 | −0.07 |
| LDLR | HB-219 | NO | NO | NO | 0 | 1 | 1 | −0.09 |
| CLDN1 | HB-059 | NO | NO | NO | 0 | 0 | 0 | −0.10 |
| PSEN1 | HB-262 | NO | NO | NO | 0 | 2 | 2 | −0.23 |
| PSAT1 | HB-231 | NO | NO | NO | 0 | 1 | 0 | −0.27 |
| DIRAS3 | HB-043 | NO | NO | NO | 0 | 15 | 14 | −0.43 |
| CCND1 | HB-146 | NO | NO | NO | 0 | 1 | 0 | −1.03 |
| CDKN2B | HB-173 | NO | NO | NO | 0 | 2 | 1 | −1.13 |
| DAPK1 | HB-046 | NO | NO | NO | 0 | 2 | 1 | −1.40 |
| SYK | HB-241 | NO | NO | NO | 0 | 3 | 1 | −1.64 |
| CDH1 | HB-050 | NO | NO | NO | 0 | 2 | 0 | −1.99 |
| MT1G | HB-204 | NO | NO | NO | 0 | 3 | 1 | −2.09 |
| MSH4 | HB-096 | NO | NO | NO | 0 | 21 | 19 | −2.34 |
| TNFRSF10D | HB-309 | NO | NO | NO | 0 | 3 | 0 | −2.94 |
| ERBB2 | HB-233 | NO | NO | NO | 0 | 22 | 18 | −3.31 |
| PTGS2 | HB-065 | NO | NO | NO | 0 | 4 | 1 | −3.51 |
| TNFRSF10A | HB-306 | NO | NO | NO | 0 | 5 | 2 | −3.62 |
| PAX8 | HB-211 | YES | YES | YES | 3 | 40 | 36 | −4.21 |
| ONECUT2 | HB-242 | YES | YES | YES | 3 | 5 | 0 | −4.49 |
| HLA-G | HB-215 | NO | YES | NO | 1 | 26 | 21 | −4.88 |
| DNAJC15 | HB-048 | NO | NO | NO | 0 | 14 | 8 | −5.87 |
| MTHFR | HB-058 | NO | NO | NO | 0 | 43 | 36 | −6.49 |
| IFNG | HB-311 | NO | NO | NO | 0 | 11 | 3 | −7.67 |
| LZTS1 | HB-200 | NO | NO | NO | 0 | 46 | 36 | −9.60 |
| SASH1 | HB-220 | NO | NO | NO | 0 | 11 | 1 | −10.04 |
| SFN | HB-174 | NO | NO | NO | 0 | 80 | 68 | −11.08 |
| TNFRSF25 | HB-080 | NO | YES | NO | 1 | 303 | 289 | −13.77 |
| NTF3 | HB-251 | NO | NO | NO | 0 | 121 | 101 | −20.28 |
| CGA | HB-237 | NO | NO | NO | 0 | 142 | 117 | −24.81 |
| RARB | HB-176 | NO | NO | NO | 0 | 112 | 79 | −32.98 |
| CDX1 | HB-195 | NO | NO | YES | 1 | 106 | 61 | −45.28 |
| PLAGL1 | HB-199 | NO | NO | NO | 0 | 387 | 323 | −64.08 |
| % OCCUPANCY | | 5 | 6 | 4 | 3 | | | |

EXAMPLE 3

Ovarian Cancer DNA Methylation Data and Stem Cell PRC2 Occupancy were Analyzed

Table 2 lists DNA methylation values (PMR) of 35 genes analyzed in 18 normal ovaries and 22 ovarian cancers. These genes were selected for their potential utility as cancer-specific DNA methylation markers without prior knowledge of their PRC2 occupancy status. P-values of genes that demonstrate significant higher DNA methylation levels (Mann Whitney U test) in cancer compared to normal ovaries are shaded and referred as to "cancer genes". Applicants defined "Stem cell genes" as genes which are occupied with at least two of the three components (SUZ12, EED and H3K27me3) in human embryonic stem cells. Nine genes demonstrated higher frequencies of densely methylated alleles (as reflected in the listed values for PMR) in cancer tissues compared to normal ovaries. 56% (5/9) of these "cancer genes" were "stem cell genes", whereas only 15% (4/26) of the "non-cancer genes" were "stem cell genes" (P=0.03). In addition, genes that are methylated in normal tissue are much more likely to show a quantitative increase in DNA methylation frequency in cancer (P=0.002) as opposed to genes that are not detectably methylated in normal tissues.

TABLE 2

Ovarian cancer DNA Methylation Data and PRC2 Occupancy

| Genes | Occupancy in ES cells with | | | Methylation values (PMR) | | | | |
|---|---|---|---|---|---|---|---|---|
| | | | | normal ovary (n = 18) | | ovarian cancer (n = 22) | | |
| | | | | Median | 25th and 75th percentile | Median | 25th and 75th percentile | |
| APC | NO | NO | NO | 0.01 | 0.00 ; 0.13 | 0.03 | 0.00 ; 0.43 | 0.274 |
| CCND2 | NO | NO | NO | 0.00 | 0.00 ; 0.00 | 0.00 | 0.00 ; 0.02 | 0.492 |
| CDH1 | NO | NO | NO | 0.00 | 0.00 ; 0.11 | 0.11 | 0.00 ; 0.41 | 0.042 |
| CXCR4 | NO | NO | NO | 0.03 | 0.02 ; 0.05 | 0.02 | 0.01 ; 0.06 | 0.251 |
| DAPK1 | NO | NO | NO | 0.00 | 0.00 ; 0.05 | 0.00 | 0.00 ; 0.10 | 0.697 |
| ESR2 | NO | NO | NO | 0.00 | 0.00 ; 0.02 | 0.00 | 0.00 ; 0.00 | 0.613 |
| GSTP1 | NO | NO | NO | 0.00 | 0.00 ; 0.00 | 0.00 | 0.00 ; 0.00 | 0.638 |
| HSD17B4 | NO | NO | NO | 0.00 | 0.00 ; 0.00 | 0.00 | 0.00 ; 0.00 | 0.925 |
| HSPA2 | NO | NO | NO | 0.00 | 0.00 ; 0.00 | 0.00 | 0.00 ; 0.58 | 0.199 |
| MGMT | NO | NO | NO | 0.00 | 0.00 ; 0.00 | 0.00 | 0.00 ; 0.00 | 0.878 |
| MLH1 | NO | NO | NO | 0.00 | 0.00 ; 0.03 | 0.00 | 0.00 ; 0.00 | 0.476 |
| PTGS2 | NO | NO | NO | 0.09 | 0.03 ; 0.20 | 0.18 | 0.04 ; 0.50 | 0.163 |
| REV3L | NO | NO | NO | 0.00 | 0.00 ; 0.00 | 0.00 | 0.00 ; 0.00 | 1.000 |
| SFRP2 | NO | NO | NO | 0 | 0 ; 0 | 3 | 1 ; 18 | 0.002 |
| SOCS1 | NO | NO | NO | 0.00 | 0.00 ; 0.01 | 0.01 | 0.00 ; 1.31 | 0.140 |
| SOCS2 | NO | NO | NO | 1 | 0 ; 3 | 10 | 4 ; 28 | 0.000 |
| SYK | NO | NO | NO | 0.00 | 0.00 ; 0.00 | 0.00 | 0.00 ; 0.00 | 0.677 |
| TERT | NO | NO | NO | 0.00 | 0.00 ; 0.09 | 0.00 | 0.00 ; 0.06 | 0.925 |
| TFF1 | NO | NO | NO | 98 | 92 ; 109 | 79 | 62 ; 108 | 0.010 |
| TGFB3 | NO | NO | NO | 0.00 | 0.00 ; 0.00 | 0.00 | 0.00 ; 0.00 | 0.778 |
| TIMP3 | NO | NO | NO | 0.00 | 0.00 ; 0.28 | 0.00 | 0.00 ; 0.16 | 0.861 |
| TP53BP2 | NO | NO | NO | 0.00 | 0.00 ; 0.00 | 0.00 | 0.00 ; 0.00 | 1.000 |
| ESR1 | NO | NO | YES | 1 | 1 ; 3 | 1 | 0 ; 1 | 0.022 |
| MT3 | NO | NO | YES | 0.00 | 0.00 ; 0.00 | 0.00 | 0.00 ; 0.00 | 0.813 |
| CDH13 | YES | NO | NO | 0.02 | 0.00 ; 0.10 | 0.09 | 0.00 ; 1.57 | 0.055 |
| GSTM3 | YES | NO | NO | 0.00 | 0.00 ; 0.00 | 0.00 | 0.00 ; 0.00 | 0.677 |
| HIC1 | NO | YES | YES | 8 | 5 ; 10 | 37 | 9 ; 60 | 0.002 |
| SFRP4 | NO | YES | YES | 1 | 1 ; 3 | 3 | 1 ; 5 | 0.106 |
| TWIST1 | NO | YES | YES | 0.00 | 0.00 ; 0.42 | 0.00 | 0.00 ; 0.33 | 0.726 |
| CALCA | YES | YES | YES | 0 | 0 ; 1 | 1 | 1 ; 6 | 0.000 |
| MYOD1 | YES | YES | YES | 0.01 | 0.00 ; 0.10 | 0.17 | 0.01 ; 0.53 | 0.012 |
| PGR | YES | YES | YES | 0.13 | 0.02 ; 0.26 | 0.74 | 0.11 ; 1.45 | 0.010 |
| SFRP1 | YES | YES | YES | 0.00 | 0.00 ; 0.12 | 0.00 | 0.00 ; 0.16 | 0.757 |

TABLE 2-continued

Ovarian cancer DNA Methylation Data and PRC2 Occupancy

| Genes | Occupancy in ES cells with | | | Methylation values (PMR) | | | | |
|---|---|---|---|---|---|---|---|---|
| | | | | normal ovary (n = 18) | | ovarian cancer (n = 22) | | |
| | | | | Median | 25th and 75th percentile | Median | 25th and 75th percentile | |
| SFRP5 | YES | YES | YES | 0 | 0 ; 1 | 1 | 1 ; 6 | 0.002 |
| TITF1 | YES | YES | YES | 0.00 | 0.00 ; 0.00 | 0.00 | 0.00 ; 0.10 | 0.163 |

EXAMPLE 4

Breast Cancer DNA Methylation Data and Stem Cell PRC2 Occupancy were Analyzed Table 3 lists DNA methylation values (PMR) of 61 genes (with known PRC2 component occupancy status in human embryonic stem cells) analyzed in 15 non-neoplastic breast and 15 breast cancers. P-values of genes that demonstrate significant higher DNA methylation levels (Mann Whitney U test) in cancer compared to non-neoplastic breast are shaded and referred as to "cancer genes". Applicants defined "Stem cell genes" as genes which are occupied with at least two of the three components (SUZ12, EED and H3K27me3) in human embryonic stem cells. Eighteen genes demonstrated higher frequencies of densely methylated alleles in breast cancer tissues compared to non-neoplastic breast. 56% (10/18) of these "cancer genes" were "stem cell genes", whereas only 23% (10/43) of the "non-cancer were "stem cell genes" (P=0.02).

TABLE 3

Breast cancer DNA Methylation Data and PRC2 Occupancy

| Genes | Occupancy in ES cells with | | | Methylation values (PMR) | | | | |
|---|---|---|---|---|---|---|---|---|
| | | | | non-neoplastic breast (n = 15) | | breast cancer (n = 15) | | |
| | | | | Median | 25th and 75th percentile | Median | 25th and 75th percentile | |
| ABCB1 | NO | NO | NO | 61 | 50 70 | 69 | 58 105 | 0.089 |
| APC | NO | NO | NO | 0.12 | 0.00 0.26 | 0.14 | 0.05 4.64 | 0246 |
| BDNF | NO | NO | NO | 0.00 | 0.00 0.00 | 0.00 | 0.00 0.02 | 0.085 |
| CARD15 | NO | NO | NO | 66 | 56 85 | 56 | 48 82 | 0.412 |
| CCND2 | NO | NO | NO | 0.00 | 0.00 0.08 | 0.64 | 0.03 10.94 | 0.011 |
| CDH1 | NO | NO | NO | 0.01 | 0.00 0.14 | 0.09 | 0.00 0.33 | 0.310 |
| CDKN1C | NO | NO | NO | 0.00 | 0.00 0.07 | 0.07 | 0.00 0.14 | 0.274 |
| CDNK2B | NO | NO | NO | 0.13 | 0.04 0.20 | 0.23 | 0.14 0.36 | 0.061 |
| CXCR4 | NO | NO | NO | 0.03 | 0.01 0.05 | 0.04 | 0.02 0.07 | 0.461 |
| DAPK1 | NO | NO | NO | 0.45 | 0.25 0.83 | 1.20 | 0.27 12.83 | 0.067 |
| ESR2 | NO | NO | NO | 0.00 | 0.00 0.06 | 0.03 | 0.00 0.05 | 0.775 |
| FOXO1A | NO | NO | NO | 0.00 | 0.00 0.00 | 0.00 | 0.00 0.00 | 1.000 |
| GSTP1 | NO | NO | NO | 0.00 | 0.00 0.15 | 0.00 | 0.00 16.21 | 0.377 |
| HRAS | NO | NO | NO | 202 | 137 240 | 199 | 84 307 | 1.000 |
| HSD17B4 | NO | NO | NO | 0.08 | 0.01 0.38 | 0.04 | 0.00 0.31 | 0.400 |
| MGMT | NO | NO | NO | 0.00 | 0.00 0.01 | 0.00 | 0.00 0.00 | 0.874 |
| MLH1 | NO | NO | NO | 0.01 | 0.00 0.51 | 0.00 | 0.00 0.02 | 0.376 |
| NR3C1 | NO | NO | NO | 0.00 | 0.00 0.00 | 0.00 | 0.00 0.00 | 1.000 |
| OPCML | NO | NO | NO | 0.67 | 0.05 3.13 | 13.46 | 3.53 59.66 | 0.000 |
| PTGS2 | NO | NO | NO | 0.71 | 0.35 1.35 | 1.91 | 1.09 9.86 | 0.021 |

TABLE 3-continued

Breast cancer DNA Methylation Data and PRC2 Occupancy

| Genes | Occupancy in ES cells with | | | Methylation values (PMR) | | | | |
|---|---|---|---|---|---|---|---|---|
| | | | | non-neoplastic breast (n = 15) | | breast cancer (n = 15) | | |
| | | | | Median | 25th and 75th percentile | Median | 25th and 75th percentile | |
| RARB | NO | NO | NO | 0.06 | 0.04 0.12 | 0.12 | 0.05 0.14 | 0.481 |
| SCGB3A1 | NO | NO | NO | 0.43 | 0.16 1.39 | 1.11 | 0.44 31.23 | 0.067 |
| SEZ6L | NO | NO | NO | 0.14 | 0.07 0.21 | 1.17 | 0.30 9.53 | 0.000 |
| SFRP2 | NO | NO | NO | 1.03 | 0.56 2.28 | 3.39 | 1.39 27.54 | 0.006 |
| SMAD3 | NO | NO | NO | 0.00 | 0.00 0.00 | 0.00 | 0.00 0.00 | 1.000 |
| SOCS1 | NO | NO | NO | 0.00 | 0.00 0.82 | 0.00 | 0.00 0.27 | 0.583 |
| SYK | NO | NO | NO | 0.08 | 0.01 0.31 | 0.00 | 0.00 0.07 | 0.012 |
| TACSTD1 | NO | NO | NO | 0.04 | 0.03 0.05 | 0.04 | 0.03 0.07 | 0.512 |
| TERT | NO | NO | NO | 0.00 | 0.00 0.00 | 1.56 | 0.00 4.34 | 0.046 |
| TFF1 | NO | NO | NO | 44 | 29 84 | 37 | 18 64 | 0.477 |
| TGFB3 | NO | NO | NO | 0.00 | 0.00 0.00 | 0.00 | 0.00 0.00 | 1.000 |
| TGFBR2 | NO | NO | NO | 0.00 | 0.00 0.00 | 0.00 | 0.00 0.00 | 0.967 |
| THBS1 | NO | NO | NO | 0.00 | 0.00 0.00 | 0.00 | 0.00 0.00 | 1.000 |
| THRB | NO | NO | NO | 0.09 | 0.00 0.38 | 0.13 | 0.04 0.42 | 0.744 |
| TIMP3 | NO | NO | NO | 0.42 | 0.04 0.72 | 0.75 | 0.21 1.60 | 0.077 |
| TYMS | NO | NO | NO | 0.00 | 0.00 0.00 | 0.00 | 0.00 0.00 | 0.539 |
| ESR1 | NO | NO | YES | 0 | 0 18 | 1 | 0 1 | 0.899 |
| CDH13 | YES | NO | NO | 0.22 | 0.01 1.05 | 1.18 | 0.43 15.04 | 0.020 |
| GATA5 | YES | NO | NO | 1.17 | 0.39 1.96 | 5.34 | 3.92 19.59 | 0.000 |
| RARRES1 | YES | NO | NO | 0.00 | 0.00 0.04 | 0.03 | 0.01 0.12 | 0.126 |
| TNFRSF25 | NO | YES | NO | 115 | 59 149 | 94 | 64 140 | 0.461 |
| SLC6A20 | YES | NO | YES | 0.06 | 0.00 0.11 | 0.15 | 0.00 0.68 | 0.331 |
| HOXA1 | NO | YES | YES | 0.61 | 0.24 1.10 | 17.97 | 0.93 66.22 | 0.001 |
| HOXA10 | NO | YES | YES | 13.11 | 3.30 18.37 | 38.17 | 5.73 87.77 | 0.033 |
| SFRP4 | NO | YES | YES | 1 | 0 2 | 3 | 3 8 | 0.000 |
| CYP1B1 | YES | YES | NO | 0.00 | 0.00 0.00 | 0.00 | 0.00 0.00 | 0.274 |
| TWIST | NO | YES | YES | 0.08 | 0.00 0.47 | 0.34 | 0.00 3.55 | 0.210 |

TABLE 3-continued

Breast cancer DNA Methylation Data and PRC2 Occupancy

| Genes | Occupancy in ES cells with | | | Methylation values (PMR) | | | | |
|---|---|---|---|---|---|---|---|---|
| | | | | non-neoplastic breast (n = 15) | | breast cancer (n = 15) | | |
| | | | | Median | 25th and 75th percentile | Median | 25th and 75th percentile | |
| BCL2 | YES | YES | YES | 0.00 | 0.00 0.00 | 0.00 | 0.00 0.10 | 0.496 |
| CALCA | YES | YES | YES | 1 | 0 2 | 2 | 1 3 | 0.185 |
| CDKN2C | YES | YES | YES | 0.00 | 0.00 0.00 | 0.00 | 0.00 0.00 | 1.000 |
| DCC | YES | YES | YES | 0.08 | 0.01 0.53 | 0.46 | 0.17 1.63 | 0.102 |
| GDNF | YES | YES | YES | 0.14 | 0.01 1.18 | 0.35 | 0.09 0.93 | 0.325 |
| ITGA4 | YES | YES | YES | 0.00 | 0.00 0.00 | 0.05 | 0.00 0.91 | 0.037 |
| MYOD1 | YES | YES | YES | 0.45 | 0.19 1.37 | 1.56 | 0.49 3.80 | 0.046 |
| NEUROD1 | YES | YES | YES | 0.25 | 0.10 1.34 | 5.49 | 3.00 34.05 | 0.000 |
| NEUROG2 | YES | YES | YES | 0.00 | 0.00 0.00 | 0.00 | 0.00 0.38 | 0.089 |
| PGR | YES | YES | YES | 0.32 | 0.24 0.89 | 0.69 | 0.26 1.12 | 0.539 |
| SFRP1 | YES | YES | YES | 0.25 | 0.00 1.26 | 0.89 | 0.31 21.50 | 0.019 |
| SFRP5 | YES | YES | YES | 0.63 | 0.51 1.36 | 3.13 | 1.83 13.09 | 0.000 |
| SLIT2 | YES | YES | YES | 1.11 | 0.64 1.94 | 6.18 | 2.15 26.31 | 0.000 |
| ZBTB16 | YES | YES | YES | 0.07 | 0.03 0.44 | 0.57 | 0.29 1.34 | 0.007 |

EXAMPLE 5

CD34-Positive Hematopoietic Progenitor Cell DNA Methylation Data and Stem Cell PRC2 Occupancy were Analyzed Table 4 lists DNA methylation values (PMR) of 35 genes (with known PRC2 component occupancy status in human embryonic stem cells) analyzed in CD34 positive hematopoietic progenitor cells from nine patients. Applicants defined "Stem cell genes" as genes which are occupied with at least two of the three components (SUZ12, EED and H3K27me3) in human embryonic stem cells. Stem-cell repressed genes, containing at least two of the PRC2 marks demonstrated detectable DNA methylation in CD34-positive cells in twice the number of subjects compared to genes lacking these marks (Mean: 6.1 vs 3.2, respectively, P=0.02). Cancer genes (as identified in ovarian cancer; Table 2) are much more likely to be methylated in CD34 pos. cells (P=0.001).

TABLE 4

DNA methylation in CD34-positive hematopoietic progenitor cells from nine subjects.

| Genes | Occupancy in ES cells with | | | Methylation values (PMR) of CD34+ haematopoietic stem cells | | | | | | | | | # pos | | |
|---|---|---|---|---|---|---|---|---|---|---|---|---|---|---|---|
| | SUZ12 | EED | H3K27me3 | 1 | 2 | 3 | 4 | 5 | 6 | 7 | 8 | 9 | | | |
| APC | NO | NO | NO | 0 | 0 | 0.1 | 0 | 0 | 0 | 0 | 0 | 0 | 1 | Average positive: 3.2 | NON-STEM CELL GENES |
| CCND2 | NO | NO | NO | 0 | 0 | 0 | 0 | 8 | 0 | 0 | 0 | 0 | 1 | Average positive: 3.2 | NON-STEM CELL GENES |
| CDH1 | NO | NO | NO | 0 | 0.2 | 1 | 0.03 | 25 | 0.002 | 0.4 | 0.1 | 0.002 | 8 | Average positive: 3.2 | NON-STEM CELL GENES |
| CXCR4 | NO | NO | NO | 0 | 0.1 | 0.01 | 0.004 | 0.01 | 0.02 | 0.004 | 0 | 0.01 | 7 | Average positive: 3.2 | NON-STEM CELL GENES |
| DAPK1 | NO | NO | NO | 0.00001 | 0 | 0.0024 | 0 | 16 | 0 | 0.2 | 0 | 0 | 3 | Average positive: 3.2 | NON-STEM CELL GENES |
| ESR2 | NO | NO | NO | 0 | 0.00001 | 0.03 | 0.001 | 0 | 0 | 0.02 | 0.001 | 0 | 5 | Average positive: 3.2 | NON-STEM CELL GENES |
| GSTP1 | NO | NO | NO | 0 | 0 | 0 | 0 | 0 | 0 | 0 | 0 | 0 | 0 | Average positive: 3.2 | NON-STEM CELL GENES |
| HSD17B4 | NO | NO | NO | 0 | 0.02 | 0 | 0 | 0 | 0 | 0 | 0 | 0 | 1 | Average positive: 3.2 | NON-STEM CELL GENES |
| HSPA2 | NO | NO | NO | 0 | 0.00001 | 0.00001 | 0.00001 | 5 | 0 | 0 | 0 | 0.00001 | 5 | Average positive: 3.2 | NON-STEM CELL GENES |
| MGMT | NO | NO | NO | 0 | 0 | 0 | 5 | 0 | 1 | 0.2 | 0.03 | 0 | 4 | Average positive: 3.2 | NON-STEM CELL GENES |
| MLH1 | NO | NO | NO | 0 | 0 | 0 | 0 | 0 | 0 | 0 | 0 | 0 | 0 | Average positive: 3.2 | NON-STEM CELL GENES |
| PTSG2 | NO | NO | NO | 0.001 | 0.04 | 0.5 | 0.2 | 2 | 0.3 | 1 | 0.4 | 0.001 | 9 | Average positive: 3.2 | NON-STEM CELL GENES |
| REV3L | NO | NO | NO | 0 | 0 | 0 | 0 | 0 | 0 | 0 | 0 | 0 | 0 | Average positive: 3.2 | NON-STEM CELL GENES |

TABLE 4-continued

DNA methylation in CD34-positive hematopoietic progenitor cells from nine subjects.

| Genes | Occupancy in ES cells with | | | Methylation values (PMR) of CD34+ haematopoietic stem cells | | | | | | | | | # pos | | |
|---|---|---|---|---|---|---|---|---|---|---|---|---|---|---|---|
| | SUZ12 | EED | H3K27me3 | 1 | 2 | 3 | 4 | 5 | 6 | 7 | 8 | 9 | | | |
| SFRP2 | NO | NO | NO | 0.1 | 0.5 | 1 | 0.2 | 67 | 0.1 | 1 | 1 | 0.1 | 9 | Average positive: 3.2 | NON-STEM CELL GENES |
| SOCS1 | NO | NO | NO | 0 | 0 | 0 | 0 | 0 | 0 | 0 | 0 | 0 | 0 | Average positive: 3.2 | NON-STEM CELL GENES |
| SOCS2 | NO | NO | NO | 0 | 0 | 5 | 3 | 1 | 0 | 1 | 0 | 0 | 4 | Average positive: 3.2 | NON-STEM CELL GENES |
| SYK | NO | NO | NO | 0 | 0 | 0.02 | 0 | 0 | 0 | 0 | 0 | 0 | 1 | Average positive: 3.2 | NON-STEM CELL GENES |
| TERT | NO | NO | NO | 0 | 0 | 0 | 0 | 0 | 0 | 0 | 0 | 0 | 0 | Average positive: 3.2 | NON-STEM CELL GENES |
| TFF1 | NO | NO | NO | 79 | 50 | 15 | 49 | 51 | 60 | 60 | 0.00001 | 53 | 9 | Average positive: 3.2 | NON-STEM CELL GENES |
| TGFB3 | NO | NO | NO | 0 | 0 | 0 | 0 | 0 | 0 | 0 | 0 | 0 | 0 | Average positive: 3.2 | NON-STEM CELL GENES |
| TIMP3 | NO | NO | NO | 0 | 0.02 | 0.1 | 0 | 4 | 0 | 0.01 | 0.00001 | 0 | 5 | Average positive: 3.2 | NON-STEM CELL GENES |
| TP53BP2 | NO | NO | NO | 0 | 0 | 0 | 0 | 0 | 0 | 0 | 0 | 0 | 0 | Average positive: 3.2 | NON-STEM CELL GENES |
| ESR1 | NO | NO | YES | 0 | 0.02 | 0.004 | 0 | 6 | 0.01 | 0.02 | 0 | 0 | 4 | Average positive: 3.2 | NON-STEM CELL GENES |
| MT3 | NO | NO | YES | 0 | 0 | 0.2 | 0 | 0 | 0 | 0 | 0 | 0 | 1 | Average positive: 3.2 | NON-STEM CELL GENES |
| CDH13 | YES | NO | NO | 0 | 0 | 0.2 | 0 | 15 | 0 | 0.01 | 0 | 0.00001 | 4 | Average positive: 3.2 | NON-STEM CELL GENES |
| GSTM3 | YES | NO | NO | 0 | 0 | 0.1 | 0 | 5 | 0 | 0 | 0 | 0 | 2 | Average positive: 3.2 | NON-STEM CELL GENES |

TABLE 4-continued

DNA methylation in CD34-positive hematopoietic progenitor cells from nine subjects.

| Genes | Occupancy in ES cells with | | | Methylation values (PMR) of CD34+ haematopoietic stem cells | | | | | | | | | # pos | |
|---|---|---|---|---|---|---|---|---|---|---|---|---|---|---|
| | SUZ12 | EED | H3K27me3 | 1 | 2 | 3 | 4 | 5 | 6 | 7 | 8 | 9 | | |
| HIC1 | NO | YES | YES | 0 | 1 | 12 | 2 | 0.04 | 5 | 10 | 2 | 0.02 | 8 | Average positive: 6.1 STEM CELL GENES |
| SFRP4 | NO | YES | YES | 2 | 1 | 2 | 1 | 1 | 0.04 | 1 | 1 | 0.3 | 9 | Average positive: 6.1 STEM CELL GENES |
| TWIST1 | NO | YES | YES | 0 | 0 | 0.2 | 0 | 0 | 1 | 0 | 0 | 0 | 2 | Average positive: 6.1 STEM CELL GENES |
| CALCA | YES | YES | YES | 0 | 1 | 0.1 | 0.1 | 5 | 0 | 1 | 0 | 0 | 5 | Average positive: 6.1 STEM CELL GENES |
| MYOD1 | YES | YES | YES | 0.02 | 0.004 | 0.3 | 0.0013 | 12 | 0 | 0 | 0 | 0 | 7 | Average positive: 6.1 STEM CELL GENES |
| PGR | YES | YES | YES | 0.1 | 0.2 | 0.4 | 0.3 | 23 | 0.1 | 0.1 | 0.3 | 0.1 | 9 | Average positive: 6.1 STEM CELL GENES |
| SFRP1 | YES | YES | YES | 0 | 0 | 0.5 | 0 | 112 | 0.4 | 1 | 1 | 0 | 4 | Average positive: 6.1 STEM CELL GENES |
| SFRP5 | YES | YES | YES | 0.3 | 1 | 1 | 0.3 | 1 | 1 | 1 | 1 | 0.2 | 9 | Average positive: 6.1 STEM CELL GENES |
| TITF1 | YES | YES | YES | 0 | 0 | 0.002 | 0 | 2 | 0 | 0 | 0 | 0 | 2 | Average positive: 6.1 STEM CELL GENES |

PMR = 0     0 < PMR < 1     PMR > 1

TABLE S5

List of MethyLight Primers and Probes

| REACTION ID | GENE SYMBOL | Aplicon Location Start (UCSC Genome Coordinates, Assembly Date May, 2004) | Amplicon Location End (UCSC Genome Coordinates, Assembly Date May, 2004) | Forward Primer Sequence | SEQ ID NO. |
|---|---|---|---|---|---|
| HB-040 | CCND2 | 4252120 | 4252184 | GGAGGGTCGGCGAGGAT | SEQ ID NO: 19 |
| HB-041 | FHIT | 61211898 | 61211972 | GGCGCGGGTTTGGG | SEQ ID NO: 22 |
| HB-042 | SOCS1 | 11256473 | 11256558 | GCGTCGAGTTCGTGGGTATTT | SEQ ID NO: 25 |
| HB-043 | DIRAS3 | 68228349 | 68228434 | GCGTAAGCGGAATTTATGTTTGT | SEQ ID NO: 28 |
| HB-046 | DAPK1 | 87342485 | 87342552 | TCGTCGTCGTTTCGGTTAGTT | SEQ ID NO: 31 |
| HB-047 | TWIST1 | 18929791 | 18929865 | GTAGCGCGGCGAACGT | SEQ ID NO: 34 |
| HB-048 | DNAJC15 | 42495746 | 42495826 | TTTCGGGTCGTTTTGTTATGG | SEQ ID NO: 37 |
| HB-049 | DPH1 | 1880101 | 1880170 | ACGCGGAGAGCGTAGATATTG | SEQ ID NO: 40 |
| HB-050 | CDH1 | 67328528 | 67328623 | AGGGTTATCGCGTTTATGCG | SEQ ID NO: 43 |
| HB-051 | ABCB1 | 86874884 | 86874962 | TCGGGTCGGGAGTAGTTATTTG | SEQ ID NO: 46 |
| HB-052 | PTTG1 | 159781430 | 159781499 | GCGTTCGTTTATCGCGGT | SEQ ID NO: 49 |
| HB-053 | SMAD3 | 65145579 | 65145653 | CGTGAAGCGTTTGTTGGGT | SEQ ID NO: 52 |
| HB-054 | CXADR | 17807103 | 17807169 | TACGCGGTTGGAGAAGTCG | SEQ ID NO: 55 |
| HB-058 | MTHFR | 11797288 | 11797377 | TGGTAGTGAGAGTTTTAAAGATAGTTCGA | SEQ ID NO: 58 |
| HB-059 | CLDN1 | 191522936 | 191523032 | CGGTGAGTCGTTTTGAAATCG | SEQ ID NO: 61 |
| HB-060 | PPARG | 12304350 | 12304465 | GCGTTCGCGTTCGTTTTC | SEQ ID NO: 64 |
| HB-061 | S100A2 | 150354273 | 150354354 | TGTTTGAGTCGTAAGTAGGGCGT | SEQ ID NO: 67 |
| HB-062 | CLIC4 | 24817200 | 24817272 | GGCGGTGTTGAGGAGTTGA | SEQ ID NO: 70 |
| HB-063 | STAT1 | 191704255 | 191704343 | GCGTAGGATTCGGAAGGGTTA | SEQ ID NO: 73 |
| HB-065 | PTGS2 | 183381471 | 183381545 | CGGAAGCGTTCGGGTAAAG | SEQ ID NO: 76 |
| HB-066 | HSD17B4 | 118816177 | 118816247 | TATCGTTGAGGTTCGACGGG | SEQ ID NO: 79 |
| HB-067 | NR3C1 | 142763209 | 142763279 | GGGTGGAAGGAGACGTCGTAG | SEQ ID NO: 82 |
| HB-068 | VDR | 46585350 | 46585440 | ACGTATTTGGTTTAGGCGTTCGTA | SEQ ID NO: 85 |
| HB-069 | CADM1 | 114880288 | 114880369 | GGGTTTCGGAGGTAGTTAACGTC | SEQ ID NO: 88 |
| HB-074 | TERT | 1348267 | 1348382 | GGATTCGCGGGTATAGACGTT | SEQ ID NO: 91 |
| HB-075 | CDH13 | 81218210 | 81218312 | AATTTCGTTCGTTTTGTGCGT | SEQ ID NO: 94 |
| HB-077 | NCL | 232154778 | 232154864 | CGTGTCGTTTCGGTTCGTT | SEQ ID NO: 97 |
| HB-078 | CYP1B1 | 38214997 | 38215082 | GTGCGTTTGGACGGGAGTT | SEQ ID NO: 100 |
| HB-079 | SLC6A20 | 45812864 | 45812998 | AGGCGAATACGAATTGTAGCG | SEQ ID NO: 103 |
| HB-080 | TNFRSF25 | 6460427 | 6460495 | GCGGAATTACGACGGGTAGA | SEQ ID NO: 106 |
| HB-082 | UNG | 107998395 | 107998490 | GTTTGACGGAGGGCGTGTA | SEQ ID NO: 109 |
| HB-083 | MBD4 | 130641365 | 130641480 | TCGTGTTTATCGAGTAGGGTTCG | SEQ ID NO: 112 |
| HB-084 | MSH6 | 47921669 | 47921753 | GGAGTGTTTCGGTTCGGTTAGT | SEQ ID NO: 115 |
| HB-087 | OGG1 | 9766425 | 9766556 | TAGGGTGGGCGGGTCG | SEQ ID NO: 118 |
| HB-088 | MUTYH/TOE1 | 45474733 | 45474807 | TCGGGTGGATTCGAGTTACG | SEQ ID NO: 121 |

TABLE S5-continued

List of MethyLight Primers and Probes

| HB-089 | NTHL1 | 2037891 | 2038004 | CGGGACGTCGTCGGAAG | SEQ ID NO: 124 |
|---|---|---|---|---|---|
| HB-090 | APEX1 | 19993146 | 19993280 | CGTATTTGTATCGGTTCGATGGTA | SEQ ID NO: 127 |
| HB-092 | XRCC1 | 48771564 | 48771673 | CGTTGTTAAGGAACGTAGCGTTTT | SEQ ID NO: 130 |
| HB-093 | PARP1 | 222902100 | 222902168 | CGGGTTAGGGAGCGAGC | SEQ ID NO: 133 |
| HB-094 | PARP2 | 19881678 | 19881744 | GGGCGAGAGGTTCGGAGT | SEQ ID NO: 136 |
| HB-095 | MSH2 | 48542284 | 47542370 | TTTTAGTGCGGAGGTACGGG | SEQ ID NO: 139 |
| HB-096 | MSH4 | 75974790 | 75974880 | CGGATTTTAGGAGATTTTATAGAGTCG | SEQ ID NO: 142 |
| HB-097 | MSH5 | 31815771 | 31815853 | TTCGTGGCGGTCGGTTA | SEQ ID NO: 145 |
| HB-098 | PILRB | 99578411 | 99578495 | TCGTGGTTTGGCGTGGAT | SEQ ID NO: 148 |
| HB-099 | MLH3 | 74587699 | 74587769 | TGATGATGGTTGCGCGTAGT | SEQ ID NO: 151 |
| HB-100 | XPC | 14195020 | 14195117 | GTCGGGTGCGTTATTCGC | SEQ ID NO: 154 |
| HB-101 | RAD23A | 12917467 | 12917552 | TATCGATAACGGGTATGGCGTT | SEQ ID NO: 157 |
| HB-102 | XPA | 97539016 | 97539079 | CGCGGAGTTGTTTGTTTCG | SEQ ID NO: 160 |
| HB-103 | RPA2 | 27925472 | 27925546 | TGGCGCGAATTTGAGTACG | SEQ ID NO: 163 |
| HB-104 | RPA3 | 7453370 | 7453448 | AGCGCGATTGCGATTTAGG | SEQ ID NO: 166 |
| HB-105 | ERCC2 | 50565643 | 50565727 | CGAGTTTTCGAGGATGTTTACGA | SEQ ID NO: 169 |
| HB-109 | ERCC5 | 102296112 | 102296188 | TAAGCGTAGAAAATATACGTTATGTGCG | SEQ ID NO: 172 |
| HB-110 | ERCC1 | 50618574 | 50618664 | GGGCGAGTCGAAGGTGG | SEQ ID NO: 175 |
| HB-111 | ERCC4 | 13921544 | 13921615 | TCGACGGATTGTTATGGCG | SEQ ID NO: 178 |
| HB-113 | NDUFA12L | 60277058 | 60277170 | GGTTAAGGCGTTTAGAGTCGGG | SEQ ID NO: 181 |
| HB-114 | ERCC6 | 50417137 | 50417262 | ACGTAAGTAGAAAGGCGTTGTTGAG | SEQ ID NO: 184 |
| HB-115 | XAB2 | 7600520 | 7600597 | GACGGATAGGTTTACGTTATTGATTTT | SEQ ID NO: 187 |
| HB-116 | DDB1 | 60857034 | 60857134 | GGGCGGAGGTAGCGGT | SEQ ID NO: 190 |
| HB-117 | MMS19L | 99248168 | 99248271 | TTAGGTAGAAGTCGGTAGGTACGTGA | SEQ ID NO: 193 |
| HB-126 | BRCA2 | 31787586 | 31787652 | CGTTACGGCGTTACGTGGT | SEQ ID NO: 196 |
| HB-133 | DCLRE1C | 15036151 | 15036236 | CGAAGCGCGGGTGATTTA | SEQ ID NO: 199 |
| HB-139 | POLD1 | 55579103 | 55579174 | GGGACGCGGAGGATGC | SEQ ID NO: 202 |
| HB-140 | BCL2 | 59136618 | 59136701 | TCGTATTTCGGGATTCGGTC | SEQ ID NO: 205 |
| HB-141 | TSHR | 80491125 | 80491211 | TTGAGGGTTAGAGGCGGGTA | SEQ ID NO: 208 |
| HB-142 | MBD2 | 50005060 | 50005138 | AGGCGGAGATAAGATGGTCGT | SEQ ID NO: 211 |
| HB-144 | HRAS | 524232 | 524327 | GAGCGATGACGGAATATAAGTTGG | SEQ ID NO: 214 |
| HB-145 | TFF1 | 42659974 | 42660121 | TAAGGTTACGGTGGTTATTTCGTGA | SEQ ID NO: 217 |
| HB-146 | CCND1 | 69164885 | 69164967 | GGTAATTTCGTCGTAGGGTAGGC | SEQ ID NO: 220 |
| HB-147 | CTSD | 1741982 | 1742072 | TACGTTTCGCGTAGGTTTGGA | SEQ ID NO: 223 |
| HB-149 | PGR | 100503526 | 100503701 | GGCGGTGACGGTCGTATTC | SEQ ID NO: 226 |

TABLE S5-continued

List of MethyLight Primers and Probes

| HB-150 | MLH1 | 37009766 | 37009849 | AGGAAGAGCGGATAGCGATTT | SEQ ID NO: 229 |
| --- | --- | --- | --- | --- | --- |
| HB-151 | FBXW7 | 153814403 | 153814526 | TGTCGTTGCGGTTGGGAT | SEQ ID NO: 232 |
| HB-152 | EPM2AIP1 | 37009363 | 37009450 | CGTTATATATCGTTCGTAGTATTCGTGTTT | SEQ ID NO: 235 |
| HB-153 | APC | 112101379 | 112101452 | TTATATGTCGGTTACGTGCGTTTATAT | SEQ ID NO: 238 |
| HB-154 | MYOD1 | 17697363 | 17697435 | GAGCGCGCGTAGTTAGCG | SEQ ID NO: 241 |
| HB-157 | PTEN | 89612994 | 89613081 | GTTTCGCGTTGTTGTAAAAGTCG | SEQ ID NO: 244 |
| HB-158 | CACNA1G | 45993464 | 45993530 | TTTTTTCGTTTCGCGTTTAGGT | SEQ ID NO: 247 |
| HB-160 | MGMT | 131155503 | 131155585 | GCGTTTCGACGTTCGTAGGT | SEQ ID NO: 250 |
| HB-163 | PENK | 57521694 | 57521792 | GGTTAATTATAAAGTGGTTTTAGTAGTCGTTAAG | SEQ ID NO: 253 |
| HB-164 | ESR1 | 152220942 | 152221042 | GGCGTTCGTTTTGGGATTG | SEQ ID NO: 256 |
| HB-165 | ESR2 | 63830670 | 63830741 | TTTGAAATTTGTAGGGCGAAGAGTAG | SEQ ID NO: 259 |
| HB-166 | CALCA | 14950501 | 14950601 | GTTTTGGAAGTATGAGGGTGACG | SEQ ID NO: 262 |
| HB-167 | TIMP3 | N/A | N/A | GCGTCGGAGGTTAAGGTTGTT | SEQ ID NO: 265 |
| HB-168 | HIC1 | 1906660 | 1906760 | GTTAGGCGGTTAGGGCGTC | SEQ ID NO: 268 |
| HB-170 | CTNNB1 | 41215587 | 41215667 | GGAAAGGCGCGTCGAGT | SEQ ID NO: 271 |
| HB-172 | GSTP1 | 67107783 | 67107882 | GTCGGCGTCGTGATTTAGTATTG | SEQ ID NO: 274 |
| HB-173 | CDKN2B | 21998980 | 21999060 | AGGAAGGAGAGAGTGCGTCG | SEQ ID NO: 277 |
| HB-174 | SFN | 26874056 | 26874136 | GAGGAGGGTTCGGAGGAGAA | SEQ ID NO: 280 |
| HB-175 | KL | 32488560 | 32488687 | AGTTTGGTTTTCGCGTAGTATGTTC | SEQ ID NO: 283 |
| HB-176 | RARB | 25444834 | 25444919 | TTTATGCGAGTTGTTTGAGGATTG | SEQ ID NO: 286 |
| HB-177 | TP73 | 3592223 | 3592304 | GGGTCGGGTAGTTCGTTTTG | SEQ ID NO: 289 |
| HB-178 | DCC | 48121053 | 48121210 | GGGTTCGGCGCGTGT | SEQ ID NO: 292 |
| HB-179 | ATM | 107599021 | 107599090 | ACGGAGAAAAGAAGTCGTGGTC | SEQ ID NO: 295 |
| HB-180 | ATR | 143780282 | 143780372 | AGCGGTTTTCGGGAGGAGT | SEQ ID NO: 298 |
| HB-181 | RUNX3 | 25001393 | 25001509 | CGTTCGATGGTGGACGTGT | SEQ ID NO: 301 |
| HB-183 | STK11 | 1156690 | 1156793 | AATTAACGGGTGGGTACGTCG | SEQ ID NO: 304 |
| HB-184 | SEZ6L | 24889734 | 24889836 | GCGTTAGTAGGGAGAGAAAACGTTC | SEQ ID NO: 307 |
| HB-185 | RBP1 | 140741145 | 140741234 | CGCGTTGGGAATTTAGTTGTC | SEQ ID NO: 310 |
| HB-186 | ARPC1B | 98616846 | 98616917 | TGCGCGGGTATCGGTAGTAT | SEQ ID NO: 313 |
| HB-190 | CHFR | 132074209 | 132074312 | CGGGAGTTTTTATGGGCGT | SEQ ID NO: 316 |
| HB-191 | VHL | 10158449 | 10158542 | CGGGAGCGCGTACGTAGTT | SEQ ID NO: 319 |
| HB-192 | TGFBR1 | 98946812 | 98946910 | ACGCGCGTTTATTGGTTGTC | SEQ ID NO: 322 |
| HB-193 | COL1A2 | 93668865 | 93668953 | CGGTAGTAGGAGGTTTCGGTTAAGT | SEQ ID NO: 325 |
| HB-194 | SCGB3A1 | 179950956 | 179951042 | GGCGTAGCGGGCGTC | SEQ ID NO: 328 |
| HB-195 | CDX1 | 149526555 | 149526622 | TGAGCGGTTGTTCGTCGTC | SEQ ID NO: 331 |
| HB-197 | CRABP1 | 76419794 | 76419875 | TCGAAATTTTCGTTGTTGCGT | SEQ ID NO: 334 |

TABLE S5-continued

List of MethyLight Primers and Probes

| HB-199 | PLAGL1 | 1443711135 | 144371211 | ATCGACGGGTTGAATGATAAATG | SEQ ID NO: 337 |
|---|---|---|---|---|---|
| HB-200 | LZTS1 | 20154741 | 20154825 | GCGGCGTTGTAGGGACG | SEQ ID NO: 340 |
| HB-201 | SFRP1 | 41286207 | 41286276 | GAATTCGTTCGCGAGGGA | SEQ ID NO: 343 |
| HB-203 | JUP | 37196423 | 37196513 | GGATAGCGAATTGAGTTCGGC | SEQ ID NO: 346 |
| HB-204 | MT1G | 55259560 | 55259636 | CGTTTAAGGGATTTTGTATTTGGTTTAT | SEQ ID NO: 349 |
| HB-205 | MT1A | 55229471 | 55229550 | CGTGTTTTCGTGTTATTGTGTACG | SEQ ID NO: 352 |
| HB-206 | MT2A | 55199620 | 55199708 | GCGTTTTCGTCGTGTGTATAGTTT | SEQ ID NO: 355 |
| HB-207 | MT3 | 55180944 | 55181018 | GGTTTTAGGGTTTATGTCGAGGAGA | SEQ ID NO: 358 |
| HB-208 | SERPINB5 | 59295148 | 59295227 | GAAAAGGAATAGGTAAGCGAGGAGT | SEQ ID NO: 361 |
| HB-209 | OPCML/HNT | 132319029 | 132319100 | CGTTTCGAGGCGGTATCG | SEQ ID NO: 364 |
| HB-211 | PAX8 | 113752214 | 113752309 | GTTCGTAGTTCGTCGAGGGTTC | SEQ ID NO: 367 |
| HB-213 | TITF1 | 36058456 | 36058584 | CGAAATAAACCGAATCCTCCTTAA | SEQ ID NO: 370 |
| HB-214 | PRKAR1A | 64019490 | 64019573 | CGGATTTGTAGTAGTTGCGTTGC | SEQ ID NO: 373 |
| HB-215 | TFAP2A | N/A | N/A | CACCCCCATATACGCGCTAA | SEQ ID NO: 376 |
| HB-216 | THRB | 24511656 | 24511731 | TCGTCGTCGTTATCGTCGC | SEQ ID NO: 379 |
| HB-217 | WDR79 | 7532404 | 7532486 | TTTGTTGTCGCGGGATTTC | SEQ ID NO: 382 |
| HB-218 | DLC1 | 13034914 | 13034989 | AGTAAGGATGCGTTGAGGATCG | SEQ ID NO: 385 |
| HB-219 | LDLR | 11060912 | 11061014 | GATATCGGTTTTTTAATTCGTGAAGTT | SEQ ID NO: 388 |
| HB-220 | SASH1 | 148705411 | 148705522 | TGGAAGAGTTTATTTTGAAGAGAGGG | SEQ ID NO: 391 |
| HB-221 | GDNF | 37875633 | 37875741 | CGGTAGTTGTCGTTGAGTCGTTC | SEQ ID NO: 394 |
| HB-223 | CYP27B1 | 56446731 | 56446808 | GGGATAGTTAGAGAGAACGGATGTTT | SEQ ID NO: 397 |
| HB-224 | LRRC41 | 46480839 | 46480910 | TTCGGTTTCGGGTTTTAACG | SEQ ID NO: 400 |
| HB-225 | DLEC1 | 38055976 | 38056105 | TCGTTGCGTATTTAAGATATTTCGTATT | SEQ ID NO: 403 |
| HB-226 | CDK2AP1 | 122281168 | 122281288 | CGCGGAAAGTTTGCGGT | SEQ ID NO: 406 |
| HB-227 | AXIN1 | 342144 | 342213 | CGGTTTTTGTAGTTGTTTCGTGTT | SEQ ID NO: 409 |
| HB-228 | PYCARD | 31121237 | 31121332 | TTGGAGATTTACGGCGTCG | SEQ ID NO: 412 |
| HB-229 | EBF3 | 131652354 | 131652431 | GTAGGATATTGCGGGATCGTTC | SEQ ID NO: 415 |
| HB-231 | PSAT1 | 78141710 | 78141790 | TGGGTTTGGTTTCGTTAAGTTGT | SEQ ID NO: 418 |
| HB-233 | ERBB2 | 35109610 | 35109685 | AGTGTGAGAACGGTTGTAGGTAATTTAG | SEQ ID NO: 421 |
| HB-235 | PITX2 | 111915903 | 111916005 | AGTTCGGTTGCGCGGTT | SEQ ID NO: 424 |
| HB-237 | CGA | 87861458 | 87861547 | GGGTTTTTTGTAGGATGTGTTTAGG | SEQ ID NO: 427 |
| HB-241 | SYK | 90643286 | 90643370 | AGGGTCGTTGGGTGTTTGTG | SEQ ID NO: 430 |
| HB-242 | ONECUT2 | 53253467 | 53253547 | ACGGGCGTTAAGCGTAATTATTT | SEQ ID NO: 433 |
| HB-245 | RB1 | 47775771 | 47775890 | TTAGTTCGCGTATCGATTAGCG | SEQ ID NO: 436 |
| HB-246 | TGFBR2 | 30623298 | 30623377 | GCGCGGAGCGTAGTTAGG | SEQ ID NO: 439 |

TABLE S5-continued

List of MethyLight Primers and Probes

| HB-247 | THBS1 | 37659935 | 37660009 | GTTTTGAGTTGGTTTTACGTTCGTT | SEQ ID NO: 442 |
|---|---|---|---|---|---|
| HB-248 | TYMS | 647871 | 647946 | CGGCGTTAGGAAGGACGAT | SEQ ID NO: 445 |
| HB-250 | GRIN2B | 14025182 | 14025264 | GTCGGATTTACGCGTCGAGT | SEQ ID NO: 448 |
| HB-251 | NTF3 | 5473982 | 5474055 | TTTCGTTTTTGTATTTTATGGAGGATT | SEQ ID NO: 451 |
| HB-253 | DRD2 | 112850580 | 112850649 | GAAGTCGGAAATTTTGGTCGC | SEQ ID NO: 454 |
| HB-254 | GABRA2 | 46233296 | 46233369 | TCGTCGGAGGAGCGGA | SEQ ID NO: 457 |
| HB-256 | GAD1 | 171500487 | 171500569 | CGATTGGTTCGGCGTAGAAA | SEQ ID NO: 460 |
| HB-258 | BDNF | 27678453 | 27678525 | CGTATCGGGTTGGTTTTTTGTT | SEQ ID NO: 463 |
| HB-259 | NEUROD1 | 182370725 | 182370806 | GTTTTTTGCGTGGGCGAAT | SEQ ID NO: 466 |
| HB-260 | NEUROD2 | 35017643 | 35017731 | GGTTTGGTATAGAGGTTGGTATTTCGT | SEQ ID NO: 469 |
| HB-261 | NEUROG1 | 134899670 | 134899757 | CGTGTAGCGTTCGGGTATTGTA | SEQ ID NO: 472 |
| HB-262 | PSEN1 | 72673243 | 72673319 | GTCGGGTGGAGAGAGATTTCG | SEQ ID NO: 475 |
| HB-264 | PSEN2 | 223365485 | 223365573 | GAGGCGTGTAGTAGGCGGG | SEQ ID NO: 478 |
| HB-266 | APP | 26465290 | 26465385 | AACGAAATGCGGATAAAAACGTAT | SEQ ID NO: 481 |
| HB-268 | HOXA1 | 26908602 | 26908684 | TTGTTTATTAGGAAGCGGTCGTC | SEQ ID NO: 484 |
| HB-270 | HOXA10 | 26987339 | 26987422 | TGTATTGATGGGTTAGGAGACGTATT | SEQ ID NO: 487 |
| HB-274 | TMEFF2 | 192885270 | 192885342 | CGACGAGGAGGTGTAAGGATG | SEQ ID NO: 490 |
| HB-275 | SMAD2 | 43711755 | 43711832 | CGAGGCGGTAGGTTTTTATAGGT | SEQ ID NO: 493 |
| HB-278 | SMAD6 | 64781526 | 64781629 | ATGTTAGTTTAGATATTTTGGCGGTTTC | SEQ ID NO: 496 |
| HB-280 | SFRP2 | 155067644 | 155067735 | GCGTTTTAGTCGTCGGTTGTTAGT | SEQ ID NO: 499 |
| HB-281 | SFRP4 | 37729547 | 37729625 | GTTGTTCGGGCGGGTTC | SEQ ID NO: 502 |
| HB-282 | SFRP5 | 99521371 | 99521463 | GCGTTTGTAGTTTATCGTGTGGTAGA | SEQ ID NO: 505 |
| HB-304 | FAF1 | 51138014 | 51138088 | CGTTTTGCGGTTTTACGTGA | SEQ ID NO: 508 |
| HB-306 | TNFRSF10A | 23138801 | 23138877 | AGTTTTTGGTATTTAGTAGGCGTTCG | SEQ ID NO: 511 |
| HB-307 | TNFRSF10B | 22982682 | 22982764 | TTTTGGCGGTTGCGTTTC | SEQ ID NO: 514 |
| HB-308 | TNFRSF10C | 23016667 | 23016789 | GGGAAGAGCGTATTGGCG | SEQ ID NO: 517 |
| HB-309 | TNFRSF10D | 230770092 | 23077216 | GGGAAGAGCGTATTTGGCG | SEQ ID NO: 520 |
| HB-311 | IFNG | 66839949 | 66840111 | TGAAGAGTTAATATTTTATTAGGGCGAA | SEQ ID NO: 523 |
| HB-315 | SMAD9 | 36392381 | 36392455 | CGCGAAGTTTTATCGTTCGTATTAG | SEQ ID NO: 526 |
| HB-319 | IGF2 | 2116714 | 2116801 | GAGCGGTTTCGGTGTCGTTA | SEQ ID NO: 529 |
| HB-321 | ITGA4 | 182147511 | 182147581 | TGCGGAGGCGTAGGGTC | SEQ ID NO: 532 |
| HB-322 | RARRES1 | 159932677 | 159932741 | GGCGAGTCGGATCGGAA | SEQ ID NO: 535 |
| HB-323 | GATA4 | 11599555 | 11599628 | GATGGTGGTCGCGTGAAGTTA | SEQ ID NO: 538 |
| HB-326 | GATA5 | 60484577 | 60484661 | AGTTACGTGATTTTGGTAGGTTTTGTT | SEQ ID NO: 541 |

TABLE S5-continued

List of MethyLight Primers and Probes

| | | | | | | |
|---|---|---|---|---|---|---|
| HB-327 | GATA3 | 8136301 | 8136380 | TGTATCGGGACGGAATCGTT | SEQ ID NO: 544 | |
| HB-329 | CDKN1C | 2862551 | 2862625 | TCGAGTAGGGCGCGAATTAG | SEQ ID NO: 547 | |

| REACTION ID | Reverse Primer Sequence | SEQ ID NO. | Probe Oligo Sequence | SEQ ID NO. |
|---|---|---|---|---|
| HB-040 | TCCTTTCCCCGAAAACATAAAA | SEQ ID NO: 20 | 6FAM-CACGCTCGATCCTTCGCCCG-BHQ-1 | SEQ ID NO: 21 |
| HB-041 | CGCCCCGTAAACGACG | SEQ ID NO: 23 | 6FAM-CACTAAACTCCGAAATAATAACCTAACGCGCG-BHQ-1 | SEQ ID NO: 24 |
| HB-042 | CCGAAACCATCTTCACGCTAA | SEQ ID NO: 26 | 6FAM-ACAATTCCGCTAACGACTATCGCGCA-BHQ-1 | SEQ ID NO: 27 |
| HB-043 | CCGCGATTTTATATTCCGACTT | SEQ ID NO: 29 | 6FAM-CGCACAAAAACGAAATACGAAAACGCAAA-BHQ-1 | SEQ ID NO: 30 |
| HB-046 | TCCCTCCGAAACGCTATCG | SEQ ID NO: 32 | 6FAM-CGACCATAAACGCCAACGCCG-BHQ-1 | SEQ ID NO: 33 |
| HB-047 | AAACGCAACGAATCATAACCAAC | SEQ ID NO: 35 | 6FAM-CCAACGCACCCAATCGCTAAACGA-BHQ-1 | SEQ ID NO: 36 |
| HB-048 | ACTACAAATACTCAACGTAACGCAAACT | SEQ ID NO: 38 | 6FAM-TCGCCAACTAAAACGATAACACCACGACA-BHQ-1 | SEQ ID NO: 39 |
| HB-049 | CCGCCCAACGAATATCCC | SEQ ID NO: 41 | 6FAM-CCCGCTAACCGATCGACGATCGA-BHQ-1 | SEQ ID NO: 42 |
| HB-050 | TTCACCTACCGACCACAACCA | SEQ ID NO: 44 | 6FAM-ACTAACGACCCGCCCACCCGA-BHQ-1 | SEQ ID NO: 45 |
| HB-051 | CGACTATACTCAACCCACGCC | SEQ ID NO: 47 | 6FAM-ACGCTATTCCTACCCAACCAATCAACCTCA-BHQ-1 | SEQ ID NO: 48 |
| HB-052 | CCGCGACCCTCCCATT | SEQ ID NO: 50 | 6FAM-ACTCACGCAAATCTTAACAACCGCATTCA-BHQ-1 | SEQ ID NO: 51 |
| HB-053 | TTAACCGCCTTCTCGCACC | SEQ ID NO: 53 | 6FAM-TCCTCCTACCCGTTCTACTCGCCCTTCT-BHQ-1 | SEQ ID NO: 54 |
| HB-054 | ATAAACTCGCGTCACTTCCGA | SEQ ID NO: 56 | 6FAM-AACGACCCGAACCGAACTACGAACG-BHQ-1 | SEQ ID NO: 57 |
| HB-058 | CGCCTCATCTTCTCCCGA | SEQ ID NO: 59 | 6FAM-TCTCATACCGCTCAAAATCCAAACCCG-BHQ-1 | SEQ ID NO: 60 |
| HB-059 | ACGCAAAACCGCTAAACGC | SEQ ID NO: 62 | 6FAM-GATTTAAAACAACTCCGCCCGCCTCA-BHQ-1 | SEQ ID NO: 63 |
| HB-060 | CGCCCAAACGACGAC | SEQ ID NO: 65 | 6FAM-CCCGCCTACCCGCGACGAAA-BHQ-1 | SEQ ID NO: 66 |
| HB-061 | CGTATCATTACAATACCGACCTCCT | SEQ ID NO: 68 | 6FAM-ATCCTCCCTTTCTTATCCGCCAAACCCT-BHQ-1 | SEQ ID NO: 69 |
| HB-062 | CCGATTCCCGCCGTACTAC | SEQ ID NO: 71 | 6FAM-CGCTAAACTATCCGAAATCGAACTAACCACG-BHQ-1 | SEQ ID NO: 72 |
| HB-063 | AACAAACCCCAAACCGAACA | SEQ ID NO: 74 | 6FAM-AACGACCCAACGCGCTCGAAAA-BHQ-1 | SEQ ID NO: 75 |

TABLE S5-continued

List of MethyLight Primers and Probes

| HB-065 | AATTCCACCGCCCCAAAC | SEQ ID NO: 77 | 6FAM-TTTCCGCCAAATATCTTTTCTTCTTCGCA-BHQ-1 | SEQ ID NO: 78 |
| --- | --- | --- | --- | --- |
| HB-066 | TCCAACCTTCGCATACTCACC | SEQ ID NO: 80 | 6FAM-CCCGCGCCGATAACCAATACCA-BHQ-1 | SEQ ID NO: 81 |
| HB-067 | AAACTTCCGAACGCGCG | SEQ ID NO: 83 | 6FAM-GTCCCGATCCCAACTACTTCGACCG-BHQ-1 | SEQ ID NO: 84 |
| HB-068 | CGCTTCAACCTATATTAATCGAAAATACA | SEQ ID NO: 86 | 6FAM-CCCACCCTTCCTACCGTAATTCTACCCAA-BHQ-1 | SEQ ID NO: 87 |
| HB-069 | CACTAAAATCCGCTCGACAACAC | SEQ ID NO: 89 | 6FAM-ACACTCGCCATATCGAACACCTACCTCAAA-BHQ-1 | SEQ ID NO: 90 |
| HB-074 | CGAAATCCGCGCGAAA | SEQ ID NO: 92 | 6FAM-CCCAATCCCTCCGCCACGTAAAA-BHQ-1 | SEQ ID NO: 93 |
| HB-075 | CTACCCGTACCGAACGATCC | SEQ ID NO: 95 | 6FAM-AACGCAAAACGCGCCCGACA-BHQ-1 | SEQ ID NO: 96 |
| HB-077 | ACCAAAACTCGCGACCGTC | SEQ ID NO: 98 | 6FAM-CCATAAACCAATCGCGAACCTCTAACCGT-BHQ-1 | SEQ ID NO: 99 |
| HB-078 | AACGCGACCTAACAAAACGAA | SEQ ID NO: 101 | 6FAM-CGCCGCACACCAAACCGCTT-BHQ-1 | SEQ ID NO: 102 |
| HB-079 | TAAAACGACGCGCCTAACG | SEQ ID NO: 104 | 6FAM-CCGCGCACTAAAACTACCGTACCGAA-BHQ-1 | SEQ ID NO: 105 |
| HB-080 | ACTCCATAACCCTCCGACGA | SEQ ID NO: 107 | 6FAM-CGCCCAAAAACTTCCCGACTCCGTA-BHQ-1 | SEQ ID NO: 108 |
| HB-082 | ACAACGACGACTATTTTAAACACGTAA | SEQ ID NO: 110 | 6FAM-CCCGAATTTACCGAATCAAAAACGCGA-BHQ-1 | SEQ ID NO: 111 |
| HB-083 | TCGATTACAACCCGATACCGTAA | SEQ ID NO: 113 | 6FAM-CACACCCTAAACGTTACGACGCTAAACTCG-BHQ-1 | SEQ ID NO: 114 |
| HB-084 | CTACCGCCGACGCCTAAA | SEQ ID NO: 116 | 6FAM-CCCTTCCCTCACGCCGCGA-BHQ-1 | SEQ ID NO: 117 |
| HB-087 | CCGCGAAACGCCCAA | SEQ ID NO: 119 | 6FAM-CAATACCGACCAACCGCGCGA-BHQ-1 | SEQ ID NO: 120 |
| HB-088 | AAAATTACCTCCCGCGAACTCTA | SEQ ID NO: 122 | 6FAM-CGCGCCCGACTTTCCGACG-BHQ-1 | SEQ ID NO: 123 |
| HB-089 | CCGACCTTTCCGCCAAA | SEQ ID NO: 125 | 6FAM-CGACCCTCCGCGCAATACCG-BHQ-1 | SEQ ID NO: 126 |
| HB-090 | GCGCATTCTTCGACCACG | SEQ ID NO: 128 | 6FAM-CAAACGCGCCTCTAATCACGTAACCAAAT-BHQ-1 | SEQ ID NO: 129 |
| HB-092 | GCGCGAAACTCGAACCTTT | SEQ ID NO: 131 | 6FAM-CCAATCGCGCCTCTCCAAAACG-BHQ-1 | SEQ ID NO: 132 |
| HB-093 | AAACGACCGCGAACCCATA | SEQ ID NO: 134 | 6FAM-CGCTCCGAAAACCCGAACCGAA-BHQ-1 | SEQ ID NO: 135 |
| HB-094 | TCGTTCCTTTCTAACTACCCGC | SEQ ID NO: 137 | 6FAM-CCCGCATACCGTCCCGCGATA-BHQ-1 | SEQ ID NO: 138 |
| HB-095 | AAACGATCCTCCGAAACCAAA | SEQ ID NO: 140 | 6FAM-CCGCACAAACACCAACGTTCCG-BHQ-1 | SEQ ID NO: 141 |

TABLE S5-continued

List of MethyLight Primers and Probes

| HB-096 | CCGATCGCCCGCAAC | SEQ ID NO: 143 | 6FAM-AACGTACCAAAACAAATAAATACAAAAACCACCTAAACCG-BHQ-1 | SEQ ID NO: 144 |
|---|---|---|---|---|
| HB-097 | CCGCCATCGCAACGTT | SEQ ID NO: 146 | 6FAM-CCCGCCTTTTCAATAACCTAAATCGCTACA-BHQ-1 | SEQ ID NO: 147 |
| HB-098 | CCTAATACATCGAAATAACGCGTACC | SEQ ID NO: 149 | 6FAM-CCAACGATCGAAAACCGCCAAACA-BHQ-1 | SEQ ID NO: 150 |
| HB-099 | CGACCGCCAAACCGC | SEQ ID NO: 152 | 6FAM-CGAAACCCTCGCGCATCCGA-BHQ-1 | SEQ ID NO: 153 |
| HB-100 | CTACGCAATTCGCGTCCC | SEQ ID NO: 155 | 6FAM-ACCGCGCGTTTCCGAACCATATTACT-BHQ-1 | SEQ ID NO: 156 |
| HB-101 | GCAAACTAAACTCCGCGCTATAA | SEQ ID NO: 158 | 6FAM-TTACTCGACCCGCACACGTAATCTCCTAAA-BHQ-1 | SEQ ID NO: 159 |
| HB-102 | CAACATCAATACCCGCTACCG | SEQ ID NO: 161 | 6FAM-CCGCTCGATACTCGCCCGCA-BHQ-1 | SEQ ID NO: 162 |
| HB-103 | CGTATAATCCCACCCTCGTCA | SEQ ID NO: 164 | 6FAM-CGCGACTTCTACCGTCACTTCCTTTATTCG-BHQ-1 | SEQ ID NO: 165 |
| HB-104 | TTTCTCGACACCAATCAACGAA | SEQ ID NO: 167 | 6FAM-TCCAACTTCGCCAATTAAATACGCGAAA-BHQ-1 | SEQ ID NO: 168 |
| HB-105 | CCGACCGAACTATACAACGAAAT | SEQ ID NO: 170 | 6FAM-ACCCGCCTCCCTCATAAATATTCAACGAA-BHQ-1 | SEQ ID NO: 171 |
| HB-109 | CCCGCTCGATTTCCGTCT | SEQ ID NO: 173 | 6FAM-CGACGCGCAAAACGAAAACTCCG-BHQ-1 | SEQ ID NO: 174 |
| HB-110 | CTCCGAAAACTCCATAACGTCAA | SEQ ID NO: 176 | 6FAM-CCCAACGCTAAAAACTCTATAACGCCACG-BHQ-1 | SEQ ID NO: 177 |
| HB-111 | CCGTCAATATCGAACAATTCCA | SEQ ID NO: 179 | 6FAM-CACCAACTATCGCTCGTACTCCAACAACG-BHQ-1 | SEQ ID NO: 180 |
| HB-113 | TCATACGACACTTAAAATATCACCGAAA | SEQ ID NO: 182 | 6FAM-CCCTTCACTCTAACATCGAAACCCTACCCG-BHQ-1 | SEQ ID NO: 183 |
| HB-114 | CGACTCCGACTTCTACTAATACGAAA | SEQ ID NO: 185 | 6FAM-CCCGTAACGCATACGCCTAACTCAACG-BHQ-1 | SEQ ID NO: 186 |
| HB-115 | CGCATCTTCTAACGCCTCTATTC | SEQ ID NO: 188 | 6FAM-ACTTCCGATCGCTAACGTCGTCGAAA-BHQ-1 | SEQ ID NO: 189 |
| HB-116 | CCCGTCGAAACTCGAACG | SEQ ID NO: 191 | 6FAM-CCAACAACGCGCAACGAACTCCA-BHQ-1 | SEQ ID NO: 192 |
| HB-117 | ATAACTCGAAACGAACTCTCCGC | SEQ ID NO: 194 | 6FAM-CGCCTCCCGAACCAATCTCCG-BHQ-1 | SEQ ID NO: 195 |
| HB-126 | CCGCCTCTACCGCCTAATTT | SEQ ID NO: 197 | 6FAM-CGCGCCACAAACCCGCG-BHQ-1 | SEQ ID NO: 198 |
| HB-133 | AAAATCCGAAAACCGAAAACAA | SEQ ID NO: 200 | 6FAM-ATCCGATCGAATTCTAAACGCCCGCTACT-BHQ-1 | SEQ ID NO: 201 |
| HB-139 | GATCTAAACGCCGCGATTCTAT | SEQ ID NO: 203 | 6FAM-TCCTCCCACCCTCGAATATTACGCG-BHQ-1 | SEQ ID NO: 204 |

TABLE S5-continued

List of MethyLight Primers and Probes

| | | | | | |
|---|---|---|---|---|---|
| HB-140 | AACTAAACGCAAACCCCGC | SEQ ID NO: 206 | 6FAM-ACGACGCCGAAAACAACCGAAATCTACA-BHQ-1 | SEQ ID NO: 207 |
| HB-141 | ACAACGAAAATCCTCCTCCAAAAATACA | SEQ ID NO: 209 | 6FAM-AACGACGACTTCGACCGCACCG-BHQ-1 | SEQ ID NO: 210 |
| HB-142 | CCCTCCTACCCGAAACGTAAC | SEQ ID NO: 212 | 6FAM-CGACCACCGCCTCTTAAATCCTCCAAA-BHQ-1 | SEQ ID NO: 213 |
| HB-144 | CGTCCACAAAATAATTCTAAATCAACTAA | SEQ ID NO: 215 | 6FAM-CACTCTTACCCACACCGCCGACG-BHQ-1 | SEQ ID NO: 216 |
| HB-145 | ACCTTAATCCAAATCCTACTCATATCTAAAA | SEQ ID NO: 218 | 6FAM-CCCTCCCGCCAAAATAAATACTATACTCACTACAAAA-BHQ-1 | SEQ ID NO: 219 |
| HB-146 | GAACGCCAAACGCCGA | SEQ ID NO: 221 | 6FAM-ACCCAAAAACCATCCCTAAAACGCCG-BHQ-1 | SEQ ID NO: 222 |
| HB-147 | TCGTAAAACGACCCACCCTAA | SEQ ID NO: 224 | 6FAM-CCTATCCCGACCGCCGCGA-BHQ-1 | SEQ ID NO: 225 |
| HB-149 | ACAAACCGTCCCGCGAA | SEQ ID NO: 227 | 6FAM-AACAACCGCTCGCGCCCGA-BHQ-1 | SEQ ID NO: 228 |
| HB-150 | TCTTCGTCCCTCCCTAAAACG | SEQ ID NO: 230 | 6FAM-CCCGCTACCTAAAAAAATATACGCTTACGCG-BHQ-1 | SEQ ID NO: 231 |
| HB-151 | CGAAAATAAATAACTACTCCGCGATAA | SEQ ID NO: 233 | 6FAM-ACGCCAAAACTTCTACCTCGTCCCGTAA-BHQ-1 | SEQ ID NO: 234 |
| HB-152 | CTATCGCCGCCTCATCGT | SEQ ID NO: 236 | 6FAM-CGCGACGTCAAACGCCACTACG-BHQ-1 | SEQ ID NO: 237 |
| HB-153 | GAACCAAAACGCTCCCCAT | SEQ ID NO: 239 | 6FAM-CCCGTCGAAAACCCGCCGATTA-BHQ-1 | SEQ ID NO: 240 |
| HB-154 | TCCGACACGCCCTTTCC | SEQ ID NO: 242 | 6FAM-CTCCAACACCCGACTACTATATCCGCGAAA-BHQ-1 | SEQ ID NO: 243 |
| HB-157 | CAATATAACTACCTAAAACTTACTCGAACCG | SEQ ID NO: 245 | 6FAM-TTCCCAACCGCCAACCTACAACTACACTTA-BHQ-1 | SEQ ID NO: 246 |
| HB-158 | CTCGAAACGACTTCGCCG | SEQ ID NO: 248 | 6FAM-AAATAACGCCGAATCCGACAACCGA-BHQ | SEQ ID NO: 249 |
| HB-160 | CACTCTTCCGAAAACGAAACG | SEQ ID NO: 251 | 6FAM-CGCAAACGATACGCACCGCGA-BHQ-1 | SEQ ID NO: 252 |
| HB-163 | CAACGTCTCTACGAAATCACGAAC | SEQ ID NO: 254 | 6FAM-AACGCCTACCTCGCCGTCCCG-BHQ-1 | SEQ ID NO: 255 |
| HB-164 | GCCGACACGCGAACTCTAA | SEQ ID NO: 257 | 6FAM-CGATAAAACCGAACGACCCGACGA-BHQ-1 | SEQ ID NO: 258 |
| HB-165 | ACCCGTCGCAACTCGAATAA | SEQ ID NO: 260 | 6FAM-CCGACCCAACGCTCGCCG-BHQ-1 | SEQ ID NO: 261 |
| HB-166 | TTCCCGCCGCTATAAATCG | SEQ ID NO: 263 | 6FAM-ATTCCGCCAATACACAACAACCAATAAACG-BHQ-1 | SEQ ID NO: 264 |
| HB-167 | CTCTCCAAAATTACCGTACGCG | SEQ ID NO: 266 | 6FAM-AACTCGCTCGCCCGCCGAA-BHQ-1 | SEQ ID NO: 267 |
| HB-168 | CCGAACGCCTCCATCGTAT | SEQ ID NO: 269 | 6FAM-CAACATCGTCTACCCAACACACTCTCCTACG-BHQ-1 | SEQ ID NO: 270 |
| HB-170 | TCCCCTATCCCAAACCCG | SEQ ID NO: 272 | 6FAM-CGCGCGTTTCCCGAACCG-BHQ-1 | SEQ ID NO: 273 |

TABLE S5-continued

List of MethyLight Primers and Probes

| HB-172 | AAACTACGACGACGAAACTCCAA | SEQ ID NO: 275 | 6FAM-AAACCTCGCGACCTCCGAACCTTATAAAA-BHQ-1 | SEQ ID NO: 276 |
| HB-173 | CGAATAATCCACCGTTAACCG | SEQ ID NO: 278 | 6FAM-TTAACGACACTCTTCCCTTCTTTCCCACG-BHQ-1 | SEQ ID NO: 279 |
| HB-174 | ATCGCACACGCCCTAAAACT | SEQ ID NO: 281 | 6FAM-TCTCCCGATACTCACGCACCTCGAA-BHQ-1 | SEQ ID NO: 282 |
| HB-175 | CGCCCGACTCCGCAC | SEQ ID NO: 284 | 6FAM-CGAACGACGCGACGAAACGCT-BHQ-1 | SEQ ID NO: 285 |
| HB-176 | CGAATCCTACCCCGACGATAC | SEQ ID NO: 287 | 6FAM-CTCGAATCGCTCGCGTTCTCGACAT-BHQ-1 | SEQ ID NO: 288 |
| HB-177 | CGATTTCGCTACGTCCCCT | SEQ ID NO: 290 | 6FAM-AACCTCCGAACGAATACGCGAACGAA-BHQ-1 | SEQ ID NO: 291 |
| HB-178 | CGAAAAATACAAAAACCAACTTAAATACC | SEQ ID NO: 293 | 6FAM-ACCAAAAATCGCGAACAACGACAACACT-BHQ-1 | SEQ ID NO: 294 |
| HB-179 | GCGACGATAACTACAACGCAAAT | SEQ ID NO: 296 | 6FAM-CGACTCCTCTCGCCTCCTCCCG-BHQ-1 | SEQ ID NO: 297 |
| HB-180 | GAATTCCCGACGTCTCCAAA | SEQ ID NO: 299 | 6FAM-CGACGCCCGACGAAACCGTATAA-BHQ-1 | SEQ ID NO: 300 |
| HB-181 | GACGAACAACGTCTTATTACAACGC | SEQ ID NO: 302 | 6FAM-CGCACGAACTCGCCTACGTAATCCG-BHQ-1 | SEQ ID NO: 303 |
| HB-183 | GCCATCTTATTTACCTCCCTCCC | SEQ ID NO: 305 | 6FAM-CGCACGCCCGACCGCAA-BHQ-1 | SEQ ID NO: 306 |
| HB-184 | ATACCAACCGCCTCCTCTAACC | SEQ ID NO: 308 | 6FAM-CCGTCGACCCTACAAAATTTAACGCCA-BHQ-1 | SEQ ID NO: 309 |
| HB-185 | GATACTACGCGAATAATAAACGACCC | SEQ ID NO: 311 | 6FAM-ACGCCCTCCGAAAACAAAAAACTCTACG-BHQ-1 | SEQ ID NO: 312 |
| HB-186 | ACCTAAAACAACGATCGCGAAAT | SEQ ID NO: 314 | 6FAM-CAAATCCCGCCCTCCCTTCGAAAT-BHQ-1 | SEQ ID NO: 315 |
| HB-190 | AACCGTCCCCAAAACTACGAC | SEQ ID NO: 317 | 6FAM-CCTCGAACCGCTCCATCGAAATTCA-BHQ | SEQ ID NO: 318 |
| HB-191 | CTCCGAAACATTCCCTCCG | SEQ ID NO: 320 | 6FAM-CGAACCGAACGCCGCGAAA-BHQ | SEQ ID NO: 321 |
| HB-192 | ACGAACCCGCAAACGAAA | SEQ ID NO: 323 | 6FAM-TAAATCCCGCTTAACAACTCGCGACGA-BHQ-1 | SEQ ID NO: 324 |
| HB-193 | CCTAAATCACCGACGAAAATATCA | SEQ ID NO: 326 | 6FAM-CGAACGCGAACATACAATCGTAACCAATACCT-BHQ | SEQ ID NO: 327 |
| HB-194 | CTACGTAACCCTATCCTACAACTCCG | SEQ ID NO: 329 | 6FAM-CGAACTCCTAACGCGCACGATAAAACCTAA-BHQ | SEQ ID NO: 330 |
| HB-195 | AAATCCCCGCGCATACTA | SEQ ID NO: 332 | 6FAM-CCTAAAACCGCCGCTACCGACCG-BHQ-1 | SEQ ID NO: 333 |
| HB-197 | TATCCGTACCTACCGCCGC | SEQ ID NO: 335 | 6FAM-ACCATACCCAACTTCGCCGACACCTAA-BHQ | SEQ ID NO: 336 |

TABLE S5-continued

List of MethyLight Primers and Probes

| HB-199 | CTCGACGCAACCATCCTCTT | SEQ ID NO: 338 | 6FAM-ACTACCGCGAACGACAAAACCCACG-BHQ-1 | SEQ ID NO: 339 |
| --- | --- | --- | --- | --- |
| HB-200 | CGCGCGCTAACTCTTCTACG | SEQ ID NO: 341 | 6FAM-ATTACCGCCTTTAAACTCCGAACCCTCCA-BHQ-1 | SEQ ID NO: 342 |
| HB-201 | AAACGAACCGCACTCGTTACC | SEQ ID NO: 344 | 6FAM-CCGTCACCGACGCGAAAACCAAT-BHQ-1 | SEQ ID NO: 345 |
| HB-203 | CTCTTCGCCTTTTATTCGATTACTAAAT | SEQ ID NO: 347 | 6FAM-AACAACCGCCGCCCGACCA-BHQ-1 | SEQ ID NO: 348 |
| HB-204 | CCGCTAAATCCGCACCG | SEQ ID NO: 350 | 6FAM-CGCGATCCCGACCTAAACTATACGCA-BHQ-1 | SEQ ID NO: 351 |
| HB-205 | CTCGCTATCGCCTTACCTATCC | SEQ ID NO: 353 | 6FAM-TCCACACCTAAATCCCTCGAACCCACT-BHQ-1 | SEQ ID NO: 354 |
| HB-206 | TTCCCAAATCCCGCTTTCA | SEQ ID NO: 356 | 6FAM-CGCGCGCTAACGACTCAAATTCG-BHQ-1 | SEQ ID NO: 357 |
| HB-207 | CCGCGCGTCCAATTACTTA | SEQ ID NO: 359 | 6FAM-AAAACCCGTTCACCGCCTCCAACTACTA-BHQ-1 | SEQ ID NO: 360 |
| HB-208 | ATAAACCACCGCTACTTCTACCCA | SEQ ID NO: 362 | 6FAM-CACGATCGCCTCCACATCCAAATCTTT-BHQ-1 | SEQ ID NO: 363 |
| HB-209 | CGAACCGCCGAAATTATCAT | SEQ ID NO: 365 | 6FAM-AACAACTCCATCCCTAACCGCCACTTTCT-BHQ-1 | SEQ ID NO: 366 |
| HB-211 | CGCATCTCATACCCTTCTCCTAAAT | SEQ ID NO: 368 | 6FAM-CAAACGCGACCCGAACCTACGAAAA-BHQ-1 | SEQ ID NO: 369 |
| HB-213 | TGTTTTGTTGTTTTAGCGTTTACGT | SEQ ID NO: 371 | 6FAM-CTCGCGTTTATTTTAACCCGACGCCA-BHQ-1 | SEQ ID NO: 372 |
| HB-214 | ACCGAACACAAAATACGCGAC | SEQ ID NO: 374 | 6FAM-CATCCCGACCATCCGCCCG-BHQ-1 | SEQ ID NO: 375 |
| HB-215 | GGTCGTTACGTTTCGGGTAGTTTA | SEQ ID NO: 377 | 6FAM-CGCGCTCACACGCTCAAAAACCT-BHQ-1 | SEQ ID NO: 378 |
| HB-216 | GCGTCTACGAACCGATAACCTAAT | SEQ ID NO: 380 | 6FAM-CCCTCCAACCCTCACGACTATCCGACTTA-BHQ-1 | SEQ ID NO: 381 |
| HB-217 | CGAATTCCGTAAATCGCCC | SEQ ID NO: 383 | 6FAM-TAATCCGAAATACGACGACCCAATCGAAAA-3'BHQ | SEQ ID NO: 384 |
| HB-218 | ACGACTCGACTTCCGCGTC | SEQ ID NO: 386 | 6FAM-AACCCACGACGACACCCGAAACG-BHQ-1 | SEQ ID NO: 387 |
| HB-219 | TTCACCGAAAACCCAAATACAA | SEQ ID NO: 389 | 6FAM-ATCAAATCGCCTACCCTAACGACACTTTCG-BHQ-1 | SEQ ID NO: 390 |
| HB-220 | GCGACTCGTTCCTTCTAACAAATC | SEQ ID NO: 392 | 6FAM-AAACCCGACAAAAATAACCGCGAAACCT-BHQ-1 | SEQ ID NO: 393 |
| HB-221 | AACAACCGCCGCTACTTTAAATA | SEQ ID NO: 395 | 6FAM-CGCGCGTCGCGCTCTTAACTAAAA-BHQ-1 | SEQ ID NO: 396 |

TABLE S5-continued

List of MethyLight Primers and Probes

| | | | | |
|---|---|---|---|---|
| HB-223 | CCGAATATAACCACACCGCC | SEQ ID NO: 398 | 6FAM-CCAACCTCAACTCGCCTTTTCCTTATTTCA-BHQ-1 | SEQ ID NO: 399 |
| HB-224 | CCCATATAAACGCTCACCGC | SEQ ID NO: 401 | 6FAM-CCCGCACAACTCGAACAAAACGAAA-BHQ-1 | SEQ ID NO: 402 |
| HB-225 | CGTAACGCTCATTCTCGCTACC | SEQ ID NO: 404 | 6FAM-TAATCAAACTTACGCTCACTTCGTCGCCG-BHQ-1 | SEQ ID NO: 405 |
| HB-226 | CGCACTTTTTATTATCGACGACTC | SEQ ID NO: 407 | 6FAM-CGACAAATATAACCGTCCGCGCCCTA-BHQ-1 | SEQ ID NO: 408 |
| HB-227 | CGACGCGATAACCGCTTAAA | SEQ ID NO: 410 | 6FAM-ATCCGAAACCTCGAACGCGTCTCG-BHQ-1 | SEQ ID NO: 411 |
| HB-228 | ACCCTAATACGTAACCGCCTACAA | SEQ ID NO: 413 | 6FAM-CATCTCCTACAAACCCATATCGCGCAA-BHQ-1 | SEQ ID NO: 414 |
| HB-229 | GCAACACTCACTACCCCGTTTAT | SEQ ID NO: 415 | 6FAM-TCTTTAAAACAAACGAACCGCGCCAA-BHQ-1 | SEQ ID NO: 417 |
| HB-231 | ACGTACTCCCGCCTAAACCTC | SEQ ID NO: 419 | 6FAM-ACGCCCGCTCGCGAAAACTTACTAAATA-BHQ-1 | SEQ ID NO: 420 |
| HB-233 | CCCTCTCTTCGCGCAAAC | SEQ ID NO: 422 | 6FAM-AAATACGTCCCTCCTAACGCCGAAACG-BHQ-1 | SEQ ID NO: 423 |
| HB-235 | TACTTCCCTCCCCTACCTCGTT | SEQ ID NO: 425 | 6FAM-CGACGCTCGCCCGAACGCTA-BHQ-1 | SEQ ID NO: 426 |
| HB-237 | AACTACAATTACTAAAAACTCATAAAACGAAACT | SEQ ID NO: 428 | 6FAM-TCCCTCTTCGAATCCACAATCAACCG-BHQ-1 | SEQ ID NO: 429 |
| HB-241 | AACATAAACCGCATCGATCCC | SEQ ID NO: 431 | 6FAM-CGCCAACGCGATAACTTCTATAACTACCCAA-BHQ-1 | SEQ ID NO: 432 |
| HB-242 | CCACAACCACTAATAACTTCCCGTA | SEQ ID NO: 434 | 6FAM-CCCGCCTCCCGAAACAACTACGA-BHQ-1 | SEQ ID NO: 435 |
| HB-245 | ACTAAACGCCGCGTCCAA | SEQ ID NO: 437 | 6FAM-TCACGTCCGCGAAACTCCCGA-BHQ-1 | SEQ ID NO: 438 |
| HB-246 | CAAACCCCGCTACTCGTCAT | SEQ ID NO: 440 | 6FAM-CACGAACGACGCCTTCCCGAA-BHQ-1 | SEQ ID NO: 441 |
| HB-247 | CGACGCACCAACCTACCG | SEQ ID NO: 443 | 6FAM-ACGCCGCGCTCACCTCCCT-BHQ-1 | SEQ ID NO: 444 |
| HB-248 | TCTCAAACTATAACGCGCCTACAT | SEQ ID NO: 446 | 6FAM-CCGAATACCGACAAAATACCGATACCCGT-BHQ-1 | SEQ ID NO: 447 |
| HB-250 | CTACCGCCGCGCTAAAATAC | SEQ ID NO: 449 | 6FAM-ACGCACGAAACTTCACCTACAACGTATCG-BHQ-1 | SEQ ID NO: 450 |
| HB-251 | CCGTTTCCGCCGTAATATTC | SEQ ID NO: 452 | GFAM-TCGCCACCACGAAACTACCCACG-BHQ-1 | SEQ ID NO: 453 |
| HB-253 | ATCTCGAAAAAACACTTCCCCC | SEQ ID NO: 455 | 6FAM-ACACCCAAACGCGAAACCCGAAACT-BHQ-1 | SEQ ID NO: 456 |
| HB-254 | AACCTCTCGAAAACCCCAACA | SEQ ID NO: 456 | 6FAM-ACGACCTCGAAAAACAACCCGAAACTACG-BHQ-1 | SEQ ID NO: 459 |

TABLE S5-continued

List of MethyLight Primers and Probes

| | | | | |
|---|---|---|---|---|
| HB-256 | CCCTCCGATATACAAAACCCC | SEQ ID NO: 461 | 6FAM-CCCGCACAACTCTCGCTTCTCTTTACAA-BHQ-1 | SEQ ID NO: 462 |
| HB-258 | CGCCCGCTCGCTATCC | SEQ ID NO: 464 | 6FAM-CCGTAACGCCTCGAACTCCCGA-BHQ-1 | SEQ ID NO: 465 |
| HB-259 | CCGCGCTTAACATCACTAACTAAA | SEQ ID NO: 467 | 6FAM-CGCGCGACCACGACACGAAA-BHQ-1 | SEQ ID NO: 468 |
| HB-260 | ACGAACGCCGACGTCTTC | SEQ ID NO: 470 | 6FAM-CGCCATACGAACCGCGAAACGAATATAA-BHQ-1 | SEQ ID NO: 471 |
| HB-261 | CGATAATTACGAACACACTCCGAAT | SEQ ID NO: 473 | 6FAM-CGATAACGACCTCCCGCGAACATAAA-BHQ-1 | SEQ ID NO: 474 |
| HB-262 | AACACCTACGCCCTAAAACGTC | SEQ ID NO: 476 | 6FAM-TCGAACAAACAACATTTCCGAACCAAAACT-BHQ-1 | SEQ ID NO: 477 |
| HB-264 | CCGATACTAAAAACCGAATAAACTCG | SEQ ID NO: 479 | 6FAM-CGCAACGAAAATCTCCGACGAAAAAA-BHQ-1 | SEQ ID NO: 480 |
| HB-266 | TCGTCCCCGTAAACTTAAATCATC | SEQ ID NO: 482 | 6FAM-CCCGCAAACCTCCCGAAAATATCGTATAAA-BHQ-1 | SEQ ID NO: 483 |
| HB-268 | TCGAACCATAAAATTACAACTTTCCA | SEQ ID NO: 485 | 6FAM-TCGTACGCGATCAACGCCAACAATTA-BHQ-1 | SEQ ID NO: 486 |
| HB-270 | CCCACCAACCACGTTAAAACA | SEQ ID NO: 488 | 6FAM-CAACTCCCGACCTTCGAACCAAAATATCG-BHQ-1 | SEQ ID NO: 489 |
| HB-274 | CAACGCCTAACGAACGAACC | SEQ ID NO: 491 | 6FAM-TATAACTTCCGCGACCGCCTCCTCCT-BHQ-1 | SEQ ID NO: 492 |
| HB-275 | CGCATTAAAACGATTCCCGAT | SEQ ID NO: 494 | 6FAM-CCGATCCCTCGCCAACGTCGTAA-BHQ-1 | SEQ ID NO: 495 |
| HB-278 | CGACCCTACAATAAAACGTATTCTCCT | SEQ ID NO: 497 | 6FAM-AAACCTTATTTACGCAACAATCAACGCCG-BHQ-1 | SEQ ID NO: 496 |
| HB-280 | AAACGACCGAAATTCGAACTTATC | SEQ ID NO: 500 | 6FAM-CGAACCCGCTCTCTTCGCTAAATACGA-BHQ-1 | SEQ ID NO: 501 |
| HB-281 | GCGAAACTCCGCCGTCTA | SEQ ID NO: 503 | 6FAM-AAACACGAACAACGCCAACTCTCAACCT-BHQ-1 | SEQ ID NO: 504 |
| HB-282 | GAACCGCTACACGACCGCT | SEQ ID NO: 506 | 6FAM-CGCCGCAATACCTTAACATCCCTACCG-BHQ-1 | SEQ ID NO: 507 |
| HB-304 | CAACGCAAAAATCCTAACCGAA | SEQ ID NO: 509 | 6FAM-CGCGCGCTAACGCTTAACAAAAAAATA-BHQ-1 | SEQ ID NO: 510 |
| HB-306 | CAAACCCCGCAATAACCTCTATATC | SEQ ID NO: 512 | 6FAM-ATTCCGCCACCCATCCGTCCA-BHQ-1 | SEQ ID NO: 513 |
| HB-307 | CTCATTTCCCCCAAATTTCGAT | SEQ ID NO: 515 | 6FAM-ATCCTAACGCGAACAAAACCCAAAACAA-BHQ-1 | SEQ ID NO: 516 |
| HB-308 | TCCCCTAACTCCGACGACG | SEQ ID NO: 518 | 6FAM-CGAACATACCCGACCGCAAATAACCA-BHQ-1 | SEQ ID NO: 519 |
| HB-309 | TCCCCTAACTCCGACGACG | SEQ ID NO: 521 | 6FAM-TACCCGACCGCAAACGACCCG-BHQ-1 | SEQ ID NO: 522 |

TABLE S5-continued

List of MethyLight Primers and Probes

| | | | | |
|---|---|---|---|---|
| HB-311 | TTCCTTTAAACTCCTTAAATCCTTTAACG | SEQ ID NO: 524 | 6FAM-ACAAACCCATTATACCCACCTA-MGBNFQ | SEQ ID NO: 525 |
| HB-315 | CGAAAACGAACCGCAAACA | SEQ ID NO: 527 | 6FAM-AACTCCCTAACCGCTTTCCAAATCGACG-BHQ | SEQ ID NO: 528 |
| HB-319 | CCAACTCGATTTAAACCGACG | SEQ ID NO: 530 | 6FAM-CCCTCTACCGTCGCGAACCCGA-BHQ-1 | SEQ ID NO: 531 |
| HB-321 | CAACCGAAATTCCCCAACG | SEQ ID NO: 533 | 6FAM-CCTACAACCGCGCGTAAACAAAAACG-BHQ-1 | SEQ ID NO: 534 |
| HB-322 | CGCAAACTCCTACAACAAACGA | SEQ ID NO: 536 | 6FAM-CGCGCGACGCTTCACTTCTTCAA-BHQ-1 | SEQ ID NO: 537 |
| HB-323 | TTCCCTCCATATACGAACTACCG | SEQ ID NO: 539 | 6FAM-CCTATCCCGAATCCGTCAATCCCG-BHQ-1 | SEQ ID NO: 540 |
| HB-326 | TAATCCGAACTCCGCGCTA | SEQ ID NO: 542 | 6FAM-CCCGTATCGTACGTCCTTATCGCCAAA-BHQ | SEQ ID NO: 543 |
| HB-327 | ACGCGCGCTCTAACCCTT | SEQ ID NO: 545 | 6FAM-AAATATAACCGCGACTCCTACCAATTCATTCG-BHQ | SEQ ID NO: 546 |
| HB-329 | GTCCCGAAATCCCCGAAT | SEQ ID NO: 548 | 6FAM-AACTAATCAACGAAAAACTCCTAACCGCGCT-BHQ | SEQ ID NO: 549 |

EXAMPLE 7

Identification/Enrichment for Candidate Cancer-Specific DNA Methylation Markers, Based on Subsets of PRC2 Targets, or Based on Other than ES-Cell PRC2 Targets Particular examples and embodiments disclosed herein provide an efficient way to identify/enrich for candidate cancer-specific DNA methylation markers, based on ES-cell PRC2 targets, and in certain aspects, based on a subset of ES-cell PRC2 targets that also bind at least one of the transcription factors: OCT4, SOX2, Nanog.

In additional embodiments of the present invention, various stem or precursor cells are used to identify transcriptional repressor (e.g., transcription factor) occupancy sites (e.g., by chromatin immunoprecipation chip analysis) and status for not only PRC2, but also for other repressors and repressor complexes as well (e.g., at least one transcription factor of the Dlx, Irx, Lhx and Pax gene families (neurogenesis, hematopoiesis and axial patterning), or the Fox, Sox, Gata and Tbx families (developmental processes)), and these ChIP-Chip targets as then used as a means of enrichment for cancer-specific DNA methylation markers as taught herein using the exemplary combination of embryonic stems cells and PRC2 targets.

According to further aspects, therefore, the instant approach has substantial utility for various types of stem and precursor cells (ES cell, somatic stem cells, hematopoietic stem cells, leukemic stem cells, skin stem cells, intestinal stem cells, gonadal stem cells, brain stem cells, muscle stem cells (muscle myoblasts, etc.), mammary stem cells, neural stem cells (e.g., cerebellar granule neuron progenitors, etc.), etc) and for various stem- or precursor cell repressor complexes as discussed above, and for various types of cancer (e.g., as discussed herein above and further including basal carcinoma, pancreatic adenocarcinoma, small cell lung cancer and metastatic prostate cancer), where the requirements are that the repressor occupancy sites/loci and corresponding occupancy status are defined/established, and a characteristic methylation status (e.g., hypermethylation) is established at corresponding sites/loci in one or more cellular proliferative disorders or cancers of interest, or, in particular embodiments, in cells of a developmental stage of interest.

EXAMPLE 8

A Method for Identifying, Screening, Selecting or Enriching for Preferred DNA Methylation Markers for a Cellular Proliferative Disorder and/or Cancer, or for Selecting or Enriching for Preferred DNA Methylation Markers for a Developmental Cell Lineage or Stage Particular embodiments provide a method for identifying, screening, selecting or enriching for preferred DNA methylation markers for a cellular proliferative disorder and/or cancer, comprising: identifying, within a precursor cell population, one or a plurality of genomic target loci for at least one polycomb group protein (PcG) or Polycomb repressive complex; obtaining a sample of genomic DNA from cells of a cellular proliferative disorder and/or cancer; and determining, by analyzing the genomic DNA from the cells of the cellular proliferative disorder and/or cancer using a suitable assay, the DNA methylation status of at least one CpG dinucleotide sequence within at least one region of at least one of the polycomb group protein (PcG) target loci, wherein the presence of said CpG methylation status identifies the at least one region of at least one of the polycomb group protein (PcG) target loci as a preferred DNA methylation marker for the cellular proliferative disorder and/or cancer.

In particular embodiments, identifying one or a plurality of polycomb group protein (PcG) target loci comprises identifying a plurality of said target loci using genomic DNA from stem cells. In certain embodiments, the stem cells consist of, or comprise embryonic stem (ES) cells. In particular preferred embodiments, the CpG methylation status is that of hypermethylation. In particular identifying comprises chromatin immunoprecipitation. In certain aspects, determining the methylation status comprises use of a high-throughput methylation assay. In particular aspects, the at least one region of at least one of the polycomb group protein (PcG) target loci comprises a CpG island or a portion thereof. In certain embodiments, the cellular proliferative disorder and/or cancer is at least one selected from the group consisting of human colorectal cancer, ovarian cancer, breast cancer, and proliferative disorders and/or cancers associated with haematopoietic stem cells.

Particular embodiments provide a method for identifying, screening, selecting or enriching for preferred DNA methylation markers for cells of a particular developmental lineage or stage, comprising: identifying, within a precursor cell population, one or a plurality of genomic target loci for at least one polycomb group protein (PcG) or polycomb repressive complex; obtaining a sample of genomic DNA from cells of a particular developmental lineage or stage; and determining, by analyzing the genomic DNA from the cells of the particular developmental lineage or stage using a suitable assay, the methylation status of at least one CpG dinucleotide sequences within at least one region of at least one of the polycomb group protein (PcG) target loci, wherein the presence of said CpG methylation status identifies the at least one region of at least one of the polycomb group protein (PcG) target loci as a preferred DNA methylation marker for the particular developmental lineage or stage. In particular aspects, identifying one or a plurality of polycomb group protein (PcG) target loci comprises identifying a plurality of said target loci using genomic DNA from stem cell-derived cells of a particular developmental lineage or stage. In certain embodiments, the stem cells comprise embryonic stem (ES) cells. In particular aspects, the CpG methylation status is that of hypermethylation.

EXAMPLE 9

A Method for Validating and/or Monitoring a Precursor Cell Population (e.g., Therapeutic Precursor Cell Population)

The remarkable demonstration herein of a role for stem-cell PRC2 complexes in the genesis of oncogenic epigenetic abnormalities entails that it will be imperative to monitor not only the generalized epigenetic state of human ES cells in culture and upon differentiation, but also to apply highly sensitive screens for oncogenic epigenetic abnormalities in cells derived from human ES cells, intended for introduction into patients receiving stem-cell therapy.

Particular embodiments provide a method for validating and/or monitoring a precursor cell population, comprising: identifying, within a reference precursor cell population, one or a plurality of genomic target loci for at least one polycomb group protein (PcG) or polycomb repressive complex; identifying one or a plurality of said target loci having a characteristic (disorder-specific, cancer-specific, etc.) DNA methylation status (e.g., at one or more CpG dinucleotide sequence positions of said at least one loci) in a cellular proliferative disorder and/or cancer to provide a set of preferred disorder and/or cancer-related diagnostic/prognostic loci; obtaining genomic DNA from a first test therapeutic precursor cell population of interest; and determining, by analyzing the genomic DNA of the first test therapeutic precursor cell population using a suitable assay, the methylation status of at least one CpG dinucleotide sequence position within the at least one region of the at least one of the polycomb group protein (PcG) preferred diagnostic/prognostic loci, wherein the first test therapeutic precursor cell population is validated and/or monitored with respect to the presence or absence of the characteristic methylation status of the one or a plurality of said target loci having a disorder-specific and/or cancer-specific methylation status in the cellular proliferative disorder and/or cancer, or with respect to the presence or absence of cells of the cellular proliferative disorder and/or cancer, or with respect to the presence or absence of cells or cells having a predispostion thereto.

In particular embodiments, identifying one or a plurality of polycomb group protein (PcG) target loci within a reference precursor cell population comprises identifying a plurality of said target loci of genomic DNA of stem cells. In particular aspects, the stem cells consist of, or comprise embryonic stem (ES) cells. In certain embodiments, the CpG methylation status is that of DNA hypermethylation. In other embodiments the status is DNA hypomethylation. In certain aspects, identifying one or a plurality of said target loci having a characteristic (disorder-specific and/or cancer-specific, etc.) DNA methylation status in a cellular proliferative disorder and/or cancer comprises obtaining a sample of genomic DNA from cells of a cellular proliferative disorder and/or cancer, and determining, by analyzing the genomic DNA using a suitable assay, the methylation status of at least one CpG dinucleotide sequence within the at least one region of the at least one of the polycomb group protein (PcG) target locus. Preferably, determining the methylation status comprises use of a high-throughput DNA methylation assay. In particular embodiments, the at least one region of at least one of the polycomb group protein (PcG) target loci comprises a CpG island or a portion thereof. In certain aspects, the cellular proliferative disorder and/or cancer is at least one selected from the group consisting of human colorectal cancer, ovarian cancer, breast cancer, and cellular proliferative disorders and/or cancers associated with hematopoietic stem cells.

In particular embodiments, the methods further comprise: obtaining genomic DNA from a second test precursor cell population; applying the method steps to said second stem cell population; and comparing the methylation status of the first and second test precursor cell populations to provide for distinguishing or selecting a preferred precursor cell population. In certain aspects, the first and second test precursor cell populations consist of, or comprise stem cells, cultured stem cells, or cells derived from stem cells or cultured stem cells. In certain embodiments, the stem cells consist of, or comprise embryonic stem (ES) cells. In certain aspects, the CpG methylation status of the first and second test precursor cell populations is that of hypermethylation.

In certain embodiments, validating and/or monitoring is of the precursor cell population in culture, subjected to one or more differentiation protocols, or in storage, etc. In particular aspects, the precursor cell population consists of, or comprises stem cells. In certain embodiments, validating and/or monitoring (e.g., validation monitoring) is of the precursor cell population during or after differentiation of the precursor cell population. In certain aspects, the precursor cell population consists of, or comprises stem cells. In certain aspects, validating and/or monitoring comprises validating and/or monitoring during culture or differentiation of the stem cells population for a presence or absence of rogue cells of the cellular proliferative disorder and/or cancer, or of cells having a predisposition thereto, or for cells of a particular developmental lineage of stage.

Further aspects provide a method for validating and/or monitoring a precursor cell population, comprising: identifying, within a reference precursor cell population, one or a plurality of genomic target loci for at least one polycomb group protein (PcG) or polycomb repressive complex; identifying one or a plurality of said target loci having a characteristic (lineage-specific and/or stage-specific) DNA methylation status of at least one CpG dinucleotide sequence position within at least one region of the at least one of the polycomb group protein (PcG) target loci in a cell of a particular developmental lineage or stage, and wherein the one or the plurality of said target loci also has a cellular proliferative disorder-specific and/or cancer-specific methylation status, to provide a set of preferred diagnostic/prognostic loci for the lineage and/or stage; obtaining genomic DNA from a first test cell population of interest; and determining, by analyzing the genomic DNA of the first test cell population using a suitable assay, the DNA methylation status of the at least one CpG dinucleotide sequence within the at least one region of the at least one of the polycomb group protein (PcG) preferred diagnostic/prognostic loci, wherein the first test cell population is validated and/or monitored with respect to the presence or absence of the characteristic methylation status of the one or a plurality of said target loci having a lineage-specific and/or stage-specific methylation status of cells of a particular developmental lineage or stage or with respect to the presence or absence of cells of the particular developmental lineage or stage, or with respect to the presence or absence of cells or cells having a developmental predispostion thereto.

ES Cell Maintenance and Differentiation.

Human ES cell lines are, for example, maintained according to the specific directions for each cell line.

For example, WA09 (H9) are cultured on MEFs in 80% DMEM/F12, 20% KSR, 1 mM L-glutamine, 1×NEAA, 4 ng/ml FGF-2. The cells are passaged by treatment with collagenase IV, 5-7 minutes at 37° C., and scraping to remove colonies, washed 1× in DMEM/F12 and plated on inactivated MEF feeder layer in 60 mm plates or 6-well plates every 5-7 days.

ES02 (HES-2) are, for example, cultured on MEFs in 80% DMEM, 20% FBS, 2 mM L glutamine, 1×NEAA, 50/50 Pen/Strep, 1×ITS, 0.1 mM 2-ME. The cells are cultured in 1 ml organ culture dishes, by carefully cutting undifferentiated pieces from hESC colonies placing them onto inactivated MEFs every 5-7 days. HUES cell lines will be cultured on MEFs in 80% KO-DMEM, 10% Plasmanate (Talecris Biotherapeutics, Inc. formerly Bayer Corporation), 10% KSR, 2 mM L-glutamine, 1×NEAA, 0.1 mM 2-ME, 10 ng/ml FGF-2. The cells are passaged by short treatment with 0.05% trypsin/EDTA and retitration every 4-5 days. The DNA methylation assays are species-specific, so the use of mouse embryonic fibroblasts will not interfere with the epigenetic analysis.

All cells are, for example, monitored daily for morphology and medium exchange. Additional analysis and validation is optionally performed for stem cell markers on a routine basis, including Alkaline Phosphatase every 5 passages, OCT4, NANOG, TRA-160, TRA-181, SEAA-4, CD30 and Karyotype by G-banding every 10-15 passages.

In additional aspects, culture conditions and differentiation protocols are analyzed for their tendency to predispose ES cells to the acquisition of aberrant epigenetic alterations. For example, undirected differentiation by maintenance in suboptimal culture conditions, such as the cultivation to high density for four to seven weeks without replacement of a feeder layer is analyzed as an exemplary condition having such a tendency. For this or other culture conditions and/or protocols, DNA samples are, for example, taken at regular intervals from parallel differentiation cultures to investigate progression of abnormal epigenetic alterations. Likewise, directed differentiation protocols, such as differentiation to neural lineages[32,33] can be analyzed for their tendency to predispose ES cells to the acquisition of aberrant epigenetic alterations. pancreatic lineages (Segev et al., *J. Stem Cells* 22:265-274, 2004; and Xu, X. et al. *Cloning Stem Cells* 8:96-107, 2006, incorporated by reference herein) and/or cardiomyocytes (Yoon, B. S. et al. *Differentiation* 74:149-159, 2006; and Beqqali et al., *Stem Cells* 24:1956-1967, 2006, incorporated by reference herein).

Profiling Technologies.

A large number of different epigenetic profiling technologies have been developed (e.g., Laird, P. W. Hum Mol Genet 14, R65-R76, 2005; Laird, P. W. Nat Rev Cancer 3, 253-66, 2003; Squazzo, S. L. et al. Genome Res 16, 890-900, 2006; and Lieb, J. D. et al. Cytogenet Genome Res 114, 1-15, 2006, all incorporated by reference herein). These can be divided broadly into chromatin interrogation techniques, which rely primarily on chromatin immunoprecipitation with antibodies directed against specific chromatin components or histone modifications, and DNA methylation analysis techniques. Chromatin immunoprecipitation can be combined with hybridization to high-density genome tiling microarrays (ChIP-Chip) to obtain comprehensive genomic data. However, chromatin immunoprecipitation is not able to detect epigenetic abnormalities in a small percentage of cells, whereas DNA methylation analysis has been successfully applied to the highly sensitive detection of tumor-derived free DNA in the bloodstream of cancer patients (Laird, P. W. Nat Rev Cancer 3, 253-66, 2003). Prefereably, a sensitive, accurate, fluorescence-based methylation-specific PCR assay (e.g., MethyLight™) is used, which can detect abnormally methylated molecules in a 10.000-fold excess of unmethylated molecules (Eads, C. A. et al., *Nucleic Acids Res* 28, E32, 2000), or an even more sensitive variation of MethyLight™ that allows detection of a single abnormally methylated DNA molecule in a very large volume or excess of unmethylated molecules. In particular aspects, MethyLight™ analyses are performed as previously described by the present applicants (e.g., Weisenberger, D. J. et al. Nat Genet 38:787-793, 2006; Weisenberger et al., *Nucleic Acids Res* 33:6823-6836, 2005; Siegmund et al., *Bioinformatics* 25, 25, 2004; Eads et al., *Nucleic Acids Res* 28, E32, 2000; Virmani et al., *Cancer Epidemiol Biomarkers Prev* 11:291-297, 2002; Uhlmann et al., *Int J Cancer* 106:52-9, 2003; Ehrlich et al., *Oncogene* 25:2636-2645, 2006; Eads et al., *Cancer Res* 61:3410-3418, 2001; Ehrlich et al., *Oncogene* 21; 6694-6702, 2002; Marjoram et al., *BMC Bioinformatics* 7, 361, 2006; Eads et al., *Cancer Res* 60:5021-5026, 2000; Marchevsky et al., *J Mol Diagn* 6:28-36, 2004; Sarter et al., *Hum Genet* 117:402-403, 2005; Trinh et al., *Methods* 25:456-462, 2001; Ogino et al., Gut 55:1000-1006, 2006; Ogino et al., *J Mol Diagn* 8:209-217, 2006, and Woodson, K. et al. *Cancer Epidemiol Biomarkers Prev* 14:1219-1223, 2005).

High-throughput Illumina platforms, for example, can be used to screen PRC2 targets (or other targets) for aberrant DNA methylation in a large collection of human ES cell DNA samples (or other derivative and/or precursor cell populations), and then MethyLight™ and MethyLight™ variations can be used to sensitively detect abnormal DNA methylation at a limited number of loci (e.g., in a particular number of cell lines during cell culture and differentiation).

Illumina DNA Methylation Profiling.

Illumina, Inc. (San Diego) has recently developed a flexible DNA methylation analysis technology based on their GoldenGate™ platform, which can interrogate 1,536 different loci for 96 different samples on a single plate (Bibikova, M. et al. *Genome Res* 16:383-393, 2006). Recently, Illumina reported that this platform can be used to identify unique epigenetic signatures in human embryonic stem cells (Bibikova, M. et al. *Genome Res* 16:1075-83, 200)). Therefore, Illumina analysis platforms are preferably used. High-throughput Illumina platforms, for example, can be used to screen PRC2 targets (or other targets) for aberrant DNA methylation in a large collection of human ES cell DNA samples (or other derivative and/or precursor cell populations), and then MethyLight™ and MethyLight™ variations can be used to sensitively detect abnormal DNA methylation at a limited number of loci (e.g., in a particular number of cell lines during cell culture and differentiation).

Cluster Analysis and Selection of Markers.

There is extensive experience in the analysis and clustering of DNA methylation data, and in DNA methylation marker selection that can be preferably used (e.g., Weisenberger, D. J. et al. Nat Genet 38:787-793, 2006; Siegmund et al., *Bioinformatics* 25, 25, 2004; Virmani et al. *Cancer Epidemiol Biomarkers Prev* 11:291-297, 2002; Marjoram et al., *Bioinformatics* 7, 361, 2006); Siegmund et al., *Cancer Epidemiol Biomarkers Prev* 15:567-572, 2006); and Siegmun & Laird, *Methods* 27:170-178, 2002, all incorporated herein by reference). For example, stepwise strategies (e.g., Weisenberger et al., *Nat Genet* 38:787-793, 2006, incorporated herein) are used as taught by the methods exemplified herein to provide DNA methylation markers that are targets for oncogenic epigenetic silencing in ES cells.

EXAMPLE 10

Methods for Therapeutically Administering a Precursor Cell Population

Particular embodiments provide methods for providing a validated cell population (e.g., precursor cell population) for therapeutic administration, comprising, prior to therapeutically administering a cell population, screening or monitoring the cell population using methods as described herein to validate the cells to be administered with respect to the presence or absence of cells of a cellular proliferative disorder and/or cancer (e.g., rogue cancer cells) or cells having a developmental predisposition thereto, or the presence or absence of cells of a particular development lineage or stage, or to validate that cells population to be delivered as being of a particular development lineage or stage, to provide for a validated precursor cell population.

For example, cell populations for therapeutic administration may be stem cells, or early progenitor cells, or typically may be cell populations derived from stem cells or from early progenitor cells. In particular embodiments, it is desired to know that the cell population to be administered is free of cancer cells, or cells having a predisposition to become cancer cells. In other embodiments, it is desired to know that the cell population to be administered is free of cells of a particular type, developmental lineage or stage, or cells having a predisposition to become cells of a particular type, developmental lineage or stage. In further embodiments, it is desired to know that the cell population to be administered is of cells of a particular type, developmental lineage or stage, or is of cells having a predisposition to become cells of a particular type, developmental lineage or stage. Generally, for purposes of determining the presence or absence of cells of a cellular proliferative disorder and/or cancer (e.g., rogue cancer cells) or cells having a developmental predisposition thereto, or the presence or absence of cells of a particular development lineage or stage, a sensitive DNA methylation assay is preferably used that is suitable to detect a characteristic DNA methylation pattern or status in one or fewer than one abnormal cells among about 1,000 or more normal cells, or among about 5,000 or more normal cells, and preferably that allows the detection of a single abnormally methylated promoter in a background of 10,000 cells without this epigenetic abnormality (e.g., MethyLight™ or suitable variations thereof).

Typically, stem cells (e.g., embryonic stem cells) are strategically differentiated to further developed cell types or lineages that suitable and appropriate for the particular therapeutic administration. Typically, it is such differentiated cell populations that will be screened or monitored or validated using methods of the present invention.

EXAMPLE 11

DNA Methylation of the PGCTs HOXA10 and/or HOXA11 were Shown Herein to be Novel and Useful Discriminators Between Ovarian Cancer and Non-Neoplastic Tissue, and HOXA11 DNA Methylation in Ovarian Cancer was Demonstrated Herein to Provide a Novel Prognostic Marker for Ovarian Cancer Example Overview The present applicants have reported that stem cell Polycomb group targets (PGCTs) are up to 12-fold more likely to have cancer-specific promoter DNA hypermethylation than non-targets (see herein, and see also reference 7 below). This observation supports the idea of a stem cell origin of cancer where a reversible gene repression is replaced by an eternal silencing, forcing the cell into a never-ending state of self-renewal and so increasing the possibility for subsequent malignant transformation (7-10). A large number of PCGT genes have not yet been described to play a role in cancer and this could explain why non-tumor suppressor genes are found to be frequently hypermethylated in adult epithelial cancers.

In the present EXAMPLE, the methylation status of 71 genes in ovarian cancer and non-neoplastic ovarian tissues of 22 patients or 18 healthy controls, respectively, was analyzed. The methylation of 35 genes included in this study was recently described with regard to PCGT (7). After ranking the genes according to their strength to discriminate between non-neoplastic and cancer tissue the top ranked genes HOXA10 and HOXA11 both stem cell PCGT genes (7), were shown to be novel and useful discriminators between cancer and non-neoplastic tissue. An independent analysis of a set consisting of 92 ovarian cancer specimens further confirmed the utility of these genes as surrogate markers for cancer stem cells and as prognostic indicators, and demonstrated that HOXA11 DNA methylation is [1] strongly associated with the residual tumor after cytoreductive surgery and [2] a valuable prognostic marker (associated with a poor prognosis; HOXA11 DNA methylation was independently associated with poor outcome [relative risk for death 3.4 (95% CI 1.2-9.9; p=0.03)]). These findings support the view that the technical inability to optimally cytoreduce ovarian cancer is associated with particular molecular alterations in the tumor which per se define a subgroup of patients with poor outcome.

Materials and Methods.
Patients and Samples.

All patients for this study were treated at the Department of Obstetrics and Gynaecology of the Innsbruck Medical University, Austria between 1989 and 2000 and staged according to the International Federation of Gynaecology and Obstetrics (FIGO) system. Ovarian cancer specimens had been prospectively collected from patients operated for gynaecological cancers in compliance with and approved by the Institutional Review Board. Specimens were brought to our pathologist, and a part of the tissue was pulverized under cooling with liquid nitrogen and stored at −70° C. Clinical, pathological and follow-up data were stored in a database in accordance with hospital privacy rules.

For the gene evaluation (TABLE 5), ovarian cancer specimens were analyzed from 22 patients (age range: 30.1 to 80.9 yrs.; mean: 61.8 yrs.; 7 serous cystadeno, 6 mucinous, 6 endometrioid and 3 clear cell cancers) and apparently normal ovaries from 18 patients (age range: 24.1 to 76.9 yrs.; mean: 61.6 yrs.; 13, 4 and 1 had endometrial and cervical cancer and fibroids, respectively). For HOXA10 and HOXA11 methylation analysis, 92 primary ovarian cancer cases were studied; details are provided in Supplementary TABLE 51 and TABLE 6. 77 patients received platinum-based chemotherapy.

After primary treatment, all patients were followed up at intervals increasing from three months to one year until death or the end of the study. Follow-up information was available for all patients.

DNA isolation and methylation analysis. Genomic DNA from lyophilized, quick-frozen specimens was isolated using the DNeasy™ tissue kit (Qiagen, Hilden, Germany). Sodium bisulfite conversion of genomic DNA and the MethyLight™ assay were performed as previously described, and PMR (Percentage of Methylated Reference) values were determined (11). For methylation analysis, ACTB was used as reference gene. Most of the primers and probes for the MethyLight™ reactions have been published (11-14, incorporated by reference herein; (HOXA10; (SEQ ID NO: 598) AC004080. e.g., amplicon position 47850-47933 (SEQ ID NO: 595)); HOXA11; (SEQ ID NO: 599) AC004080. e.g., amplicon position 59150-59249 (SEQ ID NO: 596))). Primer and probes for the remaining genes analyzed by MethyLight™ are listed in Supplementary TABLE S2.

Statistical Analysis.

Differences of PMR values between non-neoplastic and cancer specimens or primary cancer were assessed using the Mann-Whitney U test. For further analysis in the frozen ovarian cancer specimens, applicants used the highest level of HOXA10 and HOXA11 methylation detected in non-neoplastic ovaries as a cut-off level (PMR >12) and dichotomized cases with methylation scores of <12 and >12. Associations of methylation and clinicopathological features were determined using the chi-square contingency test and Spearman rank coefficient. For univariate survival analysis, Kaplan-Meier curves and an univariate proportional Hazard model was used. Multivariate survival analysis was done using a time independent proportional Hazard model adjusted for age, grade, tumor stage and remaining tumor after surgery. All statistical calculations were performed using SPSS, version 10.0.

Results.

DNA methylation of 71 different genes in 18 non-neoplastic ovarian specimens and 22 ovarian cancer cases were analyzed and ranked according to their strength to discriminate between non-neoplastic and cancer tissue (TABLE 5). 21 genes (29%) demonstrated differences between cases and controls ($p<0.05$), whereas 9 genes still remained significant after adjustment for multiple testing ($p<0.0007$). HOXA10 and HOXA11 methylation showed the most significant differences between cancer and non-cancer specimens.

To further elucidate the role of HOXA10 and HOXA11 methylation and to evaluate the findings of the gene selection set, an independent set consisting of 92 ovarian cancer specimens was analyzed in more detail. HOXA11 demonstrated higher methylation levels in patients >60 years of age, whereas HOXA10 methylation was higher in poorly differentiated cancers (Supplementary TABLE S1). HOXA10 and HOXA11 methylation could be observed already in the normal frozen specimens (highest PMR value was 11.39 and 11.02 for HOXA10 and HOXA11, respectively). In light of applicants' previous data (herein and see reference 7 below), applicants reasoned that methylation of these genes is a marker for stem cells which are unable to differentiate and also resistant to therapy. A PMR of 12 was therefore taken as a cut-off to study whether patients whose tumors have higher methylation levels at these particular loci have a worse outcome compared to patients whose tumor methylation levels are comparable with the normal ovaries. This would indirectly confirm that HOXA10 and/or HOXA11 methylation is a marker for cancer stem cells. 26 (28.3%) and 27 (29.3%) of the cancer cases demonstrated PMR <12 for HOXA10 and HOXA11 methylation, respectively. 45.5% ($15/33$) of the mucinous cancer cases demonstrated low HOXA10 methylation whereas 80.5%, 78.6% and 100% of serous, endometrioid and clear cell cases showed PMR levels >12 (TABLE 6). Interestingly, 38.5% ($25/65$) of ovarian cancer cases with no or <2 cm residual tumor after surgery demonstrated low HOXA11 methylation whereas only 7% ($2/27$) of the tumors with more than 2 cm remaining after surgery had HOXA11 PMR values <12 (TABLE 6).

Figures 2A, 2B:
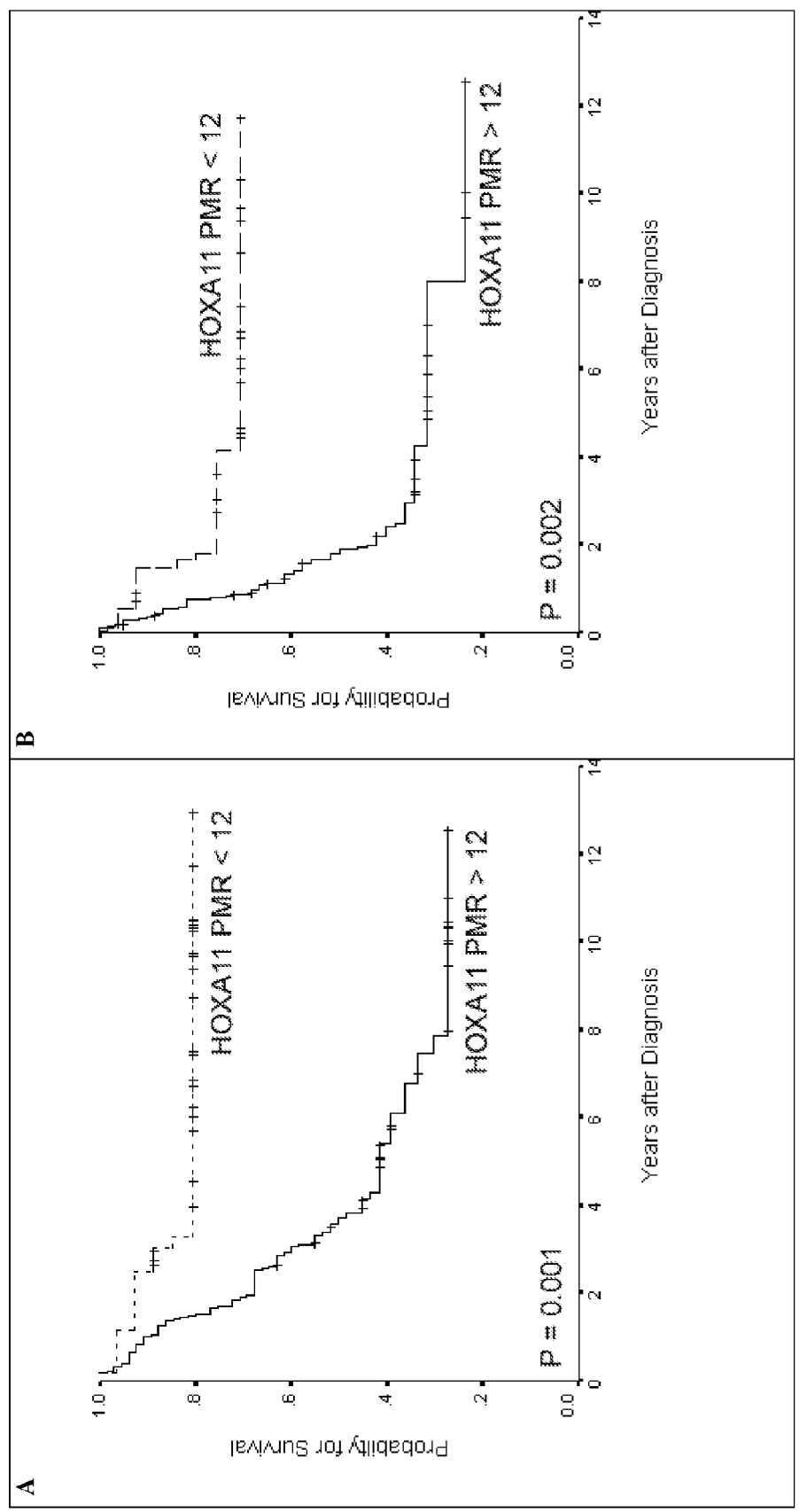
FIGS. 2A and B show Kaplan Meier survival curves and HOXA11 DNA methylation (dichotomized cases with methylated scores of PMR<12 and PMR>12). (A) Overall and (B) relapse-free survival of 92 ovarian cancer patients.

In an univariate analysis, age, grade, remaining tumor after debulking surgery and HOXA11 methylation were associated with overall survival (TABLE 7A, FIG. 2), whereas in the multivariate analysis only age, grade and HOXA11 methylation remain as independent prognostic markers (TABLE 7B). Relapse-free survival was associated with age, stage, grade, remaining tumor after debulking surgery and HOXA11 methylation in the univariate analysis, and with age and HOXA11 methylation in the multivariate analysis (Supplementary TABLE S3).

In this EXAMPLE, applicants showed aberrant HOXA10 and HOXA11 DNA methylation in ovarian cancer patients. It has been demonstrated that HOX genes, which are known to be the key players in the development of the mullerian duct (15), are dysregulated in endometrial (16) and in ovarian cancer (17). Recently, using a genome-wide CHIP-chip approach, Lee et al. (10) demonstrated that in embryonic stem (ES) cells, genes which encode transcription factors with a role in development (e.g. HOXA family) are targets (and thereby silenced) by the Polycomb group proteins (PcG) SUZ12 and EED and associated with nucleosomes that are trimethylated at histone H3 lysine-27 (H3K27me3) for maintenance of transcriptional suppression in human embryonic stem cells. PcG control is critical for long term gene silencing essential for development and adult cell renewal. The observation that HOXA10 and HOXA11 are epigenetically silenced in embryonic stem cells in conjunction with our observation that both genes are already methylated at a low level in normal ovarian tissue and increasingly methylated in ovarian cancers, indicated to applicants that HOXA10 and HOXA11 methylation acts as a tag for ovarian cancer's cell of origin and as a marker for cancer stem cells.

TABLE 5

Gene evaluation: Methylation levels in ovarian tissue samples of indicated genes.

| Gene name | Methylation values (PMR; Median) non-neoplastic ovary (n = 18) | ovarian cancer (n = 22) | p-value[a] |
|---|---|---|---|
| HOXA10 | 2 | 54 | 0.0000000 |
| HOXA11 | 5 | 50 | 0.0000000 |
| TNFRSF25 | 42 | 121 | 0.0000002 |
| LTB4R | 4 | 92 | 0.0000002 |
| OPCML | 0.1 | 2.1 | 0.0000007 |
| SOCS2 | 1 | 10 | 0.0000159 |
| CALCA | 0.2 | 1.3 | 0.0001404 |
| SEZ6L | 0.03 | 0.41 | 0.0004896 |
| NEUROD1 | 0.1 | 4.1 | 0.0004896 |
| DCC | 0 | 0.2 | 0.0012068 |
| HOXA1 | 0.2 | 3.1 | 0.0015495 |
| SFRP2 | 0.3 | 2.7 | 0.0016588 |
| HIC1 | 8 | 37 | 0.0022563 |
| SFRP5 | 0.5 | 1.4 | 0.0024944 |
| SLIT2 | 0.1 | 0.3 | 0.0044509 |
| PGR | 0.1 | 0.7 | 0.0098997 |
| MYOD1 | 0.01 | 0.17 | 0.0116989 |
| ESR1 | 1 | 1 | 0.0219985 |
| ABCB1 | 52 | 70 | 0.0219985 |
| CDH1 | 0 | 0.1 | 0.0418989 |
| RARRES1 | 0 | 0.01 | 0.0450343 |
| CDH13 | 0.02 | 0.09 | 0.0546192 |
| IGSF4 | 0.01 | 0.05 | 0.0794201 |
| TFF1 | 98 | 79 | 0.1011312 |
| SFRP4 | 1 | 3 | 0.1062841 |
| RARB | 0.01 | 0.02 | 0.1062841 |
| SOCS1 | 0.003 | 0.013 | 0.1396932 |
| TACSTD1 | 0.06 | 0.04 | 0.1550693 |
| PTGS2 | 0.1 | 0.2 | 0.1632122 |
| TITF1 | 0 | 0 | 0.1632122 |
| GDNF | 0 | 0.03 | 0.1737981 |
| HSPA2 | 0 | 0 | 0.1989375 |
| CXCR4 | 0.03 | 0.02 | 0.2510146 |
| APC | 0.01 | 0.03 | 0.2742382 |
| ZBTB16 | 0.03 | 0.15 | 0.3116839 |
| GATA5 | 0.2 | 0.4 | 0.3248644 |
| MLH1 | 0 | 0 | 0.4755239 |
| CCND2 | 0 | 0 | 0.4924007 |
| CDKN1C | 0 | 0 | 0.4924007 |
| SCGB3A1 | 0.07 | 0.01 | 0.5676904 |
| CDKN2B | 0.04 | 0.08 | 0.5812665 |
| MLLT7 | 88 | 99 | 0.6083959 |
| ESR2 | 0 | 0 | 0.6128700 |
| GSTP1 | 0 | 0 | 0.6378732 |
| SYK | 0 | 0 | 0.6768196 |
| GSTM3 | 0 | 0 | 0.6768196 |
| NEUROG1 | 0 | 0 | 0.6768196 |
| DAPK1 | 0 | 0 | 0.6966224 |
| TWIST1 | 0 | 0 | 0.7263596 |
| ITGA4 | 0 | 0 | 0.7368281 |
| CARD15 | 55 | 58 | 0.7368281 |
| CYP1B1 | 0 | 0 | 0.7572063 |
| SFRP1 | 0 | 0 | 0.7572063 |
| THRB | 0 | 0 | 0.7572063 |
| FGF18 | 0 | 0 | 0.7777505 |
| TGFB3 | 0 | 0 | 0.7777505 |
| MT3 | 0 | 0 | 0.8128928 |
| TGFBR2 | 0 | 0 | 0.8402464 |
| TIMP3 | 0 | 0 | 0.8613197 |
| MGMT | 0 | 0 | 0.8776666 |
| TERT | 0 | 0 | 0.9250627 |
| HSD17B4 | 0 | 0 | 0.9250627 |
| SLC6A20 | 0 | 0 | 0.9464355 |
| BCL2 | 0 | 0 | 0.9888932 |
| TP53BP2 | 0 | 0 | 1.0000000 |
| REV3L | 0 | 0 | 1.0000000 |
| NR3C1 | 0 | 0 | 1.0000000 |
| THBS1 | 0 | 0 | 1.0000000 |
| BDNF | 0 | 0 | 1.0000000 |
| CDKN2C | 0 | 0 | 1.0000000 |
| FOXO1A | 0 | 0 | 1.0000000 |

[a]Mann-Whitney U test

TABLE 6

Characteristics and HOXA10 and HOXA11 methylation levels of 92 ovarian cancer patients.

| Characteristics | Patients (N = 92) no. | HOXA10 methylation[a] PMR <12 (n = 26) | PMR >12 (n = 66) | p-value[b] | HOXA11 methylation[a] PMR <12 (n = 27) | PMR >12 (n = 65) | p-value[b] |
|---|---|---|---|---|---|---|---|
| Age | | | | | | | |
| <60 a | 44 | 10 | 34 | 0.35 | 17 | 27 | 0.071 |
| >60 a | 48 | 16 | 32 | | 10 | 38 | |
| Tumor stage | | | | | | | |
| I/II | 30 | 10 | 20 | 0.47 | 7 | 23 | 0.47 |
| III | 62 | 16 | 46 | | 20 | 42 | |
| Tumor grade | | | | | | | |
| I/II | 63 | 21 | 42 | 0.14 | 22 | 41 | 0.092 |
| III | 29 | 5 | 24 | | 5 | 24 | |
| Histologic type | | | | | | | |
| serous | 41 | 8 | 33 | 0.041[c] | 13 | 28 | 0.25[c] |
| mucinous | 33 | 15 | 18 | | 12 | 21 | |
| endometrioid | 14 | 3 | 11 | | 2 | 12 | |
| clear cell | 4 | | 4 | | | 4 | |
| Size of remaining tumor | | | | | | | |
| <2 cm | 65 | 19 | 46 | 0.81 | 25 | 40 | 0.002 |
| >2 cm | 27 | 7 | 20 | | 2 | 25 | |

TABLE 6-continued

Characteristics and HOXA10 and HOXA11 methylation levels of 92 ovarian cancer patients.

| Characteristics | Patients (N = 92) no. | HOXA10 methylation[a] PMR <12 (n = 26) | HOXA10 methylation[a] PMR >12 (n = 66) | p-value[b] | HOXA11 methylation[a] PMR <12 (n = 27) | HOXA11 methylation[a] PMR >12 (n = 65) | p-value[b] |
|---|---|---|---|---|---|---|---|
| chemotherapy | | | | | | | |
| no | 15 | 6 | 9 | 0.35 | 3 | 12 | 0.54 |
| yes | 77 | 20 | 57 | | 24 | 53 | |

[a] Cut-off for ovarian cancers (PMR >12<) has been chosen due to the fact that the highest PMR in normal ovaries was <12
[b] Fisher exact test
[c] Pearson Chi Quadrat test

TABLE 7

Overall survival in ovarian cancer patients.

A

| Variable | No. of patients who died/total no. | RR of death (95% CI) | P |
|---|---|---|---|
| Age | | | |
| <60 a | 14/44 | 3 (1.6-5.5) | 0.001 |
| >60 a | 33/48 | | |
| Tumor stage | | | |
| I/II | 12/30 | 1.7 (0.9-3.3) | 0.11 |
| III | 35/62 | | |
| Tumor grade | | | |
| I/II | 27/63 | 2.5 (1.4-4.6) | 0.003 |
| III | 20/29 | | |
| Size of remaining tumor | | | |
| <2 cm | 25/65 | 3.5 (2-6.3) | <0.001 |
| >2 cm | 22/27 | | |
| HOXA10 methylation | | | |
| PMR <12 | 12/26 | 1.2 (0.6-2.3) | 0.58 |
| PMR >12 | 35/66 | | |
| HOXA11 methylation | | | |
| PMR <12 | 5/27 | 4.8 (1.9-12.2) | 0.001 |
| PMR >12 | 42/65 | | |

B

| Variable | No. of patients who died/total no. | RR of death (95% CI) | P |
|---|---|---|---|
| Age | | | |
| <60 a | 14/44 | 2.7 (1.4-5.1) | <0.001 |
| >60 a | 33/48 | | |
| Tumour stage | | | |
| I/II | 12/30 | 1.4 (0.6-3.3) | 0.46 |
| III | 35/62 | | |
| Tumour grade | | | |
| I/I | 27/63 | 1.6 (0.8-3) | 0.16 |
| III | 20/29 | | |
| Size of remaining tumour | | | |
| <2 cm | 25/65 | 2.3 (1.1-4.9) | 0.04 |
| >2 cm | 22/27 | | |
| HOXA10 methylation | | | |
| PMR <12 | 12/26 | 0.7 (0.3-1.4) | 0.29 |
| PMR >12 | 35/66 | | |
| HOXA11 methylation | | | |
| PMR <12 | 5/27 | 3.4 (1.2-9.9) | 0.03 |
| PMR >12 | 42/65 | | |

(A) Univariate and (B) multivariate analysis.

Supplementary TABLE S1:

Characteristics and HOXA10 and HOXA11 methylation levels of 92 ovarian cancer patients.

| Charateristics | Patients (N = 92) no. | HOXA10 methylation (PMR) Median | p-value[a] | HOXA11 methylation (PMR) Median | p-value[a] |
|---|---|---|---|---|---|
| Age | | | | | |
| <60 a | 44 | 29 | 0.16 | 20 | 0.00 |
| >60 a | 48 | 49 | | 56 | |
| Tumor stage | | | | | |
| I/II | 30 | 42 | 0.90 | 50 | 0.11 |
| III | 62 | 32 | | 23 | |
| Tumor grade | | | | | |
| I/II | 63 | 29 | 0.043 | 26 | 0.16 |
| III | 29 | 60 | | 38 | |

Supplementary TABLE S1:
Characteristics and HOXA10 and
HOXA11 methylation levels of 92 ovarian cancer patients.

| Charateristics | Patients (N = 92) no. | HOXA10 methylation (PMR) Median | p-value[a] | HOXA11 methylation (PMR) Median | p-value[a] |
|---|---|---|---|---|---|
| Histologic type | | | | | |
| serous | 41 | 48 | 0.08[b] | 32 | 0.42[b] |
| mucinous | 33 | 15 | | 22 | |
| endometrioid | 14 | 37 | | 27 | |
| clear cell | 4 | 69 | | 55 | |
| Size of remaining tumor | | | | | |
| <2 cm | 65 | 32 | 0.72 | 27 | 0.51 |
| >2 cm | 27 | 38 | | 29 | |

[a] Mann-Whitney U test
[b] Kruskal Wallis test

SUPPLEMENTARY TABLE S2

MethyLight reaction information

| HUGO Gene Nomenclature | Alternate Gene Name | Chromosomal Location | Amplicon Location Relative to Transcription Start (bp) | Mean Distance from Transcription Start (bp) | Forward Primer Sequence | SEQ ID NO: |
|---|---|---|---|---|---|---|
| CARD15 | NOD2; caspase recruitment domain family, member 15 | 16p12-q21 | −3421/−3303 | −3362 | GTCTCACTTCCCATCTA CATTCTAAAACT | SEQ ID NO: 550 |
| CDKN1B | Cyclin-dependent kinase inhibitor 1B (p27, Kip 1); KIP1, P27KIP1 | 12p13.1-p12 | −370/−299 | −334.5 | AAATTCGAAACCCGACG CTA | SEQ ID NO: 553 |
| CDKN2C | Cyclin-dependent kinase inhibitor 2C, p18; INK4C; p18-INK4C | 1p32.3 | −85/+4 | −40.5 | AAATTACAACGCCGCGA AAA | SEQ ID NO: 556 |
| CXCR4 | chemokine (C-X-C motif) receptor 4; FB22; HM89; LAP3; LCR1; NPYR; WHIM; CD 184; LESTER; NPY3R; NPYRL; HSY3RR; NPYY3R; D2S201E | 2q21 | −15/+86 | +35.5 | CGCTAATTCTCCAAATA CGATAACTACTAAA | SEQ ID NO: 559 |
| FGF18 | Fibroblast growth factor 18; ZFGF5; FGF-18 | 5q34 | −54/+29 | −12.5 | ATCTCCTCCTCCGCGTC TCT | SEQ ID NO: 562 |

SUPPLEMENTARY TABLE S2-continued

MethyLight reaction information

| | | | | | | |
|---|---|---|---|---|---|---|
| FOXO1A | Forkhead box O1A (rhabdomyo sarcoma); FKH1; FKHR; FOXO1 | 13q14.1 | −33/+113 | +40 | GCCGCGCTCCAACTAACA | SEQ ID NO. 565 |
| GSTM3 | Glutathione S-transferase M3 (brain); GST5; GSTB; GTM3; GSTM3-3; MGC3310; MGC3704 | 1p13.3 | 46/+139 | +92.5 | GCGCGAACGCCCTAACT | SEQ ID NO: 568 |
| HSPA2 | Heat shock 70 kDa protein 2 | 14q24.1 | −176/−89 | −132.5 | CACGAACACTACCAACAACTCAACT | SEQ ID NO: 571 |
| LTB4R | Leukotriene B4 receptor; BLT1 | 14q11.2-q12 | −87/−12 | −49.5 | GCGTTGGTTTTATCGGAAGG | SEQ ID NO: 574 |
| MT3 | Metallothionein 3 (growth inhibitory factor (neurotrophic)); GIF; GIFB; GRIF | 16q13 | −72/+47 | −12.5 | CGATAAACGAACTTCTCCAAACAA | SEQ ID NO: 577 |
| OPCML | Opinoid binding protein/cell adhesion molecule-like; OPCM, OBCAM | 11q25 | −848/−781 | −814.5 | CGAACCGCCGAAATTATCA | SEQ ID NO: 580 |
| SFRP1 | Secreted frizzled-related protein 1; FRP; FRP1; FrzA; FRP-1; SARP2 | 8p12-p11.1 | −130/−58 | −94 | CAACTCCCGACGAAACGAA | SEQ ID NO: 583 |
| SFRP2 | Secreted frizzled-related protein 2; FRP-2; SARP1; SDF-5 | 4q31.3 | −599/−533 | −566 | AAACCTACCCGCCCGAAA | SEQ ID NO: 586 |
| SFRP4 | Secreted frizzled-related protein 4; FRP-4 | 7p14-p13 | −40/64 | +12 | TCCGCCGTCTAACACACAAA | SEQ ID NO: 589 |
| SFRP5 | Secreted frizzled-related protein 5; SARP3 | 10q24.1 | −59/27 | −16 | GAACGCCCCGACTAATCCTAA | SEQ ID NO: 592 |
| SLIT2 | slit homolog 2 (Drosophila); SLIL3; Slit-2; FLJ14420 | 4p15.2 | −390/−489 | −439.5 | CAATTCTAAAAACGCACGACTCTAAA | SEQ ID NO: 595 |

SUPPLEMENTARY TABLE S2-continued

| | | MethyLight reaction information | | | | |
|---|---|---|---|---|---|---|
| TACSTD1 | tumor-associated calcium signal transducer 1; EGP; KSA; M4S1; MK-1; CD326; EGP40; MIC18; TROP1; Ep-CAM; Hegp-2; C017-1A; GA733-2 | 2p21 | +35/+37 | +86 | CACACCTACCCGACCTAACGA | SEQ ID NO: 598 |
| TITF-1 | Thyroid transcription factor 1; NKX2A; BCH; TTF-1 | 14q13 | -74/+54 | -10 | CGAAATAAACCGAATCCTCCTTAA | SEQ ID NO: 601 |
| ZBTB16 | Zinc finger and BTB domain containing 16; PLZF | 11q23 | -32/+55 | +11.5 | ATCACGACGACAACGACAACAT | SEQ ID NO: 604 |

| | HUGO Gene Nomenclature | Reverse Primer Sequence | SEQ ID NO: | Probe Oligo Sequence (5'FAM; 3'BHQ-1) | SEQ ID NO: |
|---|---|---|---|---|---|
| | CARD15 | GGGTTTTATTTTCGGGATTTGAATAT | SEQ ID NO: 551 | CAACCCTTACCCAAACCCTACGACCAAAA | SEQ ID NO: 552 |
| | CDKN1B | GAGGAGCGGGAGGGAGG | SEQ ID NO: 554 | GAATTCGCCGCGACGCCTA | SEQ ID NO: 555 |
| | CDKN2C | CGTGCGAGATTGCGAGC | SEQ ID NO: 557 | AAACCGAACGCCGCCCACG | SEQ ID NO: 558 |
| | CXCR4 | TCGGTCGCGGTTAGAAATTTT | SEQ ID NO: 560 | TCGACGTCACTTTACTACCTACTACCGCAACCA | SEQ ID NO: 561 |
| | FGF18 | TCGCGCGTAGAAAACGTTT | SEQ ID NO: 563 | CGACCGTACGCATCGCCGC | SEQ ID NO: 564 |
| | FOX01A | TCGGGCGGTTTGGTAGTC | SEQ ID NO: 566 | CGAACGCCGCGAACCGCTT | SEQ ID NO: 567 |
| | GSTM3 | AACGTCGGTATTAGTCGCGTTT | SEQ ID NO: 569 | CCCCGTTCTCCGTCCCTTACCTCC | SEQ NO: 570 |
| | HSPA2 | GGGAGCGGATTGGGTTTG | SEQ ID NO: 572 | CCGCGCCCAATTCCCGATTCT | SEQ ID NO: 573 |
| | LTB4R | AAACCGTAATTCCCGCTCG | SEQ ID NO: 575 | GACTCCGCCCAACTTCGCCAAAA | SEQ ID NO: 576 |
| | MT3 | GCGCGGTGCGTAGGG | SEQ ID NO: 578 | AAACGCGCGACTTAACTAATAACAACAAATAACGA | SEQ ID NO: 579 |
| | OPCML | GAGGCGGTATCGGGAGAAAG | SEQ ID NO: 581 | AACAACAACTCCATCCCTAAGGC | SEQ ID NO: 582 |
| | SFRP1 | CGCGAGGGAGGCGATT | SEQ ID NO: 584 | CACTCGTTACCACGTCCGTCACCG | SEQ ID NO: 585 |
| | SFRP2 | GTTGAACGGTGGTTGGAGATTC | SEQ ID NO: 587 | CGCCTCGACGAACTTCGTTTTCCCT | SEQ ID NO: 588 |
| | SFRP4 | TTCGTAATGGTCGTGGTTGGT | SEQ ID NO: 590 | CAACGCCAACTCTCAACCTTCGAAACG | SEQ ID NO: 591 |
| | SFRP5 | TAGGCGGTCGGAGATTGGT | SEQ ID NO: 593 | CTCCCACCTCGAAACTCCAACCCG | SEQ ID NO: 594 |

SUPPLEMENTARY TABLE S2-continued

MethyLight reaction information

| | | | | | |
|---|---|---|---|---|---|
| SLIT2 | CGGGAGATCGC GAGGAT | SEQ ID NO: 596 | CGACCTCTCCCTCGCCCT CGACT | SEQ ID NO: 597 |
| TACSTD1 | AATTTTCGGGCG GTGATTTA | SEQ ID NO: 599 | CCCTTCCCGAAACTACTC ACCTCTAACCG | SEQ ID NO: 600 |
| TITF-1 | TGTTTTGTTGTTT TAGCGTTTACGT | SEQ ID NO: 602 | CTCGCGTTTATTTTAACCC GACGCCA | SEQ ID NO: 603 |
| ZBTB16 | TGATTTGTTAATT TCGTAGTAGAGA GGAGTT | SEQ ID NO: 605 | CGACAATTCGCAATACCC GCTCTCA | SEQ ID NO: 606 |

Supplementary Table S3
Relapse free survival in ovarian cancer patients.

| Variable | No. of patients with relapse/total no. | RR of death (95% CI) | P |
|---|---|---|---|
| A | | | |
| Age | | | |
| <60 a | 14/44 | 2.2 (1.2-3.9) | 0.01 |
| >60 a | 33/48 | | |
| Tumor stage | | | |
| I/II | 12/30 | 2.7 (1.2-6.1) | 0.01 |
| III | 35/62 | | |
| Tumor grade | | | |
| I/II | 27/63 | 2.8 (1.5-5) | <0.001 |
| III | 20/29 | | |
| Size of remaining tumor | | | |
| <2 cm | 25/65 | 3.5 (1.9-6.4) | <0.001 |
| >2 cm | 22/27 | | |
| HOXA10 methylation | | | |
| PMR <12 | 12/26 | 1.1 (0.5-2.2) | 0.85 |
| PMR >12 | 35/66 | | |
| HOXA11 methylation | | | |
| PMR <12 | 5/27 | 3.5 (1.6-7.9) | 0.002 |
| PMR >12 | 42/65 | | |
| B | | | |
| Age | | | |
| <60 a | 14/44 | 2.0 (1.1-3.7) | 0.03 |
| >60 a | 33/48 | | |
| Tumour stage | | | |
| I/II | 12/30 | 2.3 (0.9-5.9) | 0.08 |
| III | 35/62 | | |
| Tumour grade | | | |
| I/II | 27/63 | 1.9 (1-3.6) | 0.06 |
| III | 20/29 | | |
| Size of remaining tumour | | | |
| <2 cm | 25/65 | 1.9 (0.9-4) | 0.09 |
| >2 cm | 22/27 | | |
| HOXA10 methylation | | | |
| PMR <12 | 12/26 | 0.5 (0.2-1.1) | 0.09 |
| PMR >12 | 35/66 | | |
| HOXA11 methylation | | | |
| PMR <12 | 5/27 | 2.9 (1.1-7.7) | 0.035 |
| PMR >12 | 42/65 | | |

(A) Univariate and (B) multivariate analysis.

HOXA11 is a factor which is of paramount importance in Mullerian Duct biology (15) and is known to be occupied and thereby suppressed by PRC2 in human embryonic stem cells. The interesting finding that 93% of the tumors with more than 2 cm residual after surgery had HOXA11 PMR values >12 shows that HOXA11 may act also as a marker for the tumor distribution. This would support the view that the technical ability to cytoreduce the cancer simply identifies a biologically more favourable patient subgroup (18). Maurie Markman recently speculated that the multiple factors (both currently defined and still unknown) that likely determine the manner in which a cancer progresses throughout the peritoneal cavity and that might substantially influence a surgeon's ability to remove the majority of visible tumor may also define such critically important features as the presence of de novo, or development of acquired, cytotoxic drug resistance (18). In particular aspects of the present invention, therefore, HOXA11 provides a surrogate marker for cancer stem cells, and its methylation is a factor which determines cancer progression.

In the present EXAMPLE, applicants identified a steady increase of HOXA11 DNA methylation frequency from normal ovaries towards primary ovarian cancer—in particular those with suboptimal debulking surgery—as well as an independent association between high frequency of HOXA11 methylation and poor overall survival in ovarian cancer patients. Future research will need to elucidate whether epigenetic aberration of other HOX genes are also involved in ovarian carcinogenesis.

REFERENCES CITED IN THIS EXAMPLE 11, AND INCORPORATED HEREIN BY REFERENCE

1. Jemal A, Siegel R, Ward E, et al. Cancer statistics, 2006. C A Cancer J. Clin., 56(2):106-30, 2006.
2. Holschneider C, Berek J S. Ovarian cancer: epidemiology, biology, and prognostic factors. Semin Surg. Oncol., 19:3-10, 2000.
3. Teodoridis J M, Hall J, Marsh S, et al. CpG island methylation of DNA damage response genes in advanced ovarian cancer. Cancer Res., 65:8961-7, 2005.
4. Muller H M, Millinger S, Fiegl H, et al. Analysis of methylated genes in peritoneal fluids of ovarian cancer patients: a new prognostic tool. Clin. Chem., 50:2171-3, 2004.
5. Wei S H, Balch C, Paik H H, et al. Prognostic DNA methylation biomarkers in ovarian cancer. Clin. Cancer Res., 12:2788-94, 2006.
6. Laird P W. The power and the promise of DNA methylation markers. Nat. Rev. Cancer, 3:253-66, 2003.

7. Widschwendter M, Fiegl H, Egle D, et al. Epigenetic stem cell signature in cancer. Nat Genet., 39:157-58, 2007.
8. Ohm J E, McGarvey K M, Yu X, et al. A stem cell-like chromatin pattern may predispose tumor suppressor genes to DNA hypermethylation and heritable silencing. Nat Genet., 39:237-42, 2007.
9. Schlesinger Y, Straussman R, Keshet I, et al. Polycomb-mediated methylation on Lys27 of histone H3 pre-marks genes for de novo methylation in cancer. Nat Genet., 39:232-6, 2007.
10. Lee T I, Jenner R G, Boyer L A, et al. Control of developmental regulators by Polycomb in human embryonic stem cells. Cell, 125:301-13, 2006.
11. Weisenberger D J, Siegmund K D, Campan M, et al. CpG island methylator phenotype underlies sporadic microsatellite instability and is tightly associated with BRAF mutation in colorectal cancer. Nat. Genet., 38:787-93, 2006.
12. Fiegl H, Gattringer C, Widschwendter A, et al. Methylated DNA collected by tampons—a new tool to detect endometrial cancer. Cancer Epidemiol Biomarkers Prev., 13:882-8, 2004.
13. Spizzo G, Gastl G, Obrist P, et al. Methylation status of the Ep-CAM promoter region in human breast cancer cell lines and breast cancer tissue. Cancer Lett., 246:253-61, 2007.
14. Oberwalder M, Zitt M, Wontner C, et al. SFRP2 methylation in fecal DNA—a marker for colorectal polyps. Int J Colorectal Dis., Epub ahead of print, 2007.
15. Du H, Taylor H S. Molecular regulation of mullerian development by Hox genes. Ann. N.Y. Acad. Sci., 1034: 152-65, 2004.
16. Yoshida H, Broaddus R, Cheng W, Xie S, Naora H. Deregulation of the HOXA10 homeobox gene in endometrial carcinoma: role in epithelial-mesenchymal transition. Cancer Res., 66:889-97, 2006.
17. Cheng W, Liu J, Yoshida H, Rosen D, Naora, H. Lineage infidelity of epithelial ovarian cancers is controlled by HOX genes that specify regional identity in the reproductive tract. Nat. Med., 11: 531-37, 2005.
18. Markman M. Concept of optimal surgical cytoreduction in advanced ovarian cancer: a brief critique and a call for action. J Clin Oncol. 20; 25:4168-70, 2007.

EXAMPLE 12

NEUROD1 Methylation was Shown Herein to be a Novel Chemosensitivity Marker in Breast Cancer (e.g., ER Negative Breast Cancer)

Example Overview

Applicants have reported that stem cell Polycomb group targets (PGCTs) are up to 12-fold more likely to have cancer-specific promoter DNA hypermethylation than non-targets (see herein and see also reference 4 below). This supports the idea of a stem cell origin of cancer whereby reversible gene repression is replaced by permanent silencing, forcing the cell into a perpetual state of self-renewal and so increasing the possibility for subsequent malignant transformation (4). A large number of PCGT genes have not yet been described to play a role in cancer and this could explain why non-tumor suppressor genes are found to be frequently hypermethylated in adult epithelial cancers. Applicants have analyzed the methylation status of 61 genes in breast cancer and non-neoplastic breast tissues of 15 patients and 15 healthy controls, respectively. NEUROD1 DNA methylation was the best discriminator between these different groups (4). In this EXAMPLE we focused on the role of NEUROD1 methylation in breast cancer biology, and analyzed tumor samples, pre-treatment core biopsies and pre- and post-therapeutic serum samples by means of MethyLight™, a sensitive fluorescence-based real-time PCR technique (5).

In this EXAMPLE, applicants used MethyLight™ and analyzed NEUROD1 methylation in [1] 74 breast cancer tissue samples, [2] two independent sets of pre-treatment core biopsies of 23 (training set) and 21 (test set) neoadjuvantly treated breast cancer patients and [3] pre- and post-therapeutic serum samples from 107 breast cancer patients treated with adjuvant chemotherapy. High grade tumors demonstrated higher NEUROD1 methylation levels. Estrogen receptor (ER) negative breast cancers with high NEUROD1 methylation were 10.8 fold more likely to respond with a complete pathological response following neoadjuvant chemotherapy. Patients with positive serum pretreatment NEUROD1 methylation, which persisted after chemotherapy indicated poor relapse-free and overall survival in uni- and multivariate analysis [relative risk for relapse 6.2 (95% CI 1.6-24; p=0.008), relative risk for death 14 (95% CI 1.6-120; p=0.02)]. Therefore, in particular aspects, NEUROD1 methylation is provided as a chemosensitivity marker in breast cancer (e.g., ER negative breast cancer).

Materials and Methods.

Patients and Samples.

The following samples have been analyzed:

(1) Frozen breast tissue samples from 74 breast cancer patients. All samples were collected during surgery at the Department of Obstetrics and Gynecology of the Innsbruck Medical University, Austria in compliance with and approved by the Institutional Review Board. Breast cancer specimens were obtained immediately after resection of the breast or lumpectomy. Specimens were brought to our pathologist, and a part of the tissue was pulverized under cooling with liquid nitrogen and stored at −70° C. Patients were 35 to 90 years old (mean age at diagnosis, 62 years). Other clinicopathological features are shown in TABLE 8.

(2) Paraffin embedded pre-treatment core biopsies (formalin fixed 16 gauge cores) from breast cancer patients. Samples were obtained from the Department of Pathology, and Gynecology, General Hospital and Paracelsus University Salzburg (training set samples), the Department of Obstetrics and Gynecology, Medical University Innsbruck, Austria and the Royal Marsden Hospital, London, United Kingdom (test set samples). All samples were collected at diagnosis prior to chemotherapy in compliance with and approved by the Institutional Review Boards. In the training set applicants analyzed samples from 23 patients who received 6 cycles of anthracycline-based therapy. 21/23 samples yielded sufficient amount of DNA. 7/21 patients demonstrated a complete pathological response (CR; disappearance of the invasive cancer in the breast). Clinicopathological features are shown in TABLE 9A. For further evaluation applicants analysed samples from an independent test set from 21 patients. One patient received 3 cycles of a combination of cyclophosphamide, methotrexate and 5-fluorouracil, 10 patients received 4 cycles, 9 patients 6 cycles and 1 patient 3 cycles of an anthracycline-based therapy. Clinicopathological features are shown in TABLE 9B.

(3) Pre- and post-therapeutic serum samples from 107 breast cancer patients, treated at the Department of Gynecology and Obstetrics, Medical University Innsbruck, Austria, with primary non-metastatic breast cancer. Serum samples were recruited from all patients diagnosed with breast cancer between September 1992 and February 2002 who met all the following criteria: (a) primary breast cancer without metastasis at diagnosis, (b) adjuvant treatment with chemotherapy (41 patients received an anthracycline-based therapy, 64 patients received a combination of cyclophospamide, methotrexate and 5-fluorouracil and 2 patients received another kind of chemotherapy), (c) availability of serum samples at diagnosis and 1 year after treatment (a time when the patient has completed her chemotherapy) and (d) no relapse after one year. Hormone receptor status was determined by either radioligand binding assay or immunohistochemistry. Clinicopathological features are shown TABLE 10. Patients' blood samples were drawn before or 1 year after therapeutic intervention. Blood was centrifuged at 2,000×g for 10 minutes at room temperature and 1 mL aliquots of serum samples were stored at ±30° C.

DNA Isolation, Bisulfite Modification and MethyLight Analysis.

Genomic DNA from fresh frozen tissue samples or paraffin embedded tissue sample respectively was isolated using the DNeasy Tissue Kit (Qiagen, Hilden, Germany) according to the manufacturer s protocol. DNA isolation from serum samples, bisulfite modification, and MethyLight analysis was done as described previously (2). Primers and Probe for NEUROD1 (AC013733; e.g., amplicon position 78576-78657 (SEQ ID NO: 597)) have been described recently (6, incorporated by reference herein).

RNA Isolation and RT-PCR. Total cellular RNA was extracted from the tumor specimens as previously described by the acid guanidium thiocyanate-phenol-chlorophorm method.

Reverse Transcription of RNA was performed as previously described. The following primers were used for COX-2 expression analysis: Forward: 5-TGCTGCTGTGCGCGG-3 (SEQ ID NO: 592), Reverse: 5-GGTTTTGACATGGGTGG-GAAC-3 (SEQ ID NO: 593), Probe: 5 FAM-CCTGGCGCT-CAGCCATACAG CAAA-3 TAMRA (SEQ ID NO 594). Primers and probes for the TATA box-binding protein (TBP) were used according to Bieche et al (7).

Real-time PCR was performed using an ABI Prism 7900HT Detection System (Applied Biosystems, Foster City, Calif.) as recently described. The standard curves were generated using serially diluted solutions of standard cDNA derived from the HBL-100 breast carcinoma cell-line.

Statistics.

Descriptive analysis of obtained data was performed and median as well as interquartile ranges were given. Data of parametric distributed variables were shown as mean and standard deviation. Differences of PMR (Percentage of Methylated Reference) values between groups were analyzed by means of a two-sided Mann-Whitney-U-test. Survival analysis was done by using univariate Kaplan-Meier curves and Cox Regression Models. All statistical analyses were done applying SPSS Software 10.0.

Results.

Based on our recent study, NEUROD1 methylation is the best discriminator between breast cancer and non-neoplastic tissue samples (4; Supplementary TABLE S4). To further explore the role of NEUROD1 methylation in primary breast cancer, in this EXAMPLE, applicants first analyzed NEUROD1 methylation in 74 frozen primary breast cancer specimens. High grade tumors demonstrated higher NEUROD1 methylation levels (p=0.03), whereas no other clinicopathological feature was associated with NEUROD1 methylation (TABLE 8). The promoter of NEUROD1 is occupied by repressive regulators in human embryonic stem cells (8) which would be consistent with NEUROD1 DNA methylation marking cancer stem cells in the tumor. Although there is a highly significant increase in NEUROD1 methylation from non-neoplastic to breast cancer tissue (Supplementary Table S1) with higher levels in high grade tumors (TABLE 8), surprisingly NEUROD1 methylation in breast cancer is not an indicator of tumor aggressiveness which is demonstrated in a lack of association of NEUROD1 methylation and lymphnode metastasis (TABLE 8) or survival (TABLE 11). This rather surprising finding led applicants to the conclusion that NEUROD1 methylation is associated with other tumor features like responsiveness to systemic treatment in breast cancer.

Figures 3A, 3B:
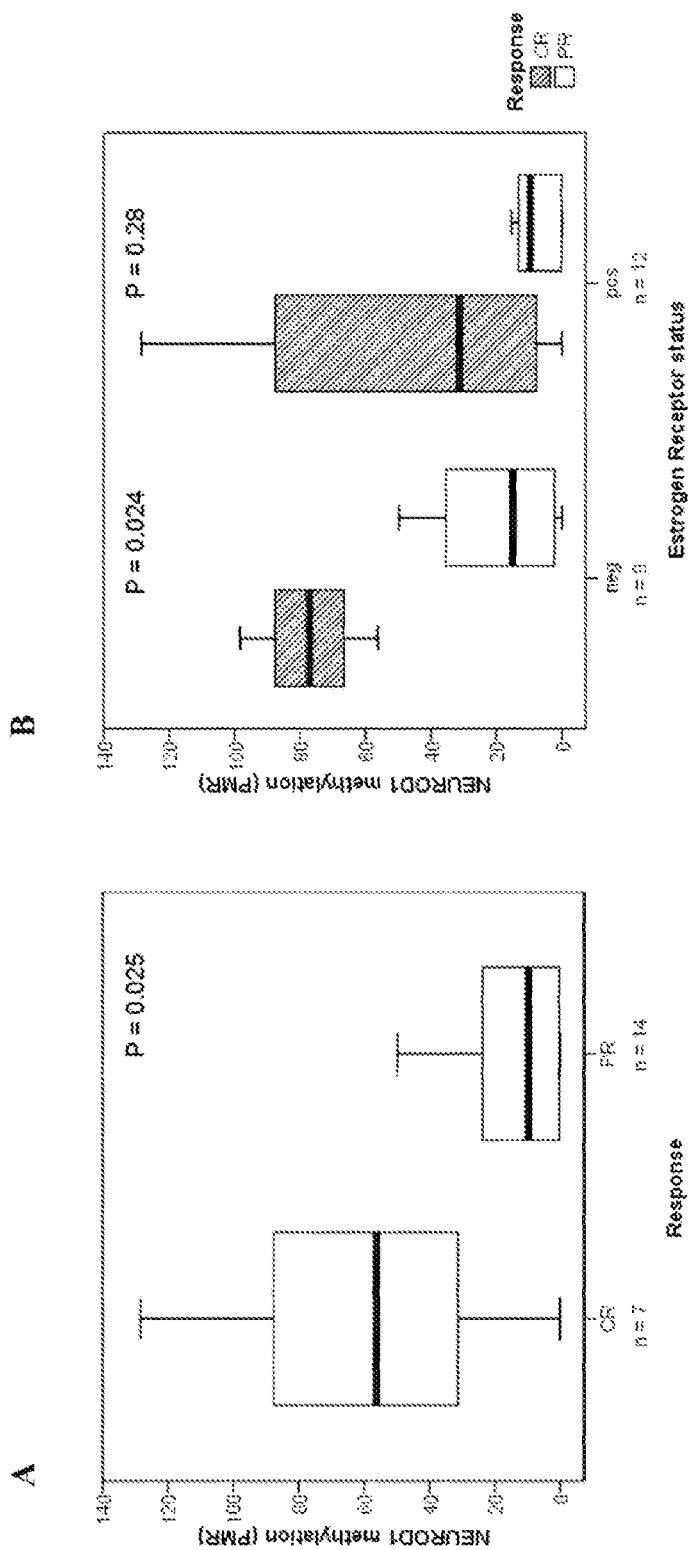
FIGS. 3A and B show NEUROD1 DNA methylation in the pretreatment breast cancer core biopsies of the training set. A, Samples stratified by response (PMR, Percentage of Methylated Reference; CR, complete pathological response; PR, partial response; Mann-Whitney-U-test, p=0.025). B, Samples stratified by ER status (Mann-Whitney-U-test, p=0.024 for ER-neg. samples, p=0.28 for ER-pos. samples).

To confirm this aspect, applicants used two in vivo experiments: NEUROD1 methylation analysis in core breast cancer biopsies taken prior to preoperative chemotherapy with complete pathological response as the endpoint (model 1) and seroconversion of NEUROD1 methylation in serum DNA during adjuvant chemotherapy with survival as the endpoint (model 2). For model 1, applicants first analyzed DNA from pretreatment core biopsies from 23 breast cancer patients (training set). 21/23 samples yielded sufficient DNA and 7/21 patients demonstrated a CR (TABLE 9A). Patients with a CR demonstrated significantly higher NEUROD1 methylation levels in their pretreatment cancer cores (FIG. 3A). To exclude the possibility that this association was merely a reflection of cellularity in the core, an adjustment was made for percentage of tumor cells (reviewed by G.H., a pathologist who was blinded for the chemotherapy response) and still observed a significant (p=0.006) association between pretreatment core NEUROD1 methylation and response to neoadjuvant chemotherapy.

As ER-negative tumors are more likely to respond to neoadjuvant chemotherapy (9-11), applicants analyzed the association of CR and NEUROD1 methylation separately, in ER negative and ER positive tumor samples. Although the numbers are small, the association between NEUROD1 methylation and response to neoadjuvant chemotherapy was retained in ER negative cancers (Mann-Whitney-U-test; p=0.02; FIG. 3B).

Figures 4A, 4B:
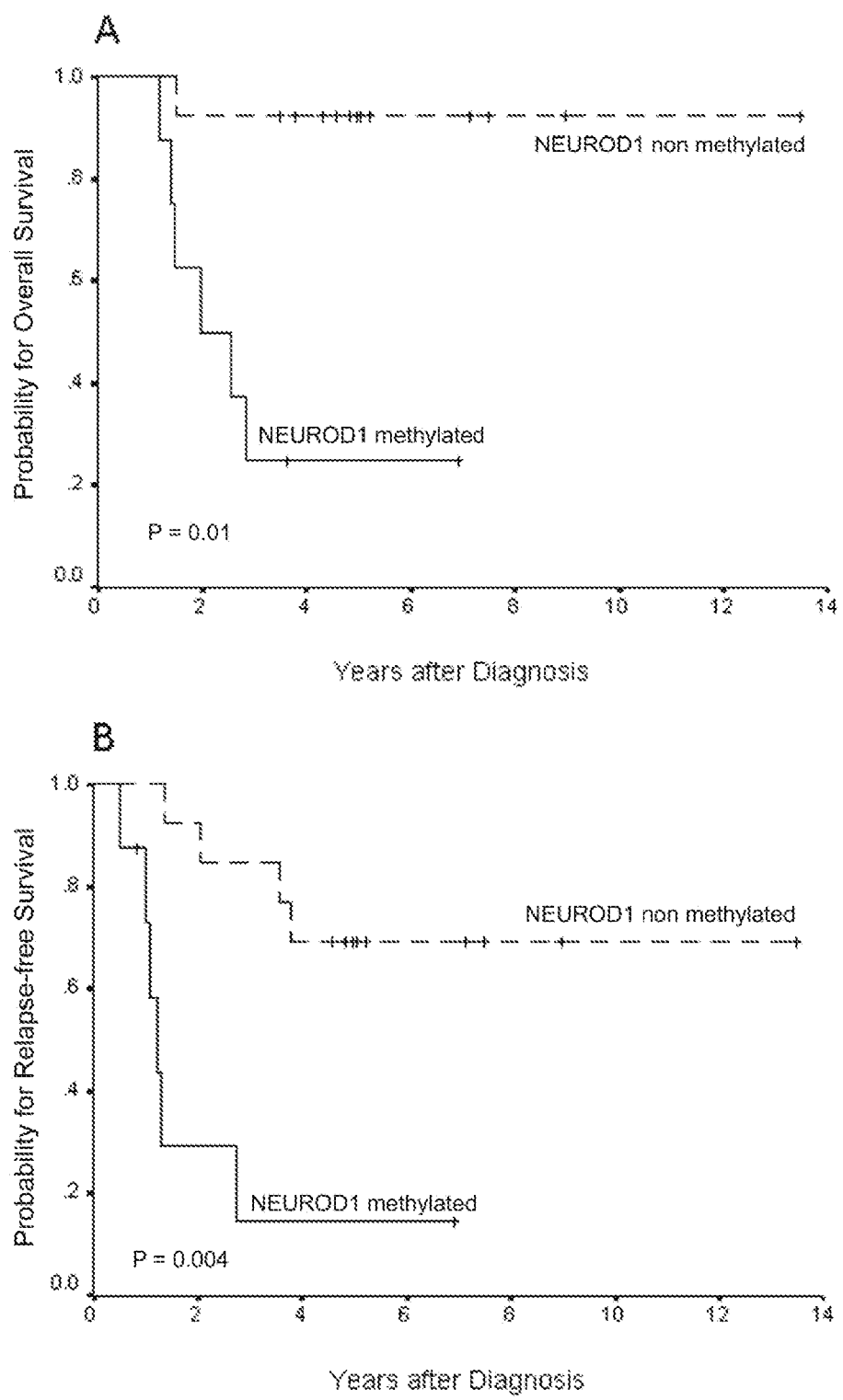
FIGS. 4A and B show Kaplan Meier survival curves and NEUROD1 DNA methylation status in serum samples. A, Overall and B, relapse-free survival of 21 ER negative primary breast cancer patients with positive NEUROD1 methylation in pre-treatment serum. Broken and continuous lines represent negative and positive serum NEUROD1 methylation after chemotherapy, respectively.

In order to further validate these findings and to calculate the predictive potential of NEUROD1 methylation, applicants analyzed an independent test set of 21 core biopsies taken prior to the start of neoadjuvant chemotherapy from ER negative breast cancer patients (TABLE 9B). NEUROD1 methylation was classified as low (n=11) and high (n=10) using the median PMR value (PMR=2.18) as the cut-off. 8/10 (80%) women with high and 3/11 (27%) women with low NEUROD1 methylation in their core biopsy had a CR. Using a logistic regression model and adjusting for age and HER2 status, high NEUROD1 methylation in ER negative pretreatment breast cancer biopsies was associated with a 10.8-fold increased likelihood for a CR following neoadjuvant chemotherapy (95% CI 1.1-106.4; p=0.042). This means that NEUROD1 methylation had a sensitivity of 80% (44.0, 96.0) and a specificity of 72% (39.0, 92.0) to predict complete pathological response in women treated with neoadjuvant chemotherapy. In applicants' second model, applicants assessed whether serum NEUROD1 methylation is able to predict the response to adjuvant chemotherapy in patients with primary breast cancer. Applicants have previously demonstrated that DNA methylation of specific genes in circulating serum DNA is a marker for poor prognosis (2) and a tool to monitor adjuvant tamoxifen treatment (3). For confirming that NEUROD1 methylation is a marker for chemosensitivity in breast cancer, we would expect that women whose serum NEUROD1 methylation is positive before, but not detectable after adjuvant chemotherapy have an improved relapse-free and overall survival as their chemosensitive tumor cells have been eliminated. 107 patients were identified who received adjuvant chemotherapy due to primary non-metastatic breast cancer and from whom both pretreatment and post-chemotherapy serum samples have been stored. Characteristics of these patients are shown in TABLE 10A. Pretreatment NEUROD1 serum DNA methylation was more prevalent in postmenopausal women, whereas no difference in any of the other clinicopathological features could be observed. In the group of 21 ER negative patients with positive pretreatment NEUROD1 methylation in their serum, persistence of NEUROD1 DNA methylation after chemotherapy indicated poor overall and relapse-free survival in the univariate analysis (FIG. 4, and TABLE 12). Characteristics of these patients are shown in TABLE 10B. Using a Cox multiple-regression analysis which included tumor size, grade, lymph node metastasis and menopausal status, persistence of methylated NEUROD1 serum DNA was the only predictor of poor outcome (relative risk for relapse 6.2 (95% CI 1.6-24; p=0.008), relative risk for death 14 (95% CI 1.6-120; p=0.02)). No association between serum NEUROD1 DNA methylation and response to adjuvant chemotherapy could be observed for ER positive breast cancer patients (data not shown).

TABLE 8

Association of NEUROD1 methylation of 74 primary breast cancer patients with clinicopathological features.

| | | | | NEUROD1 methylation values (PMR) | | |
|---|---|---|---|---|---|---|
| | | n | Median | 25th; 75th percentile | p-value | |
| Size | T1 | 14 | 19 | 0.7; 52 | 0.6 | |
| | T2/3/4 | 60 | 26 | 5.4; 61 | | |
| LN | negative | 23 | 18 | 3.2; 48 | 0.8 | |
| | positive | 46 | 26 | 7.0; 65 | | |
| | n.a. | 5 | | | | |
| Grade | grade I | 31 | 13 | 3.2; 37 | 0.03 | |
| | grade II/III | 41 | 34 | 8.9; 75 | | |
| | n.a. | 2 | | | | |
| MP | premenopausal | 18 | 24 | 5.6; 39 | 0.8 | |
| | postmenopausal | 56 | 19 | 4.5; 63 | | |
| ER | neg | 27 | 25 | 6.9; 40 | 1.0 | |
| | pos | 47 | 18 | 3.6; 71 | | |
| PR | neg | 31 | 25 | 3.6; 52 | 0.7 | |
| | pos | 43 | 19 | 6.9; 75 | | |
| HER2 | score 0/+ | 49 | 16 | 4.0; 54 | 0.1 | |
| | score ++/+++ | 23 | 34 | 13; 62 | | |
| | n.a. | 2 | | | | | n.a. not available

TABLE 9

Characteristics of neoadjuvantly treated primary breast cancer patients.

| | | | n |
|---|---|---|---|
| A | Clinicopathological features of training set | | |
| | Age (y +/− SD) | 46.9 (+/−10.1) | |
| | Histological type | invasive ductal | 17 |
| | | invasive lobular | 4 |
| | ER | neg | 9 |
| | | pos | 12 |
| | HER2 | score 0/+ | 15 |
| | | score ++/+++ | 5 |
| | | n.a. | 1 |
| | Pathological response | PR | 14 |
| | | CR | 7 |
| | Percentage of tumor cells in sample (% +/− SD) | 51 (+/−24.6) | |
| | Type of chemotherapy | Anthracyclines | 21 |
| | Cycle number of chemotherapy | 6 | 21 |

TABLE 9-continued

Characteristics of neoadjuvantly treated primary breast cancer patients.

| | | | n |
|---|---|---|---|
| B | Clinicopathological features of test set | | |
| | Age (y +/− SD) | 50 (+/−10.3) | |
| | Histologic type | invasive ductal | 18 |
| | | other | 3 |
| | ER | neg | 21 |
| | | pos | 0 |
| | HER2 | score 0/+ | 11 |
| | | score ++/+++ | 10 |
| | Pathological response | PR | 10 |
| | | CR | 11 |
| | Type of chemotherapy | Anthracyclines | 20 |
| | | Cyclophosphamide, Methotrexat, Fluorouracil | 1 |
| | Number of chemotherapy cycles | 3 | 2 |
| | | 4 | 10 |
| | | 6 | 9 |

Core Biopsy Samples of (A) training and (B) test set.

TABLE 10

Characteristics of adjuvantly treated non-metastatic primary breast cancer patients.

| | | | n |
|---|---|---|---|
| A | Clinicopathological features | | |
| | Age at diagnosis | 55.5 | |
| | SD | 11.3 | |
| | Size | T1 | 40 |
| | | T2/3/4 | 66 |
| | | n.a. | 1 |
| | LN | negative | 27 |
| | | positive | 78 |
| | | n.a. | 2 |
| | Grade | grade I | 16 |
| | | grade II/III | 89 |
| | | n.a. | 2 |
| | MP | premenopausal | 38 |
| | | postmenopausal | 69 |
| | ER | neg | 57 |
| | | pos | 50 |
| | PR | neg | 55 |
| | | pos | 52 |
| | OP-Mode | BE | 38 |
| | | ME | 68 |
| | | n.a. | 1 |
| | Endocrinetherapy | no | 55 |
| | | tamoxifen | 52 |
| | Radiationtherapy | no | 44 |
| | | yes | 63 |
| | Type of Chemotherapy | Anthracyclines | 41 |
| | | Cyclophosphamide, Methotrexat, Fluorouracil | 64 |
| | | others | 2 |
| B | Clinicopathological features | | |
| | Age at diagnosis | 57.6 | |
| | SD | 10.7 | |
| | Size | T1 | 9 |
| | | T2/3/4 | 11 |
| | | n.a. | 1 |
| | LN | negative | 5 |
| | | positive | 15 |
| | | n.a. | 1 |
| | Grade | grade I | 4 |
| | | grade II/III | 17 |
| | MP | premenopausal | 3 |
| | | postmenopausal | 18 |
| | PR | neg | 18 |
| | | pos | 3 |

TABLE 10-continued

Characteristics of adjuvantly treated non-metastatic primary breast cancer patients.

| | | n |
|---|---|---|
| OP-Mode | BE | 6 |
| | ME | 14 |
| | n.a. | 1 |
| Endocrine therapy | no | 18 |
| | tamoxifen | 3 |
| Radiation therapy | no | 7 |
| | yes | 14 |

TABLE 10-continued

Characteristics of adjuvantly treated non-metastatic primary breast cancer patients.

| | | n |
|---|---|---|
| Type of Chemotherapy | Anthracyclines | 7 |
| | Cyclophosphamide, Methotrexat, Fluorouracil | 14 |

Serum samples of A, all patients and B, 21 ER negative patients with positive NEUROD1 methylation in pre-treatment serum.

TABLE 11

Univariate survival analysis of 74 patients with primary breast cancer.

A

| | | OVERALL SURVIVAL | | |
|---|---|---|---|---|
| | | No.Patients (died/total) | RR of death (95% CI) | P |
| Size | T1 | 4/14 | 1.8 (0.6-5.2) | 0.3 |
| | T2/3/4 | 26/60 | | |
| LN | negative | 6/23 | 2 (0.8-5.1) | 0.1 |
| | positive | 21/46 | | |
| Grade | grade I | 14/31 | 0.9 (0.4-1.8) | 0.7 |
| | grade II/III | 16/41 | | |
| MP | premenopausal | 6/18 | 1.5 (0.6-3.7) | 0.4 |
| | postmenopausal | 24/56 | | |
| HR | neg | 7/24 | 1.7 (0.7-4.0) | 0.2 |
| | pos | 23/50 | | |
| Chemo | no | 16/38 | 0.9 (0.5-1.9) | 0.8 |
| | yes | 14/36 | | |
| Endocrine therapy | no | 10/28 | 1.4 (0.7-3.0) | 0.4 |
| | tamoxifen | 20/46 | | |
| Radiation therapy | no | 12/29 | 0.7 (0.4-1.6) | 0.4 |
| | yes | 18/45 | | |
| NEUROD1 | low methylation | 16/37 | 0.8 (0.4-1.7) | 0.6 |
| | high methylation | 14/37 | | |

B

| | | RELAPSE FREE SURVIVAL | | |
|---|---|---|---|---|
| | | No. Patients (relapsed/total) | RR of relapse (95% CI) | P |
| Size | T1 | 3/14 | 1.7 (0.5-5.7) | 0.4 |
| | T2/3/4 | 18/60 | | |
| LN | negative | 2/23 | 5.7 (1.3-24.4) | 0.02 |
| | positive | 19/46 | | |
| Grade | grade I | 8/31 | 1.1 (0.5-2.8) | 0.8 |
| | grade II/III | 13/41 | | |
| MP | premenopausal | 6/18 | 1.0 (0.40-2.6) | 1.0 |
| | postmenopausal | 15/56 | | |
| HR | neg | 5/24 | 1.5 (0.5-4.0) | 0.5 |
| | pos | 16/50 | | |
| Chemo | no | 4/38 | 4.0 (1.3-11.8) | 0.01 |
| | yes | 17/36 | | |
| Endocrine therapy | no | 5/28 | 1.9 (0.7-5.2) | 0.2 |
| | tamoxifen | 16/46 | | |
| Radiation therapy | no | 5/29 | 1.3 (0.5-3.6) | 0.6 |
| | yes | 16/45 | | |
| NEUROD1 | low methylation | 10/37 | 0.8 (0.3-1.8) | 0.6 |
| | high methylation | 11/37 | | |

A, Overall survival. B, Relapse free survival.

TABLE 12

Univariate analysis of 21 ER negative primary breast cancer patients with positive NEVROD1 methylation in pre-treatment serum.

A

| | | OVERALL SURVIVAL | | |
|---|---|---|---|---|
| | | No. Patients (died/total) | RR of death (95% CI) | P |
| Size | T1 | 2/9 | 2.4 (0.5-12.6) | 0.3 |
| | T2/3/4 | 5/11 | | |
| LN | negative | 2/5 | 0.6 (0.1-3.4) | 0.6 |
| | positive | 4/15 | | |
| Grade | grade I | 1/4 | 1.8 (0.2-14.5) | 0.6 |
| | grade II/III | 6/17 | | |
| MP | premenopausal | 1/3 | 1.2 (0.2-10.2) | 0.9 |
| | postmenopausal | 6/18 | | |
| PR | neg | 7/18 | 0.04 (0.0-196) | 0.5 |
| | pos | 0/3 | | |
| OP-Mode | BE | 1/6 | 2.5 (0.3-22) | 0.4 |
| | ME | 5/14 | | |
| radiation | no | 3/7 | 0.7 (0.2-3.0) | 0.6 |
| | yes | 4/14 | | |
| NEUROD1 | neg after chemo | 1/13 | 15 (1.8-125) | 0.01 |
| | pos after chemo | 6/8 | | |

B

| | | RELAPSE FREE SURVIVAL | | |
|---|---|---|---|---|
| | | No. Patients (relapsed/total) | RR of relapse (95% CI) | P |
| Size | T1 | 4/9 | 1.5 (0.4-5.4) | 0.5 |
| | T2/3/4 | 6/11 | | |
| LN | negative | 4/5 | 0.4 (0.1-1.3) | 0.1 |
| | positive | 5/15 | | |
| Grade | grade I | 1/4 | 2.3 (0.3-18.5) | 0.4 |
| | grade II/III | 9/17 | | |
| MP | premenopausal | 2/3 | 0.6 (0.1-2.8) | 0.5 |
| | postmenopausal | 8/18 | | |
| PR | neg | 9/18 | 0.5 (0.1-3.7) | 0.5 |
| | pos | 1/3 | | |
| OP-Mode | BE | 4/6 | 0.6 (0.2-2.4) | 0.5 |
| | ME | 5/14 | | |
| radiation | no | 4/7 | 0.6 (0.2-2.0) | 0.4 |
| | yes | 6/14 | | |
| NEUROD1 | neg after chemo | 4/13 | 6.9 (1.9-26) | 0.004 |
| | pos after chemo | 6/8 | | |

A, Overall survival. B, Relapse free survival.

Supplementary Table S4.
Methylation values (PMR) of 61 genes analyzed in 15 non-neoplastic breast samples and 15 breast cancers.

| | Methylation values (PMR) | | | | |
|---|---|---|---|---|---|
| | non-neoplastic breast (n = 15) | | breast cancer (n = 15) | | |
| Genes | Median | 25th; 75th percentile | Median | 25th; 75th percentile | p-value[a] |
| NEUROD1 | 0.25 | 0.10; 1.34 | 5.49 | 3.00; 34.05 | 0.000027 |
| SEZ6L | 0.14 | 0.07; 0.21 | 1.17 | 0.30; 9.53 | 0.000044 |
| SFRP4 | 1.04 | 0; 2 | 3 | 3; 8 | 0.000044 |
| OPCML | 0.67 | 0.05; 3.13 | 13.46 | 3.53; 59.66 | 0.000113 |

Supplementary Table S4.
Methylation values (PMR) of 61 genes analyzed in 15
non-neoplastic breast samples and 15 breast cancers.

| | Methylation values (PMR) | | | | |
|---|---|---|---|---|---|
| | non-neoplastic breast (n = 15) | | breast cancer (n = 15) | | |
| Genes | Median | 25th; 75th percentile | Median | 25th; 75th percentile | p-value[a] |
| GATA5 | 1.17 | 0.39; 1.96 | 5.34 | 3.92; 19.59 | 0.000174 |
| SLIT2 | 1.11 | 0.64; 1.94 | 6.18 | 2.15; 26.31 | 0.000215 |
| SFRP5 | 0.63 | 0.51; 1.36 | 3.13 | 1.83; 13.09 | 0.000478 |
| HOXA1 | 0.61 | 0.24; 1.10 | 17.97 | 0.93; 66.22 | 0.001 |
| SFRP2 | 1.03 | 0.56; 2.28 | 3.39 | 1.39; 27.54 | 0.006 |
| ZBTB16 | 0.07 | 0.03; 0.44 | 0.57 | 0.29; 1.34 | 0.007 |
| CCND2 | 0.00 | 0.00; 0.08 | 0.64 | 0.03; 10.94 | 0.011 |
| SYK | 0.08 | 0.01; 0.31 | 0.00 | 0.00; 0.07 | 0.012 |
| SFRP1 | 0.25 | 0.00; 1.26 | 0.89 | 0.31; 21.50 | 0.019 |
| CDH13 | 0.22 | 0.01; 1.05 | 1.18 | 0.43; 15.04 | 0.020 |
| PTGS2 | 0.71 | 0.35; 1.35 | 1.91 | 1.09; 9.86 | 0.021 |
| HOXA10 | 13.1 | 3.30; 18.37 | 38.17 | 5.73; 87.77 | 0.033 |
| ITGA4 | 0.00 | 0.00; 0.00 | 0.05 | 0.00; 0.91 | 0.037 |
| MYOD1 | 0.45 | 0.19; 1.37 | 1.56 | 0.49; 3.80 | 0.046 |
| TERT | 0.00 | 0.00; 0.00 | 1.56 | 0.00; 4.34 | 0.046 |
| CDKN2B | 0.13 | 0.04; 0.20 | 0.23 | 0.14; 0.36 | 0.061 |
| DAPK1 | 0.45 | 0.25; 0.83 | 1.20 | 0.27; 12.83 | 0.067 |
| SCGB3A1 | 0.43 | 0.16; 1.39 | 1.11 | 0.44; 31.23 | 0.067 |
| TIMP3 | 0.42 | 0.04; 0.72 | 0.75 | 0.21; 1.60 | 0.077 |
| BDNF | 0.00 | 0.00; 0.00 | 0.00 | 0.00; 0.02 | 0.085 |
| ABCB1 | 60.6 | 50; 70 | 69 | 58; 105 | 0.089 |
| NEUROG1 | 0.00 | 0.00; 0.00 | 0.00 | 0.00; 0.38 | 0.089 |
| DCC | 0.08 | 0.01; 0.53 | 0.46 | 0.17; 1.63 | 0.102 |
| RARRES1 | 0.00 | 0.00; 0.04 | 0.03 | 0.01; 0.12 | 0.126 |
| CALCA | 1.11 | 0; 2 | 2 | 1; 3 | 0.185 |
| TWIST1 | 0.08 | 0.00; 0.47 | 0.34 | 0.00; 3.55 | 0.210 |
| APC | 0.12 | 0.00; 0.26 | 0.14 | 0.05; 4.64 | 0.246 |
| CDKN1C | 0.00 | 0.00; 0.07 | 0.07 | 0.00; 0.14 | 0.274 |
| CYP1B1 | 0.00 | 0.00; 0.00 | 0.00 | 0.00; 0.00 | 0.274 |
| CDH1 | 0.01 | 0.00; 0.14 | 0.09 | 0.00; 0.33 | 0.310 |
| GDNF | 0.14 | 0.01; 1.18 | 0.35 | 0.09; 0.93 | 0.325 |
| SLC6A20 | 0.06 | 0.00; 0.11 | 0.15 | 0.00; 0.68 | 0.331 |
| MLH1 | 0.01 | 0.00; 0.51 | 0.00 | 0.00; 0.02 | 0.376 |
| GSTP1 | 0.00 | 0.00; 0.15 | 0.00 | 0.00; 16.21 | 0.377 |
| HSD17B4 | 0.08 | 0.01; 0.38 | 0.04 | 0.00; 0.31 | 0.400 |
| CARD15 | 66.3 | 56; 85 | 56 | 48; 82 | 0.412 |
| CXCR4 | 0.03 | 0.01; 0.05 | 0.04 | 0.02; 0.07 | 0.461 |
| TNFRSF25 | 115 | 59; 149 | 94 | 64; 140 | 0.461 |
| TFF1 | 43.8 | 29; 84 | 37 | 18; 64 | 0.477 |
| RARB | 0.06 | 0.04; 0.12 | 0.12 | 0.05; 0.14 | 0.481 |
| BCL2 | 0.00 | 0.00; 0.00 | 0.00 | 0.00; 0.10 | 0.496 |
| TACSTD1 | 0.04 | 0.03; 0.05 | 0.04 | 0.03; 0.07 | 0.512 |
| TYMS | 0.00 | 0.00; 0.00 | 0.00 | 0.00; 0.00 | 0.539 |
| PGR | 0.32 | 0.24; 0.89 | 0.69 | 0.26; 1.12 | 0.539 |
| SOCS1 | 0.00 | 0.00; 0.82 | 0.00 | 0.00; 0.27 | 0.583 |
| THRB | 0.09 | 0.00; 0.38 | 0.13 | 0.04; 0.42 | 0.744 |
| ESR2 | 0.00 | 0.00; 0.06 | 0.03 | 0.00; 0.05 | 0.775 |
| MGMT | 0.00 | 0.00; 0.01 | 0.00 | 0.00; 0.00 | 0.874 |
| ESR1 | 0.42 | 0; 18 | 1 | 0; 1 | 0.899 |
| TGFBR2 | 0.00 | 0.00; 0.00 | 0.00 | 0.00; 0.00 | 0.967 |
| FOXO1A | 0.00 | 0.00; 0.00 | 0.00 | 0.00; 0.00 | 1.000 |
| HRAS | 202 | 137; 240 | 199 | 84; 307 | 1.000 |
| NR3C1 | 0.00 | 0.00; 0.00 | 0.00 | 0.00; 0.00 | 1.000 |
| SMAD3 | 0.00 | 0.00; 0.00 | 0.00 | 0.00; 0.00 | 1.000 |
| TGFB3 | 0.00 | 0.00; 0.00 | 0.00 | 0.00; 0.00 | 1.000 |
| THBS1 | 0.00 | 0.00; 0.00 | 0.00 | 0.00; 0.00 | 1.000 |
| CDKN2C | 0.00 | 0.00; 0.00 | 0.00 | 0.00; 0.00 | 1.000 |

Data have been shown in Ref. 3.
[a]Mann-Whitney U Test

TABLE 13

MethyLight Reaction Details (taken from Supplementary Table 1, Weisenberger et al., Nature Genetics 38 787-793, 2006, which is incorporated herein by reference in its entirety).

| HUGO Gene Name (If Available) | Reaction ID | Reaction Design Code | Aliases | Cancer Specific? (Y/N) | end 5 Toyota Markers? (Y/N) |
|---|---|---|---|---|---|
| ABCB1 | ABCB1-M1B | HB-051 | MDR1; PGY1/ATP-binding cassette, sub-family B (WOR/TAP), member 1 | Y | N |
| ALU[b] | ALU-M8B | HB-086 | ALU repeat within Single-strand selective monofunctional uracil DNA glycoslase (SMUG1) focus | N | N |
| APC | APC-M1B | HB-153 | Adenomatous polypoeis coli | Y | N |
| APEX1 | APEX1-M1B | HB-090 | APEX nuclease (multifunctional DNA repair enzyme 1) | Y | N |
| APP | APP-M1B | HB-266 | Amyloid beta (A4) precursor protein (protease nexin-IL, Alzheimer disease) | N | N |
| ARF/CDKN2A | ARF-M1B | HB-196 | p14 ARF; alternate reading frame of CDKN2A | Y | N |
| ARPC1B | ARPC1B-M1B | HB-186 | Actin related protein 2/3 complex, subunit 1B, 41 kDa; ARC41 | N | N |
| ATM | ATM-M1B | HB-178 | Ataxia telenoiestasis mutated (includes complemantation groups A, C and D) | N | N |
| ATR | ATR-M1B | HB-180 | Ataxia telenoiestasis and Red3 related: FRP1; SCKL; SCKL1 | N | Y |
| AXIN1 | AXIN1-M1B | HB-227 | Axin 1 | N | N |
| BCL2 | BCL2-M1B | HB-140 | Bcl-2; B-ce-1I CLUlvrnchome 2 | Y | N |
| BDNF | BDNF-M2B | HB-258 | Brain derived neurotrophic factor | N | Y |
| BRCA1 | BRCA1-M1B | HB-045 | Breast cancer 1, early onset RNF53; BRCC1 | Y | N |
| BRCA2 | BRCA2-M1B | HB-126 | breast cancer 2, early onset | N | N |
| CACNA1G | CACNA1G-M1B | HB-158 | Caldum channel, voltage-dependent, alpha 1G subunit | Y | Y |
| CALCA | CALCA-M1B | HB-166 | Caldtonin/calcxornin-related polypeptide, alpha: CALC1 | Y | Y |
| CCND1 | CCND1-M1B | HB-146 | Cydin D1 (PRAD1: parethvoid adonontosis 1); BCL 1: D11S287E | N | N |
| CCND2 | CCND2-M1B | HB-040 | Cydin D2 | Y | N |
| CDH1 | CDH1-M1B | HB-050 | E-cadherin(epithellel)/Cadheprin 1, type 1 | Y | N |
| CDH13 | CDH13-M1B | HB-075 | H-Cadherin/Cadherin 13, H-cadherin (heart)/T-cadherin; CDHH | Y | Y |
| CDK2AP1 | CDK2AP1-M1B | HB-228 | CDK2-associated protein 1; DOC-1 (Deleted in oral cancer); DORC1; ST18 | N | N |
| CDKN1A | CDKN1A-M1B | HB-230 | Cyclin-dependent kinase inhibitor 1A:p21; C1p1p21; C1p1; SOI1; WAF1; CAP20; CDKN1 | N | N |
| CDKN1C | CDKN1C-M2B | HB-329 | Cyclin-dependent kinase inhibitor 1C 9p57, Kp12VBWS; WBS; BWCR; KIP2 | Y | N |
| CDKN2A | CDKN2A-M2B | HB-081 | p18/Cyclin-dependent kinase inhibitor 2A; CDKN2; CDK4I; p18; INK4e; MTS1: CMM2 | Y | N |
| CDKN2B | CDKN2B-M1B | HB-173 | p16/Cyclin-dependent kinase inhibitor 2B; P15; MT52; INK4B | N | N |
| CDX1 | CDX1-M1B | HB-196 | Caudal type homeo box transcription factor 1 | Y | N |
| CGA | CGA-M1B | HB-237 | Glycoprotein hormones, a;pha polypeptides; GPHa; GPHA1 | Y | N |
| CHFR | CHFR-M1B | HB-190 | Checkpoint with forkhead and ring finger domains; FLJ10798 | N | N |
| CLDN1 | CLDN1-M1B | HB-059 | Claudin-1 | N | N |
| CLIC4 | CLIC4-M1B | HB-062 | Chloride intracellular channel 4 | N | N |
| COL1A2 | COL1A2-M1B | HB-193 | Collagen, type I, alpha 2; C14 | Y | N |
| CRABP1 | CRABP1-M1B | HB-197 | Cellular retinoic acid binding protein 1; RBP5; CRABP; CRABP1; CRABP-1 | Y | Y |
| CTNNB1 | CTNNB1-M1B | HB-170 | Caterin (cadherin-associated protein), beat 1, 88 kDa; CTNNB | N | N |
| CTSD | CTSD-M1B | HB-147 | Cathepain D (lysosomal ascentyl protease); CPSD | N | N |
| CXADR | CXADR-M1B | HB-054 | Coxsackie virus and adenovirus receptor; CAR | N | N |
| CYP1B1 | CYP1B1-M1B | HB-078 | Cytochrome P450, family 1, subfamily B, polypeptide 1; GLC3A; CP1B | Y | N |
| CYP27B1 | CYP27B1-M1B | HB-223 | Cytochrome P450, family 27, subfamily B, polypeptide 1; CYP1; VDD1; PDDR | Y | N |
| DAPK1 | DAPK1-M1B | HB-046 | Death-associated protein kinase 1 | Y | Y |
| DCC | DCC-M1B | HB-178 | Deleted in colorectal carcinomas | Y | N |
| DCLRE1C | DCLRE1C-M1B | HB-133 | ARTEMIS/hypothetical protein RLJ11260; PSO2 horndoa, S. cerevisae; SNM1C; A-SCID | N | N |
| DOB1 | DOB1-M1B | HB-118 | Damage-specific DNA binding protein 1, 1271dDa | Y | N |
| DIRAS3 | DIRAS3-M1B | HB-043 | Ras homolog gene family, member VNOEY2; DIRAS family, GTP-binding RAS-line 3; ARHI | Y | N |
| DLC1 | DLC1-M1B | HB-218 | Deleted in liver cancer 1; HP; ARHGAP7; STARD12; FLJ21120; DLC-1; pf22-RhoGAP | Y | N |

TABLE 13-continued

MethyLight Reaction Details (taken from Supplementary Table 1, Weisenberger et al., Nature Genetics 38 787-793, 2006, which is incorporated herein by reference in its entirety).

| | | | | | |
|---|---|---|---|---|---|
| DLEC1 | DLEC1-M1B | HB-225 | Deleted in lung and esophageal cancer 1 | | Y |
| DNAJC15 | DNAJC15-M1B | HB-048 | DnaJ (Hap40) homolog, subfamily C, member 15; DNAJD1; MCJ | Y | N |
| DPH2L1 | DPH2L1-M1B | HB-049 | Diphamide Bicevnthesis Protein 2; OVCA2; DHP21.1; DPH2I. | N | N |
| DRD1 | DRD1-M1B | HB-252 | Dopamine receptor D1 | Y | N |
| DRD2 | DRD2-M1B | HB-253 | Dopamine receptor D2 | Y | N |
| EBF3 | EBF3-M1B | HB-229 | COE3; Early B-cell factoe 3; DKFZc867B0210 | Y | N |
| EPM2AIP1 | EPM2AIP1-M1B | HB-152 | EPM2A (leforin) interacting protein 1; KIAA0766; FLJ11207 | Y | N |
| ERBB2 | ERBB2-M2B | HB-233 | Epidermal growth factor receptor; y-arb-b crcogene homolog, avain); NGL; HER-2; NEU | Y | N |
| ERCC1 | ERCC1-M1B | HB-110 | ERCC complemeantation group 1 (includes overlapping and sense sequences) | Y | N |
| ERCC2 | ERCC2-M1B | HB-105 | ERCC complementation group 2 (xeroderma plamantoqum D; XPD) | Y | N |
| ERCC4 | ERCC4-M1B | HB-111 | Excision repair cross-complementing rodent repair deficiency, complementation group 4; RAD1; XPF | N | N |
| ERCC5 | ERCC5-M1B | HB-109 | ERCC complementation group 5; XP complementstion group G (Cockeyne syndeomel) ERCM2; | N | N |
| ERCC6 | ERCC6-M1B | HB-114 | ERCC complementation group 6 (PG8D3); CKN2; CSB; RAD28 | N | N |
| ERCC8 | ERCC8-M1B | HB-113 | ERCC complementation group 8 (ERCC8); Cocksyne syndrome 1 (classical), CKN1; CSA | N | N |
| ESR1 | ESR1-M1B | HB-164 | Estrogen Receptor Alpha; NR3A1; Era | Y | N |
| ERR2 | ERR2-M1B | HB-185 | Estrogen receptor 2 (ER beta); NR3A2; Erb | Y | N |
| FAF1 | FAF1-M1B | HB-304 | Fas (TNFRSF6) associated factor 1; CGI-03; hFAF1 | Y | Y |
| FBXW7 | FBXW7-M1B | HB-151 | F-box and WD-40 domain protein 7:AGO; FLJ11071; SEL-10; SEL10; FBW7; CDC4; FBXW6 | Y | N |
| FHIT | FHIT-M2B | HB-041 | Fragile Histidine Triad; FRA3B; AP3Asse | Y | N |
| GABRA2 | GABRA2-M1B | HB-254 | Gamma-aminobutyric acid A receptor, alpha 2 | Y | N |
| GAD1 | GAD1-M2B | HB-256 | Glutamine decarboxylase 1 (87 kda) | Y | N |
| GATA3 | GATA3-M1B | HB-327 | GATA binding protein 3/HDR; MGC5445 | Y | N |
| GATA4 | GATA4-M1B | HB-323 | GATA binding protein 4 | Y | N |
| GATA5 | GATA5-M1B | HB-328 | GATA binding protein 5; hB379Q24.1 | Y | N |
| GDNF | GDNF-M1B | HB-221 | Glial cell derived neurotrophic factor | Y | N |
| GRIN2B | GRIN2B-M1B | HB-250 | Glutamate receptor, Ionotrophic, N-methyl-D-aspartate 28 (NR3); NMDAR2B | Y | Y |
| GSTP1 | GSTP1-M1B | HB-172 | Glutathione-S transferase d1; FAEES; GST3 | Y | N |
| HIC1 | HIC1-M1B | HB-188 | Hypermethylated in cancer 1; ZBTB29 | Y | N |
| HLA-G | HLA-G-M1B | HB-215 | HLA-G histoconpentibility antigen, class I, G | Y | N |
| HOXA1 | HOXA1-M2B | HB-268 | Homeo box A1; HOX1F | N | N |
| HOXA10 | HOXA10-M1B | HB-270 | Homeo box A10; HOX1H | Y | Y |
| HOXA11 | HOXA11-M1B | HB-272 | Homeo box A11; HOX1I | Y | N |
| HRAS | HRAS-M1B | HB-144 | V-Hs-ras Harvey rat sarcoma viral onconene homolog HRAS1 | Y | N |
| HSO17B4 | HSO17B4-M1B | HB-066 | 17beta-hydroxysteroid dehydroganese IV | Y | N |
| ICAM1 | ICAM1-M1B | HB-076 | Intercellular adhesion molecule 1 (CD54L human rhinovirus recepter; BB2; CD54 | Y | N |
| IFNG | IFNG-M1B | HB-311 | Interferon Gamma | Y | N |
| IGF2 | IGF2-M2B | HB-319 | IGF2; Insulin-like growth factor 2 (somatomedin A) | Y | N |
| IGSF4 | IGSF4-M1B | HB-069 | Immunoclobulin superfamily, member 4; TSLC1; NECL2; ST17; BL2; SYNCAM; IGSF4A | Y | Y |
| ITGA4 | ITGA4-M1B | HB-321 | Integrin, alpha 4 (antigen CD49D, alpha 4 subunit of VLA-4 receptor)1 CD49D | Y | N |
| JUP | JUP-M1B | HB-203 | Junction Piskoglobin; CTNNG; PDGB; PKGB; DP1II | Y | N |
| KL | KL-M1B | HB-175 | human Kictho gene | Y | Y |
| LDUR | LDUR-M1B | HB-219 | Low density locoprotein receptor (familisi hypercholesterolemia) | N | N |
| LIG3 | LIG3-M1B | HB-091 | Ilasse I11, DNA, ATP-dependent | Y | N |
| LPHN2 | LPHN2-M1B | HB-202 | Latrophillin 2; LEC1; LPHH1; Kiaa0786 | Y | N |
| LZTS1 | LZTS1-M1B | HB-200 | Lauche zipper, putative tumor suppressor 1 F37; FEZ1 | Y | N |
| MBD2 | MBD2-M1B | HB-142 | Methyl-CpG binding domain protein 2 | Y | Y |
| MBD4 | MBD4-M1B | HB-083 | Methyl-CpG binding domain protein 4 | Y | N |
| MGMT | MGMT-M2B | HB-160 | 0-8-methylqueninue-DNA methyltransferase | Y | Y |
| MINT1 | MINT1-M1B | HB-161 | Colon cancer differentially methylated CpG Island genomic | Y | Y |

TABLE 13-continued

MethyLight Reaction Details (taken from Supplementary Table 1, Weisenberger et al., Nature Genetics 38 787-793, 2006, which is incorporated herein by reference in its entirety).

| | | | | | |
|---|---|---|---|---|---|
| MINT2[f] | MINT2-M1B | HB-187 | sequence; PROTEIN 2C (SV2C) in rats | | Y |
| MINT31[f] | MINT31-M1B | HB-162 | Colon cancer differentially methylated CpG Island genomic sequence | Y | Y |
| MLH1 | MLH1-M2B | HB-150 | Colon cancer differentially methylated CpG Island genomic sequence | Y | Y |
| MLH3 | MLH3-M1B | HB-099 | Mut L Homolog 1 (E. coli)(colon cancer, nonpolypoels type 2); COCA2 | Y | Y |
| MMS19L | MMS19L-M1B | HB-117 | MutL (E. coli) homolog 3 | N | N |
| MSH2 | MSH2-M1B | HB-096 | MMS19 (MET18 S. cerevisiae)-like MET-18, hMMS19 | N | N |
| MSH4 | MSH4-M1B | HB-096 | MutS (E. coli) homolog 2 (colon cancer, nonpolyposis type 1); COCA1 | N | N |
| MSH6 | MSH6-M1B | HB-097 | MutS (E. coli) homolog 4 | N | N |
| MSH8 | MSH8-M1B | HB-084 | MutS (E. coli) homolog 5 | N | N |
| MT1A | MT1A-M1B | HB-206 | MutS (E. coli) homolog 6; GTBP | N | Y |
| MT1G | MT1G-M1B | HB-204 | Metallothionein 1A; MT1S; K01383 | N | Y |
| MT2A | MT2A-M1B | HB-208 | Metallothionein 1G | N | Y |
| MT3 | MT3-M1B | HB-207 | Metallothionein 2A; Metallothionein-II; MT2 | N | Y |
| MTHFR | MTHFR-M1B | HB-058 | Metallothionein 3 (growth inhibitory factor (neurotrophic)) | N | N |
| MUTYH | MUTYH-M1B | HB-088 | 5,10-methylenetetrahydrofolate reductase (NADPH) | N | N |
| MYOD1 | MYOD1-M1B | HB-154 | MutY (E. coli) homolog MYH | Y | Y |
| NCL | NCL-M1B | HB-077 | Myogenic determining factor 3; MYF3 | Y | Y |
| NEUROD1 | NEUROD1-M1B | HB-259 | Nude olin | N | N |
| NEUROD2 | NEUROD2-M1B | HB-260 | Neurogenic differentiation 1; NeuroD; BETA2, BHF-1 | N | Y |
| NEUROG1 | NEUROG1-M1B | HB-261 | Neurogenic differentiation 2; NDRF | N | Y |
| NR3C1 | NR3C1-M1B | HB-067 | Neurogenic 1; NEUROD3; AKA | N | Y |
| NTF3 | NTF3-M1B | HB-251 | Glucocorticoid Receptor Nuclear receptor subfamily 2, group C, member 1; GRL; GR | N | N |
| NTHL1 | NTHL1-M1B | HB-089 | Neurotrophin 3 | N | Y |
| OGG1 | OGG1-M1B | HB-087 | Nth (E. coli endonuclease III)-line 1; NTH1; OCTS3 | N | Y |
| ONECUT2 | ONECUT2-M1B | HB-242 | 8-oxoccoumine DNA glycosylase | N | Y |
| OPCML[c] | OPCML-M1B | HB-209 | One out domain, family member 2, OC-2 | N | N |
| PARP1[d] | PARP1-M1B | HB-093 | Opioid binding protein/cell adhesion molecule-line; OPCM, OBCAM | N | Y |
| PARP2 | PARP2-M1B | HB-094 | Poly (ADP-ribose) polymerase family, member 1; PPOL; ADPRT; PARP | N | Y |
| PAX8 | PAX8-M2B | HB-211 | Poly (ADP-ribose) polymerase) family, member 2; ADPRTL2 | N | Y |
| PENK | PENK-M1B | HB-163 | Paired Box Gene B; Paired Domaon Gene 5 | N | N |
| PGR | PGR-M1B | HB-140 | ppENK/Proenkephelin precursor | N | Y |
| PITX2 | PITX2-M2B | HB-235 | Progesterone Receptor A; PR; NR3C3 | N | N |
| PLAGL1 | PLAGL1-M1B | HB-199 | Paired-like homoeodomain transcription factor 2; IRID2; IHG2; RIEG; RG8; IGD8 | N | N |
| PMS2 | PMS2-M1B | HB-098 | Pieiomorphic adename gene-like 1; LOT1 | N | N |
| POLD1 | POLD1-M1B | HB-139 | Postmeiotic segregation increased 2 (S. cerevisiae); PMSL2 | N | Y |
| PPARG | PPARG-M1B | HB-060 | Polymerase (DNA directed), delta 1, catalytic subunit (125 kD); POLD | N | N |
| PRKAR1A | PRKAR1A-M1B | HB-214 | Peroxlsome proliferative activated receptor, gamma isoform 1: PPARG1, PPARG2; NR1C3 | N | N |
| | | | protein kinase. cAMP-dependent, regulatory, type I, alpha (tissue specific extinquisher 1); TSE | | |
| PSAT1 | PSAT1-M1B | HB-231 | Phosphoserine aminotransferase 1 | N | N |
| PSEN1 | PSEN1-M1B | HB-262 | Presenlin 1 (Alzheimer disease 3); AD3 | N | N |
| PSEN2 | PSEN2-M1B | HB-264 | Presenlin 2 (Alzheimer disease 4); AD4 | N | N |
| PTEN | PTEN-M1B | HB-157 | Phosphatase and tensin homolog (mutated in multiple advanced cancers 1); MMAC1; BZS; MHAM | N | N |
| PTGS2 | PTGS2-M1B | HB-065 | protaglandin-endocerodide synthase 2 (protagandin G/H synthase and cyclooxygenase); COX2 | N | Y |
| PTTG1 | PTTG1-M1B | HB-052 | Pituitary tumor-transforming 1; TUTR1; SECURIN; PTTG; HPTTG | N | Y |
| PYCARD | PYCARD-M1B | HB-228 | PYD and CARF domain containing; ASC; TMS1; CARD5; MGC10332 | N | Y |
| RAD23A | RAD23A-M1B | HB-101 | RAD23 (S. cerevisiae) homolog A; HHR23A | N | N |
| RARB | RARB-M1B | HB-176 | retinoic acid receptor, beta; Hap; RRB2; NR1B2 | N | N |
| RARRES1 | RARRES1-M1B | HB-322 | Retinoic acid receptor responder (tazarotene induced) 1; TIG1 | N | Y |
| RASSF1 | RASSF1A-M1B | HB-044 | Res association (REIGDS/AF-6) domain family 1; NORE2A; REH3P21; RDA32 | N | Y |

TABLE 13-continued

MethyLight Reaction Details (taken from Supplementary Table 1, Weisenberger et al., Nature Genetics 38 787-793, 2006, which is incorporated herein by reference in its entirety).

| | | | | | |
|---|---|---|---|---|---|
| RB1 | RB1-M1B | HB-245 | Retinoblastoma 1 (including osteosarcoma); OSRC | N | N |
| RBP1 | RBP1-M1B | HB-186 | Retinol binding protein 1, cellular | N | Y |
| RNR1 | RNR1-M1B | HB-071 | Ribosomal RNA | N | N |
| RPA2 | RPA2-M1B | HB-103 | Replication protein A2 (32 kD) | N | N |
| RPA3 | RPA3-M1B | HB-104 | Replication protein A3 (14 kD) | N | Y |
| RUNX3 | RUNX3-M1B | HB-181 | Runt-related transcription factor 1 (acute myeloid leukemia 1; aml1 oncogene); CBFA3; AML2 | Y | Y |
| S100A2 | S100A2-M1B | HB-061 | S100 calcium binding protein A2; S100L; CAN19 | N | N |
| SASH1 | H-SASH1-M1B | HB-220 | SAM and SH3 domain containing; KIAA0790 | N | Y |
| SCAM-1 | SCAM-1-M1B | HB-064 | Vinexin beta (SH3-containing adaptor molecule-1 | N | Y |
| SCGB3A1 | SCGB3A1-M1B | HB-194 | Secretoglobin, family 3A, member 1; HIN-1; HIN1; LU105; UGRP2 | N | Y |
| SERPINB6 | SERPINB6-M1B | HB-206 | Serine (or cystine) proteinase inhibitor, clade B (ovalbumin), member 5; PI5; MASPIN | N | Y |
| SEZ6L | SEZ6L-M1B | HB-184 | Seizure related 6 homolog (mouse)-like; KIAA0927 | N | Y |
| SFN | SFN-M1B | HB-174 | Stratifin; 14-3-3 stoma | N | Y |
| SFRP1 | SFRP1-M1B | HB-201 | Secreted frizzled-related protein 1; FRP-1; SARP2 | N | Y |
| SFRP2 | SFRP2-M2B | HB-280 | Secreted frizzled-related protein 2; FRP-2; SARP1; SDF-5 | Y | Y |
| SFRP4 | SFRP4-M1B | HB-281 | Secreted frizzled-related protein 4; FRP-4 | N | N |
| SFRP5 | SFRP5-M1B | HB-282 | Secreted frizzled-related protein 5; SARP3 | N | Y |
| SLC8A20 | SLC8A20-M1B | HB-079 | solute carrier family 6 (proline IMINO transporter), member 20; XT3 | N | Y |
| SMAD2 | SMAD2-M1B | HB-275 | SMAD, mothers against DPP homolog 2 (Drosophila); MACH2 | N | N |
| SMAD3 | SMAD3-M1B | HB-053 | SMAD, mothers against DPP homolog 3 (Drosophila); MACH3 | N | N |
| SMAD4 | SMAD4-M1B | HB-277 | SMAD, mothers against DPP homolog 4 (Drosophila); MACH4; DPC4 | N | N |
| SMAD6 | SMAD6-M1B | HB-278 | SMAD, mothers against DPP homolog 6 (Drosophila); MACH6; Hs17432 | N | Y |
| SMAD9 | SMAD9-M1B | HB-315 | SMAD, mothers against DPP homolog 9 (Drosophila); MACH9 | N | N |
| SOCS1 | SOCS1-M1B | HB-042 | Suppressor of cytokine signal nc 1; SOCS-1; SSI-1; JAB; TIP3; Cish1 | Y | Y |
| STAT1 | STAT1-M1B | HB-063 | Signal transducer and activator of transcription 1, 91 kDa; STAT91 | N | N |
| STK11 | STK11-M2B | HB-183 | Serine/phsonine idnase 11 (Psutz-Jeghers syndrome); PJS; LKB1 | N | Y |
| SYK | SYK-M2B | HB-241 | Spleen tyrosine kinase | Y | Y |
| TERT | TERT-M1B | HB-074 | Telomerase reverse transcriptase; TRT; TP2; TCS1; EST2 | Y | Y |
| TFAP2A | TFAP2A-M1B | HB-314 | Transcription factor AP-2 alpha (actylin enhancer binding protein 2 alpha); AP-2; TFAP2; AP2TF | N | Y |
| TFF1 | TFF1-M1B | HB-146 | Trefoil factor 1 (breast cancer, estrogen-induced sequence expresses in); BCE-1; D21S21 | N | N |
| TGFBR1 | TGFBR1-M1B | HB-192 | Transforming growth factor, beta receptor I (actylin A receptor type II-like idnase. 53 kDa); ALK-5 | N | N |
| TGFBR2 | TGFBR2-M1B | HB-246 | Transforming growth factor, beta receptor II (70/80 kDa); MFS2 | N | N |
| THBS1 | THBS1-M1B | HB-247 | Thrombospondin 1; TsP1 | N | Y |
| THRB | THRB-M1B | HB-216 | Thyroid hormone receptor, beta; ERBA2; THRB1; THRB2; NR1A2 | Y | Y |
| TIMP3 | TIMP3-M1B | HB-167 | TIMP metallopeptidase Inhibitor 3 (Scrsby fundus dystrophy, pseudoinflammatory); SFD | Y | Y |
| TITF1 | TITF1-M1B | HB-213 | Thyroid transcription factor 1; NKX2A; BCH; TTF-1 | N | Y |
| TMEFF2 | TMEFF2-M1B | HB-274 | Transmembrane protein with EGF-like and two follistatin-like domains 2; TENB2 | N | Y |
| TNFRSF 10A | TNFRSF 10A- | HB-306 | Tumor necrosis factor receptor superfamily, member 10a; DR4; Apo2; TRAILR-1; CD261 | N | N |
| TNFRSF 10B | TNFRSF 10B- | HB-307 | Tumor necrosis factor receptor superfamily, member 10bc; DR5; KILLER; TRICK2A; TRAIL-R2 | N | Y |
| TNFRSF 10C | TNFRSF 10C- | HB-308 | Tumor necrosis factor receptor superfamily, member 10c; DcR1; TRAILR3; LIT; TRID; CD263 | N | Y |
| TNFRSF 10D | TNFRSF 10D- | HB-309 | Tumor necrosis factor receptor superfamily, member 10d; DcR2; TRUNOD; TRAILR4; CD264 | N | Y |
| TNFRSF 25 | TNFRSF 25-M1B | HB-080 | TNF receptor superfamily, member 25; TNFRSF12; DR3; APO-3 | N | N |
| TP63 | TP63-M1B | HB-217 | Tumor protein p53 | N | Y |
| TP73 | TP73-M1B | HB-177 | Tumor protein p73 | N | Y |
| TSHR | TSHR-M1B | HB-141 | Thyroid stimulating hormone receptor; LGR3 | N | Y |
| TWIST1 | TWIST1-M1B | HB-047 | Twist homolog (agrocachalosyndactyly 3; Seethre-Chotzen syndrome) (Drosophilia) | N | N |
| TYMS | TYMS-M1B | HB-248 | Thymidylate Synthese | N | N |
| UNG | UNG-M1B | HB-082 | Uracil-DNA glycosylase; DGU; UDG; ING1 | N | N |

TABLE 13-continued

MethyLight Reaction Details (taken from Supplementary Table 1, Weisenberger et al., Nature Genetics 38 787-793, 2006, which is incorporated herein by reference in its entirety).

| | | | |
|---|---|---|---|
| UQCRH | UQCRH-M1B | Ubiquiltinol cyctochrome c reductase hinge protein | N |
| VDR | VDR-M1B | Vitamin D (1.25- dihydroxy vitamin D3) receptoR; NR1I1 | N |
| VHL | VHL-M1B | Von Hippel-Linday syndrome tumor suppressor; VHL1 | N |
| XAB2 | XAB2-M1B | XPA binding protein 2; HCNP | N |
| XPA | XPA-M1B | Xeroderma pigmentosum, complementation group A; XPAC; XP1 | N |
| XPC | XPC-M1B | Xeroderma pigmentosum, complementation group C; XPCC | N |
| XRCC1 | XRCC1-M1B | X-ray repair complementing defective repair in Chinese hamster cells; RCC | N |
| COL2A1 | COL2A1-C1B | Collagen, type II, alpha 1 (primary osteoarthyritis, spondylpepiphysed dysplasia, congenital) | N/A |
| ALU | ALU-C4M | Interspersed A. U repeat sequence | N/A |

| HUGO Gene Name (If Available) | Chromosomal Location | Forward Primer Sequence | Reverse Primer Sequence |
|---|---|---|---|
| ABCB1 | 7q21.1 | TCGGGTCGGAGTAGTTATTTG | CGACTATACTCAACCCACGCC |
| ALU[b] | 12q13.11-q13.3 | GGATTATAGGCGCGGGTTATT | TCACACCCGTAATCCGAACA |
| APC | 5q21-q22 | GAACCAAAACGCTCCCCAT | TTATATGTCGGTTACGTGCGTTTATAT |
| APEX1 | 14q11.2-q12 | CGTATTTGTATCGGTTCGATGGTA | GCGCATTCTTCGACCACG |
| APP | 21q21.2 | AACGAAATGCGGATAAAAACGTAT | TCGTCCCGTAAACTTAAAATCATC |
| ARF/CDKN2A | 9p21 | ACGGGCGTTTTCGGTAGTT | CCGAACCTCCAAAATCGA |
| ARPC1B | 7q22.1 | TGCCGGGTATCGGTAGTAT | ACCTAAAACAACGATCGCGAAAT |
| ATM | 11q22-q23 | ACGGAGAAAAGAAGTCGTGGTC | GCGACGATAACTACAACGCAAAT |
| ATR | 3q22-q24 | AGCGGTTTTCGGGAGGAGT | GAATTCCGACGCTCTCCAAA |
| AXIN1 | 16p13.3 | CGGTTTTTGTAGTTGTTTCGTGTT | CGACGCGATAACCGCTTAAA |
| BCL2 | 18q21.3 | TCGTATTTCGGATTCGGTC | AACTAAACGCAAACCCCGC |
| BDNF | 11p13 | CGTATCGGGTTGTTGTTTTTGTT | CGCCCGTCGCTATCC |
| BRCA1 | 17q21 | GAGAGGTTGTTGTTTAGCGGTAGTT | CGGCAATCGCAATTTTAAT |
| BRCA2 | 13q12.3 | CGTTACGGCGTTACGTGGT | CCGCCCTTACCGCCTAATTT |
| CACHA1G | 17q22 | TTTTTCGTTCGCCGTTTAAGGT | CTCGAAACGACTTCGCCG |
| CALCA | 11p15.2-p16.1 | GTTTTGGAAGTATGAGGGTGACG | TTCCGCCGTATAAATCG |
| CCND1 | 11q13 | GGTAATTTCGTCGTAGGGTAGGC | GAACGCCAAACGCCGA |
| CCND2 | 12p13 | GGAGGGTCGGCGAGGAT | TCCTTTCCCCAAAACATAAAA |
| CDH1 | 16q22.1 | AGGGTTATCGCGTTTATCGG | TTCACCTACCGACCAACCA |
| CDH13 | 16q24.2-q24.3 | AATTTCGTTCGTTTTGTGCGT | CTACCGTACCGAACGATCC |
| CDK2AP1 | 12p14.1 | CGCGGAAAGTTTCGGT | CGCACTTTTTATTATCGACGACTC |
| CDKN1A | 8p21.2 | CGCGTTCGGTTTCGCGTAT | TTATATCGCGTCTTCCGCC |
| CDKN1C | 11p15.5 | TCGAGTAGGGCGCGAATTAG | GTCCCGAAATCCCGAAT |
| CDKN2A | 9p21 | TGGAGTTTTCGGTTGATTGGTT | AACAACGCCCGCCACTCCT |
| CDKN2B | 9p21 | AGGAAGGAGAGAGTCGTCG | CGAATAATCCACCGTTAACCG |
| CDX1 | 5q31-q33 | TGAGCGGTTGTTCGTCGTC | AAATCCCCGCGCATACTA |
| CGA | 6q12-q21 | GGGTTTTTTGTAGGATGTGTTTAGG | AACTACAATTACTAAAAACTCATAAAACGA |
| CHFR | 12q24.33 | CGGGAGTTTTTATGGGCGT | AACCGTCCCCAAAACTACGAC |
| CLDN1 | eq28-q29 | CGGTGAGTCGTTTTGAAATCG | ACGCAAAACCGCTAAACGC |
| CLIC4 | 1p36.11 | GGCGGTGTTGAGGAGTTGA | CCGATTCCCGCCGTACTAC |
| COL1A2 | 7q22.1 | CGGTAGTAGGAGTTTCGGTTAAGT | CCTAAATCACCGACGAAAATATCA |
| CRABP1 | 15q24 | TCGAAATTTTCGTTCGTTGCGT | TATCCGTACCTACCGCCGC |
| CTNNB1 | 3p22-21.3 | GGAAAGGCGCGTCGAGT | TCCCTATCCCAAACCCG |
| CTSD | 11p15.5 | TACGTTTCGCGTAGGTTTGGA | TCGTAAAACGACCCACCCTAA |
| CXADR | 21q11.2 | TACGCGGTTGGAGAAGTCG | ATAAACTCGCCTCACTTCCGA |

TABLE 13-continued

MethyLight Reaction Details (taken from Supplementary Table 1, Weisenberger et al., Nature Genetics 38 787-793, 2006, which is incorporated herein by reference in its entirety).

| Gene | Location | Sequence 1 | Sequence 2 |
|---|---|---|---|
| CYP1B1 | 2p21 | GTGCGTTTGGACGGAGTT | AACGCGACCTAACAAACGAA |
| CYP27B1 | 12q14.1 | GGATAGTTAGGAGGAACGGATGTTT | CCGAATATAACCACCACCGCC |
| DAPK1 | 9q34.1 | TCGTCGTCGTTTCGGTTAGTT | TCCCTCCGAAACGCTATCG |
| DCC | 18q21.3 | GGGTTCGGCGCGTGT | CGAAAATACAAAAACCAACTTAAATACC |
| DCLRE1C | 10p13 | CGAAGCGCGGGTGATTTA | AAAATCCGAAAACCGAAAACAA |
| DOB1 | 11q12-q13 | GGGCGGAGGTAGCGGT | CCCGTCGAAACTCGAACG |
| DIRAS3 | 1p31 | GCGTAAGCGGAATTTATGTTGT | CCGGTCGATTTTATATTCCGACTT |
| DLC1 | 8p22-p21.3 | AGTAAGCGGATGCGTTGAGGATCG | ACGACTCGACTTCCGGTC |
| DLEC1 | 3p22-p21.3 | TCGTTGCGTATTTAAGATATATTCGTATT | CGTAACGCTCATTCTCGCTACC |
| DNAJC15 | 13q13 | TTTCGGGTCGTTTTGTTATGG | ACTACAAATACTCACGTAACGCAAACT |
| DPH2L1 | 17p13.3 | ACCGGAGACGGTAGATATTG | CCGCCAACGAATATCC |
| DRD1 | 5q35.1 | GGCGCGCTTGGTTC | TACCCGTAAACGCCTATACTTCACC |
| DRD2 | 11q23 | GAAGTCGGAAATTTTGGTCGC | ATCTCGAAAAAACACTTCCCCC |
| EBF3 | 10q26 | GTAGGATATTGCGGGATCGTTC | GCAACACTCACTACCCCGTTTAT |
| EPM2AIP1 | 3p21.3 | CGTTATATATCGTTCGTAGTATTCGTGTTT | CTATCGCCGCCTCATCGT |
| ERBB2 | 17q21.1 | AGTGTGAGAACGTGTTGTAGGTAATTTAG | CCCTCCTTCGCGCAAAC |
| ERCC1 | 19q13.2-q13.3 | GGGCGAGTCGAAGGTGG | CTCCGAAACTCCATAACGTCAA |
| ERCC2 | 19qq13.3 | CGAGTTTTCGAGGATGTTTACGA | CCGACCGAACTATACAACGAAAT |
| ERCC4 | 16p13.3-p13.11 | TCGACGGATTGTTATGCG | CGTCAATATCGAACAATTCCA |
| ERCC5 | 13q22 | TAAGCGTAGAAAATATACGTTATGTGCG | CCCGCTCGATTTCCGTCT |
| ERCC6 | 10q11 | ACGTAAGTAGAAAAGGCGTTGTTGAG | CGACTCCGACTTCTACTAATACGAAA |
| ERCC8 | 5q12.1 | GGTTAAGCGTTTAGAGTCGGG | TCATACGACACTTAAAATATCACCGAAA |
| ESR1 | 8q26.1 | GGCGTTCGTTTTGGGATTG | ACCCGTCGTTTGGAACTCTAA |
| ESR2 | 14q | TTTGAAATTTGTAGGGCGAAGAGTAG | ACCGACACGCGAACTCTAA |
| FAF1 | 1p33 | CGTTTTGCGTTTTACGTGA | CAACGCAAAATCCTAACGAA |
| FBXW7 | 4q31.23 | TGTCGTTGCGGTTGGAT | CGAAAATAAATAACTACTCCGCGATAA |
| FHIT | 3p14.2 | GGCGCGGTTTGGG | CGCCCGTAAACGACG |
| GABRA2 | 4p12 | TCGTCGAGGACGGA | AACCTTCGAAAACCCCAACA |
| GAD1 | 2q31 | CGATTGGTTCGGCGAGAAA | CCCTCCGATATACAAAACCC |
| GATA3 | 10p15 | TGTATCGGGACGGAATCGTT | ACGCGCGCTCTAACCTT |
| GATA4 | 8p23.1-8p22 | GATGGTGCTCGCGTGAAGTTA | TTCCCTCCATATACGAACTACCG |
| GATA5 | 20q13.33 | AGTTACGTGATTTTCGGTAGGTTTTGTT | TAATCCGAACTCCGGCTA |
| GDNF | 5p13.1-p12 | CGGTAGTTGTCGTTGAGTCGTTC | AACAACCGCCGCTACTTTAAATA |
| GRIN2A | 12p12 | GTCGGATTTTACGCGTCGAGT | CTACCGCCGCGCTAAAATAC |
| GSTP1 | 11q13 | GTCGGCGTCGTGATTTAGTATATG | AAACTACGACGAGAAACTCCAA |
| HIC1 | 17p13.3 | GTTAGGCCGGTTAGGGCGTC | CCGAACGCCTCCATCGTAT |
| HLA-G | 8p21.3 | CACCCCATATACGCCGTAA | GGTCGTTACGTTTCGGTAGTTTA |
| HOXA1 | 7p15 | TTGTTTATTAGGAAGCGGTCGTC | TCGAACCATAAAATTACAACTTTCCA |
| HOXA10 | 7p15-p14 | TATTGATGGGTTAGGAGACGTATT | CCCACCAACCACGTTAAAACA |
| HOXA11 | 7p15-p14 | TTTTGTTTTCGATTTTAGTCGGAAT | TAATCAAATCACCGTACAAATCGAAC |
| HRAS | 11p15.5 | GAGCGAGTACGGAATATAAGTTGG | CGTCCACAAAATAATTCTAAATCAACTAA |
| HSD17B4 | 5q21 | TATCGTTGAGGTTCGCACGG | TCCAACTTCGCATAGTACC |
| ICAM1 | 19p13.3-p13.2 | GGTTAGCGAGGAGGATGATT | TCCCTCCGAAACAAATACTACAA |
| IFNG | 12q14 | TGAAGAGTTAATATTTATTAGGGCGAA | TTCCTTTAACTCCTTAAATCCTTTAACG |
| IGF2 | 11p15.5 | GAGCGGTTTCGGTGTCGTTA | CCAACTCGATTTAAACCGACG |
| IGSF4 | 11q23.2 | GGGTTTCGGAGGTAGTTAACGTC | CACTAAATCCGCTCGACAACAC |
| ITGA4 | 2q31-q32 | TGCGGAGGCGTAGGGTC | CAACCGAAATTCCCCAACG |
| JUP | 17q21 | TATCGTTGAGGTTCGCACGG | CTCTTCGCCTTTATTCGATTACTAAAT |
| KL | 13q12 | AGTTTCGGTTTCCGTAGTATGTTC | CGCCGACTCCGAC |
| LDUR | 19p13.3 | GATATCGTTTTTAATTCGTGAAGTT | TTCACCGAAACCCAAATACAA |

TABLE 13-continued

MethyLight Reaction Details (taken from Supplementary Table 1, Weisenberger et al., Nature Genetics 38 787-793, 2006, which is incorporated herein by reference in its entirety).

| Gene | Location | Sequence 1 | Sequence 2 |
|---|---|---|---|
| LIG3 | 17q11.2-q12 | GTCGCGGTAGTTTACGACG | CGACTTAACTCTTACGCCTACG |
| LPHN2 | 1p31.1 | GAGGATTTAGCGCGTAGTGAGTG | AATCCCGAACTCTACCTCCA |
| LZTS1 | 8p22 | GCGCGTTGTAGGGACG | CGCGCCTAACTCTTCTACG |
| MBD2 | 18q21 | AGGCGGAGATAAGATGGTCGT | CCCTCCTACCGAAACGTAAC |
| MBD4 | 3q21-q22 | TCGTGTTTATCGAGTAGGGTTCG | TCGATTACAACCCGATACCGTAA |
| MGMT | 10q28 | GCGTTTCGACGTTCGTAGT | CACTCTTCCGAAAACGAAACG |
| MINT1[f] | 5q13-14 | GGGTTGAGGTTTTTTGTTAGCG | CCCCTCTAAACTTCACAACCTCG |
| MINT2[f] | 2p22-21 | TTGAGTGGCGCGTTTCGT | TCCCCGCCTAAACCACCC |
| MINT31[f] | 17q22 | GTCGTCGGCGTTATTTTAGAAAGTT | CACGACGCCCAACACA |
| MLH1 | 3p21.3 | AGGAAGAGCGGATAGCGATTT | TCTTCGTCCCTCCCTAAAACG |
| MLH3 | 14q24.3 | TGATGATGGTTGCGCGTAGT | CGACCCGCCAAACGC |
| MMS19L | 10q24-10q25 | TTAGGTAGAAGTCGGTAGTACGTGA | ATAACTGAAACGAACTCTCCGC |
| MSH2 | 2p22-p21 | TTTTAGTGCGGAGGTACGGG | AAACGATCTCCGAAACCAAA |
| MSH4 | 1p31 | CGGATTTTAGGAGATTTTATAGAGTCG | CCGATCGCCCGCAAC |
| MSH6 | 8p21.3 | TTCGTGGCGGTCGGTTA | CCGCCATCGCAACGTT |
| MSH8 | 2p16 | GGAGTGTTTCGGTTCGGTTAGT | CTACCGCGACGCCTAAA |
| MT1A | 16q13 | CGTGTTTTCGGTTTATTGTACG | CTCGCTATCGCCTTACCTATCC |
| MT1G | 16q13 | CGTTTAAGGGATTTTGTATTTGGTTTAT | CCGCTAAATCCGCACCG |
| MT2A | 16q13 | GCGTTTTCGTGTGTGTATAGTTT | TTCCCAAATCCCGCTTTCA |
| MT3 | 16q13 | GGTTTTAGGGTTTATGTCGAGGAAGA | CCGGCGCGTCCAATTACTTA |
| MTHFR | 1p36.3 | TGGTAGTGAGAGTTTAAAGATAGTTCGA | CGCCTCATCTTCTCCGA |
| MUTYH | 1p34.3-p32.1 | TCGGGTGGATTCGAGTTACG | AAAATTACCTCCCGCGAACTCTA |
| MYOD1 | 11p15.4 | GAGCGCGCGTAGTTAGCG | TCCGACACGCCCTTTCC |
| NCL | 2q12-qter | CGTGTCGTTTCCGTTCGTT | ACCAAAACTCGCGACCGTC |
| NEUROD1 | 2q32 | GTTTTTTTCGTGTGGGCGAAT | CCGGCGTTAACATCACTAACTAAA |
| NEUROD2 | 17q12 | GGTTTGGTATAGAGGTTGGTATTTCGT | ACGAACGCCGACGTCTTC |
| NEUROG1 | 5q23-q31 | CCTGTAGCGTTCGGGTATTTGTA | CGATAATTACGAACACACTCCGAAT |
| NR3C1 | 5q31 | GGGTGAAGGAGAGCGTCGTAG | CAACGTCTTACGAAATCACGAAC |
| NTF3 | 12p13 | TTTCGTTTTGTATTTTATGGAGGATT | AAACTTCCGAACGCGCG |
| NTHL1 | 16p13.3 | CGGGACGTCGTCGGAAG | CCGTTTCGCCGTAATATTC |
| OGG1 | 3p26.2 | TAGGGTGGGCGGGTCG | CCGACCTTTCCGCAAA |
| ONECUT2 | 18q21.1- | ACGGGCGTTAAGCGTAATTATTT | CCGGAAACGCCCAA |
| OPCML[c] | 11q25 | CGTTTCGAGGCGGTATCG | CCACACCACTAATAACTTCCCGTA |
| PARP1[d] | 1q41-q42 | CGGGTTTAGGGAGCGAGC | CGAACGCCGAAATTATCAT |
| PARP2 | 14q11.2-q12 | GGGCGAGAGGTTCGGAGT | AAACGACCGCGAACCATA |
| PAXB | 2q12 | GTTCGTAGTTTCGTCGAGGGTTC | TCGTTCCTTTCTAACTACCGC |
| PENK | 8q23-q24 | GGTTAATTATAAGTGGTTTTAGTAGTCGT | CGCATCTCATACCCTTCTCCTAAAT |
| PGR | 11q22-q23 | GGCCGGTGACGGTCGTATTC | CAACGTCTTACGAAATCACGAAC |
| PITX2 | 4q25-27 | AGTTCGGTTGCGCGGTT | ACAAACCGTCCCGGAA |
| PLAGL1 | 6q24-q25 | ATCGACGGGTTGAATGATAAATG | TACTTCCCTCCCTACCTCGTT |
| PMB2 | 7p22 | TCGTGGTTTGGCGTGGAT | CTCGACGCAACCATCCTCTT |
| POLD1 | 19q13.3 | GGGACGCCGAGGATGC | CCTAATACATCGAAATAACGCGTACC |
| PPARG | 3p25 | GCGTTTCCGTTCGTTTTC | GATCTAAAACGCCGGATTCTAT |
| PRKAR1A | 17q23 | CGGATTTGTAGTAGTTGCGTTGC | CGCCCAAACGACGAC |
| PSAT1 | 9q21 | TGGGTTTGGTTTCGTTAAGTTGT | ACGTACCCCGCCTAAACCTC |
| PSEN1 | 14q24.3 | GTCGGGTGGAGAGAGATTTCG | AACACCTACGCCCTAAAACGTC |
| PSEN2 | 1q31-q42 | GAGGCGTGTAGTAGGCGGG | CCGATACTAAAAACCGAATAAACTCG |
| PTEN | 10q23.3 | GTTTCGCGTTGTGTGAAAGTCG | CAATATAACTACCTAAAACTTACTCGAACC |
| PTGS2 | 1q25.2-q25.3 | CGGAAGCTTCGGGTAAAG | AATTCACCGCCCCAAAC |
| PTTG1 | 5q35.1 | GCGTTCGTTTATCGCGT | CCGGCGACCCTCCATT |

TABLE 13-continued

MethyLight Reaction Details (taken from Supplementary Table 1, Weisenberger et al., Nature Genetics 38 787-793, 2006, which is incorporated herein by reference in its entirety).

| | | | |
|---|---|---|---|
| PYCARD | 16p12-p11.2 | TTGGAGATTTACGGCGTCG | ACCCTAATACGTAACCGCTACAA |
| RAD23A | 19p13.2 | TATCGATAACGGGTATGCGTT | GCAAACTAAACTCCCGCGCTATAA |
| RARB | 3p24 | TTTATGCGAGTTGTTTGAGGATTG | CGAATCCTACCCCGACGATAC |
| RARRES1 | 3q25.31-3q26.1 | GGCGAGTCGGATCGAA | CGCAAACTCCTACAACAAGA |
| RASSF1 | 3p21.3 | ATTGAGTTGCGGAGTTGGT | ACACGCTCCAACCGAATACG |
| RB1 | 13q14.2 | TTAGTTCGCGTATCGATTAGCG | ACTAAACGCCGCGTCAA |
| RBP1 | 3q23 | CGCGTTGGGAATTTAGTTGTC | GATACTACGCGAATAATAAACGACCC |
| RNR1 | 13p12 | CGTTTTGGAGATACGGGTCG | AAACAACGCCGAACCGAA |
| RPA2 | 1p35 | TGGCGCGAATTTGAGTACG | CGTATAATCCCACCCTCGTCA |
| RPA3 | 7p22 | AGCCGATTGCGATTTAGG | TTTCTGCACACCAATCAACGAA |
| RUNX3 | 1p36 | CGTTCGATGGTGACGTGT | GACGAACAACGTCTTATTACAACGC |
| S100A2 | 1q21 | TGTTTGAGTCGTAAGTAGGGCGT | CGTATCATTACAATACCGACCTCCT |
| SASH1 | 6q23 | TGGAAGAGTTTATTTGAAGAGAGGG | GCGACTCGTTCCTTCTAACAAATC |
| SCAM-1 | 8p21 | GTTTCGGTTGTCGTTGGGTT | ACGCCGACGAACTCTACGC |
| SCGB3A1 | 6q36-qter | GGCGTAGGCGGGCGTC | CTACGTAACCCTATCCTACAACTCCG |
| SERPINB6 | 18q21.3 | GAAAAGGAATAGGTAAGCGAGGAGT | ATAAACCACCGCTACTTCTACCA |
| SEZ6L | 22q12.1 | GCGTTAGTAGGGAGAGAAAACGTTC | ATACCAACCGCTCCTCCTAACC |
| SFN | 1p35.3 | GAGGAGGGTTCGAGAGAGAA | ATGGCACACGCCTAAAACT |
| SFRP1 | 8p12-p11.1 | GAATTCGTTCGCCGAGGGA | AAACGAACCGCACTCGTTACC |
| SFRP2 | 4q31.3 | GCGTTTTAGTCGTCGGTTGTTAGT | AAACGACCGAAATTCGAACTTATC |
| SFRP4 | 7p14-p13 | GTTGTTCGGGCGGGTTC | GCGAAACTCCCGGTCTA |
| SFRP5 | 10q24.1 | GCGTTTGTAGTTTATCGTCGTGGTAGA | GAACCGCTACGACGACCGCT |
| SLC8A20 | 3p21.3 | AGGCGCGAATACGAATTGTAGCG | TAAAACGACCGGCCTAACG |
| SMAD2 | 18q21.1 | CGAGGCCGTAGGTTTTATAGGT | CGCAATAAAACGATTCCCGAT |
| SMAD3 | 15q22-15q23 | CGTGAAGCGTTTCGTTGGGT | TTAACGCCTTCTCCGACC |
| SMAD4 | 18q21.1 | GTTTGCCGTAGAGCGATTTTTTC | GCAACTTTCCTTTCTCCCGACT |
| SMAD6 | 15q21.3-22.2 | ATGTTAGTTTAGATATTTTGGCGGTTTC | CGACCCTACAATAAAACGTATTCTCCT |
| SMAD8 | 13q12-q14 | CGCGAAGTTTTATCGTCGTATTAG | CGAAAACGAACCGCAACA |
| SOCS1 | 16p13.13 | GCGTCGAGTTCGTGGGTATTT | CCGAAACCATCTTCACGCTAA |
| STAT1 | 2q32.2 | GCGTAGGATTCGGAAGGGTTA | AACAAACCCCAAACCGAACA |
| STK11 | 19p13.3 | AATTAACGGGTGGGTACGTCG | GCCATCTTATTTACCTCCCTCCC |
| SYK | 9q22 | AGGGTCGTTGGGTGTTTGTG | AACATAAACCGCATCGATCCC |
| TERT | 5p15.37 | GGATTCGCGGGTATAGACGTT | CGAAATCCGCGCGAAA |
| TFAP2A | 6p24 | CGTTAATTTTTAAAGTATTTTTATGGATCG | CCGACAACCAACACTTTACGC |
| TFF1 | 21q22.3 | TAAGGTTACGGTGGTTATTTCGTGA | ACTTAATCCAAATCCTACTACATATCTAAAA |
| TGFBR1 | 9q22 | ACCGCGTTTATTGGTTGTC | ACGAACCCGCAAACGAAA |
| TGFBR2 | 3p22 | GGCGGAGCGTAGTTAGG | CAAACCCGCTACTCGTCAT |
| THBS1 | 15q15 | CGACGCACCAACCTACCG | GTTTTGAGTTGGTTTTACGTTCGTT |
| THRB | 3p24.3 | TCGTCGTCGTTATCGTCGC | GCGTCTACGAACCGATAACCTAAT |
| TIMP3 | 22q12.3 | GCGTCGGAGGTTAAGGTTGTT | CTCTCCAAAATTACCGTACGCG |
| TITF1 | 14q13 | CGAAATAAACCGAATCCTCCTTAA | TGTTTTGTTGTTTTAGCGTTTACGT |
| TMEFF2 | 2q32.3 | CGACGAGGAGGTGTAAGGATG | CAACGCCTAACGAACGAACC |
| TNFRSF 10A | 8p21 | AGTTTTTGGTATTTAGTAGGCGTTCG | CAAACCCGCAATAACCTCTATATC |
| TNFRSF 10B | 8p22-p21 | TTTTGGCCGTTGCGTTTC | CTCATTTCCCCAAATTCGAT |
| TNFRSF 10C | 8p22-p21 | GGGAAGCGCGTATTTGCCG | TCCCCTAACTCCGACGACG |
| TNFRSF 10D | 8p21 | GGGAAGAGCGTATTTGGCG | TCCCTAACTCCGACGACG |
| TNFRSF 25 | 1p36.2 | GCGGAATTACGACGGGTAGA | ACTCCATAACCCTCCGACGA |
| TP63 | 17p13.1 | TTTGTTGTCGCGGGATTTC | CGAATTCGTACGTCCCCT |
| TP73 | 1p36.3 | GGGTCGGTAGTTCGTTTG | CGATTCGCTACGTCCCCT |
| TSHR[e] | 14q31 | TTGAGGGTTAGAGGCGGTA | ACAACGAAAATCCTCCTCCAAAAATACA |

TABLE 13-continued

MethyLight Reaction Details (taken from Supplementary Table 1, Weisenberger et al., Nature Genetics 38 787-793, 2006, which is incorporated herein by reference in its entirety).

| | | | |
|---|---|---|---|
| TWIST1 | 7p21.2 | GTAGCGCGGCGAACGT | AAACGCAACGAATCATAACCAAC |
| TYMS | 18p11.32 | CGGCGTTAAGGAAGGACGAT | TCTCAAACTATAACGCGCCTACAT |
| UNG | 12q23-q24.1 | GTTTGACGGAGGCGTGTA | ACAACGACGACTATTTTAAACACGTAA |
| UQCRH | 1p33.1 | TTCGGTTTCGGGTTTAACG | CCCATATAAACGCTCACGC |
| VDR | 12q12-q14 | ACGTATTTGGTTTAGGCGTTCGTA | CGCTTCAACCTATATTAATCGAAAATACA |
| XAB2 | 3p26-p25 | CGGGAGCGCGTACGTAGTT | CTCCGAAACATTCCCTCCG |
| XPA | 19p13.2 | GACGGATAGGTTTACGTTATTGATTTT | CGCATCTTCTAACGCCTCTATTC |
| XPC | 9q22.3 | CGCGAGTTGTTTGTTTCG | CAACATCAATACCCGCTACCG |
| XRCC1 | 3p26.3 | GTCGGGTGCGTTATTCGC | CTACGCAATTCGCGTCC |
| COL2A1 | 19q13.2 | CGTTGTTAAGGAACGTAGCGTTTT | GCGCGAAACTCGAACCTTT |
| ALU | 12q13.11-q13.2 | TCTAACAATTATAAACTCCAACCACCAA | GGGAAGATGGGATAGAAGGGAATAT |
| ALU | N/A | GGTTAGGTATAGTGGTTTATATTTGTAATTT | ATTAACTAAACTAATCTTAAACTCCTAACCT |

| HUGO Gene Name (If Available) | Probe Oligo Sequence[a] | Source |
|---|---|---|
| ABCB1 | 6FAM-ACGCTATTCCTACCAACCAATCAACCTCA-BHQ-1 | Ehrlich, M. et al. Oncogene 21, 8694-8702 (2002) |
| ALU[b] | 6FAM-ACCGAAACGAACGAATCACGAAATCAA-BHQ-1 | GenBank Number AC023794; Amplicon Location; 156022-156187 |
| APC | 6FAM-CCCGTCGAAAACCCGCCGATTA-BHQ-1 | Eads, C. A. et al. Cancer Res 61, 3410-3418 (2001) |
| APEX1 | 6FAM-CAAACGCGCCTCTAATCACGTAACCAAAT-BHQ-1 | GenBank Number AL355076; Amplicon Location; 64818-64684 |
| APP | 6FAM-CCCGCAAACCTCCCGAAAATATCGTATAAA-BHQ-1 | GenBank Number D67675; Amplicon Location: 8572-8667 |
| ARF/CDKN2A | 6FAM-CGACTCTAAACCTCTACGCACGCGAAA-BHQ-1 | Eads, C. A. et al. Cancer Res 61, 3410-3418 (2001) |
| ARPC1B | 6FAM-CAAATCCCGCCCTCCCCTTCGAAAT-BHQ-1 | GenBank Number AC004922; Amplicon Location; 57135-57206 |
| ATM | 6FAM-CGACTCCTCTCGCCTCCTCCG-BHQ-1 | GenBank Number U62828; Amplicon Location; 10785-10854 |
| ATR | 6FAM-CGACGCCCGACGAAACCGTATAA-BHQ-1 | GenBank Number AC1345084; Amplicon Location; 58222-59312 |
| AXIN1 | 6FAM-ATCCGAAACCTCGAACGCGTCTCG-BHQ-1 | GenBank Number AE006483; Amplicon Location; 84738-84807 |
| BCL2 | 6FAM-ACGACGCCCGAAAACAACCGAAAATCTACA-BHQ-1 | Widschwendter, M. et al. Cancer Res 84, 3807-3813 (2004) |
| BDNF | 6FAM-CCGTAACGCCTCGAATCCCGA-BHQ-1 | GenBank Number AC103796; Amplicon Location; 3794-3866 |
| BRCA1 | 6FAM-CCCGCGTTTTCCGTTACCACGA-BHQ-1 | Fiegl, H. et al Cancer Epidermiol Biomarkers Prev 13, 882-888 (2004) |
| BRCA2 | 6FAM-CGGCCCACAAACCCGCGG-BHQ-1 | GenBank Number AL445212; Amplicon Location; 83637-83703 |
| CACHA1G | 6FAM-AAATAACGCGGAATCCGACAACCGA-BHQ-1 | GenBank Number AC021491; Amplicon Location; 46346-48411 |
| CALCA | 6FAM-ATTCCGCCAATACCACAACAACCAATAAACG-BHQ-1 | Eads, C. A. et al. Cancer Res 61, 3410-3418 (2001) |
| CCND1 | 6FAM-ACCCAAAAAACATTCCCTAAAACGCCG-BHQ-1 | GenBank Number AF511593; Amplicon Location; 1211-1293 |
| CCND2 | 6FAM-CACGCTCGATCTTCGCCCG-BHQ-1 | Ehrlich, M. et al. Oncogene 21, 6694-6702 (2002) |
| CDH1 | 6FAM-ACTAACGACCCCGCCCACCCGA-BHQ-1 | GenBank Number AC099314; Amplicon Location; 80648-80743 |
| CDH13 | 6FAM-AACGCAAAACGCGCCCGACA-BHQ-1 | Fiegl, H. et al Cancer Epidermiol Biomarkers Prev 13, 882-888 (2004) |
| CDK2AP1 | 6FAM-CGACAAATTATAAACCGTCCGCGCCTA-BHQ-1 | GenBank Number AC087768; Amplicon Location; 51406-51528 |
| CDKN1A | 6FAM-AAATTCCGACACATCCGACTCTCGT-BHQ-1 | GenBank Number Z86996; Amplicon Location: 3483-3664 |
| CDKN1C | 6FAM-AACTAATCAACGAAAAACTCCTAACCGCGCT-BHQ-1 | GenBank Number AC013791; Amplicon Location; 57564-57838 |
| CDKN2A | 6FAM-ACCCGACCCCGAACCGCG-BHQ-1 | Eads, C. A. et al. Cancer Res 61, 3410-3418 (2001) |
| CDKN2B | 6FAM-TTAACGACACTCTTCCCTTCTTTCCACG-BHQ-1 | Eads, C. A. et al. Cancer Res 61, 3410-3418 (2001) |
| CDX1 | 6FAM-CCTAAAACCGCCGTACCGACCG-BHQ-1 | GenBank Number AC005896; Amplicon Location; 36199-35266 |
| CGA | 6FAM-TCCCTCTTTCGAATCCAATCAACCG-BHQ-1 | GenBank Number AC138827; Amplicon Location; 56007-58096 |
| CHFR | 6FAM-CCTCGAACCGCTCCATCGAAATTCA-BHQ-1 | GenBank Number AC127070; Amplicon Location; 62442-62645 |
| CLDN1 | 6FAM-GATTTAAAACAACTCCGCCCGCCTCA-BHQ-1 | GenBank Number AC009520; Amplicon Location; 27434-27530 |
| CLIC4 | 6FAM-CGCTAAACTATCCGAATCGAACTAACCACG-BHQ-1 | GenBank Number AL117424; Amplicon Location; 47-119 |
| COL1A2 | 6FAM-ACGACGCGAACATACAATCGTAACCAATACCT-BHQ-1 | GenBank Number AF004877; Amplicon Location; 2302-2390 |
| CRABP1 | 6FAM-ACCATAACCACTTCGCCGACACCTAA-BHQ-1 | GenBank Number AC011270; Amplicon Location; 122142-122223 |
| CTNNB1 | 6FAM-CGGCCGTTTCCCGAACCG-BHQ-1 | Eads, C. A. et al. Cancer Res 61, 3410-3418 (2001) |

TABLE 13-continued

MethyLight Reaction Details (taken from Supplementary Table 1, Weisenberger et al., Nature Genetics 38 787-793, 2006, which is incorporated herein by reference in its entirety).

| Gene | Probe/Primer | Reference |
|---|---|---|
| CTSD | 6FAM-CCTATCCGACCGCCGGA-BHQ-1 | GenBank Number AC088580; Amplicon Location; 43075-43166 |
| CXADR | 6FAM-AACGACCCGAACCGAACTACGAACG-BHQ-1 | Ehrlich, M. et al. Oncogene 21, 8694-8702 (2002) |
| CYP1B1 | 6FAM-CGCCGCCACCAAACCGCTT-BHQ-1 | Fiegl, H. et al Cancer Epidermiol Biomarkers Prev 13,882-888 (2004) |
| CYP27B1 | 6FAM-CCAACCTCAACTCGCCTTTCCTTATTCA-BHQ-1 | GenBank Number AY286918; Amplicon Location; 1728-1805 |
| DAPK1 | 6FAM-CGACCATAAACGCCAACGCCG-BHQ-1 | Muller, H. M. et al. Cancer Lec 200, 231-236 (2004) |
| DCC | 6FAM-ACCAAAATCGGAACAACGACAACACT-BHQ-1 | GenBank Number AC011156; Amplicon Location; 118296-118443 |
| DCLRE1C | 6FAM-ATCCGATCGAATTCTAAACGCCGCTACT-BHQ-1 | GenBank Number AL380083; Amplicon Location; 54518-54803 |
| DOB1 | 6FAM-CCAACAACGCGCAACGAACTCCA-BHQ-1 | GenBank Number AC090584; Amplicon Location; 202441-202541 |
| DIRAS3 | 6FAM-CGCACAAAAACGAAATACGAAAACGCAAA-BHQ-1 | Previously described as ARHI in Fiegl, H. et al Cancer Epidermiol Biomarkers Prev 13,882- |
| DLC1 | 6FAM-AACCCACGACGACCCGAAACG-BHQ-1 | GenBank Number AC015841; Amplicon Location; 115709-115784 |
| DLEC1 | 6FAM-TAATCAAACTTACGCTCACTTCGTCGCCG-BHQ-1 | GenBank Number AP006309; Amplicon Location; 19969-20088 |
| DNAJC15 | 6FAM-TCGCCAACTAAAACGATAACCGACCGAACA-BHQ-1 | Previously described as MCJ in Ehrlich, M. et al. Oncogene 21, 8694-8702 (2002) |
| DPH2L1 | 6FAM-CCCCGTAACCGATCGACGATCGA-BHQ-1 | GenBank Number AC090617; Amplicon Location; 196986-197057 |
| DRD1 | 6FAM-CTCGCAAAAAAACGCGACGCAACTA-BHQ-1 | GenBank Number AC091393; Amplicon Location; 111358-111429 |
| DRD2 | 6FAM-ACACCCAAAACGCGAACCCGAAACT-BHQ-1 | GenBank Number AP002840; Amplicon Location; 110939-111008 |
| EBF3 | 6FAM-TCTTTAAAACAACGAACCGCCAA-BHQ-1 | GenBank Number AL364950; Amplicon Location; 144175-144252 |
| EPM2AIP1 | 6FAM-CGGCACGTCAAACGCCCACTACG-BHQ-1 | Originally described as MLH1-M1 in Eads, C. A. et al. Cancer Res 61, 3410-3418 (2001) |
| ERBB2 | 6FAM-AAATACGTCCCTCCTACGCGAAACG-BHQ-1 | GenBank Number AC079199; Amplicon Location; 44277-44362 |
| ERCC1 | 6FAM-CCCAACGCTAAAAACTTCTATAACGCCACG-BHQ-1 | GenBank Number M63796; Amplicon Location; 22088-22178 |
| ERCC2 | 6FAM-ACCCGCCTCCCTCCCTATAAATATTCAAGAA-BHQ-1 | GenBank Number AC023424; Amplicon Location; 113422-113545 |
| ERCC4 | 6FAM-CACTAAACTATCGCTCGTACTCCAACAACG-BHQ-1 | GenBank Number AC092309; Amplicon Location; 4166-4250 |
| ERCC5 | 6FAM-CACCAACTATCGCTCGTACTCCAACAACG-BHQ-1 | GenBank Number L76588; Amplicon Location; 2113-2184 |
| ERCC6 | 6FAM-CGACGCGCAAAACGAAAACTCCG-BHQ-1 | GenBank Number AL157769; Amplicon Location; 130480-130558 |
| ERCC8 | 6FAM-CCCTAACGCATACGCCTAACTCAACG-BHQ-1 | GenBank Number AC073366; Amplicon Location; 164190-164315 |
| ESR1 | 6FAM-CCCTTCACTTCAACATCGAAAACCTACCCG-BHQ-1 | GenBank Number AC073546; Amplicon Location; 21088-21200 |
| ESR2 | 6FAM-CGATAAACCGACGACCCGACCGA-BHQ-1 | Eads, C. A. et al. Cancer Res 61, 5021-5028 (2000) |
| FAF1 | 6FAM-CCGACCCAACGCTCGCC-BHQ-1 | Fiegl, H. et al Cancer Epidermiol Biomarkers Prev 13,882-888 (2004) |
| FBXW7 | 6FAM-CGCGCGTCAACGCTTAACAAAAAATA-BHQ-1 | GenBank Number AL359977; Amplicon Location; 63234-63308 |
| FHIT | 6FAM-ACGCCAAAACTTCACCTCGCCGTATCG-BHQ-1 | GenBank Number AC023424; Amplicon Location; 113422-113545 |
| GABRA2 | 6FAM-CACTAAACCTCCGAAATAATAACCTAACGCG-BHQ-1 | GenBank Number AC097357; Amplicon Location; 121650-121724 |
| GAD1 | 6FAM-ACGACCTTCGAAAAAACAACCCGAAACTACG-BHQ-1 | GenBank Number AC085060; Amplicon Location; 42381-42454 |
| GATA3 | 6FAM-CCCGCACAACTTCGCTTCTTCTTTACA-BHQ-1 | GenBank Number AC007405; Amplicon Location; 70850-70932 |
| GATA4 | 6FAM-AAATATAACCGGACGACTCCTSCCAATTCATTCG-BHQ-1 | GenBank Number AL390294; Amplicon Location; 51880-51969 |
| GATA5 | 6FAM-CCTATCCCGAATCCGTCAATCCCG-BHQ-1 | GenBank Number AC069185; Amplicon Location; 28567-28630 |
| GDNF | 6FAM-CCCGTATCGTCTACGTCCTTATGCCAAA-BHQ-1 | GenBank Number AL499827; Amplicon Location; 19744-19828 |
| GRIN2A | 6FAM-CGGCGTCGCGCTTCACGTCTAACTAAAA-BHQ-1 | GenBank Number AC008869; Amplicon Location; 108758-108866 |
| GSTP1 | 6FAM-ACGCACGAAACTTCACCTCGAACCTATCG-BHQ-1 | GenBank Number AC007916; Amplicon Location; 111645-111727 |
| HIC1 | 6FAM-AAACCTCGCGAACCTCCGAACCTTAACCGA-BHQ-1 | Eads, C. A. et al. Cancer Res 61, 3410-3418 (2001) |
| HLA-G | 6FAM-CAACATCGTCTACCCAACACACTCCTCTACG-BHQ-1 | Eads, C. A. et al. Cancer Res 61, 3410-3418 (2001) |
| HOXA1 | 6FAM-CGCGCTTCACGCCTCAAAACCT-BHQ-1 | Muller, H. M. et al Ann NY Acad Sci 1022, 44-49 (2004) |
| HOXA10 | 6FAM-TCGTACGCGATCAACGCCAACAATTA-BHQ-1 | GenBank Number AC004079; Amplicon Location; 78138-78220 |
| HOXA11 | 6FAM-CAACTCCCGACCTTCGAACCAACAATATCG-BHQ-1 | GenBank Number AC004080; Amplicon Location; 47850-47933 |
| HRAS | 6FAM-ACCAACAAAACACATCCACGACTTCA-BHQ-1 | GenBank Number AC004080; Amplicon Location; 58150-58249 |
| HSD17B4 | 6FAM-CACTCTTACCCACCACCGCCGACG-BHQ-1 | Widschwendter, M. et al. Cancer Res 84, 3807-3813 (2004) |
| ICAM1 | 6FAM-CCGCGCCGATAACCAATACCA-BHQ-1 | GenBank Number AC109319; Amplicon Location; 231-236 (2004) |
| IFNG | 6FAM-TTCCGAACTAAACAAAATACCCGAACCGAAA-BHQ-1 | Ehrlich, H. M. et al. Cancer Lec 208, 231-236 (2004) |
| IGF2 | 6FAM-ACAAACCCATTATTACCCACCTA-MGBNFQ | GenBank Number AF37590; Amplicon Location; 1245-1407 |
| IGSF4 | 6FAM-CCCTTCTACCGTCGCGAACCCGA-BHQ-1 | GenBank Number AC132217; Amplicon Location; 108663-108720 |
| ITGA4 | 6FAM-CCACTCGCCCATATCGAACCTAACCTACCTCAAA-BHQ-1 | Widschwendter, M. et al Cancer Res 84, 4472-4480 (2004) |
| JUP | 6FAM-ACTTACAACGCGGCTAAACAAAACG-BHQ-1 | GenBank Number AC020585; Amplicon Location; 148589-146639 |
| | 6FAM-AACAACCCGCGCCCGACCA-BHQ-1 | GenBank Number AC109319; Amplicon Location; 81609-81698 |

TABLE 13-continued

MethyLight Reaction Details (taken from Supplementary Table 1, Weisenberger et al., Nature Genetics 38 787-793, 2006, which is incorporated herein by reference in its entirety).

| Gene | Probe/Primer | Reference |
|---|---|---|
| KL | 6FAM-CGAACGACGCGACGAAACGCT-BHQ-1 | GenBank Number AC132217; Amplicon Location; 2082-2189 |
| LDLR | 6FAM-ATCAAATCGCCTACCCTAACGACACTTTCG-BHQ-1 | GenBank Number AC011485; Amplicon Location; 90572-90674 |
| LIG3 | 6FAM-CGCTACCTCCCCGCTCTAAAACCGA-BHQ-1 | GenBank Number AC022903; Amplicon Location; 14538-14829 |
| LPHN2 | 6FAM-CCCATTAACACACCATTCAACCGCTAA-BHQ-1 | GenBank Number AL358939; Amplicon Location; 143237-143336 |
| LZTS1 | 6FAM-ATTACCGCCTTTAAACTCCGAACCCTCCA-BHQ-1 | GenBank Number AC025853; Amplicon Location; 24463-24547 |
| MBD2 | 6FAM-CGACCACCGCCTCTTAAATCCTCCAAA-BHQ-1 | GenBank Number AC093462; Amplicon Location; 143589-143667 |
| MBD4 | 6FAM-CACACCCTAAACGTTACGACGCTAAACTCG-BHQ-1 | GenBank Number AL449212; Amplicon Location; 59670-58965 |
| MGMT | 6FAM-CGCAAACGATACGCACCGA-BHQ-1 | Virnmil, A. K. et al. Cancer Epidermiol Biomarkers Prev 11, 291-297 (2002) |
| MINT1[f] | 6FAM-CTACTTCGCCTAACCTAACGCACCAACAAACG-BHQ-1 | GenBank Number AF135601; Amplicon Location; 233-358 |
| MINT2[f] | 6FAM-CTTACGCCACCGCCTCCGA-BHQ-1 | GenBank Number AC007236; Amplicon Location; 74436-74524 |
| MINT31[f] | 6FAM-ACGCTCCGCTCCGAATACCCA-BHQ-1 | GenBank Number AC021491; Amplicon Location; 50060-50130 |
| MLH1 | 6FAM-CCCGCCTACTAAAAAAATAACGTTACGCG-BHQ-1 | Fiegl, H. et al Cancer Epidermiol Biomarkers Prev 13,882-888 (2004) |
| MLH3 | 6FAM-CGAAACCCTCGCGCATCCGA-BHQ-1 | GenBank Number AL049780; Amplicon Location; 110441-110511 |
| MMS19L | 6FAM-CGCCTCCCGAACCAATCTCCG-BHQ-1 | GenBank Number AL359388; Amplicon Location; 11495-11598 |
| MSH2 | 6FAM-CCCACACAAACACCAACGTTCCG-BHQ-1 | GenBank Number AC079775; Amplicon Location; 98483-98569 |
| MSH4 | 6FAM-AACGTACCAAAACAAATAAATAACAAAAACCACCTAAACCG- | GenBank Number AL359206; Amplicon Location; 16736-16826 |
| MSH6 | 6FAM-CCCGCCTTTTCAATAACCTAAATCGCTACA-BHQ-1 | GenBank Number AC020768; Amplicon Location; 86997-87079 |
| MSH8 | 6FAM-CCCTTTCCTCACGCCGGA-BHQ-1 | GenBank Number AC008509; Amplicon Location; 34144-34228 |
| MT1A | 6FAM-TCCACACCTAAATCCCTCGAACCCACT-BHQ-1 | GenBank Number AC106779; Amplicon Location; 18175-18254 |
| MT1G | 6FAM-CGCGATCCCGAACCTAAACTATACGCA-BHQ-1 | GenBank Number AC026461; Amplicon Location; 19549-19625 |
| MT2A | 6FAM-CGGCGCTAACGACTCAAATTCG-BHQ-1 | GenBank Number AC026461; Amplicon Location; 79477-79686 |
| MT3 | 6FAM-AAAACCCGTTCACCGCCTCCAACTACTA-BHQ-1 | GenBank Number AC024461; Amplicon Location; 98167-98241 |
| MTHFR | 6FAM-TCTCATACCGCTCAAAATCAAACCCG-BHQ-1 | Eads, C. A. et al. Cancer Res 61, 3410-3418 (2001) |
| MUTYH | 6FAM-CCCGCCCACACTTTCCGACG-BHQ-1 | GenBank Number AL369540; Amplicon Location; 54075-54149 |
| MYOD1 | 6FAM-CTCCAACACCCGACTACTATATCCGCGAAA-BHQ-1 | Eads, C. A. et al. Cancer Res 61, 3410-3418 (2001) |
| NCL | 6FAM-CCATAAACCAATCGCGAACCCTCTAACCGT-BHQ-1 | GenBank Number M60868; Amplicon Location; 888-975 |
| NEUROD1 | 6FAM-CGCGACCACCACGACACGAAA-BHQ-1 | GenBank Number AC013733; Amplicon Location; 78578-78857 |
| NEUROD2 | 6FAM-CGCCATACGAACCGCGAAACGAATATA-BHQ-1 | GenBank Number AC087491; Amplicon Location; 38463-38561 |
| NEUROG1 | 6FAM-CGATAACGACGCTCCCGCGAACATAA-BHQ-1 | GenBank Number AC005736; Amplicon Location; 75342-75429 |
| NR3C1 | 6FAM-GTCCCGATCCCAACTACTTCGACCG-BHQ-1 | GenBank Number AY436590; Amplicon Location; 1786-1860 |
| NTF3 | 6FAM-TCGCCACCACGAAACTACCACG-BHQ-1 | GenBank Number AC135586; Amplicon Location; 7503-7576 |
| NTHL1 | 6FAM-CCCCCTCCGGCAATACCG-BHQ-1 | GenBank Number AC005800; Amplicon Location; 24583-24678 |
| OGG1 | 6FAM-CAATACCGACCAACCGCGA-BHQ-1 | GenBank Number AJ131341; Amplicon Location; 1723-1954 |
| ONECUT2 | 6FAM-CCCGCCTCCCGAAACAACTACGA-BHQ-1 | GenBank Number AC090340; Amplicon Location; 75569-75839 |
| OPCML[c] | 6FAM-AACAACTTCCATCCTAACCGCCACTTTCT-BHQ-1 | GenBank Number AC017066; Amplicon Location; 158706-156777 |
| PARP1[d] | 6FAM-CGCTTCCGAAAACCCGAACCGAA-BHQ-1 | GenBank Number AL358704; Amplicon Location; 146947-147015 |
| PARP2 | 6FAM-CGATAACGCCGCCAAACA-BHQ-1 | GenBank Number AL365075; Amplicon Location; 176220-176286 |
| PAXB | 6FAM-GTCCCGATCCCAACTACTTCGACCG-BHQ-1 | GenBank Number AC018683; Amplicon Location; 115663-115758 |
| PENK | 6FAM-AACGCCTACCTCGCCGTCCG-BHQ-1 | GenBank Number AC012349; Amplicon Location; 61412-61510 |
| PGR | 6FAM-AACAACCGCTCGCGCCGA-BHQ-1 | Woodson, K. et al Cancer Epidermiol Biomarkers Prev 14, 1219-1223 (2005) |
| PITX2 | 6FAM-CGACGCTCGCCGAACGCTA-BHQ-1 | GenBank Number AC017066; Amplicon Location; 117302-117404 |
| PLAGL1 | 6FAM-ACTACCGCGAACGACAAAAGCCACG-BHQ-1 | GenBank Number AL109766; Amplicon Location; 52969-53045 |
| PMB2 | 6FAM-CCAACGATCGAAAACCGCCAAACA-BHQ-1 | GenBank Number AC005073; Amplicon Location; 150289-150373 |
| POLD1 | 6FAM-TCCTCCACCCTCGAATATTACGCG-BHQ-1 | GenBank Number AC073646; Amplicon Location; 121539-121607 |
| PPARG | 6FAM-CAAACGCCTACCTGCCGTCCG-BHQ-1 | GenBank Number AC091482; Amplicon Location; 136096-138211 |
| PRKAR1A | 6FAM-CATCCGACCATCCGCCCG-BHQ-1 | GenBank Number AC079210; Amplicon Location; 118231-118314 |
| PSAT1 | 6FAM-ACGCCCGCTCGCGAAAACTTACTAAATA-BHQ-1 | GenBank Number AL363584; Amplicon Location; 5611-5691 |
| PSEN1 | 6FAM-TCGAACAACAACATTTCCGAACCAAAGT-BHQ-1 | GenBank Number AF205692; Amplicon Location; 6663-6739 |

TABLE 13-continued

MethyLight Reaction Details (taken from Supplementary Table 1, Weisenberger et al., Nature Genetics 38 787-793, 2006, which is incorporated herein by reference in its entirety).

| Gene | Probe | Reference |
|---|---|---|
| PSEN2 | 6FAM-CGAACGAAAATCTCCGACGAAAAA-BHQ-1 | GenBank Number U50871; Amplicon Location; 26196-26284 |
| PTEN | 6FAM-TTCCAACCGCCAACCTACAACTACACTTA-BHQ-1 | GenBank Number AF143312; Amplicon Location; 1060-114 |
| PTGS2 | 6FAM-TTTCCGCCAAATATCTTTTCTTCTTCGCA-BHQ-1 | Fiegl, H. et al Cancer Epidermiol Biomarkers Prev 13,882-888 (2004) |
| PTTG1 | 6FAM-ACTCACGCAAATCTTAACACCGCATTCA-BHQ-1 | GenBank Number AC091842; Amplicon Location; 88212-88261 |
| PYCARD | 6FAM-CATCTCCTACAAACCCATATCGCGCAA-BHQ-1 | GenBank Number AC009066; Amplicon Location; 85330-85425 |
| RAD23A | 6FAM-TTACTCGACCCGCACACGTAATCTCCTAAA-BHQ-1 | GenBank Number AD000082; Amplicon Location; 82213-82298 |
| RARB | 6FAM-CTCGAATCGCTCGCGTTCTCGACAT-BHQ-1 | GenBank Number X58649; Amplicon Location; 921-1006 |
| RARRES1 | 6FAM-CGGCGACGACGCTTCACTTCTTCAA-BHQ-1 | GenBank Number AC080013; Amplicon Location; 66080-66144 |
| RASSF1 | 6FAM-CCCTTCCCAAGCGCGCCCS-BHQ-1 | Previously described as RASSF1A in Ehrlich, M. et al. Oncogene 21, 8694-8702 (2002) |
| RB1 | 6FAM-TCACGTCCGCGAAACTCCCGA-BHQ-1 | Eads, C. A. et al. Cancer Res 61, 3410-3418 (2001) |
| RBP1 | 6FAM-ACGCCCTCGAAAACAAAAAACTCTACG-BHQ-1 | GenBank Number AC046134; Amplicon Location; 137423-137512 |
| RNR1 | 6FAM-ACCGCCGTACCACACGCAA-BHQ-1 | Muller, H. M. et al. Cancer Lec 208, 231-236 (2004) |
| RPA2 | 6FAM-CGGCACTTCTACCGTCACTTCCTTTATTCG-BHQ-1 | GenBank Number AL109927; Amplicon Location; 71845-71919 |
| RPA3 | 6FAM-TCCAACTTCGCCAATTAAATACGCGAAA-BHQ-1 | GenBank Number AC004948; Amplicon Location; 23978-24056 |
| RUNX3 | 6FAM-CGACGAACTTCGCCTACGTAATCCG-BHQ-1 | GenBank Number AC023096; Amplicon Location; 64646-64762 |
| S100A2 | 6FAM-CTCGAACGCTCCGTCCCAAACCCT-BHQ-1 | Muller, H. M. et al. Cancer Lec 208, 231-236 (2004) |
| SASH1 | 6FAM-AAACCCGACAAAAATAACCGCGAAACCT-BHQ-1 | GenBank Number AL513164; Amplicon Location; 97419-97530 |
| SCAM-1 | 6FAM-ACGACGCAATCAAAACCCGCA-BHQ-1 | GenBank Number AC037458; Amplicon Location; 86588-86640 |
| SCGB3A1 | 6FAM-CGAACTCCTAACGCGCACGATAAAACCTAA-BHQ-1 | GenBank Number AC122714; Amplicon Location; 80825-80911 |
| SERPINB6 | 6FAM-CACGACGCTCCCACATCCAAATCTTT-BHQ-1 | GenBank Number AC038176; Amplicon Location; 51709-51788 |
| SEZ6L | 6FAM-CCGTCGACCCTACAAAATTTAACGCCA-BHQ-1 | GenBank Number AL022337; Amplicon Location; 87324-87426 |
| SFN | 6FAM-TCTCCCGATACTCACGCACCTCGAA-BHQ-1 | GenBank Number AF029061; Amplicon Location; 8848-8826 |
| SFRP1 | 6FAM-CCGTGACCGACGCGAAAACCAAT-BHQ-1 | GenBank Number AC103363; Amplicon Location; 1133-1202 |
| SFRP2 | 6FAM-CGAACCCGCTCTCTTCGCTAAATACGA-BHQ-1 | GenBank Number AC020703; Amplicon Location; 71046-71137 |
| SFRP4 | 6FAM-AAACACGAACAAGCCAACTCCAACTCCAACT-BHQ-1 | GenBank Number AC018834; Amplicon Location; 76448-76526 |
| SFRP5 | 6FAM-CGGCCGCAATACTTAACATCCCTACCG-BHQ-1 | GenBank Number AL368938; Amplicon Location; 45204-45296 |
| SLC8A20 | 6FAM-CCGGCACTAAAACTACCGTACCGAA-BHQ-1 | GenBank Number AJ289880; Amplicon Location; 86407-86641 |
| SMAD2 | 6FAM-CGAACCCCCGCAAGCGTCGTAA-BHQ-1 | GenBank Number AC120349; Amplicon Location; 27348-27425 |
| SMAD3 | 6FAM-TCCTCCTACCCGTTCTACTCGCCCTTCTT-BHQ-1 | Previously described as MADH3 in Ehrlich, M. et al. Oncogene 21, 8694-8702 (2002) |
| SMAD4 | 6FAM-CCCGCCCTCCCGCTCCGAATA-BHQ-1 | GenBank Number AB043547; Amplicon Location; 119423-119482 |
| SMAD6 | 6FAM-AAACCTTATTACGCAACAATCAACGCCG-BHQ-1 | GenBank Number AC013564; Amplicon Location; 57206-57309 |
| SMAD8 | 6FAM-AACTTCCCTAACCGCTTTCCAAATCGACG-BHQ-1 | GenBank Number AL138706; Amplicon Location; 77288-77362 |
| SOCS1 | 6FAM-ACAATTCCGCTAACGACTATCGCGCA-BHQ-1 | Fiegl, H. et al Cancer Epidermiol Biomarkers Prev 13,882-888 (2004) |
| STAT1 | 6FAM-AACGACCCAAGCGCCTCGAAA-BHQ-1 | GenBank Number AY865620; Amplicon Location; 2091-2179 |
| STK11 | 6FAM-CGACAGCCCGACCCGCAA-BHQ-1 | GenBank Number AC011544; Amplicon Location; 26084-26187 |
| SYK | 6FAM-CCCAACGCGATAACTTCTATAACTACCCAA-BHQ-1 | GenBank Number AL364862; Amplicon Location; 50529-50613 |
| TERT | 6FAM-CCCATCCCTCCGCCCACGTAAAA-BHQ-1 | Fiegl, H. et al Cancer Epidermiol Biomarkers Prev 13,882-888 (2004) |
| TFAP2A | 6FAM-CGAAACCCGAAAAAAACATATCCGTTCACG-BHQ-1 | GenBank Number AL138885; Amplicon Location; 105985-106093 |
| TFF1 | 6FAM-CCCTCCGCCCAAAATAAATAATACTATACTCACTACAAAA-BHQ-1 | Fiegl, H. et al Cancer Epidermiol Biomarkers Prev 13,882-888 (2004) |
| TGFBR1 | 6FAM-TAAATCCCGCTTAACAACTCGGCGACGA-BHQ-1 | GenBank Number AL162427; Amplicon Location; 68257-68355 |
| TGFBR2 | 6FAM-CACGAACGACGCGTTCCCGAA-BHQ-1 | Fiegl, H. et al Cancer Epidermiol Biomarkers Prev 13,882-888 (2004) |
| THBS1 | 6FAM-ACGCGCGCTCACTCCCT-BHQ-1 | Eads, C. A. et al. Cancer Res 61, 3410-3418 (2001) |
| THRB | 6FAM-CCCTCCAACCCTCACGACTATCCGACTTA-BHQ-1 | Widschwendter, M. et al Cancer Res 84, 3807-3813 (2004) |
| TIMP3 | 6FAM-AACTCGCTTCCGACCCGCCGAA-BHQ-1 | GenBank Number AC011087; Amplicon Location; 123758-123833 |
| TITF1 | 6FAM-CTCGCGTTTATTTAACCGACGCCA-BHQ-1 | Eads, C. A. et al. Cancer Res 61, 3410-3418 (2001) |
| TMEFF2 | 6FAM-TATAACTTCCGCGACCGCCTCCTCCT-BHQ-1 | Fiegl, H. et al Cancer Epidermiol Biomarkers Prev 13,882-888 (2004) |
| TNFRSF10A | 6FAM-ATTCCGCCACCCATCCGTCCA-BHQ-1 | GenBank Number AC092644; Amplicon Location; 149017-149069 |
| TNFRSF10B | 6FAM-ATCCTAACGCGAACCAAAACCCAAAACAA-BHQ-1 | GenBank Number AC100861; Amplicon Location; 53847-53923 |
| | | GenBank Number AC107959; Amplicon Location; 131919-132001 |

TABLE 13-continued

MethyLight Reaction Details (taken from Supplementary Table 1, Weisenberger et al., Nature Genetics 38 787-793, 2006, which is incorporated herein by reference in its entirety).

| Gene | Probe Sequence | Reference / Location |
|---|---|---|
| TNFRSF 10C | 6FAM-CGAACATACCCGACCGCAAATAACCA-BHQ-1 | GenBank Number AC107959; Amplicon Location; 185904-166026 |
| TNFRSF 10D | 6FAM-TACCCGACCGCAAACGACCCG-BHQ-1 | GenBank Number AC100861; Amplicon Location; 115508-115632 |
| TNFRSF 25 | 6FAM-CGCCCAAAAACTTCCCGACTCCGTA-BHQ-1 | Formerly described as TNFRSF-12 in Ehrlich, M. et al. Oncogene 21, 8694-8702 (2002) |
| TP63 | 6FAM-TAATCCGAAATACGACGACCAATCGAAAA-BHQ-1 | GenBank Number AC087388; Amplicon Location; 868887-86746 |
| TP73 | 6FAM-AACCTCCGAACGAATACGCGAACGAA-BHQ-1 | GenBank Number AF235000; Amplicon Location; 3977-4058 |
| TSHR$^c$ | 6FAM-AACGACGACTTCGACCGCACCG-BHQ-1 | GenBank Number AC010072; Amplicon Location; 103024-103110 |
| TWIST1 | 6FAM-CCAACGCACCCAATCGCTAAACGA-BHQ-1 | Muller, H. M. et al. Cancer Res 208, 231-236 (2004) |
| TYMS | 6FAM-CCGAATACCGACAAAATACCGATACCCGT-BHQ-1 | Eads, C. A. et al. Cancer Res 61, 3410-3418 (2001) |
| UNG | 6FAM-CCCGAATTTACCGAATCAAAAACGCGA-BHQ-1 | GenBank Number AC007637; Amplicon Location; 4765-4860 |
| UQCRH | 6FAM-CCCGCACAACTCGAACAAAACGAAA-BHQ-1 | GenBank Number AL122001; Amplicon Location; 120731-120802 |
| VDR | 6FAM-CCCACCCTTCCTACCGTAATTCTACCCAA-BHQ-1 | Muller, H. M. et al. Cancer Lec 208, 231-236 (2004) |
| VHL | 6FAM-CGAACCGAACGCCGAAA-BHQ-1 | GenBank Number AF010238; Amplicon Location; 632-725 |
| XAB2 | 6FAM-ACTTCCGATCGCTAACGTCGTCGAAA-BHQ-1 | GenBank Number AC008763; Amplicon Location; 60446-60523 |
| XPA | 6FAM-CCGCTCGATACTCGCCCGCA-BHQ-1 | GenBank Number AL445531; Amplicon Location; 26708-16771 |
| XPC | 6FAM-ACCGCGCGTTTCCGAACCATATTACT-BHQ-1 | GenBank Number AC093495; Amplicon Location; 81528-81625 |
| XRCC1 | 6FAM-CCAATCGCGCCTCTGCAAACG-BHQ-1 | GenBank Number L34079; Amplicon Location; 4045-4154 |
| COL2A1 | 6FAM-CCTTCATTCTAACCCAATACCTATCCCCACCTCTAAA-BHQ-1 | Widschwendter, M. et al Cancer Res 84, 4472-4480 (2004) |
| ALU | 6FAM-CCTACCTTAACCTCCC-MGBNFQ | Weisoniceroer, D. J. et al Nucleic Acids Res 33, 6823-6838 (2005) |

$^a$All primer and probe sequences are listed 5' to 3'. All probes have a 5' 6FAM fluorophore, and either a Black Hole Quencher (BHQ-1) or a Minor Groove Binding Non-Fluorescent Quencher (MGBNFQ) at the 3' end.
$^b$This reaction was originally designed towards the promoter-associated CpG island of the OPCML gene. However, the MethyLight PCR primers cover an ALU repeat sequence within intron 1 of SMUG1. The reaction was designed towards the promoter-associated CpG island of the OPCML gene. However, the MethyLight PCR primers and probe share 99% identity to the CpG island associated with the HNT genomic locus. Therefore, this reaction likely recognizes methylation at either locus.
$^c$The antisense primer used in this study has a mismatch compared to the current GenBank sequence for the genomic locus. The correct antisense primer sequence should read: 5-AAACGACCGCGA CCCCATA-3'. Also, the final three nucleotides of the probe oligomer (GAA) are mismatched with the genomic DNA sequence. The correct sequence should read: 5'-CGCTCCGAAAACCCGAACCCGC-3'.
$^d$However, in order to correctly meet the melting temperature PCR requirements, we recommend the probe sequence to be: 5'-CGCTCCGAAAACCCGAACCCG-3'. The correct nucleotide(s) are underlined for both the antisense and probe oligomers.
$^e$The antisense primer contains an extra 5'-TCC-3' trinucleotide that is not present in the current version of the GenBank genomic sequence. The correct antisense primer sequence should read: 5'-ACAACGAAAATCCTCCAAAATACA-3'.
$^f$The MINT designations are not HGNC-approved gene names, but loci identified as cancer-specifically methylated. MINT1 is located in intron1 of SV2C. The dose % locus to MINT2 is FANCL at 187 kb distance. MINT31 is located near CACNA1G, but in a different CoG island from the MethyLight reaction designed for the CACNA1G locus (HB-158).

Neoadjuvant chemotherapy has been widely used prior to surgery for locally advanced breast cancer (12, 13). Response to this kind of therapy has been shown to be a valid surrogate marker of survival and facilitates breast conserving surgery (14-16). But current clinical and pathological markers poorly predict response to neoadjuvant chemotherapy. In applicants EXAMPLE study, ER negative breast cancers with high NEUROD1 methylation are more likely to respond with a complete pathological response following neoadjuvant chemotherapy.

Predictive factors in adjuvant breast cancer therapy are limited to ER, progesterone receptor, and HER-2/neu. These markers are used to predict response to hormonal treatment and herceptin, respectively (17, 18). Recently HER-2/neu in serum was shown to be a significant predictor of response to neoadjuvant anthracycline-based chemotherapy for breast cancer, whereas the HER-2/neu status of tumor tissue did not correlate with response to treatment (19). Furthermore HER-2/neu overexpression was identified as a major prognostic factor in stage II and III breast cancer patients treated with a neoadjuvant docetaxel and epirubicin combination (20). Despite these findings a more extensive range of predictive markers is highly needed in order to extend the range of individualized therapies for breast cancer patients.

Figure 5:
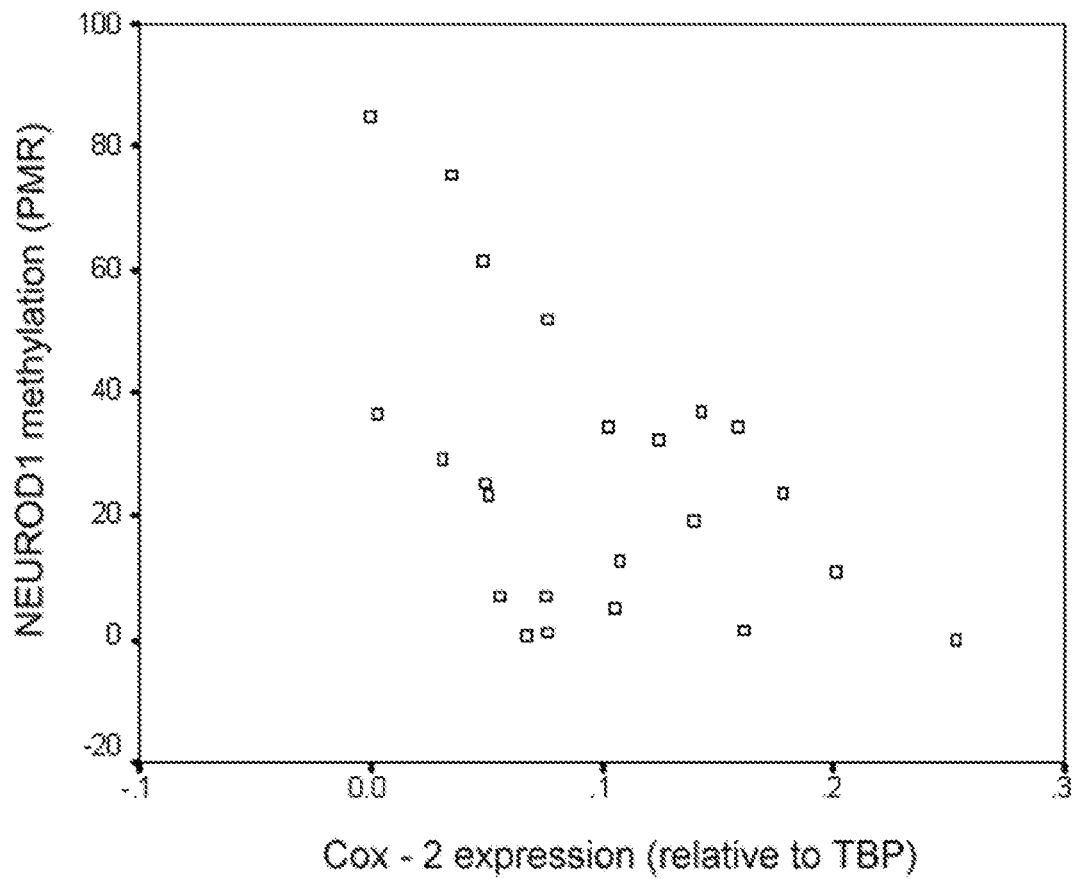
FIG. 5 shows association of COX-2 mRNA expression and NEUROD1 DNA methylation in ER negative primary breast cancer specimens (outliers excluded).

The biological characteristics of circulating tumor cells are poorly understood despite their potential contribution towards the formation of distant metastases. Up until recently, only a limited number of reports examined the occurrence of circulating tumor cells in the context of systemic therapy for primary or metastatic breast cancer. It has been demonstrated that circulating tumor cells are present in a substantial fraction of patients with breast cancer undergoing systemic therapy (21). These circulating tumor cells are usually non-proliferative, and a fraction of these cells seem to be resistant to chemotherapy (21). Only very limited data is available regarding specific characterization of these circulating tumor cells. In our EXAMPLE study applicants described NEUROD1 methylation as a marker for breast cancer cells which are responsive to chemotherapy. Expression of cyclooxygenase-2 (COX-2) has recently been demonstrated to be a marker of doxorubicin-resistant breast cancer (22). In addition, inhibitors of COX-2 increase doxorubicin-induced cytotoxicity (23) and this is at least in part due to COX-2 mediated upregulation of MDR1/P-glycoprotein (MDR1/P-gp) (24, 25), an energy-dependent pump that participates in multidrug resistance. In addition COX-2 derived Prostaglandin E2 protects embryonic stem cells from apoptosis (26). Interestingly, applicants observed a strong inverse correlation of COX-2 expression and NEUROD1 methylation in ER negative breast cancer specimens (correlation coefficient $r=-0.4$; $p=0.03$; Supplementary FIG. 5), which supports our conclusion that NEUROD1 methylation is a surrogate for the status of the cell associated with chemosensitivity.

In particular aspects, this is the first study describing a DNA based marker which is able to predict the response to neoadjuvant as well as adjuvant chemotherapy in a solid tumor independent of gene transcription and the source of DNA analyzed.

REFERENCES CITED IN THIS EXAMPLE 12, AND INCOPORATED HEREIN BY REFERENCE

1. Goldhirsch A, Glick J H, Gelber R D, Coates A S, Senn H J. Meeting highlights: International Consensus Panel on the Treatment of Primary Breast Cancer. Seventh International Conference on Adjuvant Therapy of Primary Breast Cancer. J Clin Oncol 2001; 19:3817-27.
2. Mueller H M, Widschwendter A, Fiegl H, et al. DNA methylation in serum of breast cancer patients: an independent prognostic marker. Cancer Res 2003; 63:7641-45.
3. Fiegl H, Millinger S, Mueller-Holzner E, et al. Circulating tumor-specific DNA: a marker for monitoring efficacy of adjuvant therapy in cancer patients. Cancer Res 2005; 65:1141-45.
4. Widschwendter M, Fiegl H, Egle D, et al. Epigenetic stem cell signature in cancer. Nat Genet 2007; 39:157-58.
5. Eads C A, Danenberg K D, Kawakami K, et al. MethyLight: a high-throughput assay to measure DNA methylation. Nucleic Acids Res 2000; 28: E32.
6. Weisenberger D J, Siegmund K D, Campan M, et al. CpG island methylator phenotype underlies sporadic microsatellite instability and is tightly associated with BRAF mutation in colorectal cancer. Nat Genet. 2006; 38:787-93.
7. Bieche I, Franc B, Vidaud D, Vidaud M, Lidereau R. Analyses of MYC, ERBB2, and CCND1 genes in benign and malignant thyroid follicular cell tumors by real-time polymerase chain reaction. Thyroid 2001; 11:147-52.
8. Lee T I, Jenner R G, Boyer L A, et al. Control of developmental regulators by Polycomb in human embryonic stem cells. Cell 2006; 125:301-13.
9. Gianni L, Zambetti M, Clark K, et al. Gene expression profiles in paraffin-embedded core biopsy tissue predict response to chemotherapy in women with locally advanced breast cancer. J Clin Oncol 2005; 23:7265-77.
10. Fernandez-Morales L A, Segui M A, Andreu X, et al. Analysis of the pathologic response to primary chemotherapy in patients with locally advanced breast cancer grouped according to estrogen receptor, progesterone receptor, and HER2 status. Clin Breast Cancer. 2007; 7:559-64.
11. Sarid D, Ron I G, Sperber F, et al. Neoadjuvant treatment with paclitaxel and epirubicin in invasive breast cancer: a phase II study. Clin Drug Investig. 2006; 26:691-701.
12. Bonadonna G, Veronesi U, Brambilla C, et al. Primary chemotherapy to avoid mastectomy in tumors with diameters of three centimeters or more. J Natl Cancer Inst. 1990; 82:1539-45.
13. Smith I E, Jones A L, O'Brien M E, McKinna J A, Sacks N, Baum M. Primary medical (neo-adjuvant) chemotherapy for operable breast cancer. Eur J. Cancer. 1993; 29A:1796-9.
14. Fisher B, Bryant J, Wolmark N, et al. Effect of preoperative chemotherapy on the outcome of women with operable breast cancer. J Clin Oncol. 1998; 16:2672-85.
15. Kuerer H M, Newman L A, Smith T L, et al. Clinical course of breast cancer patients with complete pathologic primary tumor and axillary lymph node response to doxorubicin-based neoadjuvant chemotherapy. J Clin Oncol. 1999; 17:460-9.
16. Chollet P, Amat S, Cure H, et al. Prognostic significance of a complete pathological response after induction chemotherapy in operable breast cancer. Br J. Cancer. 2002; 86:1041-6.
17. Goldhirsch A, Wood W C, Gelber R D, et al. Meeting highlights: updated international expert consensus on the primary therapy of early breast cancer. J Clin Oncol 2003; 21:3357-65.
18. Marty M, Cognetti F, Marianinchi D, et al. Randomized phase II trial of the efficacy and safety of trastuzumab combined with docetaxel in patients with human epidermal growth factor receptor 2-positive metastatic breast cancer administered as first-line treatment: the M77001 study group. J Clin Oncol. 2005; 23:4265-74.
19. Schippinger W, Dandachi N, Regitnig P, et al. The predictive value of EGFR and HER-2/neu in tumor tissue and serum for response to anthracycline-based neoadjuvant chemotherapy of breast cancer. Am J Clin Pathol. 2007; 128:630-7.
20. Tiezzi D G, Andrade J M, Ribeiro-Silva A, Zola F E, Marana H R, Tiezzi M G. HER-2, p53, p21 and hormonal receptors proteins expression as predictive factors of response and prognosis in locally advanced breast cancer treated with neoadjuvant docetaxel plus epirubicin combination. BMC Cancer. 2007; 7:36.
21. Muller V et al. Circulating tumor cells in breast cancer: correlation to bone marrow micrometastases, heterogeneous response to systemic therapy and low proliferative activity. Clin Cancer Res. 2005; 11:3678-85.
22. Park K, Han S, Shin E, et al. Cox-2 expression on tissue microarray of breast cancer. Eur J Surg Oncol 2006; 32:1093-96.
23. van Wijngaarden J, van Beek E, van Rossum G, et al. Celecoxib enhances doxorubicin-induced cytotoxicity in MDA-MB231 cells by NF-kappaB-mediated increase of intracellular doxorubicin accumulation. Eur J Cancer 2007; 43:433-42.
24. Patel V A, Dunn M J, Sorokin A, et al. Regulation of MDR-1 (P-glycoprotein) by cyclooxygenase-2. Biol Chem 2002; 277:38915-20.
25. Surowiak P, Materna V, Matkowski R, et al. Relationship between the expression of cyclooxygenase 2 and MDR1/P-glycoprotein in invasive breast cancers and their prognostic significance. Breast Cancer Res 2005; 7:R862-70.
26. Liou J Y, Ellent D P, Lee S, et al. Cyclooxygenase-2-derived prostaglandin e2 protects mouse embryonic stem cells from apoptosis. Stem Cells 2007; 25:1096-103.

The invention claimed is:

1. A method for validating or providing a validated precursor cell population culture, comprising:
   identifying, with respect to a reference precursor cell population, one or a plurality of genomic target loci for at least one polycomb group protein (PcG) or polycomb repressive complex;
   identifying one or a plurality of said target loci having a disorder-specific and/or cancer-specific methylation status for at least one CpG dinucleotide sequence position within at least one region of the at least one of the polycomb group protein (PcG) target loci in a cellular proliferative disorder and/or cancer to provide a set of preferred diagnostic/prognostic loci for the disorder and/or cancer;
   obtaining genomic DNA from a first cultured test precursor cell population of interest; and
   determining, by analyzing the genomic DNA of the first cultured test precursor cell population using a suitable assay, the methylation status of the at least one CpG dinucleotide sequence position within the at least one region of the at least one of the polycomb group protein (PcG) preferred diagnostic/prognostic loci, wherein the first cultured test precursor cell population is validated with respect to the presence or absence of the characteristic methylation status of the at least one target loci having a disorder-specific and/or cancer-specific methylation status in the cellular proliferative disorder and/or cancer, or is validated with respect to the presence or absence of cells of the cellular proliferative disorder and/or cancer, or is validated with respect to the presence or absence of cells having a predisposition thereto, wherein validating the first cultured test precursor cell population comprises validating for a presence or absence, in the first cultured test precursor cell population, of rogue cells having the methylation status of the cellular proliferative disorder and/or cancer, or of cells, in the first cultured test precursor cell population, having a predisposition thereto.

2. A method for validating or providing a validated precursor cell population culture, comprising:
   identifying, with respect to a reference precursor cell population, one or a plurality of genomic target loci for at least one polycomb group protein (PcG) or polycomb repressive complex;
   identifying one or a plurality of said target loci having a lineage-specific and/or stage-specific methylation status for at least one CpG dinucleotide sequence position within at least one region of the at least one of the polycomb group protein (PcG) target loci in a cell of a particular developmental lineage or stage to provide a set of preferred diagnostic/prognostic loci for the lineage and/or stage, and wherein the one or the plurality of said target loci also has a cellular proliferative disorder-specific and/or cancer-specific methylation status;
   obtaining genomic DNA from a first cultured test precursor cell population of interest; and
   determining, by analyzing the genomic DNA of the first cultured test precursor cell population using a suitable assay, the methylation status of the at least one CpG dinucleotide sequence position within the at least one region of the at least one polycomb group protein (PcG) preferred diagnostic/prognostic loci, wherein the first cultured test precursor cell population is validated with respect to the presence or absence of the characteristic methylation status of the one or the plurality of target loci having a lineage-specific and/or stage-specific methylation status of cells of a particular developmental lineage or stage, or with respect to the presence or absence of cells of the particular developmental lineage or stage, or with respect to the presence or absence of cells having a developmental predisposition thereto, wherein validating the first cultured test precursor cell population comprises validating for a presence or absence, in the first cultured test precursor cell population, of rogue cells having the methylation status of the cellular proliferative disorder and/or cancer, or of cells, in the first cultured test precursor cell population, having a predisposition thereto.

3. The method of any one of claims 1 and 2, wherein the at least one PcG target locus comprises a PRC2 developmental repressor locus characterized by occupancy, in the reference precursor cell population, by at least one of SUZ 12, EED, and H3K27me3.

4. The method of any one of claims 1 and 2, wherein the at least one PcG target locus comprises a PRC2 developmental repressor locus characterized by occupancy, in the reference precursor cell population, by at least two of SUZ 12, EED, and H3K27me3.

5. The method of any one of claims 1 and 2, wherein the at least one PcG target locus comprises a PRC2 developmental repressor locus characterized by occupancy, in the reference precursor cell population, by all three of SUZ 12, EED, and H3K27me3.

6. The method of any one of claims 1 and 2, wherein identifying one or a plurality of polycomb group protein (PcG) target loci with respect to the reference precursor cell population comprises identifying a plurality of said target loci of genomic DNA of cultured stem cells.

7. The method of claim 6, wherein the cultured stem cells comprise cultured embryonic stem (ES) cells.

8. The method of any one of claims 1 and 2, wherein the CpG methylation status is that of hypermethylation.

9. The method of any one of claims 1 and 2, wherein identifying one or a plurality of said target loci in the cultured test precursor cell population having the respective characteristic methylation status comprises obtaining a sample of genomic DNA, and determining, by analyzing the genomic DNA using a suitable assay, the methylation status of at least one CpG dinucleotide sequence within the at least one region of the at least one of the polycomb group protein (PcG) target locus.

10. The method of any one of claims 1 and 2, wherein determining the methylation status comprises use of a high-throughput methylation assay.

11. The method of any one of claims 1 and 2, wherein the at least one region of at least one of the polycomb group protein (PcG) target loci comprises a CpG island or a portion thereof.

12. The method of claim 1, wherein the cellular proliferative disorder and/or cancer is at least one selected from the group consisting of human colorectal cancer, ovarian cancer, breast cancer, and cellular proliferative disorders and/or cancers associated with hematopoietic stem cells.

13. The method of any one of claims 1 and 2, wherein validating the precursor cell population culture comprises validation of a cultured precursor cell population, or of a precursor cell population subsequent to subjecting said population to one or more differentiation protocols.

14. The method of claim 13, wherein the precursor cell population culture is a therapeutic precursor cell population comprising cultured stem cells.

15. The method of any one of claims 1 and 2, further comprising therapeutic administration, to a subject in need thereof, of the validated cultured precursor cells.

16. The method of claim 1, wherein the proliferative disorder and/or cancer associated with hematopoietic stem cells is at least one selected from the group consisting of leukemia, myeloid leukemia, lymphoblastic leukemia, medulloblastoma, T non-Hodgkin's lymphoma and idiopathic thrombocytopenic purpura.

17. A method for validating or providing a validated precursor cell population culture, comprising:
identifying, with respect to a reference precursor cell population, one or a plurality of genomic target loci for at least one polycomb group protein (PcG) or polycomb repressive complex;
identifying one or a plurality of said target loci having a disorder-specific and/or cancer-specific methylation status for at least one CpG dinucleotide sequence position within at least one region of the at least one of the polycomb group protein (PcG) target loci in a cellular proliferative disorder and/or cancer to provide a set of preferred diagnostic/prognostic loci for the disorder and/or cancer;
obtaining genomic DNA from a first cultured test precursor cell population of interest;
determining, by analyzing the genomic DNA of the first cultured test precursor cell population using a suitable assay, the methylation status of the at least one CpG dinucleotide sequence position within the at least one region of the at least one of the polycomb group protein (PcG) preferred diagnostic/prognostic loci, wherein the first cultured test precursor cell population is validated with respect to the presence or absence, in the first cultured test precursor cell population, of the characteristic methylation status of the at least one target loci having a disorder-specific and/or cancer-specific methylation status in the cellular proliferative disorder and/or cancer, or is validated with respect to the presence or absence, in the first cultured test precursor cell population, of cells of the cellular proliferative disorder and/or cancer, or is validated with respect to the presence or absence, in cultured test precursor cell population, of cells having a predisposition thereto;
obtaining genomic DNA from a second test precursor cell population;
determining, by analyzing the genomic DNA of the second cultured test precursor cell population using a suitable assay, the methylation status of the at least one CpG dinucleotide sequence position within the at least one region of the at least one of the polycomb group protein (PcG) preferred diagnostic/prognostic loci, wherein the second cultured test precursor cell population is validated with respect to the presence or absence, in the second cultured test precursor cell population, of the characteristic methylation status of the at least one target loci having a disorder-specific and/or cancer-specific methylation status in the cellular proliferative disorder and/or cancer, or is validated with respect to the presence or absence, in the second cultured test precursor cell population, of cells of the cellular proliferative disorder and/or cancer, or is validated with respect to the presence or absence, in the second cultured test precursor cell population, of cells having a predisposition thereto; and comparing the methylation status of the first and second cultured test precursor cell populations to provide for distinguishing or selecting a preferred precursor cell population culture.

18. A method for validating or providing a validated precursor cell population culture, comprising:

identifying, with respect to a reference precursor cell population, one or a plurality of genomic target loci for at least one polycomb group protein (PcG) or polycomb repressive complex;

identifying one or a plurality of said target loci having a lineage-specific and/or stage-specific methylation status for at least one CpG dinucleotide sequence position within at least one region of the at least one of the polycomb group protein (PcG) target loci in a cell of a particular developmental lineage or stage to provide a set of preferred diagnostic/prognostic loci for the lineage and/or stage, and wherein the one or the plurality of said target loci also has a cellular proliferative disorder-specific and/or cancer-specific methylation status;

obtaining genomic DNA from a first cultured test precursor cell population of interest;

determining, by analyzing the genomic DNA of the first test precursor cell population using a suitable assay, the methylation status of the at least one CpG dinucleotide sequence position within the at least one region of the at least one polycomb group protein (PcG) preferred diagnostic/prognostic loci, wherein the first test precursor cell population is validated with respect to the presence or absence of the characteristic methylation status of the one or the plurality of target loci having a lineage-specific and/or stage-specific methylation status of cells of a particular developmental lineage or stage, or with respect to the presence or absence of cells of the particular developmental lineage or stage, or with respect to the presence or absence of cells having a developmental predisposition thereto;

obtaining genomic DNA from a second test precursor cell population;

determining, by analyzing the genomic DNA of the second cultured test precursor cell population using a suitable assay, the methylation status of the at least one CpG dinucleotide sequence position within the at least one region of the at least one polycomb group protein (PcG) preferred diagnostic/prognostic loci, wherein the second cultured test precursor cell population is validated with respect to the presence or absence, in the second cultured test precursor cell population, of the characteristic methylation status of the one or the plurality of target loci having a lineage-specific and/or stage-specific methylation status of cells of a particular developmental lineage or stage, or with respect to the presence or absence, in the second cultured test precursor cell population, of cells of the particular developmental lineage or stage, or with respect to the presence or absence, in the second cultured test precursor cell population, of cells having a developmental predisposition thereto; and comparing the methylation status of the first and second cultured test precursor cell populations to provide for distinguishing or selecting a preferred precursor cell population culture.

19. The method of claim 17 or 18, wherein the first and second cultured test precursor cell populations comprise cultured stem cells.

20. The method of claim 19, wherein the cultured stem cells comprise cultured embryonic stem (ES) cells.

21. The method of claim 17 or 18, wherein the CpG methylation status of the first and second cultured test precursor cell populations is that of hypermethylation.

22. A method for identifying preferred DNA methylation markers for validating or providing a validated precursor cell population culture, comprising:

identifying, with respect to a precursor cell population culture, one or a plurality of genomic target loci for at least one polycomb group protein (PcG) or polycomb repressive complex; and determining a disorder-specific and/or cancer-specific methylation status of at least one CpG dinucleotide sequence position within at least one region of at least one of the polycomb group protein (PcG) target loci, wherein the presence of said CpG methylation status in the precursor cell population culture identifies the at least one polycomb group protein (PcG) target locus as a preferred DNA methylation marker for the cellular proliferative disorder and/or cancer, and wherein the at least one PcG target locus comprises a PRC2 developmental repressor locus characterized by occupancy by at least EED.

23. A method for identifying preferred DNA methylation markers for cultured cells of a particular developmental lineage or stage, comprising:

identifying, with respect to a precursor cell population culture, one or a plurality of genomic target loci for at least one polycomb group protein (PcG) or polycomb repressive complex; and determining a developmental lineage-specific and/or stage-specific methylation status of at least one CpG dinucleotide sequence position within at least one region of at least one of the polycomb group protein (PcG) target loci, wherein the presence of said CpG methylation status in the precursor cell population culture identifies the at least one polycomb group protein (PcG) target locus as a preferred DNA methylation marker for the particular developmental lineage or stage, and wherein the at least one of the polycomb group protein (PcG) target loci also has a cellular proliferative disorder-specific and/or cancer-specific methylation status in the precursor cell population culture, and wherein the at least one PcG target locus comprises a PRC2 developmental repressor locus characterized by occupancy by at least EED.

24. The method of any one of claims 22 and 23, wherein the at least one PcG target locus comprises a PRC2 developmental repressor locus characterized by occupancy, in the precursor cell population culture, by at least two of SUZ 12, EED, and H3K27me3.

25. The method of any one of claims 22 and 23, wherein the at least one PcG target locus comprises a PRC2 developmental repressor locus characterized by occupancy, in the precursor cell population culture, by all three of SUZ 12, EED, and H3K27me3.

26. The method of any one of claims 22 and 23, wherein identifying one or a plurality of polycomb group protein (PcG) target loci comprises identifying a plurality of said target loci of genomic DNA of cultured stem cells.

27. The method of claim 26, wherein the cultured stem cells comprise cultured embryonic stem (ES) cells.

28. The method of any one of claims 22 and 23, wherein the one CpG methylation status is that of hypermethylation.

29. The method of any one of claims 22 and 23, wherein identifying one or a plurality of genomic target loci comprises in silico database identification or correlation, or comprises chromatin immunoprecipitation.

30. The method of any one of claims 22 and 23, wherein determining the methylation status comprises use of a high-throughput methylation assay.

31. The method of any one of claims 22 and 23, wherein the at least one region of at least one of the polycomb group protein (PcG) target loci comprises a CpG island or a portion thereof.

32. The method of any one of claims 22 and 23, wherein the cellular proliferative disorder and/or cancer is at least one selected from the group consisting of human colorectal cancer, ovarian cancer, breast cancer, and proliferative disorders and/or cancers associated with hematopoietic stem cells.

33. The method of claim 32, wherein the proliferative disorder and/or cancer associated with hematopoietic stem cells is at least one selected from the group consisting of leukemia, myeloid leukemia, lymphoblastic leukemia, medulloblastoma, T non-Hodgkin's lymphoma and idiopathic thrombocytopenic purpura.

34. A method for validating or providing a validated precursor cell population culture, comprising validating the precursor cell population culture using the method of claim 23.

35. The method of claim 34, further comprising therapeutic administration, to a subject in need thereof, of the validated precursor cell culture.

36. A method for the diagnosis or prognosis of ovarian cancer comprising: performing methylation analysis of genomic DNA of a subject tissue sample; and determining the methylation state of a HOX genomic DNA sequence relative to a control HOX genomic DNA sequence, wherein the control methylation state is an averaged methylation state based on genomic DNA derived from selected multiple individual control subjects, and wherein diagnosis or prognosis of ovarian cancer is provided.

37. The method of claim 36, wherein the HOX genomic DNA sequence is that of HOXA10 or HOXA11, and wherein hypermethylation is used to provide the ovarian cancer related diagnosis or prognosis.

38. The method of claim 37, wherein the HOX genomic DNA sequence is that of HOXA11, and wherein hypermethylation is used to provide an ovarian cancer related prognosis of poor outcome.

39. The methods of any one of claims 36 through 38, wherein the diagnostic or prognosic marker is for at least one selected from the group consisting of: for stem cells that are unable to differentiate; for stem cell that are resistant to therapy; for residual tumor after cytoreductive surgery; for cancer stem cells; for mucinous cancer cases; for serous cancer cases; for endometrioid cancer cases; for clear cell cases; and for tumor distribution.

40. A method for predicting the response to neoadjuvant and/or adjuvant chemotherapy in a solid tumor, comprising performing methylation analysis of genomic DNA of a subject tissue sample; and determining the methylation state of a NEUROD1 genomic DNA sequence relative to a control NEUROD1 genomic DNA sequence, wherein the control methylation state is an averaged methylation state based on genomic DNA derived from selected multiple individual control subjects, and wherein predicting the response to neoadjuvant and/or adjuvant chemotherapy in breast cancer is provided.

41. A method for determining chemosensitivity in breast cancer, comprising: performing methylation analysis of genomic DNA of a subject tissue sample; and determining the methylation state of a NEUROD1 genomic DNA sequence relative to a control NEUROD1 genomic DNA sequence, wherein the control meth date is an averaged methylation state based on genomic DNA derived from selected multiple individual con subjects, and wherein determining chemosensitivity in breast cancer is provided.

42. The method of claim 41, wherein NEUROD1 methylation is a chemosensitivity marker in estrogen receptor (ER) negative breast cancer.

43. The method of any one of claims 40 through 42, wherein methylation analysis is at least one of: methylation analysis in core breast cancer biopsies taken prior to preoperative chemotherapy with complete pathological response as the endpoint; and seroconversion of NEUROD1 methylation in serum DNA during adjuvant chemotherapy with survival as the endpoint.

44. The method of any one of claims 40 through 42, wherein the chemosensitivity is with respect to at least one of cyclophosphamide, methotrexate, 5-fluorouracil, anthracycline, and combinations thereof.

45. A method for validating or providing a validated precursor cell population culture, comprising:
identifying, with respect to a reference precursor cell population, one or a plurality of genomic target loci for at least one polycomb group protein (PcG) or polycomb repressive complex;
identifying one or a plurality of said target loci having a disorder-specific and/or cancer-specific methylation status for at least one CpG dinucleotide sequence position within at least one region of the at least one of the polycomb group protein (PcG) target loci in a cellular proliferative disorder and/or cancer associated with hematopoietic stem cells to provide a set of preferred diagnostic/prognostic loci for the disorder and/or cancer associated with hematopoietic stem cells, wherein the cellular proliferative disorder and/or cancer associated with hematopoietic stem cells is at least one selected from the group consisting of leukemia, myeloid leukemia, lymphoblastic leukemia, medulloblastoma, T non-Hodgkin's lymphoma and idiopathic thrombocytopenic purpura; obtaining genomic DNA from a first test precursor cell population of interest; and
determining, by analyzing the genomic DNA of a first cultured test precursor cell population using a suitable assay, the methylation status of the at least one CpG dinucleotide sequence position within the at least one region of the at least one of the polycomb group protein (PcG) preferred diagnostic/prognostic loci, wherein the first test cultured precursor cell population is validated with respect to the presence or absence of the characteristic methylation status of the at least one target loci having the disorder-specific and/or cancer-specific methylation status in the cellular proliferative disorder and/or cancer associated with hematopoietic stem cells, or is validated with respect to the presence or absence of cells, in the first cultured test precursor cell population, of rogue cells having the methylation status of the cellular proliferative disorder and/or cancer associated with hematopoietic stem cells, or is validated with respect to the presence or absence of cells, in the first cultured test precursor cell population, having a predisposition thereto.

* * * * *

UNITED STATES PATENT AND TRADEMARK OFFICE
CERTIFICATE OF CORRECTION

PATENT NO.       : 8,586,313 B2                                      Page 1 of 1
APPLICATION NO. : 12/520841
DATED            : November 19, 2013
INVENTOR(S)      : Laird et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 854 days.

Signed and Sealed this
Twenty-second Day of September, 2015

Michelle K. Lee
*Director of the United States Patent and Trademark Office*